(12) United States Patent
Wiltzius et al.

(10) Patent No.: US 11,505,613 B2
(45) Date of Patent: Nov. 22, 2022

(54) BCMA BINDING MOLECULES AND METHODS OF USE THEREOF

(71) Applicant: KITE PHARMA, INC., Santa Monica, CA (US)

(72) Inventors: Jed Wiltzius, Woodland Hills, CA (US); Ruben Alvarez Rodriguez, Los Angeles, CA (US); Jonathan Belk, Lebanon, NJ (US)

(73) Assignee: Kite Pharma, Inc., Santa Monica, CA (US)

( * ) Notice: Subject to any disclaimer, the term of this patent is extended or adjusted under 35 U.S.C. 154(b) by 126 days.

(21) Appl. No.: 16/569,341

(22) Filed: Sep. 12, 2019

(65) Prior Publication Data

US 2020/0109209 A1   Apr. 9, 2020

Related U.S. Application Data

(63) Continuation of application No. 15/476,309, filed on Mar. 31, 2017, now Pat. No. 10,689,450.

(60) Provisional application No. 62/317,334, filed on Apr. 1, 2016.

(51) Int. Cl.
| | |
|---|---|
| C07K 16/28 | (2006.01) |
| C07K 14/705 | (2006.01) |
| A61K 31/675 | (2006.01) |
| A61K 31/7076 | (2006.01) |
| A61K 31/7088 | (2006.01) |
| A61P 35/00 | (2006.01) |
| A61P 35/02 | (2006.01) |
| A61K 45/06 | (2006.01) |
| A61K 35/00 | (2006.01) |

(52) U.S. Cl.
CPC ........ *C07K 16/2878* (2013.01); *A61K 31/675* (2013.01); *A61K 31/7076* (2013.01); *A61K 31/7088* (2013.01); *A61K 45/06* (2013.01); *A61P 35/00* (2018.01); *A61P 35/02* (2018.01); *C07K 14/70521* (2013.01); *A61K 35/00* (2013.01); *C07K 2317/53* (2013.01); *C07K 2317/565* (2013.01); *C07K 2317/622* (2013.01); *C07K 2317/92* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 4,946,778 A | 8/1990 | Ladner et al. |
| 5,260,203 A | 11/1993 | Ladner et al. |
| 5,728,388 A | 3/1998 | Terman |
| 5,827,642 A | 10/1998 | Riddell et al. |
| 5,830,462 A | 11/1998 | Crabtree et al. |
| 5,834,266 A | 11/1998 | Crabtree et al. |
| 5,869,337 A | 2/1999 | Crabtree et al. |
| 6,040,177 A | 3/2000 | Riddell et al. |
| 6,165,787 A | 12/2000 | Crabtree et al. |
| 6,319,494 B1 | 11/2001 | Capon et al. |
| 6,797,514 B2 | 9/2004 | Berenson et al. |
| 6,867,041 B2 | 3/2005 | Berenson et al. |
| 6,905,874 B2 | 6/2005 | Berenson et al. |
| 7,709,226 B2 | 5/2010 | Foote |
| 7,741,465 B1 | 6/2010 | Eshhar et al. |
| 8,465,743 B2 | 6/2013 | Rosenberg et al. |
| 8,486,693 B2 | 7/2013 | Park et al. |
| 8,536,310 B2 | 9/2013 | Abo et al. |
| 9,034,324 B2 | 5/2015 | Kalled et al. |
| 9,163,090 B2 | 10/2015 | Jiang et al. |
| 9,845,362 B2 | 12/2017 | Mukherjee |
| 10,597,456 B2 | 3/2020 | Wiltzius et al. |
| 2002/0006409 A1 | 1/2002 | Wood |
| 2002/0164588 A1 | 11/2002 | Eisenberg et al. |
| 2004/0014194 A1 | 1/2004 | Beyer et al. |
| 2004/0043401 A1 | 3/2004 | Sadelain et al. |
| 2004/0197328 A1 | 10/2004 | Young et al. |
| 2010/0285037 A1 | 11/2010 | Abo et al. |
| 2011/0280889 A1 | 11/2011 | Schendel et al. |
| 2011/0286980 A1 | 11/2011 | Brenner |
| 2012/0130076 A1 | 5/2012 | Holt et al. |
| 2012/0213783 A1 | 8/2012 | Rosenberg et al. |
| 2012/0227134 A1 | 9/2012 | Schon et al. |

(Continued)

FOREIGN PATENT DOCUMENTS

| | | |
|---|---|---|
| CL | 2017000590 A1 | 10/2017 |
| CL | 201802797 | 3/2019 |

(Continued)

OTHER PUBLICATIONS

US 5,830,482 A, 11/1998, Crabtree et al. (withdrawn)

(Continued)

*Primary Examiner* — Peter J Reddig

(74) *Attorney, Agent, or Firm* — Sheppard Mullin Richter & Hampton LLP

(57) ABSTRACT

The invention provides antibodies, antigen binding fragments thereof, chimeric antigen receptors (CARs), and engineered T cell receptors, polynucleotides encoding the same, and in vitro cells comprising the same. The polynucleotides, polypeptides, and in vitro cells described herein can be used in an engineered CAR T cell therapy for the treatment of a patient suffering from a cancer. In one embodiment, the polynucleotides, polypeptides, and in vitro cells described herein can be used for the treatment of multiple myeloma.

22 Claims, 51 Drawing Sheets

Specification includes a Sequence Listing.

(56) References Cited

U.S. PATENT DOCUMENTS

| | | |
|---|---|---|
| 2013/0079246 A1 | 3/2013 | De Smedt et al. |
| 2013/0156769 A1 | 6/2013 | Kufer et al. |
| 2013/0287748 A1 | 10/2013 | June et al. |
| 2013/0295118 A1 | 11/2013 | Jiang et al. |
| 2014/0010861 A1 | 1/2014 | Bancel et al. |
| 2014/0050708 A1 | 2/2014 | Powell et al. |
| 2014/0099309 A1 | 4/2014 | Powell, Jr. et al. |
| 2014/0105915 A1 | 4/2014 | Algate et al. |
| 2014/0154228 A1 | 6/2014 | Volk et al. |
| 2014/0171649 A1 | 6/2014 | Li et al. |
| 2014/0227237 A1 | 8/2014 | June et al. |
| 2014/0286987 A1 | 9/2014 | Spencer et al. |
| 2014/0328812 A1 | 11/2014 | Campana et al. |
| 2015/0051266 A1 | 2/2015 | Kochenderfer |
| 2015/0225480 A1 | 8/2015 | Powell, Jr. |
| 2015/0266973 A1 | 9/2015 | Jarjour et al. |
| 2015/0368351 A1 | 12/2015 | Vu et al. |
| 2015/0368360 A1 | 12/2015 | Liang et al. |
| 2016/0046700 A1 | 2/2016 | Foster et al. |
| 2016/0046724 A1 | 2/2016 | Brogdon et al. |
| 2016/0051651 A1 | 2/2016 | Brogdon et al. |
| 2016/0297884 A1 | 10/2016 | Kuo et al. |
| 2016/0297885 A1 | 10/2016 | Kuo et al. |
| 2016/0311907 A1 | 10/2016 | Brogdon et al. |
| 2016/0340649 A1 | 11/2016 | Brown et al. |
| 2016/0370649 A1 | 12/2016 | Zhang et al. |
| 2017/0183418 A1 | 6/2017 | Galletto |
| 2017/0281766 A1 | 10/2017 | Wiltzius |
| 2017/0283500 A1 | 10/2017 | Wiltzius et al. |
| 2017/0283504 A1 | 10/2017 | Wiltzius |
| 2020/0108142 A1 | 4/2020 | Wiltzius |
| 2020/0115457 A1 | 4/2020 | Wiltzius et al. |

FOREIGN PATENT DOCUMENTS

| | | | |
|---|---|---|---|
| CL | 2019002310 A1 | 8/2019 | |
| CL | 2018002797 A1 | 6/2020 | |
| CN | 105384825 A | 3/2016 | |
| EP | 3436079 B1 | 8/2021 | |
| JP | 2014-520088 B2 | 8/2014 | |
| JP | 2014-534242 | 12/2014 | |
| JP | 2015-513920 B | 5/2015 | |
| JP | 2015-519337 A | 7/2015 | |
| JP | 2016-507523 | 3/2016 | |
| JP | 3262724 B2 | 1/2018 | |
| WO | 88/01649 A1 | 3/1988 | |
| WO | 2005000894 A1 | 1/2005 | |
| WO | 2008081035 A1 | 7/2008 | |
| WO | 2012/031744 A1 | 3/2012 | |
| WO | 2012033885 A1 | 3/2012 | |
| WO | 2012079000 A1 | 6/2012 | |
| WO | 2012/129514 A1 | 9/2012 | |
| WO | 2012/163805 A1 | 12/2012 | |
| WO | 2013/072406 A1 | 5/2013 | |
| WO | 2013/142034 A1 | 9/2013 | |
| WO | 2013139625 A1 | 9/2013 | |
| WO | 2013/154760 A1 | 10/2013 | |
| WO | 2013169691 A1 | 11/2013 | |
| WO | 2014/089335 A2 | 6/2014 | |
| WO | 2014/122143 A1 | 8/2014 | |
| WO | 2014127261 A1 | 8/2014 | |
| WO | 2014186469 A1 | 11/2014 | |
| WO | 2015077789 A2 | 5/2015 | |
| WO | 2015080981 A1 | 6/2015 | |
| WO | 2015090229 A1 | 6/2015 | |
| WO | 2015120096 A2 | 8/2015 | |
| WO | 2015142675 A2 | 9/2015 | |
| WO | 2015/158671 A1 | 10/2015 | |
| WO | 2016/014789 A2 | 1/2016 | |
| WO | 2016014535 A1 | 1/2016 | |
| WO | 2016014565 A1 | 1/2016 | |
| WO | 2016/040868 A1 | 3/2016 | |
| WO | 2016040868 A1 | 3/2016 | |
| WO | 2016044745 A1 | 3/2016 | |
| WO | 2016090320 A1 | 6/2016 | |
| WO | 2016/094304 A2 | 6/2016 | |
| WO | 2016090369 A1 | 6/2016 | |
| WO | WO-2016090320 A1 * | 6/2016 | ............ A61K 35/17 |
| WO | 2017025038 A1 | 2/2017 | |
| WO | 2017173256 A1 | 10/2017 | |
| WO | 2017173349 A1 | 10/2017 | |
| WO | 2017173384 A1 | 10/2017 | |
| WO | 2017173410 A1 | 10/2017 | |

OTHER PUBLICATIONS

Tramontano A et al., "Framework residue 71 is a major determinant of the position and conformation of the second hypervariable region in the VH domains of immunoglobulins," J Mal Biol, 215(1):175-182 (1990).

Wu et al., "Remote control of therapeutic T Cells through a small molecule-gated chimeric receptor," Science, 350 5258):293 (2015).

International Search Report for PCT/US2017/025351 dated Aug. 22, 2017 (6 pages).

Ashwood-Smith, "Preservation of mouse bone marrow at -79 degrees C. with dimethyl sulphoxide," Nature, 190:1204-1205 (1961).

Bakker et al., "C-type lectin-like molecule-1: a novel myeloid cell surface marker associated with acute myeloid leukemia," Cancer Res., 64:8443-8450 (2004).

Chothia et al., "Conformations of immunoglobulin hypervariable regions," Nature, 342:877-883 (1989).

Chu et al., "SV40 DNA transfection of cells in suspension: analysis of efficiency of transcription and translation of T-antigen," Gene, 13:197-202 (1981).

C-type lectin domain family 12 member A isoform 1 [*Homo sapiens*], NCBI Reference Sequence: NP_612210.4, https://www.ncbi.nlm.nih.gov/protein/NP_61221.4, retrieved on Oct. 2, 2017.

Davis et al., "Basic Methods in Molecular Biology," 1986, Elsevier, Table of Contents only.

Eshhar et al., "Tumor-specific T-bodies: towards clinical application," Cancer Immunol Immunotherapy, 45:131-136 (1997).

Evans et al., "Design of nonpeptidal ligands for a peptide receptor: cholecystokinin antagonists," J_Med. Chem., 30:1229-1239 (1987).

Fauchere, J., Adv. Drug Res., 15:29 (1986).

Gautier et al., "Site-Specific Protein Labeling, Methods and Protocols," Springer 2015, pp. 1-267.

Golub et al., "Immunology—A Synthesis {2nd Edition)," Sinauer Association., Sunderland, Mass. (1991 ), table of contents only, 13 pages.

Graham et al., "A new technique for the assay of infectivity of human adenovirus 5 DNA," Virology, 52:456-467 (1973).

Guedan et al., "ICOS-based chimeric antigen receptors program bipolar TH17fTH1 cells," Blood, 124(7):1070-1080 (2014).

Harlow et al., "Antibodies: A Laboratory Manual," Cold Spring Harbor Laboratory, eds., 1988.

Hartl et al., "Genetics: Principles and Analysis," 1997, Jones and Bartlett Publishers.

Hornbach et al., "OX40 costimulation by a chimeric antigen receptor abrogates CD28 and IL-2 induced IL-10 secretion by redirected CD4{+) T cells," Oncoimmunology, 1(4): 458-466 (2012).

Hornbach et al., "Tumor-specific T cell activation by recombinnt immunorceptors: CD3 zeta signaling and CD28 :: ostimulation are simultaneously required for efficient IL-2 secretion and can be integrated into one combined CD28/CD3 zeta signaling receptor molecule," Journal of Immun., 167:6123-6131 (2001).

Kabat et al., "Sequences of Proteins of Immunological Interest," 1991, 5th Ed., NIH Publication 91-3242, Bethesda, MD title page, publication page, and table of contents only, 10 pages.

Restriction Requirement for U.S. Appl. No. 15/476,699 dated Jan. 18, 2019 (11 pages).

Non-Final Office Action for U.S. Appl. No. 15/476,309 dated Mar. 1, 2019 (35 pages).

Restriction Requirement for U.S. Appl. No. 15/476,309 dated Sep. 4, 2018 (12 pages).

Written Opinion for PCT/US2017/025573 dated Aug. 11, 2017 (8 pages).

Written Opinion for PCT/US2017/025351 dated Aug. 22, 2017 (6 pages).

(56) References Cited

OTHER PUBLICATIONS

Written Opinion for PCT/US2017/025516 dated Aug. 25, 2017 (8 pages).
Dotti et al., "Design and Development of Therapies using Chimeric Antigen Receptor-Expressing T cells", Immunol Rev. Jan. 2014; vol. 257(1); pp. 1-28 (29 pages).
Geldres et al., "Chimeric antigen receptor-redirected T cells return to the bench", Seminars in Immunology, Jan. 12, 2016, vol. 28; pp. 3-9 (6 pages).
Fesnak et al., "Engineered T cells: the promise and challenges of cancer immunotherapy", Nature Reviews Cancer Sep. 2016; vol. 16: pp. 566-581 (15 pages).
De Oliveira et al., "Modification of Hematopoietic Stem/Progenitor Cells with CD19-Specific Chimeric Antigen Receptors as a Novel Approach for Cancer Immunotherapy", Human Gene Therapy; Oct. 2013; vol. 24: pp. 24-39 (8 pages).
Kariv et al., "Analysis of the Site of Interaction of CD28 with Its Counter-Receptors COBO and CD86 and Correlation , with Function", Journal of lmmunology_ Apr. 8, 1996; vol. 157: pp. 29-38 (9 pages).
Non-Final Office Action for U.S. Appl. No. 15/475,681, dated Dec. 5, 2018 (42 pages).
Notice of Allowance for U.S. Appl. No. 15/475,681, dated Jun. 24, 2019 (37 pages).
Kowolik, Claudia M., "CD28 Costimulation Provided through a CD19-Specific ChimericAntigen Receptor EnhancesInvivoPersistence and AntitumorEfficacy of Adoptively Transferred T Cells", Cancer Res 2006; 66: (22). Nov. 15, 2006.
Sadelain, M., et al., "The Basic Principles of Chimeric Antigen Receptor Design", Cancer Discovery, Apr. 2, 2013, pp. 388-398.
Evans, E., et al., "Crystal Structure of a Soluble CD28-Fab Complex", Nature Immunology, vol. 6, No. 3 Mar. 2005, pp. 271-279.
Lovelock & Bishop, "Prevention of freezing damage to living cells by dimethyl sulphoxide.," Nature, 183:1394-1395 (1959).
Lu et al., "Targeting Human C-Type Lectin-like Molecule-1 (CLL 1) with a Bispecific Antibody for Immunotherapy of II cute Myeloid Leukemia," Angew Chem Int. Ed. Engl., 53(37):9841-9845 (2014).
Marshall et al., "Identification and characterization of a novel human myeloid inhibitory C-type lectin-like receptor MIGL) that is predominantly expressed on granulocytes and monocytes," J. Biol. Chem. 279:14792-14802 (2004).
Martin and Thornton, "Structural families in loops of homologous proteins: automatic classification, modelling and application to antibodies," J. Mol. Biol, 263:800-815 (1996).
Rinfret, Ann. NY., "Factors affecting the erythrocyte during rapid freezing and thawing," Acad. Sci., 85:576-594 (1960).
Sambrook et al., "Molecular Cloning A Laboratory Manual," 2001, Third Edition, Cold Spring Harbor Laboratory Press, Table of Contents Only.
Shen et al., "Chimeric antigen receptor containing ICOS signaling domain mediates specific and efficient antitumor affect of T cells against EGFRvIII expressing glioma,"Journal of Hematology & Oncology, 6:33 (2013).
Sloviter & Ravdin, "Recovery and transfusion of human erythrocytes after freezing in polyglycol solutions," Nature, 196:899-900 (1962).
Song et al., "Pro-survival signaling via CD27 costimulation drives effective CAR T-cell therapy," Oncoimmunology,1;11): 547-549 (2012).
Tashiro et al., "Treatment of Acute Myeloid Leukemia with T Cells Expressing Chimeric Antigen Receptors Directed to C-type Lectin-like Molecule 1," Molecular Therapy, Jul. 1, 2017 {entire document).
UniProtKB—Q5QGZ9 {CL 12A_HUMAN), (2008), http://www.uniprol.org/Q5QGZ9, retrieved on Oct. 2, 2017.
Van Rhenen et al., "The novel AML stem cell associated antigen CLL-1 aids in discrimination between normal and leukemic stem cells" Blood, 110(7):2659-2666 (2007).
Veber& Freidinger, TINS, p. 392 (1985).

English translation and original Office Action in counterpart Japanese Application No. 12018-550679, dated Apr. 21, 2021.
Office Action dated Feb. 18, 2021 for European Patent Application No. 17776859.5.
Sagar, D et al. (2015), "Antibody blocking of CLEC12A delays the course and attenuates EAE severity by impairing myeloid cell CNS infiltration: A potential new therapy for multiple sclerosis (CAM4P. 158)," The Journal of Immunology, 194(1 supplement), 185.16.
Office Action dated Feb. 16, 2021 for counterpart Australian Patent Application No. 2017240150.
Office Action dated Jan. 8, 2019 for Cuban Appl. No. 2018-0121.
Communication 70a and 70a(2) dated Nov. 22, 2019 for European Appl. No. 17776766.2.
Notification Prior to Examination dated Nov. 17, 2019 for Israeli Appl. No. 261941.
Office Action dated Sep. 23, 2019 for Taiwanese Appl. No. 106111228.
Communication Pursuant to Rule 164(1) EPC dated Oct. 2, 2019 for European Appl. 17776833.0.
Office Action dated Oct. 2, 2019 for Taiwanese Appl. No. 106111226.
Notification Prior to Examination dated Nov. 17, 2019 for Israeli Appl. No. 261942.
Supplementary European Search Report dated Oct. 7, 2019 for European Appl. No. 17776859.
Partial European Search Report dated Sep. 19, 2019 for European Appl. 17776833.
Extended European Search Report dated Feb. 18, 2020 for European Appl. No. 17776833.0.
Addition of Inventor dated Nov. 6, 2019 for Singaporean Patent Application Serial No. 11201808403S.
Request for Correction dated Oct. 4, 2019 for New Zealand Appl. No. 746700.
Grant of Request to add Co-lnventor dated Oct. 29, 2019 (Jonathan Bellk added as an inventor to the application) for Thailand Appl. 1801006120.
Office Action dated Jan. 6, 2020 for Korean Appl. No. 10-2018-7031572.
Office Action dated Mar. 2, 2021 for related Chilean Patent Application No. 201802797, English Translation and Original Version.
Office Action dated Feb. 17, 2021 for related Eurasian Patent Application No. 201891992, English Translation and Original Version.
Office Action dated Mar. 30, 2021 for related Japanese Patent Application No. 2018-550787, English Translation and Original Version.
Nyckoff et al., eds., Methods in Enzymology vol. 114—Diffraction Methods for Biological Macromolecules, Academic Dress, Orlando, FL; title page, publication page, and table of contents only, 5 pages (1985).
Zhao et al., "Targeting C-type lectin-like molecule-1 for antibody-mediated immunotherapy in acute myeloid leukemia," Haematologica, 95(1):71-78 (2010).
International Search Report for PCT/US2017/025516 dated Jul. 21, 2017 (6 pages).
International Search Report for PCT/US2017/025573 dated Jul. 25, 2017 (6 pages).
Office Action for Cuban application No. 2018-0120 dated Jan. 8, 2019 (2 pages).
International Search Report for PCT/US2017/025613 dated Jun. 27, 2017 (13 pages).
Al-Lazikani Bet al., Standard conformations for the canonical structures of immunoglobulins, J Mol Biol, 273:927-948 (1997).
Bricogne G., "Bayesian statistical viewpoint on structure determination: Basic concepts and examples," Meth Enzymol J76A:361-423 (1997).
Bricogne G., "Direct phase determination by entropy maximization and likelihood ranking: status report and perspectives," Acta Crystallogr D Biol Crystallogr, 49{Pt 1):37-60 (1993).
Champe M et al., "Monoclonal antibodies that block the activity of leukocyte function-associated antigen 1 recognize three discrete epitopes in the inserted domain of CD11a," J Biol Chem, 270:1388-1394 (1995).

(56) References Cited

OTHER PUBLICATIONS

Cheung, et al., "Epitope-specific antibody response to the surface antigen of duck hepatitis B virus in infected ducks," Virology, 176:546-552(1990).
Chayen NE, "The role of oil in macromolecular crystallization," Structure, 5:1269-1274 (1997).
Chothia C & Lesk AM, "Canonical structures for the hypervariable regions of immunoglobulins," J Mol Biol 196:901-91, 1987).
Chothia C et al., "Structural repertoire of the human VH segments," J Mol Biol, 227:799-817 (1992).
Cunningham BC & Wells JA, "High-resolution epitope mapping of hGH-receptor interactions by alanine-scanning mutagenesis," Science, 244:1081-1085 (1989).
Dayhoff et al., 1978, Atlas of Protein Sequence and Structure 5:345-352.
Devereux et al., "A comprehensive set of sequence analysis programs for the VAX," Nucl. Acid Res., 12:387-395 (1984).
Fegan et al., "Chemically controlled protein assembly: techniques and applications," Chem. Rev., 110:3315-3336 ] (2010).
Finney et al., "Chimeric receptors providing both primary and costimulatory signaling in T cells from a single gene product," Journal of Immunology, 161 :2791-2797 (1998).
Giege R. et al., "Crystallogenesis of biological macromolecules: facts and perspectives," Acta Crystallogr D Biol :; Crystallogr, 50(PI 4):339-350 (1994).
Gross et al., "Therapeutic Potential of T Cell Chimeric Antigen Receptors {CARs) in Cancer Treatment: Counteracting : :Off-Tumor Toxicities for Safe CAR T Cell Therapy," Annu. Rev. Pharmacol. Toxicol., 56:59-83 (2016).
Henikoff et al., "Amino acid substitution matrices from protein blocks," Proc. Nall. Acad. Sci. U.S.A., 89:10915-10919 (1992).
Kabat EA & Wu TT, "Attempts to locate complementarity-determining residues in the variable positions of light and heavy chains," Ann NY Acad Sci, 190:382-391 (1971).
Kalos et al., "T cells with chimeric antigen receptors have potent antitumor effects and can establish memory in patients with advanced leukemia," Sci Transl. Med., 3:95 (2011).
Kirkland et al., "Analysis of the fine specificity and cross-reactivity of monoclonal anti-lipid A antibodies," J. Immunol. 137:3614-3619(1986).
Krause et al., "Antigen-dependent CD28 signaling selectively enhances survival and proliferation in genetically modified activated human primary T lymphocytes," J. Exp Med., 188(4):619-626 (1998).
McPherson A., "Crystallization of proteins from polyethylene glycol.," J Biol Chem, 251 :6300-6303 (1976).
McPherson A., "Current approaches to macromolecular crystallization," Eur J Biochem, 189:1-23 (1990.
Moldenhauer et al., "Identity of HML-1 antigen on intestinal intraepithelial T cells and of B-ly7 antigen on hairy cell leukaemia," Scand. J. Immunol., 32:77-82 (1990).
Morel et al., "Monoclonal antibodies to bovine serum albumin: affinity and specificity determinations," Molec. Immunol., J5:7-15 (1988).
Porter et al., "Chimeric antigen receptor-modified T cells in chronic lymphoid leukemia," N. EngL J. Med., 365:725-33 (2011).
Roversi Pet al., "Modelling prior distributions of atoms for macromolecular refinement and completion," Acta :; :; Crystallogr D Biol Crystallogr, 56{Pt 10):1316-1323 (2000).
Song et al., "CD27 costimulation augments the survival and anti-tumor activity of redirected human T cells in vivo," Blood, 119:696-706 (2012).
Stahli et al., "Distinction of epitopes by monoclonal antibodies," Methods in Enzymology, 9:242-253 (1983).
Hipp, S., et al. "A Novel BCMA/CD3 Bispecific T-Cell Engager for the Treatment of Multiple Myeloma Induces Selective Lysis In Vitro and In Vivo", Leukemia (2017), p. 1743-1751, 31, www.nature.com/leu, doi: 10.1038/eu.2016.388.
Hymowitz, S.G et al., "Structures of APRIL-Receptor Complexes", J. Biol. Chem. (2005), 280, pp. 7218-7227, doi 10.1074/jbc.M411714200 originally published online Nov. 12, 2004.
Kochenderfer J N et al: "Construction and preclinicial evaluation of an anti-CD19 chimeric antigen receptor", Journal of Immunotherapy, Lippincott Williams & Wilkins, Hagerstown, MD, US, vol. 32, No. 7, Sep. 1, 2009 (Sep. 1, 2009), pp. 689-702, ISSN: 1524-9557.
Kochenderfer J N et al: "A Phase | Clinical Trial of Treatment of B-Cell Maglinancies with Autologus Anti-CD19-CAR-Transduced T-Cells", Blood, vol. 116, No. 21, Nov. 2010 (Nov. 2010), pp. 1179-1180, & 52nd Annual Meeting of the American-Society-Ofhematology (ASH); Orlando, FL, USA; Dec. 4-7, 2010.
Yu, G., et al., "APRIL and TALL-1 and receptors BCMA and TACI: system for regulating humeral immunity", Nature Immunology, Sep. 2000, vol. 1, Issue 3, pp. 252-256, ISBN: 15292908.
Jena et al.(2010) "Redirecting T-cell specificity by introducing a tumor-specific chimeric antigen receptor", Blood 19, 116(7): 1035-1044.
Bonini et al. (2015) "Adoptive T-cell therapy for cancer: The era of engineered T cells", European Journal of Immunology, 45: 2457-2469.
Chames et al. (2009), "Therapeutic antibodies: successes, limitations and hopes for the future", British Journal of Pharmacology, 157: 220-233.
Gura et al. (1997) "Systems for Identifying New Drugs Are Olien Faulty", Science, 278: 1041-1042.
Kaiser et al. (2006) "First Pass at Cancer Genome Reveals Complex Landscape", Science, 313: 1370.
Leong et al. (2017) "An anti-CD3/anti-CLL-1 bispecific antibody for the treatment of acute myeloid leukemia" Blood, 129(5): 609-618.
Rudikoff et al. (1982) "Single amino acid substitution altering antigen-binding specificity," Proc. Nall. Acad. Sci. USA, 79: 1979-1983.
Colman (1994) "Effects of amino acid sequence changes on antibody-antigen interactions," A Structural View of Immune Recognition by Antibodies, 33-36.
Ibragimova et al. (1999), "Stability of the beta-Sheet of the WW Domain: A Molecular Dynamics Simulation Study," Biophysical Journal, 77:2191-2198.
Prazma et al. (2008) "Dendritic cell CD83: A therapeutic target or innocent bystander?", Immunology Letters, 115:1-8.
Wyckoff et al. (1985), "Methods in Enzymology vol. 115. Diffraction Methods for Biological Macromolecules", Academic Press, Orlando, FL; title page, publication page, and table of contents only.
Guest et al. (2005),"The Role of Extracellular Spacer Regions in the Optimal Design of Chimeric Immune Receptors—Evaluation of Four Different SCFVS and ANTIGENS11", Journal of Immunotherapy, Lippincott williams & Wilkins, US, 28(3): 203-211.
Decision of Rejection dated Feb. 20, 2020 for Taiwanese Appl. No. 106111226.
Wiersma et al. (2015) "C-type lectin-like molecule-1 (CLL 1)-targeted TRAIL augments the tumoricidal activity of granulocytes and potentiates therapeutic antibody-dependent cell-mediated cytotoxicity," MAbs, 7(2): 321-330.
Notice of Allowance dated Jul. 22, 2019 for U.S. Appl. No. 15/476,699.
Notice of Allowance dated Oct. 7, 2019 for U.S. Appl. No. 15/476,699.
Final Office Action dated Sep. 10, 2019 for U.S. Appl. No. 15/476,309.
Final Office Action dated Apr. 23, 2019 for U.S. Appl. No. 15/475,681.
Examiner initiated interview summary dated Jun. 14, 2019 for U.S. Appl. No. 15/476,699.
Notice of Acceptance dated Jun. 18, 2019 for U.S. Appl. No. 15/476,309.
Notice of Allowance dated Jun. 24, 2019 for U.S. Appl. No. 15/475,681.
Restriction Requirement dated Aug. 7, 2018 for U.S. Appl. No. 15/475,681.
Notice to File Missing Parts dated Sep. 24, 2019 for U.S. Appl. No. 16/570,645.
Notice To File Corrected Application Papers dated Sep. 25, 2019 for U.S. Appl. No. 16/569,341.
Notice To File Corrected Application Papers dated Oct. 29, 2019 for U.S. Appl. No. 16/658,480.
Notice To File Corrected Application Papers dated Aug. 14, 2018 for U.S. Appl. No. 15/476,699.

(56) References Cited

OTHER PUBLICATIONS

Third Notice of Allowance dated Oct. 23, 2019 for U.S. Appl. No. 15/476,699.
Notice of Allowance dated Oct. 24, 2019 for U.S. Appl. No. 15/475,681.
Examination Report dated May 24, 2019 for Australian Appl. No. 2017240788.
Examination Report dated Sep. 19, 2019 for Canadian Appl. No. 3019650.
Office Action dated Nov. 7, 2019 for Eurasian Appl. No. 201891992.
Communication pursuant to rule 70a and 70a(2) dated Oct. 24, 2019 for European Appl. No. 17776859.5.
Office Action dated Oct. 29, 2019 for Japanese Appl. No. 2018-551953.
Examination Report dated Mar. 14, 2018 for Moroccan Appl. No. 43603.
Examination Report dated Mar. 3, 2018 for Moroccan Appl. No. 43603.
First Examination Report dated Aug. 29, 2019 for NewZealand Appl. No. 747172.
Office Action dated Mar. 14, 2019 for Panamanian Appl. No. PI/2018/92399-01.
Office Action dated Oct. 19, 2019 for Peru Appl. No. 001934-2018/DIN.
Office Action and Search Report dated Sep. 20, 2019 for Taiwanese Appl. No. 106111224.
Office Action dated Oct. 31, 2019 for Ukrainian Appl. No. a 2018 09953.
Granting Resolution dated Nov. 25, 2019 for Colombian Appl. No. NC2018/0010547.
Office Action dated Dec. 6, 2019 for Colombian Appl. No. NC2019/0008646.
Notification prior to examination dated Nov. 17, 2019 for Israeli Appl. No. 262041.
Office Action dated Mar. 24, 2020 for Israeli Appl. No. 262041.
Office Action dated Jun. 2, 2020 for Chinese Appl. No. 201780022074.7.
Communication Pursuant to Article 94(3) dated Jul. 6, 2020 for European Appl. No. 17776766.2.
Office Action dated Jul. 17, 2020 for Korean Appl. No. 10-2020-7015941.
Office Action dated May 5, 2020 for Indonesian Appl. No. P00201808813.
Office Action dated Jul. 12, 2020 for Eurasian Appl. No. 201891992.
Office Action dated Nov. 20, 2020 for Argentina Patent Application No. P20170100823, English Translation and original Version.
Office Action dated Dec. 7, 2020 for Candaian Patent Application No. 3,019,650.
Notice of Allowance dated Sep. 17, 2020 for Taiwan Application. No. 109107507.
Office Action in related Korean Application No. 10-2020-7015941, dated Apr. 6, 2021.
English translation Office Action of related Korean Application No. 10-2020-7015941, dated Apr. 6, 2021 and translated on Apr. 15, 2021.
Office Action (and English Translation) issued in Brazilian Patent Application No. BR 11 2018 070260 9, dated Oct. 22, 2021; Office Action 4 pages, English Translation 3 pages, total 7 pages.
Office Action dated Nov. 30, 2020 for Chilean Patent Application. No 201802797, English Translation and original version.
Office Action dated Dec. 19, 2020 for Chilean Patent Application. No 201902310, English Translation and original version.
Office Action (and English Translation) issued in Israeli Application No. 260012.6, dated Jul. 29, 2021; Office Action 3 pages, English Translation 3 pages, total pp. 6.
English translation and original Notice of Preliminary Rejection in counterpart Korean Application No. 10-2018-7031269, dated Jun. 30, 2021.
Examination Report No. 2 in related Australian Application No. 2017240667, dated Jul. 2, 2021.
Office Action (and English translation) issued in Chilean Patent Application No. 201902310, dated May 16, 2021, 21 pages.
Notification of Defects in Patent Application (and English translation) issued in Israeli Patent Application No. 262041, dated Jul. 29, 2021, 6 pages.
Office Action issued in Indian Patent Application No. 201817040512, dated Aug. 26, 2021, 7 pages.
Office Action (and English translation) issued in Taiwanese Patent Application No. 109115604, 9 pages.
Substantive Examination Report (and English translation) issued in Saudi Arabian Patent Application No. 518400135, 5 pages.
Office Action (with English translation) and search report dated Aug. 30, 2021 in TW Application No. 109112511, 11 pages.
Office Action (and English translation) issued in Chilean Patent Application No. 202002677, 28 pages.
Office Action (and English translation) issued in Mexican Patent Application No. MX/a/2018/012017, dated Sep. 13, 2021, 11 pages.
Decision of Final Rejection (and English translation) issued in Japanese Patent Application No. 2018-550679, dated Oct. 12, 2021, 6 pages.
Notice of Preliminary Rejection (and English Translation) issued in Korean Patent Application No. 10-2021-7021089, dated Sep. 6, 2021, 5 pages.
Office Action dated Dec. 3, 2021 for Chinese Appl. No. 201780030900.2.
Notice of Allowance dated Feb. 10, 2022 for Korean Appl. No. 10-2018-7031269.
Final Rejection dated Jan. 5, 2022 for Korean Appl. No. 10-2018-7031269.
Notice of Acceptance dated Feb. 15, 2022 for Australian Appl. No. 2017240150.
Official Action dated Dec. 11, 2018 for Panamanian Appl. No. 92398-01.
Notice of Allowance dated Jul. 9, 2020 for Taiwanese Appl. No. 106111226.
Notice of Allowance dated Jan. 6, 2022 for Taiwanese Appl. No. 109115604.
Notice of Allowance dated Feb. 25, 2020 for U.S. Appl. No. 15/476,309.
Office Action dated Oct. 29, 2021 for Vietnamese Appl. No. 1-2018-04880.
Notice of Acceptance dated Jun. 14, 2021 for South African Appl. No. 2018/06962.
Non-Final Office Action dated Feb. 28, 2022 for U.S. Appl. No. 16/658,480.
Non-Final Office Action dated Jan. 4, 2022 for U.S. Appl. No. 16/570,645.
Finlay, W.J.J et al. (2012) "Natural and man-made V-gene repertoires for antibody discovery," Front. Immunol. 3(342):1-18.

\* cited by examiner

FIG. 1A – Anti-BCMA Binding Molecules

```
                FR1                          CDR1          FR2              CDR2
FS-21495_VH  EVQLLESGGGLVQPGGSLRLSCAAS G--FTFSSY AMSWVRQAPGKLEWVS AISGSGGST
PC-21497_VH  QVQLVESGGGVVQPGRSLRLSCAAS G--FTFSSY GMHWVRQAPGKLEWVA VISYDGSNK
AJ-21508_VH  QVQLVQSGAEVKKPGASVKVSCKAS G--YTFTSY YMHWVRQAPGQGLEWMG IINPGGGST
NM-21517_VH  QLQLQESGPGLVKPSETLSLTCTVS GGSISSSSY YWGWIRQPPGKGLEWIG SISYSG-ST
TS-21522_VH  EVQLVESGGGLVQPGGSLRLSCAAS G--FTFSSY SMNWVRQAPGKGLEWVS FISSSSTI
RY-21527_VH  QVQLVESGGGVVQPGRSLRLSCAAS G--FTFSSY GMHWVRQAPGKGLEWVA VISYDGSNK
PP-21528_VH  QVQLVQSGAEVKKPGSSVKVSCKAS G--GTFSSY AISWVRQAPGQGLEWMG GIIPIFGTA
RD-21530_VH  QVQLVESGGGVVQPGRSLRLSCAAS G--FTFSSY GMHWVRQAPGKLEWVA VISYDGSNK

CDR2                              FR3                          CDR3
FS-21495_VH  YYADSVKG RFTISRDNSKNTLYLQMNSLRAEDTAVYYC AR-AEM--------GAVFDI WGQ
PC-21497_VH  YYADSVKG RFTISRDNSKNTLYLQMNSLRAEDTAVYYC ARDGTYLGGL---WY-FDL WGR
AJ-21508_VH  SYAQKFQG RVTMTRDTSTSTVYMELSSLRSEDTAVYYC AR----------ESWPMDV WGQ
NM-21517_VH  YYNPSLKS RVTISVDTSKNQFSLKLSSVTAADTAVYYC ARGRGYATS-----LAFDI WGQ
TS-21522_VH  YYADSVKG RFTISRDNAKNSLYLQMNSLRAEDTAVYYC ARGSQE-------HLIFDY WGQ
RY-21527_VH  YYADSVKG RFTISRDNSKNTLYLQMNSLRAEDTAVYYC ARTFWSGSP---PG-LDY WGQ
PP-21528_VH  NYAQKFQG RVTITADESTSTAYMELSSLPSEDTAVYYC ARTPEYSSSIWHYYGMDV WGQ
RD-21530_VH  YYADSVKG RFTISRDNSKNTLYLQMNSLRAEDTAVYYC VKGPLQEPPY---DYGMDV WGQ

FR4
FS-21495_VH  GTMVTVSS
PC-21497_VH  GTLVTVSS
AJ-21508_VH  GTTVTVSS
NM-21517_VH  GTMVTVSS
TS-21522_VH  GTLVTVSS
RY-21527_VH  GTLVTVSS
PP-21528_VH  GTTVTVSS
RD-21530_VH  GTTVTVSS
```

FIG. 1B

| | SEQ ID NO: | | | | | | | |
|---|---|---|---|---|---|---|---|---|
| | VH | FR1 | CDR1 | FR2 | CDR2 | FR3 | CDR3 | FR4 |
| FS-21495 VH | 65 | 1 | 9 | 17 | 25 | 33 | 41 | 49 |
| PC-21497 VH | 66 | 2 | 10 | 18 | 26 | 34 | 42 | 50 |
| AJ-21508 VH | 67 | 3 | 11 | 19 | 27 | 35 | 43 | 51 |
| NM-21517 VH | 68 | 4 | 12 | 20 | 28 | 36 | 44 | 52 |
| TS-21522 VH | 69 | 5 | 13 | 21 | 29 | 37 | 45 | 53 |
| RY-21527 VH | 70 | 6 | 14 | 22 | 30 | 38 | 46 | 54 |
| PP-21528 VH | 71 | 7 | 15 | 23 | 31 | 39 | 47 | 55 |
| RD-21530 VH | 72 | 8 | 16 | 24 | 32 | 40 | 48 | 56 |

FIG. 1C – Anti-BCMA Binding Molecules

```
                   FR1                        CDR1          FR2              CDR2
FS-21495_VH   EVQLLESGGGLVQPGGSLRLSCAASG--FTFSSYAMS WVRQAPGKGLEWVS AISGSGGST
PC-21497_VH   QVQLVESGGGVVQPGRSLRLSCAASG--FTFSSYGMH  WVRQAPGKGLEWVA VISYDGSNK
AJ-21508_VH   QVQLVQSGAEVKKPGASVKVSCKASG--YTFTSYYMH  WVRQAPGQGLEWMG IINPGGGST
NM-21517_VH   QLQLQESGPGLVKPSETLSLTCTVSGGSISSSSYYWG  WIRQPPGKGLEWIG SISYSG-ST
TS-21522_VH   EVQLVESGGGLVQPGGSLRLSCAASG--FTFSSYSMN  WVRQAPGKGLEWVS TISSSSSTI
RY-21527_VH   QVQLVESGGGVVQPGRSLRLSCAASG--FTFSSYGMH  WVRQAPGKGLEWVA VISYDGSNK
PP-21528_VH   QVQLVQSGAEVKKPGSSVKVSCKASG--GTFSSYAIS  WVRQAPGQGLEWMG GIIPIFGTA
RD-21530_VH   QVQLVESGGGVVQPGRSLRLSCAASG--FTFSSYGMH  WVRQAPGKGLEWVA VISYDGSNK
                :.** .**  : . *,  :: ::* .**    :.*** *:**,**;****:.  *     .

CDR2           FR3                                   CDR3
FS-21495_VH   YYADSVKG RFTISRDNSKNTLYLQMNSLRAEDTAVYYC AR-AEM-------GAVFDI WGQ
PC-21497_VH   YYADSVKG RFTISRDNSKNTLYLQMNSLRAEDTAVYYC APDGTYLGGL---WY-FDL WGR
AJ-21508_VH   SYAQKFQG RVTMTRDTSTSTVYMELSSLRSEDTAVYYC AR----------ESWPMDV WGQ
NM-21517_VH   YYNPSLKS RVTISVDTSKNQFSLKLSSVTAADTAVYYC ARGRGYATS-----LAFDI WGQ
TS-21522_VH   YYADSVKG RFTISRDNAKNSLYLQMNSLRAEDTAVYYC ARGSQE-------HLIFDY WGQ
RY-21527_VH   YYADSVKG RFTISRDNSKNTLYLQMNSLRAEDTAVYYC ARTFWSGSP---PG-LDY WGQ
PP-21528_VH   NYAQKFQG RVTITADESTSTAYMELSSLRSEDTAVYC ARTPEYSSIWHYYYGMDV WGQ
RD-21530_VH   YYADSVKG RFTISRDNSKNTLYLQMNSLRAEDTAVYYC VKGPLQEPPY---DYGMDV WGQ
                 ..:..  .*::  *  :..   :::.*:   *******     ,:           ;*  **:

FR4
FS-21495_VH   GTMVTVSS
PC-21497_VH   GTLVTVSS
AJ-21508_VH   GTTVTVSS
NM-21517_VH   GTMVTVSS
TS-21522_VH   GTLVTVSS
RY-21527_VH   GTLVTVSS
PP-21528_VH   GTTVTVSS
RD-21530_VH   GTTVTVSS
              ** *****
```

| FIG. 1D | SEQ ID NO: | | | | | | | |
|---|---|---|---|---|---|---|---|---|
|  | VH | FR1 | CDR1 | FR2 | CDR2 | FR3 | CDR3 | FR4 |
| FS-21495 VH | 65 | 207 | 215 | 223 | 231 | 239 | 247 | 255 |
| PC-21497 VH | 66 | 208 | 216 | 224 | 232 | 240 | 248 | 256 |
| AJ-21508 VH | 67 | 209 | 217 | 225 | 233 | 241 | 249 | 257 |
| NM-21517 VH | 68 | 210 | 218 | 226 | 234 | 242 | 250 | 258 |
| TS-21522 VH | 69 | 211 | 219 | 227 | 235 | 243 | 251 | 259 |
| RY-21527 VH | 70 | 212 | 220 | 228 | 236 | 244 | 252 | 260 |
| PP-21528 VH | 71 | 213 | 221 | 229 | 237 | 245 | 253 | 261 |
| RD-21530 VH | 72 | 214 | 222 | 230 | 238 | 246 | 254 | 262 |

FIG. 1E – Anti-BCMA Binding Molecules

```
                    FR1                    CDR1              FR2         CDR2
FS-21495_VL  EIVLTQSPATLSLSPGERATLSC RASQSVSR------YLA WYQQKPGQAPRLLIY DASNR
PC-21497_VL  DIVMTQSPLSLPVTPGEPASISC KSSQSLLHSNG-YNYLD WYLQKPGQSPQLLIY LGSNR
AJ-21508_VL  EIVMTQSPATLSVSPGERATLSC RASQSVSS------NLA WYQQKPGQAPRLLIY GASTR
NM-21517_VL  EIVLTQSPATLSLSPGERATLSC RASQSVSS------YLA WYQQKPGQAPRLLIY DASNR
TS-21522_VL  EIVLTQSPATLSLSPGERATLSC RASQSVSR------YLA WYQQKPGQAPRLLIY DASNR
RY-21527_VL  DIQLTQSPSSVSASVGDPVTITC RASQGISS------WLA WYQQKPGKAPKLLIY GASSL
PP-21528_VL  DIVMTQSPDSLAVSLGERATINC KSSQSVLYSSNNKNYLA WYQQKPGQPPKLLIY WASTR
RD-21530_VL  EIVMTQSPATLSVSPGERATLSC RASQSVSS------NLA WYQQKPGQAPRLLIY GASTR

CDR2             FR3                  CDR3           FR4
FS-21495_VL  AT GIPARFSGSGSGTDFTLTISSLEPEDFAVYYC QQRISWPFT FGGGTKVEIK
PC-21497_VL  AS GVPDRFSGSGSGTDFTLKISRVEAEDVGVYYC QQGLGLFLT FGGGTKVEIK
AJ-21508_VL  AT GIPARFSGSGSGTEFTLTISSLQSEDFAVYYC QQYAAYP-T FGGGTKVEIK
NM-21517_VL  AT GIPARFSGSGSGTDFTLTISSLEPEDFAVYYC QQRHVWPPT FGGGTKVEIK
TS-21522_VL  AT GIPARFSGSGSGTDFTLTISSLEPEDFAVYYC QQRFYYPWT FGGGTKVEIK
RY-21527_VL  QS GVPSPFSGSGSGTDFTLTISSLQPEDFATYYC QQIYTFPFT FGGGTKVEIK
PP-21528_VL  ES GVPDRFSGSGSGTDFTLTISSLQAEDVAVYYC QQFAHTFFT FGGGTKVEIK
RD-21530_VL  AT GIPARFSGSGSGTEFTLTISSLQSEDFAVYYC QQHHVWPLT FGGGTKVEIK
```

| FIG. 1F | SEQ ID NO: | | | | | | | |
|---|---|---|---|---|---|---|---|---|
| | VL | FR1 | CDR1 | FR2 | CDR2 | FR3 | CDR3 | FR4 |
| FS-21495 VL | 137 | 73 | 81 | 89 | 97 | 105 | 113 | 121 |
| PC-21497 VL | 138 | 74 | 82 | 90 | 98 | 106 | 114 | 122 |
| AJ-21508 VL | 139 | 75 | 83 | 91 | 99 | 107 | 115 | 123 |
| NM-21517 VL | 140 | 76 | 84 | 92 | 100 | 108 | 116 | 124 |
| TS-21522 VL | 141 | 77 | 85 | 93 | 101 | 109 | 117 | 125 |
| RY-21527 VL | 142 | 78 | 86 | 94 | 102 | 110 | 118 | 126 |
| PP-21528 VL | 143 | 79 | 87 | 95 | 103 | 111 | 119 | 127 |
| RD-21530 VL | 144 | 80 | 88 | 96 | 104 | 112 | 120 | 128 |

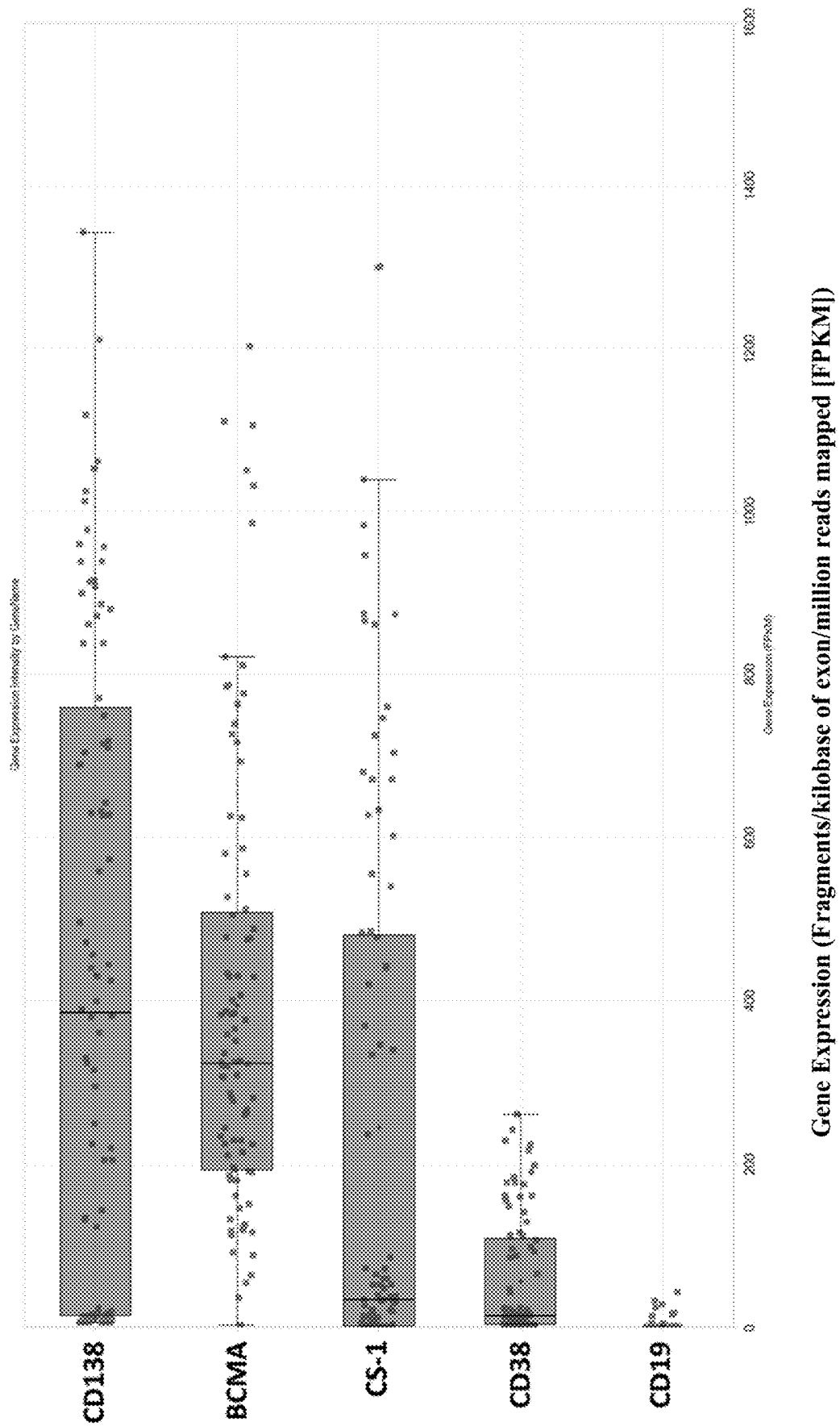
FIG. 2A – Gene Expression in Multiple Myeloma Cells

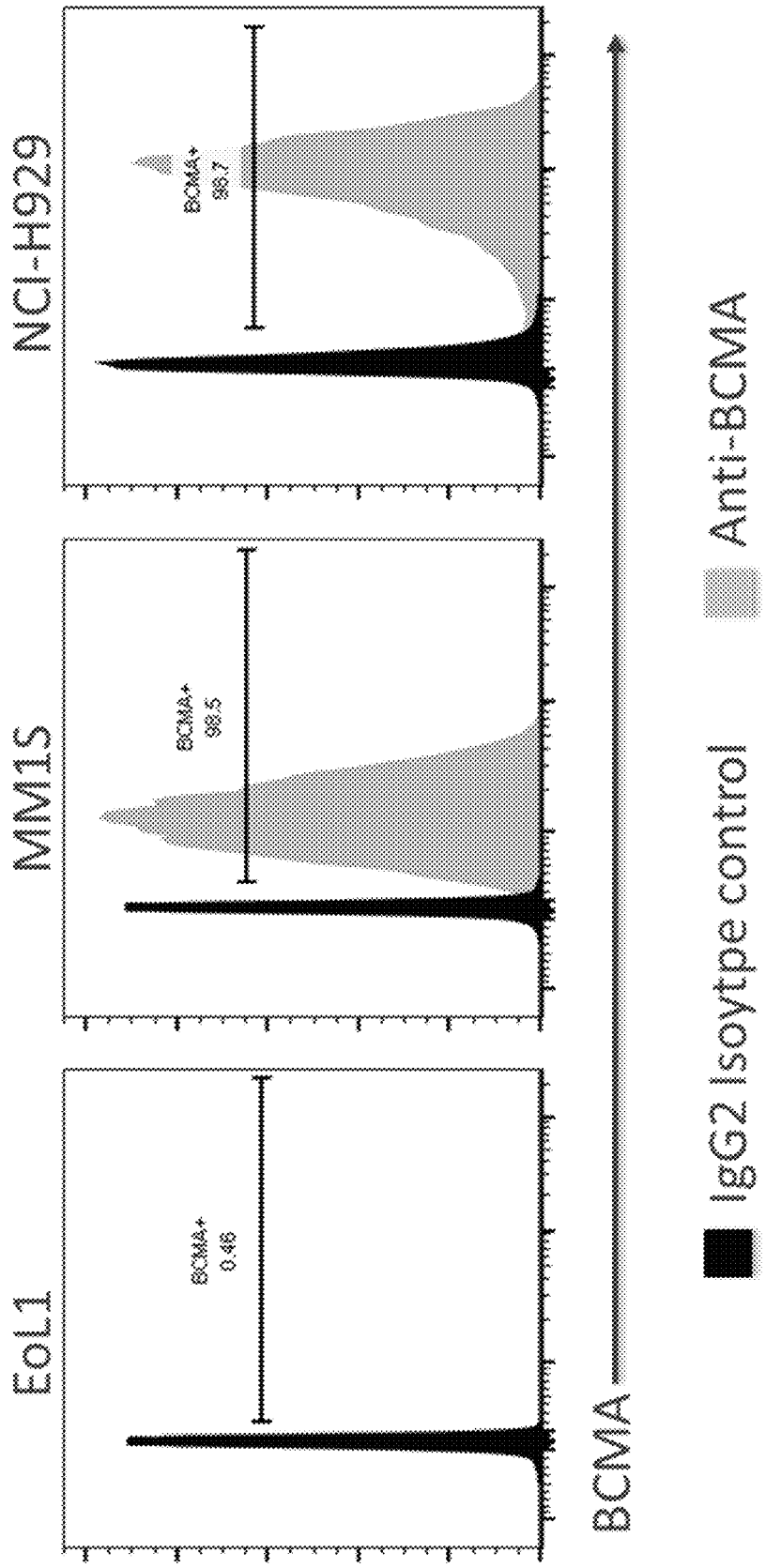

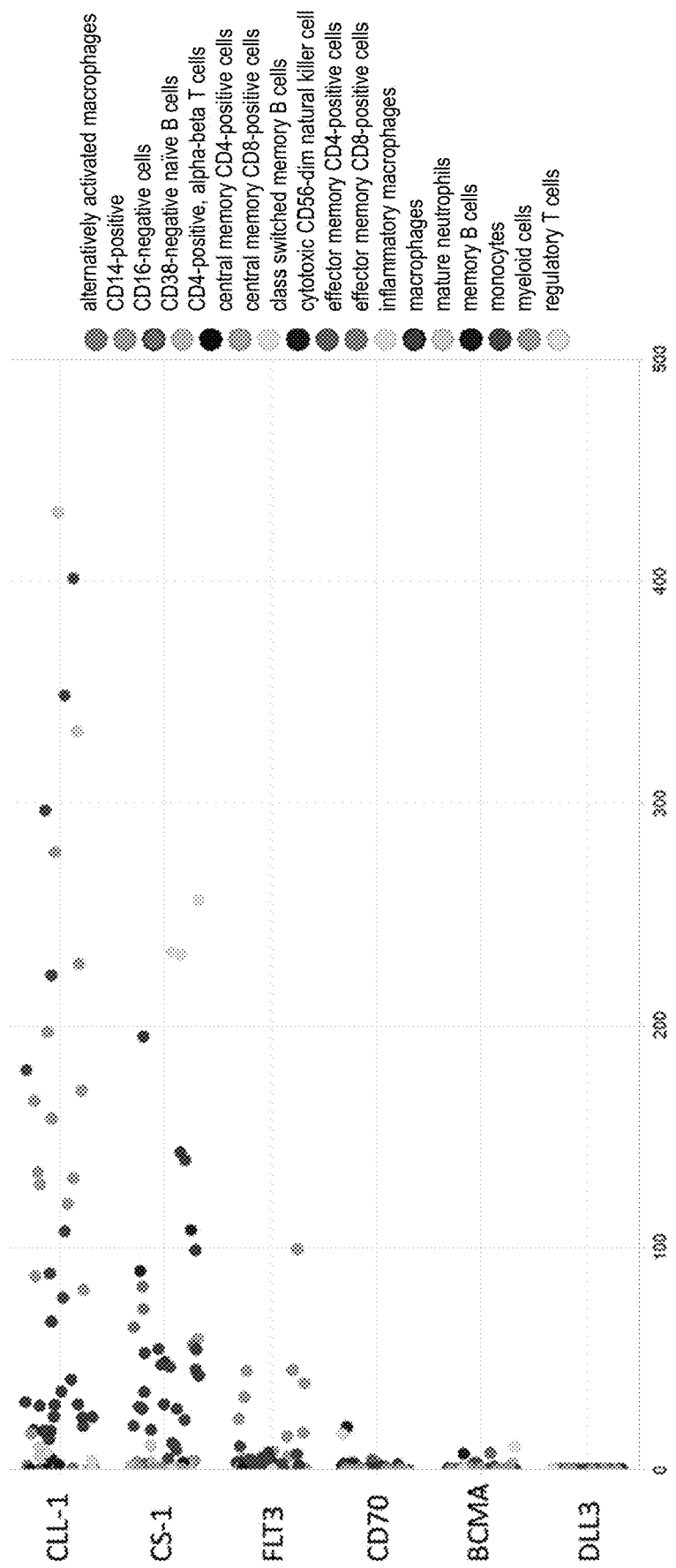

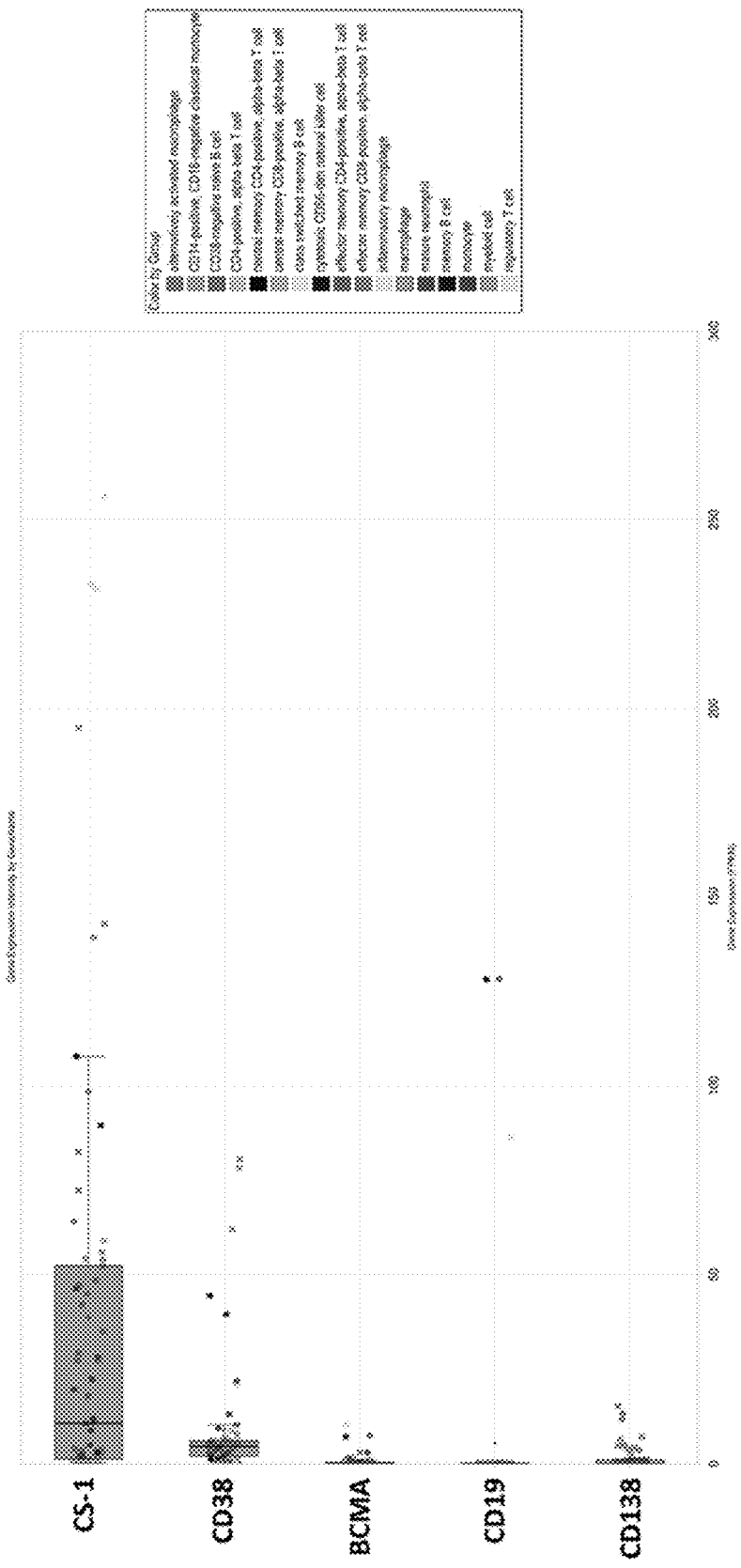

IR = Irrelevant CAR (Negative Control)
BM = Positive Control

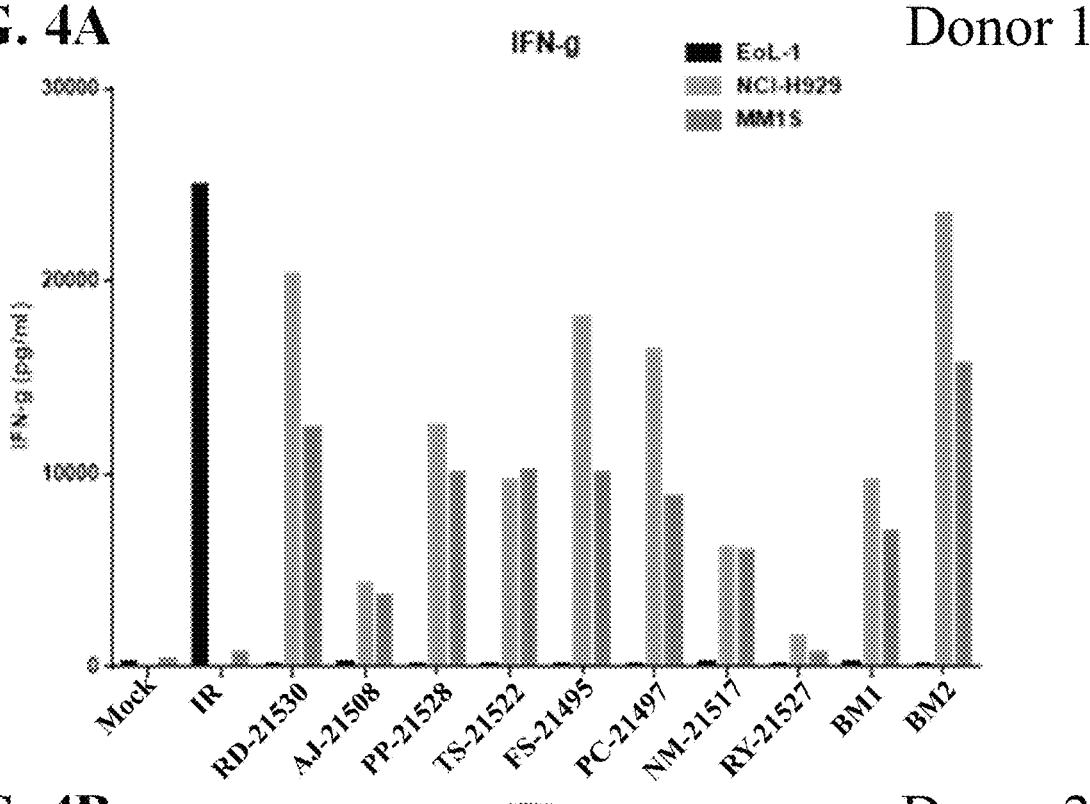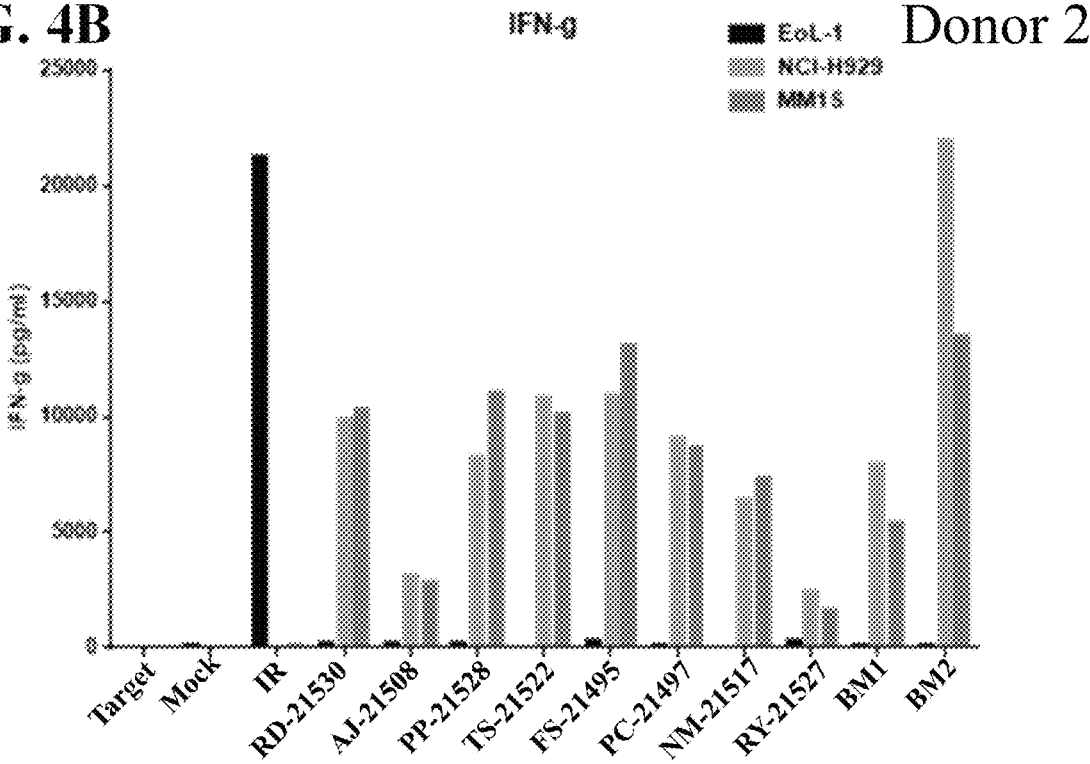

FIG. 7A

Clone FS-26528 HC DNA (SEQ ID NO: 271)
GAGGTGCAGCTGTTGGAGTCTGGGGGAGGCTTGGTACAGCCTGGGGGGTCCCTGAGACTCTCC
TGTGCAGCCTCTGGATTCACCTTTGACGACTATGCCATGGCATGGGTCCGCCAGGCTCCAGGG
AAGGGGCTGGAGTGGGTCTCAGCTATTAGTGATGCAGGTGACAGAACATACTACGCAGACTCC
GTGAGGGGCCGGTTCACCATCTCCAGAGACAATTCCAAGAACACACTGTATCTGCAAATGAAC
AGCCTGAGAGCCGAGGACACGGCGGTGTACTACTGCGCAAGAGCCGAGATGGGAGCCGTATTC
GACATATGGGGTCAGGGTACAATGGTCACCGTCTCCTCA

FIG. 7B

Clone FS-26528 HC (SEQ ID NO: 272). CDRs 1, 2, and 3 are underlined.
EVQLLESGGG LVQPGGSLRL SCAASGFTFD DYAMAWVRQA PGKGLEWVSA
ISDAGDRTYY ADSVRGRFTI SRDNSKNTLY LQMNSLRAED TAVYYCARAE
MGAVFDIWGQ GTMVTVSS

FIG. 7C

SCAASGFTFDDYAMA (SEQ ID NO: 273) [HC CDR1]

AISDAGDRTYYADSVRG (SEQ ID NO: 274) [HC CDR2]

ARAEMGAVFDI (SEQ ID NO: 275) [HC CDR3]

FIG. 7D

Clone FS-26528 LC DNA (SEQ ID NO: 276)
GAAATTGTGTTGACACAGTCTCCAGCCACCCTGTCTTTGTCTCCAGGGGAAAGAGCCACCCTC
TCCTGCAGGGCCAGTCAGAGTGTTAGCAGGTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGAATCTCCTGGCCTTTCACTTTTGGCGGAGGGACCAAGGTTGAG
ATCAAACGG

FIG. 7E

Clone FS-26528 LC (SEQ ID NO: 277). CDRs 1, 2, and 3 are underlined.
EIVLTQSPAT LSLSPGERAT LSCRASQSVS RYLAWYQQKP GQAPRLLIYD
ASNRATGIPA RFSGSGSGTD FTLTISSLEP EDFAVYYCQQ RISWPFTFGG GTKVEIKR

FIG. 7F

RASQSVSRYLA (SEQ ID NO: 278) [LC CDR1]

DASNRAT    (SEQ ID NO: 279) [LC CDR2]

QQRISWPFT  (SEQ ID NO: 280) [LC CDR3]

FIG. 7G

Clone FS-26528 CAR DNA HxL (SEQ ID NO: 281)
ATGGCACTCCCCGTAACTGCTCTGCTGCTGCCGTTGGCATTGCTCCTGCACGCCGCACGCCCG
GAGGTGCAGCTGTTGGAGTCTGGGGGAGGCTTGGTACAGCCTGGGGGGTCCCTGAGACTCTCC
TGTGCAGCCTCTGGATTCACCTTTGACGACTATGCCATGGCATGGGTCCGCCAGGCTCCAGGG
AAGGGGCTGGAGTGGGTCTCAGCTATTAGTGATGCAGGTGACAGAACATACTACGCAGACTCC
GTGAGGGGCCGGTTCACCATCTCCAGAGACAATTCCAAGAACACACTGTATCTGCAAATGAAC
AGCCTGAGAGCCGAGGACACGGCGGTGTACTACTGCGCAAGAGCCGAGATGGGAGCCGTATTC
GACATATGGGGTCAGGGTACAATGGTCACCGTCTCCTCAGGGTCTACATCCGGCTCCGGGAAG
CCCGGAAGTGGCGAAGGTAGTACAAAGGGGGAAATTGTGTTGACACAGTCTCCAGCCACCCTG
TCTTTGTCTCCAGGGGAAAGAGCCACCCTCTCCTGCAGGGCCAGTCAGAGTGTTAGCAGGTAC
TTAGCCTGGTACCAACAGAAACCTGGCCAGGCTCCCAGGCTCCTCATCTATGATGCATCCAAC
AGGGCCACTGGCATCCCAGCCAGGTTCAGTGGCAGTGGGTCTGGGACAGACTTCACTCTCACC
ATCAGCAGCCTAGAGCCTGAAGATTTTGCAGTTTATTACTGTCAGCAGAGAATCTCCTGGCCT
TTCACTTTTGGCGGAGGGACCAAGGTTGAGATCAAACGGGCCGCTGCCCTTGATAATGAAAAG
TCAAACGGAACAATCATTCACGTGAAGGGCAAGCACCTCTGTCCGTCACCCTTGTTCCCTGGT
CCATCCAAGCCATTCTGGGTGTTGGTCGTAGTGGGTGGAGTCCTCGCTTGTTACTCTCTGCTC
GTCACCGTGGCTTTTATAATCTTCTGGGTTAGATCCAAAAGAAGCCGCCTGCTCCATAGCGAT
TACATGAATATGACTCCACGCCGCCCTGGCCCCACAAGGAAACACTACCAGCCTTACGCACCA
CCTAGAGATTTCGCTGCCTATCGGAGCAGGGTGAAGTTTTCCAGATCTGCAGATGCACCAGCG
TATCAGCAGGGCCAGAACCAACTGTATAACGAGCTCAACCTGGGACGCAGGGAAGAGTATGAC
GTTTTGGACAAGCGCAGAGGACGGGACCCTGAGATGGGTGGCAAACCAAGACGAAAAAACCCC
CAGGAGGGTCTCTATAATGAGCTGCAGAAGGATAAGATGGCTGAAGCCTATTCTGAAATAGGC
ATGAAAGGAGAGCGGAGAAGGGGAAAAGGGCACGACGGTTTGTACCAGGGACTCAGCACTGCT
ACGAAGGATACTTATGACGCTCTCCACATGCAAGCCCTGCCACCTAGG

FIG. 7H

Clone FS-26528 CAR HxL (SEQ ID NO: 282)
MALPVTALLL PLALLLHAAR PEVQLLESGG GLVQPGGSLR LSCAASGFTF
DDYAMAWVRQ APGKGLEWVS AISDAGDRTY YADSVRGRFT ISRDNSKNTL
YLQMNSLRAE DTAVYYCARA EMGAVFDIWG QGTMVTVSSG STSGSGKPGS
GEGSTKGEIV LTQSPATLSL SPGERATLSC RASQSVSRYL AWYQQKPGQA
PRLLIYDASN RATGIPARFS GSGSGTDFTL TISSLEPEDF AVYYCQQRIS
WPFTGGGTK VEIKRAAALD NEKSNGTIIH VKGKHLCPSP LFPGPSKPFW
VLVVVGGVLA CYSLLVTVAF IIFWVRSKRS RLLHSDYMNM TPRRPGPTRK
HYQPYAPPRD FAAYRSRVKF SRSADAPAYQ QGQNQLYNEL NLGRREEYDV
LDKRRGRDPE MGGKPRRKNP QEGLYNELQK DKMAEAYSEI GMKGERRRGK
GHDGLYQGLS TATKDTYDAL HMQALPPR

FIG. 7I

Clone FS-26528 CAR DNA LxH (SEQ ID NO: 283)
ATGGCACTCCCCGTAACTGCTCTGCTGCTGCCGTTGGCATTGCTCCTGCACGCCGCACGCCCG
GAAATTGTGTTGACACAGTCTCCAGCCACCCTGTCTTTGTCTCCAGGGGAAAGAGCCACCCTC
TCCTGCAGGGCCAGTCAGAGTGTTAGCAGGTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGAATCTCCTGGCCTTTCACTTTTGGCGGAGGGACCAAGGTTGAG
ATCAAACGGGGTCTACATCCGGCTCCGGAAGCCCGGAAGTGGCGAAGGTAGTACAAAGGGG
GAGGTGCAGCTGTTGGAGTCTGGGGGAGGCTTGGTACAGCCTGGGGGGTCCCTGAGACTCTCC
TGTGCAGCCTCTGGATTCACCTTTGACGACTATGCCATGGCATGGGTCCGCCAGGCTCCAGGG
AAGGGGCTGGAGTGGGTCTCAGCTATTAGTGATGCAGGTGACAGAACATACTACGCAGACTCC
GTGAGGGGCCGGTTCACCATCTCCAGAGACAATTCCAAGAACACACTGTATCTGCAAATGAAC
AGCCTGAGAGCCGAGGACACGGCGGTGTACTACTGCGCAAGAGCCGAGATGGGAGCCGTATTC
GACATATGGGGTCAGGGTACAATGGTCACCGTCTCCTCAGCCGCTGCCCTTGATAATGAAAAG
TCAAACGGAACAATCATTCACGTGAAGGGCAAGCACCTCTGTCCGTCACCCTTGTTCCCTGGT
CCATCCAAGCCATTCTGGGTGTTGGTCGTAGTGGGTGGAGTCCTCGCTTGTTACTCTCTGCTC
GTCACCGTGGCTTTTATAATCTTCTGGGTTAGATCCAAAAGAAGCCGCCTGCTCCATAGCGAT
TACATGAATATGACTCCACGCCGCCCTGGCCCCACAAGGAAACACTACCAGCCTTACGCACCA
CCTAGAGATTTCGCTGCCTATCGGAGCAGGGTGAAGTTTTCCAGATCTGCAGATGCACCAGCG
TATCAGCAGGGCCAGAACCAACTGTATAACGAGCTCAACCTGGGACGCAGGGAAGAGTATGAC
GTTTTGGACAAGCGCAGAGGACGGGACCCTGAGATGGGTGGCAAACCAAGACGAAAAAACCCC
CAGGAGGGTCTCTATAATGAGCTGCAGAAGGATAAGATGGCTGAAGCCTATTCTGAAATAGGC
ATGAAAGGAGAGCGGAGAAGGGGAAAAGGGCACGACGGTTTGTACCAGGGACTCAGCACTGCT
ACGAAGGATACTTATGACGCTCTCCACATGCAAGCCCTGCCACCTAGG

FIG. 7J

Clone FS-26528 CAR LxH (SEQ ID NO: 284)
MALPVTALLL PLALLLHAAR PEIVLTQSPA TLSLSPGERA TLSCRASQSV
SRYLAWYQQK PGQAPRLLIY DASNRATGIP ARFSGSGSGT DFTLTISSLE
PEDFAVYYCQ QRISWPFTFG GGTKVEIKRG STSGSGKPGS GEGSTKGEVQ
LLESGGGLVQ PGGSLRLSCA ASGFTFDDYA MAWVRQAPGK GLEWVSAISD
AGDRTYYADS VRGRFTISRD NSKNTLYLQM NSLRAEDTAV YYCARAEMGA
VFDIWGQGTM VTVSSAALD NEKSNGTIIH VKGKHLCPSP LFPGPSKPFW
VLVVVGGVLA CYSLLVTVAF IIFWVRSKRS RLLHSDYMNM TPRRPGPTRK
HYQPYAPPRD FAAYRSRVKF SRSADAPAYQ QGQNQLYNEL NLGRREEYDV
LDKRRGRDPE MGGKPRRKNP QEGLYNELQK DKMAEAYSEI GMKGERRRGK
GHDGLYQGLS TATKDTYDAL HMQALPPR

FIG. 8A

Clone PC-26534 HC DNA (SEQ ID NO: 285)
CAGGTGCAGCTGGTGGAGTCTGGGGGAGGCGTGGTCCAGCCTGGGAGGTCCCTGAGACTCTCC
TGTGCAGCGTCTGGATTCACCTTCAGTGAGCATGGCATGCACTGGGTCCGCCAGGCTCCAGGC
AAGGGGCTGGAGTGGGTGGCAGCTATATCTTATGATGGAAGGAATAAACACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGCCAGAGACGGTACTTATCTAGGTGGT
CTCTGGTACTTCGACTTATGGGGAGAGGTACCTTGGTCACCGTCTCCTCA

FIG. 8B

Clone PC-26534 HC (SEQ ID NO: 286). CDRs 1, 2, and 3 are underlined.
QVQLVESGGG VVQPGRSLRL SCAASG<u>FTFS</u> <u>EHGMH</u>WVRQA PGKGLEWVA<u>A</u>
<u>ISYDGRNKHY</u> <u>ADSVKG</u>RFTI SRDNSKNTLY LQMNSLRAED TAVYYC<u>ARDG</u>
<u>TYLGGLWYFD</u> <u>L</u>WGRGTLVTV SS

FIG 8C

FTFSEHGMH (SEQ ID NO: 287) [HC CDR1]

AISYDGRNKHYADSVKG (SEQ ID NO: 288) [HC CDR2]

ARDGTYLGGLWYFDL (SEQ ID NO: 289) [HC CDR3]

FIG. 8D

Clone PC-26534 LC DNA (SEQ ID NO: 290)
GATATTGTGATGACTCAGTCTCCACTCTCCCTGCCCGTCACCCCTGGAGAGCCGGCCTCCATC
TCCTGCAGGTCTAGTCAGAGCCTCCTGCATAGTAATGGATACAACTATTTGGATTGGTACCTG
CAGAAGCCAGGGCAGTCTCCACAGCTCCTGATCTATTTGGGTTCTAATCGGGCCTCCGGGGTC
CCTGACAGGTTCAGTGGCAGTGGATCAGGCACAGATTTTACACTGAAAATCAGCAGAGTGGAG
GCTGAGGATGTTGGGGTTTATTACTGCATGCAGGGACTCGGCCTCCCTCTCACTTTTGGCGGA
GGGACCAAGGTTGAGATCAAACGG

FIG. 8E

Clone PC-26534 LC (SEQ ID NO: 291). CDRs 1, 2, and 3 are underlined.
DIVMTQSPLS LPVTPGEPAS ISC<u>RSSQSLL</u> <u>HSNGYNYLD</u>W YLQKPGQSPQ
LLIY<u>LGSNRA</u> SGVPDRFSGS GSGTDFTLKI SRVEAEDVGV YYC<u>MQGLGLP</u>
<u>LT</u>FGGGTKVE IKR

FIG. 8F

RSSQSLLHSNGYNYLD (SEQ ID NO: 292) [LC CDR1]

FIG. 8F(continued)

LGSNRAS (SEQ ID NO: 293) [LC CDR2]

MQGLGLPLT (SEQ ID NO: 294) [LC CDR3]

FIG. 8G

Clone PC-26534 CAR DNA HxL (SEQ ID NO: 295)
ATGGCACTCCCCGTAACTGCTCTGCTGCTGCCGTTGGCATTGCTCCTGCACGCCGCACGCCCG
CAGGTGCAGCTGGTGGAGTCTGGGGGAGGCGTGGTCCAGCCTGGGAGGTCCCTGAGACTCTCC
TGTGCAGCGTCTGGATTCACCTTCAGTGAGCATGGCATGCACTGGGTCCGCCAGGCTCCAGGC
AAGGGGCTGGAGTGGGTGGCAGCTATATCTTATGATGGAAGGAATAAACACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGCCAGAGACGGTACTTATCTAGGTGGT
CTCTGGTACTTCGACTTATGGGGAGAGGTACCTTGGTCACCGTCTCCTCAGGGTCTACATCC
GGCTCCGGGAAGCCCGGAAGTGGCGAAGGTAGTACAAAGGGGGATATTGTGATGACTCAGTCT
CCACTCTCCCTGCCCGTCACCCCTGGAGAGCCGGCCTCCATCTCCTGCAGGTCTAGTCAGAGC
CTCCTGCATAGTAATGGATACAACTATTTGGATTGGTACCTGCAGAAGCCAGGGCAGTCTCCA
CAGCTCCTGATCTATTTGGGTTCTAATCGGGCCTCCGGGGTCCCTGACAGGTTCAGTGGCAGT
GGATCAGGCACAGATTTTACACTGAAAATCAGCAGAGTGGAGGCTGAGGATGTTGGGGTTTAT
TACTGCATGCAGGGACTCGGCCTCCCTCTCACTTTTGGCGGAGGGACCAAGGTTGAGATCAAA
CGGGCCGCTGCCCTTGATAATGAAAAGTCAAACGGAACAATCATTCACGTGAAGGGCAAGCAC
CTCTGTCCGTCACCCTTGTTCCCTGGTCCATCCAAGCCATTCTGGGTGTTGGTCGTAGTGGGT
GGAGTCCTCGCTTGTTACTCTCTGCTCGTCACCGTGGCTTTTATAATCTTCTGGGTTAGATCC
AAAAGAAGCCGCCTGCTCCATAGCGATTACATGAATATGACTCCACGCCGCCCTGGCCCCACA
AGGAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGCTC
AACCTGGGACGCAGGGAAGAGTATGACGTTTTGGACAAGCGCAGAGGACGGGACCCTGAGATG
GGTGGCAAACCAAGACGAAAAAACCCCCAGGAGGGTCTCTATAATGAGCTGCAGAAGGATAAG
ATGGCTGAAGCCTATTCTGAAATAGGCATGAAAGGAGAGCGGAGAAGGGGAAAAGGGCACGAC
GGTTTGTACCAGGGACTCAGCACTGCTACGAAGGATACTTATGACGCTCTCCACATGCAAGCC
CTGCCACCTAGG

FIG. 8H

Clone PC-26534 CAR HxL (SEQ ID NO: 296)
MALPVTALLL PLALLLHAAR PQVQLVESGG GVVQPGRSLR LSCAASGFTF
SEHGMHWVRQ APGKGLEWVA AISYDGRNKH YADSVKGRFT ISRDNSKNTL
YLQMNSLRAE DTAVYYCARD GTYLGGLWYF DLWGRGTLVT VSSGSTSGSG
KPGSGEGSTK GDIVMTQSPL SLPVTPGEPA SISCRSSQSL LHSNGYNYLD
WYLQKPGQSP QLLIYLGSNR ASGVPDRFSG SGSGTDFTLK ISRVEAEDVG
VYYCMQGLGL PLTFGGGTKV EIKRAAALDN EKSNGTIIHV KGKHLCPSPL
FPGPSKPFWV LVVVGGVLAC YSLLVTVAFI IFWVRSKRSR LLHSDYMNMT
PRRPGPTRKH YQPYAPPRDF AAYRSRVKFS RSADAPAYQQ GQNQLYNELN
LGRREEYDVL DKRRGRDPEM GGKPRRKNPQ EGLYNELQKD KMAEAYSEIG
MKGERRRGKG HDGLYQGLST ATKDTYDALH MQALPPR

FIG. 8I

Clone PC-26534 CAR DNA LxH (SEQ ID NO: 297)
ATGGCACTCCCCGTAACTGCTCTGCTGCTGCCGTTGGCATTGCTCCTGCACGCCGCACGCCCG
GATATTGTGATGACTCAGTCTCCACTCTCCCTGCCCGTCACCCCTGGAGAGCCGGCCTCCATC
TCCTGCAGGTCTAGTCAGAGCCTCCTGCATAGTAATGGATACAACTATTTGGATTGGTACCTG
CAGAAGCCAGGGCAGTCTCCACAGCTCCTGATCTATTTGGGTTCTAATCGGGCCTCCGGGGTC
CCTGACAGGTTCAGTGGCAGTGGATCAGGCACAGATTTTACACTGAAAATCAGCAGAGTGGAG
GCTGAGGATGTTGGGGTTTATTACTGCATGCAGGGACTCGGCCTCCCTCTCACTTTTGGCGGA
GGGACCAAGGTTGAGATCAAACGGGGGTCTACATCCGGCTCCGGGAAGCCCGGAAGTGGCGAA
GGTAGTACAAAGGGGCAGGTGCAGCTGGTGGAGTCTGGGGGAGGCGTGGTCCAGCCTGGGAGG
TCCCTGAGACTCTCCTGTGCAGCGTCTGGATTCACCTTCAGTGAGCATGGCATGCACTGGGTC
CGCCAGGCTCCAGGCAAGGGGCTGGAGTGGGTGGCAGCTATATCTTATGATGGAAGGAATAAA
CACTATGCAGACTCCGTGAAGGGCCGATTCACCATCTCCAGAGACAATTCCAAGAACACGCTG
TATCTGCAAATGAACAGCCTGAGAGCCGAGGACACGGCGGTGTACTACTGCGCCAGAGACGGT
ACTTATCTAGGTGGTCTCTGGTACTTCGACTTATGGGGAGAGGTACCTTGGTCACCGTCTCC
TCAGCCGCTGCCCTTGATAATGAAAAGTCAAACGGAACAATCATTCACGTGAAGGGCAAGCAC
CTCTGTCCGTCACCCTTGTTCCCTGGTCCATCCAAGCCATTCTGGGTGTTGGTCGTAGTGGGT
GGAGTCCTGCTTGTTACTCTCTGCTCGTCACCGTGGCTTTTATAATCTTCTGGGTTAGATCC
AAAAGAAGCCGCCTGCTCCATAGCGATTACATGAATATGACTCCACGCCGCCCTGGCCCCACA
AGGAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGCTC
AACCTGGGACGCAGGGAAGAGTATGACGTTTTGGACAAGCGCAGAGGACGGGACCCTGAGATG
GGTGGCAAACCAAGACGAAAAAACCCCAGGAGGGTCTCTATAATGAGCTGCAGAAGGATAAG
ATGGCTGAAGCCTATTCTGAAATAGGCATGAAAGGAGAGCGGAGAAGGGGAAAAGGGCACGAC
GGTTTGTACCAGGGACTCAGCACTGCTACGAAGGATACTTATGACGCTCTCCACATGCAAGCC
CTGCCACCTAGG

FIG. 8J

Clone PC-26534 CAR LxH (SEQ ID NO: 298)
MALPVTALLL PLALLLHAAR PDIVMTQSPL SLPVTPGEPA SISCRSSQSL
LHSNGYNYLD WYLQKPGQSP QLLIYLGSNR ASGVPDRFSG SGSGTDFTLK
ISRVEAEDVG VYYCMQGLGL PLTFGGGTKV EIKRGSTSGS GKPGSGEGST
KGQVQLVESG GGVVQPGRSL RLSCAASGFT FSEHGMHWVR QAPGKGLEWV
AAISYDGRNK HYADSVKGRF TISRDNSKNT LYLQMNSLRA EDTAVYYCAR
DGTYLGGLWY FDLWGRGTLV TVSSAALDN EKSNGTIIHV KGKHLCPSPL
FPGPSKPFWV LVVVGGVLAC YSLLVTVAFI IFWVRSKRSR LLHSDYMNMT
PRRPGPTRKH YQPYAPPRDF AAYRSVKFS RSADAPAYQQ GQNQLYNELN
LGRREEYDVL DKRRGRDPEM GGKPRRKNPQ EGLYNELQKD KMAEAYSEIG
MKGERRRGKG HDGLYQGLST ATKDTYDALH MQALPPR

FIG. 9A

Clone AJ-26545 HC DNA (SEQ ID NO: 299)
CAGGTGCAGCTGGTGCAGTCTGGGGCTGAGGTGAAGAAGCCTGGGGCCTCAGTGAAGGTTTCC
TGCAGGGCATCTGGATACACCTTCATGGAGCACTATATGCACTGGGTGCGACAGGCCCCTGGA
CAAGGGCTTGAGTGGATGGGAGTAATCGGGCCTAGTGGTGGTAAGACAAGCTACGCACAGAAG
TTCCAGGGCAGAGTCACCATGACCAGGGACACGTCCACGAGCACAGTCTACATGGAGCTGAGC
AGCCTGAGATCTGAGGACACGGCGGTGTACTACTGCGCCAGAGAGAATTGGCCAATGGACGTA
TGGGGCCAGGGAACAACTGTCACCGTCTCCTCA

FIG. 9B

Clone AJ-26545 HC (SEQ ID NO: 300). CDRs 1, 2, and 3 are underlined.
QVQLVQSGAE VKKPGASVKV SCRASG<u>YTFM</u> <u>EHYMH</u>WVRQA PGQGLEWMG<u>V</u>
<u>IGPSGGKTSY</u> <u>AQKFQG</u>RVTM TRDTSTSTVY MELSSLRSED TAVYYC<u>ARES</u>
<u>WPMDV</u>WGQGT TVTVSS

FIG. 9C

YTFMEHYMH (SEQ ID NO: 301) (HC CDR1)

VIGPSGGKTSYAQKFQG (SEQ ID NO: 302) (HC CDR2)

ARESWPMDV (SEQ ID NO: 303) (HC CDR3)

FIG. 9D

Clone AJ-26545 LC DNA (SEQ ID NO: 304)
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATGGTGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGTACGCCGCCTACCCTACTTTTGGCGGAGGGACCAAGGTTGAGATC
AAACGG

FIG. 9E

Clone AJ-26545 LC (SEQ ID NO: 305). CDRs 1, 2, and 3 are underlined.
EIVMTQSPAT LSVSPGERAT LSC<u>RASQSVS</u> <u>SNLA</u>WYQQKP GQAPRLLIY<u>G</u>
<u>ASTRAT</u>GIPA RFSGSGSGTE FTLTISSLQS EDFAVYYC<u>QQ</u> <u>YAAYPT</u>FGGG TKVEIKR

FIG. 9F

RASQSVSSNLA (SEQ ID NO: 306) (LC CDR1)

GASTRAT (SEQ ID NO: 307) (LC CDR2)

QQYAAYPT (SEQ ID NO: 308) (LC CDR3)

FIG. 9G

Clone AJ-26545 CAR DNA HxL (SEQ ID NO: 309)
ATGGCACTCCCCGTAACTGCTCTGCTGCTGCCGTTGGCATTGCTCCTGCACGCCGCACGCCCG
CAGGTGCAGCTGGTGCAGTCTGGGGCTGAGGTGAAGAAGCCTGGGGCCTCAGTGAAGGTTTCC
TGCAGGGCATCTGGATACACCTTCATGGAGCACTATATGCACTGGGTGCGACAGGCCCCTGGA
CAAGGGCTTGAGTGGATGGGAGTAATCGGGCCTAGTGGTGGTAAGACAAGCTACGCACAGAAG
TTCCAGGGCAGAGTCACCATGACCAGGGACACGTCCACGAGCACAGTCTACATGGAGCTGAGC
AGCCTGAGATCTGAGGACACGGCGGTGTACTACTGCGCCAGAGAGAATTGGCCAATGGACGTA
TGGGGCCAGGGAACAACTGTCACCGTCTCCTCAGGGTCTACATCCGGCTCCGGGAAGCCCGGA
AGTGGCGAAGGTAGTACAAAGGGGGAAATAGTGATGACGCAGTCTCCAGCCACCCTGTCTGTG
TCTCCAGGGGAAAGAGCCACCCTCTCCTGCAGGGCCAGTCAGAGTGTTAGCAGCAACTTAGCC
TGGTACCAGCAGAAACCTGGCCAGGCTCCCAGGCTCCTCATCTATGGTGCATCCACCAGGGCC
ACTGGTATCCCAGCCAGGTTCAGTGGCAGTGGGTCTGGGACAGAGTTCACTCTCACCATCAGC
AGCCTGCAGTCTGAAGATTTTGCAGTTTATTACTGTCAGCAGTACGCCGCCTACCCTACTTTT
GGCGGAGGGACCAAGGTTGAGATCAAACGGGCCGCTGCCCTTGATAATGAAAGTCAAACGGA
ACAATCATTCACGTGAAGGGCAAGCACCTCTGTCCGTCACCCTTGTTCCCTGGTCCATCCAAG
CCATTCTGGGTGTTGGTCGTAGTGGGTGGAGTCCTCGCTTGTTACTCTCTGCTCGTCACCGTG
GCTTTTATAATCTTCTGGGTTAGATCCAAAAGAAGCCGCCTGCTCCATAGCGATTACATGAAT
ATGACTCCACGCCGCCCTGGCCCCACAAGGAAACACTACCAGCCTTACGCACCACCTAGAGAT
TTCGCTGCCTATCGGAGCAGGGTGAAGTTTTCCAGATCTGCAGATGCACCAGCGTATCAGCAG
GGCCAGAACCAACTGTATAACGAGCTCAACCTGGGACGCAGGGAAGAGTATGACGTTTTGGAC
AAGCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAGGA
GAGCGGAGAAGGGGAAAAGGGCACGACGGTTTGTACCAGGGACTCAGCACTGCTACGAAGGAT
ACTTATGACGCTCTCCACATGCAAGCCCTGCCACCTAGG

FIG. 9H

Clone AJ-26545 CAR HxL (SEQ ID NO: 310)
MALPVTALLL PLALLLHAAR PQVQLVQSGA EVKKPGASVK VSCRASGYTF
MEHYMHWVRQ APGQGLEWMG VIGPSGGKTS YAQKFQGRVT MTRDTSTSTV
YMELSSLRSE DTAVYYCARE SWPMDVWGQG TTVTVSSGST SGSGKPGSGE
GSTKGEIVMT QSPATLSVSP GERATLSCRA SQSVSSNLAW YQQKPGQAPR
LLIYGASTRA TGIPARFSGS GSGTEFTLTI SSLQSEDFAV YYCQQYAAYP
TFGGGTKVEI KRAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

FIG. 9I

Clone AJ-26545 CAR DNA LxH (SEQ ID NO: 311)
ATGGCACTCCCCGTAACTGCTCTGCTGCTGCCGTTGGCATTGCTCCTGCACGCCGCACGCCCG
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATGGTGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGTACGCCGCCTACCCTACTTTTGGCGGAGGGACCAAGGTTGAGATC
AAACGGGGGTCTACATCCGGCTCCGGGAAGCCCGGAAGTGGCGAAGGTAGTACAAAGGGGCAG
GTGCAGCTGGTGCAGTCTGGGGCTGAGGTGAAGAAGCCTGGGGCCTCAGTGAAGGTTTCCTGC
AGGGCATCTGGATACACCTTCATGGAGCACTATATGCACTGGGTGCGACAGGCCCCTGGACAA
GGGCTTGAGTGGATGGGAGTAATCGGGCCTAGTGGTGGTAAGACAAGCTACGCACAGAAGTTC
CAGGGCAGAGTCACCATGACCAGGGACACGTCCACGAGCACAGTCTACATGGAGCTGAGCAGC
CTGAGATCTGAGGACACGGCGGTGTACTACTGCGCCAGAGAGAATTGGCCAATGGACGTATGG
GGCCAGGGAACAACTGTCACCGTCTCCTCAGCCGCTGCCCTTGATAATGAAAGTCAAACGGA
ACAATCATTCACGTGAAGGGCAAGCACCTCTGTCCGTCACCCTTGTTCCCTGGTCCATCCAAG
CCATTCTGGGTGTTGGTCGTAGTGGGTGGAGTCCTCGCTTGTTACTCTCTGCTCGTCACCGTG
GCTTTTATAATCTTCTGGGTTAGATCCAAAAGAAGCCGCCTGCTCCATAGCGATTACATGAAT
ATGACTCCACGCCGCCCTGGCCCCACAAGGAAACACTACCAGCCTTACGCACCACCTAGAGAT
TTCGCTGCCTATCGGAGCAGGGTGAAGTTTTCCAGATCTGCAGATGCACCAGCGTATCAGCAG
GGCCAGAACCAACTGTATAACGAGCTCAACCTGGGACGCAGGGAAGAGTATGACGTTTTGGAC
AAGCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAGGA
GAGCGGAGAAGGGGAAAAGGGCACGACGGTTTGTACCAGGGACTCAGCACTGCTACAAGGAT
ACTTATGACGCTCTCCACATGCAAGCCCTGCCACCTAGG

FIG. 9J

Clone AJ-26545 CAR LxH (SEQ ID NO: 312)
MALPVTALLL PLALLLHAAR PEIVMTQSPA TLSVSPGERA TLSCRASQSV
SSNLAWYQQK PGQAPRLLIY GASTRATGIP ARFSGSGSGT EFTLTISSLQ
SEDFAVYYCQ QYAAYPTFGG GTKVEIKRGS TSGSGKPGSG EGSTKGQVQL
VQSGAEVKKP GASVKVSCRA SGYTFMEHYM HWVRQAPGQG LEWMGVIGPS
GGKTSYAQKF QGRVTMTRDT STSTVYMELS SLRSEDTAVY YCARESWPMD
VWGQGTTVTV SSAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

FIG. 10A

Clone AJ-26554 HC DNA (SEQ ID NO: 313)
CAGGTGCAGCTGGTGCAGTCTGGGGCTGAGGTGAAGAAGCCTGGGGCCTCAGTGAAGGTTTCC
TGCAAGGCATCTGGATACACCTTCACGGAGCACTATATGCACTGGGTGCGACAGGCCCCTGGA
CAAAGGCTTGAGTGGATGGGAGTAATCGGGCCTAGTGGTGGTAAGACAAGCTACGCACAGAAG
TTCCAGGGCAGAGTCACCATGACCAGGGACACGTCCACGAGCACAGTCTACATGGAGCTGAGC
AGCCTGAGATCTGAGGACACGGCGGTGTACTACTGCGCCAGAGAGAGTTGGCCAATGGACGTA
TGGGGCCAGGGAACAACTGTCACCGTCTCCTCA

FIG. 10B

Clone AJ-26554 HC (SEQ ID NO: 314). CDRs 1, 2, and 3 are underlined.
QVQLVQSGAE VKKPGASVKV SCKASG<u>YTFT</u> <u>EHYMH</u>WVRQA PGQRLEWMG<u>V</u>
<u>IGPSGGKTSY</u> <u>AQKFQG</u>RVTM TRDTSTSTVY MELSSLRSED TAVYYC<u>ARES</u>
<u>WPMDV</u>WGQGT TVTVSS

FIG. 10C

YTFTEHYMH (SEQ ID NO: 315) (HC CDR1)

VIGPSGGKTSYAQKFQG (SEQ ID NO: 316) (HC CDR2)

ARESWPMDV (SEQ ID NO: 317) (HC CDR3)

FIG. 10D

Clone AJ-26554 LC DNA (SEQ ID NO: 318)
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATGGTGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGTACGCCGCCTACCCTACTTTTGGCGGAGGGACCAAGGTTGAGATC
AAACGG

FIG. 10E

Clone AJ-26554 LC (SEQ ID NO: 319). CDRs 1, 2, and 3 are underlined.
EIVMTQSPAT LSVSPGERAT LSC<u>RASQSVS</u> <u>SNLA</u>WYQQKP GQAPRLLIY<u>G</u>
<u>ASTRAT</u>GIPA RFSGSGSGTE FTLTISSLQS EDFAVYYC<u>QQ</u> <u>YAAYPTFGGG</u> TKVEIKR

FIG. 10F

RASQSVSSNLA (SEQ ID NO: 320) (LC CDR1)

FIG. 10F (continued)

GASTRAT (SEQ ID NO: 321) (LC CDR2)

QQYAAYPT (SEQ ID NO: 322) (LC CDR3)

FIG. 10G

Clone AJ-26554 CAR DNA HxL (SEQ ID NO: 323)
ATGGCACTCCCCGTAACTGCTCTGCTGCTGCCGTTGGCATTGCTCCTGCACGCCGCACGCCCG
CAGGTGCAGCTGGTGCAGTCTGGGGCTGAGGTGAAGAAGCCTGGGGCCTCAGTGAAGGTTTCC
TGCAAGGCATCTGGATACACCTTCACGGAGCACTATATGCACTGGGTGCGACAGGCCCCTGGA
CAAAGGCTTGAGTGGATGGGAGTAATCGGGCCTAGTGGTGGTAAGACAAGCTACGCACAGAAG
TTCCAGGGCAGAGTCACCATGACCAGGGACACGTCCACGAGCACAGTCTACATGGAGCTGAGC
AGCCTGAGATCTGAGGACACGGCGGTGTACTACTGCGCCAGAGAGAGTTGGCCAATGGACGTA
TGGGGCCAGGGAACAACTGTCACCGTCTCCTCAGGGTCTACATCCGGCTCCGGGAAGCCCGGA
AGTGGCGAAGGTAGTACAAAGGGGGAAATAGTGATGACGCAGTCTCCAGCCACCCTGTCTGTG
TCTCCAGGGGAAAGAGCCACCCTCTCCTGCAGGGCCAGTCAGAGTGTTAGCAGCAACTTAGCC
TGGTACCAGCAGAAACCTGGCCAGGCTCCCAGGCTCCTCATCTATGGTGCATCCACCAGGGCC
ACTGGTATCCCAGCCAGGTTCAGTGGCAGTGGGTCTGGGACAGAGTTCACTCTCACCATCAGC
AGCCTGCAGTCTGAAGATTTTGCAGTTTATTACTGTCAGCAGTACGCCGCCTACCCTACTTTT
GGCGGAGGGACCAAGGTTGAGATCAAACGGGCCGCTGCCCTTGATAATGAAAAGTCAAACGGA
ACAATCATTCACGTGAAGGGCAAGCACCTCTGTCCGTCACCCTTGTTCCTGGTCCATCCAAG
CCATTCTGGGTGTTGGTCGTAGTGGGTGGAGTCCTCGCTTGTTACTCTCTGCTCGTCACCGTG
GCTTTTATAATCTTCTGGGTTAGATCCAAAAGAAGCCGCCTGCTCCATAGCGATTACATGAAT
ATGACTCCACGCCGCCCTGGCCCCACAAGGAAACACTACCAGCCTTACGCACCACCTAGAGAT
TTCGCTGCCTATCGGAGCAGGGTGAAGTTTTCCAGATCTGCAGATGCACCAGCGTATCAGCAG
GGCCAGAACCAACTGTATAACGAGCTCAACCTGGGACGCAGGGAAGAGTATGACGTTTTGGAC
AAGCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAGGA
GAGCGGAGAAGGGGAAAAGGGCACGACGGTTTGTACCAGGGACTCAGCACTGCTACGAAGGAT
ACTTATGACGCTCTCCACATGCAAGCCCTGCCACCTAGG

FIG. 10H

Clone AJ-26554 CAR HxL (SEQ ID NO: 324)
MALPVTALLL PLALLLHAAR PQVQLVQSGA EVKKPGASVK VSCKASGYTF
TEHYMHWVRQ APGQRLEWMG VIGPSGGKTS YAQKFQGRVT MTRDTSTSTV
YMELSSLRSE DTAVYYCARE SWPMDVWGQG TTVTVSSGST SGSGKPGSGE
GSTKGEIVMT QSPATLSVSP GERATLSCRA SQSVSSNLAW YQQKPGQAPR
LLIYGASTRA TGIPARFSGS GSGTEFTLTI SSLQSEDFAV YYCQQYAAYP
TFGGGTKVEI KRAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

FIG. 10I

Clone AJ-26554 CAR DNA LxH (SEQ ID NO: 325)
ATGGCACTCCCCGTAACTGCTCTGCTGCTGCCGTTGGCATTGCTCCTGCACGCCGCACGCCCG
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATGGTGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGTACGCCGCCTACCCTACTTTTGGCGGAGGGACCAAGGTTGAGATC
AAACGGGGGTCTACATCCGGCTCCGGGAAGCCCGGAAGTGGCGAAGGTAGTACAAAGGGGCAG
GTGCAGCTGGTGCAGTCTGGGGCTGAGGTGAAGAAGCCTGGGGCCTCAGTGAAGGTTTCCTGC
AAGGCATCTGGATACACCTTCACGGAGCACTATATGCACTGGGTGCGACAGGCCCCTGGACAA
AGGCTTGAGTGGATGGGAGTAATCGGGCCTAGTGGTGGTAAGACAAGCTACGCACAGAAGTTC
CAGGGCAGAGTCACCATGACCAGGGACACGTCCACGAGCACAGTCTACATGGAGCTGAGCAGC
CTGAGATCTGAGGACACGGCGGTGTACTACTGCGCCAGAGAGAGTTGGCCAATGGACGTATGG
GGCCAGGGAACAACTGTCACCGTCTCCTCAGCCGCTGCCCTTGATAATGAAAGTCAAACGGA
ACAATCATTCACGTGAAGGGCAAGCACCTCTGTCCGTCACCCTTGTTCCCTGGTCCATCCAAG
CCATTCTGGGTGTTGGTCGTAGTGGGTGGAGTCCTCGCTTGTTACTCTCTGCTCGTCACCGTG
GCTTTTATAATCTTCTGGGTTAGATCCAAAAGAAGCCGCCTGCTCCATAGCGATTACATGAAT
ATGACTCCACGCCGCCCTGGCCCCACAAGGAAACACTACCAGCCTTACGCACCACCTAGAGAT
TTCGCTGCCTATCGGAGCAGGGTGAAGTTTTCCAGATCTGCAGATGCACCAGCGTATCAGCAG
GGCCAGAACCAACTGTATAACGAGCTCAACCTGGGACGCAGGGAAGAGTATGACGTTTTGGAC
AAGCGCAGAGGACGGGACCCTGAGATGGGTGGCAAACCAAGACGAAAAAACCCCCAGGAGGGT
CTCTATAATGAGCTGCAGAAGGATAAGATGGCTGAAGCCTATTCTGAAATAGGCATGAAAGGA
GAGCGGAGAAGGGGAAAAGGGCACGACGGTTTGTACCAGGGACTCAGCACTGCTACGAAGGAT
ACTTATGACGCTCTCCACATGCAAGCCCTGCCACCTAGG

FIG. 10J

Clone AJ-26554 CAR LxH (SEQ ID NO: 326)
MALPVTALLL PLALLLHAAR PEIVMTQSPA TLSVSPGERA TLSCRASQSV
SSNLAWYQQK PGQAPRLLIY GASTRATGIP ARFSGSGSGT EFTLTISSLQ
SEDFAVYYCQ QYAAYPTFGG GTKVEIKRGS TSGSGKPGSG EGSTKGQVQL
VQSGAEVKKP GASVKVSCKA SGYTFTEHYM HWVRQAPGQR LEWMGVIGPS
GGKTSYAQKF QGRVTMTRDT STSTVYMELS SLRSEDTAVY YCARESWPMD
VWGQGTTVTV SSAAALDNEK SNGTIIHVKG KHLCPSPLFP GPSKPFWVLV
VVGGVLACYS LLVTVAFIIF WVRSKRSRLL HSDYMNMTPR RPGPTRKHYQ
PYAPPRDFAA YRSRVKFSRS ADAPAYQQGQ NQLYNELNLG RREEYDVLDK
RRGRDPEMGG KPRRKNPQEG LYNELQKDKM AEAYSEIGMK GERRRGKGHD
GLYQGLSTAT KDTYDALHMQ ALPPR

FIG. 11A

Clone NM-26562 HC DNA (SEQ ID NO: 327)
CAGGTGCAGCTGCAGGAGTCGGGCCCAGGACTGGTGAAGCCTTCACAGACCCTGTCCCTCACC
TGTACTGTCTCTGGTGGCTCCATCGGGAGTGGTGGTAGTTACTGGAGCTGGATCCGCCAGCAC
CCAGGGAAGGGCCTGGAGTGGATTGGGTTGATCTATTACGATGGGAGCACCTACTACAACCCG
TCCCTCAAGAGTCGAGTTACCATATCAGTAGACACGTCTAAGAACCAGTTCTCCCTGAAGCTG
AGTTCTGTGACCGCCGCAGACACGGCGGTGTACTACTGCGCCAGAGGCAGGGGATATGAGACT
TCTTTAGCCTTCGATATCTGGGGTCAGGGTACAATGGTCACCGTCTCCTCA

FIG. 11B

Clone NM-26562 HC (SEQ ID NO: 328). CDRs 1, 2, and 3 are underlined.
QVQLQESGPG LVKPSQTLSL TCTVSG<u>GSIG</u> <u>SGGSYWS</u>WIR QHPGKGLEWI
G<u>LIYYDGSTY</u> <u>YNPSLKS</u>RVT ISVDTSKNQF SLKLSSVTAA DTAVYYC<u>ARG</u>
<u>RGYETSLAFD</u> <u>I</u>WGQGTMVTV SS

FIG. 11C

GSIGSGGSYWS (SEQ ID NO: 329) (HC CDR1)

LIYYDGSTYYNPSLKS (SEQ ID NO: 330) (HC CDR2)

ARGRGYETSLAFDI (SEQ ID NO: 331) (HC CDR3)

FIG. 11D

Clone NM-26562 LC DNA (SEQ ID NO: 332)
GAAATTGTGTTGACACAGTCTCCAGCCACCCTGTCTTTGTCTCCAGGGGAAAGAGCCACCCTC
TCCTGCAGGGCCAGTCAGAGTGTTAGCAGCTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGACACGTCTGGCCTCCTACTTTTGGCGGAGGGACCAAGGTTGAG
ATCAAACGG

FIG. 11E

Clone NM-26562 LC (SEQ ID NO: 333). CDRs 1, 2, and 3 are underlined.
EIVLTQSPAT LSLSPGERAT LSC<u>RASQSVS</u> <u>SYLA</u>WYQQKP GQAPRLLIY<u>D</u>
<u>ASNRAT</u>GIPA RFSGSGSGTD FTLTISSLEP EDFAVYYC<u>QQ</u> <u>RHVWPPT</u>FGG GTKVEIKR

FIG. 11F

RASQSVSSYLA (SEQ ID NO: 334) (LC CDR1)

DASNRAT (SEQ ID NO: 335) (LC CDR2)

FIG. 11F (continued)

QQRHVWPPT (SEQ ID NO: 336) (LC CDR3)

FIG. 11G

Clone NM-26562 CAR DNA HxL (SEQ ID NO: 337)
ATGGCACTCCCCGTAACTGCTCTGCTGCTGCCGTTGGCATTGCTCCTGCACGCCGCACGCCCG
CAGGTGCAGCTGCAGGAGTCGGGCCCAGGACTGGTGAAGCCTTCACAGACCCTGTCCCTCACC
TGTACTGTCTCTGGTGGCTCCATCGGGAGTGGTGGTAGTTACTGGAGCTGGATCCGCCAGCAC
CCAGGGAAGGGCCTGGAGTGGATTGGGTTGATCTATTACGATGGGAGCACCTACTACAACCCG
TCCCTCAAGAGTCGAGTTACCATATCAGTAGACACGTCTAAGAACCAGTTCTCCCTGAAGCTG
AGTTCTGTGACCGCCGCAGACACGGCGGTGTACTACTGCGCCAGAGGCAGGGGATATGAGACT
TCTTTAGCCTTCGATATCTGGGGTCAGGGTACAATGGTCACCGTCTCCTCAGGGTCTACATCC
GGCTCCGGGAAGCCCGGAAGTGGCGAAGGTAGTACAAAGGGGGAAATTGTGTTGACACAGTCT
CCAGCCACCCTGTCTTTGTCTCCAGGGGAAAGAGCCACCCTCTCCTGCAGGGCCAGTCAGAGT
GTTAGCAGCTACTTAGCCTGGTACCAACAGAAACCTGGCCAGGCTCCCAGGCTCCTCATCTAT
GATGCATCCAACAGGGCCACTGGCATCCCAGCCAGGTTCAGTGGCAGTGGGTCTGGGACAGAC
TTCACTCTCACCATCAGCAGCCTAGAGCCTGAAGATTTTGCAGTTTATTACTGTCAGCAGAGA
CACGTCTGGCCTCCTACTTTTGGCGGAGGGACCAAGGTTGAGATCAAACGGGCCGCTGCCCTT
GATAATGAAAAGTCAAACGGAACAATCATTCACGTGAAGGGCAAGCACCTCTGTCCGTCACCC
TTGTTCCCTGGTCCATCCAAGCCATTCTGGGTGTTGGTCGTAGTGGGTGGAGTCCTCGCTTGT
TACTCTCTGCTCGTCACCGTGGCTTTTATAATCTTCTGGGTTAGATCCAAAAGAAGCCGCCTG
CTCCATAGCGATTACATGAATATGACTCCACGCCGCCCTGGCCCCACAAGGAAACACTACCAG
CCTTACGCACCACCTAGAGATTTCGCTGCCTATCGGAGCAGGGTGAAGTTTTCCAGATCTGCA
GATGCACCAGCGTATCAGCAGGGCCAGAACCAACTGTATAACGAGCTCAACCTGGGACGCAGG
GAAGAGTATGACGTTTTGGACAAGCGCAGAGGACGGGACCCTGAGATGGGTGGCAAACCAAGA
CGAAAAAACCCCCAGGAGGGTCTCTATAATGAGCTGCAGAAGGATAAGATGGCTGAAGCCTAT
TCTGAAATAGGCATGAAAGGAGAGCGGAGAAGGGGAAAAGGGCACGACGGTTTGTACCAGGGA
CTCAGCACTGCTACGAAGGATACTTATGACGCTCTCCACATGCAAGCCCTGCCACCTAGG

FIG. 11H

Clone NM-26562 CAR HxL (SEQ ID NO: 338)
MALPVTALLL PLALLLHAAR PQVQLQESGP GLVKPSQTLS LTCTVSGGSI
GSGGSYWSWI RQHPGKGLEW IGLIYYDGST YYNPSLKSRV TISVDTSKNQ
FSLKLSSVTA ADTAVYYCAR GRGYETSLAF DIWGQGTMVT VSSGSTSGSG
KPGSGEGSTK GEIVLTQSPA TLSLSPGERA TLSCRASQSV SSYLAWYQQK
PGQAPRLLIY DASNRATGIP ARFSGSGSGT DFTLTISSLE PEDFAVYYCQ
QRHVWPPTFG GGTKVEIKRA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

FIG. 11I

Clone NM-26562 CAR DNA LxH (SEQ ID NO: 339)
ATGGCACTCCCCGTAACTGCTCTGCTGCTGCCGTTGGCATTGCTCCTGCACGCCGCACGCCCG
GAAATTGTGTTGACACAGTCTCCAGCCACCCTGTCTTTGTCTCCAGGGGAAAGAGCCACCCTC
TCCTGCAGGGCCAGTCAGAGTGTTAGCAGCTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGACACGTCTGGCCTCCTACTTTTGGCGGAGGGACCAAGGTTGAG
ATCAAACGGGGGTCTACATCCGGCTCCGGGAAGCCCGGAAGTGGCGAAGGTAGTACAAAGGGG
CAGGTGCAGCTGCAGGAGTCGGGCCCAGGACTGGTGAAGCCTTCACAGACCCTGTCCCTCACC
TGTACTGTCTCTGGTGGCTCCATCGGGAGTGGTGGTAGTTACTGGAGCTGGATCCGCCAGCAC
CCAGGGAAGGGCCTGGAGTGGATTGGGTTGATCTATTACGATGGGAGCACCTACTACAACCCG
TCCCTCAAGAGTCGAGTTACCATATCAGTAGACACGTCTAAGAACCAGTTCTCCCTGAAGCTG
AGTTCTGTGACCGCCGCAGACACGGCGGTGTACTACTGCGCCAGAGGCAGGGGATATGAGACT
TCTTTAGCCTTCGATATCTGGGGTCAGGGTACAATGGTCACCGTCTCCTCAGCCGCTGCCCTT
GATAATGAAAAGTCAAACGGAACAATCATTCACGTGAAGGGCAAGCACCTCTGTCCGTCACCC
TTGTTCCCTGGTCCATCCAAGCCATTCTGGGTGTTGGTCGTAGTGGGTGGAGTCCTCGCTTGT
TACTCTCTGCTCGTCACCGTGGCTTTTATAATCTTCTGGGTTAGATCCAAAAGAAGCCGCCTG
CTCCATAGCGATTACATGAATATGACTCCACGCCGCCCTGGCCCCACAAGGAAACACTACCAG
CCTTACGCACCACCTAGAGATTTCGCTGCCTATCGGAGCAGGGTGAAGTTTTCCAGATCTGCA
GATGCACCAGCGTATCAGCAGGGCCAGAACCAACTGTATAACGAGCTCAACCTGGGACGCAGG
GAAGAGTATGACGTTTTGGACAAGCGCAGAGGACGGGACCCTGAGATGGGTGGCAAACCAAGA
CGAAAAAACCCCCAGGAGGGTCTCTATAATGAGCTGCAGAAGGATAAGATGGCTGAAGCCTAT
TCTGAAATAGGCATGAAAGGAGAGCGGAGAAGGGGAAAAGGGCACGACGGTTTGTACCAGGGA
CTCAGCACTGCTACGAAGGATACTTATGACGCTCTCCACATGCAAGCCCTGCCACCTAGG

FIG. 11J

Clone NM-26562 CAR LxH (SEQ ID NO: 340)
MALPVTALLL PLALLLHAAR PEIVLTQSPA TLSLSPGERA TLSCRASQSV
SSYLAWYQQK PGQAPRLLIY DASNRATGIP ARFSGSGSGT DFTLTISSLE
PEDFAVYYCQ QRHVWPPTFG GGTKVEIKRG STSGSGKPGS GEGSTKGQVQ
LQESGPGLVK PSQTLSLTCT VSGGSIGSGG SYWSWIRQHP GKGLEWIGLI
YYDGSTYYNP SLKSRVTISV DTSKNQFSLK LSSVTAADTA VYYCARGRGY
ETSLAFDIWG QGTMVTVSSA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

FIG. 12A

Clone TS-26564 HC DNA (SEQ ID NO: 341)
GAGGTGCAGCTGGTGGAGTCTGGGGGAGGCTTGGTACAGCCTGGGGGGTCCCTGAGACTCTCC
TGTGCAGCCTCTGGATTCACCTTCAGTAGCTATAGCATGAACTGGGTCCGCCAGGCTCCAGGG
AAGGGGCTGGAGTGGGTTTCAACCATTAGTAGTAGTAGTAGTATCATATACTACGCAGACTCT
GTGAAGGGCCGATTCACCATCTCCAGAGACAATGCCAAGAACTCACTGTATCTGCAAATGAAC
AGCCTGAGAGCTGAGGACACGGCGGTGTACTACTGCGCCAGAGGTTCTCAGGAGCACCTGATT
TTCGATTATTGGGGACAGGGTACATTGGTCACCGTCTCCTCA

FIG. 12B

Clone TS-26564 HC (SEQ ID NO: 342). CDRs 1, 2, and 3 are underlined.
EVQLVESGGG LVQPGGSLRL SCAASG<u>FTFS</u> <u>SYSMN</u>WVRQA PGKGLEWVS<u>T</u>
<u>ISSSSSIIYY</u> <u>ADSVKG</u>RFTI SRDNAKNSLY LQMNSLRAED TAVYYC<u>ARGS</u>
<u>QEHLIFDY</u>WG QGTLVTVSS

FIG. 12C

FTFSSYSMN (SEQ ID NO: 343) (HC CDR1)

TISSSSSIIYYADSVKG (SEQ ID NO: 344) (HC CDR2)

ARGSQEHLIFDY (SEQ ID NO: 345) (HC CDR3)

FIG. 12D

Clone TS-26564 LC DNA (SEQ ID NO: 346)
GAAATTGTGTTGACACAGTCTCCAGCCACCCTGTCTTTGTCTCCAGGGGAAAGAGCCACCCTC
TCCTGCAGGGCCAGTCAGAGTGTTAGCAGGTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGATTCTACTACCCTTGGACTTTTGGCGGAGGGACCAAGGTTGAG
ATCAAACGG

FIG. 12E

Clone TS-26564 LC (SEQ ID NO: 347). CDRs 1, 2, and 3 are underlined.
EIVLTQSPAT LSLSPGERAT LSC<u>RASQSVS</u> <u>RYLA</u>WYQQKP GQAPRLLIY<u>D</u>
<u>ASNRAT</u>GIPA RFSGSGSGTD FTLTISSLEP EDFAVYYC<u>QQ</u> <u>RFYYPWT</u>FGG GTKVEIKR

FIG. 12F

RASQSVSRYLA (SEQ ID NO: 347) (LC CDR1)

DASNRAT (SEQ ID NO: 349) (LC CDR2)

QQRFYYPWT (SEQ ID NO: 350) (LC CDR3)

FIG. 12G

Clone TS-26564 CAR DNA HxL (SEQ ID NO: 351)
ATGGCACTCCCCGTAACTGCTCTGCTGCTGCCGTTGGCATTGCTCCTGCACGCCGCACGCCCG
GAGGTGCAGCTGGTGGAGTCTGGGGGAGGCTTGGTACAGCCTGGGGGGTCCCTGAGACTCTCC
TGTGCAGCCTCTGGATTCACCTTCAGTAGCTATAGCATGAACTGGGTCCGCCAGGCTCCAGGG
AAGGGGCTGGAGTGGGTTTCAACCATTAGTAGTAGTAGTAGTATCATATACTACGCAGACTCT
GTGAAGGGCCGATTCACCATCTCCAGAGACAATGCCAAGAACTCACTGTATCTGCAAATGAAC
AGCCTGAGAGCTGAGGACACGGCGGTGTACTACTGCGCCAGAGGTTCTCAGGAGCACCTGATT
TTCGATTATTGGGGACAGGGTACATTGGTCACCGTCTCCTCAGGGTCTACATCCGGCTCCGGG
AAGCCCGGAAGTGGCGAAGGTAGTACAAAGGGGGAAATTGTGTTGACACAGTCTCCAGCCACC
CTGTCTTTGTCTCCAGGGGAAAGAGCCACCCTCTCCTGCAGGGCCAGTCAGAGTGTTAGCAGG
TACTTAGCCTGGTACCAACAGAAACCTGGCCAGGCTCCCAGGCTCCTCATCTATGATGCATCC
AACAGGGCCACTGGCATCCCAGCCAGGTTCAGTGGCAGTGGGTCTGGGACAGACTTCACTCTC
ACCATCAGCAGCCTAGAGCCTGAAGATTTTGCAGTTTATTACTGTCAGCAGAGATTCTACTAC
CCTTGGACTTTTGGCGGAGGGACCAAGGTTGAGATCAAACGGGCCGCTGCCCTTGATAATGAA
AAGTCAAACGGAACAATCATTCACGTGAAGGGCAAGCACCTCTGTCCGTCACCCTTGTTCCCT
GGTCCATCCAAGCCATTCTGGGTGTTGGTCGTAGTGGGTGGAGTCCTCGCTTGTTACTCTCTG
CTCGTCACCGTGGCTTTTATAATCTTCTGGGTTAGATCCAAAAGAAGCCGCCTGCTCCATAGC
GATTACATGAATATGACTCCACGCCGCCCTGGCCCCACAAGGAAACACTACCAGCCTTACGCA
CCACCTAGAGATTTCGCTGCCTATCGGAGCAGGGTGAAGTTTTCCAGATCTGCAGATGCACCA
GCGTATCAGCAGGGCCAGAACCAACTGTATAACGAGCTCAACCTGGGACGCAGGGAAGAGTAT
GACGTTTTGGACAAGCGCAGAGGACGGGACCCTGAGATGGGTGGCAAACCAAGACGAAAAAAC
CCCCAGGAGGGTCTCTATAATGAGCTGCAGAAGGATAAGATGGCTGAAGCCTATTCTGAAATA
GGCATGAAAGGAGAGCGGAGAAGGGGAAAAGGGCACGACGGTTTGTACCAGGGACTCAGCACT
GCTACGAAGGATACTTATGACGCTCTCCACATGCAAGCCCTGCCACCTAGG

FIG. 12H

Clone TS-26564 CAR HxL (SEQ ID NO: 352)

| | | | | |
|---|---|---|---|---|
| MALPVTALLL | PLALLLHAAR | PEVQLVESGG | GLVQPGGSLR | LSCAASGFTF |
| SSYSMNWVRQ | APGKGLEWVS | TISSSSSIIY | YADSVKGRFT | ISRDNAKNSL |
| YLQMNSLRAE | DTAVYYCARG | SQEHLIFDYW | GQGTLVTVSS | GSTSGSGKPG |
| SGEGSTKGEI | VLTQSPATLS | LSPGERATLS | CRASQSVSRY | LAWYQQKPGQ |
| APRLLIYDAS | NRATGIPARF | SGSGSGTDFT | LTISSLEPED | FAVYYCQQRF |
| YYPWTFGGGT | KVEIKRAAAL | DNEKSNGTII | HVKGKHLCPS | PLFPGPSKPF |
| WVLVVVGGVL | ACYSLLVTVA | FIIFWVRSKR | SRLLHSDYMN | MTPRRPGPTR |
| KHYQPYAPPR | DFAAYRSRVK | FSRSADAPAY | QQGQNQLYNE | LNLGRREEYD |
| VLDKRRGRDP | EMGGKPRRKN | PQEGLYNELQ | KDKMAEAYSE | IGMKGERRRG |
| KGHDGLYQGL | STATKDTYDA | LHMQALPPR | | |

FIG. 12I

Clone TS-26564 CAR DNA LxH (SEQ ID NO: 353)
ATGGCACTCCCCGTAACTGCTCTGCTGCTGCCGTTGGCATTGCTCCTGCACGCCGCACGCCCG
GAAATTGTGTTGACACAGTCTCCAGCCACCCTGTCTTTGTCTCCAGGGGAAAGAGCCACCCTC
TCCTGCAGGGCCAGTCAGAGTGTTAGCAGGTACTTAGCCTGGTACCAACAGAAACCTGGCCAG
GCTCCCAGGCTCCTCATCTATGATGCATCCAACAGGGCCACTGGCATCCCAGCCAGGTTCAGT
GGCAGTGGGTCTGGGACAGACTTCACTCTCACCATCAGCAGCCTAGAGCCTGAAGATTTTGCA
GTTTATTACTGTCAGCAGAGATTCTACTACCCTTGGACTTTTGGCGGAGGGACCAAGGTTGAG
ATCAAACGGGGTCTACATCCGGCTCCGGGAAGCCCGGAAGTGGCGAAGGTAGTACAAAGGGG
GAGGTGCAGCTGGTGGAGTCTGGGGGAGGCTTGGTACAGCCTGGGGGGTCCCTGAGACTCTCC
TGTGCAGCCTCTGGATTCACCTTCAGTAGCTATAGCATGAACTGGGTCCGCCAGGCTCCAGGG
AAGGGGCTGGAGTGGGTTTCAACCATTAGTAGTAGTAGTAGTATCATATACTACGCAGACTCT
GTGAAGGGCCGATTCACCATCTCCAGAGACAATGCCAAGAACTCACTGTATCTGCAAATGAAC
AGCCTGAGAGCTGAGGACACGGCGGTGTACTACTGCGCCAGAGGTTCTCAGGAGCACCTGATT
TTCGATTATTGGGGACAGGGTACATTGGTCACCGTCTCCTCAGCCGCTGCCCTTGATAATGAA
AAGTCAAACGGAACAATCATTCACGTGAAGGGCAAGCACCTCTGTCCGTCACCCTTGTTCCCT
GGTCCATCCAAGCCATTCTGGGTGTTGGTCGTAGTGGGTGGAGTCCTCGCTTGTTACTCTCTG
CTCGTCACCGTGGCTTTTATAATCTTCTGGGTTAGATCCAAAAGAAGCCGCCTGCTCCATAGC
GATTACATGAATATGACTCCACGCCGCCCTGGCCCCACAAGGAAACACTACCAGCCTTACGCA
CCACCTAGAGATTTCGCTGCCTATCGGAGCAGGGTGAAGTTTTCCAGATCTGCAGATGCACCA
GCGTATCAGCAGGGCCAGAACCAACTGTATAACGAGCTCAACCTGGGACGCAGGGAAGAGTAT
GACGTTTTGGACAAGCGCAGAGGACGGGACCCTGAGATGGGTGGCAAACCAAGACGAAAAAAC
CCCCAGGAGGGTCTCTATAATGAGCTGCAGAAGGATAAGATGGCTGAAGCCTATTCTGAAATA
GGCATGAAAGGAGAGCGGAGAAGGGGAAAAGGGCACGACGGTTTGTACCAGGGACTCAGCACT
GCTACGAAGGATACTTATGACGCTCTCCACATGCAAGCCCTGCCACCTAGG

FIG. 12J

Clone TS-26564 CAR LxH (SEQ ID NO: 354)
MALPVTALLL PLALLLHAAR PEIVLTQSPA TLSLSPGERA TLSCRASQSV
SRYLAWYQQK PGQAPRLLIY DASNRATGIP ARFSGSGSGT DFTLTISSLE
PEDFAVYYCQ QRFYYPWTFG GGTKVEIKRG STSGSGKPGS GEGSTKGEVQ
LVESGGGLVQ PGGSLRLSCA ASGFTFSSYS MNWVRQAPGK GLEWVSTISS
SSSIIYYADS VKGRFTISRD NAKNSLYLQM NSLRAEDTAV YYCARGSQEH
LIFDYWGQGT LVTVSSAAAL DNEKSNGTII HVKGKHLCPS PLFPGPSKPF
WVLVVVGGVL ACYSLLVTVA FIIFWVRSKR SRLLHSDYMN MTPRRPGPTR
KHYQPYAPPR DFAAYRSRVK FSRSADAPAY QQGQNQLYNE LNLGRREEYD
VLDKRRGRDP EMGGKPRRKN PQEGLYNELQ KDKMAEAYSE IGMKGERRRG
KGHDGLYQGL STATKDTYDA LHMQALPPR

FIG. 13A

Clone RY-26568 HC DNA (SEQ ID NO: 355)
CAGGTGCAGCTGGTGGAGTCTGGGGGAGGCGTGGTCCAGCCTGGGAGGTCCCTGAGACTCTCC
TGTGCAGCGTCTGGATTCACCTTCGGGAGCTATGGCATGCACTGGGTCCGCCAGGCTCCAGGC
AAGGGGCTGGAGTGGGTGGCAGTTATACATTATGATGGAAGTGTTGAATACTATGCAGACTCC
GTGAAGGGCCGATTCACCATCTCCAGAGACAATTCCAAGGACACGCTGTATCTGCAAATGAAC
AGCCTGAGAGCCGAGGACACGGCGGTGTACTACTGCGCCAGAACTGACTTCTGGAGCGGATCC
CCTCCAAGCTTAGATTACTGGGGACAGGGTACATTGGTCACCGTCTCCTCA

FIG. 13B

Clone RY-26568 HC (SEQ ID NO: 356). CDRs 1, 2, and 3 are underlined.
QVQLVESGGG VVQPGRSLRL SCAASG<u>FTFG</u> <u>SYGMH</u>WVRQA PGKGLEWVA<u>V</u>
<u>IHYDGSVEYY</u> <u>ADSVKG</u>RFTI SRDNSKDTLY LQMNSLRAED TAVYYC<u>ARTD</u>
<u>FWSGSPPSLD</u> <u>Y</u>WGQGTLVTV SS

FIG. 13C

FTFGSYGMH (SEQ ID NO: 357) (HC CDR1)

VIHYDGSVEYYADSVKG (SEQ ID NO: 358) (HC CDR2)

ARTDFWSGSPPSLDY (SEQ ID NO: 359) (HC CDR3)

FIG. 13D

Clone RY-26568 LC DNA (SEQ ID NO: 360)
GACATCCAGTTGACCCAGTCTCCATCTTCCGTGTCTGCATCTGTAGGAGACAGAGTCACCATC
ACTTGTCGGGCGAGTCGGGGTATTAGCAGCTGGTTAGCCTGGTATCAGCAGAAACCAGGGAAA
GCCCCTAAGCTCCTGATCTATGGTGCATCCAGTTTGCAAAGTGGGGTCCCATCAAGGTTCAGC
GGCAGTGGATCTGGGACAGATTTCACTCTCACCATCAGCAGCCTGCAGCCTGAAGATTTTGCA
ACTTATTACTGTCAGCAGATATACACCTTCCCTTTCACTTTTGGCGGAGGGACCAAGGTTGAG
ATCAAACGG

FIG. 13E

Clone RY-26568 LC (SEQ ID NO: 361). CDRs 1, 2, and 3 are underlined.
DIQLTQSPSS VSASVGDRVT ITC<u>RASRGIS</u> <u>SWLA</u>WYQQKP GKAPKLLIY<u>G</u>
<u>ASSLQS</u>GVPS RFSGSGSGTD FTLTISSLQP EDFATYYC<u>QQ</u> <u>IYTFPFT</u>FGG GTKVEIKR

FIG. 13F

RASRGISSWLA (SEQ ID NO: 362) (LC CDR1)

GASSLQS (SEQ ID NO: 363) (LC CDR2)

QQIYTFPFT (SEQ ID NO: 364) (LC CDR3)

FIG. 13G

Clone RY-26568 CAR DNA HxL (SEQ ID NO: 365)
ATGGCACTCCCCGTAACTGCTCTGCTGCTGCCGTTGGCATTGCTCCTGCACGCCGCACGCCCG
CAGGTGCAGCTGGTGGAGTCTGGGGGAGGCGTGGTCCAGCCTGGGAGGTCCCTGAGACTCTCC
TGTGCAGCGTCTGGATTCACCTTCGGGAGCTATGGCATGCACTGGGTCCGCCAGGCTCCAGGC
AAGGGGCTGGAGTGGGTGGCAGTTATACATTATGATGGAAGTGTTGAATACTATGCAGACTCC
GTGAAGGGCCGATTCACCATCTCCAGAGACAATTCCAAGGACACGCTGTATCTGCAAATGAAC
AGCCTGAGAGCCGAGGACACGGCGGTGTACTACTGCGCCAGAACTGACTTCTGGAGCGGATCC
CCTCCAAGCTTAGATTACTGGGGACAGGGTACATTGGTCACCGTCTCCTCAGGGTCTACATCC
GGCTCCGGGAAGCCCGGAAGTGGCGAAGGTAGTACAAAGGGGGACATCCAGTTGACCCAGTCT
CCATCTTCCGTGTCTGCATCTGTAGGAGACAGAGTCACCATCACTTGTCGGGCGAGTCGGGGT
ATTAGCAGCTGGTTAGCCTGGTATCAGCAGAAACCAGGGAAAGCCCCTAAGCTCCTGATCTAT
GGTGCATCCAGTTTGCAAAGTGGGGTCCCATCAAGGTTCAGCGGCAGTGGATCTGGACAGAT
TTCACTCTCACCATCAGCAGCCTGCAGCCTGAAGATTTTGCAACTTATTACTGTCAGCAGATA
TACACCTTCCCTTTCACTTTTGGCGGAGGGACCAAGGTTGAGATCAAACGGGCCGCTGCCCTT
GATAATGAAAAGTCAAACGGAACAATCATTCACGTGAAGGGCAAGCACCTCTGTCCGTCACCC
TTGTTCCCTGGTCCATCCAAGCCATTCTGGGTGTTGGTCGTAGTGGGTGGAGTCCTCGCTTGT
TACTCTCTGCTCGTCACCGTGGCTTTTATAATCTTCTGGGTTAGATCCAAAAGAAGCCGCCTG
CTCCATAGCGATTACATGAATATGACTCCACGCCGCCCTGGCCCCACAAGGAAACACTACCAG
CCTTACGCACCACCTAGAGATTTCGCTGCCTATCGGAGCAGGGTGAAGTTTTCCAGATCTGCA
GATGCACCAGCGTATCAGCAGGGCCAGAACCAACTGTATAACGAGCTCAACCTGGGACGCAGG
GAAGAGTATGACGTTTTGGACAAGCGCAGAGGACGGGACCCTGAGATGGGTGGCAAACCAAGA
CGAAAAAACCCCCAGGAGGGTCTCTATAATGAGCTGCAGAAGGATAAGATGGCTGAAGCCTAT
TCTGAAATAGGCATGAAAGGAGAGCGGAGAAGGGGAAAAGGGCACGACGGTTTGTACCAGGGA
CTCAGCACTGCTACGAAGGATACTTATGACGCTCTCCACATGCAAGCCCTGCCACCTAGG

FIG. 13H

Clone RY-26568 CAR HxL (SEQ ID NO: 366)
MALPVTALLL PLALLLHAAR PQVQLVESGG GVVQPGRSLR LSCAASGFTF
GSYGMHWVRQ APGKGLEWVA VIHYDGSVEY YADSVKGRFT ISRDNSKDTL
YLQMNSLRAE DTAVYYCART DFWSGSPPSL DYWGQGTLVT VSSGSTSGSG
KPGSGEGSTK GDIQLTQSPS SVSASVGDRV TITCRASRGI SSWLAWYQQK
PGKAPKLLIY GASSLQSGVP SRFSGSGSGT DFTLTISSLQ PEDFATYYCQ
QIYTFPFTFG GGTKVEIKRA AALDNEKSNG TIIHVKGKHL CPSPLFPGPS
KPFWVLVVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

FIG. 13I

Clone RY-26568 CAR DNA LxH (SEQ ID NO: 367)
ATGGCACTCCCCGTAACTGCTCTGCTGCTGCCGTTGGCATTGCTCCTGCACGCCGCACGCCCG
GACATCCAGTTGACCCAGTCTCCATCTTCCGTGTCTGCATCTGTAGGAGACAGAGTCACCATC
ACTTGTCGGGCGAGTCGGGGTATTAGCAGCTGGTTAGCCTGGTATCAGCAGAAACCAGGGAAA
GCCCCTAAGCTCCTGATCTATGGTGCATCCAGTTTGCAAAGTGGGGTCCCATCAAGGTTCAGC
GGCAGTGGATCTGGACAGATTTCACTCTCACCATCAGCAGCCTGCAGCCTGAAGATTTTGCA
ACTTATTACTGTCAGCAGATATACACCTTCCCTTTCACTTTTGGCGGAGGGACCAAGGTTGAG
ATCAAACGGGGTCTACATCCGGCTCCGGAAGCCCGGAAGTGGCGAAGGTAGTACAAAGGGG
CAGGTGCAGCTGGTGGAGTCTGGGGGAGGCGTGGTCCAGCCTGGGAGGTCCCTGAGACTCTCC
TGTGCAGCGTCTGGATTCACCTTCGGGAGCTATGGCATGCACTGGGTCCGCCAGGCTCCAGGC
AAGGGGCTGGAGTGGGTGGCAGTTATACATTATGATGGAAGTGTTGAATACTATGCAGACTCC
GTGAAGGGCCGATTCACCATCTCCAGAGACAATTCCAAGGACACGCTGTATCTGCAAATGAAC
AGCCTGAGAGCCGAGGACACGGCGGTGTACTACTGCGCCAGAACTGACTTCTGGAGCGGATCC
CCTCCAAGCTTAGATTACTGGGGACAGGGTACATTGGTCACCGTCTCCTCAGCCGCTGCCCTT
GATAATGAAAAGTCAAACGGAACAATCATTCACGTGAAGGGCAAGCACCTCTGTCCGTCACCC
TTGTTCCCTGGTCCATCCAAGCCATTCTGGGTGTTGGTCGTAGTGGGTGGAGTCCTCGCTTGT
TACTCTCTGCTCGTCACCGTGGCTTTTATAATCTTCTGGGTTAGATCCAAAAGAAGCCGCCTG
CTCCATAGCGATTACATGAATATGACTCCACGCCGCCTGGCCCCACAAGGAAACACTACCAG
CCTTACGCACCACCTAGAGATTTCGCTGCCTATCGGAGCAGGGTGAAGTTTTCCAGATCTGCA
GATGCACCAGCGTATCAGCAGGGCCAGAACCAACTGTATAACGAGCTCAACCTGGGACGCAGG
GAAGAGTATGACGTTTTGGACAAGCGCAGAGGACGGGACCCTGAGATGGGTGGCAAACCAAGA
CGAAAAAACCCCCAGGAGGGTCTCTATAATGAGCTGCAGAAGGATAAGATGGCTGAAGCCTAT
TCTGAAATAGGCATGAAGGAGAGCGGAGAAGGGGAAAAGGGCACGACGGTTTGTACCAGGGA
CTCAGCACTGCTACGAAGGATACTTATGACGCTCTCCACATGCAAGCCCTGCCACCTAGG

FIG. 13J

Clone RY-26568 CAR LxH (SEQ ID NO: 368)
MALPVTALLL PLALLLHAAR PDIQLTQSPS SVSASVGDRV TITCRASRGI
SSWLAWYQQK PGKAPKLLIY GASSLQSGVP SRFSGSGSGT DFTLTISSLQ
PEDFATYYCQ QIYTFPFTFG GGTKVEIKRG STSGSGKPGS GEGSTKGQVQ
LVESGGGVVQ PGRSLRLSCA ASGFTFGSYG MHWVRQAPGK GLEWVAVIHY
DGSVEYYADS VKGRFTISRD NSKDTLYLQM NSLRAEDTAV YYCARTDFWS
GSPPSLDYWG QGTLVTVSSA AALDNEKSNG TIIHVKGKHL CPSPLFPGPS
KPFWVLVVG GVLACYSLLV TVAFIIFWVR SKRSRLLHSD YMNMTPRRPG
PTRKHYQPYA PPRDFAAYRS RVKFSRSADA PAYQQGQNQL YNELNLGRRE
EYDVLDKRRG RDPEMGGKPR RKNPQEGLYN ELQKDKMAEA YSEIGMKGER
RRGKGHDGLY QGLSTATKDT YDALHMQALP PR

FIG. 14A

Clone PP-26575 HC DNA (SEQ ID NO: 369)
CAGGTGCAGCTGGTGCAGTCTGGGGCTGAGGTGAAGAAGCCTGGGTCCTCGGTGAAGGTCTCC
TGCAAGGCTTCTGGAGGCACCCTCAGCAGCCTGGCTATCAGCTGGGTGCGACAGGCCCCTGGA
CAAGGGCTTGAGTGGATGGGAGGGGTCATCCCTATCTTGGGTCGGGCAAACTACGCACAGAAG
TTCCAGGGCAGAGTCACGATTACCGCGGACGAGTCCACGAGCACAGCCTACATGGAGCTGAGC
AGCCTGAGATCTGAGGACACGGCGGTGTACTACTGCGCCAGAACTCCTGAATACTCCTCCAGC
ATATGGCACTATTACTACGGCATGGACGTATGGGGCCAGGGAACAACTGTCACCGTCTCCTCA

FIG. 14B

Clone PP-26575 HC (SEQ ID NO: 370). CDRs 1, 2, and 3 are underlined.
QVQLVQSGAE VKKPGSSVKV SCKASG<u>GTLS</u> <u>SLAIS</u>WVRQA PGQGLEWMGG
<u>VIPILGRANY</u> <u>AQKFQG</u>RVTI TADESTSTAY MELSSLRSED TAVYYC<u>ARTP</u>
<u>EYSSSIWHYY</u> <u>YGMDV</u>WGQGT TVTVSS

FIG. 14C

GTLSSLAIS (SEQ ID NO: 371) (HC CDR1)

GVIPILGRANYAQKFQG (SEQ ID NO: 372) (HC CDR2)

ARTPEYSSSIWHYYYGMDV (SEQ ID NO: 373) (HC CDR3)

FIG. 14D

Clone PP-26575 LC DNA (SEQ ID NO: 374)
GACATCGTGATGACCCAGTCTCCAGACTCCCTGGCTGTGTCTCTGGGCGAGAGGGCCACCATC
AACTGCAAGTCCAGCCAGAGTGTTTTATACAGCTCCAACAATAAGAACTACTTAGCTTGGTAC
CAGCAGAAACCAGGACAGCCTCCTAAGCTGCTCATTTACTGGGCATCTACCCGGGAATCCGGG
GTCCCTGACCGATTCAGTGGCAGCGGGTCTGGGACAGATTTCACTCTCACCATCAGCAGCCTG
CAGGCTGAAGATGTGGCAGTTTATTACTGTCAGCAGTTCGCCCACACTCCTTTCACTTTTGGC
GGAGGGACCAAGGTTGAGATCAAACGG

FIG. 14E

Clone PP-26575 LC (SEQ ID NO: 375). CDRs 1, 2, and 3 are underlined.
DIVMTQSPDS LAVSLGERAT INC<u>KSSQSVL</u> <u>YSSNNKNYLA</u> WYQQKPGQPP
KLLIY<u>WASTR</u> <u>␣</u>ESGVPDRFSG SGSGTDFTLT ISSLQAEDVA VYYC<u>QQFAHT</u>
<u>PFT</u>FGGGTKV EIKR

FIG. 14F

KSSQSVLYSSNNKNYLA (SEQ ID NO: 376) (LC CDR1)

FIG. 14F (continued)

WASTRES (SEQ ID NO: 377) (LC CDR2)

QQFAHTPFT (SEQ ID NO: 378) (LC CDR3)

FIG. 14G

Clone PP-26575 CAR DNA HxL (SEQ ID NO: 379)
ATGGCACTCCCCGTAACTGCTCTGCTGCTGCCGTTGGCATTGCTCCTGCACGCCGCACGCCCG
CAGGTGCAGCTGGTGCAGTCTGGGGCTGAGGTGAAGAAGCCTGGGTCCTCGGTGAAGGTCTCC
TGCAAGGCTTCTGGAGGCACCCTCAGCAGCCTGGCTATCAGCTGGGTGCGACAGGCCCCTGGA
CAAGGGCTTGAGTGGATGGGAGGGGTCATCCCTATCTTGGGTCGGGCAAACTACGCACAGAAG
TTCCAGGGCAGAGTCACGATTACCGCGGACGAGTCCACGAGCACAGCCTACATGGAGCTGAGC
AGCCTGAGATCTGAGGACACGGCGGTGTACTACTGCGCCAGAACTCCTGAATACTCCTCCAGC
ATATGGCACTATTACTACGGCATGGACGTATGGGGCCAGGGAACAACTGTCACCGTCTCCTCA
GGGTCTACATCCGGCTCCGGGAAGCCCGGAAGTGGCGAAGGTAGTACAAAGGGGGACATCGTG
ATGACCCAGTCTCCAGACTCCCTGGCTGTGTCTCTGGGCGAGAGGGCCACCATCAACTGCAAG
TCCAGCCAGAGTGTTTTATACAGCTCCAACAATAAGAACTACTTAGCTTGGTACCAGCAGAAA
CCAGGACAGCCTCCTAAGCTGCTCATTTACTGGGCATCTACCCGGGAATCCGGGGTCCCTGAC
CGATTCAGTGGCAGCGGGTCTGGGACAGATTTCACTCTCACCATCAGCAGCCTGCAGGCTGAA
GATGTGGCAGTTTATTACTGTCAGCAGTTCGCCCACACTCCTTTCACTTTTGGCGGAGGGACC
AAGGTTGAGATCAAACGGGCCGCTGCCCTTGATAATGAAAGTCAAACGGAACAATCATTCAC
GTGAAGGGCAAGCACCTCTGTCCGTCACCCTTGTTCCCTGGTCCATCCAAGCCATTCTGGGTG
TTGGTCGTAGTGGGTGGAGTCCTCGCTTGTTACTCTCTGCTCGTCACCGTGGCTTTTATAATC
TTCTGGGTTAGATCCAAAAGAAGCCGCCTGCTCCATAGCGATTACATGAATATGACTCCACGC
CGCCCTGGCCCCACAAGGAAACACTACCAGCCTTACGCACCACCTAGAGATTTCGCTGCCTAT
CGGAGCAGGGTGAAGTTTTCCAGATCTGCAGATGCACCAGCGTATCAGCAGGGCCAGAACCAA
CTGTATAACGAGCTCAACCTGGGACGCAGGGAAGAGTATGACGTTTTGGACAAGCGCAGAGGA
CGGGACCCTGAGATGGGTGGCAAACCAAGACGAAAAAACCCCCAGGAGGGTCTCTATAATGAG
CTGCAGAAGGATAAGATGGCTGAAGCCTATTCTGAAATAGGCATGAAAGGAGAGCGGAGAAGG
GGAAAAGGGCACGACGGTTTGTACCAGGGACTCAGCACTGCTACGAAGGATACTTATGACGCT
CTCCACATGCAAGCCCTGCCACCTAGG

FIG. 14H

Clone PP-26575 CAR HxL (SEQ ID NO: 380)
```
MALPVTALLL PLALLLHAAR PQVQLVQSGA EVKKPGSSVK VSCKASGGTL
SSLAISWVRQ APGQGLEWMG GVIPILGRAN YAQKFQGRVT ITADESTSTA
YMELSSLRSE DTAVYYCART PEYSSSIWHY YYGMDVWGQG TTVTVSSGST
SGSSKPGSGE GSTKGDIVMT QSPDSLAVSL GERATINCKS SQSVLYSSNN
KNYLAWYQQK PGQPPKLLIY WASTRESGVP DRFSGSGSGT DFTLTISSLQ
AEDVAVYYCQ QFAHTPFTFG GGTKVEIKRA AALDNEKSNG TIIHVKGKHL
CPSPLPPGPS KPFWVLVVVG GVLACYSLLV TVAFIIFWVR SKRSRLLHSD
YMNMTPRRPG PTRKHYQPYA PPRDFAAYRS RVKFSRSADA PAYQQGQNQL
YNELNLGRRE EYDVLDKRRG RDPEMGGKPR RKNPQEGLYN ELQKDKMAEA
YSEIGMKGER RRGKGHDGLY QGLSTATKDT YDALHMQALP PR
```

FIG. 14I

Clone PP-26575 CAR DNA LxH (SEQ ID NO: 381)
ATGGCACTCCCCGTAACTGCTCTGCTGCTGCCGTTGGCATTGCTCCTGCACGCCGCACGCCCG
GACATCGTGATGACCCAGTCTCCAGACTCCCTGGCTGTGTCTCTGGGCGAGAGGGCCACCATC
AACTGCAAGTCCAGCCAGAGTGTTTTATACAGCTCCAACAATAAGAACTACTTAGCTTGGTAC
CAGCAGAAACCAGGACAGCCTCCTAAGCTGCTCATTTACTGGGCATCTACCCGGGAATCCGGG
GTCCCTGACCGATTCAGTGGCAGCGGGTCTGGGACAGATTTCACTCTCACCATCAGCAGCCTG
CAGGCTGAAGATGTGGCAGTTATTACTGTCAGCAGTTCGCCCACACTCCTTTCACTTTTGGC
GGAGGGACCAAGGTTGAGATCAAACGGGGGTCTACATCCGGCTCCGGGAAGCCCGGAAGTGGC
GAAGGTAGTACAAAGGGGCAGGTGCAGCTGGTGCAGTCTGGGGCTGAGGTGAAGAAGCCTGGG
TCCTCGGTGAAGGTCTCCTGCAAGGCTTCTGGAGGCACCCTCAGCAGCCTGGCTATCAGCTGG
GTGCGACAGGCCCCTGGACAAGGGCTTGAGTGGATGGGAGGGGTCATCCCTATCTTGGGTCGG
GCAAACTACGCACAGAAGTTCCAGGGCAGAGTCACGATTACCGCGGACGAGTCCACGAGCACA
GCCTACATGGAGCTGAGCAGCCTGAGATCTGAGGACACGGCGGTGTACTACTGCGCCAGAACT
CCTGAATACTCCTCCAGCATATGGCACTATTACTACGGCATGGACGTATGGGGCCAGGGAACA
ACTGTCACCGTCTCCTCAGCCGCTGCCCTTGATAATGAAAAGTCAAACGGAACAATCATTCAC
GTGAAGGGCAAGCACCTCTGTCCGTCACCCTTGTTCCCTGGTCCATCCAAGCCATTCTGGGTG
TTGGTCGTAGTGGGTGGAGTCCTCGCTTGTTACTCTCTGCTCGTCACCGTGGCTTTTATAATC
TTCTGGGTTAGATCCAAAAGAAGCCGCCTGCTCCATAGCGATTACATGAATATGACTCCACGC
CGCCCTGGCCCCACAAGGAAACACTACCAGCCTTACGCACCACCTAGAGATTTCGCTGCCTAT
CGGAGCAGGGTGAAGTTTTCCAGATCTGCAGATGCACCAGCGTATCAGCAGGGCCAGAACCAA
CTGTATAACGAGCTCAACCTGGACGCAGGAAGAGTATGACGTTTTGGACAAGCGCAGAGGA
CGGGACCCTGAGATGGGTGGCAAACCAAGACGAAAAAACCCCCAGGAGGGTCTCTATAATGAG
CTGCAGAAGGATAAGATGGCTGAAGCCTATTCTGAAATAGGCATGAAAGGAGAGCGGAGAAGG
GGAAAAGGGCACGACGGTTTGTACCAGGGACTCAGCACTGCTACGAAGGATACTTATGACGCT
CTCCACATGCAAGCCCTGCCACCTAGG

FIG. 14J

Clone PP-26575 CAR LxH (SEQ ID NO: 382)
MALPVTALLL PLALLLHAAR PDIVMTQSPD SLAVSLGERA TINCKSSQSV
LYSSNNKNYL AWYQQKPGQP PKLLIYWAST RESGVPDRFS GSGSGTDFTL
TISSLQAEDV AVYYCQQFAH TPFTFGGGTK VEIKRGSTSG SGKPGSGEGS
TKGQVQLVQS GAEVKKPGSS VKVSCKASGG TLSSLAISWV RQAPGQGLEW
MGGVIPILGR ANYAQKFQGR VTITADESTS TAYMELSSLR SEDTAVYYCA
RTPEYSSSIW HYYYGMDVWG QGTTVTVSSA AALDNEKSNG TIIHVKGKHL
CPSPLFPGPS KPFWVLVVVG GVLACYSLLV TVAFIIFWVR SKRSRLLHSD
YMNMTPRRPG PTRKHYQPYA PPRDFAAYRS RVKFSRSADA PAYQQGQNQL
YNELNLGRRE EYDVLDKRRG RDPEMGGKPR RKNPQEGLYN ELQKDKMAEA
YSEIGMKGER RRGKGHDGLY QGLSTATKDT YDALHMQALP PR

FIG. 15A

Clone RD-26576 HC DNA (SEQ ID NO: 383)
CAGGTGCGGCTGGTGGAGTCTGGGGGGGGCGTGGTCCAGCCTGGGAGGTCCCTGAGACTCTCC
TGTGCAGCGTCTGGATTCACCTTCAGTAGCTATGGCATACACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGCTTTTGGGATGGACGTATGGGGCCAGGGAACAACTGTCACCGTCTCCTCA

FIG. 15B

Clone RD-26576 HC (SEQ ID NO: 384). CDRs 1, 2, and 3 are underlined.
QVRLVESGGG VVQPGRSLRL SCAASG<u>FTFS</u> <u>SYGIH</u>WVRQA PGKGLEWVA<u>V</u>
<u>IGYDGQEKYY</u> <u>ADSVKG</u>RFTI SRDNSKNTLY LQMNSLRAED TAVYYC<u>VKGP</u>
<u>LQEPPYAFGM</u> <u>DV</u>WGQGTTVT VSS

FIG. 15C

FTFSSYGIH (SEQ ID NO: 385) (HC CDR1)

VIGYDGQEKYYADSVKG (SEQ ID NO: 386) (HC CDR2)

VKGPLQEPPYAFGMDV (SEQ ID NO: 387) (HC CDR3)

FIG. 15D

Clone RD-26576 LC DNA (SEQ ID NO: 388)
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATAGCGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGCACCACGTCTGGCCTCTCACTTTTGGCGGAGGGACCAAGGTTGAG
ATCAAACGG

FIG. 15E

Clone RD-26576 LC (SEQ ID NO: 389). CDRs 1, 2, and 3 are underlined.
EIVMTQSPAT LSVSPGERAT LSC<u>RASQSVS</u> <u>SNLA</u>WYQQKP GQAPRLLIY<u>S</u>
<u>ASTRAT</u>GIPA RFSGSGSGTE FTLTISSLQS EDFAVYYC<u>QQ</u> <u>HHVWPLT</u>FGG GTKVEIKR

FIG. 15F

RASQSVSSNLA (SEQ ID NO: 390) (LC CDR1)

SASTRAT (SEQ ID NO: 391) (LC CDR2)

FIG. 15F (continued)

QQHHVWPLT (SEQ ID NO: 392) (LC CDR3)

FIG. 15G

Clone RD-26576 CAR DNA HxL (SEQ ID NO: 393)
ATGGCACTCCCCGTAACTGCTCTGCTGCTGCCGTTGGCATTGCTCCTGCACGCCGCACGCCCG
CAGGTGCGGCTGGTGGAGTCTGGGGGGGGCGTGGTCCAGCCTGGGAGGTCCCTGAGACTCTCC
TGTGCAGCGTCTGGATTCACCTTCAGTAGCTATGGCATACACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGCTTTTGGGATGGACGTATGGGGCCAGGGAACAACTGTCACCGTCTCCTCAGGGTCTACA
TCCGGCTCCGGGAAGCCCGGAAGTGGCGAAGGTAGTACAAAGGGGGAAATAGTGATGACGCAG
TCTCCAGCCACCCTGTCTGTGTCTCCAGGGGAAAGAGCCACCCTCTCCTGCAGGGCCAGTCAG
AGTGTTAGCAGCAACTTAGCCTGGTACCAGCAGAAACCTGGCCAGGCTCCCAGGCTCCTCATC
TATAGCGCATCCACCAGGGCCACTGGTATCCCAGCCAGGTTCAGTGGCAGTGGGTCTGGGACA
GAGTTCACTCTCACCATCAGCAGCCTGCAGTCTGAAGATTTTGCAGTTTATTACTGTCAGCAG
CACCACGTCTGGCCTCTCACTTTTGGCGGAGGGACCAAGGTTGAGATCAAACGGGCCGCTGCC
CTTGATAATGAAAAGTCAAACGGAACAATCATTCACGTGAAGGGCAAGCACCTCTGTCCGTCA
CCCTTGTTCCCTGGTCCATCCAAGCCATTCTGGGTGTTGGTCGTAGTGGGTGGAGTCCTCGCT
TGTTACTCTCTGCTCGTCACCGTGGCTTTTATAATCTTCTGGGTTAGATCCAAAAGAAGCCGC
CTGCTCCATAGCGATTACATGAATATGACTCCACGCCGCCCTGGCCCCACAAGGAAACACTAC
CAGCCTTACGCACCACCTAGAGATTTCGCTGCCTATCGGAGCAGGGTGAAGTTTTCCAGATCT
GCAGATGCACCAGCGTATCAGCAGGGCCAGAACCAACTGTATAACGAGCTCAACCTGGGACGC
AGGGAAGAGTATGACGTTTTGGACAAGCGCAGAGGACGGGACCCTGAGATGGGTGGCAAACCA
AGACGAAAAAACCCCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGACGGTTTGTACCAG
GGACTCAGCACTGCTACGAAGGATACTTATGACGCTCTCCACATGCAAGCCCTGCCACCTAGG

FIG. 15H

Clone RD-26576 CAR HxL (SEQ ID NO: 394)
MALPVTALLL PLALLLHAAR PQVRLVESGG GVVQPGRSLR LSCAASGFTF
SSYGIHWVRQ APGKGLEWVA VIGYDGQEKY YADSVKGRFT ISRDNSKNTL
YLQMNSLRAE DTAVYYCVKG PLQEPPYAFG MDVWGQGTTV TVSSGSTSGS
GKPGSGEGST KGEIVMTQSP ATLSVSPGER ATLSCRASQS VSSNLAWYQQ
KPGQAPRLLI YSASTRATGI PARFSGSGSG TEFTLTISSL QSEDFAVYYC
QQHHVWPLTF GGGTKVEIKR AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

FIG. 15I

Clone RD-26576 CAR DNA LxH (SEQ ID NO: 395)
ATGGCACTCCCCGTAACTGCTCTGCTGCTGCCGTTGGCATTGCTCCTGCACGCCGCACGCCCG
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATAGCGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGCACCACGTCTGGCCTCTCACTTTTGGCGGAGGGACCAAGGTTGAG
ATCAAACGGGGGTCTACATCCGGCTCCGGGAAGCCCGGAAGTGGCGAAGGTAGTACAAAGGGG
CAGGTGCGGCTGGTGGAGTCTGGGGGGGCGTGGTCCAGCCTGGGAGGTCCCTGAGACTCTCC
TGTGCAGCGTCTGGATTCACCTTCAGTAGCTATGGCATACACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGCTTTTGGGATGGACGTATGGGGCCAGGGAACAACTGTCACCGTCTCCTCAGCCGCTGCC
CTTGATAATGAAAAGTCAAACGGAACAATCATTCACGTGAAGGGCAAGCACCTCTGTCCGTCA
CCCTTGTTCCCTGGTCCATCCAAGCCATTCTGGGTGTTGGTCGTAGTGGGTGGAGTCCTCGCT
TGTTACTCTCTGCTCGTCACCGTGGCTTTTATAATCTTCTGGGTTAGATCCAAAAGAAGCCGC
CTGCTCCATAGCGATTACATGAATATGACTCCACGCCGCCCTGGCCCCACAAGGAAACACTAC
CAGCCTTACGCACCACCTAGAGATTTCGCTGCCTATCGGAGCAGGGTGAAGTTTTCCAGATCT
GCAGATGCACCAGCGTATCAGCAGGGCCAGAACCAACTGTATAACGAGCTCAACCTGGGACGC
AGGGAAGAGTATGACGTTTTGGACAAGCGCAGAGGACGGGACCCTGAGATGGGTGGCAAACCA
AGACGAAAAAACCCCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGACGGTTTGTACCAG
GGACTCAGCACTGCTACGAAGGATACTTATGACGCTCTCCACATGCAAGCCCTGCCACCTAGG

FIG. 15J

Clone RD-26576 CAR LxH (SEQ ID NO: 396)
```
MALPVTALLL PLALLLHAAR PEIVMTQSPA TLSVSPGERA TLSCRASQSV
SSNLAWYQQK PGQAPRLLIY SASTRATGIP ARFSGSGSGT EFTLTISSLQ
SEDFAVYYCQ QHHVWPLTFG GGTKVEIKRG STSGSGKPGS GEGSTKGQVR
LVESGGGVVQ PGRSLRLSCA ASGFTFSSYG IHWVRQAPGK GLEWVAVIGY
DGQEKYYADS VKGRFTISRD NSKNTLYLQM NSLRAEDTAV YYCVKGPLQE
PPYAFGMDVW GQGTTVTVSS AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR
```

FIG. 16A

Clone RD-26578 HC DNA (SEQ ID NO: 397)
CAGGTGCAGCTGGTGGAGTCTGGGGGAGGCGTGGTCCAGCCTGGGAGGTCCCTGAGACTCTCC
TGTGCAGCGTCTGGATTCACCTTCAGTAGCCGTGGCATGCACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGATTATGGAATGGACGTATGGGGCCAGGGAACAACTGTCACCGTCTCCTCA

FIG. 16B

Clone RD-26578 HC (SEQ ID NO: 398) CDRs 1, 2, and 3 are underlined.
QVQLVESGGG VVQPGRSLRL SCAASG<u>FTFS</u> <u>SRGMH</u>WVRQA PGKGLEWVA<u>V</u>
<u>IGYDGQEKYY</u> <u>ADSVKG</u>RFTI SRDNSKNTLY LQMNSLRAED TAVYYC<u>VKGP</u>
<u>LQEPPYDYGM</u> <u>DV</u>WGQGTTVT VSS

FIG. 16C

FTFSSRGMH (SEQ ID NO: 399) (HC CDR1)

VIGYDGQEKYYADSVKG (SEQ ID NO: 400) (HC CDR2)

VKGPLQEPPYDYGMDV (SEQ ID NO: 401) (HC CDR3)

FIG. 16D

Clone RD-26578 LC DNA (SEQ ID NO: 402)
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATAGCGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGCACCACGTCTGGCCTCTCACTTTTGGCGGAGGGACCAAGGTTGAG
ATCAAACGG

FIG. 16E

Clone RD-26578 LC (SEQ ID NO: 403). CDRs 1, 2, and 3 are underlined.
EIVMTQSPAT LSVSPGERAT LSC<u>RASQSVS</u> <u>SNLA</u>WYQQKP GQAPRLLIY<u>S</u>
<u>ASTRAT</u>GIPA RFSGSGSGTE FTLTISSLQS EDFAVYYC<u>QQ</u> <u>HHVWPLT</u>FGG GTKVEIKR

FIG. 16F

RASQSVSSNLA (SEQ ID NO: 404) (LC CDR1)

SASTRAT (SEQ ID NO: 405) (LC CDR2)

QQHHVWPLT (SEQ ID NO: 406) (LC CDR3)

FIG. 16G

Clone RD-26578 CAR DNA HxL (SEQ ID NO: 407)
ATGGCACTCCCCGTAACTGCTCTGCTGCTGCCGTTGGCATTGCTCCTGCACGCCGCACGCCCG
CAGGTGCAGCTGGTGGAGTCTGGGGGAGGCGTGGTCCAGCCTGGGAGGTCCCTGAGACTCTCC
TGTGCAGCGTCTGGATTCACCTTCAGTAGCCGTGGCATGCACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGATTATGGAATGGACGTATGGGGCCAGGGAACAACTGTCACCGTCTCCTCAGGGTCTACA
TCCGGCTCCGGGAAGCCCGGAAGTGGCGAAGGTAGTACAAAGGGGGAAATAGTGATGACGCAG
TCTCCAGCCACCCTGTCTGTGTCTCCAGGGGAAAGAGCCACCCTCTCCTGCAGGGCCAGTCAG
AGTGTTAGCAGCAACTTAGCCTGGTACCAGCAGAAACCTGGCCAGGCTCCCAGGCTCCTCATC
TATAGCGCATCCACCAGGGCCACTGGTATCCCAGCCAGGTTCAGTGGCAGTGGGTCTGGGACA
GAGTTCACTCTCACCATCAGCAGCCTGCAGTCTGAAGATTTTGCAGTTTATTACTGTCAGCAG
CACCACGTCTGGCCTCTCACTTTTGGCGGAGGGACCAAGGTTGAGATCAAACGGGCCGCTGCC
CTTGATAATGAAAAGTCAAACGGAACAATCATTCACGTGAAGGGCAAGCACCTCTGTCCGTCA
CCCTTGTTCCCTGGTCCATCCAAGCCATTCTGGGTGTTGGTCGTAGTGGGTGGAGTCCTCGCT
TGTTACTCTCTGCTCGTCACCGTGGCTTTTATAATCTTCTGGGTTAGATCCAAAAGAAGCCGC
CTGCTCCATAGCGATTACATGAATATGACTCCACGCCGCCCTGGCCCCACAAGGAAACACTAC
CAGCCTTACGCACCACCTAGAGATTTCGCTGCCTATCGGAGCAGGGTGAAGTTTTCCAGATCT
GCAGATGCACCAGCGTATCAGCAGGGCCAGAACCAACTGTATAACGAGCTCAACCTGGGACGC
AGGGAAGAGTATGACGTTTTGGACAAGCGCAGAGGACGGGACCCTGAGATGGGTGGCAAACCA
AGACGAAAAAACCCCCAGGAGGGTCTCTATAATGAGCTGCAGAAGGATAAGATGGCTGAAGCC
TATTCTGAAATAGGCATGAAGGAGAGCGGAGAAGGGGAAAAGGGCACGACGGTTTGTACCAG
GGACTCAGCACTGCTACGAAGGATACTTATGACGCTCTCCACATGCAAGCCCTGCCACCTAGG

FIG. 16H

Clone RD-26578 CAR HxL (SEQ ID NO: 408)

MALPVTALLL PLALLLHAAR PQVQLVESGG GVVQPGRSLR LSCAASGFTF
SSRGMHWVRQ APGKGLEWVA VIGYDGQEKY YADSVKGRFT ISRDNSKNTL
YLQMNSLRAE DTAVYYCVKG PLQEPPYDYG MDVWGQGTTV TVSSGSTSGS
GKPGSGEGST KGEIVMTQSP ATLSVSPGER ATLSCRASQS VSSNLAWYQQ
KPGQAPRLLI YSASTRATGI PARFSGSGSG TEFTLTISSL QSEDFAVYYC
QQHHVWPLTF GGGTKVEIKR AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

FIG. 16I

Clone RD-26578 CAR DNA LxH (SEQ ID NO: 409)

ATGGCACTCCCCGTAACTGCTCTGCTGCTGCCGTTGGCATTGCTCCTGCACGCCGCACGCCCG
GAAATAGTGATGACGCAGTCTCCAGCCACCCTGTCTGTGTCTCCAGGGGAAAGAGCCACCCTC
TCCTGCAGGGCCAGTCAGAGTGTTAGCAGCAACTTAGCCTGGTACCAGCAGAAACCTGGCCAG
GCTCCCAGGCTCCTCATCTATAGCGCATCCACCAGGGCCACTGGTATCCCAGCCAGGTTCAGT
GGCAGTGGGTCTGGGACAGAGTTCACTCTCACCATCAGCAGCCTGCAGTCTGAAGATTTTGCA
GTTTATTACTGTCAGCAGCACCACGTCTGGCCTCTCACTTTTGGCGGAGGGACCAAGGTTGAG
ATCAAACGGGGTCTACATCCGGCTCCGGGAAGCCCGGAAGTGGCGAAGGTAGTACAAAGGGG
CAGGTGCAGCTGGTGGAGTCTGGGGGAGGCGTGGTCCAGCCTGGAGGTCCCTGAGACTCTCC
TGTGCAGCGTCTGGATTCACCTTCAGTAGCCGTGGCATGCACTGGGTCCGCCAGGCTCCAGGC
AAGGGGCTGGAGTGGGTGGCAGTTATAGGGTATGATGGACAGGAGAAATACTATGCAGACTCC
GTGAAGGGCCGATTCACCATCTCCAGAGACAATTCCAAGAACACGCTGTATCTGCAAATGAAC
AGCCTGAGAGCCGAGGACACGGCGGTGTACTACTGCGTCAAGGGGCCGTTGCAGGAGCCGCCA
TACGATTATGGAATGGACGTATGGGGCCAGGGAACAACTGTCACCGTCTCCTCAGCCGCTGCC
CTTGATAATGAAAAGTCAAACGGAACAATCATTCACGTGAAGGGCAAGCACCTCTGTCCGTCA
CCCTTGTTCCCTGGTCCATCCAAGCCATTCTGGGTGTTGGTCGTAGTGGGTGGAGTCCTCGCT
TGTTACTCTCTGCTCGTCACCGTGGCTTTTATAATCTTCTGGGTTAGATCCAAAAGAAGCCGC
CTGCTCCATAGCGATTACATGAATATGACTCCACGCCGCCTGGCCCCACAAGGAAACACTAC
CAGCCTTACGCACCACCTAGAGATTTCGCTGCCTATCGGAGCAGGGTGAAGTTTTCCAGATCT
GCAGATGCACCAGCGTATCAGCAGGGCCAGAACCAACTGTATAACGAGCTCAACCTGGGACGC
AGGGAAGAGTATGACGTTTTGGACAAGCGCAGAGGACGGGACCCTGAGATGGGTGGCAAACCA
AGACGAAAAAACCCCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGACGGTTTGTACCAG
GGACTCAGCACTGCTACGAAGGATACTTATGACGCTCTCCACATGCAAGCCCTGCCACCTAGG

FIG. 16J

Clone RD-26578 CAR LxH (SEQ ID NO: 410)
MALPVTALLL PLALLLHAAR PEIVMTQSPA TLSVSPGERA TLSCRASQSV
SSNLAWYQQK PGQAPRLLIY SASTRATGIP ARFSGSGSGT EFTLTISSLQ
SEDFAVYYCQ QHHVWPLTFG GGTKVEIKRG STSGSGKPGS GEGSTKGQVQ
LVESGGGVVQ PGRSLRLSCA ASGFTFSSRG MHWVRQAPGK GLEWVAVIGY
DGQEKYYADS VKGRFTISRD NSKNTLYLQM NSLRAEDTAV YYCVKGPLQE
PPYDYGMDVW GQGTTVTVSS AAALDNEKSN GTIIHVKGKH LCPSPLFPGP
SKPFWVLVVV GGVLACYSLL VTVAFIIFWV RSKRSRLLHS DYMNMTPRRP
GPTRKHYQPY APPRDFAAYR SRVKFSRSAD APAYQQGQNQ LYNELNLGRR
EEYDVLDKRR GRDPEMGGKP RRKNPQEGLY NELQKDKMAE AYSEIGMKGE
RRRGKGHDGL YQGLSTATKD TYDALHMQAL PPR

BCMA BINDING MOLECULES AND METHODS OF USE THEREOF

CROSS REFERENCE TO RELATED APPLICATIONS

This application is a continuation of U.S. patent application Ser. No. 15/476,309, filed Mar. 31, 2017, issued as U.S. Pat. No. 10,689,450, and claims the benefit of U.S. Provisional Patent Application 62/317,334, filed Apr. 1, 2016, both of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 30, 2017, is named K-1030_02_SL.txt and is 387,353 bytes in size.

FIELD OF THE INVENTION

This invention relates to chimeric antigen receptors (CARs) and engineered T cell receptors (TCRs) comprising an antigen binding molecule which binds to B-cell maturation antigen (BCMA), polynucleotides encoding the same, and methods of treating a cancer or other disease or disorder in a patient using the same.

BACKGROUND OF THE INVENTION

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen.

Current therapies for hematologic malignancies have shown varying levels of effectiveness with undesired side effects. Therefore, a need exists to identify novel and improved therapies for treating BCMA related diseases and disorders.

SUMMARY OF THE INVENTION

The present invention is directed to an isolated polynucleotide encoding a chimeric antigen receptor (CAR) or T cell receptor (TCR) comprising a binding molecule that specifically binds to B-cell maturation antigen (BCMA), wherein the binding molecule comprises: (a) a heavy chain variable region (VH) complementarity determining region (CDR) 1 comprising, consisting of, or consisting essentially of the amino acid sequence $GX_2X_3X_4X_5X_6X_7SY$ (SEQ ID NO: 145) wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$, is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y; and/or (d) a light chain variable region (VL) CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; (e) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (f) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In another embodiment, the invention is directed to an isolated polynucleotide encoding an antibody or an antigen binding molecule thereof that specifically binds to BCMA, wherein the antibody or the antigen binding molecule thereof comprises: (a) a heavy chain variable region (VH) complementarity determining region (CDR) 1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$, is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y; and/or (d) a light chain variable region (VL) CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; (e) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (f) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In some embodiments, the VH CDR1 comprises an amino acid sequence selected from the group consisting of SEQ ID NO: 9-16. In some embodiments, the VH CDR2 comprises an amino acid sequence selected from the group consisting of SEQ ID NO: 25-32. In some embodiments, the VL CDR1 comprises an amino acid sequence selected from the group consisting of SEQ ID NO: 81-88. In some embodiments, the VL CDR2 comprises an amino acid sequence selected from the group consisting of SEQ ID NO: 97-104. In some embodiments, the VL CDR3 comprises an amino acid sequence selected from the group consisting of SEQ ID NO: 113-120.

In some embodiments, the binding molecule comprises: (a) a VH CDR1 region comprising the amino acid sequence of SEQ ID NO: 9; a VH CDR2 region comprising the amino acid sequence of SEQ ID NO: 25; a VH CDR3 region comprising the amino acid sequence of SEQ ID NO: 41; a VL CDR1 region comprising the amino acid sequence of SEQ ID NO: 81; a VL CDR2 region comprising the amino acid sequence of SEQ ID NO: 97; and a VL CDR3 region comprising the amino acid sequence of SEQ ID NO: 113; (b) a VH CDR1 region comprising the amino acid sequence of SEQ ID NO: 10; a VH CDR2 region comprising the amino acid sequence of SEQ ID NO: 26; a VH CDR3 region comprising the amino acid sequence of SEQ ID NO: 42; a VL CDR1 region comprising the amino acid sequence of SEQ ID NO: 82; a VL CDR2 region comprising the amino acid sequence of SEQ ID NO: 98; and a VL CDR3 region comprising the amino acid sequence of SEQ ID NO: 114; (c) a VH CDR1 region comprising the amino acid sequence of SEQ ID NO: 11; a VH CDR2 region comprising the amino acid sequence of SEQ ID NO: 27; a VH CDR3 region comprising the amino acid sequence of SEQ ID NO: 43; a VL CDR1 region comprising the amino acid sequence of SEQ ID NO: 83; a VL CDR2 region comprising the amino acid sequence of SEQ ID NO: 99; and a VL CDR3 region comprising the amino acid sequence of SEQ ID NO: 115; (d) a VH CDR1 region comprising the amino acid sequence of SEQ ID NO: 12; a VH CDR2 region comprising the amino acid sequence of SEQ ID NO: 28; a VH CDR3 region comprising the amino acid sequence of SEQ ID NO: 44; a VL CDR1 region comprising the amino acid sequence of SEQ ID NO: 84; a VL CDR2 region comprising the amino acid sequence of SEQ ID NO: 100; and a VL CDR3 region comprising the amino acid sequence of SEQ ID NO: 116; (e) a VH CDR1 region comprising the amino acid sequence of SEQ ID NO: 13; a VH CDR2 region comprising the amino acid sequence of SEQ ID NO: 29; a VH CDR3 region comprising the amino acid sequence of SEQ ID NO: 45; a VL CDR1 region comprising the amino acid sequence of SEQ ID NO: 85; a VL CDR2 region comprising the amino acid sequence of SEQ ID NO: 101; and a VL CDR3 region comprising the amino acid sequence of SEQ ID NO: 117; (f) a VH CDR1 region comprising the amino acid sequence of SEQ ID NO: 14; a VH CDR2 region comprising the amino acid sequence of SEQ ID NO: 30; a VH CDR3 region comprising the amino acid sequence of SEQ ID NO: 46; a VL CDR1 region comprising the amino acid sequence of SEQ ID NO: 86; a VL CDR2 region comprising the amino acid sequence of SEQ ID NO: 102; and a VL CDR3 region comprising the amino acid sequence of SEQ ID NO: 118; (g) a VH CDR1 region comprising the amino acid sequence of SEQ ID NO: 15; a VH CDR2 region comprising the amino acid sequence of SEQ ID NO: 31; a VH CDR3 region comprising the amino acid sequence of SEQ ID NO: 47; a VL CDR1 region comprising the amino acid sequence of SEQ ID NO: 87; a VL CDR2 region comprising the amino acid sequence of SEQ ID NO: 103; and a VL CDR3 region comprising the amino acid sequence of SEQ ID NO: 119; or (h) a VH CDR1 region comprising the amino acid sequence of SEQ ID NO: 16; a VH CDR2 region comprising the amino acid sequence of SEQ ID NO: 32; a VH CDR3 region comprising the amino acid sequence of SEQ ID NO: 48; a VL CDR1 region comprising the amino acid sequence of SEQ ID NO: 88; a VL CDR2 region comprising the amino acid sequence of SEQ ID NO: 104; and a VL CDR3 region comprising the amino acid sequence of SEQ ID NO: 120.

In some embodiments, the binding molecule is single chained. In some embodiments, the binding molecule comprises an scFv.

In some embodiments, the CAR comprises a transmembrane domain. In some embodiments, the transmembrane domain is a transmembrane domain of CD28, 4-1BB/CD137, CD8 (e.g., CD8 alpha, CD4, CD19, CD3 epsilon, CD45, CD5, CD9, CD16, CD22, CD33, CD37, CD64, CD80, CD86, CD134, CD137, CD154, an alpha chain of a T cell receptor, a beta chain of a T cell receptor, a zeta chain of a T cell receptor, or any combination thereof. In some embodiments, the CAR comprises a hinge region between the transmembrane domain and the binding molecule. In some embodiments, the hinge region is of IgG1, IgG2, IgG3, IgG4, IgA, IgD, IgE, IgM, CD28, or CD8 alpha. In some embodiments, the CAR or TCR comprises a costimulatory region. In some embodiments, the costimulatory region is a signaling region of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1 (CDl la/CD18), CD3 gamma, CD3 delta, CD3 epsilon, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. In some embodiments, the CAR or TCR comprises an activation domain. In some embodiments, the activation domain is a CD3 zeta domain.

In other embodiments, the invention is directed to a vector comprising the polynucleotide or a polypeptide encoded by the polynucleotide.

In certain embodiments, the invention is directed to a cell comprising the polynucleotide, the vector, the polypeptide, or any combination thereof. In other embodiments, the invention is directed to a cell, e.g., an immune cell, e.g., a tumor-infiltrating lymphocyte (TIL), autologous T cell, engineered autologous T cell (eACT), an allogeneic T cell, or any combination thereof.

In other embodiments, the invention is directed to a method of inducing an immunity against a tumor comprising administering to a subject an effective amount of a cell comprising the polynucleotide, the vector, the polypeptide, or any combination thereof. Other aspects of the invention include a method of treating a cancer in a subject in need thereof comprising administering to the subject the polynucleotide, the vector, the polypeptide, the cell, or the composition. The cancer treatable by the method can be a hematologic cancer.

BRIEF DESCRIPTION OF THE FIGURES

FIG. 1A-1F show CLUTSTAL W (1.83) multiple sequence alignments of eight example anti-BCMA binding molecules disclosed herein. FIG. 1A shows a sequence alignment of example anti-BCMA binding molecules comprising a VH domain. Complementarity determining regions (CDRs) and framework regions (FRs) are shown, as determined by Chothia FIG. 1B is a table providing the SEQ ID NO for each VH, CDR, and FR sequence illustrated in FIG. 1A. FIG. 1C shows a sequence alignment of example anti-BCMA binding molecules comprising a VH domain, with alternate CDRs and FRs shown. FIG. 1D is a table providing the SEQ ID NO for each VH, CDR, and FR sequence illustrated in FIG. 1C. FIG. 1E shows a sequence alignment of example anti-BCMA binding molecules comprising a VL domain. CDRs and FRs are shown, as determined by Chothia. FIG. 1F is a table providing the SEQ ID NO for each VH, CDR, and FR sequence illustrated in FIG. 1E.

FIGS. 2A-2F show BCMA expression in various cells. FIG. 2A shows multiple myeloma cell expression of BCMA, CD138, CS-1, CD38, and CD19. Box-plot analysis shows the distribution of gene expression levels in the various multiple myeloma cell lines tested (FIG. 2A). FIGS. 2B-2D show BCMA expression in EoL1 (FIG. 2B), MM1S (FIG. 2C), and NCI-H929 (FIG. 2D) cancer cell lines as measured by flow cytometric analysis of BCMA cell surface expression on the respective cell lines. FIG. 2E shows the expression of BCMA, CS-1, CLL-1, DLL3, CD70, and FLT3 in alternatively activated macrophages; CD14-positive, CD16-negative cells; CD38-negative naïve B cells; CD4-positive, alpha-beta T cells; central memory CD4-positive cells; central memory CD8-positive cells; class switched memory B cells; cytotoxic CD56-dim natural killer cell; effector memory CD4-positive cells; effector memory CD8-positive cells; inflammatory macrophages; macrophages; mature neutrophils; memory B cells; monocytes; myeloid cells; and regulatory T cells. FIG. 2F shows the expression of BCMA, CD138, CS-1, CD38, and CD19 in the same cell types as in FIG. 2E. Gene expression is shown as fragments per kilobase of exon per million reads mapped (FPKM) (FIG. 2A, FIG. 2E, and FIG. 2F).

FIGS. 4A-4F shows IFNγ, TNFα, and IL-2 production by lentivirus transduced CAR T cells from two healthy donors following 16 hours of co-cultured with EoL-1 (Black), NCI-H929 (light grey), or MM1S (grey) target cell lines. FIGS. 4A and 4B show the IFNγ (pg/ml; y-axis) production in lentivirus transduced CAR T cells from a first donor (FIG. 4A) and a second donor (FIG. 4B). FIGS. 4C and 4D show the TNFα (pg/ml; y-axis) production in lentivirus transduced CAR T cells from a first donor (FIG. 4C) and a second donor (FIG. 4D). FIGS. 4E and 4F show the IL-2 production (pg/ml; y-axis) in lentivirus transduced CAR T cells from a first donor (FIG. 4E) and a second donor (FIG. 4F).

FIGS. 5A and 5B show the average cytolytic activity of transduced CAR T cells from a first donor (FIG. 5A) and a second donor (FIG. 5B) co-cultured with EoL1 target cells for 16 hours, 40 hours, 64 hours, 88 hours, or 112 hours. FIGS. 5C and 5D show the average cytolytic activity of transduced CAR T cells from a first donor (FIG. 5C) and a second donor (FIG. 5D) co-cultured with NCI-H929 target cells for 16 hours, 40 hours, 64 hours, 88 hours, or 112 hours. FIGS. 5E and 5F show the average cytolytic activity of transduced CAR T cells from a first donor (FIG. 5E) and a second donor (FIG. 5F) co-cultured with MM1S target cells for 16 hours, 40 hours, 64 hours, 88 hours, or 112 hours.

Figure 3A:
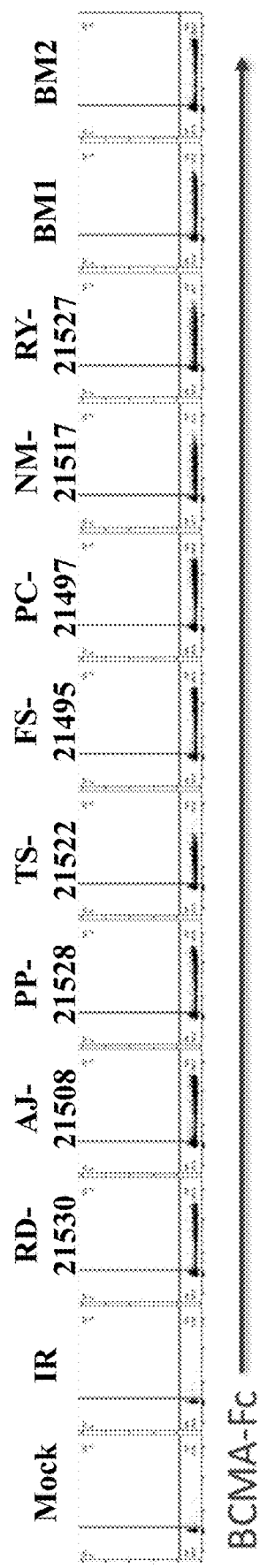
FIG. 3A and FIG. 3B show CAR expression in lend virus transduced primary human T cells from a first healthy donor (FIG. 3A) and a second healthy donor (FIG. 3B).

In the Figure descriptions below, underlined sequences denote CDR regions calculated using Chothia.

FIG. 7A shows Clone FS-26528 HC DNA sequence (SEQ ID NO: 271)

FIG. 7B shows Clone FS-26528 HC AA sequence (SEQ ID NO: 272)

FIG. 7C shows HC CDR sequences for clone FS-26528.

FIG. 7D shows Clone FS-26528 LC DNA sequence (SEQ ID NO: 276).

FIG. 7E shows Clone FS-26528 LC AA sequence (SEQ ID NO: 277).

FIG. 7F shows LC CDR sequences for clone FS-26S28.

FIG. 7G shows Clone FS-26528 CAR DNA HxL sequences (SEQ ID NO: 281)

FIG. 7H shows Clone FS-26528 CAR HxL AA sequences (SEQ ID NO: 282)

FIG. 7I shows Clone FS-26528 CAR DNA LxH sequences (SEQ ID NO: 283).

FIG. 7J shows Clone FS-26528 CAR LxH sequences (SEQ ID NO: 284).

FIG. 8A shows Clone PC-26534 HC DNA sequence (SEQ ID NO: 285).

FIG. 8B shows Clone PC-26534 HC sequence (SEQ ID NO: 286).

FIG. 8C shows HC CDR sequences for clone FS-26528.

FIG. 8D shows Clone PC-26534 LC DNA sequences (SEQ ID NO: 290).

FIG. 8E shows the Clone PC-26534 LC sequence (SEQ ID NO: 291).

FIG. 8F shows LC CDR sequences for Clone PC-26534.

FIG. 8G shows the Clone PC-26534 CAR DNA HxL sequence (SEQ ID NO: 295).

FIG. 8H shows the Clone PC-26534 CAR HxL AA sequence (SEQ ID NO: 296)

FIG. 8I shows the Clone PC-26534 CAR DNA LxH sequence (SEQ ID NO: 297).

FIG. 8J shows Clone PC-26534 CAR LxH sequence (SEQ ID NO: 298).

FIG. 9A shows Clone AJ-26545 HC DNA sequence (SEQ ID NO: 299).

FIG. 9B shows Clone AJ-26545 variable HC sequence (SEQ ID NO: 300).

FIG. 9C shows HC CDR sequences for Clone AJ-26545.

FIG. 9D shows Clone AJ-26545 variable LC DNA sequence (SEQ ID NO: 304).

FIG. 9E shows Clone AJ-26545 variable LC AA sequence (SEQ ID NO: 305)

FIG. 9F shows Clone AJ-26545 LC CDR sequences.

FIG. 9G shows Clone AJ-26545 CAR DNA HxL sequence (SEQ ID NO: 309).

FIG. 9H shows Clone AJ-26545 CAR HxL AA sequence (SEQ ID NO: 310)

FIG. 9I shows Clone AJ-26545 CAR DNA LxH sequence (SEQ ID NO: 311)

FIG. 9J shows Clone AJ-26545 CAR LxH sequence (SEQ ID NO: 312).

FIG. 10A shows Clone AJ-26554 HC DNA sequence (SEQ ID NO: 313)

FIG. 10B shows Clone AJ-26554 HC AA sequence (SEQ ID NO: 314).

FIG. 10C shows Clone AJ-26554 HC CDR sequences

FIG. 10D shows Clone AJ-26554 LC DNA sequence (SEQ ID NO: 318).

FIG. 10E shows Clone AJ-26554 LC AA sequence (SEQ ID NO: 319).

FIG. 10F shows Clone AJ-26554 LC CDR sequences.

FIG. 10G shows Clone AJ-26554 CAR DNA HxL chain sequences (SEQ ID NO: 323).

FIG. 10H shows Clone AJ-26554 CAR HxL chain AA sequences (SEQ ID NO: 324).

FIG. 10I shows Clone AJ-26554 CAR DNA LxH chain sequences (SEQ ID NO: 325).

FIG. 10J shows Clone AJ-26554 CAR LxH AA sequences (SEQ ID NO: 326).

FIG. 11A shows Clone NM-26562 HC DNA sequence (SEQ ID NO: 327).

FIG. 11B shows Clone NM-26562 HC AA sequence (SEQ ID NO: 328).

FIG. 11C shows Clone NM-26562 HC CDR sequences.

FIG. 11D shows Clone NM-26562 LC DNA sequence (SEQ ID NO: 332).

FIG. 11E shows Clone NM-26562 LC AA sequence (SEQ ID NO: 333).

FIG. 11F shows the Clone NM-26562 LC CDR sequences.

FIG. 11G shows the Clone NM-26562 CAR DNA HxL sequences (SEQ ID NO: 337)

FIG. 11H shows Clone NM-26562 CAR HxL AA sequences (SEQ ID NO: 338).

FIG. 11I shows Clone NM-26562 CAR DNA LxH sequences (SEQ ID NO: 339).

FIG. 11J shows Clone NM-26562 CAR LxH AA sequences (SEQ ID NO: 340).

FIG. 12A shows Clone TS-26564 HC DNA sequence (SEQ ID NO: 341).

FIG. 12B shows Clone TS-26564 HC AA sequence (SEQ ID NO: 342).

FIG. 12C shows the Clone TS-26564 HC CDR sequences.

FIG. 12D shows the Clone TS-26564 LC DNA sequence (SEQ ID NO: 346).

FIG. 12E shows the Clone TS-26564 LC AA sequence (SEQ ID NO: 347).

FIG. 12F shows the Clone TS-26564 LC CDR sequences.

FIG. 12G shows the Clone TS-26564 CAR DNA HxL sequences (SEQ ID NO: 351).

FIG. 12H shows the Clone TS-26564 CAR HxL chain AA sequences (SEQ ID NO: 352).

FIG. 12I shows the Clone TS-26564 CAR DNA LxH sequences (SEQ ID NO: 353)

FIG. 12J shows the Clone TS-26564 CAR LxH AA sequences (SEQ ID NO: 354)

FIG. 13A shows the Clone RY-26568 HC DNA sequence (SEQ ID NO: 355)

FIG. 13B shows the Clone RY-26568 HC AA sequence (SEQ ID NO: 356).

FIG. 13C shows the Clone RY-26568 HC CDR sequences.

FIG. 13D shows the Clone RY-26568 LC DNA sequence (SEQ ID NO: 360).

FIG. 13E shows the Clone RY-26568 LC AA sequence (SEQ ID NO: 361).

FIG. 13F shows the Clone RY-26568 LC CDR AA sequences.

FIG. 13G shows the Clone RY-26568 CAR DNA HxL sequences (SEQ ID NO: 365)

FIG. 13H shows the Clone RY-26568 CAR HxL AA sequences (SEQ ID NO: 366).

FIG. 13I shows the Clone RY-26568 CAR DNA LxH sequences (SEQ ID NO: 367).

FIG. 13J shows the Clone RY-26568 CAR LxH AA sequences (SEQ ID NO: 368).

FIG. 14A shows the Clone PP-26575 HC DNA sequence (SEQ ID NO: 369).

FIG. 14B shows the Clone PP-26575 HC AA sequence (SEQ ID NO: 370).

FIG. 14C shows the Clone PP-26575 HC CDR AA sequences.

FIG. 14D shows the Clone PP-26575 LC DNA sequence (SEQ ID NO: 374).

FIG. 14E shows the Clone PP-26575 LC AA sequence (SEQ ID NO: 375).

FIG. 14F shows the Clone PP-26575 LC CDR AA sequences.

FIG. 14G shows the Clone PP-26575 CAR DNA HxL sequences (SEQ ID NO: 379).

FIG. 14H shows the Clone PP-26575 CAR HxL AA sequences (SEQ ID NO: 380).

FIG. 14I shows Clone PP-26575 CAR DNA LxH sequence (SEQ ID NO: 381).

FIG. 14J shows the Clone PP-26575 CAR LxH AA sequence (SEQ ID NO: 382).

FIG. 15A shows the Clone RD-26576 HC DNA sequence (SEQ ID NO: 383)

FIG. 15B shows Clone RD-26576 HC AA sequence (SEQ ID NO: 384).

FIG. 15C shows the Clone RD-26576 HC CDR sequences.

FIG. 15D shows the Clone RD-26576 LC DNA sequence (SEQ ID NO: 388)

FIG. 15E shows the Clone RD-26576 LC AA sequence (SEQ ID NO: 389).

FIG. 15F shows the Clone RD-26576 LC CDR sequences.

FIG. 15G shoes the Clone RD-26576 CAR DNA HxL sequences (SEQ ID NO: 393).

FIG. 15H shows the Clone RD-26576 CAR HxL chain AA sequences (SEQ ID NO: 394).

FIG. 15I shows the Clone RD-26576 CAR DNA LxH sequences (SEQ ID NO: 395).

FIG. 15J shows the Clone RD-26576 CAR LxH AA sequences (SEQ ID NO: 3%).

FIG. 16A shows the Clone RD-26578 HC DNA sequences (SEQ ID NO: 397).

FIG. 16B shows the Clone RD-26578 HC AA sequence (SEQ ID NO: 398).

FIG. 16C shows the Clone RD-26578 HC CDR AA sequences.

FIG. 16D shows the Clone RD-26578 LC DNA sequence (SEQ ID NO: 402).

FIG. 16E shows the Clone RD-26578 LC AA sequence (SEQ ID NO: 403)

FIG. 16F shows the Clone RD-26578 LC CDR sequences.

FIG. 16G shows the Clone RD-26578 CAR DNA HxL chain sequence (SEQ ID NO: 407).

FIG. 16H shows the Clone RD-26578 CAR HxL AA sequence (SEQ ID NO: 408).

FIG. 16I shows the Clone RD-26578 CAR DNA LxH sequences (SEQ ID NO: 409).

FIG. 16J shows the Clone RD-26578 CAR LxH AA sequence (SEQ ID NO: 410).

Figure 17:
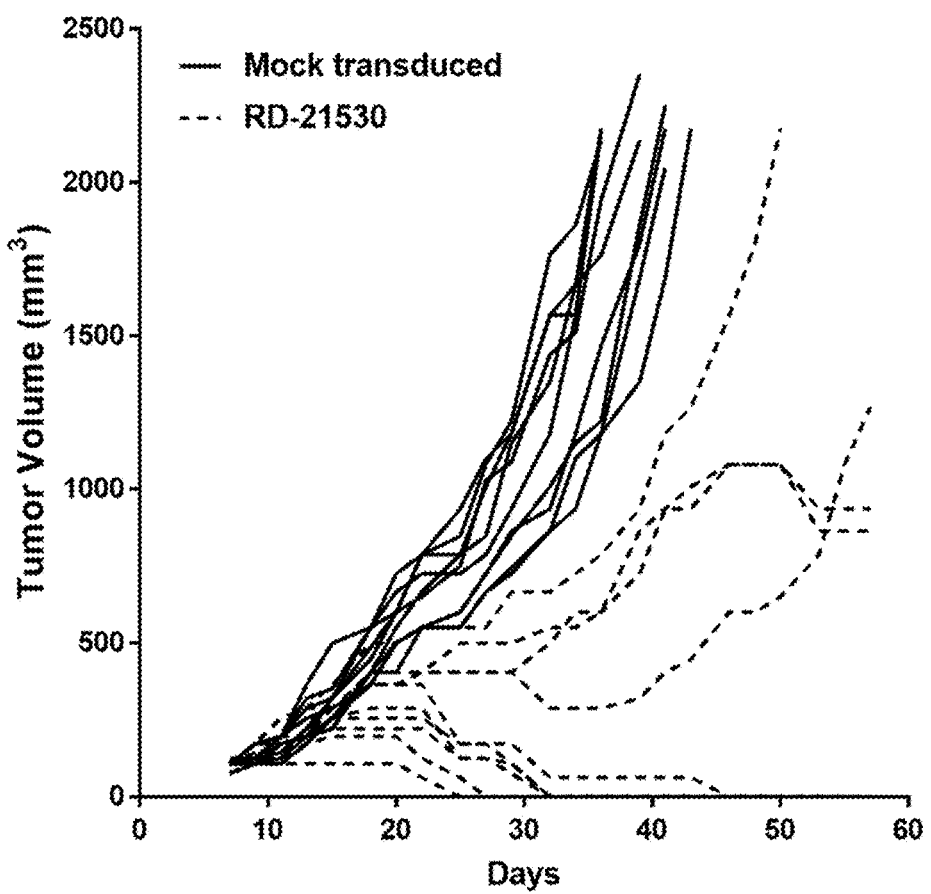

FIG. 17 shows the outcome of an in vivo study examining the efficacy of clone RD-21530 in a subcutaneous RPMI-8226 mouse model. Cohorts of 10 mice each were tested for the CAR (dashed lines) and mock transduced (bolded lines) T cells.

Figure 18A:
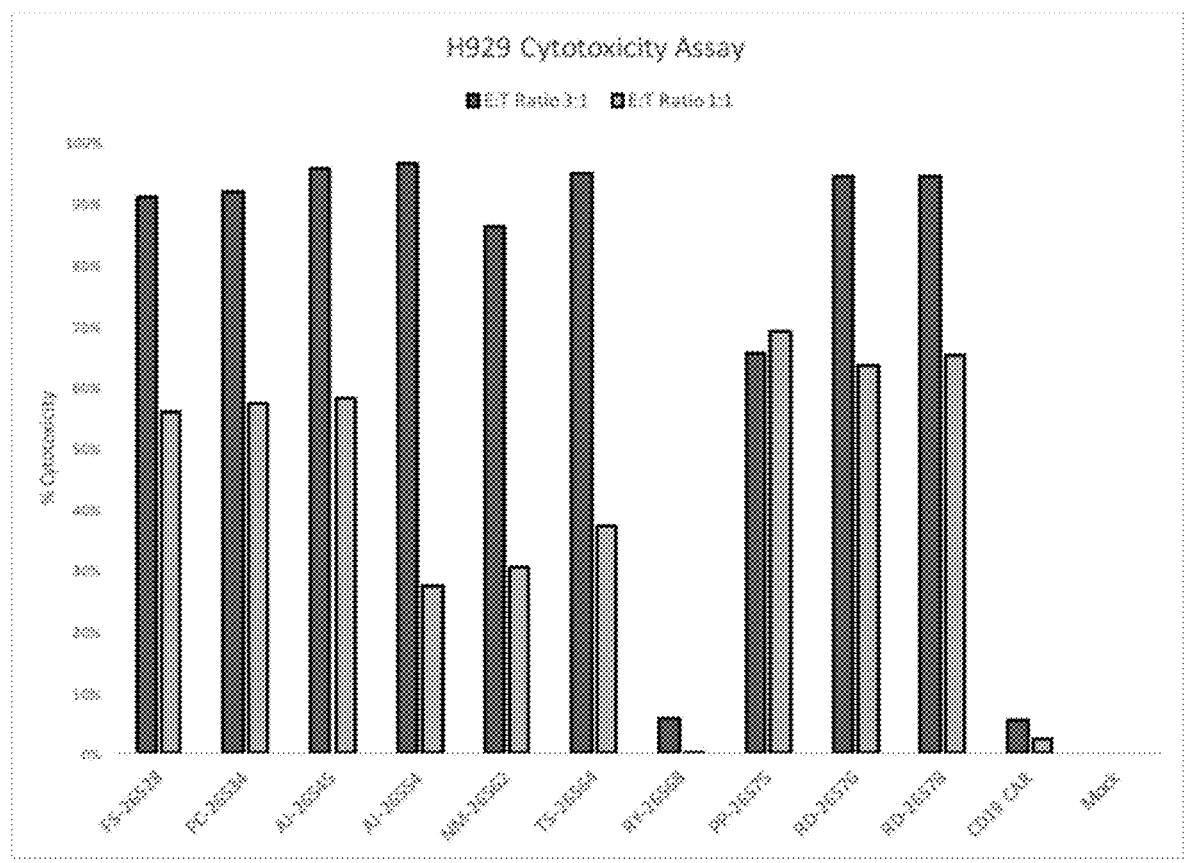
Figure 18B:
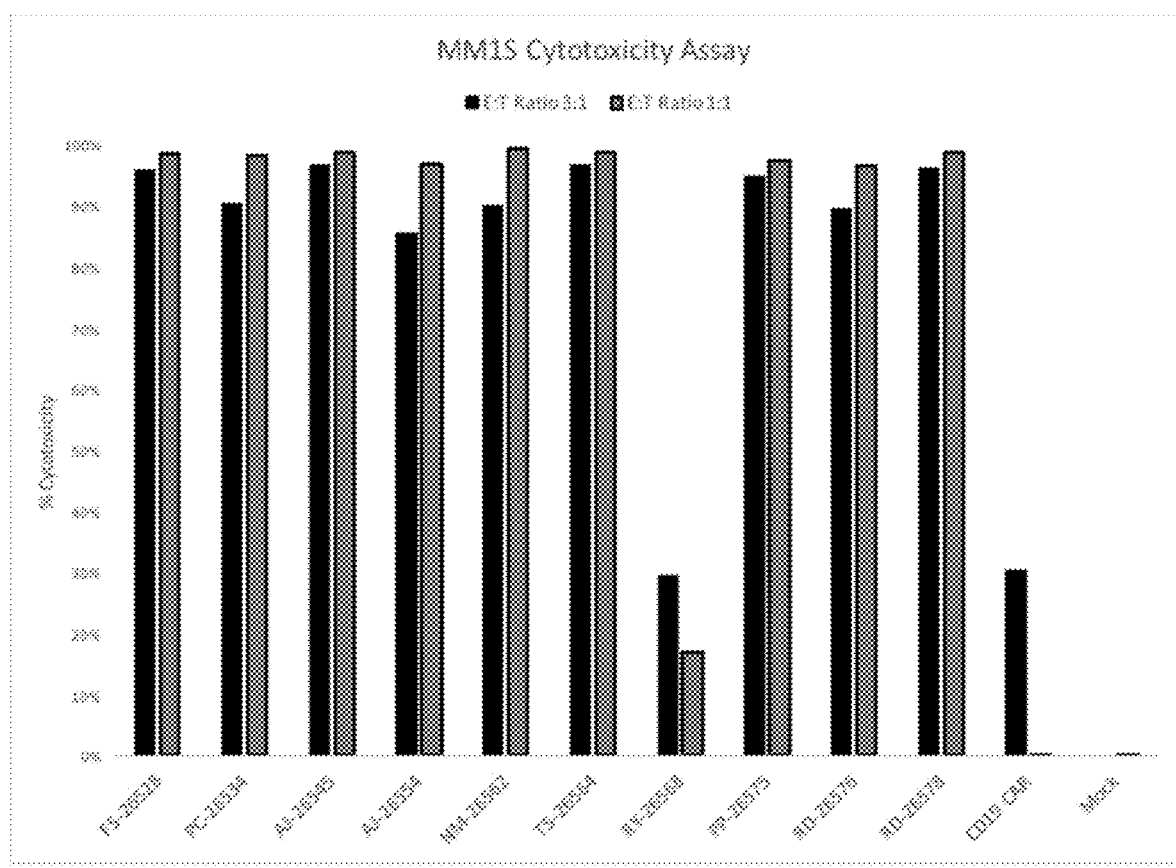

FIG. 18A and FIG. 18B show the outcome of an in vitro cytotoxicity assay using the optimized BCMA scFv variants cocultured with NCI-H929 and MM.1S cells, respectively. CAR T cells using these optimized scFvs were incubated overnight with luciferase labeled target cells in 3:1 and 1:1 effector to target cell ratios.

Figure 19:
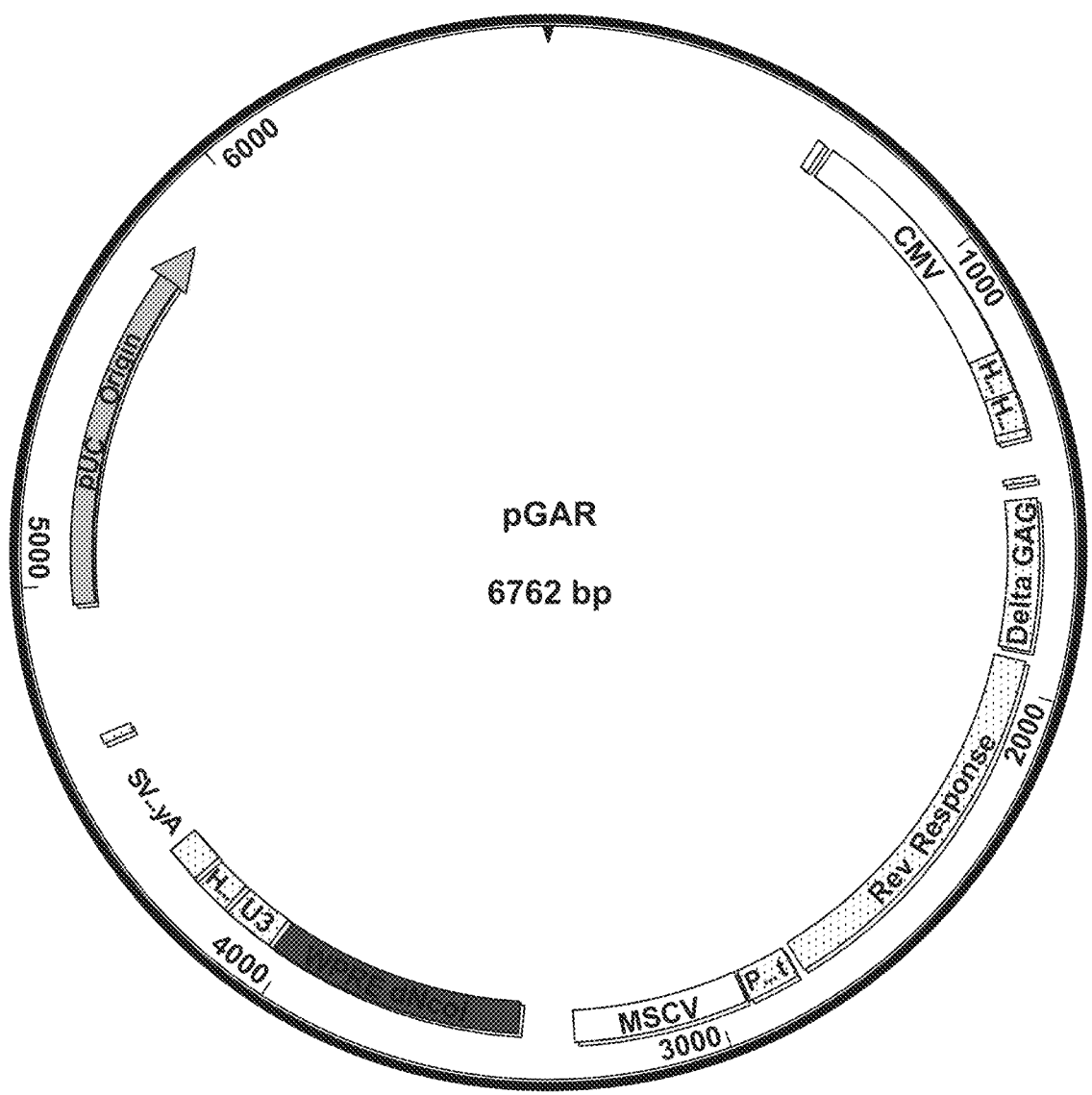

FIG. 19 shows the pGAR vector map.

DETAILED DESCRIPTION OF THE INVENTION

The present invention relates to antibodies, antigen binding molecules thereof, chimeric antigen receptors (CARs), and engineered T cell receptors, which bind BCMA, polynucleotides encoding the same, and in vitro cells comprising the same. The polynucleotides, polypeptides, and in vitro cells described herein can be used in an engineered CAR T cell therapy, e.g., an autologous cell therapy (eACT™), for the treatment of a patient suffering from a cancer. In particular, the polynucleotides, polypeptides, and in vitro cells described herein can be used for the treatment of multiple myeloma.

Definitions

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system Antibodies can include, for example, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-id) antibodies (including, e.g., anti-anti-Id antibodies), minibodies, domain antibodies, synthetic antibodies (sometimes referred to herein as "antibody mimetics"), and antigen-binding fragments of any of the above. In certain embodiments, antibodies described herein refer to polyclonal antibody populations.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by wav of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen binding molecule of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, the antigen binding molecule binds to BCMA. In further embodiments, the antigen binding molecule is an antibody of fragment thereof, including one or more of the complementarity determining regions (CDRs) thereof. In further embodiments, the antigen binding molecule is a single chain variable fragment (scFv). In some embodiments, the antigen binding molecule comprises or consists of avimers.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding fragment thereof.

The terms "VH" and "VH domain" are used interchangeably to refer to the heavy chain variable region of an antibody or an antigen-binding fragment thereof.

A number of definitions of the CDRs are commonly in use: Rabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

CDR Numbering

| Loop | Kabat | AbM | Chothia | Contact |
|---|---|---|---|---|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |

TABLE 1-continued

CDR Numbering

| Loop | Kabat | AbM | Chothia | Contact |
|---|---|---|---|---|
| H1 | H31--H35B (Kabat Numbering) | H26--H35B | H26--H32 ... 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Rabat numbering" and like terms are recognized in the art and refer to a system of numbering amino acid residues in the heavy and light chain variable regions of an antibody, or an antigen binding molecule thereof. In certain aspects, the CDRs of an antibody can be determined according to the Rabat numbering system (see, e.g., Rabat E A & Wu T T (1971) Ann NY Acad Sci 190: 382-391 and Rabat E A et al., (1991) Sequences of Proteins of Immunological Interest, Fifth Edition, U.S. Department of Health and Human Services, NIH Publication No. 91-3242). Using the Rabat numbering system, CDRs within an antibody heavy chain molecule are typically present at amino acid positions 31 to 35, which optionally can include one or two additional amino acids, following 35 (referred to in the Rabat numbering scheme as 35A and 35B) (CDR1), amino acid positions 50 to 65 (CDR2), and amino acid positions 95 to 102 (CDR3). Using the Rabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Rabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Rabat numbering convention, the Chothia CDR-H1 loop is present at heavy chain amino acids 26 to 32,33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Rabat numbering convention varies between H32 and H34 depending on the length of the loop (this is because the Rabat numbering scheme places the insertions at H35A and H35B; if neither 35A nor 35B is present, the loop ends at 32; if wily 35A is present, the loop ends at 33; if both 35A and 35B are present, the loop ends at 34). In a specific embodiment, the CDRs of the antibodies described herein have been determined according to the Chothia numbering scheme.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding fragment thereof can be replaced with an amino acid residue with a similar side chain.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Ciystallogr D Biol Ciystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

As used herein, an antigen binding molecule, an antibody, or an antigen binding molecule thereof "cross competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross competes with a reference antigen binding molecule binds the same or an overlapping epitope as the reference antigen binding molecule. In other embodiments, the antigen binding molecule that cross competes with a reference antigen binding molecule binds a different epitope as the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

In another embodiment, specific embodiment, molecules that specifically bind to an antigen bind with a dissociation constant ($K_d$) of about $1\times10^{-7}$ M. In some embodiments, the antigen binding molecule specifically binds an antigen with "high affinity" when the $K_d$ is about $1\times10^{-9}$ M to about $5\times10^{-9}$ M. In some embodiments, the antigen binding molecule specifically binds an antigen with "very high affinity" when the $K_d$ is $1\times10^{-10}$ M to about $5\times10^{-10}$ M. In one embodiment, the antigen binding molecule has a $K_d$ of $10^{-9}$ M. In one embodiment, the off-rate is less than about $1\times10^{-5}$. In other embodiments, the antigen binding molecule binds human BCMA with a $K_d$ of between about $1\times10^{-7}$ M and about $1\times10^{-13}$ M. In yet another embodiment, the antigen binding molecule binds human BCMA with a $K_d$ of about $1\times10^{-10}$ M to about $5\times10^{-10}$ M.

In another specific embodiment, molecules that specifically bind to an antigen do not cross react with other proteins under similar binding conditions. In another specific embodiment, molecules that specifically bind to an antigen do not cross react with other non-BCMA proteins. In a specific embodiment, provided herein is an antibody or fragment thereof that binds to BCMA with higher affinity than to another unrelated antigen. In certain embodiments, provided herein is an antibody or fragment thereof that binds to BCMA (e.g., human BCMA) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-BCMA antibody or antigen-binding fragment thereof described herein to an unrelated, non-BCMA protein is less than 10%, 15%, or 20% of the binding of the antibody to BCMA protein as measured by, e.g., a radioimmunoassay.

In a specific embodiment, provided herein is an antibody or fragment thereof that binds to human BCMA with higher affinity than to another species of BCMA. In certain embodiments, provided herein is an antibody or fragment thereof that binds to human BCMA with a 5%, 10%, 15%, 20%, 25%, 30%, 35%, 40%, 45%, 50%, 55%, 60%, 65%, 70% or higher affinity than to another species of BCMA as measured by, e.g., a radioimmunoassay, surface plasmon resonance, or kinetic exclusion assay. In a specific embodiment, an antibody or fragment thereof described herein, which binds to human BCMA, will bind to another species of BCMA protein with less than 10%, 15%, or 20% of the binding of the antibody or fragment thereof to the human BCMA protein as measured by, e.g., a radioimmunoassay, surface plasmon resonance, or kinetic exclusion assay.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is BCMA.

The term "neutralizing" refers to an antigen binding molecule, scFv, antibody, or a fragment thereof that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "BCMA" refers to B cell maturation antigen, which can include, but is not limited to, native BCMA, an isoform of BCMA, or an interspecies BCMA homolog of BCMA. BCMA (also known as TNFRSF17, CD269, and TNFRSF13A) is a member of the tumor necrosis factor (TNF)-receptor superfamily. BCMA is expressed on the surface of multiple myeloma cells, while highly restricted to plasma cells and a subset of mature B cells in healthy tissue (FIG. 2A and FIG. 2C). The amino acid sequence of human BCMA (hBCMA) is provided in NCBI Accession Q02223.2 (GI:313104029) (SEQ ID NO: 163). As used herein, BCMA includes human BCMA and non-human BCMA homologs, as well as variants, fragments, or post-transnationally modified forms thereof, including, but not limited to, N- and O-linked glycosylated forms of BCMA. BCMA proteins may further include fragments comprising all or a portion of the extracellular domain of BCMA (e.g., all or a portion of amino acids 1-54 of hBCMA).

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, myeloma, and other leukocyte malignancies. In some embodiments, the methods of the present invention can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-la, IL-lb, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1α), MIP-1β (MIP-1β), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+(L-selectin), CD27+, CD28+ and IL-7Rα+, but they also express large amounts of CD9S, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from, e.g., CD28, and the activating domain can be derived from, e.g., CD3-zeta. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell can include a T cell.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In some aspects, the polypeptides and/or proteins have deletions from, additions to, and/or substitutions of one or more amino acid of antigen-binding protein, and in some embodiments preferably no more than 8 amino acid substitutions therein. Useful polypeptide fragments may include immunologically functional fragments of antigen binding molecules, including not limited to one or more CDR regions, variable domains of a heavy and/or light chain, a portion of other portions of an antibody chain, and the like. Additionally, polypeptide fragments of activating and/or costimulatory molecules and the like are within the scope of the invention.

"Activation" or "Stimulation" as used herein, refers to a primary response induced by binding of an activating molecule with its cognate ligand, wherein the binding mediates a signal transduction event. An "activating molecule" or "stimulating molecule" refers to a molecule on a T cell, e.g., the TCR/CD3 complex that specifically binds with a cognate stimulatory ligand present on an antigen present cell. Suitable activating molecules are described herein.

A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class I molecule loaded with a peptide, an anti-CD3 antibody, a superagonist anti-CD28 antibody, and a superagonist anti-CD2 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, CD7, B7-1 (CD80), B7-2 (CD86), programmed death (PD) L1, PD-L2, 4-1BB ligand, OX40 ligand, inducible costimulatory ligand (ICOS-L), intercellular adhesion molecule (ICAM), CD30 ligand, CD40, CD70, CD83, human leukocyte antigen G (HLA-G), MHC class I chain-related protein A (MICA), MHC class I chain-related protein B (MICB), herpes virus entry mediator (HVEM), lymphotoxin beta receptor, 3/TR6, immunoglobulin-like transcript (ILT) 3, ILT4, an agonist or antibody that binds Toll ligand receptor and a ligand that specifically binds with B7-H3. A co-stimulatory ligand includes, without limitation, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, tumor necrosis factor superfamily member 14 (TNFSF14 or LIGHT), natural killer cell receptor C (NKG2C), B7-H3, and a ligand that specifically binds with CD83.

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, CD28, CD28T, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CDl la/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CDl-ld, ITGAE, CD103, ITGAL, CDl-la, LFA-1, ITGAM, CDl-lb, ITGAX, CDl-lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

II. Binding Molecules and Polynucleotides Encoding the Same

The present invention is directed to a polynucleotide encoding an anti-BCMA antibody or antigen binding molecule thereof which cross competes with one or more antibodies described herein (i.e., one or more described in FIG. 1) or an antibody or antigen binding molecule thereof encoded by the polynucleotide. In one embodiment, the invention is directed to a polynucleotide encoding an anti-BCMA antibody or antigen binding molecule thereof which binds to the same epitope as one or more antibodies described in FIG. 1 or an antibody or antigen binding molecule thereof encoded by the polynucleotide. In some embodiments, the polynucleotide encodes an antibody or antigen binding molecule thereof that specifically binds to BCMA, wherein the antibody or binding molecule comprises a heavy chain VH comprising: (a) a VH CDR1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K. or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y.

In one particular embodiment, the polynucleotide encodes an antibody or antigen binding molecule that specifically binds to BCMA, wherein the antibody or antigen binding molecule comprises a VH comprising: (a) a VH CDR1 comprising, consisting of, or consisting essentially of the amino acid sequence $X_1X_2X_3X_4X_5X_6SYX_9X_{10}X_{11}$ (SEQ ID NO: 263), wherein: $X_1$ is not present or G; $X_2$ is not present or S $X_3$ is F, G, I, or Y; $X_4$ is S or T; $X_5$ is F or S; $X_6$ is S or T; $X_9$ is A, G, S, or Y; $X_{10}$ is I, M, or W; and $X_{11}$ is G, H, N, or S; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is G or S; $X_8$ is not present or N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}X_{18}X_{19}DX_{21}$ (SEQ ID NO: 264), wherein: $X_1$ is A or V; $X_2$ is K. or R; $X_3$ is not present or D, G, or T; $X_4$ is not present or D, G, or P; $X_5$ is not present or F, L, or T; $X_6$, is not present or P, Q, R, W, or Y; $X_7$ is not present or E, G, L, or S; $X_8$ is not present or A, G, P, S, or Y; $X_9$ is not present or A, E, G, P, Q, or S; $X_{10}$ is not present or E, L, M, PS, T, or Y; $X_{11}$ is not present or D, G, H, P, S or W; $X_{12}$ is not present or A, G, I, L, or Y; $X_{13}$ is not present or A, G, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y.

In another embodiment, the polynucleotide encodes an antibody or antigen binding molecule that specifically binds to BCMA, wherein the antibody or antigen binding molecule comprises a VL comprising: (a) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (b) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (c) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In one particular embodiment, the polynucleotide encodes an antibody or antigen binding molecule that specifically binds to BCMA, wherein the antibody or antigen binding molecule comprises a VH comprising: (a) a VH CDR1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or D, G, P, R, or S; $X_5$ is not present or E, F, G, L, Q, or T; $X_6$, is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y; and/or (d) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (e) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (f) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In one particular embodiment, the polynucleotide encodes an antibody or antigen binding molecule that specifically binds to BCMA, wherein the antibody or antigen binding molecule comprises a VH comprising: (a) a VH CDR1 comprising, consisting of, or consisting essentially of the amino acid sequence $X_1X_2X_3X_4X_5X_6SYX_9X_{10}X_{11}$ (SEQ ID NO: 263), wherein: $X_1$ is not present or G; $X_2$ is not present or S $X_3$ is F, G, I, or Y; $X_4$ is S or T; $X_5$ is F or S; $X_6$ is S or T; $X_9$ is A, G, S, or Y; $X_{10}$ is I, M, or W; and $X_{11}$ is G, H, N, or S; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is G or S; $X_8$ is not present or N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}X_{18}X_{19}DX_{21}$ (SEQ ID NO: 264), wherein: $X_1$ is A or V; $X_2$ is K, or R; $X_3$ is not present or D, G, or T; $X_4$ is not present or D, G, or P; $X_5$ is not present or F, L, or T; $X_6$, is not present or P, Q, R, W, or Y; $X_7$ is not present or E, G, L, or S; $X_8$ is not present or A, G, P, S, or Y; $X_9$ is not present or A, E, G, P, Q, or S; $X_{10}$ is not present or E, L, M, PS, T, or Y; $X_{11}$ is not present or D, G, H, P, S or W; $X_{12}$ is not present or A, G, I, L, or Y; $X_{13}$ is not present or A, G, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y; and/or (d) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (e) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (f) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In another embodiment, the polynucleotide encodes an antibody or antigen binding molecule that specifically binds to BCMA, wherein the antibody or antigen binding molecule comprises a VH and a VL, wherein: (i) the VH comprises: (a) a VH CDR1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is not present or G or S; $X_8$ is N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147), wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y; and (ii) the VL comprises: (a) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (b) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (c) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In another embodiment, the polynucleotide encodes an antibody or antigen binding molecule that specifically binds to BCMA, wherein the antibody or antigen binding molecule comprises a VH and a VL, wherein: (i) the VH comprises: (a) a VH CDR1 comprising, consisting of, or consisting essentially of the amino acid sequence $X_1X_2X_3X_4X_5X_6SYX_9X_{10}X_{11}$ (SEQ ID NO: 263), wherein: $X_1$ is not present or G; $X_2$ is not present or S; $X_3$ is F, G, I, or Y; $X_4$ is S or T; $X_5$ is F or S; $X_6$ is S or T; $X_9$ is A, G, S, or Y; $X_{10}$ is I, M, or W; and $X_{11}$ is G, H, N, or S; and/or (b) a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is G or S; $X_8$ is not present or N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S; and/or (c) a VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}X_{18}X_{19}DX_{21}$ (SEQ ID NO: 264), wherein: $X_1$ is A or V; $X_2$ is K or R; $X_3$ is not present or D, G, or T; $X_4$ is not present or D, G, or P; $X_5$ is not present or F, L, or T; $X_6$ is not present or P, Q, R, W, or Y; $X_7$ is not present or E, G, L, or S; $X_8$ is not present or A, G, P, S, or Y; $X_9$ is not present or A, E, G, P, Q, or S; $X_{10}$ is not present or E, L, M, P, S, T, or Y; $X_{11}$ is not present or D, G, H, P, S or W; $X_{12}$ is not present or A, G, I, L, or Y; $X_{13}$ is not present or A, G, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y; and (ii) the VL comprises: (a) a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D; and/or (b) a VL CDR2 comprising, consisting of, or consisting essentially of the amino acid sequence $X_1X_2SX_4X_5X_6X_7$ (SEQ ID NO: 149), wherein $X_1$ is D, G, L, S, or W; $X_2$ is A or G; $X_4$ is N, S, or T; $X_5$ is L or R; $X_6$ is A, E, or Q; and $X_7$ is S or T; and/or (c) a VL CDR3 comprising, consisting of, or consisting essentially of the amino acid sequence $X_1QX_3X_4X_5X_6PX_8T$ (SEQ ID NO: 150), wherein $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In one embodiment, the antibody or antigen binding molecule, which specifically binds to BCMA (e.g., hBCMA), comprises a VH CDR1 comprising, consisting of, or consisting essentially of the amino acid sequence $GX_2X_3X_4X_5X_6X_7SY$ (SEQ ID NO: 145), wherein: $X_2$ is not present or G; $X_3$ is not present or S; $X_4$ is F, G, I, or Y; $X_5$ is S or T; $X_6$ is F or S; and $X_7$ is S or T.

In one embodiment, the antibody or antigen binding molecule, which specifically binds to BCMA (e.g., hBCMA), comprises a VH CDR1 comprising, consisting of, or consisting essentially of the amino acid sequence $GX_2TFSSY$ (SEQ ID NO: 151), wherein: $X_2$ is F or G.

In one embodiment, the antibody or antigen binding molecule, which specifically binds to BCMA (e.g., hBCMA), comprises a VH CDR1 comprising, consisting of, or consisting essentially of the amino acid sequence $GX_2X_3X_4X_5X_6SSY$ (SEQ ID NO: 152), wherein: $X_2$ is not present or G; $X_3$ is not present or S; $X_4$ is F, G, or I; $X_5$ is S or T; and $X_6$ is F or S.

In one embodiment, the antibody or antigen binding molecule, which specifically binds to BCMA (e.g., hBCMA), comprises a VH CDR1 comprising, consisting of, or consisting essentially of the amino acid sequence $X_1X_2X_3X_4X_5X_6SYX_9X_{10}X_{11}$ (SEQ ID NO: 263), wherein: $X_1$ is not present or G; $X_2$ is not present or S; $X_3$ is F, G, I, or Y; $X_4$ is S or T; $X_5$ is F or S; $X_6$ is S or T; $X_9$ is A, G, S, or Y; $X_{10}$ is I, M, or W; and $X_{11}$ is G, H, N, or S.

In one embodiment, the antibody or antigen binding molecule, which specifically binds to BCMA (e.g., hBCMA), comprises a VH CDR1 comprising, consisting of, or consisting essentially of the amino acid sequence $X_1TFX_4SYX_7X_8X_9$ (SEQ ID NO: 265), wherein: $X_1$ is F, G, or Y; $X_4$ is S or T; $X_7$ is A, G, S, or Y; $X_8$ is I or M; and $X_9$ is H, N, or S.

In one embodiment, the antibody or antigen binding molecule, which specifically binds to BCMA (e.g., hBCMA), comprises a VH CDR1 comprising, consisting of, or consisting essentially of the amino acid sequence $FTFSSYX_7MX_9$ (SEQ ID NO: 266), wherein: $X_7$ is A, G, or S; and $X_9$ is H, N, or S.

In one embodiment, the antibody or antigen binding molecule, which specifically binds to BCMA (e.g., hBCMA), comprises a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}X_{17}$ (SEQ ID NO: 146), wherein: $X_1$ is A, G, I, S, T, or V; $X_3$ is I, N, or S; $X_4$ is G, P, S, or Y; $X_5$ is D, G, I, or S; $X_6$ is F, G, or S; $X_7$ is G or S; $X_8$ is not present or N, S, or T; $X_9$ is A, I, K, or T; $X_{10}$ is N, S, or Y; $X_{12}$ is A or N; $X_{13}$ is D, P, or Q; $X_{14}$ is K or S; $X_{15}$ is F, L, or V; $X_{16}$ is K or Q; and $X_{17}$ is G or S.

In one embodiment, the antibody or antigen binding molecule, which specifically binds to BCMA (e.g., hBCMA), comprises a VH CDR2 comprising, consisting of, or consisting essentially of the amino acid sequence $X_1IX_3X_4X_5X_6X_7X_8X_9X_{10}YX_{12}X_{13}X_{14}X_{15}X_{16}G$ (SEQ ID NO: 153), wherein: $X_1$ is A, G, I, T, or V; $X_3$ is I, N, or S; $X_4$ is G, P, S, or Y; $X_5$ is D, G, I, or S; $X_6$ is F, G, or S; $X_7$ is G or S; $X_8$ is N, S, or T; $X_9$ is A, I, K, or T; $X_{10}$ is N, S, or Y; $X_{13}$ is D or Q; $X_{14}$ is K or S; $X_{15}$ is F or V; and $X_{16}$ is K or Q.

In one embodiment, the antibody or antigen binding molecule, which specifically binds to BCMA (e.g., hBCMA), comprises a VH CDR2 comprising, consisting of, or consisting essentially of the amino acid sequence $X_1ISX_4X_5X_6X_7X_8X_9YYADSVKG$ (SEQ ID NO: 154), wherein: $X_1$ is A, T, or V; $X_4$ is G, S, or Y; $X_5$ is D or S; $X_6$ is G or S; $X_7$ is G or S; $X_8$ is N, S, or T; and $X_9$ is I, K, or T.

In one embodiment, the antibody or antigen binding molecule, which specifically binds to BCMA (e.g., hBCMA), comprises a VH CDR2 comprising, consisting of, or consisting essentially of the amino acid sequence $X_1IX_3PX_5X_6GX_8X_9X_{10}YAQKFQG$ (SEQ ID NO: 155), wherein: $X_1$ is G or I; $X_3$ is I or N; $X_5$ is G or I; $X_6$ is F or G; $X_8$ is S or T; $X_9$ is A or T; and $X_{10}$ is N or S.

In one embodiment, the antibody or antigen binding molecule, which specifically binds to BCMA (e.g., hBCMA), comprises three VH CDRs and three VL CDRs, wherein the VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}DX_{19}$ (SEQ ID NO: 147) and wherein: $X_1$ is A or V; $X_2$ is K or R; $X_3$ is not present or D, G, or T; $X_4$ is not present or A, D, G, P, R, or S; $X_5$ is not present or E, F, G, L, Q, or T; $X_6$ is not present or E, M, Q, W, or Y; $X_7$ is not present or A, E, L, or S; $X_8$ is not present or G, P, S, or T; $X_9$ is not present or G, P, or S; $X_{10}$ is not present or I, L, P, or Y; $X_{11}$ is not present or W; $X_{12}$ is not present or H; $X_{13}$ is not present or E or Y; $X_{14}$ is not present or D, G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y.

In one embodiment, the antibody or antigen binding molecule, which specifically binds to BCMA (e.g., hBCMA), comprises three VH CDRs and three VL CDRs, wherein the VH CDR3 comprising, consisting of, or consisting essentially of the amino acid sequence $ARX_3X_4X_5X_6X_7X_8X_9X_{10}X_{11}X_{12}X_{13}X_{14}X_{15}X_{16}X_{17}DX_{19}$ (SEQ ID NO: 156) and wherein: $X_3$ is not present or D, G, or T; $X_4$ is not present or A, D, G, P, R, or S; $X_5$ is not present or E, F, G, Q, or T; $X_6$ is not present or E, M, W, or Y; $X_7$ is not present or A, L, or S; $X_8$ is not present or G, S, or T; $X_9$ is not present or G or S; $X_{10}$ is not present or I, L, or P; $X_{11}$ is not present or W; $X_{12}$ is not present or H; $X_{13}$ is not present or E or Y; $X_{14}$ is not present or G, H, P, S, W, or Y; $X_{15}$ is A, G, L, W, or Y; $X_{16}$ is not present or A, G, I, P, or V; $X_{17}$ is F, L, or M; and $X_{19}$ is I, L, V, or Y.

In one embodiment, the antibody or antigen binding molecule, which specifically binds to BCMA (e.g., hBCMA), comprises three VH CDRs and three VL CDRs, wherein the VH CDR3 comprising, consisting of, or consisting essentially of the amino acid sequence $X_1X_2X_3X_4X_5X_6X_7X_8X_9X_{10}X_{11}X_{12}X_{13}X_{14}X_{15}X_{16}X_{17}X_{18}X_{19}DX_{21}$ (SEQ ID NO: 264) and wherein: $X_1$ is A or V; $X_2$ is K or R; $X_3$ is not present or D, G, or T; $X_4$ is not present or D, G, or P; $X_5$ is not present or F, L, or T; $X_6$ is not present or P, Q, R, W, or Y; $X_7$ is not present or E, G, L, or S; $X_8$ is not present or A, G, P, S, or Y; $X_9$ is A, E, G, P, Q, or S; $X_{10}$ is E, L, M, P, S, T, or Y; $X_{11}$ is not present or D, G, H, P, S or W; $X_{12}$ is not present or A, G, I, L, or Y; $X_{13}$ is not present or A, G, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y.

In one embodiment, the antibody or antigen binding molecule, which specifically binds to BCMA (e.g., hBCMA), comprises three VH CDRs and three VL CDRs, wherein the VH CDR3 comprising, consisting of, or consisting essentially of the amino acid sequence $ARX_3X_4X_5X_6X_7X_8X_9X_{10}X_{11}X_{12}X_{13}X_{14}X_{15}X_{16}X_{17}X_{18}X_{19}DX_{21}$ (SEQ ID NO: 267), wherein: $X_3$ is not present or D or T; $X_4$ is not present or D or G; $X_5$ is not present or F or T; $X_6$ is not present or P, R, W, or Y; $X_7$ is not present or E, G, L, or S; $X_8$ is not present or A, G, S, or Y; $X_9$ is A, E, G, Q, or S; $X_{10}$ is E, L, M, P, S, or T; $X_{11}$ is not present or G, H, P, S or W; $X_{12}$ is not present or A, G, I, L, or Y; $X_{13}$ is not present or A, I, V, or W; $X_{14}$ is not present or H; $X_{15}$ is not present or Y; $X_{16}$ is not present or Y; $X_{17}$ is not present or W or Y; $X_{18}$ is not present or P or G; $X_{19}$ is F, L, or M; and $X_{21}$ is I, L, V, or Y.

In some embodiments, the polynucleotide encodes an antibody or antigen binding molecule that specifically binds to BCMA, wherein the antibody or antigen binding molecule comprises one, two, or all three of any of the VH CDRs listed above or described in FIG. 1A or FIG. 1B. In some embodiments, the antibody or antigen binding molecule comprises the VH framework regions (FRs) described herein. In specific embodiments, the antibody or antigen binding molecule comprises the VH FRs of an antibody set forth in FIG. 1A or FIG. 1B (e.g., one, two, three, or four of the FRs in one sequence of FIG. 1A).

In one embodiment, the antibody or antigen binding molecule, which specifically binds to BCMA (e.g., hBCMA), comprises a VL CDR1 comprising, consisting of, or consisting essentially of the amino acid sequence $X_1X_2SQX_5X_6X_7X_8X_9X_{10}X_{11}X_{12}X_{13}X_{14}X_{15}LX_{17}$ (SEQ ID NO: 148), wherein: $X_1$ is K or R; $X_2$ is A or S; $X_5$ is G or S; $X_6$ is I, L, or V; $X_7$ is L or S; $X_8$ is not present or H or Y; $X_9$ is not present or S; $X_{10}$ is not present or N or S; $X_{11}$ is not present or G or N; $X_{12}$ is not present or N; $X_{13}$ is not present or K or Y; $X_{14}$ is N, R, or S; $X_{15}$ is N, W, or Y; and $X_{17}$ is A or D.

In one embodiment, the antibody or antigen binding molecule, which specifically binds to BCMA (e.g., hBCMA), comprises a VL CDR1 comprising, consisting of, or consisting essentially of the amino acid sequence $RASQX_5X_6SX_8X_9LA$ (SEQ ID NO: 157), wherein: $X_5$ is G or S; $X_6$ is I or V; $X_8$ is R or S; and $X_9$ is N, W, or Y.

In one embodiment, the antibody or antigen binding molecule, which specifically binds to BCMA (e.g., hBCMA), comprises a VL CDR1 comprising, consisting of, or consisting essentially of the amino acid sequence $X_1SSQSX_6LX_8SX_{10}X_{11}X_{12}X_{13}NYLX_{17}$ (SEQ ID NO: 158), wherein: $X_1$ is K or R; $X_6$ is L or V; $X_8$ is H or Y; $X_{10}$ is N or S; $X_{11}$ is G or N; $X_{12}$ is not present or N; $X_{13}$ is K or Y; and $X_{17}$ is A or D.

In one embodiment, the antibody or antigen binding molecule, which specifically binds to BCMA (e.g., hBCMA), comprises a VL CDR2 comprising, consisting of, or consisting essentially of the amino acid sequence $X_1X_2SX_4X_5X_6X_7$ (SEQ ID NO: 149), wherein: $X_1$ is D, G, L, S, or W; $X_2$ is A or G; $X_4$ is N, S, or T; $X_5$ is L or R; $X_6$ is A, E, or Q; and $X_7$ is S or T.

In one embodiment, the antibody or antigen binding molecule, which specifically binds to BCMA (e.g., hBCMA), comprises a VL CDR2 comprising, consisting of, or consisting essentially of the amino acid sequence $X_1ASX_4RAT$ (SEQ ID NO: 159), wherein: $X_1$ is D, G, or S; and $X_4$ is N or T.

In one embodiment, the antibody or antigen binding molecule, which specifically binds to BCMA (e.g., hBCMA), comprises a VL CDR2 comprising, consisting of, or consisting essentially of the amino acid sequence $X_1ASX_4X_5X_6X_7$ (SEQ ID NO: 160), wherein: $X_1$ is D, G, or S; $X_4$ is N, S, or T; $X_5$ is L or R; $X_6$ is A or Q; and $X_1$ is S or T.

In one embodiment, the antibody or antigen binding molecule, which specifically binds to BCMA (e.g., hBCMA), comprises a VL CDR2 comprising, consisting of, or consisting essentially of the amino acid sequence $X_1X_2SX_4RX_6S$ (SEQ ID NO: 161), wherein $X_1$ is L or W; $X_2$ is A or G; $X_4$ is N or T; and $X_6$ is A or E.

In one embodiment, the antibody or antigen binding molecule, which specifically binds to BCMA (e.g., hBCMA), comprises a VL CDR3 comprising, consisting of, or consisting essentially of the amino acid sequence $X_1QX_3X_4X_5X_6PX_8T$ (SEQ ID NO: 150), wherein: $X_1$ is M or Q; $X_3$ is F, G, H, I, R, or Y; $X_4$ is A, F, H, I, L, or Y; $X_5$ is A, G, H, S, T, V, or Y; $X_6$ is F, L, T, W, or Y; and $X_8$ is not present or F, L, P, or W.

In one embodiment, the antibody or antigen binding molecule, which specifically binds to BCMA (e.g., hBCMA), comprises a VL CDR3 comprising, consisting of, or consisting essentially of the amino acid sequence $QQX_3X_4X_5X_6PX_8T$ (SEQ ID NO: 162), wherein: $X_3$ is H, I, R, or Y; $X_4$ is A, F, H, I, or Y; $X_5$ is A, S, T, V, or Y; $X_6$ is F, W, or Y; and $X_8$ is not present or F, L, P, or W.

In some embodiments, the polynucleotide encodes an antibody or antigen binding molecule that specifically binds to BCMA, wherein the antibody or antigen binding molecule comprises one, two, or all three of any of the VL CDRs listed above or described in FIG. 2. In some embodiments, the antibody or antigen binding molecule comprises the VL framework regions (FRs) described herein. In specific embodiments, the antibody or antigen binding molecule comprises the VL FRs of an antibody set forth in FIG. 4 (e.g., one, two, three, or four of the FRs in one row of FIG. 4).

In some embodiments, the polynucleotide encodes an antibody or antigen binding molecule that specifically binds to BCMA, wherein the antibody or antigen binding molecule comprises a VH CDR1, wherein the VH CDR1 comprises an amino acid sequence selected from the group consisting of SEQ ID NO: 9-16. In other embodiments, the antibody or antigen binding molecule comprises a VH CDR1, wherein the VH CDR1 comprises an amino acid sequence selected from the group consisting of SEQ ID NO: 215-222. In some embodiments, the antibody or antigen binding molecule comprises a VH CDR2, wherein the VH CDR2 comprises an amino acid sequence selected from the group consisting of SEQ ID NO: 25-32. In some embodiments, the antibody or antigen binding molecule comprises a VH CDR2, wherein the VH CDR2 comprises an amino acid sequence selected from the group consisting of SEQ ID NO: 231-238. In some embodiments, the antibody or antigen binding molecule comprises a VH CDR3, wherein the VH CDR3 comprises an amino acid sequence selected from the group consisting of SEQ ID NO: 41-48. In some embodiments, the antibody or antigen binding molecule comprises a VH CDR3, wherein the VH CDR3 comprises an amino acid sequence selected from the group consisting of SEQ ID NO: 247-254.

In some embodiments, the polynucleotide encodes an antibody or antigen binding molecule that specifically binds to BCMA, wherein the antibody or antigen binding molecule comprises a VH CDR1, a VH CDR2, and VH CDR3, wherein the VH CDR1, VH CDR2, and VH CDR3 comprise the amino acid sequence of the VH CDR1, VH CDR2, and VH CDR3 of an antibody in FIG. 1A or FIG. 1B, respectively.

In some embodiments, the polynucleotide encodes an antibody or antigen binding molecule that specifically binds to BCMA, wherein the antibody or antigen binding molecule comprises a VL CDR1, wherein the VL CDR1 comprises an amino acid sequence selected from the group consisting of SEQ ID NO: 81-88. In some embodiments, the antibody or antigen binding molecule comprises a VL CDR2, wherein the VL CDR2 comprises an amino acid sequence selected from the group consisting of SEQ ID NO: 97-104. In some embodiments, the antibody or antigen binding molecule comprises a VL CDR3, wherein the VL CDR3 comprises an amino acid sequence selected from the group consisting of SEQ ID NO: 113-120.

In some embodiments, the polynucleotide encodes an antibody or antigen binding molecule that specifically binds to BCMA, wherein the antibody or antigen binding molecule comprises a VL CDR1, a VL CDR2, and VL CDR3, wherein the VL CDR1, VL CDR2, and VL CDR3 comprise the amino acid sequence of the VL CDR1, VL CDR2, and VL CDR3 of an antibody in FIG. 1C, respectively.

In some embodiments, the polynucleotide encodes an antibody or antigen binding molecule that specifically binds to BCMA, wherein the antibody or antigen binding molecule comprises a VH framework region 1 (FR1), wherein the VH FR1 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 1-8 and 207-214. In some embodiments, the antibody or antigen binding molecule comprises a VH FR2, wherein the VH FR2 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 17-24 and 223-23. In some embodiments, the antibody or antigen binding molecule comprises a VH FR3, wherein the VH FR3 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 33-40 and 239-246. In some embodiments, the antibody or antigen binding molecule comprises a VH FR4, wherein the VH FR4 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 49-56 and 255-262.

In some embodiments, the antibody or antigen binding molecule or a fragment thereof comprises a VL FR1, wherein the VL FR1 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 73-80. In some embodiments, the antibody or antigen binding molecule or a fragment thereof comprises a VL FR2, wherein the VL FR2 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 89-96. In some embodiments, the antibody or antigen binding molecule or a fragment thereof comprises a VL FR3, wherein the VL FR3 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 105-112. In some embodiments, the antibody or antigen binding molecule or a fragment thereof comprises a VL FR4, wherein the VL FR4 comprises an amino acid sequence at least about 75%, at least about 80%, at least about 85%, at least about 90%, at least about 95%, at least about 96%, at least about 97%, at least about 98%, at least about 99%, or 100% identical to an amino acid sequence selected from SEQ ID NOs: 121-128.

In some embodiments, the polynucleotide encodes an antibody or antigen binding molecule that specifically binds to BCMA, wherein the antibody or antigen binding molecule comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule comprises: (a) a VH CDR1 region comprising the amino acid sequence of SEQ ID NO: 9; (b) a VH CDR2 region comprising the amino acid sequence of SEQ ID NO: 25; (c) a VH CDR3 region comprising the amino acid sequence of SEQ ID NO: 41; (d) a VL CDR1 region comprising the amino acid sequence of SEQ ID NO: 81; (e) a VL CDR2 region comprising the amino acid sequence of SEQ ID NO: 97; and (f) a VL CDR3 region comprising the amino acid sequence of SEQ ID NO: 113.

In one embodiment, the antibody or antigen binding molecule comprises: (a) a VH CDR1 region comprising the amino acid sequence of SEQ ID NO: 10; (b) a VH CDR2 region comprising the amino acid sequence of SEQ ID NO: 26; (c) a VH CDR3 region comprising the amino acid sequence of SEQ ID NO: 42; (d) a VL CDR1 region comprising the amino acid sequence of SEQ ID NO: 82; (e) a VL CDR2 region comprising the amino acid sequence of SEQ ID NO: 98; and (f) a VL CDR3 region comprising the amino acid sequence of SEQ ID NO: 114.

In one embodiment, the antibody or antigen binding molecule comprises: (a) a VH CDR1 region comprising the amino acid sequence of SEQ ID NO: 11; (b) a VH CDR2 region comprising the amino acid sequence of SEQ ID NO: 27; (c) a VH CDR3 region comprising the amino acid sequence of SEQ ID NO: 43; (d) a VL CDR1 region comprising the amino acid sequence of SEQ ID NO: 83; (e) a VL CDR2 region comprising the amino acid sequence of SEQ ID NO: 99; and (f) a VL CDR3 region comprising the amino acid sequence of SEQ ID NO: 115.

In one embodiment, the antibody or antigen binding molecule comprises: (a) a VH CDR1 region comprising the amino acid sequence of SEQ ID NO: 12; (b) a VH CDR2 region comprising the amino acid sequence of SEQ ID NO: 28; (c) a VH CDR3 region comprising the amino acid sequence of SEQ ID NO: 44; (d) a VL CDR1 region comprising the amino acid sequence of SEQ ID NO: 84; (e) a VL CDR2 region comprising the amino acid sequence of SEQ ID NO: 100; and (f) a VL CDR3 region comprising the amino acid sequence of SEQ ID NO: 116.

In one embodiment, the antibody or antigen binding molecule comprises: (a) a VH CDR1 region comprising the amino acid sequence of SEQ ID NO: 13; (b) a VH CDR2 region comprising the amino acid sequence of SEQ ID NO: 29; (c) a VH CDR3 region comprising the amino acid sequence of SEQ ID NO: 45; (d) a VL CDR1 region comprising the amino acid sequence of SEQ ID NO: 85; (e) a VL CDR2 region comprising the amino acid sequence of SEQ ID NO: 101; and (f) a VL CDR3 region comprising the amino acid sequence of SEQ ID NO: 117.

In one embodiment, the antibody or antigen binding molecule comprises: (a) a VH CDR1 region comprising the amino acid sequence of SEQ ID NO: 14; (b) a VH CDR2 region comprising the amino acid sequence of SEQ ID NO: 30; (c) a VH CDR3 region comprising the amino acid sequence of SEQ ID NO: 46; (d) a VL CDR1 region comprising the amino acid sequence of SEQ ID NO: 86; (e) a VL CDR2 region comprising the amino acid sequence of SEQ ID NO: 102; and (f) a VL CDR3 region comprising the amino acid sequence of SEQ ID NO: 118.

In one embodiment, the antibody or antigen binding molecule comprises: (a) a VH CDR1 region comprising the amino acid sequence of SEQ ID NO: 15; (b) a VH CDR2 region comprising the amino acid sequence of SEQ ID NO: 31; (c) a VH CDR3 region comprising the amino acid sequence of SEQ ID NO: 47; (d) a VL CDR1 region comprising the amino acid sequence of SEQ ID NO: 87; (e) a VL CDR2 region comprising the amino acid sequence of SEQ ID NO: 103; and (f) a VL CDR3 region comprising the amino acid sequence of SEQ ID NO: 119.

In one embodiment, the antibody or antigen binding molecule comprises: (a) a VH CDR1 region comprising the amino acid sequence of SEQ ID NO: 16; (b) a VH CDR2 region comprising the amino acid sequence of SEQ ID NO: 32; (c) a VH CDR3 region comprising the amino acid sequence of SEQ ID NO: 48; (d) a VL CDR1 region comprising the amino acid sequence of SEQ ID NO: 88; (e) a VL CDR2 region comprising the amino acid sequence of SEQ ID NO: 104; and (f) a VL CDR3 region comprising the amino acid sequence of SEQ ID NO: 120.

In one embodiment, the antibody or antigen binding molecule comprises: (a) a VH CDR1 region comprising the amino acid sequence of SEQ ID NO: 215; (b) a VH CDR2 region comprising the amino acid sequence of SEQ ID NO: 231; (c) a VH CDR3 region comprising the amino acid sequence of SEQ ID NO: 247; (d) a VL CDR1 region comprising the amino acid sequence of SEQ ID NO: 81; (e) a VL CDR2 region comprising the amino acid sequence of SEQ ID NO: 97; and (f) a VL CDR3 region comprising the amino acid sequence of SEQ ID NO: 113.

In one embodiment, the antibody or antigen binding molecule comprises: (a) a VH CDR1 region comprising the amino acid sequence of SEQ ID NO: 216; (b) a VH CDR2 region comprising the amino acid sequence of SEQ ID NO: 232; (c) a VH CDR3 region comprising the amino acid sequence of SEQ ID NO: 248; (d) a VL CDR1 region comprising the amino acid sequence of SEQ ID NO: 82; (e) a VL CDR2 region comprising the amino acid sequence of SEQ ID NO: 98; and (f) a VL CDR3 region comprising the amino acid sequence of SEQ ID NO: 114.

In one embodiment, the antibody or antigen binding molecule comprises: (a) a VH CDR1 region comprising the amino acid sequence of SEQ ID NO: 217; (b) a VH CDR2 region comprising the amino acid sequence of SEQ ID NO: 233; (c) a VH CDR3 region comprising the amino acid sequence of SEQ ID NO: 249; (d) a VL CDR1 region comprising the amino acid sequence of SEQ ID NO: 83; (e) a VL CDR2 region comprising the amino acid sequence of SEQ ID NO: 99; and (f) a VL CDR3 region comprising the amino acid sequence of SEQ ID NO: 115.

In one embodiment, the antibody or antigen binding molecule comprises: (a) a VH CDR1 region comprising the amino acid sequence of SEQ ID NO:218; (b) a VH CDR2 region comprising the amino acid sequence of SEQ ID NO: 234; (c) a VH CDR3 region comprising the amino acid sequence of SEQ ID NO: 250; (d) a VL CDR1 region comprising the amino acid sequence of SEQ ID NO: 84; (e) a VL CDR2 region comprising the amino acid sequence of SEQ ID NO: 100; and (f) a VL CDR3 region comprising the amino acid sequence of SEQ ID NO: 116.

In one embodiment, the antibody or antigen binding molecule comprises: (a) a VH CDR1 region comprising the amino acid sequence of SEQ ID NO: 219; (b) a VH CDR2 region comprising the amino acid sequence of SEQ ID NO: 235; (c) a VH CDR3 region comprising the amino acid sequence of SEQ ID NO: 251; (d) a VL CDR1 region comprising the amino acid sequence of SEQ ID NO: 85; (e) a VL CDR2 region comprising the amino acid sequence of SEQ ID NO: 101; and (f) a VL CDR3 region comprising the amino acid sequence of SEQ ID NO: 117.

In one embodiment, the antibody or antigen binding molecule comprises: (a) a VH CDR1 region comprising the amino acid sequence of SEQ ID NO: 220; (b) a VH CDR2 region comprising the amino acid sequence of SEQ ID NO: 236; (c) a VH CDR3 region comprising the amino acid sequence of SEQ ID NO: 252; (d) a VL CDR1 region comprising the amino acid sequence of SEQ ID NO: 86; (e) a VL CDR2 region comprising the amino acid sequence of SEQ ID NO: 102; and (f) a VL CDR3 region comprising the amino acid sequence of SEQ ID NO: 118.

In one embodiment, the antibody or antigen binding molecule comprises: (a) a VH CDR1 region comprising the amino acid sequence of SEQ ID NO: 221; (b) a VH CDR2 region comprising the amino acid sequence of SEQ ID NO: 237; (c) a VH CDR3 region comprising the amino acid sequence of SEQ ID NO: 253; (d) a VL CDR1 region comprising the amino acid sequence of SEQ ID NO: 87; (e) a VL CDR2 region comprising the amino acid sequence of SEQ ID NO: 103; and (f) a VL CDR3 region comprising the amino acid sequence of SEQ ID NO: 119.

In one embodiment, the antibody or antigen binding molecule comprises: (a) a VH CDR1 region comprising the amino acid sequence of SEQ ID NO: 222; (b) a VH CDR2 region comprising the amino acid sequence of SEQ ID NO: 238; (c) a VH CDR3 region comprising the amino acid sequence of SEQ ID NO: 254; (d) a VL CDR1 region comprising the amino acid sequence of SEQ ID NO: 88; (e) a VL CDR2 region comprising the amino acid sequence of SEQ ID NO: 104; and (f) a VL CDR3 region comprising the amino acid sequence of SEQ ID NO: 120.

In some embodiments, the antibody or antigen binding molecule comprises a heavy chain variable region sequence comprising an amino acid sequence of FIG. 1A or FIG. 1B. In some embodiments, the antibody or antigen binding molecule comprises a heavy chain variable region sequence comprising an amino acid sequence selected from the group consisting of SEQ ID NOs: 65-72. In some embodiments, the antibody or antigen binding molecule comprises a light chain variable region sequence comprising an amino acid sequence selected from FIG. 1C. In some embodiments, the antibody or antigen binding molecule comprises a light chain variable region sequence comprising an amino acid sequence selected from the group consisting of SEQ ID NOs: 137-144.

In some embodiments, the antibody or antigen binding molecule comprises (a) a heavy chain variable region comprising the amino acid sequence of SEQ ID NO: 65; and (b) a light chain variable region comprising the amino acid sequence of SEQ ID NO 137.

In some embodiments, the antibody or antigen binding molecule comprises (a) a heavy chain variable region comprising the amino acid sequence of SEQ ID NO: 66; and (b) a light chain variable region comprising the amino acid sequence of SEQ ID NO: 138.

In some embodiments, the antibody or antigen binding molecule comprises (a) a heavy chain variable region comprising the amino acid sequence of SEQ ID NO: 67; and (b) a light chain variable region comprising the amino acid sequence of SEQ ID NO: 139.

In some embodiments, the antibody or antigen binding molecule comprises (a) a heavy chain variable region comprising the amino acid sequence of SEQ ID NO: 68; and (b) a light chain variable region comprising the amino acid sequence of SEQ ID NO: 140.

In some embodiments, the antibody or antigen binding molecule comprises (a) a heavy chain variable region comprising the amino acid sequence of SEQ ID NO: 69; and (b) a light chain variable region comprising the amino acid sequence of SEQ ID NO: 141.

In some embodiments, the antibody or antigen binding molecule comprises (a) a heavy chain variable region comprising the amino acid sequence of SEQ ID NO: 70; and (b) a light chain variable region comprising the amino acid sequence of SEQ ID NO: 142.

In some embodiments, the antibody or antigen binding molecule comprises (a) a heavy chain variable region comprising the amino acid sequence of SEQ ID NO: 71; and (b) a light chain variable region comprising the amino acid sequence of SEQ ID NO: 143.

In some embodiments, the antibody or antigen binding molecule comprises (a) a heavy chain variable region comprising the amino acid sequence of SEQ ID NO: 72; and (b) a light chain variable region comprising the amino acid sequence of SEQ ID NO: 144.

In one particular embodiment, the polynucleotide of the present invention comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 57-64. In another embodiment, the polynucleotide of the present invention comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 129-136.

The antibody or antigen binding molecule encoded by the polypeptide of the present invention can be single chained or double chained. In some embodiments, the antibody or antigen binding molecule comprises is single chained. In certain embodiments, the antigen binding molecule is selected from the group consisting of an scFv, an Fab, an Fab', an Fv, an F(ab')2, a dAb, and any combination thereof. In one particular embodiment, the antibody or antigen binding molecule comprises an scFv.

In certain embodiments, the antibody or antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises at least about 18 amino acids. In certain embodiments, the linker comprises an amino acid sequence that is at least about 75%, at least about 85%, at least about 85%, at least about 90%, at least about 95%, at least about 96%, at least about 97%, at least about 98%, at least about 99%, or 100% identical to the amino acid sequence GSTSGSGKPGSGEGSTKG (SEQ ID NO: 174) or a poly-Gly linker such as the amino acid sequence GGGGSGGGGSGGGGS (SEQ ID NO: 268). Or GGGGSGGGGSGGGGSGGGGS (SEQ ID NO: 411). In one embodiment, the linker is a Whitlow linker. In certain embodiments, the antibody or antigen binding molecule comprises a single chain, wherein the heavy chain variable region and the light chain variable region are connected by a linker, wherein the linker comprises the amino acid sequence of SEQ ID NO: 174.

In some embodiments, the antibody or antigen binding molecules of the present invention specifically bind BCMA (e.g., hBCMA). In certain embodiments, an anti-BCMA antibody or antigen binding molecule of the present invention binds human BCMA with a $K_D$ of less than $1\times10^{-6}$ M, less than $1\times10^{-7}$ M, less than $1\times10^{-8}$ M, or less than $1\times10^{-9}$ M. In one particular embodiment, the anti-BCMA antibody or antigen binding molecules binds human BCMA with a $K_D$ of less than $1\times10^{-7}$ M. In another embodiment, the anti-BCMA antibody or antigen binding molecules binds human BCMA with a $K_D$ of less than $1\times10^{-8}$ M. In some embodiments, the anti-BCMA antibody or antigen binding molecules binds human BCMA with a $K_D$ of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-10}$ M. In certain embodiments, the $K_D$ is calculated as the quotient of $k_{off}/k_{on}$, and the $k_{on}$ and $k_{off}$ are determined using a monovalent antibody, such as a Fab fragment, as measured by, e.g., BIAcore® surface plasmon resonance technology. In other embodiments, the $K_D$ is calculated as the quotient of $k_{off}/k_{on}$, and the $k_{on}$ and $k_{off}$ are determined using a bivalent antibody, such as a Fab fragment, as measured by, e.g., BIAcore® surface plasmon resonance technology.

In other embodiments, the anti-BCMA antibody or antigen binding molecule binds human BCMA-Fc with a $K_D$ of less than $1\times10^{-9}$ M, less than $3\times10^{-9}$ M, less than $5\times10^{-9}$ M, less than $1\times10^{-10}$ M, less than $3\times10^{-10}$ M, or less than $5\times10^{-10}$ M. In other embodiments, the anti-BCMA antibody or antigen binding molecules binds cyno BCMA-Fc with a $K_D$ of less than $1\times10^{-5}$ M, less than $1\times10^{-6}$ M, less than $1\times10^{-7}$ M, less than $1\times10^{-8}$ M, less than $1\times10^{-9}$ M, or less than $1\times10^{-10}$ M.

In some embodiments, the anti-BCMA antibody or antigen binding molecule binds human BCMA with an association rate ($k_{on}$) of less than $1\times10^{-4}$ $M^{-1}$ $s^{-1}$, less than $2\times10^{-4}$ $M^{-1}$ $s^{-1}$ less than $3\times10^{-4}$ $M^{-1}$ $s^{-1}$ less than $4\times10^{-4}$ $M^{-1}$ $s^{-1}$ less than $5\times10^{-4}$ $M^{-1}$ $s^{-1}$ less than $6\times10^{-4}$ $M^{-1}$ $s^{-1}$, less than $7\times10^{-4}$ $M^{-1}$ $s^{-1}$, less than $8\times10^{-4}$ $M^{-1}$ $s^{-1}$, less than $9\times10^{-4}$ $M\text{-}s^{-1}$, less than $1\times10^{-5}$ $M^{-1}$ $s^{-1}$ less than $2\times10^{-5}$ $M^{-1}$ $s^{-1}$ less than $3\times10^{-5}$ $M^{-1}$ $s^{-1}$ less than $4\times10^{-5}$ $M^{-1}$ $s^{-1}$ less than $5\times10^{-5}$ $M^{-1}$ $s^{-1}$ less than $6\times10^{-5}$ $M^{-1}$ $s^{-1}$ less than $7\times10^{-5}$ $M^{-1}$ $s^{-1}$ less than $8\times10^{-5}$ $M^{-1}$ $s^{-1}$, less than $9\times10^{-5}$ $M^{-1}$ $s^{-1}$, less than $1\times10^{-6}$ $M^{-1}$ $s^{-1}$, less than $2\times10^{-6}$ $M^{-1}$ $s^{-1}$, less than $3\times10^{-6}$ $M^{-1}$ $s^{-1}$, less than $4\times10^{-6}$ $M^{-1}$ $s^{-1}$, less than $5\times10^{-6}$ $M^{-1}$ $s^{-1}$, less than $6\times10^{-6}$ $M^{-1}$ $s^{-1}$ less than $7\times10^{-6}$ $M^{-1}$ $s^{-1}$ less than $8\times10^{-6}$ $M^{-1}$ $s^{-1}$ less than $9\times10^{-6}$ $M^{-1}$ $s^{-1}$ or less than $1\times10^{-7}$ $M^{-1}$ $s^{-1}$. In certain embodiments, the $k_{on}$ is determined using a monovalent antibody, such as a Fab fragment, as measured by, e.g., BIAcore® surface plasmon resonance technology. In other embodiments, the $k_{on}$ is determined using a bivalent antibody as measured by, e.g., BIAcore® surface plasmon resonance technology.

In some embodiments, the anti-BCMA antibody or antigen binding molecule binds human BCMA with an dissociation rate ($k_{off}$) of less than $1\times10^{-2}$ $s^{-1}$, less than $2\times10^{-2}$ $s^{-1}$, less than $3\times10^{-2}$ $s^{-1}$, less than $4\times10^{-2}$ $s^{-1}$, less than $5\times10^{-2}$ $s^{-1}$, less than $6\times10^{-2}$ $s^{-1}$, less than $7\times10^{-2}$ $s^{-1}$, less than $8\times10^{-2}$ $s^{-1}$, less than $9\times10^{-2}$ $s^{-1}$, less than $1\times10^{-3}$ $s^{-1}$, less than $2\times10^{-3}$ $s^{-1}$, less than $3\times10^{-3}$ $s^{-1}$, less than $4\times10^{-3}$ $s^{-1}$, less than $5\times10^{-3}$ $s^{-1}$, less than $6\times10^{-3}$ $s^{-1}$, less than $7\times10^{-3}$ $s^{-1}$, less than $8\times10^{-3}$ $s^{-1}$, less than $9\times10^{-3}$ $s^{-1}$, less than $1\times10^{-4}$ $s^{-1}$, less than $2\times10^{-4}$ $s^{-1}$, less than $3\times10^{-4}$ $s^{-1}$, less than $4\times10^{-4}$ $s^{-1}$, less than $5\times10^{-4}$ $s^{-1}$, less than $6\times10^{-4}$ $s^{-1}$, less than $7\times10^{-4}$ $s^{-1}$, less than $8\times10^{-4}$ $s^{-1}$, less than $9\times10^{-4}$ $s^{-1}$, less than $1\times10^{-4}$ $s^{-1}$, or less than $5\times10^{-4}$ $s^{-1}$ In certain embodiments, the $k_{off}$ is determined using a monovalent antibody, such as a Fab fragment, as measured by, e.g., BIAcore® surface plasmon resonance technology. In other embodiments, the $k_{off}$ is determined using a bivalent antibody as measured by, e.g., BIAcore® surface plasmon resonance technology.

In some embodiments, the polynucleotide of the present invention encodes an antibody or antigen binding molecule that specifically binds to BCMA, wherein the antibody or antigen binding molecule cross competes with a reference antibody disclosed herein. In certain embodiments, the antibody or antigen binding molecule cross competes with a reference antibody comprising an amino acid sequence selected from the group consisting of SEQ ID NOs: 1-56, 65-128, and 137-144. In some embodiments, the antibody or antigen binding molecule cross competes with a reference antibody comprising an amino acid sequence selected from the group consisting of SEQ ID NOs: 65-72 and 137-144. In certain embodiments, the antibody or antigen binding molecule cross competes with a reference antibody, wherein the reference antibody comprises a VH CDR1 comprising an amino acid sequence selected from the group consisting of SEQ ID NOs: 9-16. In certain embodiments, the antibody or antigen binding molecule cross competes with a reference antibody, wherein the reference antibody comprises a VH CDR2 comprising an amino acid sequence selected from the group consisting of SEQ ID NOs: 25-32. In certain embodiments, the antibody or antigen binding molecule cross competes with a reference antibody, wherein the reference antibody comprises a VH CDR3 comprising an amino acid sequence selected from the group consisting of SEQ ID NOs: 41-48. In some embodiments, the antibody or antigen binding molecule cross competes with a reference antibody, wherein the reference antibody comprises a VL CDR1 comprising an amino acid sequence selected from the group consisting of SEQ ID NOs: 89-96. In certain embodiments, the antibody or antigen binding molecule cross competes with a reference antibody, wherein the reference antibody comprises a VL CDR2 comprising an amino acid sequence selected from the group consisting of SEQ ID NOs: 105-112. In certain embodiments, the antibody or antigen binding molecule cross competes with a reference antibody, wherein the reference antibody comprises a VL CDR3 comprising an amino acid sequence selected from the group consisting of SEQ ID NOs: 121-128. In one embodiment, the antibody or antigen binding molecule cross competes with a reference antibody, wherein the reference antibody comprises a VH comprising an amino acid sequence selected from the group consisting of SEQ ID NOs: 65-72. In another embodiment, the antibody or antigen binding molecule cross competes with a reference antibody, wherein the reference antibody comprises a VL comprising an amino acid sequence selected from the group consisting of SEQ ID NOs: 137-144.

In some embodiments, the polynucleotide of the present invention encodes an antibody or antigen binding molecule that specifically binds to BCMA, wherein the antibody or antigen binding molecule binds the same or an overlapping epitope as a reference antibody disclosed herein (e.g., FIG. 1). In certain embodiments, the antibody or antigen binding molecule binds the same or an overlapping epitope as a reference antibody comprising an amino acid sequence selected from the group consisting of SEQ ID NOs: 1-56, 65-128, and 137-144. In some embodiments, the antibody or antigen binding molecule binds the same or an overlapping epitope as a reference antibody comprising an amino acid sequence selected from the group consisting of SEQ ID NOs: 65-72 and 137-144.

III Polynucleotides Encoding Chimeric Antigen Receptors and T Cell Receptors

The present invention is also directed to polynucleotides encoding chimeric antigen receptors (CARs) or T cell receptors (TCRs) comprising an antigen binding molecule that specifically binds to BCMA described in Section II, and engineered T cells comprising an antigen binding molecule that specifically binds to BCMA described in Section II. In some embodiments, an anti-BCMA CAR or TCR encoded by the polynucleotide of the present invention comprises an antigen binding molecule that specifically binds to BCMA. In some embodiments, the anti-BCMA CAR or TCR encoded by the polynucleotide further comprises a costimulatory domain. In some embodiments, the costimulatory domain in the anti-BCMA CAR or TCR encoded by the polynucleotide comprises an extracellular domain (i.e., a hinge region), a transmembrane domain, and/or an intracellular (signaling) domain. In some embodiments, the anti-BCMA CAR or TCR encoded by the polynucleotide further comprises a CD3 zeta activating domain. In one particular embodiment, the anti-BCMA CAR or TCR encoded by the polynucleotide comprises an antigen binding molecule that specifically binds BCMA (e.g., hBCMA), a costimulatory domain comprising an extracellular domain, a transmembrane domain, and an intracellular domain, and a CD3 zeta activating domain.

In some embodiments, the polynucleotide of the present invention encodes a TCR, wherein the TCR comprises an antigen binding molecule that specifically binds to BCMA, and wherein the TCR further comprises a fourth complementarity determining region (CDR4). In certain embodiments, the polynucleotide encodes a TCR, wherein the TCR comprises an antigen binding molecule that specifically binds to BCMA, and a constant region. In some embodiments, the constant region is selected from a constant region of IgG1, IgG2, IgG3, IgG4, IgA, IgD, IgE, and IgM.

III.A. Costimulatory Domain

In some embodiments, the polynucleotide of the present invention encodes a CAR, wherein the CAR comprises an antigen binding molecule that specifically binds to BCMA (one or more antigen binding molecules in Section II), and wherein the CAR further comprises a costimulatory domain. In some embodiments, the costimulatory domain is positioned between the antigen binding molecule and an activating domain. In certain embodiments, the costimulatory domain can comprise an extracellular domain, a transmembrane domain, and an intracellular signaling domain.

Extracellular Domain: In one embodiment, the extracellular domain comprises a hinge region (e.g., a spacer region). In another embodiment, the extracellular domain is from or derived from (e.g., comprises) CD28, CD28T, OX40, 4-1BB/CD137, CD2, CD3 (alpha, beta, delta, epsilon, gamma, zeta), CD4, CD5, CD7, CD8, CD9, CD16, CD22, CD27, CD30, CD 33, CD37, CD40, CD 45, CD64, CD80, CD86, CD134, CD137, CD154, programmed death-1 (PD-1), ICOS, April, BAFF, lymphocyte function-associated antigen-1 (LFA-1 (CDl la/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CDl-ld, ITGAE, CD103, ITGAL, CDl-la, LFA-1, ITGAM, CDl-lb, ITGAX, CDl-lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. The extracellular domain can be derived either from a natural or from a synthetic source.

In some embodiments, the extracellular domain in the costimulatory domain is positioned between the antigen binding molecule and the transmembrane domain. In certain embodiments, the extracellular domain in the costimulatory domain is from or derived from an immunoglobulin. In some embodiments, the extracellular domain in the costimulatory domain is selected from the hinge regions of IgG1, IgG2, IgG3, IgG4, IgA, IgD, IgE, and IgM, or a fragment thereof. In other embodiments, the extracellular domain in the costimulatory domain is from or derived from the hinge region of CD8 alpha. In one particular embodiment, the extracellular domain in the costimulatory domain is from or derived from the hinge region of CD28. In certain embodiments, the extracellular domain in the costimulatory domain comprises a fragment of the hinge region of CD8 alpha or a fragment of the hinge region of CD28, wherein the fragment is anything less than the whole hinge region. In some embodiments, the fragment of the CD8 alpha hinge region or the fragment of the CD28 hinge region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge region of the CD28 hinge region.

In certain embodiments, the extracellular domain in the costimulatory domain comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence LDNEKSNGTIIHVKGKHLCPSPLFPGPSKP (SEQ ID NO: 167) or a fragment thereof. In some embodiments, the extracellular domain in the costimulatory domain comprises the amino acid sequence of SEQ ID NO: 167 or a fragment thereof.

In certain embodiments, the extracellular domain in the costimulatory domain is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence CTTGATAATGAAAAGTCAAACGGAACAATCATT CACGTGAAGGGCAAGCACCTCTGTCCGTCACCCTTGTTCCCTGGTCCATCCAAGCCA (SEQ ID NO: 166) or a fragment thereof. In some embodiments, the extracellular domain in the costimulatory domain is encoded by a nucleotide sequence that comprises the nucleotide sequence of SEQ ID NO: 166 or a fragment thereof.

In some embodiments, the CD28T domain is derived from a human CD28 hinge region. In other embodiments, the CD28T domain is derived from a rodent, murine, or primate (e.g., non-human primate) CD28 hinge region. In some embodiments, the CD28T domain is derived from a chimeric CD28 hinge region.

In some embodiments, the extracellular domain comprises some or all of a member of the immunoglobulin family such as IgG1, IgG2, IgG3, IgG4, IgA, IgD, IgE, IgM, or fragment thereof.

Transmembrane Domain: The costimulatory domain for the CAR or TCR of the invention can further comprise a transmembrane domain. The transmembrane domain can be designed to be fused to the extracellular domain in the costimulatory domain. It can similarly be fused to the intracellular domain in the costimulatory domain. In one embodiment, the transmembrane domain that naturally is associated with one of the domains in a CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain can be derived from any membrane-bound or transmembrane protein. In some embodiments, the transmembrane domain is derived from CD28, OX-40, 4-1BB/CD137, CD2, CD3 (alpha, beta, delta, epsilon, zeta), CD4, CD5, CD7, CD8, CD9, CD16, CD22, CD27, CD30, CD 33, CD37, CD40, CD 45, CD64, CD80, CD86, CD134, CD137, CD154, programmed death-1 (PD-1), ICOS, lymphocyte function-associated antigen-1 (LFA-1 (CDl la/CD18), CD3 gamma, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CDl-ld, ITGAE, CD103, ITGAL, CDl-la, LFA-1, ITGAM, CDl-lb, ITGAX, CDl-lc, ITGBl, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, CD83 ligand, or a fragment thereof.

Optionally, a short oligo or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain in the CAR of the invention comprises the CD8 transmembrane domain. In one embodiment, the CD8 transmembrane domain comprises the transmembrane portion of the nucleic acid sequence of GCTGCAGCATTGAGCAACTCAATAATGTATTTTAGTCACTTTGTACCAGTGTTCTTGCCGGCTAAGCCTACTACCACACCCGCTCCACGGCCACCTACCCCAGCTCCTA CCATCGCTTCACAGCCTCTGTCCCTGCGCCCAGAGGCTTGCCGACCGGCCGCAG GGGGCGCTGTTCATACCAGAGGACTGGATTTCGCCTGCGATATCTATATCTGGG CACCCCTGGCCGGAACCTGCGGCGTACTCCTGCTGTCCCTGGTCATCACGCTCT ATTGTAATCACAGGAAC (SEQ ID NO: 269). In one embodiment, the CD8 transmembrane domain comprises the nucleic acid sequence that encodes the transmembrane amino acid sequence contained within AAALSNSIMYFSHFVPVFLPAKPTTTPAPRPPTPAPTIASQP LSLRPEACRPAAGGAVHTRGLDFACDIYI-WAPLAGTCGVLLLSLVITLYCNHRN (SEQ ID NO: 270).

In another embodiment, the transmembrane domain in the costimulating domain is a CD28 transmembrane domain. In some embodiments, the transmembrane domain comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence FWVLVVVGGVLACYSLL-VTVAFIIFWV (SEQ ID NO: 169). In some embodiments, the transmembrane domain comprises the amino acid sequence of SEQ ID NO: 169.

In some embodiments, the transmembrane domain is encoded by a nucleotide sequence at least about 75%, at least about 80%, at least about 85%, at least about 90%, at least about 95%, at least about 96%, at least about 97%, at least about 98%, at least about 99%, or 100% identical to the nucleotide sequence TTCTGGGTGTTGGTCGTAGTGGGTG-GAGTCCTCGCTTGTTACTCTCTGCTCGTCA CCGTGGCTTTTATAATCTTCTGGGTT (SEQ ID NO: 168). In some embodiments, the transmembrane domain is encoded by a nucleotide sequence that comprises the nucleotide sequence of SEQ ID NO: 168.

Intracellular (signaling) Domain: The intracellular (signaling) domain of the engineered T cells of the invention can provide signaling to an activating domain, which then activates at least one of the normal effector functions of the immune cell. Effector function of a T cell, for example, can be cytolytic activity or helper activity including the secretion of cytokines.

In certain embodiments, suitable intracellular signaling domain include (i.e., comprise), but are not limited to CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CDl-la/CD18), CD3 gamma, CD3 delta, CD3 epsilon, CD247, CD276 (B7-H3), LIGHT, (TNFSF14), NKG2C, Ig alpha (CD79a), DAP-10, Fe gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGBl, CD29, ITGB2, CD18, LFA-1, ITGB7, NKG2D, TNFR2, TRANCE/ RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

An example of a nucleotide sequence encoding the intracellular signaling domain is set forth in SEQ ID NO: 170:

AGATCCAAAAGAAGCCGCCTGCTCCATAGCGATTACATGAATATGACTC

CACGCCGCCCTGGCCCCACAAGGAAACACTACCAGCCTTACGCACCACC

TAGAGATTTCGCTGCCTATCGGAGC

In one embodiment, the polynucleotide encoding an intracellular signaling domain within a costimulatory domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 170.

An example of an intracellular signaling domain is set forth in SEQ ID NO: 171:

RSKRSRLLHSDYMNMTPRRPGPTRKHYQPYAPPRDFAAYRS.

In one particular embodiment, the intracellular signaling domain within a costimulatory domain comprises an amino acid sequence at least about 80%, at least about 85%, at least about 90%, at least about 95%, at least about 96%, at least about 97%, at least about 98%, at least about 99%, or about 100% identical to the amino acid sequence of SEQ ID NO: 171.

The intracellular signaling sequences within the CAR of the invention can be linked to each other or to an activating domain in a random or specified order. Optionally, a short oligo- or polypeptide linker, preferably between 2 and 10 amino acids in length may form the linkage. A glycine-serine doublet provides a particularly suitable linker.

It will further be appreciated that where desired, the costimulatory regions described herein can be expressed in a separate chain from the antigen binding molecule (e.g., scFv) and activating domains, in so-called "trans" configuration.

III.B Activating Domain

In some embodiments, intracellular domains for use in the engineered T cell of the invention include cytoplasmic sequences of the T cell receptor (TCR) and co-receptors that act in concert to initiate signal transduction following antigen/receptor engagement, as well as any derivative or variant of these sequences and any synthetic sequence that has the same functional capability. CD3 is an element of the T cell receptor on native T cells, and has been shown to be an important intracellular activating element in CARs. In one embodiment, the activating domain is CD3, e.g., CD3 zeta, the nucleotide sequence of which is set forth in SEQ ID NO. 172:

AGGGTGAAGTTTTCCAGATCTGCAGATGCACCAGCGTATCAGCAGGGCC

AGAACCAACTGTATAACGAGCTCAACCTGGGACGCAGGGAAGAGTATG

ACGTTTTGGACAAGCGCAGAGGACGGGACCCTGAGATGGGTGGCAAACC

AAGACGAAAAAACCCCCAGGAGGGTCTCTATAATGAGCTGCAGAAGGA

TAAGATGGCTGAAGCCTATTCTGAAATAGGCATGAAAGGAGAGCGGAG

AAGGGGAAAAGGGCACGACGGTTTGTACCAGGGACTCAGCACTGCTACG

AAGGATACTTATGACGCTCTCCACATGCAAGCCCTGCCACCTAGG.

In some embodiments, the polynucleotide encoding an activating domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 172.

The corresponding amino acid of intracellular CD3 zeta is set forth in SEQ ID NO. 173:

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

In some embodiments, the activating domain comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of SEQ ID NO: 173.

Additionally, in certain embodiments the activating domain comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of a CD3 zeta variant as set forth in SEQ ID NO: 412:

RVKFSRSADAPAYKQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR

III.C. Leader Peptide

In some embodiments, the polynucleotide of the present invention encodes a CAR or a TCR, wherein the CAR or the TCR comprises an antigen binding molecule that specifically binds to BCMA, and wherein the CAR or the TCR further comprises a leader peptide (also referred to herein as a "signal peptide"). In certain embodiments, the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence MALPVTALLL-PLALLLHAARP (SEQ ID NO: 165). In some embodiments, the signal peptide comprises the amino acid sequence of SEQ ID NO: 165. In some embodiments, the leader peptide is encoded by a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to SEQ ID NO: 164.

In some embodiments, the polynucleotide of the present invention encodes a CAR, wherein the CAR comprises a leader peptide (P), an antigen binding molecule (B), a hinge domain (H), a transmembrane domain (T), a costimulatory region (C), and an activation domain (A), wherein the CAR is configured according to the following: P-B-H-T-C-A. In some embodiments, the antigen binding molecule comprises a VH and a VL, wherein the CAR is configured according to the following: P-VH-VL-H-T-C-A or P-VL-VH-H-T-C-A. In some embodiments, the VH and the VL are connected by a linker (L), wherein the anti-BCMA CAR is configured according to the following, from N-terminus to C-terminus: P-VH-L-VL-H-T-C-A or P-VH-L-VL-H-T-C-A.

In some embodiments, the polynucleotide of the present invention encodes a CAR, wherein the CAR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence selected from Table 2. In certain embodiments, the polynucleotide of the present invention encodes a CAR, wherein the CAR comprises an amino acid sequence selected from Table 2.

TABLE 2

Example CAR Sequences

| Anti-BCMA CAR | Nucleotide Sequence | SEQ ID NO: | Amino Acid Sequence | SEQ ID NO: |
|---|---|---|---|---|
| FS-21495CAR HxL | ATGGCACTCCCCGTAACTGCTCTGCTGCTGCCGTTGGCATTG CTCCTGCACGCCGCACGCCCGGAGGTGCAGCTGTTGGAGTCT GGGGGAGGCTTGGTACAGCCTGGGGGGTCCCTGAGACTCTCC TGTGCAGCCTCTGGATTCACCTTTAGCAGCTATGCCATGAGC TGGGTCCGCCAGGCTCCAGGGAAGGGGCTGGAGTGGGTCTCA GCTATTAGTGGTAGTGGTGGTAGCACATACTACGCAGACTCC GTGAAGGGCCGGTTCACCATCTCCAGAGACAATTCCAAGAAC ACGCTGTATCTGCAAATGAACAGCCTGAGAGCCGAGGACACG GCGGTGTACTACTGCGCAAGAGCCGAGATGGGAGCCGTATTC GACATATGGGGTCAGGGTACAATGGTCACCGTCTCCTCAGGG TCTACATCCGGCTCCGGGAAGCCCGGAAGTGGCGAAGGTAGT ACAAAGGGGGAAATTGTGTTGACACAGTCTCCAGCCACCCTG TCTTTGTCTCCAGGGGAAAGAGCCACCCTCTCCTGCAGGGCC AGTCAGAGTGTTAGCAGGTACTTAGCCTGGTACCAACAGAAA CCTGGCCAGGCTCCCAGGCTCCTCATCTATGATGCATCCAAC AGGGCCACTGGCATCCCAGCCAGGTTCAGTGGCAGTGGGTCT GGGACAGACTTCACTCTCACCATCAGCAGCCTAGAGCCTGAA GATTTTGCAGTTTATTACTGTCAGCAGAGAATCTCCTGGCCT TTCACTTTTGGCGGAGGGACCAAGGTTGAGATCAAACGGGCC GCTGCCCTTGATAATGAAAAGTCAAACGGAACAATCATTCAC GTGAAGGGCAAGCACCTCTGTCCGTCACCCTTGTTCCCTGGT CCATCCAAGCCATTCTGGGTGTTGGTCGTAGTGGGTGGAGTC CTCGCTTGTTACTCTCTGCTCGTCACCGTGGCTTTTATAATC TTCTGGGTTAGATCCAAAAGAAGCCGCCTGCTCCATAGCGAT TACATGAATATGACTCCACGCCGCCCTGGCCCCACAAGGAAA CACTACCAGCCTTACGCACCACCTAGAGATTTCGCTGCCTAT CGGAGCAGGGTGAAGTTTTCCAGATCTGCAGATGCACCAGCG TATCAGCAGGGCCAGAACCAACTGTATAACGAGCTCAACCTG GGACGCAGGGAAGAGTATGACGTTTTGGACAAGCGCAGAGGA CGGGACCCTGAGATGGGTGGCAAACCAAGACGAAAAAACCCC CAGGAGGGTCTCTATAATGAGCTGCAGAAGGATAAGATGGCT GAAGCCTATTCTGAAATAGGCATGAAAGGAGAGCGGAGAAGG GGAAAAGGGCACGACGGTTTGTACCAGGGACTCAGCACTGCT ACGAAGGATACTTATGACGCTCTCCACATGCAAGCCCTGCCA CCTAGGTAA | 175 | MALPVTALLLPLALLLHAA RPEVQLLESGGGLVQPGGS LRLSCAASGFTFSSYAMSW VRQAPGKGLEWVSAISGSG GSTYYADSVKGRFTISRDN SKNTLYLQMNSLRAEDTAV YYCARAEMGAVFDIWGQGT MVTVSSGSTSGSGKPGSGE GSTKGEIVLTQSPATLSLS PGERATLSCRASQSVSRYL AWYQQKPGQAPRLLIYDAS NRATGIPARFSGSGSGTDF TLTISSLEPEDFAVYYCQQ RISWPFTFGGGTKVEIKRA AALDNEKSNGTIIHVKGKH LCPSPLFPGPSKPFWVLVV VGGVLACYSLLVTVAFIIF WVRSKRSRLLHSDYMNMTP RRPGPTRKHYQPYAPPRDF AAYRSRVKFSRSADAPAYQ QGQNQLYNELNLGRREEYD VLDKRRGRDPEMGGKPRRK NPQEGLYNELQKDKMAEAY SEIGMKGERRRGKGHDGLY QGLSTATKDTYDALHMQAL PPR | 176 |

TABLE 2-continued

Example CAR Sequences

| Anti-BCMA CAR | Nucleotide Sequence | SEQ ID NO: | Amino Acid Sequence | SEQ ID NO: |
| --- | --- | --- | --- | --- |
| FS-21495CAR LxH | ATGGCACTCCCCGTAACTGCTCTGCTGCTGCCGTTGGCATTG CTCCTGCACGCCGCACGCCCGGAAATTGTGTTGACACAGTCT CCAGCCACCCTGTCTTTGTCTCCAGGGGAAAGAGCCACCCTC TCCTGCAGGGCCAGTCAGAGTGTTAGCAGGTACTTAGCCTGG TACCAACAGAAACCTGGCCAGGCTCCCAGGCTCCTCATCTAT GATGCATCCAACAGGGCCACTGGCATCCCAGCCAGGTTCAGT GGCAGTGGGTCTGGGACAGACTTCACTCTCACCATCAGCAGC CTAGAGCCTGAAGATTTTGCAGTTTATTACTGTCAGCAGAGA ATCTCCTGGCCTTTCACTTTTGGCGGAGGGACCAAGGTTGAG ATCAAACGGGGGTCTACATCCGGCTCCGGGAAGCCCGGAAGT GGCGAAGGTAGTACAAAGGGGGAGGTGCAGCTGTTGGAGTCT GGGGGAGGCTTGGTACAGCCTGGGGGTCCCTGAGACTCTCC TGTGCAGCCTCTGGATTCACCTTTAGCAGCTATGCCATGAGC TGGGTCCGCCAGGCTCCAGGGAAGGGGCTGGAGTGGGTCTCA GCTATTAGTGGTAGTGGTGGTAGCACATACTACGCAGACTCC GTGAAGGGCCGGTTCACCATCTCCAGAGACAATTCCAAGAAC ACGCTGTATCTGCAAATGAACAGCCTGAGAGCCGAGGACACG GCGGTGTACTACTGCGCAAGAGCCGAGATGGGAGCCGTATTC GACATATGGGGTCAGGGTACAATGGTCACCGTCTCCTCAGCC GCTGCCCTTGATAATGAAAAGTCAAACGGAACAATCATTCAC GTGAAGGGCAAGCACCTCTGTCCGTCACCCTTGTTCCCTGGT CCATCCAAGCCATTCTGGGTGTTGGTCGTAGTGGGTGGAGTC CTCGCTTGTTACTCTCTGCTCGTCACCGTGGCTTTTATAATC TTCTGGGTTAGATCCAAAAGAAGCCGCCTGCTCCATAGCGAT TACATGAATATGACTCCACGCCGCCCTGGCCCCACAAGGAAA CACTACCAGCCTTACGCACCACCTAGAGATTTCGCTGCCTAT CGGAGCAGGGTGAAGTTTTCCAGATCTGCAGATGCACCAGCG TATCAGCAGGGCCAGAACCAACTGTATAACGAGCTCAACCTG GGACGCAGGGAAGAGTATGACGTTTTGGACAAGCGCAGAGGA CGGGACCCTGAGATGGGTGGCAAACCAAGACGAAAAAACCCC CAGGAGGGTCTCTATAATGAGCTGCAGAAGGATAAGATGGCT GAAGCCTATTCTGAAATAGGCATGAAAGGAGAGCGGAGAAGG GGAAAAGGGCACGACGGTTTGTACCAGGGACTCAGCACTGCT ACGAAGGATACTTATGACGCTCTCCACATGCAAGCCCTGCCA CCTAGGTAA | 177 | MALPVTALLLPLALLLHAA RPEIVLTQSPATLSLSPGE RATLSCRASQSVSRYLAWY QQKPGQAPRLLIYDASNRA TGIPARFSGSGSGTDFTLT ISSLEPEDFAVYYCQQRIS WPFTFGGGTKVEIKRGSTS GSGKPGSGEGSTKGEVQLL ESGGGLVQPGGSLRLSCAA SGFTFSSYAMSWVRQAPGK GLEWVSAISGSGGSTYYAD SVKGRFTISRDNSKNTLYL QMNSLRAEDTAVYYCARAE MGAVFDIWGQGTMVTVSSA AALDNEKSNGTIIHVKGKH LCPSPLFPGPSKPFWVLVV VGGVLACYSLLVTVAFIIF WVRSKRSRLLHSDYMNMTP RRPGPTRKHYQPYAPPRDF AAYRSRVKFSRSADAPAYQ QGQNQLYNELNLGRREEYD VLDKRRGRDPEMGGKPRRK NPQEGLYNELQKDKMAEAY SEIGMKGERRRGKGHDGLY QGLSTATKDTYDALHMQAL PPR | 178 |
| PC-21497CAR HxL | ATGGCACTCCCCGTAACTGCTCTGCTGCTGCCGTTGGCATTG CTCCTGCACGCCGCACGCCCGCAGGTGCAGCTGGTGGAGTCT GGGGGAGGCGTGGTCCAGCCTGGGAGGTCCCTGAGACTCTCC TGTGCAGCGTCTGGATTCACCTTCAGTAGCTATGGCATGCAC TGGGTCCGCCAGGCTCCAGGCAAGGGGCTGGAGTGGGTGGCA GTTATATCGTATGATGGAAGTAATAAATACTATGCAGACTCC GTGAAGGGCCGATTCACCATCTCCAGAGACAATTCCAAGAAC ACGCTGTATCTGCAAATGAACAGCCTGAGAGCCGAGGACACG GCGGTGTACTACTGCGCCAGAGACGGTTACTTATCTAGGTGGT CTCTGGTACTTCGACTTATGGGGAGAGGTACCTTGGTCACC GTCTCCTCAGGGTCTACATCCGGCTCCGGGAAGCCCGGAAGT GGCGAAGGTAGTACAAAGGGGGATATTGTGATGACTCAGTCT CCACTCTCCCTGCCCGTCACCCCTGGAGAGCCGGCCTCCATC TCCTGCAGGTCTAGTCAGAGCCTCCTGCATAGTAATGGATAC AACTATTTGGATTGGTACCTGCAGAAGCCAGGGCAGTCTCCA CAGCTCCTGATCTATTTGGGTTCTAATCGGGCCTCCGGGGTC CCTGACAGGTTCAGTGGCAGTGGATCAGGCACAGATTTTACA CTGAAAATCAGCAGAGTGGAGGCTGAGGATGTTGGGGTTTAT TACTGCATGCAGGGTCTGGGCCTCCCTCTCACTTTTGGCGGA GGGACCAAGGTTGAGATCAAACGGGCCGCTGCCCTTGATAAT GAAAAGTCAAACGGAACAATCATTCACGTGAAGGGCAAGCAC CTCTGTCCGTCACCCTTGTTCCCTGGTCCATCCAAGCCATTC TGGGTGTTGGTCGTAGTGGGTGGAGTCCTCGCTTGTTACTCT CTGCTCGTCACCGTGGCTTTTATAATCTTCTGGGTTAGATCC AAAAGAAGCCGCCTGCTCCATAGCGATTACATGAATATGACT CCACGCCGCCCTGGCCCCACAAGGAAACACTACCAGCCTTAC GCACCACCTAGAGATTTCGCTGCCTATCGGAGCAGGGTGAAG TTTTCCAGATCTGCAGATGCACCAGCGTATCAGCAGGGCCAG AACCAACTGTATAACGAGCTCAACCTGGGACGCAGGGAAGAG TATGACGTTTTGGACAAGCGCAGAGGACGGGACCCTGAGATG GGTGGCAAACCAAGACGAAAAAACCCCCAGGAGGGTCTCTAT AATGAGCTGCAGAAGGATAAGATGGCTGAAGCCTATTCTGAA ATAGGCATGAAAGGAGAGCGGAGAAGGGGAAAAGGGCACGAC GGTTTGTACCAGGGACTCAGCACTGCTACGAAGGATACTTAT GACGCTCTCCACATGCAAGCCCTGCCACCTAGGTAA | 179 | MALPVTALLLPLALLLHAA RPQVQLVESGGGVVQPGRS LRLSCAASGFTFSSYGMHW VRQAPGKGLEWVAVISYDG SNKYYADSVKGRFTISRDN SKNTLYLQMNSLRAEDTAV YYCARDGTYLGGLWYFDLW GRGTLVTVSSGSTSGSGKP GSGEGSTKGDIVMTQSPLS LPVTPGEPASISCRSSQSL LHSNGYNYLDWYLQKPGQS PQLLIYLGSNRASGVPDRF SGSGSGTDFTLKISRVEAE DVGVYYCMQGLGLPLTFGG GTKVEIKRAAALDNEKSNG TIIHVKGKHLCPSPLFPGP SKPFWVLVVVGGVLACYSL LVTVAFIIFWVRSKRSRLL HSDYMNMTPRRPGPTRKHY QPYAPPRDFAAYRSRVKFS RSADAPAYQQGQNQLYNEL NLGRREEYDVLDKRRGRDP EMGGKPRRKNPQEGLYNEL QKDKMAEAYSEIGMKGERR RGKGHDGLYQGLSTATKDT YDALHMQALPPR | 180 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| PC-21497CAR HxL | ATGGCACTCCCCGTAACTGCTCTGCTGCTGCCGTTGGCATTG CTCCTGCACGCCGCACGCCCGGATATTGTGATGACTCAGTCT CCACTCTCCCTGCCCGTCACCCCTGGAGAGCCGGCCTCCATC TCCTGCAGGTCTAGTCAGAGCCTCCTGCATAGTAATGGATAC AACTATTTGGATTGGTACCTGCAGAAGCCAGGGCAGTCTCCA CAGCTCCTGATCTATTTGGGTTCTAATCGGGCCTCCGGGGTC CCTGACAGGTTCAGTGGCAGTGGATCAGGCACAGATTTTACA CTGAAAATCAGCAGAGTGGAGGCTGAGGATGTTGGGGTTTAT TACTGCATGCAGGGACTCGGCCTCCCTCTCACTTTTGGCGGA GGGACCAAGGTTGAGATCAAACGGGGGTCTACATCCGGCTCC GGGAAGCCCGGAAGTGGCGAAGGTAGTACAAAGGGGCAGGTG CAGCTGGTGGAGTCTGGGGGAGGCGTGGTCCAGCCTGGAGG TCCCTGAGACTCTCCTGTGCAGCGTCTGGATTCACCTTCAGT AGCTATGGCATGCACTGGGTCCGCCAGGCTCCAGGCAAGGGG CTGGAGTGGGTGGCAGTTATATCGTATGATGGAAGTAATAAA TACTATGCAGACTCCGTGAAGGGCCGATTCACCATCTCCAGA GACAATTCCAAGAACACGCTGTATCTGCAAATGAACAGCCTG AGAGCCGAGGACACGGCGGTGTACTACTGCGCCAGACGGT ACTTATCTAGGTGGTCTCTGGTACTTCGACTTATGGGGGAGA GGTACCTTGGTCACCGTCTCCTCAGCCGCTGCCCTTGATAAT GAAAAGTCAAACGGAACAATCATTCACGTGAAGGGCAAGCAC CTCTGTCCGTCACCCTTGTTCCTGGTCCATCCAAGCCATTC TGGGTGTTGGTCGTAGTGGGTGGAGTCCTCGCTTGTTACTCT CTGCTCGTCACCGTGGCTTTTATAATCTTCTGGGTTAGATCC AAAAGAAGCCGCCTGCTCCATAGCGATTACATGAATATGACT CCACGCGCCCCTGGCCCCACAAGGAAACACTACCAGCCTTAC GCACCACCTAGAGATTTCGCTGCCTATCGGAGCAGGGTGAAG TTTTCCAGATCTGCAGATGCACCAGCGTATCAGCAGGGCCAG AACCAACTGTATAACGAGCTCAACCTGGGACGCAGGGAAGAG TATGACGTTTTGGACAAGCGCAGAGGACGGGACCCTGAGATG GGTGGCAAACCAAGACGAAAAAACCCCCAGGAGGGTCTCTAT AATGAGCTGCAGAAGGATAAGATGGCTGAAGCCTATTCTGAA ATAGGCATGAAAGGAGAGCGGAGAAGGGGAAAAGGGCACGAC GGTTTGTACCAGGGACTCAGCACTGCTACGAAGGATACTTAT GACGCTCTCCACATGCAAGCCCTGCCACCTAGGTAA | 181 | MALPVTALLLPLALLLHAA RPDIVMTQSPLSLPVTPGE PASISCRSSQSLLHSNGYN YLDWYLQKPGQSPQLLIYL GSNRASGVPDRFSGSGSGT DFTLKISRVEAEDVGVYYC MQGLGLPLTFGGGTKVEIK RGSTSGSGKPGSGEGSTKG QVQLVESGGGVVQPGRSLR LSCAASGFTFSSYGMHWVR QAPGKGLEWVAVISYDGSN KYYADSVKGRFTISRDNSK NTLYLQMNSLRAEDTAVYY CARDGTYLGGLWYFDLWGR GTLVTVSSAAALDNEKSNG TIIHVKGKHLCPSPLFPGP SKPFWVLVVVGGVLACYSL LVTVAFIIFWVRSKRSRLL HSDYMNMTPRRPGPTRKHY QPYAPPRDFAAYRSRVKFS RSADAPAYQQGQNQLYNEL NLGRREEYDVLDKRRGRDP EMGGKPRRKNPQEGLYNEL QKDKMAEAYSEIGMKGERR RGKGHDGLYQGLSTATKDT YDALHMQALPPR | 182 |
| AJ-21508CAR HxL | ATGGCACTCCCCGTAACTGCTCTGCTGCTGCCGTTGGCATTG CTCCTGCACGCCGCACGCCCGCAGGTGCAGCTGGTGCAGTCT GGGGCTGAGGTGAAGAAGCCTGGGGCCTCAGTGAAGGTTTCC TGCAAGGCATCTGGATACACCTTCACCAGCTACTATATGCAC TGGGTGCGACAGGCCCCTGGACAAGGGCTTGAGTGGATGGGA ATAATCAACCCTGGTGGTGGTAGCACAAGCTACGCACAGAAG TTCCAGGGCAGAGTCACCATGACCAGGGACACGTCCACGAGC ACAGTCTACATGGAGCTGAGCAGCCTGAGATCTGAGGACACG GCGGTGTACTACTGCGCCAGAGAGAGTTGGCCAATGGACGTA TGGGGCCAGGGAACAACTGTCACCGTCTCCTCAGGGTCTACA TCCGGCTCCGGGAAGCCCGGAAGTGGCGAAGGTAGTACAAAG GGGGAAATAGTGATGACGCAGTCTCCAGCCACCCTGTCTGTG TCTCCAGGGGAAAGAGCCACCCTCTCCTGCAGGGCCAGTCAG AGTGTTAGCAGCAACTTAGCCTGGTACCAGCAGAAACCTGGC CAGGCTCCCAGGCTCCTCATCTATGGTGCATCCACCAGGGCC ACTGGTATCCCAGCCAGGTTCAGTGGCAGTGGGTCTGGGACA GAGTTCACTCTCACCATCAGCAGCCTGCAGTCTGAAGATTTT GCAGTTTATTACTGTCAGCAGTACGCCGCCTACCCTACTTTT GGCGGAGGGACCAAGGTTGAGATCAAACGGGCCGCTGCCCTT GATAATGAAAAGTCAAACGGAACAATCATTCACGTGAAGGGC AAGCACCTCTGTCCGTCACCCTTGTTCCTGGTCCATCCAAG CCATTCTGGGTGTTGGTCGTAGTGGGTGGAGTCCTCGCTTGT TACTCTCTGCTCGTCACCGTGGCTTTTATAATCTTCTGGGTT AGATCCAAAAGAAGCCGCCTGCTCCATAGCGATTACATGAAT ATGACTCCACGCGCCCCTGGCCCCACAAGGAAACACTACCAG CCTTACGCACCACCTAGAGATTTCGCTGCCTATCGGAGCAGG GTGAAGTTTTCCAGATCTGCAGATGCACCAGCGTATCAGCAG GGCCAGAACCAACTGTATAACGAGCTCAACCTGGGACGCAGG GAAGAGTATGACGTTTTGGACAAGCGCAGAGGACGGGACCCT GAGATGGGTGGCAAACCAAGACGAAAAAACCCCCAGGAGGGT CTCTATAATGAGCTGCAGAAGGATAAGATGGCTGAAGCCTAT TCTGAAATAGGCATGAAAGGAGAGCGGAGAAGGGGAAAAGGG CACGACGGTTTGTACCAGGGACTCAGCACTGCTACGAAGGAT ACTTATGACGCTCTCCACATGCAAGCCCTGCCACCTAGGTAA | 183 | MALPVTALLLPLALLLHAA RPQVQLVQSGAEVKKPGAS VKVSCKASGYTFTSYYMHW VRQAPGQGLEWMGIINPGG GSTSYAQKFQGRVTMTRDT STSTVYMELSSLRSEDTAV YYCARESWPMDVWGQGTTV TVSSGSTSGSGKPGSGEGS TKGEIVMTQSPATLSVSPG ERATLSCRASQSVSSNLAW YQQKPGQAPRLLIYGASTR ATGIPARFSGSGSGTEFTL TISSLQSEDFAVYYCQQYA AYPTFGGGTKVEIKRAAAL DNEKSNGTIIHVKGKHLCP SPLFPGPSKPFWVLVVVGG VLACYSLLVTVAFIIFWVR SKRSRLLHSDYMNMTPRRP GPTRKHYQPYAPPRDFAAY RSRVKFSRSADAPAYQQGQ NQLYNELNLGRREEYDVLD KRRGRDPEMGGKPRRKNPQ EGLYNELQKDKMAEAYSEI GMKGERRRGKGHDGLYQGL STATKDTYDALHMQALPPR | 184 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| AJ-21508CAR LxH | ATGGCACTCCCCGTAACTGCTCTGCTGCTGCCGTTGGCATTG CTCCTGCACGCCGCACGCCCGGAAATAGTGATGACGCAGTCT CCAGCCACCCTGTCTGTGTCTCCAGGGGAAAGAGCCACCCTC TCCTGCAGGGCCAGTCAGAGTGTTAGCAGCAACTTAGCCTGG TACCAGCAGAAACCTGGCCAGGCTCCCAGGCTCCTCATCTAT GGTGCATCCACCAGGGCCACTGGTATCCCAGCCAGGTTCAGT GGCAGTGGGTCTGGGACAGAGTTCACTCTCACCATCAGCAGC CTGCAGTCTGAAGATTTTGCAGTTTATTACTGTCAGCAGTAC GCCGCCTACCCTACTTTTGGCGGAGGGACCAAGGTTGAGATC AAACGGGGTCTACATCCGGCTCCGGGAAGCCCGGAAGTGGC GAAGGTAGTACAAAGGGGCAGGTGCAGCTGGTGCAGTCTGGG GCTGAGGTGAAGAAGCCTGGGGCCTCAGTGAAGGTTTCCTGC AAGGCATCTGGATACACCTTCACCAGCTACTATATGCACTGG GTGCGACAGGCCCCTGGACAAGGGCTTGAGTGGATGGGAATA ATCAACCCTGGTGGTGGTAGCACAAGCTACGCACAGAAGTTC CAGGGCAGAGTCACCATGACCAGGGACACGTCCACGAGCACA GTCTACATGGAGCTGAGCAGCCTGAGATCTGAGGACACGGCG GTGTACTACTGCGCCAGAGAGAGTTGGCCAATGGACGTATGG GGCCAGGGAACAACTGTCACCGTCTCCTCAGCCGCTGCCCTT GATAATGAAAAGTCAAACGGAACAATCATTCACGTGAAGGGC AAGCACCTCTGTCCGTCACCCTTGTTCCCTGGTCCATCCAAG CCATTCTGGGTGTTGGTCGTAGTGGGTGGAGTCCTCGCTTGT TACTCTCTGCTCGTCACCGTGGCTTTTATAATCTTCTGGGTT AGATCCAAAAGAAGCCGCCTGCTCCATAGCGATTACATGAAT ATGACTCCACGCCGCCCTGGCCCCACAAGGAAACACTACCAG CCTTACGCACCACCTAGAGATTTCGCTGCCTATCGGAGCAGG GTGAAGTTTTCCAGATCTGCAGATGCACCAGCGTATCAGCAG GGCCAGAACCAACTGTATAACGAGCTCAACCTGGGACGCAGG GAAGAGTATGACGTTTTGGACAAGCGCAGAGGACGGGACCCT GAGATGGGTGGCAAACCAAGACGAAAAAACCCCCAGGAGGGT CTCTATAATGAGCTGCAGAAGGATAAGATGGCTGAAGCCTAT TCTGAAATAGGCATGAAAGGAGAGCGGAGAAGGGGAAAAGGG CACGACGGTTTGTACCAGGGACTCAGCACTGCTACGAAGGAT ACTTATGACGCTCTCCACATGCAAGCCCTGCCACCTAGGTAA | 185 | MALPVTALLLPLALLLHAA RPEIVMTQSPATLSVSPGE RATLSCRASQSVSSNLAWY QQKPGQAPRLLIYGASTRA TGIPARFSGSGSGTEFTLT ISSLQSEDFAVYYCQQYAA YPTFGGGTKVEIKRGSTSG SGKPGSGEGSTKGQVQLVQ SGAEVKKPGASVKVSCKAS GYTFTSYYMHWVRQAPGQG LEWMGIINPGGGSTSYAQK FQGRVTMTRDTSTSTVYME LSSLRSEDTAVYYCARESW PMDVWGQGTTVTVSSAAAL DNEKSNGTIIHVKGKHLCP SPLFPGPSKPFWVLVVVGG VLACYSLLVTVAFIIFWVR SKRSRLLHSDYMNMTPRRP GPTRKHYQPYAPPRDFAAY RSRVKFSRSADAPAYQQGQ NQLYNELNLGRREEYDVLD KRRGRDPEMGGKPRRKNPQ EGLYNELQKDKMAEAYSEI GMKGERRRGKGHDGLYQGL STATKDTYDALHMQALPPR | 186 |
| NM-21517CAR HxL | ATGGCACTCCCCGTAACTGCTCTGCTGCTGCCGTTGGCATTG CTCCTGCACGCCGCACGCCCGCAGCTGCAGCTGCAGGAGTCG GGCCCAGGACTGGTGAAGCCTTCGGAGACCCTGTCCCTCACG TGCACTGTCTCTGGTGGCTCCATCAGCAGTAGTAGTTACTAC TGGGGCTGGATCCGCCAGCCCCCAGGGAAGGGGCTGGAGTGG ATTGGGAGTATCTCCTATAGTGGGAGCACCTACTACAACCCG TCCCTCAAGAGTCGAGTCACCATATCCGTAGACACGTCCAAG AACCAGTTCTCCCTGAAGCTGAGTTCTGTGACCGCTGCAGAC ACGGCGGTGTACTACTGCGCCAGAGGCAGGGGATATGCAACC AGCTTAGCCTTCGATATCTGGGGTCAGGGTACAATGGTCACC GTCTCCTCAGGGTCTACATCCGGCTCCGGGAAGCCCGGAAGT GGCGAAGGTAGTACAAAGGGGGAAATTGTGTTGACACAGTCT CCAGCCACCCTGTCTTTGTCTCCAGGGGAAAGAGCCACCCTC TCCTGCAGGGCCAGTCAGAGTGTTAGCAGCTACTTAGCCTGG TACCAACAGAAACCTGGCCAGGCTCCCAGGCTCCTCATCTAT GATGCATCCAACAGGGCCACTGGCATCCCAGCCAGGTTCAGT GGCAGTGGGTCTGGGACAGACTTCACTCTCACCATCAGCAGC CTAGAGCCTGAAGATTTTGCAGTTTATTACTGTCAGCAGAGA CACGTCTGGCCTCCTACTTTTGGCCAGGGGACCAAGGTTGAG ATCAAACGGGCCGCTGCCCTTGATAATGAAAAGTCAAACGGA ACAATCATTCACGTGAAGGGCAAGCACCTCTGTCCGTCACCC TTGTTCCCTGGTCCATCCAAGCCATTCTGGGTGTTGGTCGTA GTGGGTGGAGTCCTCGCTTGTTACTCTCTGCTCGTCACCGTG GCTTTTATAATCTTCTGGGTTAGATCCAAAAGAAGCCGCCTG CTCCATAGCGATTACATGAATATGACTCCACGCCGCCCTGGC CCCACAAGGAAACACTACCAGCCTTACGCACCACCTAGAGAT TTCGCTGCCTATCGGAGCAGGGTGAAGTTTTCCAGATCTGCA GATGCACCAGCGTATCAGCAGGGCCAGAACCAACTGTATAAC GAGCTCAACCTGGGACGCAGGGAAGAGTATGACGTTTTGGAC AAGCGCAGAGGACGGGACCCTGAGATGGGTGGCAAACCAAGA CGAAAAAACCCCCAGGAGGGTCTCTATAATGAGCTGCAGAAG GATAAGATGGCTGAAGCCTATTCTGAAATAGGCATGAAAGGA GAGCGGAGAAGGGGAAAAGGGCACGACGGTTTGTACCAGGGA CTCAGCACTGCTACGAAGGATACTTATGACGCTCTCCACATG CAAGCCCTGCCACCTAGGTAA | 187 | MALPVTALLLPLALLLHAA RPQLQLQESGPGLVKPSET LSLTCTVSGGSISSSSYYW GWIRQPPGKGLEWIGSISY SGSTYYNPSLKSRVTISVD TSKNQFSLKLSSVTAADTA VYYCARGRGYATSLAFDIW GQGTMVTVSSGSTSGSGKP GSGEGSTKGEIVLTQSPAT LSLSPGERATLSCRASQSV SSYLAWYQQKPGQAPRLLI YDASNRATGIPARFSGSGS GTDFTLTISSLEPEDFAVY YCQQRHVWPPTFGQGTKVE IKRAAALDNEKSNGTIIHV KGKHLCPSPLFPGPSKPFW VLVVVGGVLACYSLLVTVA FIIFWVRSKRSRLLHSDYM NMTPRRPGPTRKHYQPYAP PRDFAAYRSRVKFSRSADA PAYQQGQNQLYNELNLGRR EEYDVLDKRRGRDPEMGGK PRRKNPQEGLYNELQKDKM AEAYSEIGMKGERRRGKGH DGLYQGLSTATKDTYDALH MQALPPR | 188 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| NM-21517CAR LxH | ATGGCACTCCCCGTAACTGCTCTGCTGCTGCCGTTGGCATTG CTCCTGCACGCCGCACGCCCGGAAATTGTGTTGACACAGTCT CCAGCCACCCTGTCTTTGTCTCCAGGGGAAAGAGCCACCCTC TCCTGCAGGGCCAGTCAGAGTGTTAGCAGCTACTTAGCCTGG TACCAACAGAAACCTGGCCAGGCTCCCAGGCTCCTCATCTAT GATGCATCCAACAGGGCCACTGGCATCCCAGCCAGGTTCAGT GGCAGTGGGTCTGGGACAGACTTCACTCTCACCATCAGCAGC CTAGAGCCTGAAGATTTTGCAGTTTATTACTGTCAGCAGAGA CACGTCTGGCCTCCTACTTTTGGCGGAGGGACCAAGGTTGAG ATCAAACGGGGTCTACATCCGGCTCCGGGAAGCCCGGAAGT GGCGAAGGTAGTACAAAGGGGCAGCTGCAGCTGCAGGAGTCG GGCCCAGGACTGGTGAAGCCTTCGGAGACCCTGTCCCTCACC TGCACTGTCTCTGGTGGCTCCATCAGCAGTAGTAGTTACTAC TGGGGCTGGATCCGCCAGCCCCCAGGGAAGGGGCTGGAGTGG ATTGGGAGTATCTCCTATAGTGGGAGCACCTACTACAACCCG TCCCTCAAGAGTCGAGTCACCATATCCGTAGACACGTCCAAG AACCAGTTCTCCCTGAAGCTGAGTTCTGTGACCGCCGCAGAC ACGGCGGTGTACTACTGCGCCAGAGGCAGGGGATATGCAACC AGCTTAGCCTTCGATATCTGGGGTCAGGGTACAATGGTCACC GTCTCCTCAGCCGCTGCCCTTGATAATGAAAAGTCAAACGGA ACAATCATTCACGTGAAGGGCAAGCACCTCTGTCCGTCACCC TTGTTCCCTGGTCATCCAAGCCATTCTGGGTGTTGGTCGTA GTGGGTGGAGTCCTCGCTTGTTACTCTCTGCTCGTCACCGTG GCTTTTATAATCTTCTGGGTTAGATCCAAAAGAAGCCGCCTG CTCCATAGCGATTACATGAATATGACTCCACGCCGCCCTGGC CCCACAAGGAAACACTACCAGCCTTACGCACCACCTAGAGAT TTCGCTGCCTATCGGAGCAGGGTGAAGTTTTCCAGATCTGCA GATGCACCAGCGTATCAGCAGGGCCAGAACCAACTGTATAAC GAGCTCAACCTGGGACGCAGGGAAGAGTATGACGTTTTGGAC AAGCGCAGAGGACGGGACCCTGAGATGGGTGGCAAACCAAGA CGAAAAAACCCCCAGGAGGGTCTCTATAATGAGCTGCAGAAG GATAAGATGGCTGAAGCCTATTCTGAAATAGGCATGAAAGGA GAGCGGAGAAGGGGAAAAGGGCACGACGGTTTGTACCAGGGA CTCAGCACTGCTACGAAGGATACTTATGACGCTCTCCACATG CAAGCCCTGCCACCTAGGTAA | 189 | MALPVTALLLPLALLLHAA RPEIVLTQSPATLSLSPGE RATLSCRASQSVSSYLAWY QQKPGQAPRLLIYDASNRA TGIPARFSGSGSGTDFTLT ISSLEPEDFAVYYCQQRHV WPPTFGGGTKVEIKRGSTS GSGKPGSGEGSTKGQLQLQ ESGPGLVKPSETLSLTCTV SGGSISSSSYYWGWIRQPP GKGLEWIGSISYSGSTYYN PSLKSRVTISVDTSKNQFS LKLSSVTAADTAVYYCARG RGYATSLAFDIWGQGTMVT VSSAAALDNEKSNGTIIHV KGKHLCPSPLFPGPSKPFW VLVVVGGVLACYSLLVTVA FIIFWVRSKRSRLLHSDYM NMTPRRPGPTRKHYQPYAP PRDFAAYRSRVKFSRSADA PAYQQGQNQLYNELNLGRR EEYDVLDKRRGRDPEMGGK PRRKNPQEGLYNELQKDKM AEAYSEIGMKGERRRGKGH DGLYQGLSTATKDTYDALH MQALPPR | 190 |
| TS-21522CAR HxL | ATGGCACTCCCCGTAACTGCTCTGCTGCTGCCGTTGGCATTG CTCCTGCACGCCGCACGCCCGGAGGTGCAGCTGGTGGAGTCT GGGGGAGGCTTGGTACAGCCTGGGGGGTCCCTGAGACTCTCC TGTGCAGCCTCTGGATTCACCTTCAGTAGCTATAGCATGAAC TGGGTCCGCCAGGCTCCAGGGAAGGGGCTGGAGTGGGTTTCA ACCATTAGTAGTAGTAGTAGTACCATATACTACGCAGACTCT GTGAAGGGCCGATTCACCATCTCCAGAGACAATGCCAAGAAC TCACTGTATCTGCAAATGAACAGCCTGAGAGCTGAGGACACG GCCGTGTACTACTGCGCCAGAGGTTCTCAGGAGCACCTGATT TTCGATTATTGGGGACAGGGTACATTGGTCACCGTCTCCTCA GGGTCTACATCCGGCTCCGGGAAGCCCGGAAGTGGCGAAGGT AGTACAAAGGGGGAAATTGTGTTGACACAGTCTCCAGCCACC CTGTCTTTGTCTCCAGGGGAAAGAGCCACCCTCTCCTGCAGG GCCAGTCAGAGTGTTAGCAGGTACTTAGCCTGGTACCAACAG AAACCTGGCCAGGCTCCCAGGCTCCTCATCTATGATGCATCC AACAGGGCCACTGGCATCCCAGCCAGGTTCAGTGGCAGTGGG TCTGGGACAGACTTCACTCTCACCATCAGCAGCCTAGAGCCT GAAGATTTTGCAGTTTATTACTGTCAGCAGAGATTCTACTAC CCTTGGACTTTTGGCGGAGGGACCAAGGTTGAGATCAAACGG GCCGCTGCCCTTGATAATGAAAAGTCAAACGGAACAATCATT CACGTGAAGGGCAAGCACCTCTGTCCGTCACCCTTGTTCCCT GGTCCATCCAAGCCATTCTGGGTGTTGGTCGTAGTGGGTGGA GTCCTCGCTTGTTACTCTCTGCTCGTCACCGTGGCTTTTATA ATCTTCTGGGTTAGATCCAAAAGAAGCCGCCTGCTCCATAGC GATTACATGAATATGACTCCACGCCGCCCTGGCCCCACAAGG AAACACTACCAGCCTTACGCACCACCTAGAGATTTCGCTGCC TATCGGAGCAGGGTGAAGTTTTCCAGATCTGCAGATGCACCA GCGTATCAGCAGGGCCAGAACCAACTGTATAACGAGCTCAAC CTGGGACGCAGGGAAGAGTATGACGTTTTGGACAAGCGCAGA GGACGGGACCCTGAGATGGGTGGCAAACCAAGACGAAAAAAC CCCCAGGAGGGTCTCTATAATGAGCTGCAGAAGGATAAGATG GCTGAAGCCTATTCTGAAATAGGCATGAAAGGAGAGCGGAGA AGGGGAAAAGGGCACGACGGTTTGTACCAGGGACTCAGCACT GCTACGAAGGATACTTATGACGCTCTCCACATGCAAGCCCTG CCACCTAGGTAA | 191 | MALPVTALLLPLALLLHAA RPEVQLVESGGGLVQPGGS LRLSCAASGFTFSSYSMNW VRQAPGKGLEWVSTISSSS STIYYADSVKGRFTISRDN AKNSLYLQMNSLRAEDTAV YYCARGSQEHLIFDYWGQG TLVTVSSGSTSGSGKPGSG EGSTKGEIVLTQSPATLSL SPGERATLSCRASQSVSRY LAWYQQKPGQAPRLLIYDA SNRATGIPARFSGSGSGTD FTLTISSLEPEDFAVYYCQ QRFYYPWTFGGGTKVEIKR AAALDNEKSNGTIIHVKGK HLCPSPLFPGPSKPFWVLV VVGGVLACYSLLVTVAFII FWVRSKRSRLLHSDYMNMT PRRPGPTRKHYQPYAPPRD FAAYRSRVKFSRSADAPAY QQGQNQLYNELNLGRREEY DVLDKRRGRDPEMGGKPRR KNPQEGLYNELQKDKMAEA YSEIGMKGERRRGKGHDGL YQGLSTATKDTYDALHMQA LPPR | 192 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| TS-21522CAR LxH | ATGGCACTCCCCGTAACTGCTCTGCTGCTGCCGTTGGCATTG CTCCTGCACGCCGCACGCCCGGAAATTGTGTTGACACAGTCT CCAGCCACCCTGTCTTTGTCTCCAGGGGAAAGAGCCACCCTC TCCTGCAGGGCCAGTCAGAGTGTTAGCAGGTACTTAGCCTGG TACCAACAGAAACCTGGCCAGGCTCCCAGGCTCCTCATCTAT GATGCATCCAACAGGGCCACTGGCATCCCAGCCAGGTTCAGT GGCAGTGGGTCTGGGACAGACTTCACTCTCACCATCAGCAGC CTAGAGCCTGAAGATTTTGCAGTTTATTACTGTCAGCAGAGA TTCTACTACCCTTGGACTTTTGGCGGAGGGACCAAGGTTGAG ATCAAACGGGGTCTACATCCGGCTCCGGGAAGCCCGGAAGT GGCGAAGGTAGTACAAAGGGGGAGGTGCAGCTGGTGGAGTCT GGGGGAGGCTTGGTACAGCCTGGGGGTCCCTGAGACTCTCC TGTGCAGCCTCTGGATTCACCTTCAGTAGCTATAGCATGAAC TGGGTCCGCCAGGCTCCAGGGAAGGGGCTGGAGTGGGTTTCA ACCATTAGTAGTAGTAGTAGTACCATATACTACGCAGACTCT GTGAAGGGCCGATTCACCATCTCCAGAGACAATGCCAAGAAC TCACTGTATCTGCAAATGAACAGCCTGAGAGCTGAGGACACG GCGGTGTACTACTGCGCAGAGGTTCTCAGGAGCACCTGATT TTCGATTATTGGGACAGGGTACATTGGTCACCGTCTCCTCA GCCGCTGCCCTTGATAATGAAAGTCAAACGGAACAATCATT CACGTGAAGGGCAAGCACCTCTGTCCGTCACCCTTGTTCCCT GGTCCATCCAAGCCATTCTGGGTGTTGGTCGTAGTGGGTGGA GTCCTCGCTTGTTACTCTCTGCTCGTCACCGTGGCTTTTATA ATCTTCTGGGTTAGATCCAAAAGAAGCCGCCTGCTCCATAGC GATTACATGAATATGACTCCACGCCGCCCTGGCCCCACAAGG AAACACTACCAGCCTTACGCACCACCTAGAGATTTCGCTGCC TATCGGAGCAGGGTGAAGTTTTCCAGATCTGCAGATGCACCA GCGTATCAGCAGGGCCAGAACCAACTGTATAACGAGCTCAAC CTGGGACGCAGGGAAGAGTATGACGTTTTGGACAAGCGCAGA GGACGGGACCCTGAGATGGGTGGCAAACCAAGACGAAAAAAC CCCCAGGAGGGTCTCTATAATGAGCTGCAGAAGGATAAGATG GCTGAAGCCTATTCTGAAATAGGCATGAAAGGAGAGCGGAGA AGGGGAAAAGGGCACGACGGTTTGTACCAGGGACTCAGCACT GCTACGAAGGATACTTATGACGCTCTCCACATGCAAGCCCTG CCACCTAGGTAA | 193 | MALPVTALLLPLALLLHAA RPEIVLTQSPATLSLSPGE RATLSCRASQSVSRYLAWY QQKPGQAPRLLIYDASNRA TGIPARFSGSGSGTDFTLT ISSLEPEDFAVYYCQQRFY YPWTFGGGTKVEIKRGSTS GSGKPGSGEGSTKGEVQLV ESGGGLVQPGGSLRLSCAA SGFTFSSYSMNWVRQAPGK GLEWVSTISSSSSTIYYAD SVKGRFTISRDNAKNSLYL QMNSLRAEDTAVYYCARGS QEHLIFDYWGQGTLVTVSS AAALDNEKSNGTIIHVKGK HLCPSPLFPGPSKPFWVLV VVGGVLACYSLLVTVAFII FWVRSKRSRLLHSDYMNMT PRRPGPTRKHYQPYAPPRD FAAYRSRVKFSRSADAPAY QQGQNQLYNELNLGRREEY DVLDKRRGRDPEMGGKPRR KNPQEGLYNELQKDKMAEA YSEIGMKGERRRGKGHDGL YQGLSTATKDTYDALHMQA LPPR | 194 |
| RY-21527CAR HxL | ATGGCACTCCCCGTAACTGCTCTGCTGCTGCCGTTGGCATTG CTCCTGCACGCCGCACGCCCGCAGGTGCAGCTGGTGGAGTCT GGGGGAGGCGTGGTCCAGCCTGGGAGGTCCCTGAGACTCTCC TGTGCAGCGTCTGGATTCACCTTCAGTAGCTATGGCATGCAC TGGGTCCGCCAGGCTCCAGGCAAGGGGCTGGAGTGGGTGGCA GTTATATCGTATGATGGAAGTAATAAATACTATGCAGACTCC GTGAAGGGCCGATTCACCATCTCCAGAGACAATTCCAAGAAC ACGCTGTATCTGCAAATGAACAGCCTGAGAGCCGAGGACACG GCGGTGTACTACTGCGCCAGAACTGACTTCTGGAGCGGATCC CCTCCAGGCTTAGATTACTGGGGACAGGGTACATTGGTCACC GTCTCCTCAGGGTCTACATCCGGCTCCGGGAAGCCCGGAAGT GGCGAAGGTAGTACAAAGGGGGACATCCAGTTGACCCAGTCT CCATCTTCCGTGTCTGCATCTGTAGGAGACAGAGTCACCATC ACTTGTCGGGCGAGTCAGGGTATTAGCAGCTGGTTAGCCTGG TATCAGCAGAAACCAGGGAAAGCCCCTAAGCTCCTGATCTAT GGTGCATCCAGTTTGCAAAGTGGGGTCCCATCAAGGTTCAGC GGCAGTGGATCTGGGACAGATTTCACTCTCACCATCAGCAGC CTGCAGCCTGAAGATTTTGCAACTTATTACTGTCAGCAGATA TACACCTTCCCTTTCACTTTTGGCGGAGGGACCAAGGTTGAG ATCAAACGGGCCGCTGCCCTTGATAATGAAAGTCAAACGGA ACAATCATTCACGTGAAGGGCAAGCACCTCTGTCCGTCACCC TTGTTCCCTGGTCCATCCAAGCCATTCTGGGTGTTGGTCGTA GTGGGTGGAGTCCTCGCTTGTTACTCTCTGCTCGTCACCGTG GCTTTTATAATCTTCTGGGTTAGATCCAAAAGAAGCCGCCTG CTCCATAGCGATTACATGAATATGACTCCACGCCGCCCTGGC CCCACAAGGAAACACTACCAGCCTTACGCACCACCTAGAGAT TTCGCTGCCTATCGGAGCAGGGTGAAGTTTTCCAGATCTGCA GATGCACCAGCGTATCAGCAGGGCCAGAACCAACTGTATAAC GAGCTCAACCTGGGACGCAGGGAAGAGTATGACGTTTTGGAC AAGCGCAGAGGACGGGACCCTGAGATGGGTGGCAAACCAAGA CGAAAAAACCCCCAGGAGGGTCTCTATAATGAGCTGCAGAAG GATAAGATGGCTGAAGCCTATTCTGAAATAGGCATGAAGGA GAGCGGAGAAGGGGAAAAGGGCACGACGGTTTGTACCAGGGA CTCAGCACTGCTACGAAGGATACTTATGACGCTCTCCACATG CAAGCCCTGCCACCTAGGTAA | 195 | MALPVTALLLPLALLLHAA RPQVQLVESGGGVVQPGRS LRLSCAASGFTFSSYGMHW VRQAPGKGLEWVAVISYDG SNKYYADSVKGRFTISRDN SKNTLYLQMNSLRAEDTAV YYCARTDFWSGSPPGLDYW GQGTLVTVSSGSTSGSGKP GSGEGSTKGDIQLTQSPSS VSASVGDRVTITCRASQGI SSWLAWYQQKPGKAPKLLI YGASSLQSGVPSRFSGSGS GTDFTLTISSLQPEDFATY YCQQIYTFPFTFGGGTKVE IKRAAALDNEKSNGTIIHV KGKHLCPSPLFPGPSKPFW VLVVVGGVLACYSLLVTVA FIIFWVRSKRSRLLHSDYM NMTPRRPGPTRKHYQPYAP PRDFAAYRSRVKFSRSADA PAYQQGQNQLYNELNLGRR EEYDVLDKRRGRDPEMGGK PRRKNPQEGLYNELQKDKM AEAYSEIGMKGERRRGKGH DGLYQGLSTATKDTYDALH MQALPPR | 196 |

TABLE 2-continued

Example CAR Sequences

| Anti-BCMA CAR | Nucleotide Sequence | SEQ ID NO: | Amino Acid Sequence | SEQ ID NO: |
| --- | --- | --- | --- | --- |
| RY-21527CAR LxH | ATGGCACTCCCCGTAACTGCTCTGCTGCTGCCGTTGGCATTG CTCCTGCACGCCGCACGCCCGGACATCCAGTTGACCCAGTCT CCATCTTCCGTGTCTGCATCTGTAGGAGACAGAGTCACCATC ACTTGTCGGGCGAGTCAGGGTATTAGCAGCTGGTTAGCCTGG TATCAGCAGAAACCAGGGAAAGCCCCTAAGCTCCTGATCTAT GGTGCATCCAGTTTGCAAAGTGGGGTCCCATCAAGGTTCAGC GGCAGTGGATCTGGGACAGATTTCACTCTCACCATCAGCAGC CTGCAGCCTGAAGATTTTGCAACTTATTACTGTCAGCAGATA TACACCTTCCCTTTCACTTTTGGCGGAGGGACCAAGGTTGAG ATCAAACGGGGGTCTACATCCGGCTCCGGGAAGCCCGGAAGT GGCGAAGGTAGTACAAAGGGGCAGGTGCAGCTGGTGGAGTCT GGGGGAGGCGTGGTCCAGCCTGGGAGGTCCCTGAGACTCTCC TGTGCAGCGTCTGGATTCACCTTCAGTAGCTATGGCATGCAC TGGGTCCGCCAGGCTCCAGGCAAGGGGCTGGAGTGGGTGGCA GTTATATCGTATGATGGAAGTAATAAATACTATGCAGACTCC GTGAAGGGCCGATTCACCATCTCCAGAGACAATTCCAAGAAC ACGCTGTATCTGCAAATGAACAGCCTGAGAGCCGAGGACACG GCGGTGTACTACTGCGCCAGAACTGACTTCTGGAGCGGATCC CCTCCAGGCTTAGATTACTGGGGACAGGGTACATTGGTCACC GTCTCCTCAGCCGCTGCCCTTGATAATGAAAAGTCAAACGGA ACAATCATTCACGTGAAGGGCAAGCACCTCTGTCCGTCACCC TTGTTCCCTGGTCCATCCAAGCCATTCTGGGTGTTGGTCGTA GTGGGTGGAGTCCTCGCTTGTTACTCTCTGCTCGTCACCGTG GCTTTTATAATCTTCTGGGTTAGATCAAAAGAAGCCGCCTG CTCCATAGCGATTACATGAATATGACTCCACGCCGCCCTGGC CCACAAGGAAACACTACCAGCCTTACGCACCACCTAGAGAT TTCGCTGCCTATCGGAGCAGGGTGAAGTTTTCCAGATCTGCA GATGCACCAGCGTATCAGCAGGGCCAGAACCAACTGTATAAC GAGCTCAACCTGGGACGCAGGGAAGAGTATGACGTTTTGGAC AAGCGCAGAGGACGGGACCCTGAGATGGGTGGCAAACCAAGA CGAAAAAACCCCCAGGAGGGTCTCTATAATGAGCTGCAGAAG GATAAGATGGCTGAAGCCTATTCTGAAATAGGCATGAAAGGA GAGCGGAGAAGGGGAAAAGGGCACGACGGTTTGTACCAGGGA CTCAGCACTGCTACGAAGGATACTTATGACGCTCTCCACATG CAAGCCCTGCCACCTAGGTAA | 197 | MALPVTALLLPLALLLHAA RPDIQLTQSPSSVSASVGD RVTITCRASQGISSWLAWY QQKPGKAPKLLIYGASSLQ SGVPSRFSGSGSGTDFTLT ISSLQPEDFATYYCQQIYT FPFTFGGGTKVEIKRGSTS GSGKPGSGEGSTKGQVQLV ESGGGVVQPGRSLRLSCAA SGFTFSSYGMHWVRQAPGK GLEWVAVISYDGSNKYYAD SVKGRFTISRDNSKNTLYL QMNSLRAEDTAVYYCARTD FWSGSPPGLDYWGQGTLVT VSSAAALDNEKSNGTIIHV KGKHLCPSPLFPGPSKPFW VLVVVGGVLACYSLLVTVA FIIFWVRSKRSRLLHSDYM NMTPRRPGPTRKHYQPYAP PRDFAAYRSRVKFSRSADA PAYQQGQNQLYNELNLGRR EEYDVLDKRRGRDPEMGGK PRRKNPQEGLYNELQKDKM AEAYSEIGMKGERRRGKGH DGLYQGLSTATKDTYDALH MQALPPR | 198 |
| PP-21528CAR HxL | ATGGCACTCCCCGTAACTGCTCTGCTGCTGCCGTTGGCATTG CTCCTGCACGCCGCACGCCCGCAGGTGCAGCTGGTGCAGTCT GGGGCTGAGGTGAAGAAGCCTGGGTCCTCGGTGAAGGTCTCC TGCAAGGCTTCTGGAGGCACCTTCAGCAGCTATGCTATCAGC TGGGTGCGACAGGCCCCTGGACAAGGGCTTGAGTGGATGGGA GGGATCATCCCTATCTTTGGTACAGCAAACTACGCACAGAAG TTCCAGGGCAGAGTCACGATTACCGCGGACGAATCCACAGAC ACAGCCTACATGGAGCTGAGCAGCCTGAGATCTGAGGACACG GCGGTGTACTACTGCGCCAGAACTCCTGAATACTCCTCCAGC ATATGGCACTATTACTACGGCATGGACGTATGGGGCCAGGGA ACAACTGTCACCGTCTCCTCAGGGTCTACATCCGGCTCCGGG AAGCCCGGAAGTGGCGAAGGTAGTACAAAGGGGGGACATCGTG ATGACCCAGTCTCCAGACTCCCTGGCTGTGTCTCTGGGCGAG AGGGCCACCATCAACTGCAAGTCCAGCCAGAGTGTTTTATAC AGCTCCAACAATAAGAACTACTTAGCTTGGTACCAGCAGAAA CCAGGACAGCCTCCTAAGCTGCTCATTTACTGGGCATCTACC CGGGAATCCGGGGTCCCTGACCGATTCAGTGGCAGCGGGTCT GGGACAGATTTCACTCTCACCATCAGCAGCCTGCAGGCTGAA GATGTGGCAGTTTATTACTGTCAGCAGTTCGCCCACACTCCT TTCACTTTTGGCGGAGGGACCAAGGTTGAGATCAAACGGGCC GCTGCCCTTGATAATGAAAAGTCAAACGGAACAATCATTCAC GTGAAGGGCAAGCACCTCTGTCCGTCACCCTTGTTCCCTGGT CCATCCAAGCCATTCTGGGTGTTGGTCGTAGTGGGTGGAGTC CTCGCTTGTTACTCTCTGCTCGTCACCGTGGCTTTTATAATC TTCTGGGTTAGATCCAAAAGAAGCCGCCTGCTCCATAGCGAT TACATGAATATGACTCCACGCCGCCCTGGCCCCACAAGGAAA CACTACCAGCCTTACGCACCACCTAGAGATTTCGCTGCCTAT CGGAGCAGGGTGAAGTTTTCCAGATCTGCAGATGCACCAGCG TATCAGCAGGGCCAGAACCAACTGTATAACGAGCTCAACCTG GGACGCAGGGAAGAGTATGACGTTTTGGACAAGCGCAGAGGA CGGGACCCTGAGATGGGTGGCAAACCAAGACGAAAAAACCCC CAGGAGGGTCTCTATAATGAGCTGCAGAAGGATAAGATGGCT GAAGCCTATTCTGAAATAGGCATGAAAGGAGAGCGGAGAAGG GGAAAAGGGCACGACGGTTTGTACCAGGGACTCAGCACTGCT ACGAAGGATACTTATGACGCTCTCCACATGCAAGCCCTGCCA CCTAGGTAA | 199 | MALPVTALLLPLALLLHAA RPQVQLVQSGAEVKKPGSS VKVSCKASGGTFSSYAISW VRQAPGQGLEWMGGIIPIF GTANYAQKFQGRVTITADE STSTAYMELSSLRSEDTAV YYCARTPEYSSSIWHYYYG MDVWGQGTTVTVSSGSTSG SGKPGSGEGSTKGDIVMTQ SPDSLAVSLGERATINCKS SQSVLYSSNNKNYLAWYQQ KPGQPPKLLIYWASTRESG VPDRFSGSGSGTDFTLTIS SLQAEDVAVYYCQQFAHTP FTFGGGTKVEIKRAAALDN EKSNGTIIHVKGKHLCPSP LFPGPSKPFWVLVVVGGVL ACYSLLVTVAFIIFWVRSK RSRLLHSDYMNMTPRRPGP TRKHYQPYAPPRDFAAYRS RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 200 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| PP-21528CAR LxH | ATGGCACTCCCCGTAACTGCTCTGCTGCTGCCGTTGGCATTG CTCCTGCACGCCGCACGCCCGGACATCGTGATGACCCAGTCT CCAGACTCCCTGGCTGTGTCTCTGGGCGAGAGGGCCACCATC AACTGCAAGTCCAGCCAGAGTGTTTTATACAGCTCCAACAAT AAGAACTACTTAGCTTGGTACCAGCAGAAACCAGGACAGCCT CCTAAGCTGCTCATTTACTGGGCATCTACCCGGGAATCCGGG GTCCCTGACCGATTCAGTGGCAGCGGGTCTGGGACAGATTTC ACTCTCACCATCAGCAGCCTGCAGGCTGAAGATGTGGCAGTT TATTACTGTCAGCAGTTCGCCCACACTCCTTTCACTTTTGGC GGAGGGACCAAGGTTGAGATCAAACGGGGGTCTACATCCGGC TCCGGGAAGCCCGGAAGTGGCGAAGGTAGTACAAAGGGGCAG GTGCAGCTGGTGCAGTCTGGGGCTGAGGTGAAGAAGCCTGGG TCCTCGGTGAAGGTCTCCTGCAAGGCTTCTGGAGGCACCTTC AGCAGCTATGCTATCAGCTGGGTGCGACAGGCCCCTGGACAA GGGCTTGAGTGGATGGGAGGCATCATCCCTATCTTTGGTACA GCAAACTACGCACAGAAGTTCCAGGGCAGAGTCACGATTACC GCGGACGAATCCACGAGCACAGCCTACATGGAGCTGAGCAGC CTGAGATCTGAGGACACGGCGGTGTACTACTGCGCCAGAACT CCTGAATACTCCTCCAGCATATGGCATTATTACTACGGCATG GACGTATGGGGCCAGGGAACAACTGTCACCGTCTCCTCAGCC GCTGCCCTTGATAATGAAAAGTCAAACGGAACAATCATTCAC GTGAAGGGCAAGCACCTCTGTCCGTCACCCTTGTTCCCTGGT CCATCCAAGCCATTCTGGGTGTTGGTCGTAGTGGGTGGAGTC CTCGCTTGTTACTCTCTGCTCGTCACCGTGGCTTTTATAATC TTCTGGGTTAGATCCAAAAGAAGCCGCCTGCTCCATAGCGAT TACATGAATATGACTCCACGCCGCCCTGGCCCCACAAGGAAA CACTACCAGCCTTACGCACCACCTAGAGATTTCGCTGCCTAT CGGAGCAGGGTGAAGTTTTCCAGATCTGCAGATGCACCAGCG TATCAGCAGGGCCAGAACCAACTGTATAACGAGCTCAACCTG GGACGCAGGGAAGAGTATGACGTTTTGGACAAGCGCAGAGGA CGGGACCCTGAGATGGGTGGCAAACCAAGACGAAAAAACCCC CAGGAGGGTCTCTATAATGAGCTGCAGAAGGATAAGATGGCT GAAGCCTATTCTGAAATAGGCATGAAAGGAGAGCGGAGAAGG GGAAAAGGGCACGACGGTTTGTACCAGGGACTCAGCACTGCT ACGAAGGATACTTATGACGCTCTCCACATGCAAGCCCTGCCA CCTAGGTAA | 201 | MALPVTALLLPLALLLHAA RPDIVMTQSPDSLAVSLGE RATINCKSSQSVLYSSNNK NYLAWYQQKPGQPPKLLIY WASTRESGVPDRFSGSGSG TDFTLTISSLQAEDVAVYY CQQFAHTPFTFGGGTKVEI KRGSTSGSGKPGSGEGSTK GQVQLVQSGAEVKKPGSSV KVSCKASGGTFSSYAISWV RQAPGQGLEWMGGIIPIFG TANYAQKFQGRVTITADES TSTAYMELSSLRSEDTAVY YCARTPEYSSSIWHYYYGM DVWGQGTTVTVSSAAALDN EKSNGTIIHVKGKHLCPSP LFPGPSKPFWVLVVVGGVL ACYSLLVTVAFIIFWVRSK RSRLLHSDYMNMTPRRPGP TRKHYQPYAPPRDFAAYRS RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 202 |
| RD-21530CAR HxL | ATGGCACTCCCCGTAACTGCTCTGCTGCTGCCGTTGGCATTG CTCCTGCACGCCGCACGCCCGCAGGTGCAGCTGGTGGAGTCT GGGGGAGGCGTGGTCCAGCCTGGGAGGTCCCTGAGACTCTCC TGTGCAGCGTCTGGATTCACCTTCAGTAGCTATGGCATGCAC TGGGTCCGCCAGGCTCCAGGCAAGGGGCTGGAGTGGGTGGCA GTTATATCGTATGATGGAAGTAATAAATACTATGCAGACTCC GTGAAGGGCCGATTCACCATCTCCAGAGACAATTCCAAGAAC ACGCTGTATCTGCAAATGAACAGCCTGAGAGCCGAGGACACG GCGGTGTACTACTGCGTCAAGGGGCCGTTGCAGGAGCCGCCA TACGATTATGGAATGGACGTATGGGGCCAGGGAACAACTGTC ACCGTCTCCTCAGGGTCTACATCCGGCTCCGGGAAGCCCGGA AGTGGCGAAGGTAGTACAAAGGGGGAAATAGTGATGACGCAG TCTCCAGCCACCCTGTCTGTGTCTCCAGGGGAAAGAGCCACC CTCTCCTGCAGGGCCAGTCAGAGTGTTAGCAGCAACTTAGCC TGGTACCAGCAGAAACCTGGCCAGGCTCCCAGGCTCCTCATC TATAGCGCATCCACCAGGGCCACTGGTATCCCAGCCAGGTTC AGTGGCAGTGGGTCTGGGACAGAGTTCACTCTCACCATCAGC AGCCTGCAGTCTGAAGATTTTGCAGTTTATTACTGTCAGCAG CACCACGTCTGGCCTCTCACTTTTGGCGGAGGGACCAAGGTT GAGATCAAACGGGCCGCTGCCCTTGATAATGAAAGTCAAAC GGAACAATCATTCACGTGAAGGGCAAGCACCTCTGTCCGTCA CCCTTGTTCCCTGGTCCATCCAAGCCATTCTGGGTGTTGGTC GTAGTGGGTGGAGTCCTCGCTTGTTACTCTCTGCTCGTCACC GTGGCTTTTATAATCTTCTGGGTTAGATCCAAAAGAAGCCGC CTGCTCCATAGCGATTACATGAATATGACTCCACGCCGCCCT GGCCCCACAAGGAAACACTACCAGCCTTACGCACCACCTAGA GATTTCGCTGCCTATCGGAGCAGGGTGAAGTTTTCCAGATCT GCAGATGCACCAGCGTATCAGCAGGGCCAGAACCAACTGTAT AACGAGCTCAACCTGGGACGCAGGGAAGAGTATGACGTTTTG GACAAGCGCAGAGGACGGGACCCTGAGATGGGTGGCAAACCA AGACGAAAAAACCCCCAGGAGGGTCTCTATAATGAGCTGCAG AAGGATAAGATGGCTGAAGCCTATTCTGAAATAGGCATGAAA GGAGAGCGGAGAAGGGGAAAAGGGCACGACGGTTTGTACCAG GGACTCAGCACTGCTACGAAGGATACTTATGACGCTCTCCAC ATGCAAGCCCTGCCACCTAGGTAA | 203 | MALPVTALLLPLALLLHAA RPQVQLVESGGGVVQPGRS LRLSCAASGFTFSSYGMHW VRQAPGKGLEWVAVISYDG SNKYYADSVKGRFTISRDN SKNTLYLQMNSLRAEDTAV YYCVKGPLQEPPYDYGMDV WGQGTTVTVSSGSTSGSGK PGSGEGSTKGEIVMTQSPA TLSVSPGERATLSCRASQS VSSNLAWYQQKPGQAPRLL IYSASTRATGIPARFSGSG SGTEFTLTISSLQSEDFAV YYCQQHHVWPLTFGGGTKV EIKRAAALDNEKSNGTIIH VKGKHLCPSPLFPGPSKPF WVLVVVGGVLACYSLLVTV AFIIFWVRSKRSRLLHSDY MNMTPRRPGPTRKHYQPYA PPRDFAAYRSRVKFSRSAD APAYQQGQNQLYNELNLGR REEYDVLDKRRGRDPEMGG KPRRKNPQEGLYNELQKDK MAEAYSEIGMKGERRRGKG HDGLYQGLSTATKDTYDAL HMQALPPR | 204 |

TABLE 2-continued

Example CAR Sequences

| Anti-BCMA CAR | Nucleotide Sequence | SEQ ID NO: | Amino Acid Sequence | SEQ ID NO: |
|---|---|---|---|---|
| RD-21530CAR LxH | ATGGCACTCCCCGTAACTGCTCTGCTGCTGCCGTTGGCATTG CTCCTGCACGCCGCACGCCCGGAAATAGTGATGACGCAGTCT CCAGCCACCCTGTCTGTGTCTCCAGGGGAAAGAGCCACCCTC TCCTGCAGGGCCAGTCAGAGTGTTAGCAGCAACTTAGCCTGG TACCAGCAGAAACCTGGCCAGGCTCCCAGGCTCCTCATCTAT AGCGCATCCACCAGGGCCACTGGTATCCCAGCCAGGTTCAGT GGCAGTGGGTCTGGGACAGAGTTCACTCTCACCATCAGCAGC CTGCAGTCTGAAGATTTTGCAGTTTATTACTGTCAGCAGCAC CACGTCTGGCCTCTCACTTTTGGCGGAGGGACCAAGGTTGAG ATCAAACGGGGGTCTACATCCGGCTCCGGGAAGCCCGGAAGT GGCGAAGGTAGTACAAAGGGGCAGGTGCAGCTGGTGGAGTCT GGGGGAGGCGTGGTCCAGCCTGGGAGGTCCCTGAGACTCTCC TGTGCAGCGTCTGGATTCACCTTCAGTAGCTATGGCATGCAC TGGGTCCGCCAGGCTCCAGGCAAGGGGCTGGAGTGGGTGGCA GTTATATCGTATGATGGAAGTAATAAATACTATGCAGACTCC GTGAAGGGCCGATTCACCATCTCCAGAGACAATTCCAAGAAC ACGCTGTATCTGCAAATGAACAGCCTGAGAGCCGAGGACACG GCGGTGTACTACTGCGTCAAGGGGCCGTTGCAGGAGCCGCCA TACGATTATGGAATGGACGTATGGGGCCAGGGAACAACTGTC ACCGTCTCCTCAGCCGCTGCCCTTGATAATGAAAAGTCAAAC GGAACAATCATTCACGTGAAGGGCAAGCACCTCTGTCCGTCA CCCTTGTTCCCTGGTCCATCCAAGCCATTCTGGGTGTTGGTC GTAGTGGGTGGAGTCCTCGCTTGTTACTCTCTGCTCGTCACC GTGGCTTTTATAATCTTCTGGGTTAGATCCAAAAGAAGCCGC CTGCTCCATAGCGATTACATGAATATGACTCCACGCCGCCCT GGCCCCACAAGGAAACACTACCAGCCTTACGCACCACCTAGA GATTTCGCTGCCTATCGGAGCAGGGTGAAGTTTTCCAGATCT GCAGATGCACCAGCGTATCAGCAGGGCCAGAACCAACTGTAT AACGAGCTCAACCTGGGACGCAGGGAAGAGTATGACGTTTTG GACAAGCGCAGAGGACGGGACCCTGAGATGGGTGGCAAACCA AGACGAAAAAACCCCCAGGAGGGTCTCTATAATGAGCTGCAG AAGGATAAGATGGCTGAAGCCTATTCTGAAATAGGCATGAAA GGAGAGCGGAGAAGGGGAAAAGGGCACGACGGTTTGTACCAG GGACTCAGCACTGCTACGAAGGATACTTATGACGCTCTCCAC ATGCAAGCCCTGCCACCTAGGTAA | 205 | MALPVTALLLPLALLLHAA RPEIVMTQSPATLSVSPGE RATLSCRASQSVSSNLAWY QQKPGQAPRLLIYSASTRA TGIPARFSGSGSGTEFTLT ISSLQSEDFAVYYCQQHHV WPLTFGGGTKVEIKRGSTS GSGKPGSGEGSTKGQVQLV ESGGGVVQPGRSLRLSCAA SGFTFSSYGMHWVRQAPGK GLEWVAVISYDGSNKYYAD SVKGRFTISRDNSKNTLYL QMNSLRAEDTAVYYCVKGP LQEPPYDYGMDVWGQGTTV TVSSAAALDNEKSNGTIIH VKGKHLCPSPLFPGPSKPF WVLVVVGGVLACYSLLVTV AFIIFWVRSKRSRLLHSDY MNMTPRRPGPTRKHYQPYA PPRDFAAYRSRVKFSRSAD APAYQQGQNQLYNELNLGR REEYDVLDKRRGRDPEMGG KPRRKNPQEGLYNELQKDK MAEAYSEIGMKGERRRGKG HDGLYQGLSTATKDTYDAL HMQALPPR | 206 |

In some embodiments, the polynucleotide of the present invention encodes a CAR, wherein the CAR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence selected from the group consisting of SEQ ID NOs: 176, 178, 180, 182, 184, 186, 188, 190, 192, 194, 196, 198, 200, 202, 204, and 206. In certain embodiments, the CAR comprises an amino acid sequence selected from the group consisting of SEQ ID NOs: 176, 178, 180, 182, 184, 186, 188, 190, 192, 194, 196, 198, 200, 202, 204, and 206. In one embodiment, the CAR comprises the amino acid sequence of SEQ ID NO: 176. In another embodiment, the CAR comprises the amino acid sequence of SEQ ID NO: 178. In another embodiment, the CAR comprises the amino acid sequence of SEQ ID NO: 180. In another embodiment, the CAR comprises the amino acid sequence of SEQ ID NO: 182. In another embodiment, the CAR comprises the amino acid sequence of SEQ ID NO: 184. In another embodiment, the CAR comprises the amino acid sequence of SEQ ID NO: 186. In another embodiment, the CAR comprises the amino acid sequence of SEQ ID NO: 188. In another embodiment, the CAR comprises the amino acid sequence of SEQ ID NO: 190. In another embodiment, the CAR comprises the amino acid sequence of SEQ ID NO: 192. In another embodiment, the CAR comprises the amino acid sequence of SEQ ID NO: 194. In another embodiment, the CAR comprises the amino acid sequence of SEQ ID NO: 196. In another embodiment, the CAR comprises the amino acid sequence of SEQ ID NO: 198. In another embodiment, the CAR comprises the amino acid sequence of SEQ ID NO: 200. In another embodiment, the CAR comprises the amino acid sequence of SEQ ID NO: 202. In another embodiment, the CAR comprises the amino acid sequence of SEQ ID NO: 204. In another embodiment, the CAR comprises the amino acid sequence of SEQ ID NO: 206.

In some embodiments, the polynucleotide of the present invention comprises an nucleotide sequence at least about 50%, at least about 60%, at least about 65%, at least about 70%, at least about 75%, at least about 85%, at least about 85%, at least about 90%, at least about 95%, at least about 96%, at least about 97%, at least about 98%, at least about 99%, or 100% identical to an amino acid sequence selected from the group consisting of SEQ ID NOs: 175, 177, 179, 181, 183, 185, 187, 189, 191, 193, 195, 197, 199, 201, 203, and 205. In certain embodiments, the polynucleotide comprises a nucleotide sequence selected from the group consisting of SEQ ID NOs: 175, 177, 179, 181, 183, 185, 187, 189, 191, 193, 195, 197, 199, 201, 203, and 205. In one embodiment, the polynucleotide comprises the nucleotide sequence of SEQ ID NO: 175. In another embodiment, the polynucleotide comprises the nucleotide sequence of SEQ ID NO: 177. In another embodiment, the polynucleotide comprises the nucleotide sequence of SEQ ID NO: 179. In another embodiment, the polynucleotide comprises the nucleotide sequence of SEQ ID NO: 181. In another embodiment, the polynucleotide comprises the nucleotide sequence of SEQ ID NO: 183. In another embodiment, the polynucleotide comprises the nucleotide sequence of SEQ ID NO: 185. In another embodiment, the polynucleotide comprises the nucleotide sequence of SEQ ID NO: 187. In another embodiment, the polynucleotide comprises the nucleotide sequence of SEQ ID NO: 189. In another embodiment, the polynucleotide comprises the nucleotide sequence of SEQ ID NO: 191. In another embodiment, the polynucleotide comprises the nucleotide sequence of SEQ ID NO: 193. In another embodiment, the polynucleotide comprises the nucleotide sequence of SEQ ID NO: 195. In another embodiment, the polynucleotide comprises the nucleotide sequence of SEQ ID NO: 197. In another embodiment, the polynucleotide comprises the nucleotide sequence of SEQ ID NO: 199. In another embodiment, the polynucleotide comprises the nucleotide sequence of SEQ ID NO: 201. In another embodiment, the polynucleotide comprises the nucleotide sequence of SEQ ID NO: 203. In another embodiment, the polynucleotide comprises the nucleotide sequence of SEQ ID NO: 205.

In further embodiments, the invention relates to Clone FS-26528 HC DNA (SEQ ID NO: 271) as follows:

```
GAGGTGCAGCTGTTGGAGTCTGGGGGAGGCTTGGTACAGCCTGGGGGGT
CCCTGAGACTCTCCTGTGCAGCCTCTGGATTCACCTTTGACGACTATGCC
ATGGCATGGGTCCGCCAGGCTCCAGGGAAGGGGCTGGAGTGGGTCTCAG
CTATTAGTGATGCAGGTGACAGAACATACTACGCAGACTCCGTGAGGGG
CCGGTTCACCATCTCCAGAGACAATTCCAAGAACACACTGTATCTGCAA
ATGAACAGCCTGAGAGCCGAGGACACGGCGGTGTACTACTGCGCAAGA
GCCGAGATGGGAGCCGTATTCGACATATGGGGTCAGGGTACAATGGTCA
CCGTCTCCTCA
```

In further embodiments, the invention relates to the Clone FS-26528 HC amino acid sequence (SEQ ID NO: 272):

```
EVQLLESGGG LVQPGGSLRL SCAASGFTFD DYAMAWVRQA
PGKGLEWVSA ISDAGDRTYY ADSVRGRFTI SRDNSKNTLY
LQMNSLRAED TAVYYCARAE MGAVFDIWGQ GTMVTVSS
```

In further embodiments, the invention relates to HC CDR1 thereof: SCAASGFTFDDYAMA (SEQ ID NO: 273). In further embodiments, the invention relates to HC CDR2 thereof: AISDAGDRTYYADSVRG (SEQ ID NO: 274). In further embodiments, the invention relates to HC CDR3 thereof: ARAEMGAVFDI (SEQ ID NO: 275) [HC CDR3]

In further embodiments, the invention relates to Clone FS-26528 LC DNA (SEQ ID NO: 276):

```
GAAATTGTGTTGACACAGTCTCCAGCCACCCTGTCTTTGTCTCCAGGGGA
AGAGCCACCCTCTCCTGCAGGGCCAGTCAGAGTGTTAGCAGGTACTTA
GCCTGGTACCAACAGAAACCTGGCCAGGCTCCCAGGCTCCTCATCTATG
ATGCATCCAACAGGGCCACTGGCATCCCAGCCAGGTTCAGTGGCAGTGG
GTCTGGGACAGACTTCACTCTCACCATCAGCAGCCTAGAGCCTGAAGAT
TTTGCAGTTTATTACTGTCAGCAGAGAATCTCCTGGCCTTTCACTTTTGG
CGGAGGGACCAAGGTTGAGATCAAACGG
```

In further embodiments, the invention relates to Clone FS-26528 LC AA sequence (SEQ ID NO: 277):

```
EIVLTQSPAT LSLSPGERAT LSCRASQSVS RYLAWYQQKP
GQAPRLLIYD ASNRATGIPA RFSGSGSGTD FTLTISSLEP
EDFAVYYCQQ RISWPFTFGG GTKVEIKR.
```

In further embodiments, the invention relates to LC CDR1 thereof: RASQSVSRYLA (SEQ ID NO: 278). In further embodiments, the invention relates to LC CDR2 thereof: DASNRAT (SEQ ID NO: 279). In further embodiments, the invention relates to the LC CDR3 thereof: QQRISWPFT (SEQ ID NO: 280).

In further embodiments, the invention relates to Clone FS-26528 CAR DNA HxL (SEQ ID NO: 281):

```
ATGGCACTCCCCGTAACTGCTCTGCTGCTGCCGTTGGCATTGCTCCTGCA
CGCCGCACGCCCGGAGGTGCAGCTGTTGGAGTCTGGGGGAGGCTTGGTA
CAGCCTGGGGGGTCCCTGAGACTCTCCTGTGCAGCCTCTGGATTCACCTT
TGACGACTATGCCATGGCATGGGTCCGCCAGGCTCCAGGGAAGGGGCTG
GAGTGGGTCTCAGCTATTAGTGATGCAGGTGACAGAACATACTACGCAG
ACTCCGTGAGGGGCCGGTTCACCATCTCCAGAGACAATTCCAAGAACAC
ACTGTATCTGCAAATGAACAGCCTGAGAGCCGAGGACACGGCGGTGTAC
TACTGCGCAAGAGCCGAGATGGGAGCCGTATTCGACATATGGGGTCAGG
GTACAATGGTCACCGTCTCCTCAGGGTCTACATCCGGCTCCGGGAAGCCC
GGAAGTGGCGAAGGTAGTACAAAGGGGGAAATTGTGTTGACACAGTCTC
CAGCCACCCTGTCTTTGTCTCCAGGGGAAAGAGCCACCCTCTCCTGCAGG
GCCAGTCAGAGTGTTAGCAGGTACTTAGCCTGGTACCAACAGAAACCTG
GCCAGGCTCCCAGGCTCCTCATCTATGATGCATCCAACAGGGCCACTGG
CATCCCAGCCAGGTTCAGTGGCAGTGGGTCTGGGACAGACTTCACTCTC
ACCATCAGCAGCCTAGAGCCTGAAGATTTTGCAGTTTATTACTGTCAGCA
GAGAATCTCCTGGCCTTTCACTTTTGGCGGAGGGACCAAGGTTGAGATC
AAACGGGCCGCTGCCCTTGATAATGAAAAGTCAAACGGAACAATCATTC
ACGTGAAGGGCAAGCACCTCTGTCCGTCACCCTTGTTCCCTGGTCCATCC
AAGCCATTCTGGGTGTTGGTCGTAGTGGGTGGAGTCCTCGCTTGTTACTC
TCTGCTCGTCACCGTGGCTTTTATAATCTTCTGGGTTAGATCCAAAAGAA
GCCGCCTGCTCCATAGCGATTACATGAATATGACTCCACGCCGCCCTGGC
CCCACAAGGAAACACTACCAGCCTTACGCACCACCTAGAGATTTCGCTG
CCTATCGGAGCAGGGTGAAGTTTTCCAGATCTGCAGATGCACCAGCGTA
TCAGCAGGGCCAGAACCAACTGTATAACGAGCTCAACCTGGGACGCAGG
GAAGAGTATGACGTTTTGGACAAGCGCAGAGGACGGGACCCTGAGATG
GGTGGCAAACCAAGACGAAAAAACCCCCAGGAGGGTCTCTATAATGAG
CTGCAGAAGGATAAGATGGCTGAAGCCTATTCTGAAATAGGCATGAAAG
GAGAGCGGAGAAGGGGAAAAGGGCACGACGGTTTGTACCAGGGACTCA
GCACTGCTACGAAGGATACTTATGACGCTCTCCACATGCAAGCCCTGCC
ACCTAGG
```

In further embodiments, the invention relates to Clone FS-26528 CAR HxL AA sequence (SEQ ID NO: 282):

```
MALPVTALLL PLALLLHAAR PEVQLLESGG GLVQPGGSLR
LSCAASGFTF DDYAMAWVRQ APGKGLEWVS AISDAGDRTY
YADSVRGRFT ISRDNSKNTL YLQMNSLRAE DTAVYYCARA
EMGAVFDIWG QGTMVTVSSG STSGSGKPGS GEGSTKGEIV
LTQSPATLSL SPGERATLSC RASQSVSRYL AWYQQKPGQA
PRLLIYDASN RATGIPARFS GSGSGTDFTL TISSLEPEDF
AVYYCQQRIS WPFTFGGGTK VEIKRAAALD NEKSNGTIIH
VKGKHLCPSP LFPGPSKPFW VLVVVGGVLA CYSLLVTVAF
IIFWVRSKRS RLLHSDYMNM TPRRPGPTRK HYQPYAPPRD
FAAYRSRVKF SRSADAPAYQ QGQNQLYNEL NLGRREEYDV
LDKRRGRDPE MGGKPRRKNP QEGLYNELQK DKMAEAYSEI
GMKGERRRGK GHDGLYQGLS TATKDTYDAL HMQALPPR
```

In further embodiments, the invention relates to Clone FS-26528 CAR DNA LxH (SEQ ID NO: 283):

```
ATGGCACTCCCCGTAACTGCTCTGCTGCTGCCGTTGGCATTGCTCCTGCA
CGCCGCACGCCCGGAAATTGTGTTGACACAGTCTCCAGCCACCCTGTCTT
TGTCTCCAGGGGAAAGAGCCACCCTCTCCTGCAGGGCCAGTCAGAGTGT
TAGCAGGTACTTAGCCTGGTACCAACAGAAACCTGGCCAGGCTCCCAGG
CTCCTCATCTATGATGCATCCAACAGGGCCACTGGCATCCCAGCCAGGTT
CAGTGGCAGTGGGTCTGGGACAGACTTCACTCTCACCATCAGCAGCCTA
GAGCCTGAAGATTTTGCAGTTTATTACTGTCAGCAGAGAATCTCCTGGCC
TTTCACTTTTGGCGGAGGGACCAAGGTTGAGATCAAACGGGGGTCTACA
TCCGGCTCCGGGAAGCCCGGAAGTGGCGAAGGTAGTACAAAGGGGGAG
GTGCAGCTGTTGGAGTCTGGGGGAGGCTTGGTACAGCCTGGGGGGTCCC
TGAGACTCTCCTGTGCAGCCTCTGGATTCACCTTTGACGACTATGCCATG
GCATGGGTCCGCCAGGCTCCAGGGAAGGGGCTGGAGTGGGTCTCAGCTA
TTAGTGATGCAGGTGACAGAACATACTACGCAGACTCCGTGAGGGGCCG
GTTCACCATCTCCAGAGACAATTCCAAGAACACACTGTATCTGCAAATG
AACAGCCTGAGAGCCGAGGACACGGCGGTGTACTACTGCGCAAGAGCC
GAGATGGGAGCCGTATTCGACATATGGGGTCAGGGTACAATGGTCACCG
TCTCCTCAGCCGCTGCCCTTGATAATGAAAAGTCAAACGGAACAATCATT
CACGTGAAGGGCAAGCACCTCTGTCCGTCACCCTTGTTCCCTGGTCCATC
CAAGCCATTCTGGGTGTTGGTCGTAGTGGGTGGAGTCCTCGCTTGTTACT
CTCTGCTCGTCACCGTGGCTTTTATAATCTTCTGGGTTAGATCCAAAAGA
AGCCGCCTGCTCCATAGCGATTACATGAATATGACTCCACGCCGCCCTGG
CCCCACAAGGAAACACTACCAGCCTTACGCACCACCTAGAGATTTCGCT
GCCTATCGGAGCAGGGTGAAGTTTTCCAGATCTGCAGATGCACCAGCGT
ATCAGCAGGGCCAGAACCAACTGTATAACGAGCTCAACCTGGGACGCAG
GGAAGAGTATGACGTTTTGGACAAGCGCAGAGGACGGGACCCTGAGAT
GGGTGGCAAACCAAGACGAAAAAACCCCCAGGAGGGTCTCTATAATGA
GCTGCAGAAGGATAAGATGGCTGAAGCCTATTCTGAAATAGGCATGAAA
GGAGAGCGGAGAAGGGGAAAAGGGCACGACGGTTTGTACCAGGGACTC
AGCACTGCTACGAAGGATACTTATGACGCTCTCCACATGCAAGCCCTGC
CACCTAGG
```

In further embodiments, the invention relates to the Clone FS-26528 CAR LxH AA sequence (SEQ ID NO: 284):

```
MALPVTALLL PLALLLHAAR PEIVLTQSPA TLSLSPGERA
TLSCRASQSV SRYLAWYQQK PGQAPRLLIY DASNRATGIP
ARFSGSGSGT DFTLTISSLE PEDFAVYYCQ QRISWPFTFG
GGTKVEIKRG STSGSGKPGS GEGSTKGEVQ LLESGGGLVQ
PGGSLRLSCA ASGFTFDDYA MAWVRQAPGK GLEWVSAISD
AGDRTYYADS VRGRFTISRD NSKNTLYLQM NSLRAEDTAV
YYCARAEMGA VFDIWGQGTM VTVSSAAALD NEKSNGTIIH
VKGKHLCPSP LFPGPSKPFW VLVVVGGVLA CYSLLVTVAF
IIFWVRSKRS RLLHSDYMNM TPRRPGPTRK HYQPYAPPRD
FAAYRSRVKF SRSADAPAYQ QGQNQLYNEL NLGRREEYDV
LDKRRGRDPE MGGKPRRKNP QEGLYNELQK DKMAEAYSEI
GMKGERRRGK GHDGLYQGLS TATKDTYDAL HMQALPPR
```

In further embodiments, the invention relates to Clone PC-26534 HC DNA (SEQ ID NO: 285) as follows:

```
CAGGTGCAGCTGGTGGAGTCTGGGGGAGGCGTGGTCCAGCCTGGGAGGT
CCCTGAGACTCTCCTGTGCAGCGTCTGGATTCACCTTCAGTGAGCATGGC
ATGCACTGGGTCCGCCAGGCTCCAGGCAAGGGGCTGGAGTGGGTGGCAG
CTATATCTTATGATGGAAGGAATAAACACTATGCAGACTCCGTGAAGGG
CCGATTCACCATCTCCAGAGACAATTCCAAGAACACGCTGTATCTGCAA
ATGAACAGCCTGAGAGCCGAGGACACGGCGGTGTACTACTGCGCCAGAG
ACGGTACTTATCTAGGTGGTCTCTGGTACTTCGACTTATGGGGGAGAGGT
ACCTTGGTCACCGTCTCCTCA
```

In further embodiments, the invention relates to Clone PC-26534 HC (SEQ ID NO: 286):

```
QVQLVESGGG VVQPGRSLRL SCAASGFTFS EHGMHWVRQA
PGKGLEWVAA ISYDGRNKHY ADSVKGRFTI SRDNSKNTLY
LQMNSLRAED TAVYYCARDG TYLGGLWYFD LWGRGTLVTV
SS.
```

In further embodiments, the invention relates to HC CDR1 thereof: FTFSEHGMH (SEQ ID NO: 287). In further embodiments, the invention relates to HC CDR2 thereof: AISYDGRNKHYADSVKG (SEQ ID NO: 288). In further embodiments, the invention relates to HC CDR3 thereof: ARDGTYLGGLWYFDL (SEQ ID NO: 289).

In further embodiments, the invention relates to Clone PC-26534 LC DNA (SEQ ID NO: 290) as follows:

GATATTGTGATGACTCAGTCTCCACTCTCCCTGCCCGTCACCCCTGGAGA
GCCGGCCTCCATCTCCTGCAGGTCTAGTCAGAGCCTCCTGCATAGTAATG
GATACAACTATTTGGATTGGTACCTGCAGAAGCCAGGGCAGTCTCCACA
GCTCCTGATCTATTTGGGTTCTAATCGGGCCTCCGGGGTCCCTGACAGGT
TCAGTGGCAGTGGATCAGGCACAGATTTTACACTGAAAATCAGCAGAGT
GGAGGCTGAGGATGTTGGGGTTTATTACTGCATGCAGGGACTCGGCCTC
CCTCTCACTTTTGGCGGAGGGACCAAGGTTGAGATCAAACGG

In further embodiments, the invention relates to Clone PC-26534 LC AA sequence (SEQ ID NO: 291):

DIVMTQSPLS LPVTPGEPAS ISCRSSQSLL HSNGYNYLDW
YLQKPGQSPQ LLIYLGSNRA SGVPDRFSGS GSGTDFTLKI
SRVEAEDVGV YYCMQGLGLP LTFGGGTKVE IKR.

In further embodiments, the invention relates to LC CDR1 AA sequence thereof: RSSQSLLHSNGYNYLD (SEQ ID NO: 292). In further embodiments, the invention relates to LC CDR2 thereof: LGSNRAS (SEQ ID NO: 293). In further embodiments, the invention relates to LC CDR3 thereof: MQGLGLPLT (SEQ ID NO: 294).

In further embodiments, the invention relates to Clone PC-26534 CAR DNA HxL (SEQ ID NO: 295) as follows:

ATGGCACTCCCCGTAACTGCTCTGCTGCTGCCGTTGGCATTGCTCCTGCA
CGCCGCACGCCCGCAGGTGCAGCTGGTGGAGTCTGGGGGAGGCGTGGTC
CAGCCTGGGAGGTCCCTGAGACTCTCCTGTGCAGCGTCTGGATTCACCTT
CAGTGAGCATGGCATGCACTGGGTCCGCCAGGCTCCAGGCAAGGGGCTG
GAGTGGGTGGCAGCTATATCTTATGATGGAAGGAATAAACACTATGCAG
ACTCCGTGAAGGGCCGATTCACCATCTCCAGAGACAATTCCAAGAACAC
GCTGTATCTGCAAATGAACAGCCTGAGAGCCGAGGACACGGCGGTGTAC
TACTGCGCCAGAGACGGTACTTATCTAGGTGGTCTCTGGTACTTCGACTT
ATGGGGGAGAGGTACCTTGGTCACCGTCTCCTCAGGGTCTACATCCGGCT
CCGGGAAGCCCGGAAGTGGCGAAGGTAGTACAAAGGGGGATATTGTGA
TGACTCAGTCTCCACTCTCCCTGCCCGTCACCCCTGGAGAGCCGGCCTCC
ATCTCCTGCAGGTCTAGTCAGAGCCTCCTGCATAGTAATGGATACAACTA
TTTGGATTGGTACCTGCAGAAGCCAGGGCAGTCTCCACAGCTCCTGATCT
ATTTGGGTTCTAATCGGGCCTCCGGGGTCCCTGACAGGTTCAGTGGCAGT
GGATCAGGCACAGATTTTACACTGAAAATCAGCAGAGTGGAGGCTGAGG
ATGTTGGGGTTTATTACTGCATGCAGGGACTCGGCCTCCCTCTCACTTTT
GGCGGAGGGACCAAGGTTGAGATCAAACGGGCCGCTGCCCTTGATAATG
AAAAGTCAAACGGAACAATCATTCACGTGAAGGGCAAGCACCTCTGTCC
GTCACCCTTGTTCCCTGGTCCATCCAAGCCATTCTGGGTGTTGGTCGTAG
TGGGTGGAGTCCTCGCTTGTTACTCTCTGCTCGTCACCGTGGCTTTTATA

ATCTTCTGGGTTAGATCCAAAAGAAGCCGCCTGCTCCATAGCGATTACAT
GAATATGACTCCACGCCGCCCTGGCCCCACAAGGAAACACTACCAGCCTT
ACGCACCACCTAGAGATTTCGCTGCCTATCGGAGCAGGGTGAAGTTTTCC
AGATCTGCAGATGCACCAGCGTATCAGCAGGGCCAGAACCAACTGTATA
ACGAGCTCAACCTGGGACGCAGGGAAGAGTATGACGTTTTGGACAAGCG
CAGAGGACGGGACCCTGAGATGGGTGGCAAACCAAGACGAAAAAACCC
CCAGGAGGGTCTCTATAATGAGCTGCAGAAGGATAAGATGGCTGAAGCC
TATTCTGAAATAGGCATGAAAGGAGAGCGGAGAAGGGGAAAAGGGCAC
GACGGTTTGTACCAGGGACTCAGCACTGCTACGAAGGATACTTATGACG
CTCTCCACATGCAAGCCCTGCCACCTAGG

In further embodiments, the invention relates to Clone PC-26534 CAR HxL AA sequence (SEQ ID NO: 296):

MALPVTALLL PLALLLHAAR PQVQLVESGG GVVQPGRSLR
LSCAASGFTF SEHGMHWVRQ APGKGLEWVA AISYDGRNKH
YADSVKGRFT ISRDNSKNTL YLQMNSLRAE DTAVYYCARD
GTYLGGLWYF DLWGRGTLVT VSSGSTSGSG KPGSGEGSTK
GDIVMTQSPL SLPVTPGEPA SISCRSSQSL LHSNGYNYLD
WYLQKPGQSP QLLIYLGSNR ASGVPDRFSG SGSGTDFTLK
ISRVEAEDVG VYYCMQGLGL PLTFGGGTKV EIKRAAALDN
EKSNGTIIHV KGKHLCPSPL FPGPSKPFWV LVVVGGVLAC
YSLLVTVAFI IFWVRSKRSR LLHSDYMNMT PRRPGPTRKH
YQPYAPPRDF AAYRSRVKFS RSADAPAYQQ GQNQLYNELN
LGRREEYDVL DKRRGRDPEM GGKPRRKNPQ EGLYNELQKD
KMAEAYSEIG MKGERRRGKG HDGLYQGLST ATKDTYDALH
MQALPPR

In further embodiments, the invention relates to Clone PC-26534 CAR DNA LxH (SEQ ID NO: 297):

ATGGCACTCCCCGTAACTGCTCTGCTGCTGCCGTTGGCATTGCTCCTGCA
CGCCGCACGCCCGGATATTGTGATGACTCAGTCTCCACTCTCCCTGCCCG
TCACCCCTGGAGAGCCGGCCTCCATCTCCTGCAGGTCTAGTCAGAGCCTC
CTGCATAGTAATGGATACAACTATTTGGATTGGTACCTGCAGAAGCCAG
GGCAGTCTCCACAGCTCCTGATCTATTTGGGTTCTAATCGGGCCTCCGGG
GTCCCTGACAGGTTCAGTGGCAGTGGATCAGGCACAGATTTTACACTGA
AAATCAGCAGAGTGGAGGCTGAGGATGTTGGGGTTTATTACTGCATGCA
GGGACTCGGCCTCCCTCTCACTTTTGGCGGAGGGACCAAGGTTGAGATC
AAACGGGGGTCTACATCCGGCTCCGGGAAGCCCGGAAGTGGCGAAGGT
AGTACAAAGGGGCAGGTGCAGCTGGTGGAGTCTGGGGGAGGCGTGGTC
CAGCCTGGGAGGTCCCTGAGACTCTCCTGTGCAGCGTCTGGATTCACCTT
CAGTGAGCATGGCATGCACTGGGTCCGCCAGGCTCCAGGCAAGGGGCTG
GAGTGGGTGGCAGCTATATCTTATGATGGAAGGAATAAACACTATGCAG

-continued
```
ACTCCGTGAAGGGCCGATTCACCATCTCCAGAGACAATTCCAAGAACAC

GCTGTATCTGCAAATGAACAGCCTGAGAGCCGAGGACACGGCGGTGTAC

TACTGCGCCAGAGACGGTACTTATCTAGGTGGTCTCTGGTACTTCGACTT

ATGGGGGAGAGGTACCTTGGTCACCGTCTCCTCAGCCGCTGCCCTTGATA

ATGAAAAGTCAAACGGAACAATCATTCACGTGAAGGGCAAGCACCTCTGT

CCGTCACCCTTGTTCCCTGGTCCATCCAAGCCATTCTGGGTGTTGGTCGT

AGTGGGTGGAGTCCTCGCTTGTTACTCTCTGCTCGTCACCGTGGCTTTTA

TAATCTTCTGGGTTAGATCCAAAAGAAGCCGCCTGCTCCATAGCGATTAC

ATGAATATGACTCCACGCCGCCCTGGCCCCACAAGGAAACACTACCAGC

CTTACGCACCACCTAGAGATTTCGCTGCCTATCGGAGCAGGGTGAAGTTT

TCCAGATCTGCAGATGCACCAGCGTATCAGCAGGGCCAGAACCAACTGT

ATAACGAGCTCAACCTGGGACGCAGGGAAGAGTATGACGTTTTGGACAA

GCGCAGAGGACGGGACCCTGAGATGGGTGGCAAACCAAGACGAAAAAA

CCCCCAGGAGGGTCTCTATAATGAGCTGCAGAAGGATAAGATGGCTGAA

GCCTATTCTGAAATAGGCATGAAAGGAGAGCGGAGAAGGGGAAAAGGG

CACGACGGTTTGTACCAGGGACTCAGCACTGCTACGAAGGATACTTATG

ACGCTCTCCACATGCAAGCCCTGCCACCTAGG
```

In further embodiments, the invention relates to Clone PC-26534 CAR LxH chain sequences (SEQ ID NO: 298):

```
MALPVTALLL PLALLLHAAR PDIVMTQSPL SLPVTPGEPA

SISCRSSQSL LHSNGYNYLD WYLQKPGQSP QLLIYLGSNR

ASGVPDRFSG SGSGTDFTLK ISRVEAEDVG VYYCMQGLGL

PLTFGGGTKV EIKRGSTSGS GKPGSGEGST KGQVQLVESG

GGVVQPGRSL RLSCAASGFT FSEHGMHWVR QAPGKGLEWV

AAISYDGRNK HYADSVKGRF TISRDNSKNT LYLQMNSLRA

EDTAVYYCAR DGTYLGGLWY FDLWGRGTLV TVSSAAALDN

EKSNGTIIHV KGKHLCPSPL FPGPSKPFWV LVVVGGVLAC

YSLLVTVAFI IFWVRSKRSR LLHSDYMNMT PRRPGPTRKH

YQPYAPPRDF AAYRSRVKFS RSADAPAYQQ GQNQLYNELN

LGRREEYDVL DKRRGRDPEM GGKPRRKNPQ EGLYNELQKD

KMAEAYSEIG MKGERRRGKG HDGLYQGLST ATKDTYDALH

MQALPPR
```

In further embodiments, the invention relates to Clone AJ-26545 HC DNA (SEQ ID NO: 299):

```
CAGGTGCAGCTGGTGCAGTCTGGGGCTGAGGTGAAGAAGCCTGGGGCCT

CAGTGAAGGTTTCCTGCAGGGCATCTGGATACACCTTCATGGAGCACTAT

ATGCACTGGGTGCGACAGGCCCCTGGACAAGGGCTTGAGTGGATGGGAG

TAATCGGGCCTAGTGGTGGTAAGACAAGCTACGCACAGAAGTTCCAGGG

CAGAGTCACCATGACCAGGGACACGTCCACGAGCACAGTCTACATGGAG

CTGAGCAGCCTGAGATCTGAGGACACGGCGGTGTACTACTGCGCCAGAG

AGAATTGGCCAATGGACGTATGGGGCCAGGGAACAACTGTCACCGTCTC

CTCA
```

In further embodiments, the invention relates to Clone AJ-26545 HC AA sequence (SEQ ID NO: 300):

```
QVQLVQSGAE VKKPGASVKV SCRASGYTFM EHYMHWVRQA

PGQGLEWMGV IGPSGGKTSY AQKFQGRVTM TRDTSTSTVY

MELSSLRSED TAVYYCARES WPMDVWGQGT TVTVSS.
```

In further embodiments, the invention relates to HC CDR1 thereof: YTFMEHYMH (SEQ ID NO: 301). In further embodiments, the invention relates to HC CDR2 thereof: VIGPSGGKTSYAQKFQG (SEQ ID NO: 302). In further embodiments, the invention relates to HC CDR3 thereof: ARESWPMDV (SEQ ID NO: 303).

In further embodiments, the invention relates to Clone AJ-26545 LC DNA (SEQ ID NO: 304):

```
GAAATAGTGATGACGCAGTCTCCAGCCACCCTGTCTGTGTCTCCAGGGG

AAAGAGCCACCCTCTCCTGCAGGGCCAGTCAGAGTGTTAGCAGCAACTT

AGCCTGGTACCAGCAGAAACCTGGCCAGGCTCCCAGGCTCCTCATCTAT

GGTGCATCCACCAGGGCCACTGGTATCCCAGCCAGGTTCAGTGGCAGTG

GGTCTGGGACAGAGTTCACTCTCACCATCAGCAGCCTGCAGTCTGAAGA

TTTTGCAGTTTATTACTGTCAGCAGTACGCCGCCTACCCTACTTTTGGCG

GAGGGACCAAGGTTGAGATCAAACGG
```

In further embodiments, the invention relates to Clone AJ-26545 LC AA sequence (SEQ ID NO: 305):

```
EIVMTQSPAT LSVSPGERAT LSCRASQSVS SNLAWYQQKP

GQAPRLLIYG ASTRATGIPA RFSGSGSGTE FTLTISSLQS

EDFAVYYCQQ YAAYPTFGGG TKVEIKR.
```

In further embodiments, the invention relates to LC CDR1 thereof: RASQSVSSNLA (SEQ ID NO: 306). In further embodiments, the invention relates to LC CDR2 thereof: GASTRAT (SEQ ID NO: 307). In further embodiments, the invention relates to the LC CDR3 thereof: QQYAAYPT (SEQ ID NO: 308).

In further embodiments, the invention relates to Clone AJ-26545 CAR DNA HxL (SEQ ID NO: 309):

```
ATGGCACTCCCCGTAACTGCTCTGCTGCTGCCGTTGGCATTGCTCCTGCA

CGCCGCACGCCCGCAGGTGCAGCTGGTGCAGTCTGGGGCTGAGGTGAAG

AAGCCTGGGGCCTCAGTGAAGGTTTCCTGCAGGGCATCTGGATACACCT

TCATGGAGCACTATATGCACTGGGTGCGACAGGCCCCTGGACAAGGGCT

TGAGTGGATGGGAGTAATCGGGCCTAGTGGTGGTAAGACAAGCTACGCA

CAGAAGTTCCAGGGCAGAGTCACCATGACCAGGGACACGTCCACGAGCA

CAGTCTACATGGAGCTGAGCAGCCTGAGATCTGAGGACACGGCGGTGTA

CTACTGCGCCAGAGAGAATTGGCCAATGGACGTATGGGGCCAGGGAACA
```

-continued

ACTGTCACCGTCTCCTCAGGGTCTACATCCGGCTCCGGGAAGCCCGGAA

GTGGCGAAGGTAGTACAAAGGGGGAAATAGTGATGACGCAGTCTCCAG

CCACCCTGTCTGTGTCTCCAGGGGAAAGAGCCACCCTCTCCTGCAGGGC

AGTCAGAGTGTTAGCAGCAACTTAGCCTGGTACCAGCAGAAACCTGGCC

AGGCTCCCAGGCTCCTCATCTATGGTGCATCCACCAGGGCCACTGGTATC

CCAGCCAGGTTCAGTGGCAGTGGGTCTGGGACAGAGTTCACTCTCACCA

TCAGCAGCCTGCAGTCTGAAGATTTTGCAGTTTATTACTGTCAGCAGTAC

GCCGCCTACCCTACTTTTGGCGGAGGGACCAAGGTTGAGATCAAACGGG

CCGCTGCCCTTGATAATGAAAAGTCAAACGGAACAATCATTCACGTGAA

GGGCAAGCACCTCTGTCCGTCACCCTTGTTCCCTGGTCCATCCAAGCCAT

TCTGGGTGTTGGTCGTAGTGGGTGGAGTCCTCGCTTGTTACTCTCTGCTC

GTCACCGTGGCTTTTATAATCTTCTGGGTTAGATCCAAAAGAAGCCGCCT

GCTCCATAGCGATTACATGAATATGACTCCACGCCGCCCTGGCCCCACA

AGGAAACACTACCAGCCTTACGCACCACCTAGAGATTTCGCTGCCTATC

GGAGCAGGGTGAAGTTTTCCAGATCTGCAGATGCACCAGCGTATCAGCA

GGGCCAGAACCAACTGTATAACGAGCTCAACCTGGGACGCAGGGAAGA

GTATGACGTTTTGGACAAGCGCAGAGGACGGGACCCTGAGATGGGTGGC

AAACCAAGACGAAAAAACCCCCAGGAGGGTCTCTATAATGAGCTGCAG

AAGGATAAGATGGCTGAAGCCTATTCTGAAATAGGCATGAAAGGAGAG

CGGAGAAGGGGAAAAGGGCACGACGGTTTGTACCAGGGACTCAGCACT

GCTACGAAGGATACTTATGACGCTCTCCACATGCAAGCCCTGCCACCTA

GG

In further embodiments, the invention relates to Clone AJ-26545 CAR HxL AA sequence (SEQ ID NO: 310):

```
MALPVTALLL PLALLLHAAR PQVQLVQSGA EVKKPGASVK
VSCRASGYTF MEHYMHWVRQ APGQGLEWMG VIGPSGGKTS
YAQKFQGRVT MTRDTSTSTV YMELSSLRSE DTAVYYCARE
SWPMDVWGQG TTVTVSSGST SGSGKPGSGE GSTKGEIVMT
QSPATLSVSP GERATLSCRA SQSVSSNLAW YQQKPGQAPR
LLIYGASTRA TGIPARFSGS GSGTEFTLTI SSLQSEDFAV
YYCQQYAAYP TFGGGTKVEI KRAAALDNEK SNGTIIHVKG
KHLCPSPLFP GPSKPFWVLV VVGGVLACYS LLVTVAFIIF
WVRSKRSRLL HSDYMNMTPR RPGPTRKHYQ PYAPPRDFAA
YRSRVKFSRS ADAPAYQQGQ NQLYNELNLG RREEYDVLDK
RRGRDPEMGG KPRRKNPQEG LYNELQKDKM AEAYSEIGMK
GERRRGKGHD GLYQGLSTAT KDTYDALHMQ ALPPR
```

In further embodiments, the invention relates to Clone AJ-26545 CAR DNA LxH (SEQ ID NO: 311):

ATGGCACTCCCCGTAACTGCTCTGCTGCTGCCGTTGGCATTGCTCCTGCA

CGCCGCACGCCCGGAAATAGTGATGACGCAGTCTCCAGCCACCCTGTCT

GTGTCTCCAGGGGAAAGAGCCACCCTCTCCTGCAGGGCCAGTCAGAGTG

TTAGCAGCAACTTAGCCTGGTACCAGCAGAAACCTGGCCAGGCTCCCAG

GCTCCTCATCTATGGTGCATCCACCAGGGCCACTGGTATCCCAGCCAGGT

TCAGTGGCAGTGGGTCTGGGACAGAGTTCACTCTCACCATCAGCAGCCT

GCAGTCTGAAGATTTTGCAGTTTATTACTGTCAGCAGTACGCCGCCTACC

CTACTTTTGGCGGAGGGACCAAGGTTGAGATCAAACGGGGGTCTACATC

CGGCTCCGGGAAGCCCGGAAGTGGCGAAGGTAGTACAAAGGGGCAGGT

GCAGCTGGTGCAGTCTGGGGCTGAGGTGAAGAAGCCTGGGGCCTCAGTG

AAGGTTTCCTGCAGGGCATCTGGATACACCTTCATGGAGCACTATATGCA

CTGGGTGCGACAGGCCCCTGGACAAGGGCTTGAGTGGATGGGAGTAATC

GGGCCTAGTGGTGGTAAGACAAGCTACGCACAGAAGTTCCAGGGCAGA

GTCACCATGACCAGGGACACGTCCACGAGCACAGTCTACATGGAGCTGA

GCAGCCTGAGATCTGAGGACACGGCGGTGTACTACTGCGCCAGAGAGAA

TTGGCCAATGGACGTATGGGCCAGGGAACAACTGTCACCGTCTCCTCA

GCCGCTGCCCTTGATAATGAAAAGTCAAACGGAACAATCATTCACGTGA

AGGGCAAGCACCTCTGTCCGTCACCCTTGTTCCCTGGTCCATCCAAGCCA

TTCTGGGTGTTGGTCGTAGTGGGTGGAGTCCTCGCTTGTTACTCTCTGCT

CGTCACCGTGGCTTTTATAATCTTCTGGGTTAGATCCAAAAGAAGCCGCC

TGCTCCATAGCGATTACATGAATATGACTCCACGCCGCCCTGGCCCCACA

AGGAAACACTACCAGCCTTACGCACCACCTAGAGATTTCGCTGCCTATC

GGAGCAGGGTGAAGTTTTCCAGATCTGCAGATGCACCAGCGTATCAGCA

GGGCCAGAACCAACTGTATAACGAGCTCAACCTGGGACGCAGGGAAGA

GTATGACGTTTTGGACAAGCGCAGAGGACGGGACCCTGAGATGGGTGGC

AAACCAAGACGAAAAAACCCCCAGGAGGGTCTCTATAATGAGCTGCAG

AAGGATAAGATGGCTGAAGCCTATTCTGAAATAGGCATGAAAGGAGAG

CGGAGAAGGGGAAAAGGGCACGACGGTTTGTACCAGGGACTCAGCACT

GCTACGAAGGATACTTATGACGCTCTCCACATGCAAGCCCTGCCACCTA

GG

In further embodiments, the invention relates to Clone AJ-26545 CAR LxH AA sequence (SEQ ID NO: 312):

```
MALPVTALLL PLALLLHAAR PEIVMTQSPA TLSVSPGERA
TLSCRASQSV SSNLAWYQQK PGQAPRLLIY GASTRATGIP
ARFSGSGSGT EFTLTISSLQ SEDFAVYYCQ QYAAYPTFGG
GTKVEIKRGS TSGSGKPGSG EGSTKGQVQL VQSGAEVKKP
GASVKVSCRA SGYTFMEHYM HWVRQAPGQG LEWMGVIGPS
GGKTSYAQKF QGRVTMTRDT STSTVYMELS SLRSEDTAVY
YCARESWPMD VWGQGTTVTV SSAAALDNEK SNGTIIHVKG
KHLCPSPLFP GPSKPFWVLV VVGGVLACYS LLVTVAFIIF
WVRSKRSRLL HSDYMNMTPR RPGPTRKHYQ PYAPPRDFAA
```

YRSRVKFSRS ADAPAYQQGQ NQLYNELNLG RREEYDVLDK

RRGRDPEMGG KPRRKNPQEG LYNELQKDKM AEAYSEIGMK

GERRRGKGHD GLYQGLSTAT KDTYDALHMQ ALPPR

In further embodiments, the invention relates to Clone AJ-26554 HC DNA (SEQ ID NO: 313):

CAGGTGCAGCTGGTGCAGTCTGGGGCTGAGGTGAAGAAGCCTGGGGCCT

CAGTGAAGGTTTCCTGCAAGGCATCTGGATACACCTTCACGGAGCACTA

TATGCACTGGGTGCGACAGGCCCCTGGACAAAGGCTTGAGTGGATGGGA

GTAATCGGGCCTAGTGGTGGTAAGACAAGCTACGCACAGAAGTTCCAGG

GCAGAGTCACCATGACCAGGGACACGTCCACGAGCACAGTCTACATGGA

GCTGAGCAGCCTGAGATCTGAGGACACGGCGGTGTACTACTGCGCCAGA

GAGAGTTGGCCAATGGACGTATGGGGCCAGGGAACAACTGTCACCGTCT

CCTCA

In further embodiments, the invention relates to Clone AJ-26554 HC (SEQ ID NO: 314): QVQLVQSGAE VKKP-GASVKV SCKASGYTFT EHYMHWVRQA PGQR-LEWMGV IGPSGGKTSY AQKFQGRVTM TRDTST-STVY MELSSLRSED TAVYYCARES WPMDVWGQGT TVTVSS In further embodiments, the invention relates to HC CDR1 thereof: YTFTEHYMH (SEQ ID NO: 315). In further embodiments, the invention relates to HC CDR2 thereof: VIGPSGGKTSYAQKFQG (SEQ ID NO: 316). In further embodiments, the invention relates to HC CDR3 thereof: ARESWPMDV (SEQ ID NO: 317).

In further embodiments, the invention relates to Clone AJ-26554 LC DNA (SEQ ID NO: 318):

GAAATAGTGATGACGCAGTCTCCAGCCACCCTGTCTGTGTCTCCAGGGG

AAAGAGCCACCCTCTCCTGCAGGGCCAGTCAGAGTGTTAGCAGCAACTT

AGCCTGGTACCAGCAGAAACCTGGCCAGGCTCCCAGGCTCCTCATCTAT

GGTGCATCCACCAGGGCCACTGGTATCCCAGCCAGGTTCAGTGGCAGTG

GGTCTGGGACAGAGTTCACTCTCACCATCAGCAGCCTGCAGTCTGAAGA

TTTTGCAGTTTATTACTGTCAGCAGTACGCCGCCTACCCTACTTTTGGCG

GAGGGACCAAGGTTGAGATCAAACGG

In further embodiments, the invention relates to Clone AJ-26554 LC AA sequence (SEQ ID NO: 319): EIVMTQSPAT LSVSPGERAT LSCRASQSVS SNLAWYQQKP GQAPRLLIYG ASTRATGIPA RFSGSGSGTE FTLTISSLQS EDFAVYYCQQ YAAYPTFGGG TKVEIKR.

In further embodiments, the invention relates to the LC CDR1 thereof: RASQSVSSNLA (SEQ ID NO: 320). In further embodiments, the invention relates to the LC CDR2 thereof: GASTRAT (SEQ ID NO: 321). In further embodiments, the invention relates to LC CDR3 thereof: QQYAAYPT (SEQ ID NO: 322).

In further embodiments, the invention relates to Clone AJ-26554 CAR DNA HxL (SEQ ID NO: 323):

ATGGCACTCCCCGTAACTGCTCTGCTGCTGCCGTTGGCATTGCTCCTGCA

CGCCGCACGCCCGCAGGTGCAGCTGGTGCAGTCTGGGGCTGAGGTGAAG

AAGCCTGGGGCCTCAGTGAAGGTTTCCTGCAAGGCATCTGGATACACCT

TCACGGAGCACTATATGCACTGGGTGCGACAGGCCCCTGGACAAAGGCT

TGAGTGGATGGGAGTAATCGGGCCTAGTGGTGGTAAGACAAGCTACGCA

CAGAAGTTCCAGGGCAGAGTCACCATGACCAGGGACACGTCCACGAGCA

CAGTCTACATGGAGCTGAGCAGCCTGAGATCTGAGGACACGGCGGTGTA

CTACTGCGCCAGAGAGAGTTGGCCAATGGACGTATGGGGCCAGGGAACA

ACTGTCACCGTCTCCTCAGGGTCTACATCCGGCTCCGGGAAGCCCGGAA

GTGGCGAAGGTAGTACAAAGGGGGAAATAGTGATGACGCAGTCTCCAG

CCACCCTGTCTGTGTCTCCAGGGGAAAGAGCCACCCTCTCCTGCAGGGCC

AGTCAGAGTGTTAGCAGCAACTTAGCCTGGTACCAGCAGAAACCTGGCC

AGGCTCCCAGGCTCCTCATCTATGGTGCATCCACCAGGGCCACTGGTATC

CCAGCCAGGTTCAGTGGCAGTGGGTCTGGGACAGAGTTCACTCTCACCA

TCAGCAGCCTGCAGTCTGAAGATTTTGCAGTTTATTACTGTCAGCAGTAC

GCCGCCTACCCTACTTTTGGCGGAGGGACCAAGGTTGAGATCAAACGGG

CCGCTGCCCTTGATAATGAAAAGTCAAACGGAACAATCATTCACGTGAA

GGGCAAGCACCTCTGTCCGTCACCCTTGTTCCCTGGTCCATCCAAGCCAT

TCTGGGTGTTGGTCGTAGTGGGTGGAGTCCTCGCTTGTTACTCTCTGCTC

GTCACCGTGGCTTTTATAATCTTCTGGGTTAGATCCAAAAGAAGCCGCCT

GCTCCATAGCGATTACATGAATATGACTCCACGCCGCCCTGGCCCCACA

AGGAAACACTACCAGCCTTACGCACCACCTAGAGATTTCGCTGCCTATC

GGAGCAGGGTGAAGTTTTCCAGATCTGCAGATGCACCAGCGTATCAGCA

GGGCCAGAACCAACTGTATAACGAGCTCAACCTGGGACGCAGGGAAGA

GTATGACGTTTTGGACAAGCGCAGAGGACGGGACCCTGAGATGGGTGGC

AAACCAAGACGAAAAAACCCCCAGGAGGGTCTCTATAATGAGCTGCAG

AAGGATAAGATGGCTGAAGCCTATTCTGAAATAGGCATGAAAGGAGAG

CGGAGAAGGGGAAAAGGGCACGACGGTTTGTACCAGGGACTCAGCACT

GCTACGAAGGATACTTATGACGCTCTCCACATGCAAGCCCTGCCACCTA

GG

In further embodiments, the invention relates to Clone AJ-26554 CAR HxL AA sequence (SEQ ID NO: 324):

MALPVTALLL PLALLLHAAR PQVQLVQSGA EVKKPGASVK

VSCKASGYTF TEHYMHWVRQ APGQRLEWMG VIGPSGGKTS

YAQKFQGRVT MTRDTSTSTV YMELSSLRSE DTAVYYCARE

SWPMDVWGQG TTVTVSSGST SGSGKPGSGE GSTKGEIVMT

QSPATLSVSP GERATLSCRA SQSVSSNLAW YQQKPGQAPR

LLIYGASTRA TGIPARFSGS GSGTEFTLTI SSLQSEDFAV

YYCQQYAAYP TFGGGTKVEI KRAAALDNEK SNGTIIHVKG

KHLCPSPLFP GPSKPFWVLV VVGGVLACYS LLVTVAFIIF

WVRSKRSRLL HSDYMNMTPR RPGPTRKHYQ PYAPPRDFAA

YRSRVKFSRS ADAPAYQQGQ NQLYNELNLG RREEYDVLDK

RRGRDPEMGG KPRRKNPQEG LYNELQKDKM AEAYSEIGMK

GERRRGKGHD GLYQGLSTAT KDTYDALHMQ ALPPR.

In further embodiments, the invention relates to Clone AJ-26554 CAR DNA LxH (SEQ ID NO: 325):

ATGGCACTCCCCGTAACTGCTCTGCTGCTGCCGTTGGCATTGCTCCTGCA

CGCCGCACGCCCGGAAATAGTGATGACGCAGTCTCCAGCCACCCTGTCT

GTGTCTCCAGGGGAAAGAGCCACCCTCTCCTGCAGGGCCAGTCAGAGTG

TTAGCAGCAACTTAGCCTGGTACCAGCAGAAACCTGGCCAGGCTCCCAG

GCTCCTCATCTATGGTGCATCCACCAGGGCCACTGGTATCCCAGCCAGGT

TCAGTGGCAGTGGGTCTGGGACAGAGTTCACTCTCACCATCAGCAGCCT

GCAGTCTGAAGATTTTGCAGTTTATTACTGTCAGCAGTACGCCGCCTACC

CTACTTTTGGCGGAGGGACCAAGGTTGAGATCAAACGGGGGTCTACATC

CGGCTCCGGGAAGCCCGGAAGTGGCGAAGGTAGTACAAAGGGGCAGGT

GCAGCTGGTGCAGTCTGGGGCTGAGGTGAAGAAGCCTGGGGCCTCAGTG

AAGGTTTCCTGCAAGGCATCTGGATACACCTTCACGGAGCACTATATGC

ACTGGGTGCGACAGGCCCCTGGACAAAGGCTTGAGTGGATGGGAGTAAT

CGGGCCTAGTGGTGGTAAGACAAGCTACGCACAGAAGTTCCAGGGCAGA

GTCACCATGACCAGGGACACGTCCACGAGCACAGTCTACATGGAGCTGA

GCAGCCTGAGATCTGAGGACACGGCGGTGTACTACTGCGCCAGAGAGAG

TTGGCCAATGGACGTATGGGCCAGGGAACAACTGTCACCGTCTCCTCA

GCCGCTGCCCTTGATAATGAAAAGTCAAACGGAACAATCATTCACGTGA

AGGGCAAGCACCTCTGTCCGTCACCCTTGTTCCCTGGTCCATCCAAGCCA

TTCTGGGTGTTGGTCGTAGTGGGTGGAGTCCTCGCTTGTTACTCTCTGCT

CGTCACCGTGGCTTTTATAATCTTCTGGGTTAGATCCAAAAGAAGCCGCC

TGCTCCATAGCGATTACATGAATATGACTCCACGCCGCCCTGGCCCCACA

AGGAAACACTACCAGCCTTACGCACCACCTAGAGATTTCGCTGCCTATC

GGAGCAGGGTGAAGTTTTCCAGATCTGCAGATGCACCAGCGTATCAGCA

GGGCCAGAACCAACTGTATAACGAGCTCAACCTGGGACGCAGGGAAGA

GTATGACGTTTTGGACAAGCGCAGAGGACGGGACCCTGAGATGGGTGGC

AAACCAAGACGAAAAAACCCCCAGGAGGGTCTCTATAATGAGCTGCAG

AAGGATAAGATGGCTGAAGCCTATTCTGAAATAGGCATGAAAGGAGAG

CGGAGAAGGGGAAAAGGGCACGACGGTTTGTACCAGGGACTCAGCACT

GCTACGAAGGATACTTATGACGCTCTCCACATGCAAGCCCTGCCACCTA

GG

In further embodiments, the invention relates to Clone AJ-26554 CAR LxH AA sequence (SEQ ID NO: 326):

MALPVTALLL PLALLLHAAR PEIVMTQSPA TLSVSPGERA

TLSCRASQSV SSNLAWYQQK PGQAPRLLIY GASTRATGIP

ARFSGSGSGT EFTLTISSLQ SEDFAVYYCQ QYAAYPTFGG

GTKVEIKRGS TSGSGKPGSG EGSTKGQVQL VQSGAEVKKP

GASVKVSCKA SGYTFTEHYM HWVRQAPGQR LEWMGVIGPS

GGKTSYAQKF QGRVTMTRDT STSTVYMELS SLRSEDTAVY

YCARESWPMD VWGQGTTVTV SSAAALDNEK SNGTIIHVKG

KHLCPSPLFP GPSKPFWVLV VVGGVLACYS LLVTVAFIIF

WVRSKRSRLL HSDYMNMTPR RPGPTRKHYQ PYAPPRDFAA

YRSRVKFSRS ADAPAYQQGQ NQLYNELNLG RREEYDVLDK

RRGRDPEMGG KPRRKNPQEG LYNELQKDKM AEAYSEIGMK

GERRRGKGHD GLYQGLSTAT KDTYDALHMQ ALPPR

In further embodiments, the invention relates to Clone NM-26562 HC DNA (SEQ ID NO: 327):

CAGGTGCAGCTGCAGGAGTCGGGCCCAGGACTGGTGAAGCCTTCACAGA

CCCTGTCCCTCACCTGTACTGTCTCTGGTGGCTCCATCGGGAGTGGTGGT

AGTTACTGGAGCTGGATCCGCCAGCACCCAGGGAAGGGCCTGGAGTGGA

TTGGGTTGATCTATTACGATGGGAGCACCTACTACAACCCGTCCCTCAAG

AGTCGAGTTACCATATCAGTAGACACGTCTAAGAACCAGTTCTCCCTGA

AGCTGAGTTCTGTGACCGCCGCAGACACGGCGGTGTACTACTGCGCCAG

AGGCAGGGGATATGAGACTTCTTTAGCCTTCGATATCTGGGGTCAGGGT

ACAATGGTCACCGTCTCCTCA

In further embodiments, the invention relates to Clone NM-26562 HC AA sequence (SEQ ID NO: 328):
QVQLQESGPG LVKPSQTLSL TCTVSGG<u>SIG SGGSYWS</u>WIR QHPGKGLEWI G<u>LIYYDGSTY YNPSLKS</u>RVT ISVDTSKNQF SLKLSSVTAA DTAVYYC<u>ARG RGYETSLAFD</u> IWGQGTMVTV SS.

In further embodiments, the invention relates to HC CDR1 thereof: GSIGSGGSYWS (SEQ ID NO: 329). In further embodiments, the invention relates to HC CDR2 thereof: LIYYDGSTYYNPSLKS (SEQ ID NO: 330). In further embodiments, the invention relates to HC CDR3 thereof: ARGRGYETSLAFDI (SEQ ID NO: 331).

In further embodiments, the invention relates to Clone NM-26562 LC DNA (SEQ ID NO: 332):

GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGAGACACGTCTGGCCTCCTACTTTTGGCGGA

GGGACCAAGGTTGAGATCAAACGG

In further embodiments, the invention relates to Clone NM-26562 LC AA sequence (SEQ ID NO: 333):

```
EIVLTQSPAT LSLSPGERAT LSCRASQSVS SYLAWYQQKP
GQAPRLLIYD ASNRATGIPA RFSGSGSGTD FTLTISSLEP
EDFAVYYCQQ RHVWPPTFGG GTKVEIKR
```

In further embodiments, the invention relates to LC CDR1 AA sequence thereof: RASQSVSSYLA (SEQ ID NO: 334) In further embodiments, the invention relates to LC CDR2 AA sequence thereof: DASNRAT (SEQ ID NO: 335). In further embodiments, the invention relates to LC CDR3 AA sequence thereof: QQRHVWPPT (SEQ ID NO: 336) (LC CDR3).

In further embodiments, the invention relates to Clone NM-26562 CAR DNA HxL (SEQ ID NO: 337):

```
ATGGCACTCCCCGTAACTGCTCTGCTGCTGCCGTTGGCATTGCTCCTGCA
CGCCGCACGCCCGCAGGTGCAGCTGCAGGAGTCGGGCCCAGGACTGGTGA
AGCCTTCACAGACCCTGTCCCTCACCTGTACTGTCTCTGGTGGCTCCATC
GGGAGTGGTGGTAGTTACTGGAGCTGGATCCGCCAGCACCCAGGGAAGGG
CCTGGAGTGGATTGGGTTGATCTATTACGATGGGAGCACCTACTACAACC
CGTCCCTCAAGAGTCGAGTTACCATATCAGTAGACACGTCTAAGAACCAG
TTCTCCCTGAAGCTGAGTTCTGTGACCGCCGCAGACACGGCGGTGTACTA
CTGCGCCAGAGGCAGGGGATATGAGACTTCTTTAGCCTTCGATATCTGGG
GTCAGGGTACAATGGTCACCGTCTCCTCAGGGTCTACATCCGGCTCCGGG
AAGCCCGGAAGTGGCGAAGGTAGTACAAAGGGGGAAATTGTGTTGACACA
GTCTCCAGCCACCCTGTCTTTGTCTCCAGGGGAAAGAGCCACCCTCTCCT
GCAGGGCCAGTCAGAGTGTTAGCAGCTACTTAGCCTGGTACCAACAGAAA
CCTGGCCAGGCTCCCAGGCTCCTCATCTATGATGCATCCAACAGGGCCAC
TGGCATCCCAGCCAGGTTCAGTGGCAGTGGGTCTGGGACAGACTTCACTC
TCACCATCAGCAGCCTAGAGCCTGAAGATTTTGCAGTTTATTACTGTCAG
CAGAGACACGTCTGGCCTCCTACTTTTGGCGGAGGGACCAAGGTTGAGAT
CAAACGGGCCGCTGCCCTTGATAATGAAAAGTCAAACGGAACAATCATTC
ACGTGAAGGGCAAGCACCTCTGTCCGTCACCCTTGTTCCCTGGTCCATCC
AAGCCATTCTGGGTGTTGGTCGTAGTGGGTGGAGTCCTCGCTTGTTACTC
TCTGCTCGTCACCGTGGCTTTTATAATCTTCTGGGTTAGATCCAAAAGAA
GCCGCCTGCTCCATAGCGATTACATGAATATGACTCCACGCCGCCCTGGC
CCCACAAGGAAACACTACCAGCCTTACGCACCACCTAGAGATTTCGCTGC
CTATCGGAGCAGGGTGAAGTTTTCCAGATCTGCAGATGCACCAGCGTATC
AGCAGGGCCAGAACCAACTGTATAACGAGCTCAACCTGGGACGCAGGGAA
GAGTATGACGTTTTGGACAAGCGCAGAGGACGGGACCCTGAGATGGGTGG
CAAACCAAGACGAAAAACCCCCAGGAGGGTCTCTATAATGAGCTGCAGA
AGGATAAGATGGCTGAAGCCTATTCTGAAATAGGCATGAAAGGAGAGCGG
AGAAGGGGAAAAGGGCACGACGGTTTGTACCAGGGACTCAGCACTGCTAC
GAAGGATACTTATGACGCTCTCCACATGCAAGCCCTGCCACCTAGG.
```

In further embodiments, the invention relates to Clone NM-26562 CAR HxL (SEQ ID NO: 338):

```
MALPVTALLL PLALLLHAAR PQVQLQESGP GLVKPSQTLS
LTCTVSGGSI GSGGSYWSWI RQHPGKGLEW IGLIYYDGST
YYNPSLKSRV TISVDTSKNQ FSLKLSSVTA ADTAVYYCAR
GRGYETSLAF DIWGQGTMVT VSSGSTSGSG KPGSGEGSTK
GEIVLTQSPA TLSLSPGERA TLSCRASQSV SSYLAWYQQK
PGQAPRLLIY DASNRATGIP ARFSGSGSGT DFTLTISSLE
PEDFAVYYCQ QRHVWPPTFG GGTKVEIKRA AALDNEKSNG
TIIHVKGKHL CPSPLFPGPS KPFWVLVVVG GVLACYSLLV
TVAFIIFWVR SKRSRLLHSD YMNMTPRRPG PTRKHYQPYA
PPRDFAAYRS RVKFSRSADA PAYQQGQNQL YNELNLGRRE
EYDVLDKRRG RDPEMGGKPR RKNPQEGLYN ELQKDKMAEA
YSEIGMKGER RRGKGHDGLY QGLSTATKDT YDALHMQALP
PR.
```

In further embodiments, the invention relates to Clone NM-26562 CAR DNA LxH (SEQ ID NO: 339):

```
ATGGCACTCCCCGTAACTGCTCTGCTGCTGCCGTTGGCATTGCTCCTGCA
CGCCGCACGCCCGGAAATTGTGTTGACACAGTCTCCAGCCACCCTGTCTT
TGTCTCCAGGGGAAAGAGCCACCCTCTCCTGCAGGGCCAGTCAGAGTGTT
AGCAGCTACTTAGCCTGGTACCAACAGAAACCTGGCCAGGCTCCCAGGCT
CCTCATCTATGATGCATCCAACAGGGCCACTGGCATCCCAGCCAGGTTCA
GTGGCAGTGGGTCTGGGACAGACTTCACTCTCACCATCAGCAGCCTAGAG
CCTGAAGATTTTGCAGTTTATTACTGTCAGCAGAGACACGTCTGGCCTCC
TACTTTTGGCGGAGGGACCAAGGTTGAGATCAAACGGGGGTCTACATCCG
GCTCCGGGAAGCCCGGAAGTGGCGAAGGTAGTACAAAGGGGCAGGTGCAG
CTGCAGGAGTCGGGCCCAGGACTGGTGAAGCCTTCACAGACCCTGTCCCT
CACCTGTACTGTCTCTGGTGGCTCCATCGGGAGTGGTGGTAGTTACTGGA
GCTGGATCCGCCAGCACCCAGGGAAGGGCCTGGAGTGGATTGGGTTGATC
TATTACGATGGGAGCACCTACTACAACCCGTCCCTCAAGAGTCGAGTTAC
CATATCAGTAGACACGTCTAAGAACCAGTTCTCCCTGAAGCTGAGTTCTG
TGACCGCCGCAGACACGGCGGTGTACTACTGCGCCAGAGGCAGGGGATAT
GAGACTTCTTTAGCCTTCGATATCTGGGGTCAGGGTACAATGGTCACCGT
CTCCTCAGCCGCTGCCCTTGATAATGAAAAGTCAAACGGAACAATCATTC
ACGTGAAGGGCAAGCACCTCTGTCCGTCACCCTTGTTCCCTGGTCCATCC
AAGCCATTCTGGGTGTTGGTCGTAGTGGGTGGAGTCCTCGCTTGTTACTC
TCTGCTCGTCACCGTGGCTTTTATAATCTTCTGGGTTAGATCCAAAAGAA
GCCGCCTGCTCCATAGCGATTACATGAATATGACTCCACGCCGCCCTGGC
CCCACAAGGAAACACTACCAGCCTTACGCACCACCTAGAGATTTCGCTGC
CTATCGGAGCAGGGTGAAGTTTTCCAGATCTGCAGATGCACCAGCGTATC
```

-continued
AGCAGGGCCAGAACCAACTGTATAACGAGCTCAACCTGGGACGCAGGGAA

GAGTATGACGTTTTGGACAAGCGCAGAGGACGGGACCCTGAGATGGGTGG

CAAACCAAGACGAAAAAACCCCCAGGAGGGTCTCTATAATGAGCTGCAGA

AGGATAAGATGGCTGAAGCCTATTCTGAAATAGGCATGAAAGGAGAGCGG

AGAAGGGGAAAAGGGCACGACGGTTTGTACCAGGGACTCAGCACTGCTAC

GAAGGATACTTATGACGCTCTCCACATGCAAGCCCTGCCACCTAGG

In further embodiments, the invention relates to Clone NM-26562 CAR LxH (SEQ ID NO: 340):

```
MALPVTALLL PLALLLHAAR PEIVLTQSPA TLSLSPGERA

TLSCRASQSV SSYLAWYQQK PGQAPRLLIY DASNRATGIP

ARFSGSGSGT DFTLTISSLE PEDFAVYYCQ QRHVWPPTFG

GGTKVEIKRG STSGSGKPGS GEGSTKGQVQ LQESGPGLVK

PSQTLSLTCT VSGGSIGSGG SYWSWIRQHP GKGLEWIGLI

YYDGSTYYNP SLKSRVTISV DTSKNQFSLK LSSVTAADTA

VYYCARGRGY ETSLAFDIWG QGTMVTVSSA AALDNEKSNG

TIIHVKGKHL CPSPLFPGPS KPFWVLVVVG GVLACYSLLV

TVAFIIFWVR SKRSRLLHSD YMNMTPRRPG PTRKHYQPYA

PPRDFAAYRS RVKFSRSADA PAYQQGQNQL YNELNLGRRE

EYDVLDKRRG RDPEMGGKPR RKNPQEGLYN ELQKDKMAEA

YSEIGMKGER RRGKGHDGLY QGLSTATKDT YDALHMQALP

PR
```

In further embodiments, the invention relates to Clone TS-26564 HC DNA sequence (SEQ ID NO: 341):

GAGGTGCAGCTGGTGGAGTCTGGGGGAGGCTTGGTACAGCCTGGGGGGTC

CCTGAGACTCTCCTGTGCAGCCTCTGGATTCACCTTCAGTAGCTATAGCA

TGAACTGGGTCCGCCAGGCTCCAGGGAAGGGGCTGGAGTGGGTTTCAACC

ATTAGTAGTAGTAGTAGTATCATATACTACGCAGACTCTGTGAAGGGCCG

ATTCACCATCTCCAGAGACAATGCCAAGAACTCACTGTATCTGCAAATGA

ACAGCCTGAGAGCTGAGGACACGGCGGTGTACTACTGCGCCAGAGGTTCT

CAGGAGCACCTGATTTTCGATTATTGGGGACAGGGTACATTGGTCACCGT

CTCCTCA

In further embodiments, the invention relates to Clone TS-26564 HC AA sequence (SEQ ID NO: 342): EVQLVES-GGG LVQPGGSLRL SCAASG<u>FTFS SYSMN</u>WVRQA PGKGLEWVS<u>T ISSSSSIIYY ADSVKGRFTI</u> SRD-NAKNSLY LQMNSLRAED TAVYYC<u>ARGS QEHLIFDY</u>WG QGTLVTVSS In further embodiments, the invention relates to HC CDR1 AA sequence thereof: FTFSSYSMN (SEQ ID NO: 343). In further embodiments, the invention relates to HC CDR2 AA sequence thereof: TISSSSSIIYYADSVKG (SEQ ID NO: 344). In further embodiments, the invention relates to HC CDR3 AA sequence thereof: ARGSQEHLIFDY (SEQ ID NO: 345).

In further embodiments, the invention relates to Clone TS-26564 LC DNA (SEQ ID NO: 346):

GAAATTGTGTTGACACAGTCTCCAGCCACCCTGTCTTTGTCTCCAGGGGAA

AGAGCCACCCTCTCCTGCAGGGCCAGTCAGAGTGTTAGCAGGTACTTAGCC

TGGTACCAACAGAAACCTGGCCAGGCTCCCAGGCTCCTCATCTATGATGCA

TCCAACAGGGCCACTGGCATCCCAGCCAGGTTCAGTGGCAGTGGGTCTGGG

ACAGACTTCACTCTCACCATCAGCAGCCTAGAGCCTGAAGATTTTGCAGTT

TATTACTGTCAGCAGAGATTCTACTACCCTTGGACTTTTGGCGGAGGGACC

AAGGTTGAGATCAAACGG

In further embodiments, the invention relates to Clone TS-26564 LC AA sequence (SEQ ID NO: 347):

EIVLTQSPAT LSLSPGERAT LSC<u>RASQSVS RYLA</u>WYQQKP

GQAPRLLIY<u>D ASNRAT</u>GIPA RFSGSGSGTD FTLTISSLEP

EDFAVYYC<u>QQ RFYYPWT</u>FGG GTKVEIKR.

In further embodiments, the invention relates to LC CDR1 AA sequence thereof: RASQSVSRYLA (SEQ ID NO: 348). In further embodiments, the invention relates to LC CDR2 AA sequence thereof: DASNRAT (SEQ ID NO: 349). In further embodiments, the invention relates to LC CDR3 AA sequence thereof: QQRFYYPWT (SEQ ID NO: 350).

In further embodiments, the invention relates to Clone TS-26564 CAR DNA HxL (SEQ ID NO: 351):

ATGGCACTCCCCGTAACTGCTCTGCTGCTGCCGTTGGCATTGCTCCTGCA

CGCCGCACGCCCGGAGGTGCAGCTGGTGGAGTCTGGGGGAGGCTTGGTAC

AGCCTGGGGGGTCCCTGAGACTCTCCTGTGCAGCCTCTGGATTCACCTTC

AGTAGCTATAGCATGAACTGGGTCCGCCAGGCTCCAGGGAAGGGGCTGGA

GTGGGTTTCAACCATTAGTAGTAGTAGTAGTATCATATACTACGCAGACT

CTGTGAAGGGCCGATTCACCATCTCCAGAGACAATGCCAAGAACTCACTG

TATCTGCAAATGAACAGCCTGAGAGCTGAGGACACGGCGGTGTACTACTG

CGCCAGAGGTTCTCAGGAGCACCTGATTTTCGATTATTGGGGACAGGGTA

CATTGGTCACCGTCTCCTCAGGGTCTACATCCGGCTCCGGGAAGCCCGGA

AGTGGCGAAGGTAGTACAAAGGGGGAAATTGTGTTGACACAGTCTCCAGC

CACCCTGTCTTTGTCTCCAGGGGAAAGAGCCACCCTCTCCTGCAGGGCCA

GTCAGAGTGTTAGCAGGTACTTAGCCTGGTACCAACAGAAACCTGGCCAG

GCTCCCAGGCTCCTCATCTATGATGCATCCAACAGGGCCACTGGCATCCC

AGCCAGGTTCAGTGGCAGTGGGTCTGGGACAGACTTCACTCTCACCATCA

GCAGCCTAGAGCCTGAAGATTTTGCAGTTTATTACTGTCAGCAGAGATTC

TACTACCCTTGGACTTTTGGCGGAGGGACCAAGGTTGAGATCAAACGGGC

CGCTGCCCTTGATAATGAAAAGTCAAACGGAACAATCATTCACGTGAAGG

GCAAGCACCTCTGTCCGTCACCCTTGTTCCCTGGTCCATCCAAGCCATTC

TGGGTGTTGGTCGTAGTGGGTGGAGTCCTCGCTTGTTACTCTCTGCTCGT

CACCGTGGCTTTTATAATCTTCTGGGTTAGATCCAAAAGAAGCCGCCTGC

-continued

```
TCCATAGCGATTACATGAATATGACTCCACGCCGCCCTGGCCCCACAAGG

AAACACTACCAGCCTTACGCACCACCTAGAGATTTCGCTGCCTATCGGAG

CAGGGTGAAGTTTTCCAGATCTGCAGATGCACCAGCGTATCAGCAGGGCC

AGAACCAACTGTATAACGAGCTCAACCTGGGACGCAGGGAAGAGTATGAC

GTTTTGGACAAGCGCAGAGGACGGGACCCTGAGATGGGTGGCAAACCAAG

ACGAAAAAACCCCCAGGAGGGTCTCTATAATGAGCTGCAGAAGGATAAGA

TGGCTGAAGCCTATTCTGAAATAGGCATGAAAGGAGAGCGGAGAAGGGGA

AAAGGGCACGACGGTTTGTACCAGGGACTCAGCACTGCTACGAAGGATAC

TTATGACGCTCTCCACATGCAAGCCCTGCCACCTAGG
```

In further embodiments, the invention relates to Clone TS-26564 CAR HxL AA sequence (SEQ ID NO: 352):

```
MALPVTALLL PLALLLHAAR PEVQLVESGG GLVQPGGSLR

LSCAASGFTF SSYSMNWVRQ APGKGLEWVS TISSSSSIIY

YADSVKGRFT ISRDNAKNSL YLQMNSLRAE DTAVYYCARG

SQEHLIFDYW GQGTLVTVSS GSTSGSGKPG SGEGSTKGEI

VLTQSPATLS LSPGERATLS CRASQSVSRY LAWYQQKPGQ

APRLLIYDAS NRATGIPARF SGSGSGTDFT LTISSLEPED

FAVYYCQQRF YYPWTFGGGT KVEIKRAAAL DNEKSNGTII

HVKGKHLCPS PLFPGPSKPF WVLVVVGGVL ACYSLLVTVA

FIIFWVRSKR SRLLHSDYMN MTPRRPGPTR KHYQPYAPPR

DFAAYRSRVK FSRSADAPAY QQGQNQLYNE LNLGRREEYD

VLDKRRGRDP EMGGKPRRKN PQEGLYNELQ KDKMAEAYSE

IGMKGERRRG KGHDGLYQGL STATKDTYDA LHMQALPPR
```

In further embodiments, the invention relates to Clone TS-26564 CAR DNA LxH (SEQ ID NO: 353):

```
ATGGCACTCCCCGTAACTGCTCTGCTGCTGCCGTTGGCATTGCTCCTGCA

CGCCGCACGCCCGGAAATTGTGTTGACACAGTCTCCAGCCACCCTGTCTT

TGTCTCCAGGGGAAAGAGCCACCCTCTCCTGCAGGGCCAGTCAGAGTGTT

AGCAGGTACTTAGCCTGGTACCAACAGAAACCTGGCCAGGCTCCCAGGCT

CCTCATCTATGATGCATCCAACAGGGCCACTGGCATCCCAGCCAGGTTCA

GTGGCAGTGGGTCTGGGACAGACTTCACTCTCACCATCAGCAGCCTAGAG

CCTGAAGATTTTGCAGTTTATTACTGTCAGCAGAGATTCTACTACCCTTG

GACTTTTGGCGGAGGGACCAAGGTTGAGATCAAACGGGGGTCTACATCCG

GCTCCGGGAAGCCCGGAAGTGGCGAAGGTAGTACAAAGGGGGAGGTGCAG

CTGGTGGAGTCTGGGGGAGGCTTGGTACAGCCTGGGGGGTCCCTGAGACT

CTCCTGTGCAGCCTCTGGATTCACCTTCAGTAGCTATAGCATGAACTGGG

TCCGCCAGGCTCCAGGGAAGGGGCTGGAGTGGGTTTCAACCATTAGTAGT

AGTAGTAGTATCATATACTACGCAGACTCTGTGAAGGGCCGATTCACCAT

CTCCAGAGACAATGCCAAGAACTCACTGTATCTGCAAATGAACAGCCTGA
```
```
GAGCTGAGGACACGGCGGTGTACTACTGCGCCAGAGGTTCTCAGGAGCAC

CTGATTTTCGATTATTGGGGACAGGGTACATTGGTCACCGTCTCCTCAGC

CGCTGCCCTTGATAATGAAAAGTCAAACGGAACAATCATTCACGTGAAGG

GCAAGCACCTCTGTCCGTCACCCTTGTTCCCTGGTCCATCCAAGCCATTC

TGGGTGTTGGTCGTAGTGGGTGGAGTCCTCGCTTGTTACTCTCTGCTCGT

CACCGTGGCTTTTATAATCTTCTGGGTTAGATCCAAAAGAAGCCGCCTGC

TCCATAGCGATTACATGAATATGACTCCACGCCGCCCTGGCCCCACAAGG

AAACACTACCAGCCTTACGCACCACCTAGAGATTTCGCTGCCTATCGGAG

CAGGGTGAAGTTTTCCAGATCTGCAGATGCACCAGCGTATCAGCAGGGCC

AGAACCAACTGTATAACGAGCTCAACCTGGGACGCAGGGAAGAGTATGAC

GTTTTGGACAAGCGCAGAGGACGGGACCCTGAGATGGGTGGCAAACCAAG

ACGAAAAAACCCCCAGGAGGGTCTCTATAATGAGCTGCAGAAGGATAAGA

TGGCTGAAGCCTATTCTGAAATAGGCATGAAAGGAGAGCGGAGAAGGGGA

AAAGGGCACGACGGTTTGTACCAGGGACTCAGCACTGCTACGAAGGATAC

TTATGACGCTCTCCACATGCAAGCCCTGCCACCTAGG
```

In further embodiments, the invention relates to Clone TS-26564 CAR LxH AA sequence (SEQ ID NO: 354):

```
MALPVTALLL PLALLLHAAR PEIVLTQSPA TLSLSPGERA

TLSCRASQSV SRYLAWYQQK PGQAPRLLIY DASNRATGIP

ARFSGSGSGT DFTLTISSLE PEDFAVYYCQ QRFYYPWTFG

GGTKVEIKRG STSGSGKPGS GEGSTKGEVQ LVESGGGLVQ

PGGSLRLSCA ASGFTFSSYS MNWVRQAPGK GLEWVSTISS

SSSIIYYADS VKGRFTISRD NAKNSLYLQM NSLRAEDTAV

YYCARGSQEH LIFDYWGQGT LVTVSSAAAL DNEKSNGTII

HVKGKHLCPS PLFPGPSKPF WVLVVVGGVL ACYSLLVTVA

FIIFWVRSKR SRLLHSDYMN MTPRRPGPTR KHYQPYAPPR

DFAAYRSRVK FSRSADAPAY QQGQNQLYNE LNLGRREEYD

VLDKRRGRDP EMGGKPRRKN PQEGLYNELQ KDKMAEAYSE

IGMKGERRRG KGHDGLYQGL STATKDTYDA LHMQALPPR
```

In further embodiments, the invention relates to Clone RY-26568 HC DNA (SEQ ID NO: 355):

```
CAGGTGCAGCTGGTGGAGTCTGGGGGAGGCGTGGTCCAGCCTGGGAGGTC

CCTGAGACTCTCCTGTGCAGCGTCTGGATTCACCTTCGGGAGCTATGGCA

TGCACTGGGTCCGCCAGGCTCCAGGCAAGGGGCTGGAGTGGGTGGCAGTT

ATACATTATGATGGAAGTGTTAATACTATGCAGACTCCGTGAAGGGCCG

ATTCACCATCTCCAGAGACAATTCCAAGGACACGCTGTATCTGCAAATGA

ACAGCCTGAGAGCCGAGGACACGCGGTGTACTACTGCGCCAGAACTGAC

TTCTGGAGCGGATCCCCTCCAAGCTTAGATTACTGGGGACAGGGTACATT

GGTCACCGTCTCCTCA
```

In further embodiments, the invention relates to Clone RY-26568 HC AA sequence (SEQ ID NO: 356):

QVQLVESGGG VVQPGRSLRL SCAASG<u>FTFG
SYGMH</u>WVRQA PGKGLEWVA<u>V IHYDGSVEYY
ADSVKG</u>RFTI SRDNSKDTLY LQMNSLRAED TAV-
YYC<u>ARTD FWSGSPPSLD</u> YWGQGTLVTV SS

In further embodiments, the invention relates to HC CDR1 thereof: FTFGSYGMH (SEQ ID NO: 357). In further embodiments, the invention relates to HC CDR2 thereof: VIHYDGSVEYYADSVKG (SEQ ID NO: 358). In further embodiments, the invention relates to HC CDR3 thereof: ARTDFWSGSPPSLDY (SEQ ID NO: 359).

In further embodiments, the invention relates to Clone RY-26568 LC DNA (SEQ ID NO: 360):

GACATCCAGTTGACCCAGTCTCCATCTTCCGTGTCTGCATCTGTAGGAGA

CAGAGTCACCATCACTTGTCGGGCGAGTCGGGGTATTAGCAGCTGGTTAG

CCTGGTATCAGCAGAAACCAGGGAAAGCCCCTAAGCTCCTGATCTATGGT

GCATCCAGTTTGCAAAGTGGGGTCCCATCAAGGTTCAGCGGCAGTGGATC

TGGGACAGATTTCACTCTCACCATCAGCAGCCTGCAGCCTGAAGATTTTG

CAACTTATTACTGTCAGCAGATATACACCTTCCCTTTCACTTTTGGCGGA

GGGACCAAGGTTGAGATCAAACGG

In further embodiments, the invention relates to Clone RY-26568 LC AA sequence (SEQ ID NO: 361):

DIQLTQSPSS VSASVGDRVT ITC<u>RASRGIS SWLA</u>WYQQKP

GKAPKLLIYG <u>ASSLQS</u>GVPS RFSGSGSGTD FTLTISSLQP

EDFATYYC<u>QQ IYTFPFT</u>FGG GTKVEIKR.

In further embodiments, the invention relates to LC CDR1 AA sequence thereof: RASRGISSWLA (SEQ ID NO: 362). In further embodiments, the invention relates to LC CDR2 AA sequence thereof: GASSLQS (SEQ ID NO: 363). In further embodiments, the invention relates to LC CDR3 AA sequence thereof: QQIYTFPFT (SEQ ID NO: 364) (LC CDR3).

In further embodiments, the invention relates to Clone RY-26568 CAR DNA HxL (SEQ ID NO: 365):

ATGGCACTCCCCGTAACTGCTCTGCTGCTGCCGTTGGCATTGCTCCTGCA

CGCCGCACGCCCGCAGGTGCAGCTGGTGGAGTCTGGGGGAGGCGTGGTCC

AGCCTGGGAGGTCCCTGAGACTCTCCTGTGCAGCGTCTGGATTCACCTTC

GGGAGCTATGGCATGCACTGGGTCCGCCAGGCTCCAGGCAAGGGGCTGGA

GTGGGTGGCAGTTATACATTATGATGGAAGTGTTGAATACTATGCAGACT

CCGTGAAGGGCCGATTCACCATCTCCAGAGACAATTCCAAGGACACGCTG

TATCTGCAAATGAACAGCCTGAGAGCCGAGGACACGGCGGTGTACTACTG

CGCCAGAACTGACTTCTGGAGCGGATCCCCTCCAAGCTTAGATTACTGGG

GACAGGGTACATTGGTCACCGTCTCCTCAGGGTCTACATCCGGCTCCGGG

AAGCCCGGAAGTGGCGAAGGTAGTACAAAGGGGGACATCCAGTTGACCCA

GTCTCCATCTTCCGTGTCTGCATCTGTAGGAGACAGAGTCACCATCACTT

GTCGGGCGAGTCGGGGTATTAGCAGCTGGTTAGCCTGGTATCAGCAGAAA

CCAGGGAAAGCCCCTAAGCTCCTGATCTATGGTGCATCCAGTTTGCAAAG

-continued

TGGGGTCCCATCAAGGTTCAGCGGCAGTGGATCTGGGACAGATTTCACTC

TCACCATCAGCAGCCTGCAGCCTGAAGATTTTGCAACTTATTACTGTCAG

CAGATATACACCTTCCCTTTCACTTTTGGCGGAGGGACCAAGGTTGAGAT

CAAACGGGCCGCTGCCCTTGATAATGAAAAGTCAAACGGAACAATCATTC

ACGTGAAGGGCAAGCACCTCTGTCCGTCACCCTTGTTCCCTGGTCCATCC

AAGCCATTCTGGGTGTTGGTCGTAGTGGGTGGAGTCCTCGCTTGTTACTC

TCTGCTCGTCACCGTGGCTTTTATAATCTTCTGGGTTAGATCCAAAAGAA

GCCGCCTGCTCCATAGCGATTACATGAATATGACTCCACGCCGCCCTGGC

CCCACAAGGAAACACTACCAGCCTTACGCACCACCTAGAGATTTCGCTGC

CTATCGGAGCAGGGTGAAGTTTTCCAGATCTGCAGATGCACCAGCGTATC

AGCAGGGCCAGAACCAACTGTATAACGAGCTCAACCTGGGACGCAGGGAA

GAGTATGACGTTTTGGACAAGCGCAGAGGACGGGACCCTGAGATGGGTGG

CAAACCAAGACGAAAAAACCCCCAGGAGGGTCTCTATAATGAGCTGCAGA

AGGATAAGATGGCTGAAGCCTATTCTGAAATAGGCATGAAAGGAGAGCGG

AGAAGGGGAAAAGGGCACGACGGTTTGTACCAGGGACTCAGCACTGCTAC

GAAGGATACTTATGACGCTCTCCACATGCAAGCCCTGCCACCTAGG

In further embodiments, the invention relates to Clone RY-26568 CAR HxL AA sequence (SEQ ID NO: 366):

MALPVTALLL PLALLLHAAR PQVQLVESGG GVVQPGRSLR

LSCAASGFTF GSYGMHWVRQ APGKGLEWVA VIHYDGSVEY

YADSVKGRFT ISRDNSKDTL YLQMNSLRAE DTAVYYCART

DFWSGSPPSL DYWGQGTLVT VSSGSTSGSG KPGSGEGSTK

GDIQLTQSPS SVSASVGDRV TITCRASRGI SSWLAWYQQK

PGKAPKLLIY GASSLQSGVP SRFSGSGSGT DFTLTISSLQ

PEDFATYYCQ QIYTFPFTFG GGTKVEIKRA AALDNEKSNG

TIIHVKGKHL CPSPLFPGPS KPFWVLVVVG GVLACYSLLV

TVAFIIFWVR SKRSRLLHSD YMNMTPRRPG PTRKHYQPYA

PPRDFAAYRS RVKFSRSADA PAYQQGQNQL YNELNLGRRE

EYDVLDKRRG RDPEMGGKPR RKNPQEGLYN ELQKDKMAEA

YSEIGMKGER RRGKGHDGLY QGLSTATKDT YDALHMQALP

PR

In further embodiments, the invention relates to Clone RY-26568 CAR DNA LxH (SEQ ID NO: 367):

ATGGCACTCCCCGTAACTGCTCTGCTGCTGCCGTTGGCATTGCTCCTGCA

CGCCGCACGCCCGGACATCCAGTTGACCCAGTCTCCATCTTCCGTGTCTG

CATCTGTAGGAGACAGAGTCACCATCACTTGTCGGGCGAGTCGGGGTATT

AGCAGCTGGTTAGCCTGGTATCAGCAGAAACCAGGGAAAGCCCCTAAGCT

CCTGATCTATGGTGCATCCAGTTTGCAAAGTGGGGTCCCATCAAGGTTCA

GCGGCAGTGGATCTGGGACAGATTTCACTCTCACCATCAGCAGCCTGCAG

CCTGAAGATTTTGCAACTTATTACTGTCAGCAGATATACACCTTCCCTTT

-continued

```
CACTTTTGGCGGAGGGACCAAGGTTGAGATCAAACGGGGTCTACATCCG

GCTCCGGGAAGCCCGGAAGTGGCGAAGGTAGTACAAAGGGGCAGGTGCAG

CTGGTGGAGTCTGGGGGAGGCGTGGTCCAGCCTGGGAGGTCCCTGAGACT

CTCCTGTGCAGCGTCTGGATTCACCTTCGGGAGCTATGGCATGCACTGGG

TCCGCCAGGCTCCAGGCAAGGGGCTGGAGTGGGTGGCAGTTATACATTAT

GATGGAAGTGTTGAATACTATGCAGACTCCGTGAAGGGCCGATTCACCAT

CTCCAGAGACAATTCCAAGGACACGCTGTATCTGCAAATGAACAGCCTGA

GAGCCGAGGACACGGCGGTGTACTACTGCGCCAGAACTGACTTCTGGAGC

GGATCCCCTCCAAGCTTAGATTACTGGGGACAGGGTACATTGGTCACCGT

CTCCTCAGCCGCTGCCCTTGATAATGAAAAGTCAAACGGAACAATCATTC

ACGTGAAGGGCAAGCACCTCTGTCCGTCACCCTTGTTCCCTGGTCCATCC

AAGCCATTCTGGGTGTTGGTCGTAGTGGGTGGAGTCCTCGCTTGTTACTC

TCTGCTCGTCACCGTGGCTTTTATAATCTTCTGGGTTAGATCCAAAAGAA

GCCGCCTGCTCCATAGCGATTACATGAATATGACTCCACGCCGCCCTGGC

CCCACAAGGAAACACTACCAGCCTTACGCACCACCTAGAGATTTCGCTGC

CTATCGGAGCAGGGTGAAGTTTTCCAGATCTGCAGATGCACCAGCGTATC

AGCAGGGCCAGAACCAACTGTATAACGAGCTCAACCTGGGACGCAGGGAA

GAGTATGACGTTTTGGACAAGCGCAGAGGACGGGACCCTGAGATGGGTGG

CAAACCAAGACGAAAAAACCCCCAGGAGGGTCTCTATAATGAGCTGCAGA

AGGATAAGATGGCTGAAGCCTATTCTGAAATAGGCATGAAAGGAGAGCGG

AGAAGGGGAAAAGGGCACGACGGTTTGTACCAGGGACTCAGCACTGCTAC

GAAGGATACTTATGACGCTCTCCACATGCAAGCCCTGCCACCTAGG
```

In further embodiments, the invention relates to Clone RY-26568 CAR LxH AA sequence (SEQ ID NO: 368):

```
MALPVTALLL PLALLLHAAR PDIQLTQSPS SVSASVGDRV

TITCRASRGI SSWLAWYQQK PGKAPKLLIY GASSLQSGVP

SRFSGSGSGT DFTLTISSLQ PEDFATYYCQ QIYTFPFTFG

GGTKVEIKRG STSGSGKPGS GEGSTKGQVQ LVESGGGVVQ

PGRSLRLSCA ASGFTFGSYG MHWVRQAPGK GLEWVAVIHY

DGSVEYYADS VKGRFTISRD NSKDTLYLQM NSLRAEDTAV

YYCARTDFWS GSPPSLDYWG QGTLVTVSSA AALDNEKSNG

TIIHVKGKHL CPSPLFPGPS KPFWVLVVVG GVLACYSLLV

TVAFIIFWVR SKRSRLLHSD YMNMTPRRPG PTRKHYQPYA

PPRDFAAYRS RVKFSRSADA PAYQQGQNQL YNELNLGRRE

EYDVLDKRRG RDPEMGGKPR RKNPQEGLYN ELQKDKMAEA

YSEIGMKGER RRGKGHDGLY QGLSTATKDT YDALHMQALP

PR
```

In further embodiments, the invention relates to Clone PP-26575 HC DNA (SEQ ID NO: 369):

```
CAGGTGCAGCTGGTGCAGTCTGGGGCTGAGGTGAAGAAGCCTGGGTCCTC

GGTGAAGGTCTCCTGCAAGGCTTCTGGAGGCACCCTCAGCAGCCTGGCTA

TCAGCTGGGTGCGACAGGCCCCTGGACAAGGGCTTGAGTGGATGGGAGGG

GTCATCCCTATCTTGGGTCGGGCAAACTACGCACAGAAGTTCCAGGGCAG

AGTCACGATTACCGCGGACGAGTCCACGAGCACAGCCTACATGGAGCTGA

GCAGCCTGAGATCTGAGGACACGGCGGTGTACTACTGCGCCAGAACTCCT

GAATACTCCTCCAGCATATGGCACTATTACTACGGCATGGACGTATGGGG

CCAGGGAACAACTGTCACCGTCTCCTCA
```

In further embodiments, the invention relates to Clone PP-26575 HC AA sequence (SEQ ID NO: 370):

```
QVQLVQSGAE VKKPGSSVKV SCKASGGTLS SLAISWVRQA

PGQGLEWMGG VIPILGRANY AQKFQGRVTI TADESTSTAY

MELSSLRSED TAVYYCARTP EYSSSIWHYY YGMDVWGQGT

TVTVSS.
```

In further embodiments, the invention relates to HC CDR1 AA sequence thereof: GTLSSLAIS (SEQ ID NO: 371). In further embodiments, the invention relates to HC CDR2 AA sequence thereof: GVIPILGRANYAQKFQG (SEQ ID NO: 372). In further embodiments, the invention relates to HC CDR3 thereof: ARTPEYSSSIWHYYYGMDV (SEQ ID NO: 373).

In further embodiments, the invention relates to Clone PP-26575 LC DNA (SEQ ID NO: 374):

```
GACATCGTGATGACCCAGTCTCCAGACTCCCTGGCTGTGTCTCTGGGCGA

GAGGGCCACCATCAACTGCAAGTCCAGCCAGAGTGTTTTATACAGCTCCA

ACAATAAGAACTACTTAGCTTGGTACCAGCAGAAACCAGGACAGCCTCCT

AAGCTGCTCATTTACTGGGCATCTACCCGGGAATCCGGGGTCCCTGACCG

ATTCAGTGGCAGCGGGTCTGGGACAGATTTCACTCTCACCATCAGCAGCC

TGCAGGCTGAAGATGTGGCAGTTTATTACTGTCAGCAGTTCGCCCACACT

CCTTTCACTTTTGGCGGAGGGACCAAGGTTGAGATCAAACGG
```

In further embodiments, the invention relates to Clone PP-26575 LC AA sequence (SEQ ID NO: 375):

```
DIVMTQSPDS LAVSLGERAT INCKSSQSVL YSSNNKNYLA

WYQQKPGQPP KLLIYWASTR ESGVPDRFSG SGSGTDFTLT

ISSLQAEDVA VYYCQQFAHT PFTFGGGTKV EIKR.
```

In further embodiments, the invention relates to LC CDR 1 AA sequence thereof: KSSQSVLYSSNNKNYLA (SEQ ID NO: 376). In further embodiments, the invention relates to LC CDR2 AA sequence thereof: WASTRES (SEQ ID NO: 377). In further embodiments, the invention relates to LC CDR3 AA sequence thereof: QQFAHTPFT (SEQ ID NO: 378).

In further embodiments, the invention relates to Clone PP-26575 CAR DNA HxL (SEQ ID NO: 379):

ATGGCACTCCCCGTAACTGCTCTGCTGCTGCCGTTGGCATTGCTCCTGCA
CGCCGCACGCCCGCAGGTGCAGCTGGTGCAGTCTGGGGCTGAGGTGAAGA
AGCCTGGGTCCTCGGTGAAGGTCTCCTGCAAGGCTTCTGGAGGCACCCTC
AGCAGCCTGGCTATCAGCTGGGTGCGACAGGCCCCTGGACAAGGGCTTGA
GTGGATGGGAGGGGTCATCCCTATCTTGGGTCGGGCAAACTACGCACAGA
AGTTCCAGGGCAGAGTCACGATTACCGCGGACGAGTCCACGAGCACAGCC
TACATGGAGCTGAGCAGCCTGAGATCTGAGGACACGGCGGTGTACTACTG
CGCCAGAACTCCTGAATACTCCTCCAGCATATGGCACTATTACTACGGCA
TGGACGTATGGGGCCAGGGAACAACTGTCACCGTCTCCTCAGGGTCTACA
TCCGGCTCCGGGAAGCCCGGAAGTGGCGAAGGTAGTACAAAGGGGGACAT
CGTGATGACCCAGTCTCCAGACTCCCTGGCTGTGTCTCTGGGCGAGAGGG
CCACCATCAACTGCAAGTCCAGCCAGAGTGTTTTATACAGCTCCAACAAT
AAGAACTACTTAGCTTGGTACCAGCAGAAACCAGGACAGCCTCCTAAGCT
GCTCATTTACTGGGCATCTACCCGGGAATCCGGGGTCCCTGACCGATTCA
GTGGCAGCGGGTCTGGGACAGATTTCACTCTCACCATCAGCAGCCTGCAG
GCTGAAGATGTGGCAGTTTATTACTGTCAGCAGTTCGCCCACACTCCTTT
CACTTTTGGCGGAGGGACCAAGGTTGAGATCAAACGGGCCGCTGCCCTTG
ATAATGAAAAGTCAAACGGAACAATCATTCACGTGAAGGGCAAGCACCTC
TGTCCGTCACCCTTGTTCCCTGGTCCATCCAAGCCATTCTGGGTGTTGGT
CGTAGTGGGTGGAGTCCTCGCTTGTTACTCTCTGCTCGTCACCGTGGCTT
TTATAATCTTCTGGGTTAGATCCAAAAGAAGCCGCCTGCTCCATAGCGAT
TACATGAATATGACTCCACGCCGCCCTGGCCCCACAAGGAAACACTACCA
GCCTTACGCACCACCTAGAGATTTCGCTGCCTATCGGAGCAGGGTGAAGT
TTTCCAGATCTGCAGATGCACCAGCGTATCAGCAGGGCCAGAACCAACTG
TATAACGAGCTCAACCTGGGACGCAGGGAAGAGTATGACGTTTTGGACAA
GCGCAGAGGACGGGACCCTGAGATGGGTGGCAAACCAAGACGAAAAAACC
CCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGA
CGGTTTGTACCAGGGACTCAGCACTGCTACGAAGGATACTTATGACGCTC
TCCACATGCAAGCCCTGCCACCTAGG

In further embodiments, the invention relates to Clone PP-26575 CAR HxL AA sequence (SEQ ID NO: 380):

MALPVTALLL PLALLLHAAR PQVQLVQSGA EVKKPGSSVK
VSCKASGGTL SSLAISWVRQ APGQGLEWMG GVIPILGRAN
YAQKFQGRVT ITADESTSTA YMELSSLRSE DTAVYYCART
PEYSSSIWHY YGMDVWGQG TTVTVSSGST SGSGKPGSGE
GSTKGDIVMT QSPDSLAVSL GERATINCKS SQSVLYSSNN
KNYLAWYQQK PGQPPKLLIY WASTRESGVP DRFSGSGSGT
DFTLTISSLQ AEDVAVYYCQ QFAHTPFTFG GGTKVEIKRA
AALDNEKSNG TIIHVKGKHL CPSPLFPGPS KPFWVLVVVG
GVLACYSLLV TVAFIIFWVR SKRSRLLHSD YMNMTPRRPG
PTRKHYQPYA PPRDFAAYRS RVKFSRSADA PAYQQGQNQL
YNELNLGRRE EYDVLDKRRG RDPEMGGKPR RKNPQEGLYN
ELQKDKMAEA YSEIGMKGER RRGKGHDGLY QGLSTATKDT
YDALHMQALP PR

In further embodiments, the invention relates to Clone PP-26575 CAR DNA LxH (SEQ ID NO: 381):

ATGGCACTCCCCGTAACTGCTCTGCTGCTGCCGTTGGCATTGCTCCTGCA
CGCCGCACGCCCGGACATCGTGATGACCCAGTCTCCAGACTCCCTGGCTG
TGTCTCTGGGCGAGAGGGCCACCATCAACTGCAAGTCCAGCCAGAGTGTT
TTATACAGCTCCAACAATAAGAACTACTTAGCTTGGTACCAGCAGAAACC
AGGACAGCCTCCTAAGCTGCTCATTTACTGGGCATCTACCCGGGAATCCG
GGGTCCCTGACCGATTCAGTGGCAGCGGGTCTGGGACAGATTTCACTCTC
ACCATCAGCAGCCTGCAGGCTGAAGATGTGGCAGTTTATTACTGTCAGCA
GTTCGCCCACACTCCTTTCACTTTTGGCGGAGGGACCAAGGTTGAGATCA
AACGGGGGTCTACATCCGGCTCCGGGAAGCCCGGAAGTGGCGAAGGTAGT
ACAAAGGGGCAGGTGCAGCTGGTGCAGTCTGGGGCTGAGGTGAAGAAGCC
TGGGTCCTCGGTGAAGGTCTCCTGCAAGGCTTCTGGAGGCACCCTCAGCA
GCCTGGCTATCAGCTGGGTGCGACAGGCCCCTGGACAAGGGCTTGAGTGG
ATGGGAGGGGTCATCCCTATCTTGGGTCGGGCAAACTACGCACAGAAGTT
CCAGGGCAGAGTCACGATTACCGCGGACGAGTCCACGAGCACAGCCTACA
TGGAGCTGAGCAGCCTGAGATCTGAGGACACGGCGGTGTACTACTGCGCC
AGAACTCCTGAATACTCCTCCAGCATATGGCACTATTACTACGGCATGGA
CGTATGGGGCCAGGGAACAACTGTCACCGTCTCCTCAGCCGCTGCCCTTG
ATAATGAAAAGTCAAACGGAACAATCATTCACGTGAAGGGCAAGCACCTC
TGTCCGTCACCCTTGTTCCCTGGTCCATCCAAGCCATTCTGGGTGTTGGT
CGTAGTGGGTGGAGTCCTCGCTTGTTACTCTCTGCTCGTCACCGTGGCTT
TTATAATCTTCTGGGTTAGATCCAAAAGAAGCCGCCTGCTCCATAGCGAT
TACATGAATATGACTCCACGCCGCCCTGGCCCCACAAGGAAACACTACCA
GCCTTACGCACCACCTAGAGATTTCGCTGCCTATCGGAGCAGGGTGAAGT
TTTCCAGATCTGCAGATGCACCAGCGTATCAGCAGGGCCAGAACCAACTG
TATAACGAGCTCAACCTGGGACGCAGGGAAGAGTATGACGTTTTGGACAA
GCGCAGAGGACGGGACCCTGAGATGGGTGGCAAACCAAGACGAAAAAACC
CCCAGGAGGGTCTCTATAATGAGCTGCAGAAGGATAAGATGGCTGAAGCC
TATTCTGAAATAGGCATGAAAGGAGAGCGGAGAAGGGGAAAAGGGCACGA
CGGTTTGTACCAGGGACTCAGCACTGCTACGAAGGATACTTATGACGCTC
TCCACATGCAAGCCCTGCCACCTAGG

In further embodiments, the invention relates to Clone PP-26575 CAR LxH AA sequence (SEQ ID NO: 382):

```
MALPVTALLL PLALLLHAAR PDIVMTQSPD SLAVSLGERA
TINCKSSQSV LYSSNNKNYL AWYQQKPGQP PKLLIYWAST
RESGVPDRFS GSGSGTDFTL TISSLQAEDV AVYYCQQFAH
TPFTFGGGTK VEIKRGSTSG SGKPGSGEGS TKGQVQLVQS
GAEVKKPGSS VKVSCKASGG TLSSLAISWV RQAPGQGLEW
MGGVIPILGR ANYAQKFQGR VTITADESTS TAYMELSSLR
SEDTAVYYCA RTPEYSSSIW HYYYGMDVWG QGTTVTVSSA
AALDNEKSNG TIIHVKGKHL CPSPLFPGPS KPFWVLVVVG
GVLACYSLLV TVAFIIFWVR SKRSRLLHSD YMNMTPRRPG
PTRKHYQPYA PPRDFAAYRS RVKFSRSADA PAYQQGQNQL
YNELNLGRRE EYDVLDKRRG RDPEMGGKPR RKNPQEGLYN
ELQKDKMAEA YSEIGMKGER RRGKGHDGLY QGLSTATKDT
YDALHMQALP PR
```

In further embodiments, the invention relates to Clone RD-26576 HC DNA (SEQ ID NO: 383):

```
CAGGTGCGGCTGGTGGAGTCTGGGGGGGCGTGGTCCAGCCTGGGAGGTC
CCTGAGACTCTCCTGTGCAGCGTCTGGATTCACCTTCAGTAGCTATGGCA
TACACTGGGTCCGCCAGGCTCCAGGCAAGGGGCTGGAGTGGGTGGCAGTT
ATAGGGTATGATGGACAGGAGAAATACTATGCAGACTCCGTGAAGGGCCG
ATTCACCATCTCCAGAGACAATTCCAAGAACACGCTGTATCTGCAAATGA
ACAGCCTGAGAGCCGAGGACACGGCGGTGTACTACTGCGTCAAGGGGCCG
TTGCAGGAGCCGCCATACGCTTTTGGGATGGACGTATGGGGCCAGGGAAC
AACTGTCACCGTCTCCTCA
```

In further embodiments, the invention relates to Clone RD-26576 HC AA sequence (SEQ ID NO: 384):

```
QVRLVESGGG VVQPGRSLRL SCAASGFTFS SYGIHWVRQA
PGKGLEWVAV IGYDGQEKYY ADSVKGRFTI SRDNSKNTLY
LQMNSLRAED TAVYYCVKGP LQEPPYAFGM DVWGQGTTVT
VSS.
```

In further embodiments, the invention relates to HC CDR1 AA sequence thereof: FTFSSYGIH (SEQ ID NO: 385). In further embodiments, the invention relates to HC CDR2 AA sequence thereof: VIGYDGQEKYYADSVKG (SEQ ID NO: 386). In further embodiments, the invention relates to the HC CDR3 AA sequence thereof: VKGPLQEPPYAFGMDV (SEQ ID NO: 387).

In further embodiments, the invention relates to Clone RD-26576 LC DNA (SEQ ID NO: 388):

```
GAAATAGTGATGACGCAGTCTCCAGCCACCCTGTCTGTGTCTCCAGGGGA
AAGAGCCACCCTCTCCTGCAGGGCCAGTCAGAGTGTTAGCAGCAACTTAG
CCTGGTACCAGCAGAAACCTGGCCAGGCTCCCAGGCTCCTCATCTATAGC
GCATCCACCAGGGCCACTGGTATCCCAGCCAGGTTCAGTGGCAGTGGGTC
TGGGACAGAGTTCACTCTCACCATCAGCAGCCTGCAGTCTGAAGATTTTG
CAGTTTATTACTGTCAGCAGCACCACGTCTGGCCTCTCACTTTTGGCGGA
GGGACCAAGGTTGAGATCAAACGG
```

In further embodiments, the invention relates to Clone RD-26576 LC AA sequence (SEQ ID NO: 389):

```
EIVMTQSPAT LSVSPGERAT LSCRASQSVS SNLAWYQQKP
GQAPRLLIYS ASTRATGIPA RFSGSGSGTE FTLTISSLQS
EDFAVYYCQQ HHVWPLTFGG GTKVEIKR.
```

In further embodiments, the invention relates to LC CDR1 AA sequence thereof: RASQSVSSNLA (SEQ ID NO: 390). In further embodiments, the invention relates to LC CDR2 AA sequence thereof: SASTRAT (SEQ ID NO: 391). In further embodiments, the invention relates to LC CDR3 AA sequence thereof: QQHHVWPLT (SEQ ID NO: 392).

In further embodiments, the invention relates to Clone RD-26576 CAR DNA HxL (SEQ ID NO: 393):

```
ATGGCACTCCCCGTAACTGCTCTGCTGCTGCCGTTGGCATTGCTCCTGCA
CGCCGCACGCCCGCAGGTGCGGCTGGTGGAGTCTGGGGGGGCGTGGTCC
AGCCTGGGAGGTCCCTGAGACTCTCCTGTGCAGCGTCTGGATTCACCTTC
AGTAGCTATGGCATACACTGGGTCCGCCAGGCTCCAGGCAAGGGGCTGGA
GTGGGTGGCAGTTATAGGGTATGATGGACAGGAGAAATACTATGCAGACT
CCGTGAAGGGCCGATTCACCATCTCCAGAGACAATTCCAAGAACACGCTG
TATCTGCAAATGAACAGCCTGAGAGCCGAGGACACGGCGGTGTACTACTG
CGTCAAGGGGCCGTTGCAGGAGCCGCCATACGCTTTTGGGATGGACGTAT
GGGGCCAGGGAACAACTGTCACCGTCTCCTCAGGGTCTACATCCGGCTCC
GGGAAGCCCGGAAGTGGCGAAGGTAGTACAAAGGGGGAAATAGTGATGAC
GCAGTCTCCAGCCACCCTGTCTGTGTCTCCAGGGGAAAGAGCCACCCTCT
CCTGCAGGGCCAGTCAGAGTGTTAGCAGCAACTTAGCCTGGTACCAGCAG
AAACCTGGCCAGGCTCCCAGGCTCCTCATCTATAGCGCATCCACCAGGGC
CACTGGTATCCCAGCCAGGTTCAGTGGCAGTGGGTCTGGGACAGAGTTCA
CTCTCACCATCAGCAGCCTGCAGTCTGAAGATTTTGCAGTTTATTACTGT
CAGCAGCACCACGTCTGGCCTCTCACTTTTGGCGGAGGGACCAAGGTTGA
GATCAAACGGGCCGCTGCCCTTGATAATGAAAAGTCAAACGGAACAATCA
TTCACGTGAAGGGCAAGCACCTCTGTCCGTCACCCTTGTTCCCTGGTCCA
TCCAAGCCATTCTGGGTGTTGGTCGTAGTGGGTGGAGTCCTCGCTTGTTA
CTCTCTGCTCGTCACCGTGGCTTTTATAATCTTCTGGGTTAGATCCAAAA
GAAGCCGCCTGCTCCATAGCGATTACATGAATATGACTCCACGCCGCCCT
GGCCCCACAAGGAAACACTACCAGCCTTACGCACCACCTAGAGATTTCGC
TGCCTATCGGAGCAGGGTGAAGTTTTCCAGATCTGCAGATGCACCAGCGT
ATCAGCAGGGCCAGAACCAACTGTATAACGAGCTCAACCTGGGACGCAGG
```

GAAGAGTATGACGTTTTGGACAAGCGCAGAGGACGGGACCCTGAGATGGG

TGGCAAACCAAGACGAAAAAACCCCCAGGAGGGTCTCTATAATGAGCTGC

AGAAGGATAAGATGGCTGAAGCCTATTCTGAAATAGGCATGAAAGGAGAG

CGGAGAAGGGGAAAAGGGCACGACGGTTTGTACCAGGGACTCAGCACTGC

TACGAAGGATACTTATGACGCTCTCCACATGCAAGCCCTGCCACCTAGG

In further embodiments, the invention relates to Clone RD-26576 CAR HxL AA sequence (SEQ ID NO: 394);

```
MALPVTALLL PLALLLHAAR PQVRLVESGG GVVQPGRSLR

LSCAASGFTF SSYGIHWVRQ APGKGLEWVA VIGYDGQEKY

YADSVKGRFT ISRDNSKNTL YLQMNSLRAE DTAVYYCVKG

PLQEPPYAFG MDVWGQGTTV TVSSGSTSGS GKPGSGEGST

KGEIVMTQSP ATLSVSPGER ATLSCRASQS VSSNLAWYQQ

KPGQAPRLLI YSASTRATGI PARFSGSGSG TEFTLTISSL

QSEDFAVYYC QQHHVWPLTF GGGTKVEIKR AAALDNEKSN

GTIIHVKGKH LCPSPLFPGP SKPFWVLVVV GGVLACYSLL

VTVAFIIFWV RSKRSRLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL

PPR.
```

In further embodiments, the invention relates to Clone RD-26576 CAR DNA LxH (SEQ ID NO: 395):

ATGGCACTCCCCGTAACTGCTCTGCTGCTGCCGTTGGCATTGCTCCTGCA

CGCCGCACGCCCGGAAATAGTGATGACGCAGTCTCCAGCCACCCTGTCTG

TGTCTCCAGGGGAAAGAGCCACCCTCTCCTGCAGGGCCAGTCAGAGTGTT

AGCAGCAACTTAGCCTGGTACCAGCAGAAACCTGGCCAGGCTCCCAGGCT

CCTCATCTATAGCGCATCCACCAGGGCCACTGGTATCCCAGCCAGGTTCA

GTGGCAGTGGGTCTGGGACAGAGTTCACTCTCACCATCAGCAGCCTGCAG

TCTGAAGATTTTGCAGTTTATTACTGTCAGCAGCACCACGTCTGGCCTCT

CACTTTTGGCGGAGGGACCAAGGTTGAGATCAAACGGGGGTCTACATCCG

GCTCCGGGAAGCCCGGAAGTGGCGAAGGTAGTACAAAGGGGCAGGTGCGG

CTGGTGGAGTCTGGGGGGGCGTGGTCCAGCCTGGGAGGTCCCTGAGACT

CTCCTGTGCAGCGTCTGGATTCACCTTCAGTAGCTATGGCATACACTGGG

TCCGCCAGGCTCCAGGCAAGGGGCTGGAGTGGGTGGCAGTTATAGGGTAT

GATGGACAGGAGAAATACTATGCAGACTCCGTGAAGGGCCGATTCACCAT

CTCCAGAGACAATTCCAAGAACACGCTGTATCTGCAAATGAACAGCCTGA

GAGCCGAGGACACGGCGGTGTACTACTGCGTCAAGGGGCCGTTGCAGGAG

CCGCCATACGCTTTTGGGATGGACGTATGGGCCAGGGAACAACTGTCAC

CGTCTCCTCAGCCGCTGCCCTTGATAATGAAAAGTCAAACGGAACAATCA

TTCACGTGAAGGGCAAGCACCTCTGTCCGTCACCCTTGTTCCCTGGTCCA

TCCAAGCCATTCTGGGTGTTGGTCGTAGTGGGTGGAGTCCTCGCTTGTTA

CTCTCTGCTCGTCACCGTGGCTTTTATAATCTTCTGGGTTAGATCCAAAA

GAAGCCGCCTGCTCCATAGCGATTACATGAATATGACTCCACGCCGCCCT

GGCCCCACAAGGAAACACTACCAGCCTTACGCACCACCTAGAGATTTCGC

TGCCTATCGGAGCAGGGTGAAGTTTTCCAGATCTGCAGATGCACCAGCGT

ATCAGCAGGGCCAGAACCAACTGTATAACGAGCTCAACCTGGGACGCAGG

GAAGAGTATGACGTTTTGGACAAGCGCAGAGGACGGGACCCTGAGATGGG

TGGCAAACCAAGACGAAAAAACCCCCAGGAGGGTCTCTATAATGAGCTGC

AGAAGGATAAGATGGCTGAAGCCTATTCTGAAATAGGCATGAAAGGAGAG

CGGAGAAGGGGAAAAGGGCACGACGGTTTGTACCAGGGACTCAGCACTGC

TACGAAGGATACTTATGACGCTCTCCACATGCAAGCCCTGCCACCTAGG

In further embodiments, the invention relates to Clone RD-26576 CAR LxH AA sequence (SEQ ID NO: 396):

```
MALPVTALLL PLALLLHAAR PEIVMTQSPA TLSVSPGERA

TLSCRASQSV SSNLAWYQQK PGQAPRLLIY SASTRATGIP

ARFSGSGSGT EFTLTISSLQ SEDFAVYYCQ QHHVWPLTFG

GGTKVEIKRG STSGSGKPGS GEGSTKGQVR LVESGGGVVQ

PGRSLRLSCA ASGFTFSSYG IHWVRQAPGK GLEWVAVIGY

DGQEKYYADS VKGRFTISRD NSKNTLYLQM NSLRAEDTAV

YYCVKGPLQE PPYAFGMDVW GQGTTVTVSS AAALDNEKSN

GTIIHVKGKH LCPSPLFPGP SKPFWVLVVV GGVLACYSLL

VTVAFIIFWV RSKRSRLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL

PPR.
```

In further embodiments, the invention relates to Clone RD-26578 HC DNA (SEQ ID NO: 397):

CAGGTGCAGCTGGTGGAGTCTGGGGGAGGCGTGGTCCAGCCTGGGAGGTC

CCTGAGACTCTCCTGTGCAGCGTCTGGATTCACCTTCAGTAGCCGTGGCA

TGCACTGGGTCCGCCAGGCTCCAGGCAAGGGGCTGGAGTGGGTGGCAGTT

ATAGGGTATGATGGACAGGAGAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCGGTGTACTACTGCGTCAAGGGGCCG

TTGCAGGAGCCGCCATACGATTATGGAATGGACGTATGGGGCCAGGGAAC

AACTGTCACCGTCTCCTCA

In further embodiments, the invention relates to Clone RD-26578 HC AA sequence (SEQ ID NO: 398):

```
QVQLVESGGG VVQPGRSLRL SCAASGFTFS SRGMHWVRQA

PGKGLEWVAV IGYDGQEKYY ADSVKGRFTI SRDNSKNTLY

LQMNSLRAED TAVYYCVKGP LQEPPYDYGM DVWGQGTTVT

VSS.
```

In further embodiments, the invention relates to HC CDR1 AA sequence thereof: FTFSSRGMH (SEQ ID NO: 399). In further embodiments, the invention relates to HC CDR2 AA sequence thereof: VIGYDGQEKYYADSVKG (SEQ ID NO: 400). In further embodiments, the invention relates to HC CDR3 thereof: VKGPLQEPPYDYGMDV (SEQ ID NO: 401).

In further embodiments, the invention relates to Clone RD-26578 LC DNA (SEQ ID NO: 402):

```
GAAATAGTGATGACGCAGTCTCCAGCCACCCTGTCTGTGTCTCCAGGGGA

AAGAGCCACCCTCTCCTGCAGGGCCAGTCAGAGTGTTAGCAGCAACTTAG

CCTGGTACCAGCAGAAACCTGGCCAGGCTCCCAGGCTCCTCATCTATAGC

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGCACCACGTCTGGCCTCTCACTTTTGGCGGA

GGGACCAAGGTTGAGATCAAACGG
```

In further embodiments, the invention relates to Clone RD-26578 LC AA sequence (SEQ ID NO: 403):

```
EIVMTQSPAT LSVSPGERAT LSCRASQSVS SNLAWYQQKP

GQAPRLLIYS ASTRATGIPA RFSGSGSGTE FTLTISSLQS

EDFAVYYCQQ HHVWPLTFGG GTKVEIKR.
```

In further embodiments, the invention relates to LC CDR1 AA sequence: RASQSVSSNLA (SEQ ID NO: 404). In further embodiments, the invention relates to LC CDR2 AA sequence thereof: SASTRAT (SEQ ID NO: 405). In further embodiments, the invention relates to LC CDR3 AA sequence thereof: QQHHVWPLT (SEQ ID NO: 406).

In further embodiments, the invention relates to Clone RD-26578 CAR DNA HxL (SEQ ID NO: 407):

```
ATGGCACTCCCCGTAACTGCTCTGCTGCTGCCGTTGGCATTGCTCCTGCA

CGCCGCACGCCCGCAGGTGCAGCTGGTGGAGTCTGGGGGAGGCGTGGTCC

AGCCTGGGAGGTCCCTGAGACTCTCCTGTGCAGCGTCTGGATTCACCTTC

AGTAGCCGTGGCATGCACTGGGTCCGCCAGGCTCCAGGCAAGGGGCTGGA

GTGGGTGGCAGTTATAGGGTATGATGGACAGGAGAAATACTATGCAGACT

CCGTGAAGGGCCGATTCACCATCTCCAGAGACAATTCCAAGAACACGCTG

TATCTGCAAATGAACAGCCTGAGAGCCGAGGACACGGCGGTGTACTACTG

CGTCAAGGGGCCGTTGCAGGAGCCGCCATACGATTATGGAATGGACGTAT

GGGGCCAGGGAACAACTGTCACCGTCTCCTCAGGGTCTACATCCGGCTCC

GGGAAGCCCGGAAGTGGCGAAGGTAGTACAAAGGGGGAAATAGTGATGAC
```

GCAGTCTCCAGCCACCCTGTCTGTGTCTCCAGGGGAAAGAGCCACCCTCT

CCTGCAGGGCCAGTCAGAGTGTTAGCAGCAACTTAGCCTGGTACCAGCAG

AAACCTGGCCAGGCTCCCAGGCTCCTCATCTATAGCGCATCCACCAGGGC

CACTGGTATCCCAGCCAGGTTCAGTGGCAGTGGGTCTGGGACAGAGTTCA

CTCTCACCATCAGCAGCCTGCAGTCTGAAGATTTTGCAGTTTATTACTGT

CAGCAGCACCACGTCTGGCCTCTCACTTTTGGCGGAGGGACCAAGGTTGA

GATCAAACGGGCCGCTGCCCTTGATAATGAAAAGTCAAACGGAACAATCA

TTCACGTGAAGGGCAAGCACCTCTGTCCGTCACCCTTGTTCCCTGGTCCA

TCCAAGCCATTCTGGGTGTTGGTCGTAGTGGGTGGAGTCCTCGCTTGTTA

CTCTCTGCTCGTCACCGTGGCTTTTATAATCTTCTGGGTTAGATCCAAAA

GAAGCCGCCTGCTCCATAGCGATTACATGAATATGACTCCACGCCGCCCT

GGCCCCACAAGGAAACACTACCAGCCTTACGCACCACCTAGAGATTTCGC

TGCCTATCGGAGCAGGGTGAAGTTTTCCAGATCTGCAGATGCACCAGCGT

ATCAGCAGGGCCAGAACCAACTGTATAACGAGCTCAACCTGGGACGCAGG

GAAGAGTATGACGTTTTGGACAAGCGCAGAGGACGGGACCCTGAGATGGG

TGGCAAACCAAGACGAAAAAACCCCCAGGAGGGTCTCTATAATGAGCTGC

AGAAGGATAAGATGGCTGAAGCCTATTCTGAAATAGGCATGAAAGGAGAG

CGGAGAAGGGGAAAAGGGCACGACGGTTTGTACCAGGGACTCAGCACTGC

TACGAAGGATACTTATGACGCTCTCCACATGCAAGCCCTGCCACCTAGG

In further embodiments, the invention relates to Clone RD-26578 CAR HxL AA sequence (SEQ ID NO: 408):

```
MALPVTALLL PLALLLHAAR PQVQLVESGG GVVQPGRSLR

LSCAASGFTF SSRGMHWVRQ APGKGLEWVA VIGYDGQEKY

YADSVKGRFT ISRDNSKNTL YLQMNSLRAE DTAVYYCVKG

PLQEPPYDYG MDVWGQGTTV TVSSGSTSGS GKPGSGEGST

KGEIVMTQSP ATLSVSPGER ATLSCRASQS VSSNLAWYQQ

KPGQAPRLLI YSASTRATGI PARFSGSGSG TEFTLTISSL

QSEDFAVYYC QQHHVWPLTF GGGTKVEIKR AAALDNEKSN

GTIIHVKGKH LCPSPLFPGP SKPFWVLVVV GGVLACYSLL

VTVAFIIFWV RSKRSRLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL

PPR
```

In further embodiments, the invention relates to Clone RD-26578 CAR DNA LxH (SEQ ID NO: 409):

```
ATGGCACTCCCCGTAACTGCTCTGCTGCTGCCGTTGGCATTGCTCCTGCA

CGCCGCACGCCCGGAAATAGTGATGACGCAGTCTCCAGCCACCCTGTCTG

TGTCTCCAGGGGAAAGAGCCACCCTCTCCTGCAGGGCCAGTCAGAGTGTT
```

-continued
```
AGCAGCAACTTAGCCTGGTACCAGCAGAAACCTGGCCAGGCTCCCAGGCT

CCTCATCTATAGCGCATCCACCAGGGCCACTGGTATCCCAGCCAGGTTCA

GTGGCAGTGGGTCTGGGACAGAGTTCACTCTCACCATCAGCAGCCTGCAG

TCTGAAGATTTTGCAGTTTATTACTGTCAGCAGCACCACGTCTGGCCTCT

CACTTTTGGCGGAGGGACCAAGGTTGAGATCAAACGGGGGTCTACATCCG

GCTCCGGGAAGCCCGGAAGTGGCGAAGGTAGTACAAAGGGGCAGGTGCAG

CTGGTGGAGTCTGGGGGAGGCGTGGTCCAGCCTGGGAGGTCCCTGAGACT

CTCCTGTGCAGCGTCTGGATTCACCTTCAGTAGCCGTGGCATGCACTGGG

TCCGCCAGGCTCCAGGCAAGGGGCTGGAGTGGGTGGCAGTTATAGGGTAT

GATGGACAGGAGAAATACTATGCAGACTCCGTGAAGGGCCGATTCACCAT

CTCCAGAGACAATTCCAAGAACACGCTGTATCTGCAAATGAACAGCCTGA

GAGCCGAGGACACGGCGGTGTACTACTGCGTCAAGGGGCCGTTGCAGGAG

CCGCCATACGATTATGGAATGGACGTATGGGCCAGGGAACAACTGTCAC

CGTCTCCTCAGCCGCTGCCCTTGATAATGAAAAGTCAAACGGAACAATCA

TTCACGTGAAGGGCAAGCACCTCTGTCCGTCACCCTTGTTCCCTGGTCCA

TCCAAGCCATTCTGGGTGTTGGTCGTAGTGGGTGGAGTCCTCGCTTGTTA

CTCTCTGCTCGTCACCGTGGCTTTTATAATCTTCTGGGTTAGATCCAAAA

GAAGCCGCCTGCTCCATAGCGATTACATGAATATGACTCCACGCCGCCCT

GGCCCCACAAGGAAACACTACCAGCCTTACGCACCACCTAGAGATTTCGC

TGCCTATCGGAGCAGGGTGAAGTTTTCCAGATCTGCAGATGCACCAGCGT

ATCAGCAGGGCCAGAACCAACTGTATAACGAGCTCAACCTGGGACGCAGG

GAAGAGTATGACGTTTTGGACAAGCGCAGAGGACGGGACCCTGAGATGGG

TGGCAAACCAAGACGAAAAAACCCCCAGGAGGGTCTCTATAATGAGCTGC

AGAAGGATAAGATGGCTGAAGCCTATTCTGAAATAGGCATGAAAGGAGAG

CGGAGAAGGGGAAAAGGGCACGACGGTTTGTACCAGGGACTCAGCACTGC

TACGAAGGATACTTATGACGCTCTCCACATGCAAGCCCTGCCACCTAGG
```

In further embodiments, the invention relates to Clone RD-26578 CAR LxH AA sequence (SEQ ID NO: 410):

```
MALPVTALLL PLALLLHAAR PEIVMTQSPA TLSVSPGERA

TLSCRASQSV SSNLAWYQQK PGQAPRLLIY SASTRATGIP

ARFSGSGSGT EFTLTISSLQ SEDFAVYYCQ QHHVWPLTFG

GGTKVEIKRG STSGSGKPGS GEGSTKGQVQ LVESGGGVVQ

PGRSLRLSCA ASGFTFSSRG MHWVRQAPGK GLEWVAVIGY

DGQEKYYADS VKGRFTISRD NSKNTLYLQM NSLRAEDTAV

YYCVKGPLQE PPYDYGMDVW GQGTTVTVSS AAALDNEKSN

GTIIHVKGKH LCPSPLFPGP SKPFWVLVVV GGVLACYSLL

VTVAFIIFWV RSKRSRLLHS DYMNMTPRRP GPTRKHYQPY

APPRDFAAYR SRVKFSRSAD APAYQQGQNQ LYNELNLGRR
```

-continued
```
EEYDVLDKRR GRDPEMGGKP RRKNPQEGLY NELQKDKMAE

AYSEIGMKGE RRRGKGHDGL YQGLSTATKD TYDALHMQAL

PPR.
```

It will be appreciated that the sequences recited herein can be useful by themselves, in combination with one or more sequences recited herein, and/or incorporated into cells (such as CAR or TCR-based T cells) for use in immune- or other therapies. It will be further appreciated that these sequences can be used in accordance with the invention incorporated in vectors for transduction, transfection, and the like, into cells.

It will be appreciated that adverse events may be minimized by transducing the immune cells (containing one or more CARs or TCRs) with a suicide gene. It may also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present invention. Additional methods for introducing suicide genes and/or "on" switches include TALENS, zinc fingers, RNAi, siRNA, shRNA, antisense technology, and other techniques known in the art.

In accordance with the invention, additional on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO2014/127261, WO2015/090229, US2014/0286987, US2015/0266973, US2016/0046700, U.S. Pat. No. 8,486,693, US2014/0171649, and US2012/0130076, the contents of which are further incorporated by reference herein in their entirety.

IV. Vectors, Cells, and Pharmaceutical Compositions

In certain aspects, provided herein are vectors comprising a polynucleotide of the present invention. In some embodiments, the present invention is directed to a vector or a set of vectors comprising a polynucleotide encoding a CAR or a TCR, as described herein. In other embodiments, the present invention is directed to a vector or a set of vectors comprising a polynucleotide encoding an antibody or an antigen binding molecule thereof that specifically binds to BCMA, as disclosed herein.

Any vector known in the art can be suitable for the present invention. In some embodiments, the vector is a viral vector. In some embodiments, the vector is a retroviral vector (such as pMSVG1), a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector (such as pGAR), or any combination thereof.

The pGAR sequence (SEQ ID NO. 413) is as follows:

CTGACGCGCCCTGTAGCGGCGCATTAAGCGCGGCGGGTGTGGTGGTTACG
CGCAGCGTGACCGCTACACTTGCCAGCGCCCTAGCGCCCGCTCCTTTCGC
TTTCTTCCCTTCCTTTCTCGCCACGTTCGCCGGCTTTCCCCGTCAAGCTC
TAAATCGGGGCTCCCTTTAGGGTTCCGATTTAGTGCTTTACGGCACCTC
GACCCCAAAAAACTTGATTAGGGTGATGGTTCACGTAGTGGGCCATCGCC
CTGATAGACGGTTTTTCGCCCTTTGACGTTGGAGTCCACGTTCTTTAATA
GTGGACTCTTGTTCCAAACTGGAACAACACTCAACCCTATCTCGGTCTAT
TCTTTTGATTTATAAGGGATTTTGCCGATTTCGGCCTATTGGTTAAAAAA
TGAGCTGATTTAACAAAAATTTAACGCGAATTTTAACAAAATATTAACGC
TTACAATTTGCCATTCGCCATTCAGGCTGCGCAACTGTTGGGAAGGGCGA
TCGGTGCGGGCCTCTTCGCTATTACGCCAGCTGGCGAAAGGGGGATGTGC
TGCAAGGCGATTAAGTTGGGTAACGCCAGGGTTTTCCCAGTCACGACGTT
GTAAAACGACGGCCAGTGAATTGTAATACGACTCACTATAGGGCGACCCG
GGGATGGCGCGCCAGTAATCAATTACGGGGTCATTAGTTCATAGCCCATA
TATGGAGTTCCGCGTTACATAACTTACGGTAAATGGCCCGCCTGGCTGAC
CGCCCAACGACCCCCGCCCATTGACGTCAATAATGACGTATGTTCCCATA
GTAACGCCAATAGGGACTTTCCATTGACGTCAATGGGTGGAGTATTTACG
GTAAACTGCCCACTTGGCAGTACATCAAGTGTATCATATGCCAAGTACGC
CCCCTATTGACGTCAATGACGGTAAATGGCCCGCCTGGCATTATGCCCAG
TACATGACCTTATGGGACTTTCCTACTTGGCAGTACATCTACGTATTAGT
CATCGCTATTACCATGCTGATGCGGTTTTGGCAGTACATCAATGGGCGTG
GATAGCGGTTTGACTCACGGGGATTTCCAAGTCTCCACCCCATTGACGTC
AATGGGAGTTTGTTTTGGCACCAAAATCAACGGGACTTTCCAAAATGTCG
TAACAACTCCGCCCCATTGACGCAAATGGGCGGTAGGCGTGTACGGTGGG
AGGTCTATATAAGCAGAGCTGGTTTAGTGAACCGGGGTCTCTCTGGTTAG
ACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCT
GTTGTGTGACTCTGGTAACTAGAGATCCCTCAGACCCTTTTAGTCAGTGT
GGAAAATCTCTAGCAGTGGCGCCCGAACAGGGACTTGAAAGCGAAAGGA
AACCAGAGGAGCTCTCTCGACGCAGGACTCGGCTTGCTGAAGCGCGCACG
GCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGG
GGAGAATTAGATCGCGATGGGAAAAAATTCGGTTAAGGCCAGGGGGAAAG
AAAAAATATAAATTAAAACATATAGTATGGGCAAGCAGGGAGCTAGAACG
ATTCGCAGTTAATCCTGGCCTGTTAGAAACATCAGAAGGCTGTAGACAAA
TACTGGGACAGCTACAACCATCCCTTCAGACAGGATCAGAAGAACTTAGA
TCATTATATAATACAGTAGCAACCCTCTATTGTGTGCATCAAAGGATAGA
GATAAAAGACACCAAGGAAGCTTTAGACAAGATAGAGGAAGAGCAAAACA

AAAGTAAGACCACCGCACAGCAAGCCGCCGCTGATCTTCAGACCTGGAGG
AGGAGATATGAGGGACAATTGGAGAAGTGAATTATATAAATATAAAGTAG
TAAAAATTGAACCATTAGGAGTAGCACCCACCAAGGCAAAGAGAAGAGTG
GTGCAGAGAGAAAAAAGAGCAGTGGGAATAGGAGCTTTGTTCCTTGGGTT
CTTGGGAGCAGCAGGAAGCACTATGGGCGCAGCGTCAATGACGCTGACGG
TACAGGCCAGACAATTATTGTCTGGTATAGTGCAGCAGCAGAACAATTTG
CTGAGGGCTATTGAGGCGCAACAGCATCTGTTGCAACTCACAGTCTGGGG
CATCAAGCAGCTCCAGGCAAGAATCCTGGCTGTGGAAAGATACCTAAAGG
ATCAACAGCTCCTGGGGATTTGGGGTTGCTCTGGAAAACTCATTTGCACC
ACTGCTGTGCCTTGGAATGCTAGTTGGAGTAATAAATCTCTGGAACAGAT
TTGGAATCACACGACCTGGATGGAGTGGGACAGAGAAATTAACAATTACA
CAAGCTTAATACACTCCTTAATTGAAGAATCGCAAAACCAGCAAGAAAAG
AATGAACAAGAATTATTGGAATTAGATAAATGGGCAAGTTTGTGGAATTG
GTTTAACATAACAAATTGGCTGTGGTATATAAAATTATTCATAATGATAG
TAGGAGGCTTGGTAGGTTTAAGAATAGTTTTTGCTGTACTTTCTATAGTG
AATAGAGTTAGGCAGGATATTCACCATTATCGTTTCAGACCCACCTCCC
AACCCCGAGGGGACCCGACAGGCCCGAAGGAATAGAAGAAGAAGGTGGAG
AGAGAGACAGAGACAGATCCATTCGATTAGTGAACGGATCTCGACGGTAT
CGGTTAACTTTTAAAAGAAAAGGGGGGATTGGGGGGTACAGTGCAGGGGA
AAGAATAGTAGACATAATAGCAACAGACATACAAACTAAAGAATTACAAA
AACAAATTACAAAATTCAAAATTTTATCGCGATCGCGGAATGAAAGACCC
CACCTGTAGGTTTGGCAAGCTAGCTTAAGTAACGCCATTTTGCAAGGCAT
GGAAAATACATAACTGAGAATAGAGAAGTTCAGATCAAGGTTAGGAACAG
AGAGACAGCAGAATATGGGCCAAACAGGATATCTGTGGTAAGCAGTTCCT
GCCCCGGCTCAGGGCCAAGAACAGATGGTCCCCAGATGCGGTCCCGCCCT
CAGCAGTTTCTAGAGAACCATCAGATGTTTCCAGGGTGCCCCAAGGACCT
GAAAATGACCCTGTGCCTTATTTGAACTAACCAATCAGTTCGCTTCTCGC
TTCTGTTCGCGCGCTTCTGCTCCCCGAGCTCAATAAAAGAGCCCACAACC
CCTCACTCGGCGCGCCAGTCCTTCGAAGTAGATCTTTGTCGATCCTACCA
TCCACTCGACACACCCGCCAGCGGCCGCTGCCAAGCTTCCGAGCTCTCGA
ATTAATTCACGGTACCCACCATGGCCTAGGGAGACTAGTCGAATCGATAT
CAACCTCTGGATTACAAAATTTGTGAAAGATTGACTGGTATTCTTAACTA
TGTTGCTCCTTTTACGCTATGTGGATACGCTGCTTTAATGCCTTTGTATC
ATGCTATTGCTTCCCGTATGGCTTTCATTTTCTCCTCCTTGTATAAATCC
TGGTTGCTGTCTCTTTATGAGGAGTTGTGGCCCGTTGTCAGGCAACGTGG
CGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGC
TCGGCTGTTGGGCACTGACAATTCCGTGGTGTTGTCGGGGAAGCTGACGT
CCTTTTCATGGCTGCTCGCCTGTGTTGCCACCTGGATTCTGCGCGGGACG

```
TCCTTCTGCTACGTCCCTTCGGCCCTCAATCCAGCGGACCTTCCTTCCCG
CGGCCTGCTGCCGGCTCTGCGGCCTCTTCCGCGTCTTCGCCTTCGCCCTC
AGACGAGTCGGATCTCCCTTTGGGCCGCCTCCCCGCCTGGTTAATTAAAG
TACCTTTAAGACCAATGACTTACAAGGCAGCTGTAGATCTTAGCCACTTT
TTAAAAGAAAAGGGGGGACTGGAAGGGCGAATTCACTCCCAACGAAGACA
AGATCTGCTTTTTGCTTGTACTGGGTCTCTCTGGTTAGACCAGATCTGAG
CCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTC
TGGTAACTAGAGATCCCTCAGACCCTTTTAGTCAGTGTGGAAAATCTCTA
GCAGGCATGCCAGACATGATAAGATACATTGATGAGTTTGGACAAACCAC
AACTAGAATGCAGTGAAAAAAATGCTTTATTTGTGAAATTTGTGATGCTA
TTGCTTTATTTGTAACCATTATAAGCTGCAATAAACAAGTTAACAACAAC
AATTGCATTCATTTTATGTTTCAGGTTCAGGGGGAGGTGTGGGAGGTTTT
TTGGCGCGCCATCGTCGAGGTTCCCTTTAGTGAGGGTTAATTGCGAGCTT
GGCGTAATCATGGTCATAGCTGTTTCCTGTGTGAAATTGTTATCCGCTCA
CAATTCCACACAACATACGAGCCGGAAGCATAAAGTGTAAAGCCTGGGGT
GCCTAATGAGTGAGCTAACTCACATTAATTGCGTTGCGCTCACTGCCCGC
TTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTC
ACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAA
AGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAA
AAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGC
GCCTTATCCGGTAACTATCGTCTTGAGTCCAACCCGGTAAGACACGACTT
ATCGCCACTGGCAGCAGCCACTGGTAACAGGATTAGCAGAGCGAGGTATG
TAGGCGGTGCTACAGAGTTCTTGAAGTGGTGGCCTAACTACGGCTACACT
AGAAGAACAGTATTTGGTATCTGCGCTCTGCTGAAGCCAGTTACCTTCGG
AAAAAGAGTTGGTAGCTCTTGATCCGGCAAACAAACCACCGCTGGTAGCG
GTGGTTTTTTGTTTGCAAGCAGCAGATTACGCGCAGAAAAAAAGGATCT
CAAGAAGATCCTTTGATCTTTTCTACGGGGTCTGACGCTCAGTGGAACGA
AAACTCACGTTAAGGGATTTTGGTCATGAGATTATCAAAAAGGATCTTCA
CCTAGATCCTTTTAAATTAAAAATGAAGTTTTAAATCAATCTAAAGTATA
TATGAGTAAACTTGGTCTGACAGTTACCAATGCTTAATCAGTGAGGCACC
TATCTCAGCGATCTGTCTATTTCGTTCATCCATAGTTGCCTGACTCCCCG
TCGTGTAGATAACTACGATACGGGAGGGCTTACCATCTGGCCCCAGTGCT
GCAATGATACCGCGAGACCCACGCTCACCGGCTCCAGATTTATCAGCAAT
AAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATC
ACTCATGGTTATGGCAGCACTGCATAATTCTCTTACTGTCATGCCATCCG
TAAGATGCTTTTCTGTGACTGGTGAGTACTCAACCAAGTCATTCTGAGAA
TAGTGTATGCGGCGACCGAGTTGCTCTTGCCCGGCGTCAATACGGGATAA
TACCGCGCCACATAGCAGAACTTTAAAAGTGCTCATCATTGGAAAACGTT
CTTCGGGGCGAAAACTCTCAAGGATCTTACCGCTGTTGAGATCCAGTTCG
ATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGG
GAATAAGGGCGACACGGAAATGTTGAATACTCATACTCTTCCTTTTTCAA
TATTATTGAAGCATTTATCAGGGTTATTGTCTCATGAGCGGATACATATT
TGAATGTATTTAGAAAAATAAACAAATAGGGGTTCCGCGCACATTTCCCC
GAAAAGTGCCAC
```

The pGAR vector map is set forth in FIG. 19.

Suitable additional exemplary vectors include e.g., pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

In other aspects, provided herein are cells comprising a polynucleotide or a vector of the present invention. In some embodiments, the present invention is directed to cells, in vitro cells, comprising a polynucleotide encoding a CAR or a TCR, as described herein. In some embodiments, the present invention is directed to cells, e.g., in vitro cells, comprising a polynucleotide encoding an antibody or an antigen binding molecule thereof that specifically binds to BCMA, as disclosed herein. In other embodiments, the present invention is directed to in vitro cells comprising a polypeptide encoded by a polynucleotide encoding a CAR or a TCR, as disclosed herein. In other embodiments, the present invention is directed to cells, in vitro cells, comprising a polypeptide encoded by a polynucleotide encoding an antibody or an antigen binding molecule thereof that specifically binds to BCMA, as disclosed herein.

Any cell may be used as a host cell for the polynucleotides, the vectors, or the polypeptides of the present invention. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof.

The cell of the present invention can be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flowthrough centrifuge, e.g., the COBE™ 2991 cell processor, the Baxter CYTOMATE™, or the like. In some embodiments, the washed cells are resuspended in one or more biocompatible buffers, or other saline solution with or without buffer. In certain embodiments, the undesired components of the apheresis sample are removed. Additional methods of isolating T cells for a T cell therapy are disclosed in U.S. Patent Publication No. 2013/0287748, which is herein incorporated by references in its entirety.

In certain embodiments, T cells are isolated from PBMCs by lysing the red blood cells and depleting the monocytes, e.g., by using centrifugation through a PERCOLL™ gradient. In some embodiments, a specific subpopulation of T cells, such as $CD28^+$, $CD4^+$, $CD8^+$, $CD45RA^+$, and $CD45RO^+$ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for $CD4^+$ cells by negative selection, a monoclonal antibody cocktail typically includes antibodies to CD14, CD20, CD11b, CD16, HLA-DR, and CD8. In certain embodiments, flow cytometry and cell sorting are used to isolate cell populations of interest for use in the present invention.

In some embodiments, PBMCs are used directly for genetic modification with the immune cells (such as CARs or TCRs) using methods as described herein. In certain embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, $CD8^+$ cells are further sorted into naive, central memory, and effector cells by identifying cell surface antigens that are associated with each of these types of $CD8^+$ cells. In some embodiments, the expression of phenotypic markers of central memory T cells includes CD45RO, CD62L, CCR7, CD28, CD3, and CD127 and are negative for granzyme B. In some embodiments, central memory T cells are $CD45RO^+$, $CD62L^+$, $CD8^+$ T cells. In some embodiments, effector T cells are negative for CD62L, CCR7, CD28, and CD127 and positive for granzyme B and perform. In certain embodiments, $CD4^+$ T cells are further sorted into subpopulations. For example, $CD4^+$ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In certain embodiments, the T cells are obtained from a donor subject. In some embodiments, the donor subject is human patient afflicted with a cancer or a tumor. In other embodiments, the donor subject is a human patient not afflicted with a cancer or a tumor.

Other aspects of the present invention are directed to compositions comprising a polynucleotide described herein, a vector described herein, a polypeptide described herein, or an in vitro cell described herein. In some embodiments, the composition comprises a pharmaceutically acceptable carrier, diluent, solubilizer, emulsifier, preservative and/or adjuvant. In some embodiments, the composition comprises an excipient. In one embodiment, the composition comprises a polynucleotide encoding a CAR or a TCR, wherein the CAR or the TCR comprises an antigen binding molecule that specifically binds to BCMA. In another embodiment, the composition comprises a CAR or a TCR encoded by a polynucleotide of the present invention, wherein the CAR or the TCR comprises an antigen binding molecule that specifically binds to BCMA. In another embodiment, the composition comprises a T cell comprising a polynucleotide encoding a CAR or a TCR, wherein the CAR or the TCR comprises an antigen binding molecule that specifically binds to BCMA. In another embodiment, the composition comprises an antibody or an antigen binding molecule thereof encoded by a polynucleotide of the present invention. In another embodiment, the composition comprises an in vitro cell comprising a polynucleotide encoding an antibody or an antigen binding molecule thereof encoded by a polynucleotide of the present invention.

In some embodiments, the composition includes more than one different antigen binding molecule to BMCA. In some embodiments, the composition included more than one antigen binding molecule to BCMA, wherein the antigen binding molecules to BCMA bind more than one epitope. In some embodiments, the antigen binding molecules will not compete with one another for binding to BCMA. In some embodiments, any of the antigen binding molecules provided herein are combined together in a pharmaceutical composition.

In other embodiments, the composition is selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, the composition is in the form of a pyrogen-free, parenterally acceptable aqueous solution comprising a desired antigen binding molecule to BCMA, with or without additional therapeutic agents, in a pharmaceutically acceptable vehicle. In certain embodiments, the vehicle for parenteral injection is sterile distilled water in which an antigen binding molecule to BCMA, with or without at least one additional therapeutic agent, is formulated as a sterile, isotonic solution, properly preserved. In certain embodiments, the preparation involves the formulation of the desired molecule with polymeric compounds (such as polylactic acid or polyglycolic acid), beads or liposomes, that provide for the controlled or sustained release of the product, which are then be delivered via a depot injection. In certain embodiments, implantable drug delivery devices are used to introduce the desired molecule.

V. Methods of the Invention

Another aspect of the invention is directed to a method of making a cell expressing a CAR or a TCR comprising transducing a cell with a polynucleotide disclosed herein under suitable conditions. In some embodiments, the method comprises transducing a cell with a polynucleotide encoding a CAR or a TCR, wherein the CAR or the TCR comprises an antigen binding molecule that specifically binds to BCMA, as disclosed herein. In some embodiments, the method comprises transducing a cell with a vector comprising the polynucleotide encoding a CAR or a TCR, wherein the CAR or the TCR comprises an antigen binding molecule that specifically binds to BCMA. In other embodiments, the method comprises transducing a cell with a polynucleotide encoding an antibody or an antigen binding molecule thereof that specifically binds to BCMA, as disclosed herein. In some embodiments, the method comprises transducing a cell with a vector comprising the polynucleotide encoding an antibody or an antigen binding molecule thereof that specifically binds to BCMA, as described herein. In some embodiments, the method further comprises isolating the cell.

Another aspect of the present invention is directed to a method of inducing an immunity against a tumor comprising administering to a subject an effective amount of a cell comprising a polynucleotide described herein, a vector described herein, or a CAR or a TCR described herein. In one embodiment, the method comprises administering to a subject an effective amount of a cell comprising a polynucleotide encoding a CAR or a TCR, wherein the CAR or the TCR comprises an antigen binding molecule that specifically binds to BCMA, as disclosed herein. In another embodiment, the method comprises administering to a subject an effective amount of a cell comprising a vector comprising a polynucleotide encoding a CAR or a TCR, wherein the CAR or the TCR comprises an antigen binding molecule that specifically binds to BCMA, as disclosed herein. In another embodiment, the method comprises administering to a subject an effective amount of a cell comprising a CAR or a TCR encoded by a polynucleotide disclosed herein, wherein the CAR or the TCR comprises an antigen binding molecule that specifically binds to BCMA. In other embodiments, the method comprises administering to a subject an effective amount of a cell comprising a polynucleotide encoding an antibody or an antigen binding molecule thereof that specifically binds to BCMA, as disclosed herein. In another embodiment, the method comprises administering to a subject an effective amount of a cell comprising a vector comprising a polynucleotide encoding an antibody or an antigen binding molecule thereof that specifically binds to BCMA, as disclosed herein. In another embodiment, the method comprises administering to a subject an effective amount of a cell comprising an antibody or antigen binding molecule thereof encoded by a polynucleotide disclosed herein, wherein the antibody or antigen binding molecule thereof specifically binds to BCMA.

Another aspect of the present invention is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells. In some embodiments, the engineered immune cell comprises a CAR or a TCR. In some embodiments, the target cell is a tumor cell.

Another aspect of the present invention is directed to a method for treating or preventing a malignancy, said method comprising administering to a subject in need thereof an effective amount of at least one isolated antigen binding molecule described herein or at least one immune cell, wherein the immune cell comprises at least one CAR, TCR, and/or an isolated antigen binding molecule as described herein.

Another aspect of the present invention is directed to a method of treating a hyperproliferative disorder or an inflammatory disease in a subject in need thereof comprising administering to the subject a polynucleotide disclosed herein, a vector disclosed herein, a CAR or a TCR disclosed herein, a cell disclosed herein, or a composition disclosed herein. In some embodiments, the inflammatory disease is selected from the group consisting of rheumatoid arthritis, psoriasis, allergies, asthma, autoimmune diseases such as Crohn's, IBD, fibromyalga, mastocytosis, Celiac disease, and any combination thereof. Additionally, the present invention may be useful to treat diabetes, particularly Type 1 diabetes.

Another aspect of the present invention is directed to a method of treating a cancer in a subject in need thereof comprising administering to the subject a polynucleotide disclosed herein, a vector disclosed herein, a CAR or a TCR disclosed herein, a cell disclosed herein, or a composition disclosed herein. In one embodiment, the method comprises administering a polynucleotide encoding a CAR or a TCR, wherein the CAR or the TCR comprises an antigen binding molecule that specifically binds to BCMA, as disclosed herein. In another embodiment, the method comprises administering a vector comprising a polynucleotide encoding a CAR or a TCR, wherein the CAR or the TCR comprises an antigen binding molecule that specifically binds to BCMA, as disclosed herein. In another embodiment, the method comprises administering a CAR or a TCR encoded by a polynucleotide disclosed herein, wherein the CAR or the TCR comprises an antigen binding molecule that specifically binds to BCMA. In another embodiment, the method comprises administering a cell comprising the polynucleotide, or a vector comprising the polynucleotide, encoding a CAR or a TCR, wherein the CAR or the TCR comprises an antigen binding molecule that specifically binds to BCMA, as disclosed herein. In other embodiments, the method comprises administering a polynucleotide encoding an antibody or an antigen binding molecule thereof that specifically binds to BCMA, as disclosed herein. In another embodiment, the method comprises administering a vector comprising a polynucleotide encoding an antibody or an antigen binding molecule thereof that specifically binds to BCMA, as disclosed herein. In another embodiment, the method comprises administering an antibody or an antigen binding molecule thereof encoded by a polynucleotide disclosed herein, wherein the antibody or the antigen binding molecule thereof specifically binds to BCMA. In another embodiment, the method comprises administering a cell comprising the polynucleotide, or a vector comprising the polynucleotide, encoding an antibody or an antigen binding molecule thereof that specifically binds to BCMA, as disclosed herein.

In some embodiments, an antigen binding molecule to BCMA is administered alone. In certain embodiments, an antigen binding molecule to BCMA is administered as part of a CAR, TCR, or other immune cell. In such immune cells, the antigen binding molecule to BCMA can be under the control of the same promoter region, or a separate promoter. In certain embodiments, the genes encoding protein agents and/or an antigen binding molecule to BCMA can be in separate vectors.

In some embodiments, the methods of treating a cancer in a subject in need thereof comprise a T cell therapy. In one embodiment, the T cell therapy of the present invention is engineered Autologous Cell Therapy (eACT™). According to this embodiment, the method can include collecting blood cells from the patient. The isolated blood cells (e.g., T cells) can then be engineered to express an anti-BCMA CAR of the present invention ("anti-BCMA CAR T cells"). In a particular embodiment, the anti-BCMA CAR T cells are administered to the patient. In some embodiments, the anti-BCMA CAR T cells treat a tumor or a cancer in the patient. In one embodiment the anti-BCMA CAR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

The T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$ cells, at least about $10^{10}$ cells, or at least about $10^{11}$ cells. In another embodiment, the therapeutically effective amount of the T cells is about $10^4$ cells, about $10^5$ cells, about $10^6$ cells, about $10^7$ cells, or about $10^8$ cells. In one particular embodiment, the therapeutically effective amount of the anti-BCMA CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

Another aspect of the present invention is directed to methods of diagnosis, detection, or validation. In some embodiments, the antigen binding molecule is used as a diagnostic or validation tool. In certain embodiments, the antigen binding molecules disclosed herein are used to assay the amount of BCMA present in a sample and/or subject. In some embodiments, the diagnostic antigen binding molecule is not neutralizing. In some embodiments, the antigen binding molecules disclosed herein are used or provided in an assay kit and/or method for the detection of BCMA in mammalian tissues or cells in order to screen/diagnose for a disease or disorder associated with changes in levels of BCMA. In some embodiments, the kit comprises an antigen binding molecule that binds BCMA, along with means for indicating the binding of the antigen binding molecule with BCMA, if present, and optionally BCMA protein levels. Various means for indicating the presence of an antigen binding molecule can be used. For example, fluorophores, other molecular probes, or enzymes can be linked to the antigen binding molecule and the presence of the antigen binding molecule can be observed in a variety of ways. As will be appreciated by one of skill in the art, the degree of antigen binding molecule binding can be used to determine how much BCMA is in a sample.

V.A. Cancer Treatment

The methods of the invention can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In certain embodiments, the cancer is multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, myeloid diseases including but not limited to acute myeloid leukemia (AML), chronic myeloid leukemia (CML), acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome (MDS), hemophagocytic syndrome (Macrophage Activating Syndrome (MAS), and hemophagocytic lymphohistiocytosis (HLH)), chronic or acute granulomatous disease, large cell granuloma, leukocyte adhesion deficiency, plasmablastic lymphoma, plasmacytoid dendritic cell neoplasm, Waldenstrom macroglobulinemia, plasma cell proliferative disorders (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (Crow-Fukase syndrome, Takatsuki disease, PEP syndrome), or combinations thereof. In one embodiment, the cancer is a myeloma. In one particular embodiment, the cancer is multiple myeloma.

In some embodiments, the methods further comprise administering a chemotherapeutic. In certain embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). A preferred dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient.

In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR- and/or TCR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (Opdivo®), pembrolizumab (Keytruda®), pembrolizumab, pidilizumab (CureTech), and atezolizumab (Roche).

Additional therapeutic agents suitable for use in combination with the invention include, but are not limited to, ibrutinib (Imbruvica®), ofatumumab (Arzerra®), rituximab (Rituxan®), bevacizumab (Avastin®), trastuzumab (Herceptin®), trastuzumab emtansine (KADCYLA®), imatinib (Gleevec®), cetuximab (Erbitux®), panitumumab (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR- and/or TCR-containing immune are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The present invention is further illustrated by the following examples which should not be construed as further limiting. The contents of all references cited throughout this application are expressly incorporated herein by reference.

EXAMPLES

Example 1

BCMA expression was measured in various cell lines. BCMA was found to be expressed, with a fragments/kilobase of exon/million reads mapped (FPKM) greater than 35, in 99% of multiple myeloma tumor cell lines tested (FIG. 2A). BCMA expression was greater than that of CD70, CS-1, CLL-1, DLL-1 and FLT3 (FIG. 2A). To further characterize the expression of BCMA, EoL-1 (Sigma), NCI-H929 (Molecular Imaging), and MM1S (Molecular Imaging) cells were stained with an anti-BCMA antibody conjugated to PE (Biolegend, San Diego, Calif.) in stain buffer (BD Pharmingen, San Jose, Calif.) for 30 minutes at 4° C. Cells were then washed and resuspended in stain buffer with propidium iodide (BD Pharmingen) prior to data acquisition. Samples were then acquired by flow cytometry and data analyzed (FIGS. 2B-2C). BCMA expression was observed in the myeloma cell lines MMIS (FIG. 2C) and NCI-H929 (FIG. 2D), but not in the human eosinophil cell line EoL-1 (FIG. 2B). In addition, little to no BCMA expression was observed in normal immune cells (FIG. 2E).

Example 2

A third generation lentiviral transfer vector containing the BCMA CAR constructs was used along with the ViraPowerm Lentiviral Packaging Mix (Life Technologies, FIX™) to generate the lentiviral supernatants. Briefly, a transfection mix was generated by mixing 15 μg of DNA and 22.5 μl of polyethileneimine (Polysciences, 1 mg/ml) in 600 μl of OptiMEM media. The transfection mix was incubated for 5 minutes at room temperature. Simultaneously, 293T cells (ATCC) were trypsinized and counted. A total of $10 \times 10^6$ total 293T cells were then plated in a T75 flask with the transfection mix. Following culture for three days, supernatants were collected and filtered through a 0.45 μm filter and stored at −80° C.

Peripheral blood mononuclear cells (PBMCs) were isolated from two different healthy donor leukopaks (Hemacare) using ficoll-paque density centrifugation according to the manufacturer's instructions. PBMCs were stimulated using OKT3 (Muromonab-CD3, 50 ng/ml, Miltenyi Biotec) in R10 media supplemented with IL-2 (300 IU/ml, Proleukin®, Prometheus® Therapeutics and Diagnostics). Forty-eight hours post-stimulation, cells were transduced using lentivirus containing the different BCMA CAR constructs at a multiplicity of infection (MOI) of 10. Cells were maintained at $0.5 \times 10^6$-$2.0 \times 10^6$ cells/ml prior to use in activity assays.

Figure 3B:
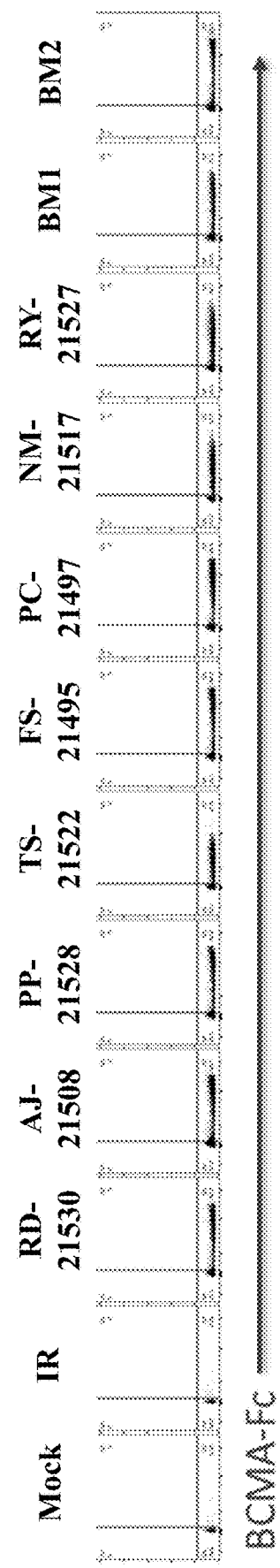

At day 12 post-stimulation, transduced T cells were stained with recombinant BCMA-Fc (R&D Systems) in stain buffer (BD Pharmingen) for 30 minutes at 4° C. Cells were then washed and stained with goat anti-human IgG Fc PE (Jackson ImmunoResearch, West Grove, Pa.) in stain buffer for 30 minutes at 4° C. Cells were then washed and resuspended in stain buffer with propidium iodide (BD Pharmingen) prior to data acquisition. All experiments were performed in two different donors. BCMA CAR expression was observed for each of the constructs in both Donor 1 (FIG. 3A) and Donor 2 (FIG. 3B) transduced cells.

Figure 4C:
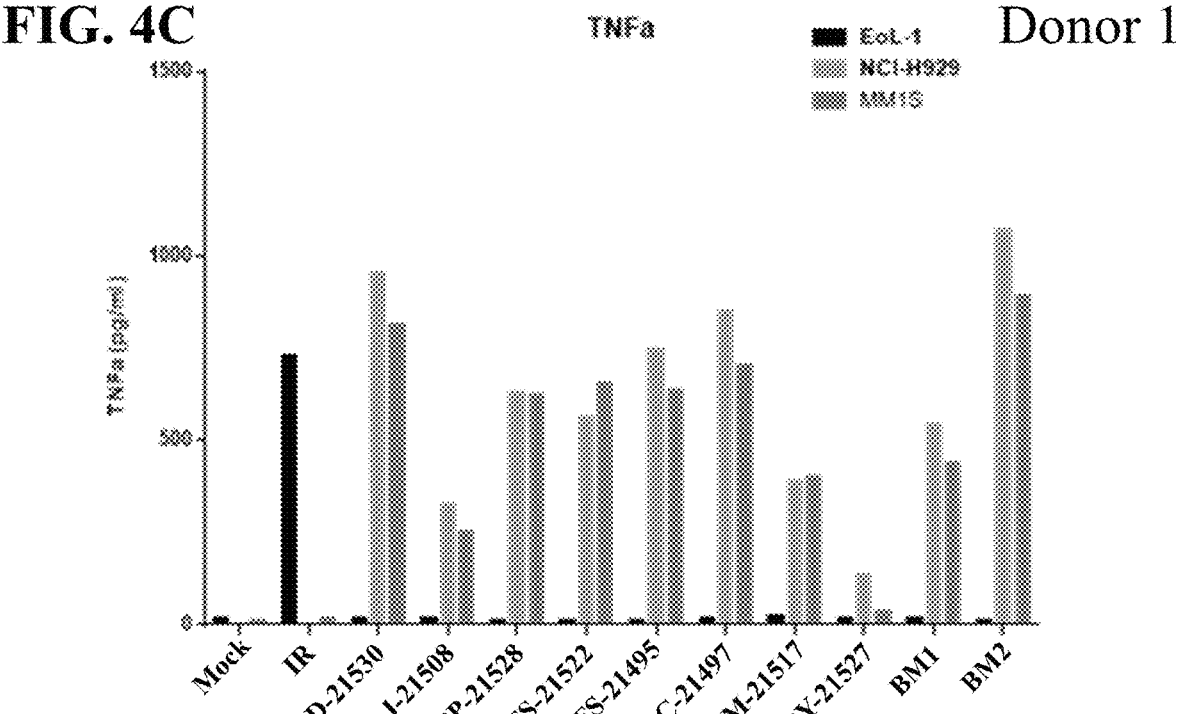
Figure 4D:
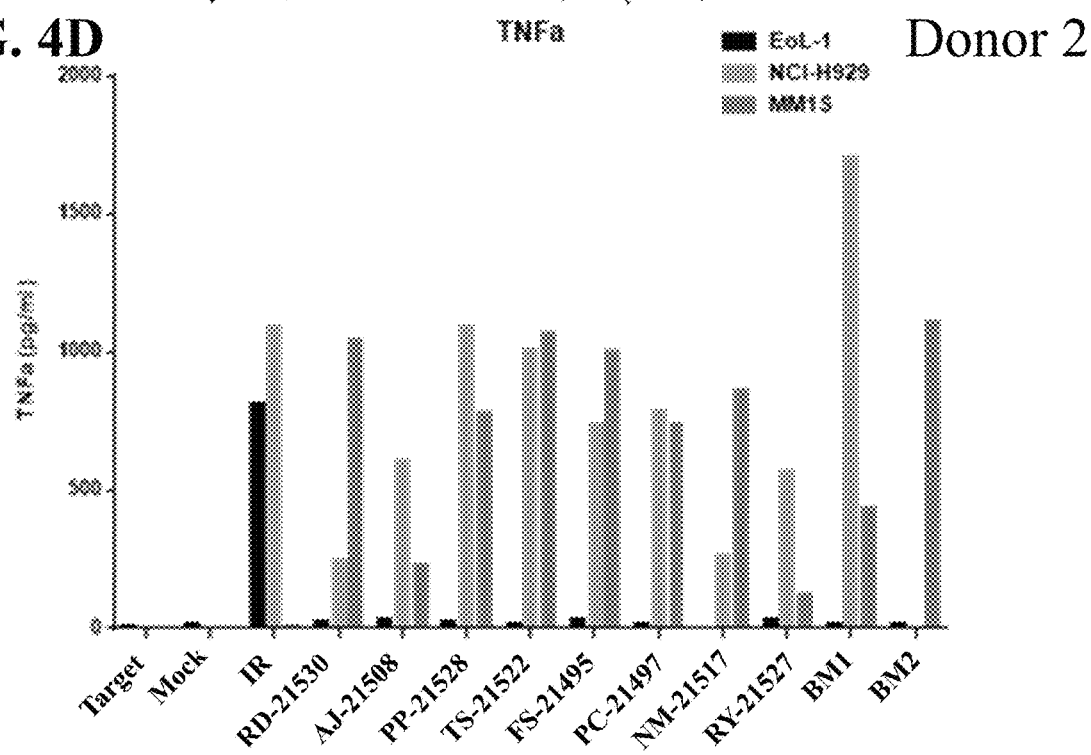
Figure 4E:
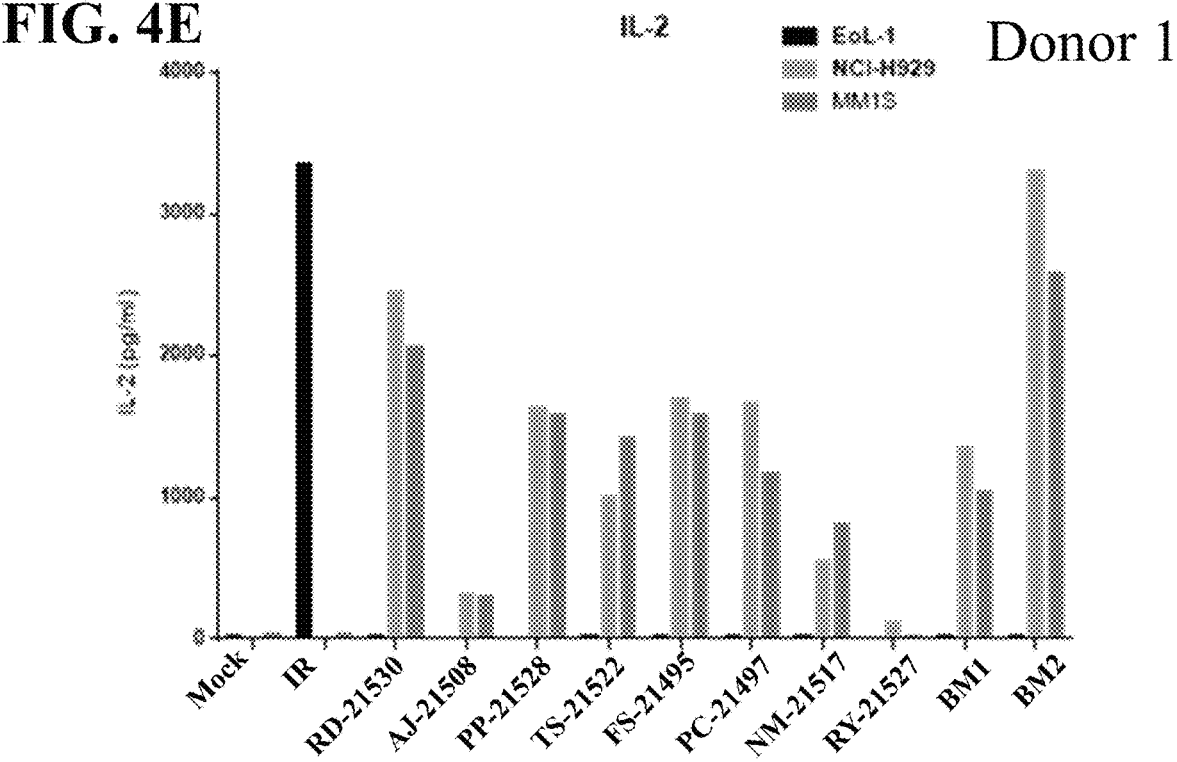
Figure 4F:
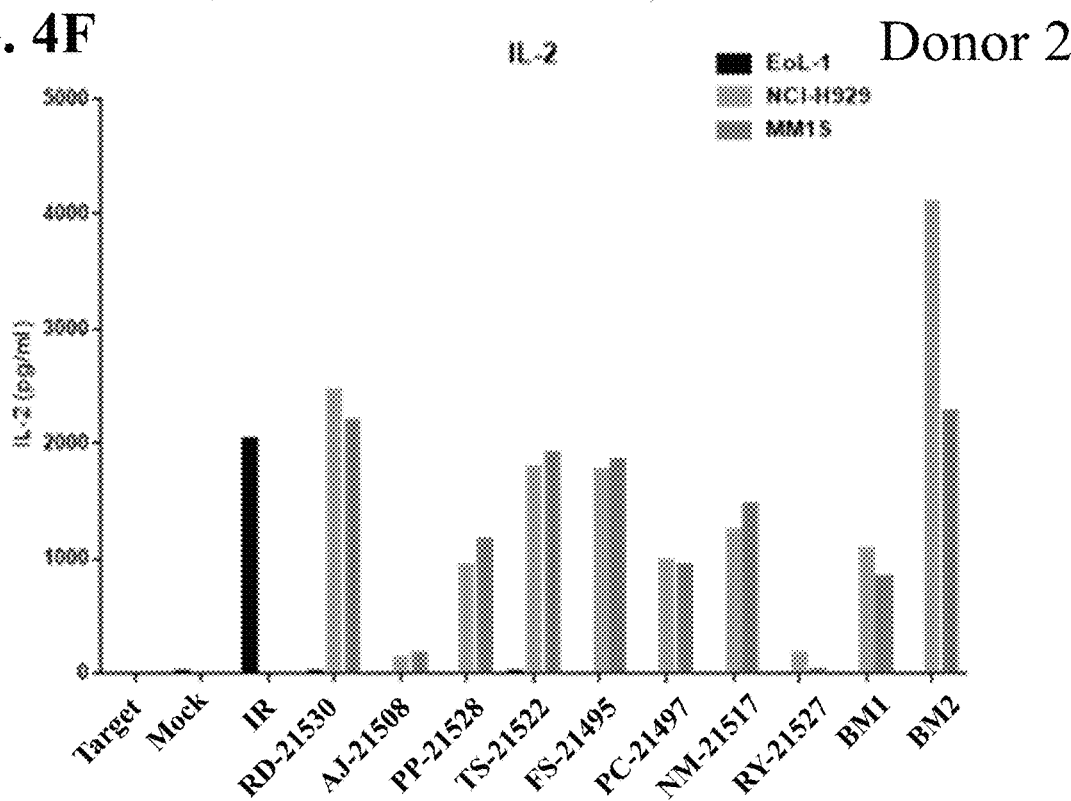

Effector cells, e.g., anti-BCMA CAR T cells, were cultured with target cells at a 1:1 effector cell to target cell (E:T) ratio in R10 media 12 days after T cell stimulation. Cell lines tested included EoL-1, NCI-H929 and MM1S. Sixteen hours post-co-culture, supernatants were analyzed by Luminex (EMD Millipore), according to the manufacturer's instructions, for production of the cytokines IFNγ (FIGS. 4A-4B), TNFα (FIG. 4C-4D), and IL-2 (FIG. 4E-4F). IFNγ (FIGS. 4A-4B), TNFα (FIG. 4C-4D), and IL-2 (FIG. 4E-4F) were observed in the supernatant of NCI-H929 and MM1S target cell co-cultures for each anti-BCMA CAR T cell tested in both donors (FIGS. 4A-4B); however, IFNγ (FIGS. 4A-4B), TNFα (FIG. 4C-4D), and IL-2 (FIG. 4E-4F) were only observed in the supernatant of EoL-1 target cell co-cultures above background for the IR negative control T cells (FIG. 4A).

Figure 5A:
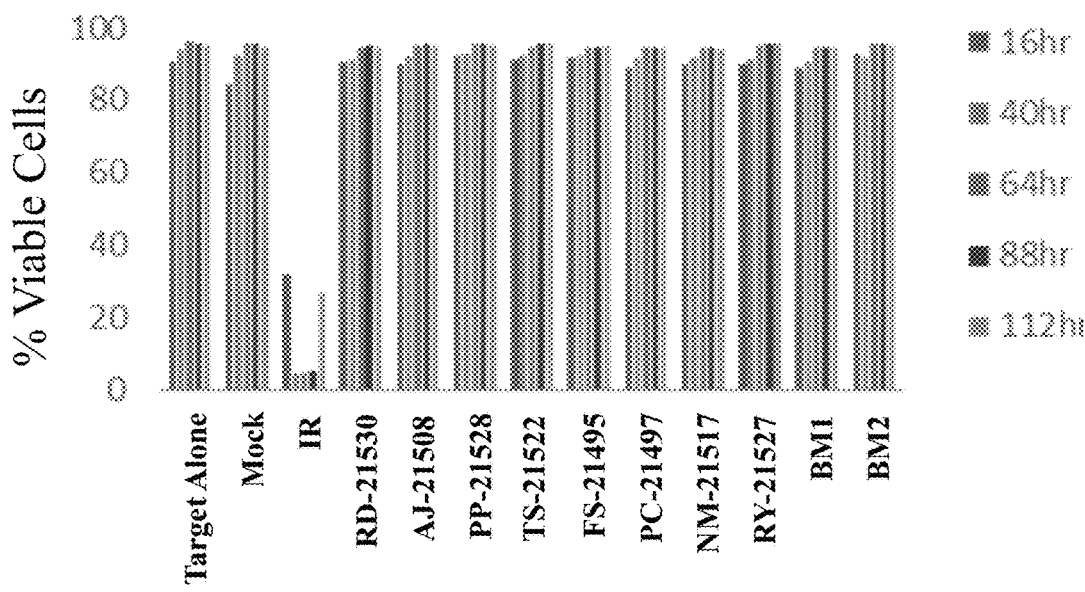
FIGS. 5A-5F show the average cytolytic activity (as a percentage of viable target cells remaining; y-axis) over time from two healthy donors expressing the indicated CARs co-cultured with EoL1 (FIGS. 5A and 5B), NCI-H929 (FIGS. 5C and 5D), or MM1S (FIGS. 5E and 5F) target cells for 16 hours, 40 hours, 64 hours, 88 hours, or 112 hours.
Figure 5B:
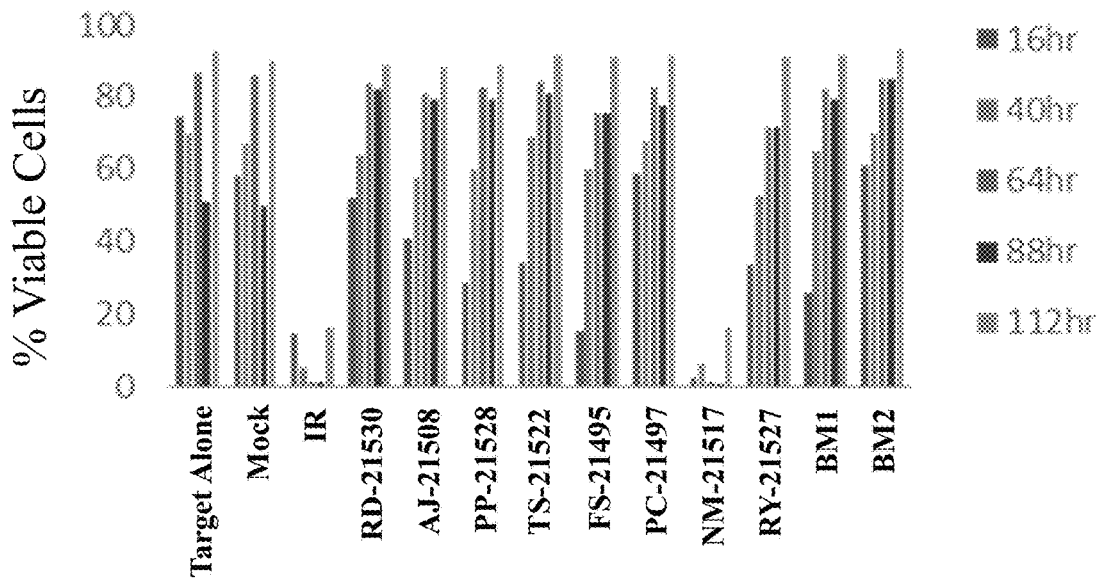
Figure 5C:
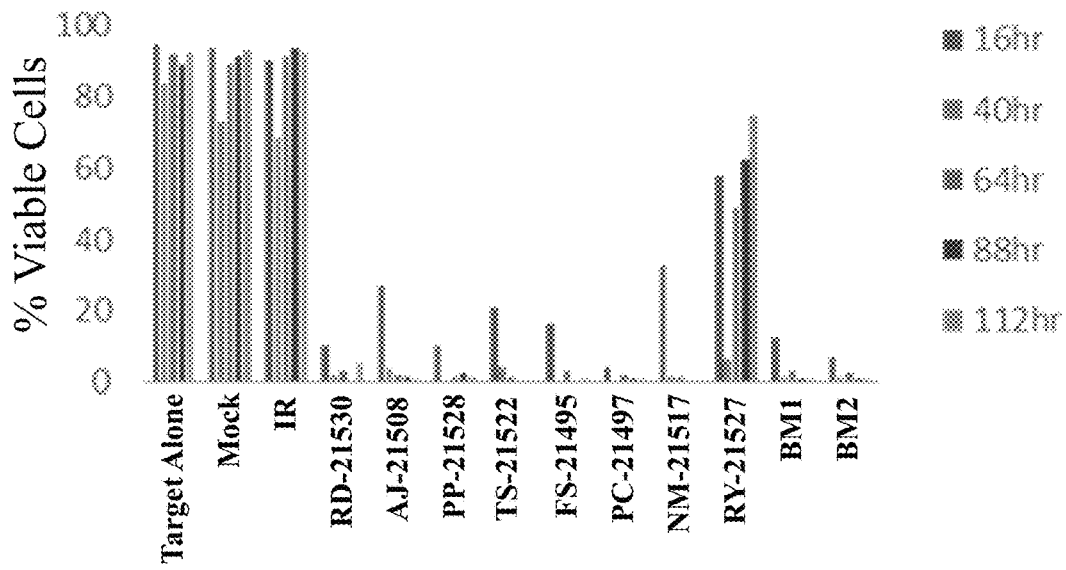
Figure 5D:
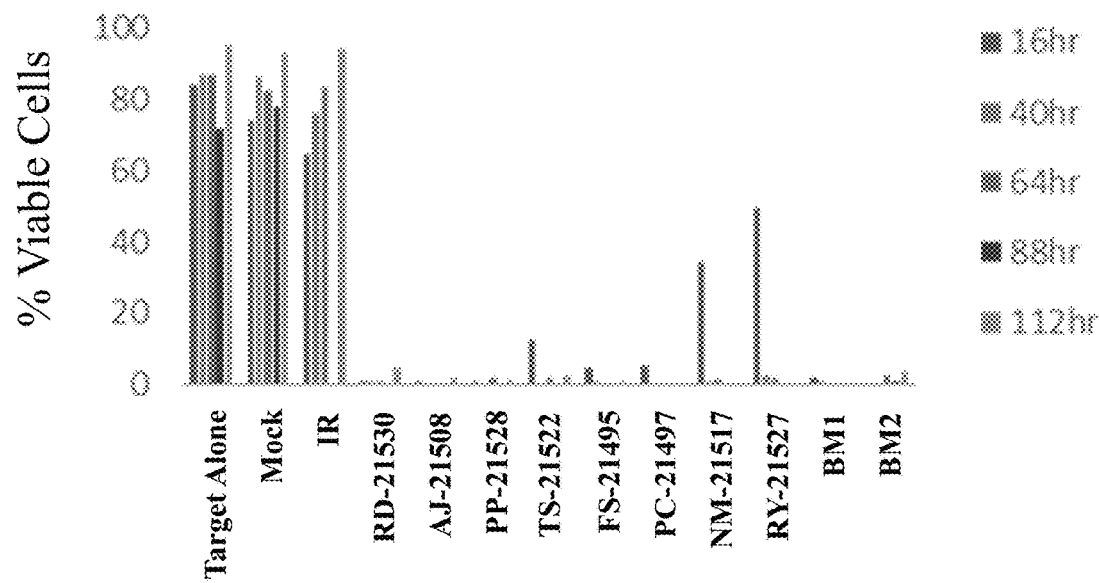
Figure 5E:
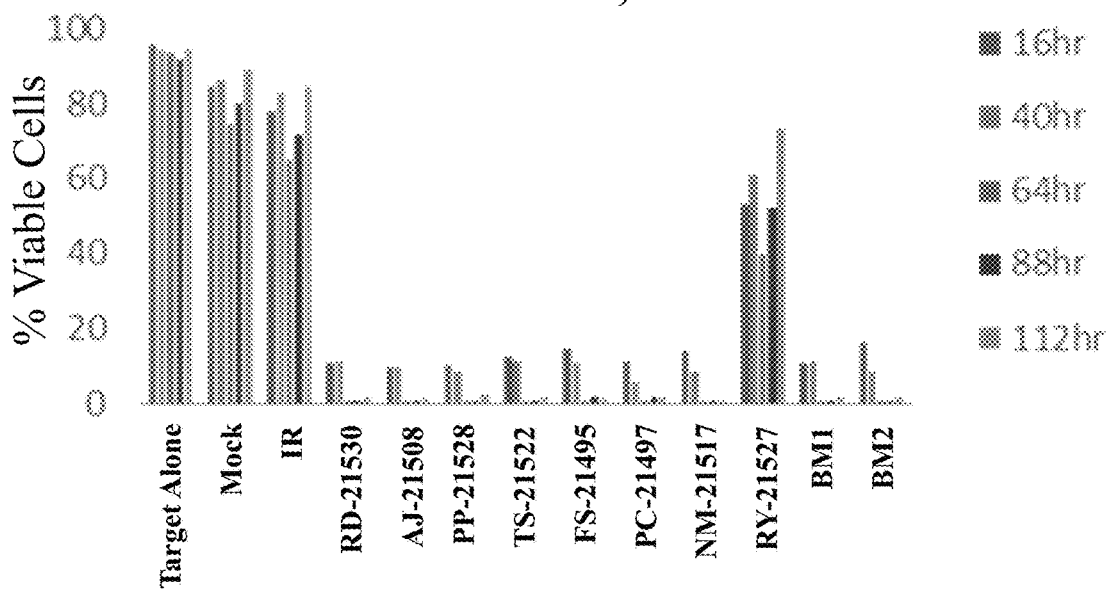
Figure 5F:
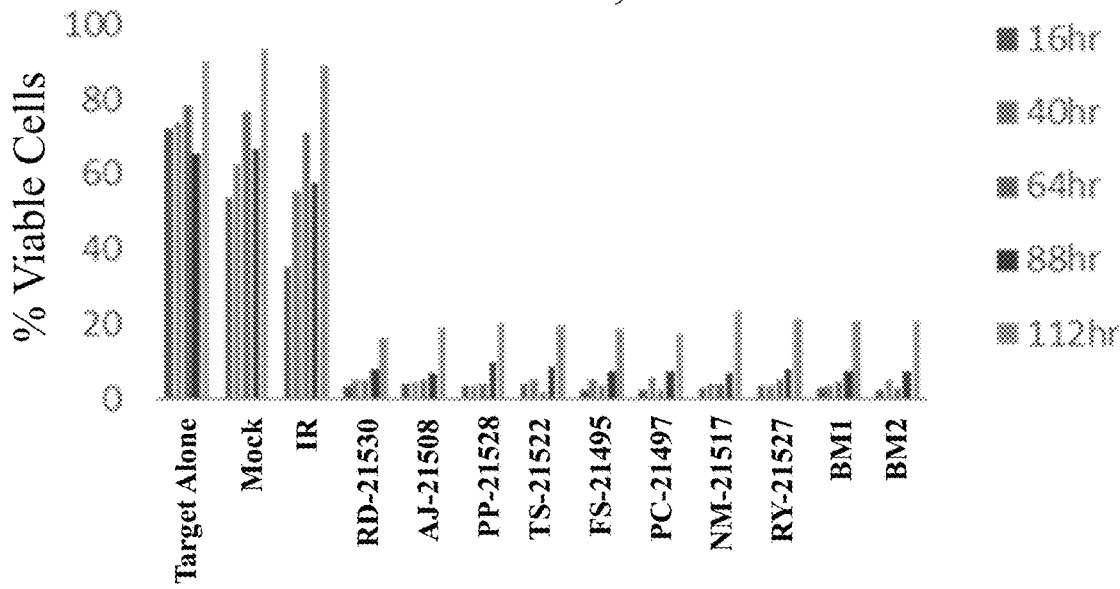

Target cell viability was assessed by flow cytometric analysis of propidium iodide (PI) uptake of CD3 negative cells. The anti-BCMA CAR T cells were co-cultured with EoL1 (FIGS. 5A-5B), NCI-H929 (FIGS. 5C-5D), or MM1S (FIGS. 5E-5F) target cells for 16 hours, 40 hours, 64 hours, 88 hours, or 112 hours. Little cytolytic activity was observed in the EoL-1 co-cultures at any time period for the anti-BCMA CAR T cells (FIG. 5A-5B). However, co-culture of the anti-BCMA CART cells and the NCI-H929 or MM1S target cells resulted in a decrease in the percentage of viable target cells at each time point measured for each of the anti-BCMA CAR T cells.

Figure 6A:
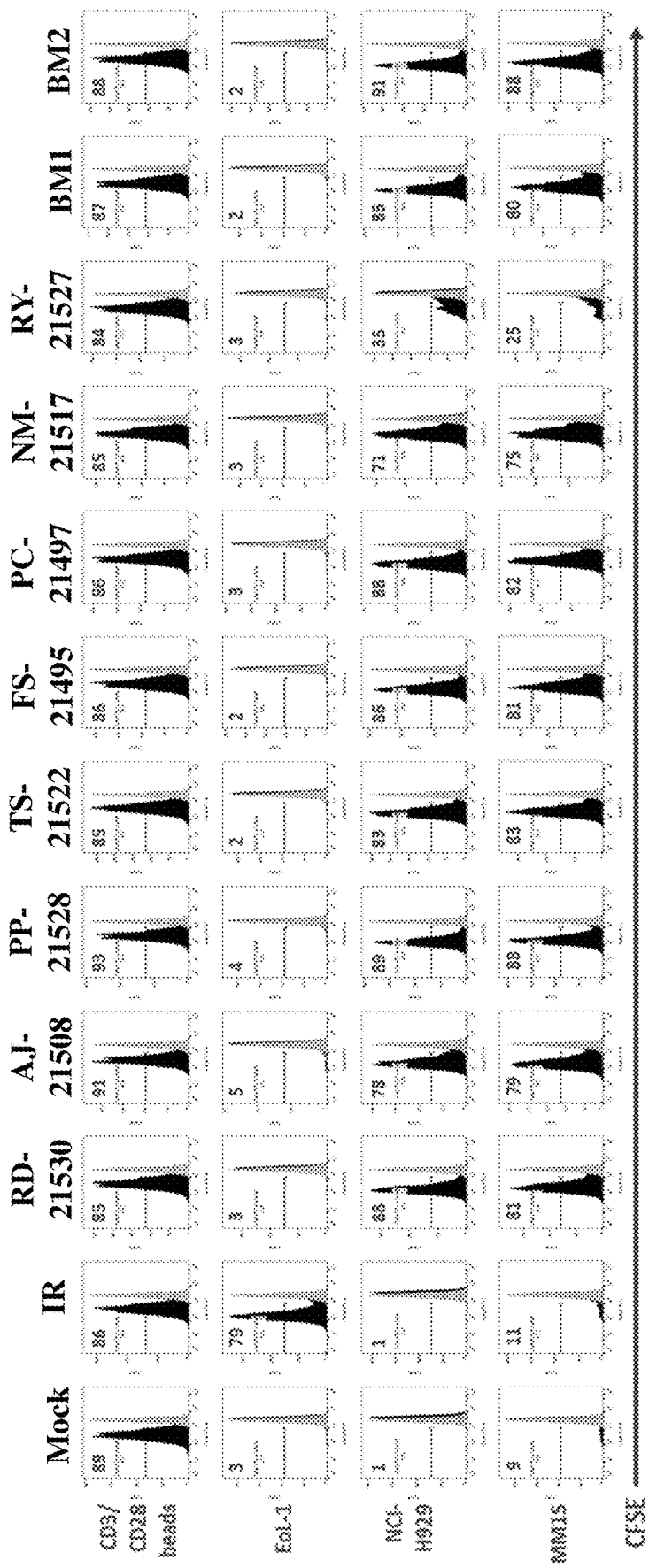
FIGS. 6A and 6B show proliferation of CFSE-labeled lentivirus transduced CAR T cells from a first healthy donor (FIG. 6A) and a second healthy donor (FIG. 6B) following 5 days of co-culture with CD3-CD28 beads (top row), EoL-1 (second row), NCI-11929 (third row), or MM1S (bottom row) target cell lines.
Figure 6B:
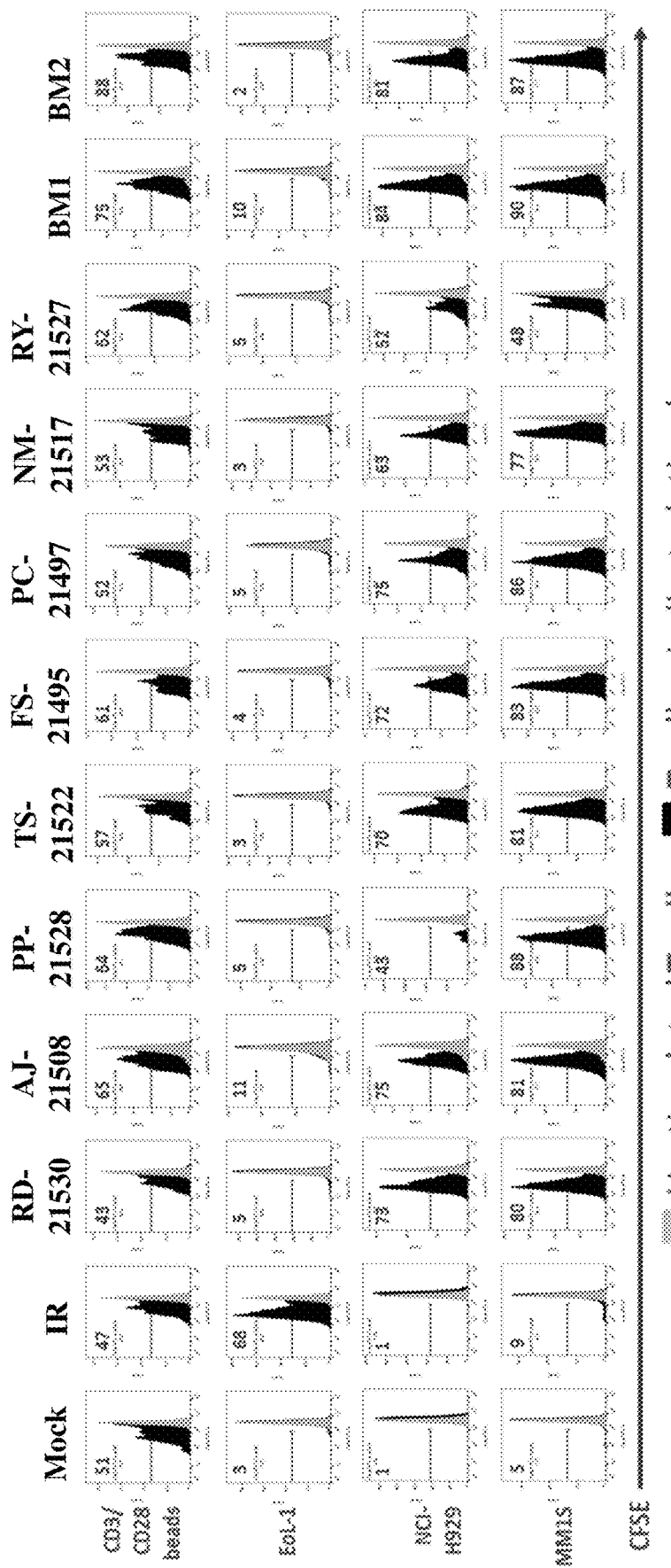

To examine proliferation, anti-BCMA CAR T cells were labeled with carboxyfluorescein succinimidyl ester (CFSE) prior to co-culture with EoL-1, NCI-H929, or MM1S target cells at a 1:1 E:T ratio in R10 media. Five days later, T cell proliferation was assessed by flow cytometric analysis of CFSE dilution. Data was analyzed and plotted as histogram using FlowJo™ (FIGS. 6A-6B). All experiments were performed in two different donors.

Example 3

Antigens were biotinylated using the EZ-Link Sulfo-NHS-Biotinylation Kit from Pierce/ThermoFisher (Waltham, Mass.). Goat anti-human F(ab')2 kappa-FITC (LC-FITC), Extravidin-PE (EA-PE) and streptavidin-633 (SA-633) were obtained from Southern Biotech (Birmingham, Ala.), Sigma (St. Louis, Mo.) and Molecular Probes/Invitrogen (Waltham, Mass.), respectively. Streptavidin MicroBeads and MACS LC separation columns were purchased from Miltenyi Biotec (Gladbachn, Germany).

Naïve Discovery

Eight naïve human synthetic yeast libraries each of ~$10^9$ diversity were propagated as described herein (see WO2009036379, WO2010105256, and WO2012009568 to Xu et al.). For the first two rounds of selection, a magnetic bead sorting technique utilizing the Miltenyi MACs system was performed, as described (Siegel et al., 2004). Briefly, yeast cells (~$10^{10}$ cells/library) were incubated with 3 ml of 100 nM biotinylated monomeric antigen or 10 nM biotinylated Fc fusion antigen for 15 minutes at room temperature in FACS wash buffer (phosphate-buffered saline (PBS)/ 0.1% bovine serum albumin (BSA)). After washing once with 50 ml ice-cold wash buffer, the cell pellet was resuspended in 40 mL wash buffer, and Streptavidin MicroBeads (500 μl) were added to the yeast and incubated for 15 minutes at 4° C. Next, the yeast were pelleted, resuspended in 5 mL wash buffer, and loaded onto a Miltenyi LS column. After the 5 mL was loaded, the column was washed 3 times with 3 ml FACS wash buffer. The column was then removed from the magnetic field, and the yeast were eluted with 5 mL of growth media and then grown overnight. The following rounds of sorting were performed using flow cytometry. Approximately $1 \times 10^8$ yeast were pelleted, washed three times with wash buffer, and incubated with decreasing concentrations of biotinylated monomeric or Fc fusion antigen (100 to 1 nM) under equilibrium conditions at room temperature. Yeast were then washed twice and stained with LC-FITC (diluted 1:100) and either SA-633 (diluted 1:500) or EA-PE (diluted 1:50) secondary reagents for 15 minutes at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences, San Jose, Calif.) and sort gates were assigned to select for specific binders relative to a background control. Subsequent rounds of selection were focused on reduction of non-specific reagent binders (utilizing soluble membrane proteins from CHO cell), as well as pressuring for affinity to BCMA. After the final round of sorting, yeast were plated and individual colonies were picked for characterization.

Affinity Maturation

Binding optimization of naïve clones was carried out using three maturation strategies: light chain diversification, diversification of VH CDRH1/CDRH2, and performing VHmut/VKmut selections.

Light Chain Diversification: Heavy chain plasmids were extracted and transformed into a light chain library with a diversity of $1 \times 10^6$. Selections were performed as described above with one round of MACS sorting and two rounds of FACS sorting using 10 nM or 1 nM biotinylated antigen for respective rounds.

CDRH1 and CDRH2 Selection: A selected donor CDRH3 was recombined into a premade library with CDRH1 and CDRH2 variants of a diversity of $1 \times 10^8$ and selections were performed as described above. Affinity pressures were applied by incubating the biotinylated antigen-antibody yeast complex with unbiotinylated antigen for varying amounts of time to select for the highest affinity antibodies.

VHmut/VKmut Selection: This round of affinity maturation included error prone PCR-based mutagenesis of the heavy chain and/or light chain. Selections were performed similar to previous cycles, but employing FACS sorting for all selection rounds. Antigen concentration was reduced and cold antigen competition times were increased to pressure further for optimal affinity.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect™ (GE Healthcare LifeSciences, Pittsburgh, Pa.).

ForteBio KD Measurements

ForteBio affinity measurements were performed generally as previously described (Estep et al., 2013). Briefly, ForteBio affinity measurements were performed by loading IgGs on-line onto AHQ sensors. Sensors were equilibrated off-line in assay buffer for 30 minutes and then monitored on-line for 60 seconds for baseline establishment. Sensors with loaded IgGs were exposed to 100 nM antigen for 5 minutes, afterwards they were transferred to assay buffer for 5 minutes for off-rate measurement. Kinetics were analyzed using the 1:1 binding model.

MSD-SET KD Measurements

Equilibrium affinity measurements performed generally as previously described (Estep et al., 2013). Briefly, solution equilibrium titrations (SET) were performed in PBS+0.1% IgG-Free BSA (PBSF) with antigen (BCMA monomer) held constant at 10-100 pM and incubated with 3- to 5-fold serial dilutions of Fab or mAbs starting at 10 pM-10 nM (experimental condition is sample dependent). Antibodies (20 nM in PBS) were coated onto standard bind MSD-ECL plates overnight at 4° C. or at room temperature for 30 minutes. Plates were then blocked by BSA for 30 minutes with shaking at 700 rpm, followed by three washes with wash buffer (PBSF+0.05% Tween 20). SET samples were applied and incubated on the plates for 150 seconds with shaking at 700 rpm followed by one wash. Antigen captured on a plate was detected with 250 ng/mL Sulfotag™-labeled streptavidin in PBSF by incubation on the plate for 3 minutes. The plates were washed three times with wash buffer and then read on the MSD Sector Imager 2400™ instrument using 1× Read Buffer T with surfactant. The percent free antigen was plotted as a function of titrated antibody in Prism™ and fit to a quadratic equation to extract the KD. To improve throughput, liquid handling robots were used throughout MSD-SET experiments, including SET sample preparation.

Octet Red384 Epitope Binning/Ligand Blocking

Epitope binning/ligand blocking was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Data was processed using ForteBio's Data Analysis Software 7.0. Additional binding by the second antibody or ligand after antigen association indicates an unoccupied epitope (non-competitor), while no binding indicates epitope blocking (competitor or ligand blocking).

Size Exclusion Chromatography

A TSKgel SuperSW mAb HTP column (22855) was used for fast SEC analysis of yeast produced mAbs at 0.4 mL/minute with a cycle time of 6 minutes/run. 200 mM Sodium Phosphate and 250 mM Sodium Chloride was used as the mobile phase.

Dynamic Scanning Fluorimetry 10 uL of 20× Sypro Orange™ is added to 20 uL of 0.2-1 mg/mL mAb or Fab solution. A RT-PCR instrument (BioRad CFX96 RT PCR) is used to ramp the sample plate temperature from 40° to 95° C. at 0.5C increment, with 2 minutes to equilibrate at each temperature. The negative of first derivative for the raw data is used to extract Tm.

```
Clone FS-26528 HC DNA
                                                   (SEQ ID NO: 271)
GAGGTGCAGCTGTTGGAGTCTGGGGGAGGCTTGGTACAGCCTGGGGGGTCCCTGAGACTCT

CCTGTGCAGCCTCTGGATTCACCTTTGACGACTATGCCATGGCATGGGTCCGCCAGGCTCC

AGGGAAGGGGCTGGAGTGGGTCTCAGCTATTAGTGATGCAGGTGACAGAACATACTACGCA

GACTCCGTGAGGGGCCGGTTCACCATCTCCAGAGACAATTCCAAGAACACACTGTATCTGC

AAATGAACAGCCTGAGAGCCGAGGACACGGCGGTGTACTACTGCGCAAGAGCCGAGATGGG

AGCCGTATTCGACATATGGGGTCAGGGTACAATGGTCACCGTCTCCTCA

Clone FS-26528 HC. CDRs 1, 2, and 3 are underlined.
                                                   (SEQ ID NO: 272)
EVQLLESGGGLVQPGGSLRLSCAASGFTFDDYAMAWVRQAPGKGLEWVSAISDAGDRTYY

ADSVRGRFTISRDNSKNTLYLQMNSLRAEDTAVYYCARAEMGAVFDIWGQGTMVTVSS (SEQ ID NO: 273)
SCAASGFTFDDYAMA [HC CDR1]

(SEQ ID NO: 274)
AISDAGDRTYYADSVRG [HC CDR2]

(SEQ ID NO: 275)
ARAEMGAVFDI [HC CDR3]

Clone FS-26528 LC DNA
                                                   (SEQ ID NO: 276)
GAAATTGTGTTGACACAGTCTCCAGCCACCCTGTCTTTGTCTCCAGGGGAAAGAGCCACCC

TCTCCTGCAGGGCCAGTCAGAGTGTTAGCAGGTACTTAGCCTGGTACCAACAGAAACCTGG
```

-continued

```
CCAGGCTCCCAGGCTCCTCATCTATGATGCATCCAACAGGGCCACTGGCATCCCAGCCAGG

TTCAGTGGCAGTGGGTCTGGGACAGACTTCACTCTCACCATCAGCAGCCTAGAGCCTGAAG

ATTTTGCAGTTTATTACTGTCAGCAGAGAATCTCCTGGCCTTTCACTTTTGGCGGAGGGAC

CAAGGTTGAGATCAAACGG
```

Clone FS-26528 LC. CDRs 1, 2, and 3 are underlined.

(SEQ ID NO: 277)
EIVLTQSPATLSLSPGERATLSC<u>RASQSVSRYLA</u>WYQQKPGQAPRLLIY<u>DASNRAT</u>GIPAR
FSGSGSGTDFTLTISSLEPEDFAVYYCQQ <u>RISWPFT</u>FGGGTKVEIKR (SEQ ID NO: 278)
RASQSVSRYLA [LC CDR1]

(SEQ ID NO: 279)
DASNRAT [LC CDR2]

(SEQ ID NO: 280)
QQRISWPFT [LC CDR3]

Clone FS-26528 CAR DNA HxL (SEQ ID NO: 281)
```
ATGGCACTCCCCGTAACTGCTCTGCTGCTGCCGTTGGCATTGCTCCTGCACGCCGCACGCC

CGGAGGTGCAGCTGTTGGAGTCTGGGGGAGGCTTGGTACAGCCTGGGGGGTCCCTGAGACT

CTCCTGTGCAGCCTCTGGATTCACCTTTGACGACTATGCCATGGCATGGGTCCGCCAGGCT

CCAGGGAAGGGGCTGGAGTGGGTCTCAGCTATTAGTGATGCAGGTGACAGAACATACTACG

CAGACTCCGTGAGGGGCCGGTTCACCATCTCCAGAGACAATTCCAAGAACACACTGTATCT

GCAAATGAACAGCCTGAGAGCCGAGGACACGGCGGTGTACTACTGCGCAAGAGCCGAGATG

GGAGCCGTATTCGACATATGGGGTCAGGGTACAATGGTCACCGTCTCCTCAGGGTCTACAT

CCGGCTCCGGGAAGCCCGGAAGTGGCGAAGGTAGTACAAAGGGGGAAATTGTGTTGACACA

GTCTCCAGCCACCCTGTCTTTGTCTCCAGGGGAAAGAGCCACCCTCTCCTGCAGGGCCAGT

CAGAGTGTTAGCAGGTACTTAGCCTGGTACCAACAGAAACCTGGCCAGGCTCCCAGGCTCC

TCATCTATGATGCATCCAACAGGGCCACTGGCATCCCAGCCAGGTTCAGTGGCAGTGGGTC

TGGGACAGACTTCACTCTCACCATCAGCAGCCTAGAGCCTGAAGATTTTGCAGTTTATTAC

TGTCAGCAGAGAATCTCCTGGCCTTTCACTTTTGGCGGAGGGACCAAGGTTGAGATCAAAC

GGGCCGCTGCCCTTGATAATGAAAAGTCAAACGGAACAATCATTCACGTGAAGGGCAAGCA

CCTCTGTCCGTCACCCTTGTTCCCTGGTCCATCCAAGCCATTCTGGGTGTTGGTCGTAGTG

GGTGGAGTCCTCGCTTGTTACTCTCTGCTCGTCACCGTGGCTTTTATAATCTTCTGGGTTA

GATCCAAAAGAAGCCGCCTGCTCCATAGCGATTACATGAATATGACTCCACGCCGCCCTGG

CCCCACAAGGAAACACTACCAGCCTTACGCACCACCTAGAGATTTCGCTGCCTATCGGAGC

AGGGTGAAGTTTTCCAGATCTGCAGATGCACCAGCGTATCAGCAGGGCCAGAACCAACTGT

ATAACGAGCTCAACCTGGGACGCAGGGAAGAGTATGACGTTTTGGACAAGCGCAGAGGACG

GGACCCTGAGATGGGTGGCAAACCAAGACGAAAAAACCCCCAGGAGGGTCTCTATAATGAG

CTGCAGAAGGATAAGATGGCTGAAGCCTATTCTGAAATAGGCATGAAAGGAGAGCGGAGAA

GGGGAAAAGGGCACGACGGTTTGTACCAGGGACTCAGCACTGCTACGAAGGATACTTATGA

CGCTCTCCACATGCAAGCCCTGCCACCTAGG
```

Clone FS-26528 CAR HxL (SEQ ID NO: 282)
MALPVTALLLPLALLLHAARPEVQLLESGGGLVQPGGSLRLSCAASGFTFDDYAMAWVRQA
PGKGLEWVSAISDAGDRTYYADSVRGRFTISRDNSKNTLYLQMNSLRAEDTAVYYCARAEM
GAVFDIWGQGTMVTVSSGSTSGSGKPGSGEGSTKGEIVLTQSPATLSLSPGERATLSCRAS -continued

QSVSRYLAWYQQKPGQAPRLLIYDASNRATGIPARFSGSGSGTDFTLTISSLEPEDFAVYY

CQQRISWPFTFGGGTKVEIKRAAALDNEKSNGTIIHVKGKHLCPSPLFPGPSKPFWVLVVV

GGVLACYSLLVTVAFIIFWVRSKRSRLLHSDYMNMTPRRPGPTRKHYQPYAPPRDFAAYRS

RVKFSRSADAPAYQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR

Clone FS-26528 CAR DNA LxH (SEQ ID NO: 283)

ATGGCACTCCCCGTAACTGCTCTGCTGCTGCCGTTGGCATTGCTCCTGCACGCCGCACGCC

CGGAAATTGTGTTGACACAGTCTCCAGCCACCCTGTCTTTGTCTCCAGGGGAAAGAGCCAC

CCTCTCCTGCAGGGCCAGTCAGAGTGTTAGCAGGTACTTAGCCTGGTACCAACAGAAACCT

GGCCAGGCTCCCAGGCTCCTCATCTATGATGCATCCAACAGGGCCACTGGCATCCCAGCCA

GGTTCAGTGGCAGTGGGTCTGGGACAGACTTCACTCTCACCATCAGCAGCCTAGAGCCTGA

AGATTTTGCAGTTTATTACTGTCAGCAGAGAATCTCCTGGCCTTTCACTTTTGGCGGAGGG

ACCAAGGTTGAGATCAAACGGGGGTCTACATCCGGCTCCGGGAAGCCCGGAAGTGGCGAAG

GTAGTACAAAGGGGGAGGTGCAGCTGTTGGAGTCTGGGGGAGGCTTGGTACAGCCTGGGGG

GTCCCTGAGACTCTCCTGTGCAGCCTCTGGATTCACCTTTGACGACTATGCCATGGCATGG

GTCCGCCAGGCTCCAGGGAAGGGGCTGGAGTGGGTCTCAGCTATTAGTGATGCAGGTGACA

GAACATACTACGCAGACTCCGTGAGGGGCCGGTTCACCATCTCCAGAGACAATTCCAAGAA

CACACTGTATCTGCAAATGAACAGCCTGAGAGCCGAGGACACGGCGGTGTACTACTGCGCA

AGAGCCGAGATGGGAGCCGTATTCGACATATGGGGTCAGGGTACAATGGTCACCGTCTCCT

CAGCCGCTGCCCTTGATAATGAAAAGTCAAACGGAACAATCATTCACGTGAAGGGCAAGCA

CCTCTGTCCGTCACCCTTGTTCCTGGTCCATCCAAGCCATTCTGGGTGTTGGTCGTAGTG

GGTGGAGTCCTCGCTTGTTACTCTCTGCTCGTCACCGTGGCTTTTATAATCTTCTGGGTTA

GATCCAAAAGAAGCCGCCTGCTCCATAGCGATTACATGAATATGACTCCACGCCGCCCTGG

CCCCACAAGGAAACACTACCAGCCTTACGCACCACCTAGAGATTTCGCTGCCTATCGGAGC

AGGGTGAAGTTTTCCAGATCTGCAGATGCACCAGCGTATCAGCAGGGCCAGAACCAACTGT

ATAACGAGCTCAACCTGGGACGCAGGGAAGAGTATGACGTTTTGGACAAGCGCAGAGGACG

GGACCCTGAGATGGGTGGCAAACCAAGACGAAAAAACCCCCAGGAGGGTCTCTATAATGAG

CTGCAGAAGGATAAGATGGCTGAAGCCTATTCTGAAATAGGCATGAAAGGAGAGCGGAGAA

GGGGAAAAGGGCACGACGGTTTGTACCAGGGACTCAGCACTGCTACGAAGGATACTTATGA

CGCTCTCCACATGCAAGCCCTGCCACCTAGG

Clone FS-26528 CAR LxH (SEQ ID NO: 284)

MALPVTALLLPLALLLHAARPEIVLTQSPATLSLSPGERATLSCRASQSVSRYLAWYQQKP

GQAPRLLIYDASNRATGIPARFSGSGSGTDFTLTISSLEPEDFAVYYCQQRISWPFTFGGG

TKVEIKRGSTSGSGKPGSGEGSTKGEVQLLESGGGLVQPGGSLRLSCAASGFTFDDYAMAW

VRQAPGKGLEWVSAISDAGDRTYYADSVRGRFTISRDNSKNTLYLQMNSLRAEDTAVYYCA

RAEMGAVFDIWGQGTMVTVSSAAALDNEKSNGTIIHVKGKHLCPSPLFPGPSKPFWVLVVV

GGVLACYSLLVTVAFIIFWVRSKRSRLLHSDYMNMTPRRPGPTRKHYQPYAPPRDFAAYRS

RVKFSRSADAPAYQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR

```
Clone PC-26534 HC DNA
                                              (SEQ ID NO: 285)
CAGGTGCAGCTGGTGGAGTCTGGGGGAGGCGTGGTCCAGCCTGGGAGGTCCCTGAGACTCT

CCTGTGCAGCGTCTGGATTCACCTTCAGTGAGCATGGCATGCACTGGGTCCGCCAGGCTCC

AGGCAAGGGGCTGGAGTGGGTGGCAGCTATATCTTATGATGGAAGGAATAAACACTATGCA

GACTCCGTGAAGGGCCGATTCACCATCTCCAGAGACAATTCCAAGAACACGCTGTATCTGC

AAATGAACAGCCTGAGAGCCGAGGACACGGCGGTGTACTACTGCGCCAGAGACGGTACTTA

TCTAGGTGGTCTCTGGTACTTCGACTTATGGGGGAGAGGTACCTTGGTCACCGTCTCCTCA

Clone PC-26534 HC. CDRs 1, 2, and 3 are underlined.
                                              (SEQ ID NO: 286)
QVQLVESGGGVVQPGRSLRLSCAASGFTFSEHGMHWVRQAPGKGLEWVAAISYDGRNKHY

ADSVKGRFTISRDNSKNTLYLQMNSLRAEDTAVYYCARDGTYLGGLWYFDLWGRGTLVTVSS (SEQ ID NO: 287)
FTFSEHGMH [HC CDR1]

(SEQ ID NO: 288)
AISYDGRNKHYADSVKG [HC CDR2]

(SEQ ID NO: 289)
ARDGTYLGGLWYFDL [HC CDR3]

Clone PC-26534 LC DNA
                                              (SEQ ID NO: 290)
GATATTGTGATGACTCAGTCTCCACTCTCCCTGCCCGTCACCCCTGGAGAGCCGGCCTCCA

TCTCCTGCAGGTCTAGTCAGAGCCTCCTGCATAGTAATGGATACAACTATTTGGATTGGTA

CCTGCAGAAGCCAGGGCAGTCTCCACAGCTCCTGATCTATTTGGGTTCTAATCGGGCCTCC

GGGGTCCCTGACAGGTTCAGTGGCAGTGGATCAGGCACAGATTTTACACTGAAAATCAGCA

GAGTGGAGGCTGAGGATGTTGGGGTTTATTACTGCATGCAGGGACTCGGCCTCCCTCTCAC

TTTTGGCGGAGGGACCAAGGTTGAGATCAAACGG

Clone PC-26534 LC. CDRs 1, 2, and 3 are underlined.
                                              (SEQ ID NO: 291)
DIVMTQSPLSLPVTPGEPASISCRSSQSLLHSNGYNYLDWYLQKPGQSPQLLIYLGSNRA

SGVPDRFSGSGSGTDFTLKISRVEAEDVGVYYCMQGLGLPLTFGGGTKVEIKR (SEQ ID NO: 292)
RSSQSLLHSNGYNYLD [LC CDR1]

(SEQ ID NO: 293)
LGSNRAS [LC CDR2]

(SEQ ID NO: 294)
MQGLGLPLT [LC CDR3]

Clone PC-26534 CAR DNA HxL
                                              (SEQ ID NO: 295)
ATGGCACTCCCCGTAACTGCTCTGCTGCTGCCGTTGGCATTGCTCCTGCACGCCGCACGCC

CGCAGGTGCAGCTGGTGGAGTCTGGGGGAGGCGTGGTCCAGCCTGGGAGGTCCCTGAGACT

CTCCTGTGCAGCGTCTGGATTCACCTTCAGTGAGCATGGCATGCACTGGGTCCGCCAGGCT

CCAGGCAAGGGGCTGGAGTGGGTGGCAGCTATATCTTATGATGGAAGGAATAAACACTATG

CAGACTCCGTGAAGGGCCGATTCACCATCTCCAGAGACAATTCCAAGAACACGCTGTATCT

GCAAATGAACAGCCTGAGAGCCGAGGACACGGCGGTGTACTACTGCGCCAGAGACGGTACT

TATCTAGGTGGTCTCTGGTACTTCGACTTATGGGGGAGAGGTACCTTGGTCACCGTCTCCT

CAGGGTCTACATCCGGCTCCGGGAAGCCCGGAAGTGGCGAAGGTAGTACAAAGGGGGATAT

TGTGATGACTCAGTCTCCACTCTCCCTGCCCGTCACCCCTGGAGAGCCGGCCTCCATCTCC

TGCAGGTCTAGTCAGAGCCTCCTGCATAGTAATGGATACAACTATTTGGATTGGTACCTGC
```

-continued

```
AGAAGCCAGGGCAGTCTCCACAGCTCCTGATCTATTTGGGTTCTAATCGGGCCTCCGGGGT

CCCTGACAGGTTCAGTGGCAGTGGATCAGGCACAGATTTTACACTGAAAATCAGCAGAGTG

GAGGCTGAGGATGTTGGGGTTTATTACTGCATGCAGGGACTCGGCCTCCCTCTCACTTTTG

GCGGAGGGACCAAGGTTGAGATCAAACGGGCCGCTGCCCTTGATAATGAAAAGTCAAACGG

AACAATCATTCACGTGAAGGGCAAGCACCTCTGTCCGTCACCCTTGTTCCCTGGTCCATCC

AAGCCATTCTGGGTGTTGGTCGTAGTGGGTGGAGTCCTCGCTTGTTACTCTCTGCTCGTCA

CCGTGGCTTTTATAATCTTCTGGGTTAGATCCAAAAGAAGCCGCCTGCTCCATAGCGATTA

CATGAATATGACTCCACGCCGCCCTGGCCCCACAAGGAAACACTACCAGCCTTACGCACCA

CCTAGAGATTTCGCTGCCTATCGGAGCAGGGTGAAGTTTTCCAGATCTGCAGATGCACCAG

CGTATCAGCAGGGCCAGAACCAACTGTATAACGAGCTCAACCTGGGACGCAGGGAAGAGTA

TGACGTTTTGGACAAGCGCAGAGGACGGGACCCTGAGATGGGTGGCAAACCAAGACGAAAA

AACCCCCAGGAGGGTCTCTATAATGAGCTGCAGAAGGATAAGATGGCTGAAGCCTATTCTG

AAATAGGCATGAAAGGAGAGCGGAGAAGGGGAAAAGGGCACGACGGTTTGTACCAGGGACT

CAGCACTGCTACGAAGGATACTTATGACGCTCTCCACATGCAAGCCCTGCCACCTAGG
```

Clone PC-26534 CAR HxL (SEQ ID NO: 296)
```
MALPVTALLLPLALLLHAARPQVQLVESGGGVVQPGRSLRLSCAASGFTFSEHGMHWVRQA

PGKGLEWVAAISYDGRNKHYADSVKGRFTISRDNSKNTLYLQMNSLRAEDTAVYYCARDGT

YLGGLWYFDLWGRGTLVTVSSGSTSGSGKPGSGEGSTKGDIVMTQSPLSLPVTPGEPASIS

CRSSQSLLHSNGYNYLDWYLQKPGQSPQLLIYLGSNRASGVPDRFSGSGSGTDFTLKISRV

EAEDVGVYYCMQGLGLPLTFGGGTKVEIKRAAALDNEKSNGTIIHVKGKHLCPSPLFPGPS

KPFWVLVVVGGVLACYSLLVTVAFIIFWVRSKRSRLLHSDYMNMTPRRPGPTRKHYQPYAP

PRDFAAYRSRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDALHMQALPPR
```

Clone PC-26534 CAR DNA LxH (SEQ ID NO: 297)
```
ATGGCACTCCCCGTAACTGCTCTGCTGCTGCCGTTGGCATTGCTCCTGCACGCCGCACGCC

CGGATATTGTGATGACTCAGTCTCCACTCTCCCTGCCCGTCACCCCTGGAGAGCCGGCCTC

CATCTCCTGCAGGTCTAGTCAGAGCCTCCTGCATAGTAATGGATACAACTATTTGGATTGG

TACCTGCAGAAGCCAGGGCAGTCTCCACAGCTCCTGATCTATTTGGGTTCTAATCGGGCCT

CCGGGGTCCCTGACAGGTTCAGTGGCAGTGGATCAGGCACAGATTTTACACTGAAAATCAG

CAGAGTGGAGGCTGAGGATGTTGGGGTTTATTACTGCATGCAGGGACTCGGCCTCCCTCTC

ACTTTTGGCGGAGGGACCAAGGTTGAGATCAAACGGGGGTCTACATCCGGCTCCGGGAAGC

CCGGAAGTGGCGAAGGTAGTACAAAGGGGCAGGTGCAGCTGGTGGAGTCTGGGGGAGGCGT

GGTCCAGCCTGGGAGGTCCCTGAGACTCTCCTGTGCAGCGTCTGGATTCACCTTCAGTGAG

CATGGCATGCACTGGGTCCGCCAGGCTCCAGGCAAGGGGCTGGAGTGGGTGGCAGCTATAT

CTTATGATGGAAGGAATAAACACTATGCAGACTCCGTGAAGGGCCGATTCACCATCTCCAG

AGACAATTCCAAGAACACGCTGTATCTGCAAATGAACAGCCTGAGAGCCGAGGACACGGCG

GTGTACTACTGCGCCAGAGACGGTACTTATCTAGGTGGTCTCTGGTACTTCGACTTATGGG

GGAGAGGTACCTTGGTCACCGTCTCCTCAGCCGCTGCCCTTGATAATGAAAAGTCAAACGG

AACAATCATTCACGTGAAGGGCAAGCACCTCTGTCCGTCACCCTTGTTCCCTGGTCCATCC

AAGCCATTCTGGGTGTTGGTCGTAGTGGGTGGAGTCCTCGCTTGTTACTCTCTGCTCGTCA

CCGTGGCTTTTATAATCTTCTGGGTTAGATCCAAAAGAAGCCGCCTGCTCCATAGCGATTA
```

-continued

```
CATGAATATGACTCCACGCCGCCCTGGCCCCACAAGGAAACACTACCAGCCTTACGCACCA

CCTAGAGATTTCGCTGCCTATCGGAGCAGGGTGAAGTTTTCCAGATCTGCAGATGCACCAG

CGTATCAGCAGGGCCAGAACCAACTGTATAACGAGCTCAACCTGGGACGCAGGGAAGAGTA

TGACGTTTTGGACAAGCGCAGAGGACGGGACCCTGAGATGGGTGGCAAACCAAGACGAAAA

AACCCCCAGGAGGGTCTCTATAATGAGCTGCAGAAGGATAAGATGGCTGAAGCCTATTCTG

AAATAGGCATGAAAGGAGAGCGGAGAAGGGGAAAAGGGCACGACGGTTTGTACCAGGGACT

CAGCACTGCTACGAAGGATACTTATGACGCTCTCCACATGCAAGCCCTGCCACCTAGG
```

Clone PC-26534 CAR LxH
(SEQ ID NO: 298)
```
MALPVTALLL PLALLLHAAR PDIVMTQSPL SLPVTPGEPA

SISCRSSQSL LHSNGYNYLD WYLQKPGQSP QLLIYLGSNR

ASGVPDRFSG SGSGTDFTLK ISRVEAEDVG VYYCMQGLGL

PLTFGGGTKV EIKRGSTSGS GKPGSGEGST KGQVQLVESG

GGVVQPGRSL RLSCAASGFT FSEHGMHWVR QAPGKGLEWV

AAISYDGRNK HYADSVKGRF TISRDNSKNT LYLQMNSLRA

EDTAVYYCAR DGTYLGGLWY FDLWGRGTLV TVSSAAALDN

EKSNGTIIHV KGKHLCPSPL FPGPSKPFWV LVVVGGVLAC

YSLLVTVAFI IFWVRSKRSR LLHSDYMNMT PRRPGPTRKH

YQPYAPPRDF AAYRSRVKFS RSADAPAYQQ GQNQLYNELN

LGRREEYDVL DKRRGRDPEM GGKPRRKNPQ EGLYNELQKD

KMAEAYSEIG MKGERRRGKG HDGLYQGLST ATKDTYDALH

MQALPPR
```

Clone AJ-26545 HC DNA
(SEQ ID NO: 299)
```
CAGGTGCAGCTGGTGCAGTCTGGGGCTGAGGTGAAGAAGCCTGGGGCCTCAGTGAAGGTTT

CCTGCAGGGCATCTGGATACACCTTCATGGAGCACTATATGCACTGGGTGCGACAGGCCCC

TGGACAAGGGCTTGAGTGGATGGGAGTAATCGGGCCTAGTGGTGGTAAGACAAGCTACGCA

CAGAAGTTCCAGGGCAGAGTCACCATGACCAGGGACACGTCCACGAGCACAGTCTACATGG

AGCTGAGCAGCCTGAGATCTGAGGACACGGCGGTGTACTACTGCGCCAGAGAGAATTGGCC

AATGGACGTATGGGGCCAGGGAACAACTGTCACCGTCTCCTCA
```

Clone AJ-26545 HC. CDRs 1, 2, and 3 are underlined.
(SEQ ID NO: 300)
QVQLVQSGAEVKKPGASVKVSCRASG<u>YTFMEHYMH</u>WVRQAPGQGLEWMG<u>VIGPSGGKTSY
AQKFQG</u>RVTMTRDTSTSTVYMELSSLRSEDTAVYYC<u>ARESWPMDV</u>WGQGTTVTVSS (SEQ ID NO: 301)
YTFMEHYMH (HC CDR1)

(SEQ ID NO: 302)
VIGPSGGKTSYAQKFQG (HC CDR2)

(SEQ ID NO: 303)
ARESWPMDV (HC CDR3)

Clone AJ-26545 LC DNA
(SEQ ID NO: 304)
```
GAAATAGTGATGACGCAGTCTCCAGCCACCCTGTCTGTGTCTCCAGGGGAAAGAGCCACCC

TCTCCTGCAGGGCCAGTCAGAGTGTTAGCAGCAACTTAGCCTGGTACCAGCAGAAACCTGG

CCAGGCTCCCAGGCTCCTCATCTATGGTGCATCCACCAGGGCCACTGGTATCCCAGCCAGG

TTCAGTGGCAGTGGGTCTGGGACAGAGTTCACTCTCACCATCAGCAGCCTGCAGTCTGAAG
```

-continued

ATTTTGCAGTTTATTACTGTCAGCAGTACGCCGCCTACCCTACTTTTGGCGGAGGGACCAA

GGTTGAGATCAAACGG

Clone AJ-26545 LC. CDRs 1, 2, and 3 are underlined.
(SEQ ID NO: 305)
EIVMTQSPATLSVSPGERATLSCRASQSVSSNLAWYQQKPGQAPRLLIYGASTRATGIPAR

FSGSGSGTEFTLTISSLQSEDFAVYYCQQYAAYPTFGGGTKVEIKR (SEQ ID NO: 306)
RASQSVSSNLA (LC CDR1)

(SEQ ID NO: 307)
GASTRAT (LC CDR2)

(SEQ ID NO: 308)
QQYAAYPT (LC CDR3)

Clone AJ-26545 CAR DNA HxL
(SEQ ID NO: 309)
ATGGCACTCCCCGTAACTGCTCTGCTGCTGCCGTTGGCATTGCTCCTGCACGCCGCACGCC

CGCAGGTGCAGCTGGTGCAGTCTGGGGCTGAGGTGAAGAAGCCTGGGGCCTCAGTGAAGGT

TTCCTGCAGGGCATCTGGATACACCTTCATGGAGCACTATATGCACTGGGTGCGACAGGCC

CCTGGACAAGGGCTTGAGTGGATGGGAGTAATCGGGCCTAGTGGTGGTAAGACAAGCTACG

CACAGAAGTTCCAGGGCAGAGTCACCATGACCAGGGACACGTCCACGAGCACAGTCTACAT

GGAGCTGAGCAGCCTGAGATCTGAGGACACGGCGGTGTACTACTGCGCCAGAGAGAATTGG

CCAATGGACGTATGGGGCCAGGGAACAACTGTCACCGTCTCCTCAGGGTCTACATCCGGCT

CCGGGAAGCCCGGAAGTGGCGAAGGTAGTACAAAGGGGGAAATAGTGATGACGCAGTCTCC

AGCCACCCTGTCTGTGTCTCCAGGGGAAAGAGCCACCCTCTCCTGCAGGGCCAGTCAGAGT

GTTAGCAGCAACTTAGCCTGGTACCAGCAGAAACCTGGCCAGGCTCCCAGGCTCCTCATCT

ATGGTGCATCCACCAGGGCCACTGGTATCCCAGCCAGGTTCAGTGGCAGTGGGTCTGGGAC

AGAGTTCACTCTCACCATCAGCAGCCTGCAGTCTGAAGATTTTGCAGTTTATTACTGTCAG

CAGTACGCCGCCTACCCTACTTTTGGCGGAGGGACCAAGGTTGAGATCAAACGGGCCGCTG

CCCTTGATAATGAAAAGTCAAACGGAACAATCATTCACGTGAAGGGCAAGCACCTCTGTCC

GTCACCCTTGTTCCCTGGTCCATCCAAGCCATTCTGGGTGTTGGTCGTAGTGGGTGGAGTC

CTCGCTTGTTACTCTCTGCTCGTCACCGTGGCTTTTATAATCTTCTGGGTTAGATCCAAAA

GAAGCCGCCTGCTCCATAGCGATTACATGAATATGACTCCACGCCGCCCTGGCCCCACAAG

GAAACACTACCAGCCTTACGCACCACCTAGAGATTTCGCTGCCTATCGGAGCAGGGTGAAG

TTTTCCAGATCTGCAGATGCACCAGCGTATCAGCAGGGCCAGAACCAACTGTATAACGAGC

TCAACCTGGGACGCAGGGAAGAGTATGACGTTTTGGACAAGCGCAGAGGACGGGACCCTGA

GATGGGTGGCAAACCAAGACGAAAAAACCCCCAGGAGGGTCTCTATAATGAGCTGCAGAAG

GATAAGATGGCTGAAGCCTATTCTGAAATAGGCATGAAAGGAGAGCGGAGAAGGGGAAAAG

GGCACGACGGTTTGTACCAGGGACTCAGCACTGCTACGAAGGATACTTATGACGCTCTCCA

CATGCAAGCCCTGCCACCTAGG

Clone AJ-26545 CAR HxL
(SEQ ID NO: 310)
MALPVTALLL PLALLLHAAR PQVQLVQSGA EVKKPGASVK

VSCRASGYTF MEHYMHWVRQ APGQGLEWMG VIGPSGGKTS

YAQKFQGRVT MTRDTSTSTV YMELSSLRSE DTAVYYCARE

SWPMDVWGQG TTVTVSSGST SGSGKPGSGE GSTKGEIVMT

QSPATLSVSP GERATLSCRA SQSVSSNLAW YQQKPGQAPR

LLIYGASTRA TGIPARFSGS GSGTEFTLTI SSLQSEDFAV

YYCQQYAAYP TFGGGTKVEI KRAAALDNEK SNGTIIHVKG

KHLCPSPLFP GPSKPFWVLV VVGGVLACYS LLVTVAFIIF

WVRSKRSRLL HSDYMNMTPR RPGPTRKHYQ PYAPPRDFAA

YRSRVKFSRS ADAPAYQQGQ NQLYNELNLG RREEYDVLDK

RRGRDPEMGG KPRRKNPQEG LYNELQKDKM AEAYSEIGMK

GERRRGKGHD GLYQGLSTAT KDTYDALHMQ ALPPR

Clone AJ-26545 CAR DNA LxH
(SEQ ID NO: 311)
ATGGCACTCCCCGTAACTGCTCTGCTGCTGCCGTTGGCATTGCTCCTGCACGCCGCACGCC

CGGAAATAGTGATGACGCAGTCTCCAGCCACCCTGTCTGTGTCTCCAGGGGAAAGAGCCAC

CCTCTCCTGCAGGGCCAGTCAGAGTGTTAGCAGCAACTTAGCCTGGTACCAGCAGAAACCT

GGCCAGGCTCCCAGGCTCCTCATCTATGGTGCATCCACCAGGGCCACTGGTATCCCAGCCA

GGTTCAGTGGCAGTGGGTCTGGGACAGAGTTCACTCTCACCATCAGCAGCCTGCAGTCTGA

AGATTTTGCAGTTTATTACTGTCAGCAGTACGCCGCCTACCCTACTTTTGGCGGAGGGACC

AAGGTTGAGATCAAACGGGGGTCTACATCCGGCTCCGGGAAGCCCGGAAGTGGCGAAGGTA

GTACAAAGGGGCAGGTGCAGCTGGTGCAGTCTGGGGCTGAGGTGAAGAAGCCTGGGGCCTC

AGTGAAGGTTTCCTGCAGGGCATCTGGATACACCTTCATGGAGCACTATATGCACTGGGTG

CGACAGGCCCCTGGACAAGGGCTTGAGTGGATGGGAGTAATCGGGCCTAGTGGTGGTAAGA

CAAGCTACGCACAGAAGTTCCAGGGCAGAGTCACCATGACCAGGGACACGTCCACGAGCAC

AGTCTACATGGAGCTGAGCAGCCTGAGATCTGAGGACACGGCGGTGTACTACTGCGCCAGA

GAGAATTGGCCAATGGACGTATGGGCCAGGGAACAACTGTCACCGTCTCCTCAGCCGCTG

CCCTTGATAATGAAAAGTCAAACGGAACAATCATTCACGTGAAGGGCAAGCACCTCTGTCC

GTCACCCTTGTTCCCTGGTCCATCCAAGCCATTCTGGGTGTTGGTCGTAGTGGGTGGAGTC

CTCGCTTGTTACTCTCTGCTCGTCACCGTGGCTTTTATAATCTTCTGGGTTAGATCCAAAA

GAAGCCGCCTGCTCCATAGCGATTACATGAATATGACTCCACGCCGCCCTGGCCCCACAAG

GAAACACTACCAGCCTTACGCACCACCTAGAGATTTCGCTGCCTATCGGAGCAGGGTGAAG

TTTTCCAGATCTGCAGATGCACCAGCGTATCAGCAGGGCCAGAACCAACTGTATAACGAGC

TCAACCTGGGACGCAGGGAAGAGTATGACGTTTTGGACAAGCGCAGAGGACGGGACCCTGA

GATGGGTGGCAAACCAAGACGAAAAAACCCCCAGGAGGGTCTCTATAATGAGCTGCAGAAG

GATAAGATGGCTGAAGCCTATTCTGAAATAGGCATGAAAGGAGAGCGGAGAAGGGGAAAAG

GGCACGACGGTTTGTACCAGGGACTCAGCACTGCTACGAAGGATACTTATGACGCTCTCCA

CATGCAAGCCCTGCCACCTAGG

Clone AJ-26545 CAR LxH
(SEQ ID NO: 312)
MALPVTALLL PLALLLHAAR PEIVMTQSPA TLSVSPGERA

TLSCRASQSV SSNLAWYQQK PGQAPRLLIY GASTRATGIP

ARFSGSGSGT EFTLTISSLQ SEDFAVYYCQ QYAAYPTFGG

GTKVEIKRGS TSGSGKPGSG EGSTKGQVQL VQSGAEVKKP

GASVKVSCRA SGYTFMEHYM HWVRQAPGQG LEWMGVIGPS

GGKTSYAQKF QGRVTMTRDT STSTVYMELS SLRSEDTAVY

YCARESWPMD VWGQGTTVTV SSAAALDNEK SNGTIIHVKG

```
KHLCPSPLFP GPSKPFWVLV VVGGVLACYS LLVTVAFIIF

WVRSKRSRLL HSDYMNMTPR RPGPTRKHYQ PYAPPRDFAA

YRSRVKFSRS ADAPAYQQGQ NQLYNELNLG RREEYDVLDK

RRGRDPEMGG KPRRKNPQEG LYNELQKDKM AEAYSEIGMK

GERRRGKGHD GLYQGLSTAT KDTYDALHMQ ALPPR

Clone AJ-26554 HC DNA
                                              (SEQ ID NO: 313)
CAGGTGCAGCTGGTGCAGTCTGGGGCTGAGGTGAAGAAGCCTGGGGCCTCAGTGAAGGTTT

CCTGCAAGGCATCTGGATACACCTTCACGGAGCACTATATGCACTGGGTGCGACAGGCCCC

TGGACAAAGGCTTGAGTGGATGGGAGTAATCGGGCCTAGTGGTGGTAAGACAAGCTACGCA

CAGAAGTTCCAGGGCAGAGTCACCATGACCAGGGACACGTCCACGAGCACAGTCTACATGG

AGCTGAGCAGCCTGAGATCTGAGGACACGGCGGTGTACTACTGCGCCAGAGAGAGTTGGCC

AATGGACGTATGGGGCCAGGGAACAACTGTCACCGTCTCCTCA

Clone AJ-26554 HC. CDRs 1, 2, and 3 are underlined.
                                              (SEQ ID NO: 314)
QVQLVQSGAE VKKPGASVKV SCKASGYTFT EHYMHWVRQA

PGQRLEWMGV IGPSGGKTSY AQKFQGRVTM TRDTSTSTVY

MELSSLRSED TAVYYCARES WPMDVWGQGT TVTVSS (SEQ ID NO: 315)
YTFTEHYMH (HC CDR1)

(SEQ ID NO: 316)
VIGPSGGKTSYAQKFQG (HC CDR2)

(SEQ ID NO: 317)
ARESWPMDV (HC CDR3)

Clone AJ-26554 LC DNA
                                              (SEQ ID NO: 318)
GAAATAGTGATGACGCAGTCTCCAGCCACCCTGTCTGTGTCTCCAGGGGAAAGAGCCACCC

TCTCCTGCAGGGCCAGTCAGAGTGTTAGCAGCAACTTAGCCTGGTACCAGCAGAAACCTGG

CCAGGCTCCCAGGCTCCTCATCTATGGTGCATCCACCAGGGCCACTGGTATCCCAGCCAGG

TTCAGTGGCAGTGGGTCTGGGACAGAGTTCACTCTCACCATCAGCAGCCTGCAGTCTGAAG

ATTTTGCAGTTTATTACTGTCAGCAGTACGCCGCCTACCCTACTTTTGGCGGAGGGACCAA

GGTTGAGATCAAACGG

Clone AJ-26554 LC. CDRs 1, 2, and 3 are underlined.
                                              (SEQ ID NO: 319)
EIVMTQSPATLSVSPGERATLSCRASQSVSSNLAWYQQKPGQAPRLLIYGASTRATGIPA

RFSGSGSGTEFTLTISSLQSEDFAVYYCQQYAAYPTFGGGTKVEIKR (SEQ ID NO: 320)
RASQSVSSNLA (LC CDR1)

(SEQ ID NO: 321)
GASTRAT (LC CDR2)

(SEQ ID NO: 322)
QQYAAYPT (LC CDR3)

Clone AJ-26554 CAR DNA HxL
                                              (SEQ ID NO: 323)
ATGGCACTCCCCGTAACTGCTCTGCTGCTGCCGTTGGCATTGCTCCTGCACGCCGCACGCC

CGCAGGTGCAGCTGGTGCAGTCTGGGGCTGAGGTGAAGAAGCCTGGGGCCTCAGTGAAGGT

TCCTGCAAGGCATCTGGATACACCTTCACGGAGCACTATATGCACTGGGTGCGACAGGCC

CCTGGACAAAGGCTTGAGTGGATGGGAGTAATCGGGCCTAGTGGTGGTAAGACAAGCTACG

CACAGAAGTTCCAGGGCAGAGTCACCATGACCAGGGACACGTCCACGAGCACAGTCTACAT
```

-continued

```
GGAGCTGAGCAGCCTGAGATCTGAGGACACGGCGGTGTACTACTGCGCCAGAGAGAGTTGG
CCAATGGACGTATGGGGCCAGGGAACAACTGTCACCGTCTCCTCAGGGTCTACATCCGGCT
CCGGGAAGCCCGGAAGTGGCGAAGGTAGTACAAAGGGGGAAATAGTGATGACGCAGTCTCC
AGCCACCCTGTCTGTGTCTCCAGGGGAAAGAGCCACCCTCTCCTGCAGGGCCAGTCAGAGT
GTTAGCAGCAACTTAGCCTGGTACCAGCAGAAACCTGGCCAGGCTCCCAGGCTCCTCATCT
ATGGTGCATCCACCAGGGCCACTGGTATCCCAGCCAGGTTCAGTGGCAGTGGGTCTGGGAC
AGAGTTCACTCTCACCATCAGCAGCCTGCAGTCTGAAGATTTTGCAGTTTATTACTGTCAG
CAGTACGCCGCCTACCCTACTTTTGGCGGAGGGACCAAGGTTGAGATCAAACGGGCCGCTG
CCCTTGATAATGAAAAGTCAAACGGAACAATCATTCACGTGAAGGGCAAGCACCTCTGTCC
GTCACCCTTGTTCCCTGGTCCATCCAAGCCATTCTGGGTGTTGGTCGTAGTGGGTGGAGTC
CTCGCTTGTTACTCTCTGCTCGTCACCGTGGCTTTTATAATCTTCTGGGTTAGATCCAAAA
GAAGCCGCCTGCTCCATAGCGATTACATGAATATGACTCCACGCCGCCCTGGCCCCACAAG
GAAACACTACCAGCCTTACGCACCACCTAGAGATTTCGCTGCCTATCGGAGCAGGGTGAAG
TTTTCCAGATCTGCAGATGCACCAGCGTATCAGCAGGGCCAGAACCAACTGTATAACGAGC
TCAACCTGGGACGCAGGGAAGAGTATGACGTTTTGGACAAGCGCAGAGGACGGGACCCTGA
GATGGGTGGCAAACCAAGACGAAAAAACCCCCAGGAGGGTCTCTATAATGAGCTGCAGAAG
GATAAGATGGCTGAAGCCTATTCTGAAATAGGCATGAAAGGAGAGCGGAGAAGGGGAAAAG
GGCACGACGGTTTGTACCAGGGACTCAGCACTGCTACGAAGGATACTTATGACGCTCTCCA
CATGCAAGCCCTGCCACCTAGG
```

Clone AJ-26554 CAR HxL
(SEQ ID NO: 324)

```
MALPVTALLL PLALLLHAAR PQVQLVQSGA EVKKPGASVK
VSCKASGYTF TEHYMHWVRQ APGQRLEWMG VIGPSGGKTS
YAQKFQGRVT MTRDTSTSTV YMELSSLRSE DTAVYYCARE
SWPMDVWGQG TTVTVSSGST SGSGKPGSGE GSTKGEIVMT
QSPATLSVSP GERATLSCRA SQSVSSNLAW YQQKPGQAPR
LLIYGASTRA TGIPARFSGS GSGTEFTLTI SSLQSEDFAV
YYCQQYAAYP TFGGGTKVEI KRAAALDNEK SNGTIIHVKG
KHLCPSPLFP GPSKPFWVLV VVGGVLACYS LLVTVAFIIF
WVRSKRSRLL HSDYMNMTPR RPGPTRKHYQ PYAPPRDFAA
YRSRVKFSRS ADAPAYQQGQ NQLYNELNLG RREEYDVLDK
RRGRDPEMGG KPRRKNPQEG LYNELQKDKM AEAYSEIGMK
GERRRGKGHD GLYQGLSTAT KDTYDALHMQ ALPPR
```

Clone AJ-26554 CAR DNA LxH
(SEQ ID NO: 325)

```
ATGGCACTCCCCGTAACTGCTCTGCTGCTGCCGTTGGCATTGCTCCTGCACGCCGCACGCC
CGGAAATAGTGATGACGCAGTCTCCAGCCACCCTGTCTGTGTCTCCAGGGGAAAGAGCCAC
CCTCTCCTGCAGGGCCAGTCAGAGTGTTAGCAGCAACTTAGCCTGGTACCAGCAGAAACCT
GGCCAGGCTCCCAGGCTCCTCATCTATGGTGCATCCACCAGGGCCACTGGTATCCCAGCCA
GGTTCAGTGGCAGTGGGTCTGGGACAGAGTTCACTCTCACCATCAGCAGCCTGCAGTCTGA
AGATTTTGCAGTTTATTACTGTCAGCAGTACGCCGCCTACCCTACTTTTGGCGGAGGGACC
AAGGTTGAGATCAAACGGGGGTCTACATCCGGCTCCGGGAAGCCCGGAAGTGGCGAAGGTA
```

-continued

```
GTACAAAGGGCAGGTGCAGCTGGTGCAGTCTGGGGCTGAGGTGAAGAAGCCTGGGGCCTC

AGTGAAGGTTTCCTGCAAGGCATCTGGATACACCTTCACGGAGCACTATATGCACTGGGTG

CGACAGGCCCCTGGACAAAGGCTTGAGTGGATGGGAGTAATCGGGCCTAGTGGTGGTAAGA

CAAGCTACGCACAGAAGTTCCAGGGCAGAGTCACCATGACCAGGGACACGTCCACGAGCAC

AGTCTACATGGAGCTGAGCAGCCTGAGATCTGAGGACACGGCGGTGTACTACTGCGCCAGA

GAGAGTTGGCCAATGGACGTATGGGGCCAGGGAACAACTGTCACCGTCTCCTCAGCCGCTG

CCCTTGATAATGAAAAGTCAAACGGAACAATCATTCACGTGAAGGGCAAGCACCTCTGTCC

GTCACCCTTGTTCCCTGGTCCATCCAAGCCATTCTGGGTGTTGGTCGTAGTGGGTGGAGTC

CTCGCTTGTTACTCTCTGCTCGTCACCGTGGCTTTTATAATCTTCTGGGTTAGATCCAAAA

GAAGCCGCCTGCTCCATAGCGATTACATGAATATGACTCCACGCCGCCCTGGCCCCACAAG

GAAACACTACCAGCCTTACGCACCACCTAGAGATTTCGCTGCCTATCGGAGCAGGGTGAAG

TTTTCCAGATCTGCAGATGCACCAGCGTATCAGCAGGGCCAGAACCAACTGTATAACGAGC

TCAACCTGGGACGCAGGGAAGAGTATGACGTTTTGGACAAGCGCAGAGGACGGGACCCTGA

GATGGGTGGCAAACCAAGACGAAAAAACCCCCAGGAGGGTCTCTATAATGAGCTGCAGAAG

GATAAGATGGCTGAAGCCTATTCTGAAATAGGCATGAAAGGAGAGCGGAGAAGGGGAAAAG

GGCACGACGGTTTGTACCAGGGACTCAGCACTGCTACGAAGGATACTTATGACGCTCTCCA

CATGCAAGCCCTGCCACCTAGG
```

Clone AJ-26554 CAR LxH (SEQ ID NO: 326)

```
MALPVTALLL PLALLLHAAR PEIVMTQSPA TLSVSPGERA

TLSCRASQSV SSNLAWYQQK PGQAPRLLIY GASTRATGIP

ARFSGSGSGT EFTLTISSLQ SEDFAVYYCQ QYAAYPTFGG

GTKVEIKRGS TSGSGKPGSG EGSTKGQVQL VQSGAEVKKP

GASVKVSCKA SGYTFTEHYM HWVRQAPGQR LEWMGVIGPS

GGKTSYAQKF QGRVTMTRDT STSTVYMELS SLRSEDTAVY

YCARESWPMD VWGQGTTVTV SSAAALDNEK SNGTIIHVKG

KHLCPSPLFP GPSKPFWVLV VVGGVLACYS LLVTVAFIIF

WVRSKRSRLL HSDYMNMTPR RPGPTRKHYQ PYAPPRDFAA

YRSRVKFSRS ADAPAYQQGQ NQLYNELNLG RREEYDVLDK

RRGRDPEMGG KPRRKNPQEG LYNELQKDKM AEAYSEIGMK

GERRRGKGHD GLYQGLSTAT KDTYDALHMQ ALPPR
```

Clone NM-26562 HC DNA (SEQ ID NO: 327)

```
CAGGTGCAGCTGCAGGAGTCGGGCCCAGGACTGGTGAAGCCTTCACAGACCCTGTCCCTCA

CCTGTACTGTCTCTGGTGGCTCCATCGGGAGTGGTGGTAGTTACTGGAGCTGGATCCGCCA

GCACCCAGGGAAGGGCCTGGAGTGGATTGGGTTGATCTATTACGATGGAGCACCTACTAC

AACCCGTCCCTCAAGAGTCGAGTTACCATATCAGTAGACACGTCTAAGAACCAGTTCTCCC
```

-continued

TGAAGCTGAGTTCTGTGACCGCCGCAGACACGGCGGTGTACTACTGCGCCAGAGGCAGGGG

ATATGAGACTTCTTTAGCCTTCGATATCTGGGGTCAGGGTACAATGGTCACCGTCTCCTCA

Clone NM-26562 HC. CDRs 1, 2, and 3 are underlined.
(SEQ ID NO: 328)
QVQLQESGPGLVKPSQTLSLTCTVSG<u>GSIGSGGSYWS</u>WIRQHPGKGLEWIG<u>LIYYDGSTY YNPSLKS</u>RVTISVDTSKNQFSLKLSSVTAADTAVYYC<u>ARGRGYETSLAFDI</u>WGQGTMVTVS

S (SEQ ID NO: 329)
GSIGSGGSYWS (HC CDR1)

(SEQ ID NO: 330)
LIYYDGSTYYNPSLKS (HC CDR2)

(SEQ ID NO: 331)
ARGRGYETSLAFDI (HC CDR3)

Clone NM-26562 LC DNA
(SEQ ID NO: 332)
GAAATTGTGTTGACACAGTCTCCAGCCACCCTGTCTTTGTCTCCAGGGGAAAGAGCCACCC

TCTCCTGCAGGGCCAGTCAGAGTGTTAGCAGCTACTTAGCCTGGTACCAACAGAAACCTGG

CCAGGCTCCCAGGCTCCTCATCTATGATGCATCCAACAGGGCCACTGGCATCCCAGCCAGG

TTCAGTGGCAGTGGGTCTGGGACAGACTTCACTCTCACCATCAGCAGCCTAGAGCCTGAAG

ATTTTGCAGTTTATTACTGTCAGCAGAGACACGTCTGGCCTCCTACTTTTGGCGGAGGGAC

CAAGGTTGAGATCAAACGG

Clone NM-26562 LC. CDRs 1, 2, and 3 are underlined.
(SEQ ID NO: 333)
EIVLTQSPATLSLSPGERATLSC<u>RASQSVSSYLA</u>WYQQKPGQAPRLLIY<u>DASNRAT</u>GIPA RFSGSGSGTDFTLTISSLEPEDFAVYYC<u>QQRHVWPPT</u>FGGGTKVEIKR (SEQ ID NO: 334)
RASQSVSSYLA (LC CDR1)

(SEQ ID NO: 335)
DASNRAT (LC CDR2)

(SEQ ID NO: 336)
QQRHVWPPT (LC CDR3)

Clone NM-26562 CAR DNA HxL
(SEQ ID NO: 337)
ATGGCACTCCCCGTAACTGCTCTGCTGCTGCCGTTGGCATTGCTCCTGCACGCCGCACGCC

CGCAGGTGCAGCTGCAGGAGTCGGGCCCAGGACTGGTGAAGCCTTCACAGACCCTGTCCCT

CACCTGTACTGTCTCTGGTGGCTCCATCGGGAGTGGTGGTAGTTACTGGAGCTGGATCCGC

CAGCACCCAGGGAAGGGCCTGGAGTGGATTGGGTTGATCTATTACGATGGGAGCACCTACT

ACAACCCGTCCCTCAAGAGTCGAGTTACCATATCAGTAGACACGTCTAAGAACCAGTTCTC

CCTGAAGCTGAGTTCTGTGACCGCCGCAGACACGGCGGTGTACTACTGCGCCAGAGGCAGG

GGATATGAGACTTCTTTAGCCTTCGATATCTGGGGTCAGGGTACAATGGTCACCGTCTCCT

CAGGGTCTACATCCGGCTCCGGGAAGCCCGGAAGTGGCGAAGGTAGTACAAAGGGGGAAAT

TGTGTTGACACAGTCTCCAGCCACCCTGTCTTTGTCTCCAGGGGAAAGAGCCACCCTCTCC

TGCAGGGCCAGTCAGAGTGTTAGCAGCTACTTAGCCTGGTACCAACAGAAACCTGGCCAGG

CTCCCAGGCTCCTCATCTATGATGCATCCAACAGGGCCACTGGCATCCCAGCCAGGTTCAG

TGGCAGTGGGTCTGGGACAGACTTCACTCTCACCATCAGCAGCCTAGAGCCTGAAGATTTT

GCAGTTTATTACTGTCAGCAGAGACACGTCTGGCCTCCTACTTTTGGCGGAGGGACCAAGG

TTGAGATCAAACGGGCCGCTGCCCTTGATAATGAAAAGTCAAACGGAACAATCATTCACGT

-continued

```
GAAGGGCAAGCACCTCTGTCCGTCACCCTTGTTCCCTGGTCCATCCAAGCCATTCTGGGTG

TTGGTCGTAGTGGGTGGAGTCCTCGCTTGTTACTCTCTGCTCGTCACCGTGGCTTTTATAA

TCTTCTGGGTTAGATCCAAAAGAAGCCGCCTGCTCCATAGCGATTACATGAATATGACTCC

ACGCCGCCCTGGCCCCACAAGGAAACACTACCAGCCTTACGCACCACCTAGAGATTTCGCT

GCCTATCGGAGCAGGGTGAAGTTTTCCAGATCTGCAGATGCACCAGCGTATCAGCAGGGCC

AGAACCAACTGTATAACGAGCTCAACCTGGGACGCAGGGAAGAGTATGACGTTTTGGACAA

GCGCAGAGGACGGGACCCTGAGATGGGTGGCAAACCAAGACGAAAAAACCCCCAGGAGGGT

CTCTATAATGAGCTGCAGAAGGATAAGATGGCTGAAGCCTATTCTGAAATAGGCATGAAAG

GAGAGCGGAGAAGGGGAAAAGGGCACGACGGTTTGTACCAGGGACTCAGCACTGCTACGAA

GGATACTTATGACGCTCTCCACATGCAAGCCCTGCCACCTAGG
```

Clone NM-26562 CAR HxL
(SEQ ID NO: 338)

```
MALPVTALLL PLALLLHAAR PQVQLQESGP GLVKPSQTLS

LTCTVSGGSI GSGGSYWSWI RQHPGKGLEW IGLIYYDGST

YYNPSLKSRV TISVDTSKNQ FSLKLSSVTA ADTAVYYCAR

GRGYETSLAF DIWGQGTMVT VSSGSTSGSG KPGSGEGSTK

GEIVLTQSPA TLSLSPGERA TLSCRASQSV SSYLAWYQQK

PGQAPRLLIY DASNRATGIP ARFSGSGSGT DFTLTISSLE

PEDFAVYYCQ QRHVWPPTFG GGTKVEIKRA AALDNEKSNG

TIIHVKGKHL CPSPLFPGPS KPFWVLVVVG GVLACYSLLV

TVAFIIFWVR SKRSRLLHSD YMNMTPRRPG PTRKHYQPYA

PPRDFAAYRS RVKFSRSADA PAYQQGQNQL YNELNLGRRE

EYDVLDKRRG RDPEMGGKPR RKNPQEGLYN ELQKDKMAEA

YSEIGMKGER RRGKGHDGLY QGLSTATKDT YDALHMQALP

PR
```

Clone NM-26562 CAR DNA LxH
(SEQ ID NO: 339)

```
ATGGCACTCCCCGTAACTGCTCTGCTGCTGCCGTTGGCATTGCTCCTGCACGCCGCACGCC

CGGAAATTGTGTTGACACAGTCTCCAGCCACCCTGTCTTTGTCTCCAGGGGAAAGAGCCAC

CCTCTCCTGCAGGGCCAGTCAGAGTGTTAGCAGCTACTTAGCCTGGTACCAACAGAAACCT

GGCCAGGCTCCCAGGCTCCTCATCTATGATGCATCCAACAGGGCCACTGGCATCCCAGCCA

GGTTCAGTGGCAGTGGGTCTGGGACAGACTTCACTCTCACCATCAGCAGCCTAGAGCCTGA

AGATTTTGCAGTTTATTACTGTCAGCAGAGACACGTCTGGCCTCCTACTTTTGGCGGAGGG

ACCAAGGTTGAGATCAAACGGGGGTCTACATCCGGCTCCGGGAAGCCCGGAAGTGGCGAAG

GTAGTACAAAGGGGCAGGTGCAGCTGCAGGAGTCGGGCCCAGGACTGGTGAAGCCTTCACA

GACCCTGTCCCTCACCTGTACTGTCTCTGGTGGCTCCATCGGGAGTGGTGGTAGTTACTGG

AGCTGGATCCGCCAGCACCCAGGGAAGGGCCTGGAGTGGATTGGGTTGATCTATTACGATG

GGAGCACCTACTACAACCCGTCCCTCAAGAGTCGAGTTACCATATCAGTAGACACGTCTAA

GAACCAGTTCTCCCTGAAGCTGAGTTCTGTGACCGCCGCAGACACGGCGGTGTACTACTGC

GCCAGAGGCAGGGGATATGAGACTTCTTTAGCCTTCGATATCTGGGGTCAGGGTACAATGG

TCACCGTCTCCTCAGCCGCTGCCCTTGATAATGAAAAGTCAAACGGAACAATCATTCACGT

GAAGGGCAAGCACCTCTGTCCGTCACCCTTGTTCCCTGGTCCATCCAAGCCATTCTGGGTG

TTGGTCGTAGTGGGTGGAGTCCTCGCTTGTTACTCTCTGCTCGTCACCGTGGCTTTTATAA
```

TCTTCTGGGTTAGATCCAAAAGAAGCCGCCTGCTCCATAGCGATTACATGAATATGACTCC

ACGCCGCCCTGGCCCCACAAGGAAACACTACCAGCCTTACGCACCACCTAGAGATTTCGCT

GCCTATCGGAGCAGGGTGAAGTTTTCCAGATCTGCAGATGCACCAGCGTATCAGCAGGGCC

AGAACCAACTGTATAACGAGCTCAACCTGGGACGCAGGGAAGAGTATGACGTTTTGGACAA

GCGCAGAGGACGGGACCCTGAGATGGGTGGCAAACCAAGACGAAAAAACCCCCAGGAGGGT

CTCTATAATGAGCTGCAGAAGGATAAGATGGCTGAAGCCTATTCTGAAATAGGCATGAAAG

GAGAGCGGAGAAGGGGAAAAGGGCACGACGGTTTGTACCAGGGACTCAGCACTGCTACGAA

GGATACTTATGACGCTCTCCACATGCAAGCCCTGCCACCTAGG

Clone NM-26562 CAR LxH
(SEQ ID NO: 340)
MALPVTALLL PLALLLHAAR PEIVLTQSPA TLSLSPGERA

TLSCRASQSV SSYLAWYQQK PGQAPRLLIY DASNRATGIP

ARFSGSGSGT DFTLTISSLE PEDFAVYYCQ QRHVWPPTFG

GGTKVEIKRG STSGSGKPGS GEGSTKGQVQ LQESGPGLVK

PSQTLSLTCT VSGGSIGSGG SYWSWIRQHP GKGLEWIGLI

YYDGSTYYNP SLKSRVTISV DTSKNQFSLK LSSVTAADTA

VYYCARGRGY ETSLAFDIWG QGTMVTVSSA AALDNEKSNG

TIIHVKGKHL CPSPLFPGPS KPFWVLVVVG GVLACYSLLV

TVAFIIFWVR SKRSRLLHSD YMNMTPRRPG PTRKHYQPYA

PPRDFAAYRS RVKFSRSADA PAYQQGQNQL YNELNLGRRE

EYDVLDKRRG RDPEMGGKPR RKNPQEGLYN ELQKDKMAEA

YSEIGMKGER RRGKGHDGLY QGLSTATKDT YDALHMQALP

PR

Clone TS-26564 HC DNA
(SEQ ID NO: 341)
GAGGTGCAGCTGGTGGAGTCTGGGGGAGGCTTGGTACAGCCTGGGGGGTCCCTGAGACTCT

CCTGTGCAGCCTCTGGATTCACCTTCAGTAGCTATAGCATGAACTGGGTCCGCCAGGCTCC

AGGGAAGGGGCTGGAGTGGGTTTCAACCATTAGTAGTAGTAGTAGTATCATATACTACGCA

GACTCTGTGAAGGGCCGATTCACCATCTCCAGAGACAATGCCAAGAACTCACTGTATCTGC

AAATGAACAGCCTGAGAGCTGAGGACACGGCGGTGTACTACTGCGCCAGAGGTTCTCAGGA

GCACCTGATTTTCGATTATTGGGGACAGGGTACATTGGTCACCGTCTCCTCA

Clone TS-26564 HC. CDRs 1, 2, and 3 are underlined.
(SEQ ID NO: 342)
EVQLVESGGGLVQPGGSLRLSCAASG<u>FTFSSYSMN</u>WVRQAPGKGLEWVS<u>TISSSSSIIYY ADSVKG</u>RFTISRDNAKNSLYLQMNSLRAEDTAVYYC<u>ARGSQEHLIFDY</u>WGQGTLVTVSS (SEQ ID NO: 343)
FTFSSYSMN (HC CDR1)

(SEQ ID NO: 344)
TISSSSSIIYYADSVKG (HC CDR2)

(SEQ ID NO: 345)
ARGSQEHLIFDY (HC CDR3)

Clone TS-26564 LC DNA
(SEQ ID NO: 346)
GAAATTGTGTTGACACAGTCTCCAGCCACCCTGTCTTTGTCTCCAGGGGAAAGAGCCACCC

TCTCCTGCAGGGCCAGTCAGAGTGTTAGCAGGTACTTAGCCTGGTACCAACAGAAACCTGG

CCAGGCTCCCAGGCTCCTCATCTATGATGCATCCAACAGGGCCACTGGCATCCCAGCCAGG

```
TTCAGTGGCAGTGGGTCTGGGACAGACTTCACTCTCACCATCAGCAGCCTAGAGCCTGAAG

ATTTTGCAGTTTATTACTGTCAGCAGAGATTCTACTACCCTTGGACTTTTGGCGGAGGGAC

CAAGGTTGAGATCAAACGG
```

Clone TS-26564 LC. CDRs 1, 2, and 3 are underlined.
(SEQ ID NO: 347)
EIVLTQSPATLSLSPGERATLSC<u>RASQSVSRYLA</u>WYQQKPGQAPRLLIY<u>DASNRAT</u>GIPA
RFSGSGSGTDFTLTISSLEPEDFAVYYC<u>QQRFYYPWT</u>FGGGTKVEIKR (SEQ ID NO: 348)
RASQSVSRYLA (LC CDR1)

(SEQ ID NO: 349)
DASNRAT (LC CDR2)

(SEQ ID NO: 350)
QQRFYYPWT (LC CDR3)

Clone TS-26564 CAR DNA HxL
(SEQ ID NO: 351)
```
ATGGCACTCCCCGTAACTGCTCTGCTGCTGCCGTTGGCATTGCTCCTGCACGCCGCACGCC

CGGAGGTGCAGCTGGTGGAGTCTGGGGGAGGCTTGGTACAGCCTGGGGGGTCCCTGAGACT

CTCCTGTGCAGCCTCTGGATTCACCTTCAGTAGCTATAGCATGAACTGGGTCCGCCAGGCT

CCAGGGAAGGGGCTGGAGTGGGTTTCAACCATTAGTAGTAGTAGTAGTATCATATACTACG

CAGACTCTGTGAAGGGCCGATTCACCATCTCCAGAGACAATGCCAAGAACTCACTGTATCT

GCAAATGAACAGCCTGAGAGCTGAGGACACGGCGGTGTACTACTGCGCCAGAGGTTCTCAG

GAGCACCTGATTTTCGATTATTGGGGACAGGGTACATTGGTCACCGTCTCCTCAGGGTCTA

CATCCGGCTCCGGGAAGCCCGGAAGTGGCGAAGGTAGTACAAAGGGGGAAATTGTGTTGAC

ACAGTCTCCAGCCACCCTGTCTTTGTCTCCAGGGGAAAGAGCCACCCTCTCCTGCAGGGCC

AGTCAGAGTGTTAGCAGGTACTTAGCCTGGTACCAACAGAAACCTGGCCAGGCTCCCAGGC

TCCTCATCTATGATGCATCCAACAGGGCCACTGGCATCCCAGCCAGGTTCAGTGGCAGTGG

GTCTGGGACAGACTTCACTCTCACCATCAGCAGCCTAGAGCCTGAAGATTTTGCAGTTTAT

TACTGTCAGCAGAGATTCTACTACCCTTGGACTTTTGGCGGAGGGACCAAGGTTGAGATCA

AACGGGCCGCTGCCCTTGATAATGAAAAGTCAAACGGAACAATCATTCACGTGAAGGGCAA

GCACCTCTGTCCGTCACCCTTGTTCCCTGGTCCATCCAAGCCATTCTGGGTGTTGGTCGTA

GTGGGTGGAGTCCTCGCTTGTTACTCTCTGCTCGTCACCGTGGCTTTTATAATCTTCTGGG

TTAGATCCAAAAGAAGCCGCCTGCTCCATAGCGATTACATGAATATGACTCCACGCCGCCC

TGGCCCCACAAGGAAACACTACCAGCCTTACGCACCACCTAGAGATTTCGCTGCCTATCGG

AGCAGGGTGAAGTTTTCCAGATCTGCAGATGCACCAGCGTATCAGCAGGGCCAGAACCAAC

TGTATAACGAGCTCAACCTGGGACGCAGGGAAGAGTATGACGTTTTGGACAAGCGCAGAGG

ACGGGACCCTGAGATGGGTGGCAAACCAAGACGAAAAAACCCCCAGGAGGGTCTCTATAAT

GAGCTGCAGAAGGATAAGATGGCTGAAGCCTATTCTGAAATAGGCATGAAAGGAGAGCGGA

GAAGGGGAAAGGGCACGACGGTTTGTACCAGGGACTCAGCACTGCTACGAAGGATACTTA

TGACGCTCTCCACATGCAAGCCCTGCCACCTAGG
```

Clone TS-26564 CAR HxL
(SEQ ID NO: 352)
MALPVTALLL PLALLLHAAR PEVQLVESGG GLVQPGGSLR

LSCAASGFTF SSYSMNWVRQ APGKGLEWVS TISSSSIIY

YADSVKGRFT ISRDNAKNSL YLQMNSLRAE DTAVYYCARG

SQEHLIFDYW GQGTLVTVSS GSTSGSGKPG SGEGSTKGEI

-continued

```
VLTQSPATLS LSPGERATLS CRASQSVSRY LAWYQQKPGQ

APRLLIYDAS NRATGIPARF SGSGSGTDFT LTISSLEPED

FAVYYCQQRF YYPWTFGGGT KVEIKRAAAL DNEKSNGTII

HVKGKHLCPS PLFPGPSKPF WVLVVVGGVL ACYSLLVTVA

FIIFWVRSKR SRLLHSDYMN MTPRRPGPTR KHYQPYAPPR

DFAAYRSRVK FSRSADAPAY QQGQNQLYNE LNLGRREEYD

VLDKRRGRDP EMGGKPRRKN PQEGLYNELQ KDKMAEAYSE

IGMKGERRRG KGHDGLYQGL STATKDTYDA LHMQALPPR
```

Clone TS-26564 CAR DNA LxH
(SEQ ID NO: 353)
```
ATGGCACTCCCCGTAACTGCTCTGCTGCTGCCGTTGGCATTGCTCCTGCACGCCGCACGCC

CGGAAATTGTGTTGACACAGTCTCCAGCCACCCTGTCTTTGTCTCCAGGGGAAAGAGCCAC

CCTCTCCTGCAGGGCCAGTCAGAGTGTTAGCAGGTACTTAGCCTGGTACCAACAGAAACCT

GGCCAGGCTCCCAGGCTCCTCATCTATGATGCATCCAACAGGGCCACTGGCATCCCAGCCA

GGTTCAGTGGCAGTGGGTCTGGGACAGACTTCACTCTCACCATCAGCAGCCTAGAGCCTGA

AGATTTTGCAGTTTATTACTGTCAGCAGAGATTCTACTACCCTTGGACTTTTGGCGGAGGG

ACCAAGGTTGAGATCAAACGGGGGTCTACATCCGGCTCCGGGAAGCCCGGAAGTGGCGAAG

GTAGTACAAAGGGGGAGGTGCAGCTGGTGGAGTCTGGGGGAGGCTTGGTACAGCCTGGGGG

GTCCCTGAGACTCTCCTGTGCAGCCTCTGGATTCACCTTCAGTAGCTATAGCATGAACTGG

GTCCGCCAGGCTCCAGGGAAGGGGCTGGAGTGGGTTTCAACCATTAGTAGTAGTAGTAGTA

TCATATACTACGCAGACTCTGTGAAGGGCCGATTCACCATCTCCAGAGACAATGCCAAGAA

CTCACTGTATCTGCAAATGAACAGCCTGAGAGCTGAGGACACGGCGGTGTACTACTGCGCC

AGAGGTTCTCAGGAGCACCTGATTTTCGATTATTGGGGACAGGGTACATTGGTCACCGTCT

CCTCAGCCGCTGCCCTTGATAATGAAAAGTCAAACGGAACAATCATTCACGTGAAGGGCAA

GCACCTCTGTCCGTCACCCTTGTTCCCTGGTCCATCCAAGCCATTCGGGTGTTGGTCGTA

GTGGGTGGAGTCCTCGCTTGTTACTCTCTGCTCGTCACCGTGGCTTTTATAATCTTCTGGG

TTAGATCCAAAAGAAGCCGCCTGCTCCATAGCGATTACATGAATATGACTCCACGCCGCCC

TGGCCCCACAAGGAAACACTACCAGCCTTACGCACCACCTAGAGATTTCGCTGCCTATCGG

AGCAGGGTGAAGTTTTCCAGATCTGCAGATGCACCAGCGTATCAGCAGGGCCAGAACCAAC

TGTATAACGAGCTCAACCTGGGACGCAGGGAAGAGTATGACGTTTTGGACAAGCGCAGAGG

ACGGGACCCTGAGATGGGTGGCAAACCAAGACGAAAAAACCCCCAGGAGGGTCTCTATAAT

GAGCTGCAGAAGGATAAGATGGCTGAAGCCTATTCTGAAATAGGCATGAAAGGAGAGCGGA

GAAGGGGAAAAGGGCACGACGGTTTGTACCAGGGACTCAGCACTGCTACGAAGGATACTTA

TGACGCTCTCCACATGCAAGCCCTGCCACCTAGG
```

Clone TS-26564 CAR LxH
(SEQ ID NO: 354)
```
MALPVTALLL PLALLLHAAR PEIVLTQSPA TLSLSPGERA

TLSCRASQSV SRYLAWYQQK PGQAPRLLIY DASNRATGIP

ARFSGSGSGT DFTLTISSLE PEDFAVYYCQ QRFYYPWTFG

GGTKVEIKRG STSGSGKPGS GEGSTKGEVQ LVESGGGLVQ

PGGSLRLSCA ASGFTFSSYS MNWVRQAPGK GLEWVSTISS

SSSIIYYADS VKGRFTISRD NAKNSLYLQM NSLRAEDTAV
```

-continued

```
YYCARGSQEH LIFDYWGQGT LVTVSSAAAL DNEKSNGTII

HVKGKHLCPS PLFPGPSKPF WVLVVVGGVL ACYSLLVTVA

FIIFWVRSKR SRLLHSDYMN MTPRRPGPTR KHYQPYAPPR

DFAAYRSRVK FSRSADAPAY QQGQNQLYNE LNLGRREEYD

VLDKRRGRDP EMGGKPRRKN PQEGLYNELQ KDKMAEAYSE

IGMKGERRRG KGHDGLYQGL STATKDTYDA LHMQALPPR

Clone RY-26568 HC DNA
                                           (SEQ ID NO: 355)
CAGGTGCAGCTGGTGGAGTCTGGGGGAGGCGTGGTCCAGCCTGGGAGGTCCCTGAGACTCT

CCTGTGCAGCGTCTGGATTCACCTTCGGGAGCTATGGCATGCACTGGGTCCGCCAGGCTCC

AGGCAAGGGGCTGGAGTGGGTGGCAGTTATACATTATGATGGAAGTGTTGAATACTATGCA

GACTCCGTGAAGGGCCGATTCACCATCTCCAGAGACAATTCCAAGGACACGCTGTATCTGC

AAATGAACAGCCTGAGAGCCGAGGACACGGCGGTGTACTACTGCGCCAGAACTGACTTCTG

GAGCGGATCCCCTCCAAGCTTAGATTACTGGGGACAGGGTACATTGGTCACCGTCTCCTCA

Clone RY-26568 HC. CDRs 1, 2, and 3 are underlined.
                                           (SEQ ID NO: 356)
QVQLVESGGG VVQPGRSLRL SCAASGFTFG SYGMHWVRQA

PGKGLEWVAV IHYDGSVEYY ADSVKGRFTI SRDNSKDTLY

LQMNSLRAED TAVYYCARTD FWSGSPPSLD YWGQGTLVTV

SS
                                           (SEQ ID NO: 357)
FTFGSYGMH (HC CDR1)

(SEQ ID NO: 358)
VIHYDGSVEYYADSVKG (HC CDR2)

(SEQ ID NO: 359)
ARTDFWSGSPPSLDY (HC CDR3)

Clone RY-26568 LC DNA
                                           (SEQ ID NO: 360)
GACATCCAGTTGACCCAGTCTCCATCTTCCGTGTCTGCATCTGTAGGAGACAGAGTCACCA

TCACTTGTCGGGCGAGTCGGGGTATTAGCAGCTGGTTAGCCTGGTATCAGCAGAAACCAGG

GAAAGCCCCTAAGCTCCTGATCTATGGTGCATCCAGTTTGCAAAGTGGGGTCCCATCAAGG

TTCAGCGGCAGTGGATCTGGGACAGATTTCACTCTCACCATCAGCAGCCTGCAGCCTGAAG

ATTTTGCAACTTATTACTGTCAGCAGATATACACCTTCCCTTTCACTTTTGGCGGAGGGAC

CAAGGTTGAGATCAAACGG

Clone RY-26568 LC. CDRs 1, 2, and 3 are underlined.
                                           (SEQ ID NO: 361)
DIQLTQSPSSVSASVGDRVTITCRASRGISSWLAWYQQKPGKAPKLLIYGASSLQSGVPSR

FSGSGSGTDFTLTISSLQPEDFATYYCQQIYTFPFTFGGGTKVEIKR (SEQ ID NO: 362)
RASRGISSWLA (LC CDR1)

(SEQ ID NO: 363)
GASSLQS (LC CDR2)

(SEQ ID NO: 364)
QQIYTFPFT (LC CDR3)

Clone RY-26568 CAR DNA HxL
                                           (SEQ ID NO: 365)
ATGGCACTCCCCGTAACTGCTCTGCTGCTGCCGTTGGCATTGCTCCTGCACGCCGCACGCC

CGCAGGTGCAGCTGGTGGAGTCTGGGGGAGGCGTGGTCCAGCCTGGGAGGTCCCTGAGACT

CTCCTGTGCAGCGTCTGGATTCACCTTCGGGAGCTATGGCATGCACTGGGTCCGCCAGGCT
```

-continued

```
CCAGGCAAGGGGCTGGAGTGGGTGGCAGTTATACATTATGATGGAAGTGTTGAATACTATG

CAGACTCCGTGAAGGGCCGATTCACCATCTCCAGAGACAATTCCAAGGACACGCTGTATCT

GCAAATGAACAGCCTGAGAGCCGAGGACACGGCGGTGTACTACTGCGCCAGAACTGACTTC

TGGAGCGGATCCCCTCCAAGCTTAGATTACTGGGGACAGGGTACATTGGTCACCGTCTCCT

CAGGGTCTACATCCGGCTCCGGGAAGCCCGGAAGTGGCGAAGGTAGTACAAAGGGGGACAT

CCAGTTGACCCAGTCTCCATCTTCCGTGTCTGCATCTGTAGGAGACAGAGTCACCATCACT

TGTCGGGCGAGTCGGGGTATTAGCAGCTGGTTAGCCTGGTATCAGCAGAAACCAGGGAAAG

CCCCTAAGCTCCTGATCTATGGTGCATCCAGTTTGCAAAGTGGGGTCCCATCAAGGTTCAG

CGGCAGTGGATCTGGGACAGATTTCACTCTCACCATCAGCAGCCTGCAGCCTGAAGATTTT

GCAACTTATTACTGTCAGCAGATATACACCTTCCCTTTCACTTTTGGCGGAGGGACCAAGG

TTGAGATCAAACGGGCCGCTGCCCTTGATAATGAAAAGTCAAACGGAACAATCATTCACGT

GAAGGGCAAGCACCTCTGTCCGTCACCCTTGTTCCCTGGTCCATCCAAGCCATTCTGGGTG

TTGGTCGTAGTGGGTGGAGTCCTCGCTTGTTACTCTCTGCTCGTCACCGTGGCTTTTATAA

TCTTCTGGGTTAGATCCAAAAGAAGCCGCCTGCTCCATAGCGATTACATGAATATGACTCC

ACGCCGCCCTGGCCCCACAAGGAAACACTACCAGCCTTACGCACCACCTAGAGATTTCGCT

GCCTATCGGAGCAGGGTGAAGTTTTCCAGATCTGCAGATGCACCAGCGTATCAGCAGGGCC

AGAACCAACTGTATAACGAGCTCAACCTGGGACGCAGGGAAGAGTATGACGTTTTGGACAA

GCGCAGAGGACGGGACCCTGAGATGGGTGGCAAACCAAGACGAAAAAACCCCCAGGAGGGT

CTCTATAATGAGCTGCAGAAGGATAAGATGGCTGAAGCCTATTCTGAAATAGGCATGAAAG

GAGAGCGGAGAAGGGGAAAAGGGCACGACGGTTTGTACCAGGGACTCAGCACTGCTACGAA

GGATACTTATGACGCTCTCCACATGCAAGCCCTGCCACCTAGG
```

Clone RY-26568 CAR HxL
(SEQ ID NO: 366)
```
MALPVTALLL PLALLLHAAR PQVQLVESGG GVVQPGRSLR

LSCAASGFTF GSYGMHWVRQ APGKGLEWVA VIHYDGSVEY

YADSVKGRFT ISRDNSKDTL YLQMNSLRAE DTAVYYCART

DFWSGSPPSL DYWGQGTLVT VSSGSTSGSG KPGSGEGSTK

GDIQLTQSPS SVSASVGDRV TITCRASRGI SSWLAWYQQK

PGKAPKLLIY GASSLQSGVP SRFSGSGSGT DFTLTISSLQ

PEDFATYYCQ QIYTFPFTFG GGTKVEIKRA AALDNEKSNG

TIIHVKGKHL CPSPLFPGPS KPFWVLVVVG GVLACYSLLV

TVAFIIFWVR SKRSRLLHSD YMNMTPRRPG PTRKHYQPYA

PPRDFAAYRS RVKFSRSADA PAYQQGQNQL YNELNLGRRE

EYDVLDKRRG RDPEMGGKPR RKNPQEGLYN ELQKDKMAEA

YSEIGMKGER RRGKGHDGLY QGLSTATKDT YDALHMQALP

PR
```

Clone RY-26568 CAR DNA LxH
(SEQ ID NO: 367)
```
ATGGCACTCCCCGTAACTGCTCTGCTGCTGCCGTTGGCATTGCTCCTGCACGCCGCACGCC

CGGACATCCAGTTGACCCAGTCTCCATCTTCCGTGTCTGCATCTGTAGGAGACAGAGTCAC

CATCACTTGTCGGGCGAGTCGGGGTATTAGCAGCTGGTTAGCCTGGTATCAGCAGAAACCA

GGGAAAGCCCCTAAGCTCCTGATCTATGGTGCATCCAGTTTGCAAAGTGGGGTCCCATCAA
```

-continued
```
GGTTCAGCGGCAGTGGATCTGGGACAGATTTCACTCTCACCATCAGCAGCCTGCAGCCTGA

AGATTTTGCAACTTATTACTGTCAGCAGATATACACCTTCCCTTTCACTTTTGGCGGAGGG

ACCAAGGTTGAGATCAAACGGGGGTCTACATCCGGCTCCGGGAAGCCCGGAAGTGGCGAAG

GTAGTACAAAGGGGCAGGTGCAGCTGGTGGAGTCTGGGGGAGGCGTGGTCCAGCCTGGGAG

GTCCCTGAGACTCTCCTGTGCAGCGTCTGGATTCACCTTCGGGAGCTATGGCATGCACTGG

GTCCGCCAGGCTCCAGGCAAGGGGCTGGAGTGGGTGGCAGTTATACATTATGATGGAAGTG

TTGAATACTATGCAGACTCCGTGAAGGGCCGATTCACCATCTCCAGAGACAATTCCAAGGA

CACGCTGTATCTGCAAATGAACAGCCTGAGAGCCGAGGACACGGCGGTGTACTACTGCGCC

AGAACTGACTTCTGGAGCGGATCCCCTCCAAGCTTAGATTACTGGGGACAGGGTACATTGG

TCACCGTCTCCTCAGCCGCTGCCCTTGATAATGAAAAGTCAAACGGAACAATCATTCACGT

GAAGGGCAAGCACCTCTGTCCGTCACCCTTGTTCCCTGGTCCATCCAAGCCATTCTGGGTG

TTGGTCGTAGTGGGTGGAGTCCTCGCTTGTTACTCTCTGCTCGTCACCGTGGCTTTTATAA

TCTTCTGGGTTAGATCCAAAAGAAGCCGCCTGCTCCATAGCGATTACATGAATATGACTCC

ACGCCGCCCTGGCCCCACAAGGAAACACTACCAGCCTTACGCACCACCTAGAGATTTCGCT

GCCTATCGGAGCAGGGTGAAGTTTTCCAGATCTGCAGATGCACCAGCGTATCAGCAGGGCC

AGAACCAACTGTATAACGAGCTCAACCTGGGACGCAGGGAAGAGTATGACGTTTTGGACAA

GCGCAGAGGACGGGACCCTGAGATGGGTGGCAAACCAAGACGAAAAAACCCCCAGGAGGGT

CTCTATAATGAGCTGCAGAAGGATAAGATGGCTGAAGCCTATTCTGAAATAGGCATGAAAG

GAGAGCGGAGAAGGGGAAAAGGGCACGACGGTTTGTACCAGGGACTCAGCACTGCTACGAA

GGATACTTATGACGCTCTCCACATGCAAGCCCTGCCACCTAGG
```

Clone RY-26568 CAR LxH
                                                    (SEQ ID NO: 368)
```
MALPVTALLL PLALLLHAAR PDIQLTQSPS SVSASVGDRV

TITCRASRGI SSWLAWYQQK PGKAPKLLIY GASSLQSGVP

SRFSGSGSGT DFTLTISSLQ PEDFATYYCQ QIYTFPFTFG

GGTKVEIKRG STSGSGKPGS GEGSTKGQVQ LVESGGGVVQ

PGRSLRLSCA ASGFTFGSYG MHWVRQAPGK GLEWVAVIHY

DGSVEYYADS VKGRFTISRD NSKDTLYLQM NSLRAEDTAV

YYCARTDFWS GSPPSLDYWG QGTLVTVSSA AALDNEKSNG

TIIHVKGKHL CPSPLFPGPS KPFWVLVVVG GVLACYSLLV

TVAFIIFWVR SKRSRLLHSD YMNMTPRRPG PTRKHYQPYA

PPRDFAAYRS RVKFSRSADA PAYQQGQNQL YNELNLGRRE

EYDVLDKRRG RDPEMGGKPR RKNPQEGLYN ELQKDKMAEA

YSEIGMKGER RRGKGHDGLY QGLSTATKDT YDALHMQALP

PR
```

Clone PP-26575 HC DNA
                                                    (SEQ ID NO: 369)
```
CAGGTGCAGCTGGTGCAGTCTGGGGCTGAGGTGAAGAAGCCTGGGTCCTCGGTGAAGGTCT

CCTGCAAGGCTTCTGGAGGCACCCTCAGCAGCCTGGCTATCAGCTGGGTGCGACAGGCCCC

TGGACAAGGGCTTGAGTGGATGGGAGGGGTCATCCCTATCTTGGGTCGGGCAAACTACGCA

CAGAAGTTCCAGGGCAGAGTCACGATTACCGCGGACGAGTCCACGAGCACAGCCTACATGG
```

-continued

AGCTGAGCAGCCTGAGATCTGAGGACACGGCGGTGTACTACTGCGCCAGAACTCCTGAATA

CTCCTCCAGCATATGGCACTATTACTACGGCATGGACGTATGGGGCCAGGGAACAACTGTC

ACCGTCTCCTCA

Clone PP-26575 HC. CDRs 1, 2, and 3 are underlined.
(SEQ ID NO: 370)
QVQLVQSGAEVKKPGSSVKVSCKASGGTLSSLAISWVRQAPGQGLEWMGGVIPILGRANYA

QKFQGRVTITADESTSTAYMELSSLRSEDTAVYYCARTPEYSSSIWHYYYGMDVWGQGTTV

TVSS (SEQ ID NO: 371)
GTLSSLAIS (HC CDR1)

(SEQ ID NO: 372)
GVIPILGRANYAQKFQG (HC CDR2)

(SEQ ID NO: 373)
ARTPEYSSSIWHYYYGMDV (HC CDR3)

Clone PP-26575 LC DNA
(SEQ ID NO: 374)
GACATCGTGATGACCCAGTCTCCAGACTCCCTGGCTGTGTCTCTGGGCGAGAGGGCCACCA

TCAACTGCAAGTCCAGCCAGAGTGTTTTATACAGCTCCAACAATAAGAACTACTTAGCTTG

GTACCAGCAGAAACCAGGACAGCCTCCTAAGCTGCTCATTTACTGGGCATCTACCCGGGAA

TCCGGGGTCCCTGACCGATTCAGTGGCAGCGGGTCTGGGACAGATTTCACTCTCACCATCA

GCAGCCTGCAGGCTGAAGATGTGGCAGTTTATTACTGTCAGCAGTTCGCCCACACTCCTTT

CACTTTTGGCGGAGGGACCAAGGTTGAGATCAAACGG

Clone PP-26575 LC. CDRs 1, 2, and 3 are underlined.
(SEQ ID NO: 375)
DIVMTQSPDSLAVSLGERATINCKSSQSVLYSSNNKNYLAWYQQKPGQPPKLLIYWASTR

ESGVPDRFSGSGSGTDFTLTISSLQAEDVAVYYCQQFAHTPFTFGGGTKVEIKR (SEQ ID NO: 376)
KSSQSVLYSSNNKNYLA (LC CDR1)

(SEQ ID NO: 377)
WASTRES (LC CDR2)

(SEQ ID NO: 378)
QQFAHTPFT (LC CDR3)

Clone PP-26575 CAR DNA HxL
(SEQ ID NO: 379)
ATGGCACTCCCCGTAACTGCTCTGCTGCTGCCGTTGGCATTGCTCCTGCACGCCGCACGCC

CGCAGGTGCAGCTGGTGCAGTCTGGGGCTGAGGTGAAGAAGCCTGGGTCCTCGGTGAAGGT

CTCCTGCAAGGCTTCTGGAGGCACCCTCAGCAGCCTGGCTATCAGCTGGGTGCGACAGGCC

CCTGGACAAGGGCTTGAGTGGATGGGAGGGGTCATCCCTATCTTGGGTCGGGCAAACTACG

CACAGAAGTTCCAGGGCAGAGTCACGATTACCGCGGACGAGTCCACGAGCACAGCCTACAT

GGAGCTGAGCAGCCTGAGATCTGAGGACACGGCGGTGTACTACTGCGCCAGAACTCCTGAA

TACTCCTCCAGCATATGGCACTATTACTACGGCATGGACGTATGGGGCCAGGGAACAACTG

TCACCGTCTCCTCAGGGTCTACATCCGGCTCCGGAAGCCCGGAAGTGGCGAAGGTAGTAC

AAAGGGGGACATCGTGATGACCCAGTCTCCAGACTCCCTGGCTGTGTCTCTGGGCGAGAGG

GCCACCATCAACTGCAAGTCCAGCCAGAGTGTTTTATACAGCTCCAACAATAAGAACTACT

TAGCTTGGTACCAGCAGAAACCAGGACAGCCTCCTAAGCTGCTCATTTACTGGGCATCTAC

CCGGGAATCCGGGGTCCCTGACCGATTCAGTGGCAGCGGGTCTGGGACAGATTTCACTCTC

ACCATCAGCAGCCTGCAGGCTGAAGATGTGGCAGTTTATTACTGTCAGCAGTTCGCCCACA

-continued

```
CTCCTTTCACTTTTGGCGGAGGGACCAAGGTTGAGATCAAACGGGCCGCTGCCCTTGATAA

TGAAAAGTCAAACGGAACAATCATTCACGTGAAGGGCAAGCACCTCTGTCCGTCACCCTTG

TTCCCTGGTCCATCCAAGCCATTCTGGGTGTTGGTCGTAGTGGGTGGAGTCCTCGCTTGTT

ACTCTCTGCTCGTCACCGTGGCTTTTATAATCTTCTGGGTTAGATCCAAAAGAAGCCGCCT

GCTCCATAGCGATTACATGAATATGACTCCACGCCGCCCTGGCCCCACAAGGAAACACTAC

CAGCCTTACGCACCACCTAGAGATTTCGCTGCCTATCGGAGCAGGGTGAAGTTTTCCAGAT

CTGCAGATGCACCAGCGTATCAGCAGGGCCAGAACCAACTGTATAACGAGCTCAACCTGGG

ACGCAGGGAAGAGTATGACGTTTTGGACAAGCGCAGAGGACGGGACCCTGAGATGGGTGGC

AAACCAAGACGAAAAAACCCCCAGGAGGGTCTCTATAATGAGCTGCAGAAGGATAAGATGG

CTGAAGCCTATTCTGAAATAGGCATGAAAGGAGAGCGGAGAAGGGGAAAAGGGCACGACGG

TTTGTACCAGGGACTCAGCACTGCTACGAAGGATACTTATGACGCTCTCCACATGCAAGCC

CTGCCACCTAGG
```

Clone PP-26575 CAR HxL
(SEQ ID NO: 380)

MALPVTALLL PLALLLHAAR PQVQLVQSGA EVKKPGSSVK

VSCKASGGTL SSLAISWVRQ APGQGLEWMG GVIPILGRAN

YAQKFQGRVT ITADESTSTA YMELSSLRSE DTAVYYCART

PEYSSSIWHY YYGMDVWGQG TTVTVSSGST SGSGKPGSGE

GSTKGDIVMT QSPDSLAVSL GERATINCKS SQSVLYSSNN

KNYLAWYQQK PGQPPKLLIY WASTRESGVP DRFSGSGSGT

DFTLTISSLQ AEDVAVYYCQ QFAHTPFTFG GGTKVEIKRA

AALDNEKSNG TIIHVKGKHL CPSPLFPGPS KPFWVLVVVG

GVLACYSLLV TVAFIIFWVR SKRSRLLHSD YMNMTPRRPG

PTRKHYQPYA PPRDFAAYRS RVKFSRSADA PAYQQGQNQL

YNELNLGRRE EYDVLDKRRG RDPEMGGKPR RKNPQEGLYN

ELQKDKMAEA YSEIGMKGER RRGKGHDGLY QGLSTATKDT

YDALHMQALP PR

Clone PP-26575 CAR DNA LxH
(SEQ ID NO: 381)

```
ATGGCACTCCCCGTAACTGCTCTGCTGCTGCCGTTGGCATTGCTCCTGCACGCCGCACGCC

CGGACATCGTGATGACCCAGTCTCCAGACTCCCTGGCTGTGTCTCTGGGCGAGAGGGCCAC

CATCAACTGCAAGTCCAGCCAGAGTGTTTTATACAGCTCCAACAATAAGAACTACTTAGCT

TGGTACCAGCAGAAACCAGGACAGCCTCCTAAGCTGCTCATTTACTGGGCATCTACCCGGG

AATCCGGGGTCCCTGACCGATTCAGTGGCAGCGGGTCTGGGACAGATTTCACTCTCACCAT

CAGCAGCCTGCAGGCTGAAGATGTGGCAGTTTATTACTGTCAGCAGTTCGCCCACACTCCT

TTCACTTTTGGCGGAGGGACCAAGGTTGAGATCAAACGGGGTCTACATCCGGCTCCGGGA

AGCCCGGAAGTGGCGAAGGTAGTACAAAGGGGCAGGTGCAGCTGGTGCAGTCTGGGGCTGA

GGTGAAGAAGCCTGGGTCCTCGGTGAAGGTCTCCTGCAAGGCTTCTGGAGGCACCCTCAGC

AGCCTGGCTATCAGCTGGGTGCGACAGGCCCCTGGACAAGGGCTTGAGTGGATGGGAGGGG

TCATCCCTATCTTGGGTCGGGCAAACTACGCACAGAAGTTCCAGGGCAGAGTCACGATTAC

CGCGGACGAGTCCACGAGCACAGCCTACATGGAGCTGAGCAGCCTGAGATCTGAGGACACG

GCGGTGTACTACTGCGCCAGAACTCCTGAATACTCCTCCAGCATATGGCACTATTACTACG

GCATGGACGTATGGGGCCAGGGAACAACTGTCACCGTCTCCTCAGCCGCTGCCCTTGATAA
```

-continued

```
TGAAAAGTCAAACGGAACAATCATTCACGTGAAGGGCAAGCACCTCTGTCCGTCACCCTTG

TTCCCTGGTCCATCCAAGCCATTCTGGGTGTTGGTCGTAGTGGGTGGAGTCCTCGCTTGTT

ACTCTCTGCTCGTCACCGTGGCTTTTATAATCTTCTGGGTTAGATCCAAAAGAAGCCGCCT

GCTCCATAGCGATTACATGAATATGACTCCACGCCGCCCTGGCCCCACAAGGAAACACTAC

CAGCCTTACGCACCACCTAGAGATTTCGCTGCCTATCGGAGCAGGGTGAAGTTTTCCAGAT

CTGCAGATGCACCAGCGTATCAGCAGGGCCAGAACCAACTGTATAACGAGCTCAACCTGGG

ACGCAGGGAAGAGTATGACGTTTTGGACAAGCGCAGAGGACGGGACCCTGAGATGGGTGGC

AAACCAAGACGAAAAACCCCCAGGAGGGTCTCTATAATGAGCTGCAGAAGGATAAGATGG

CTGAAGCCTATTCTGAAATAGGCATGAAAGGAGAGCGGAGAAGGGGAAAAGGGCACGACGG

TTTGTACCAGGGACTCAGCACTGCTACGAAGGATACTTATGACGCTCTCCACATGCAAGCC

CTGCCACCTAGG
```

Clone PP-26575 CAR LxH (SEQ ID NO: 382)

```
MALPVTALLL PLALLLHAAR PDIVMTQSPD SLAVSLGERA

TINCKSSQSV LYSSNNKNYL AWYQQKPGQP PKLLIYWAST

RESGVPDRFS GSGSGTDFTL TISSLQAEDV AVYYCQQFAH

TPFTFGGGTK VEIKRGSTSG SGKPGSGEGS TKGQVQLVQS

GAEVKKPGSS VKVSCKASGG TLSSLAISWV RQAPGQGLEW

MGGVIPILGR ANYAQKFQGR VTITADESTS TAYMELSSLR

SEDTAVYYCA RTPEYSSSIW HYYYGMDVWG QGTTVTVSSA

AALDNEKSNG TIIHVKGKHL CPSPLFPGPS KPFWVLVVVG

GVLACYSLLV TVAFIIFWVR SKRSRLLHSD YMNMTPRRPG

PTRKHYQPYA PPRDFAAYRS RVKFSRSADA PAYQQGQNQL

YNELNLGRRE EYDVLDKRRG RDPEMGGKPR RKNPQEGLYN

ELQKDKMAEA YSEIGMKGER RRGKGHDGLY QGLSTATKDT

YDALHMQALP PR
```

Clone RD-26576 HC DNA (SEQ ID NO: 383)

```
CAGGTGCGGCTGGTGGAGTCTGGGGGGGGCGTGGTCCAGCCTGGGAGGTCCCTGAGACTCT

CCTGTGCAGCGTCTGGATTCACCTTCAGTAGCTATGGCATACACTGGGTCCGCCAGGCTCC

AGGCAAGGGGCTGGAGTGGGTGGCAGTTATAGGGTATGATGGACAGGAGAAATACTATGCA

GACTCCGTGAAGGGCCGATTCACCATCTCCAGAGACAATTCCAAGAACACGCTGTATCTGC

AAATGAACAGCCTGAGAGCCGAGGACACGGCGGTGTACTACTGCGTCAAGGGGCCGTTGCA

GGAGCCGCCATACGCTTTTGGGATGGACGTATGGGGCCAGGGAACAACTGTCACCGTCTCC

TCA
```

Clone RD-26576 HC. CDRs 1, 2, and 3 are underlined.

(SEQ ID NO: 384)

QVRLVESGGGVVQPGRSLRLSCAASG<u>FTFSSYGIH</u>WVRQAPGKGLEWVA<u>VIGYDGQEKYYA
DSVKG</u>RFTISRDNSKNTLYLQMNSLRAEDTAVYYC<u>VKGPLQEPPYAFGMDV</u>WGQGTTVTVS
S

-continued

```
                                              (SEQ ID NO: 385)
FTFSSYGIH (HC CDR1)

(SEQ ID NO: 386)
VIGYDGQEKYYADSVKG (HC CDR2)

(SEQ ID NO: 387)
VKGPLQEPPYAFGMDV (HC CDR3)

Clone RD-26576 LC DNA
                                              (SEQ ID NO: 388)
GAAATAGTGATGACGCAGTCTCCAGCCACCCTGTCTGTGTCTCCAGGGGAAAGAGCCACCC

TCTCCTGCAGGGCCAGTCAGAGTGTTAGCAGCAACTTAGCCTGGTACCAGCAGAAACCTGG

CCAGGCTCCCAGGCTCCTCATCTATAGCGCATCCACCAGGGCCACTGGTATCCCAGCCAGG

TTCAGTGGCAGTGGGTCTGGGACAGAGTTCACTCTCACCATCAGCAGCCTGCAGTCTGAAG

ATTTTGCAGTTTATTACTGTCAGCAGCACCACGTCTGGCCTCTCACTTTTGGCGGAGGGAC

CAAGGTTGAGATCAAACGG

Clone RD-26576 LC. CDRs 1, 2, and 3 are underlined.
                                              (SEQ ID NO: 389)
EIVMTQSPATLSVSPGERATLSCRASQSVSSNLAWYQQKPGQAPRLLIYSASTRATGIPA

RFSGSGSGTEFTLTISSLQSEDFAVYYCQQHHVWPLTFGGGTKVEIKR (SEQ ID NO: 390)
RASQSVSSNLA (LC CDR1)

(SEQ ID NO: 391)
SASTRAT (LC CDR2)

(SEQ ID NO: 392)
QQHHVWPLT (LC CDR3)

Clone RD-26576 CAR DNA HxL
                                              (SEQ ID NO: 393)
ATGGCACTCCCCGTAACTGCTCTGCTGCTGCCGTTGGCATTGCTCCTGCACGCCGCACGCC

CGCAGGTGCGGCTGGTGGAGTCTGGGGGGGGCGTGGTCCAGCCTGGGAGGTCCCTGAGACT

CTCCTGTGCAGCGTCTGGATTCACCTTCAGTAGCTATGGCATACACTGGGTCCGCCAGGCT

CCAGGCAAGGGGCTGGAGTGGGTGGCAGTTATAGGGTATGATGGACAGGAGAAATACTATG

CAGACTCCGTGAAGGGCCGATTCACCATCTCCAGAGACAATTCCAAGAACACGCTGTATCT

GCAAATGAACAGCCTGAGAGCCGAGGACACGGCGGTGTACTACTGCGTCAAGGGGCCGTTG

CAGGAGCCGCCATACGCTTTTGGGATGGACGTATGGGGCCAGGGAACAACTGTCACCGTCT

CCTCAGGGTCTACATCCGGCTCCGGGAAGCCCGGAAGTGGCGAAGGTAGTACAAAGGGGGA

AATAGTGATGACGCAGTCTCCAGCCACCCTGTCTGTGTCTCCAGGGGAAAGAGCCACCCTC

TCCTGCAGGGCCAGTCAGAGTGTTAGCAGCAACTTAGCCTGGTACCAGCAGAAACCTGGCC

AGGCTCCCAGGCTCCTCATCTATAGCGCATCCACCAGGGCCACTGGTATCCCAGCCAGGTT

CAGTGGCAGTGGGTCTGGGACAGAGTTCACTCTCACCATCAGCAGCCTGCAGTCTGAAGAT

TTTGCAGTTTATTACTGTCAGCAGCACCACGTCTGGCCTCTCACTTTTGGCGGAGGGACCA

AGGTTGAGATCAAACGGGCCGCTGCCCTTGATAATGAAAAGTCAAACGGAACAATCATTCA

CGTGAAGGGCAAGCACCTCTGTCCGTCACCCTTGTTCCCTGGTCCATCCAAGCCATTCTGG

GTGTTGGTCGTAGTGGGTGGAGTCCTCGCTTGTTACTCTCTGCTCGTCACCGTGGCTTTTA

TAATCTTCTGGGTTAGATCCAAAAGAAGCCGCCTGCTCCATAGCGATTACATGAATATGAC

TCCACGCCGCCCTGGCCCCACAAGGAAACACTACCAGCCTTACGCACCACCTAGAGATTTC

GCTGCCTATCGGAGCAGGGTGAAGTTTTCCAGATCTGCAGATGCACCAGCGTATCAGCAGG

GCCAGAACCAACTGTATAACGAGCTCAACCTGGGACGCAGGGAAGAGTATGACGTTTTGGA
```

```
CAAGCGCAGAGGACGGGACCCTGAGATGGGTGGCAAACCAAGACGAAAAAACCCCCAGGAG

GGTCTCTATAATGAGCTGCAGAAGGATAAGATGGCTGAAGCCTATTCTGAAATAGGCATGA

AAGGAGAGCGGAGAAGGGGAAAAGGGCACGACGGTTTGTACCAGGGACTCAGCACTGCTAC

GAAGGATACTTATGACGCTCTCCACATGCAAGCCCTGCCACCTAGG
```

Clone RD-26576 CAR HxL
(SEQ ID NO: 394)

```
MALPVTALLL PLALLLHAAR PQVRLVESGG GVVQPGRSLR

LSCAASGFTF SSYGIHWVRQ APGKGLEWVA VIGYDGQEKY

YADSVKGRFT ISRDNSKNTL YLQMNSLRAE DTAVYYCVKG

PLQEPPYAFG MDVWGQGTTV TVSSGSTSGS GKPGSGEGST

KGEIVMTQSP ATLSVSPGER ATLSCRASQS VSSNLAWYQQ

KPGQAPRLLI YSASTRATGI PARFSGSGSG TEFTLTISSL

QSEDFAVYYC QQHHVWPLTF GGGTKVEIKR AAALDNEKSN

GTIIHVKGKH LCPSPLFPGP SKPFWVLVVV GGVLACYSLL

VTVAFIIFWV RSKRSLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL

PPR
```

Clone RD-26576 CAR DNA LxH
(SEQ ID NO: 395)

```
ATGGCACTCCCCGTAACTGCTCTGCTGCTGCCGTTGGCATTGCTCCTGCACGCCGCACGCC

CGGAAATAGTGATGACGCAGTCTCCAGCCACCCTGTCTGTGTCTCCAGGGGAAAGAGCCAC

CCTCTCCTGCAGGGCCAGTCAGAGTGTTAGCAGCAACTTAGCCTGGTACCAGCAGAAACCT

GGCCAGGCTCCCAGGCTCCTCATCTATAGCGCATCCACCAGGGCCACTGGTATCCCAGCCA

GGTTCAGTGGCAGTGGGTCTGGGACAGAGTTCACTCTCACCATCAGCAGCCTGCAGTCTGA

AGATTTTGCAGTTTATTACTGTCAGCAGCACCACGTCTGGCCTCTCACTTTTGGCGGAGGG

ACCAAGGTTGAGATCAAACGGGGGTCTACATCCGGCTCCGGGAAGCCCGGAAGTGGCGAAG

GTAGTACAAAGGGGCAGGTGCGGCTGGTGGAGTCTGGGGGGGCGTGGTCCAGCCTGGGAG

GTCCCTGAGACTCTCCTGTGCAGCGTCTGGATTCACCTTCAGTAGCTATGGCATACACTGG

GTCCGCCAGGCTCCAGGCAAGGGGCTGGAGTGGGTGGCAGTTATAGGGTATGATGGACAGG

AGAAATACTATGCAGACTCCGTGAAGGGCCGATTCACCATCTCCAGAGACAATTCCAAGAA

CACGCTGTATCTGCAAATGAACAGCCTGAGAGCCGAGGACACGGCGGTGTACTACTGCGTC

AAGGGGCCGTTGCAGGAGCCGCCATACGCTTTTGGGATGGACGTATGGGGCCAGGGAACAA

CTGTCACCGTCTCCTCAGCCGCTGCCCTTGATAATGAAAAGTCAAACGGAACAATCATTCA

CGTGAAGGGCAAGCACCTCTGTCCGTCACCCTTGTTCCCTGGTCCATCCAAGCCATTCTGG

GTGTTGGTCGTAGTGGGTGGAGTCCTCGCTTGTTACTCTCTGCTCGTCACCGTGGCTTTTA

TAATCTTCTGGGTTAGATCCAAAAGAAGCCGCCTGCTCCATAGCGATTACATGAATATGAC

TCCACGCCGCCCTGGCCCCACAAGGAAACACTACCAGCCTTACGCACCACCTAGAGATTTC

GCTGCCTATCGGAGCAGGGTGAAGTTTTCCAGATCTGCAGATGCACCAGCGTATCAGCAGG

GCCAGAACCAACTGTATAACGAGCTCAACCTGGGACGCAGGGAAGAGTATGACGTTTTGGA

CAAGCGCAGAGGACGGGACCCTGAGATGGGTGGCAAACCAAGACGAAAAAACCCCCAGGAG

GGTCTCTATAATGAGCTGCAGAAGGATAAGATGGCTGAAGCCTATTCTGAAATAGGCATGA
```

-continued

AAGGAGAGCGGAGAAGGGGAAAAGGGCACGACGGTTTGTACCAGGGACTCAGCACTGCTAC

GAAGGATACTTATGACGCTCTCCACATGCAAGCCCTGCCACCTAGG

Clone RD-26576 CAR LxH
(SEQ ID NO: 396)
MALPVTALLL PLALLLHAAR PEIVMTQSPA TLSVSPGERA

TLSCRASQSV SSNLAWYQQK PGQAPRLLIY SASTRATGIP

ARFSGSGSGT EFTLTISSLQ SEDFAVYYCQ QHHVWPLTFG

GGTKVEIKRG STSGSGKPGS GEGSTKGQVR LVESGGGVVQ

PGRSLRLSCA ASGFTFSSYG IHWVRQAPGK GLEWVAVIGY

DGQEKYYADS VKGRFTISRD NSKNTLYLQM NSLRAEDTAV

YYCVKGPLQE PPYAFGMDVW GQGTTVTVSS AAALDNEKSN

GTIIHVKGKH LCPSPLFPGP SKPFWVLVVV GGVLACYSLL

VTVAFIIFWV RSKRSRLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL

PPR

Clone RD-26578 HC DNA
(SEQ ID NO: 397)
CAGGTGCAGCTGGTGGAGTCTGGGGGAGGCGTGGTCCAGCCTGGGAGGTCCCTGAGACTCT

CCTGTGCAGCGTCTGGATTCACCTTCAGTAGCCGTGGCATGCACTGGGTCCGCCAGGCTCC

AGGCAAGGGGCTGGAGTGGGTGGCAGTTATAGGGTATGATGGACAGGAGAAATACTATGCA

GACTCCGTGAAGGGCCGATTCACCATCTCCAGAGACAATTCCAAGAACACGCTGTATCTGC

AAATGAACAGCCTGAGAGCCGAGGACACGGCGGTGTACTACTGCGTCAAGGGGCCGTTGCA

GGAGCCGCCATACGATTATGGAATGGACGTATGGGGCCAGGGAACAACTGTCACCGTCTCC

TCA

Clone RD-26578 HC CDRs 1, 2, and 3 are underlined.
(SEQ ID NO: 398)
QVQLVESGGGVVQPGRSLRLSCAASG<u>FTFSSRGMH</u>WVRQAPGKGLEWVA<u>VIGYDGQEKYYA
DSVKG</u>RFTISRDNSKNTLYLQMNSLRAEDTAVYYC<u>VKGPLQEPPYDYGMDV</u>WGQGTTVTVS

S (SEQ ID NO: 399)
FTFSSRGMH (HC CDR1)

(SEQ ID NO: 400)
VIGYDGQEKYYADSVKG (HC CDR2)

(SEQ ID NO: 401)
VKGPLQEPPYDYGMDV (HC CDR3)

Clone RD-26578 LC DNA
(SEQ ID NO: 402)
GAAATAGTGATGACGCAGTCTCCAGCCACCCTGTCTGTGTCTCCAGGGGAAAGAGCCACCC

TCTCCTGCAGGGCCAGTCAGAGTGTTAGCAGCAACTTAGCCTGGTACCAGCAGAAACCTGG

CCAGGCTCCCAGGCTCCTCATCTATAGCGCATCCACCAGGGCCACTGGTATCCCAGCCAGG

TTCAGTGGCAGTGGGTCTGGGACAGAGTTCACTCTCACCATCAGCAGCCTGCAGTCTGAAG

-continued

ATTTTGCAGTTTATTACTGTCAGCAGCACCACGTCTGGCCTCTCACTTTTGGCGGAGGGAC

CAAGGTTGAGATCAAACGG

Clone RD-26578 LC. CDRs 1, 2, and 3 are underlined.
(SEQ ID NO: 403)
EIVMTQSPATLSVSPGERATLSC<u>RASQSVSSNLA</u>WYQQKPGQAPRLLIY<u>S</u>

<u>ASTRAT</u>GIPARFSGSGSGTEFTLTISSLQSEDFAVYYC<u>QQHHVWPLT</u>FGGGTKVEIKR (SEQ ID NO: 404)
RASQSVSSNLA (LC CDR1)

(SEQ ID NO: 405)
SASTRAT (LC CDR2)

(SEQ ID NO: 406)
QQHHVWPLT (LC CDR3)

Clone RD-26578 CAR DNA HxL
(SEQ ID NO: 407)
ATGGCACTCCCCGTAACTGCTCTGCTGCTGCCGTTGGCATTGCTCCTGCACGCCGCACGCC

CGCAGGTGCAGCTGGTGGAGTCTGGGGGAGGCGTGGTCCAGCCTGGGAGGTCCCTGAGACT

CTCCTGTGCAGCGTCTGGATTCACCTTCAGTAGCCGTGGCATGCACTGGGTCCGCCAGGCT

CCAGGCAAGGGGCTGGAGTGGGTGGCAGTTATAGGGTATGATGGACAGGAGAAATACTATG

CAGACTCCGTGAAGGGCCGATTCACCATCTCCAGAGACAATTCCAAGAACACGCTGTATCT

GCAAATGAACAGCCTGAGAGCCGAGGACACGGCGGTGTACTACTGCGTCAAGGGGCCGTTG

CAGGAGCCGCCATACGATTATGGAATGGACGTATGGGGCCAGGGAACAACTGTCACCGTCT

CCTCAGGGTCTACATCCGGCTCCGGGAAGCCCGGAAGTGGCGAAGGTAGTACAAAGGGGGA

AATAGTGATGACGCAGTCTCCAGCCACCCTGTCTGTGTCTCCAGGGGAAAGAGCCACCCTC

TCCTGCAGGGCCAGTCAGAGTGTTAGCAGCAACTTAGCCTGGTACCAGCAGAAACCTGGCC

AGGCTCCCAGGCTCCTCATCTATAGCGCATCCACCAGGGCCACTGGTATCCCAGCCAGGTT

CAGTGGCAGTGGGTCTGGGACAGAGTTCACTCTCACCATCAGCAGCCTGCAGTCTGAAGAT

TTTGCAGTTTATTACTGTCAGCAGCACCACGTCTGGCCTCTCACTTTTGGCGGAGGGACCA

AGGTTGAGATCAAACGGGCCGCTGCCCTTGATAATGAAAAGTCAAACGGAACAATCATTCA

CGTGAAGGGCAAGCACCTCTGTCCGTCACCCTTGTTCCCTGGTCCATCCAAGCCATTCTGG

GTGTTGGTCGTAGTGGGTGGAGTCCTCGCTTGTTACTCTCTGCTCGTCACCGTGGCTTTTA

TAATCTTCTGGGTTAGATCCAAAAGAAGCCGCCTGCTCCATAGCGATTACATGAATATGAC

TCCACGCCGCCCTGGCCCCACAAGGAAACACTACCAGCCTTACGCACCACCTAGAGATTTC

GCTGCCTATCGGAGCAGGGTGAAGTTTTCCAGATCTGCAGATGCACCAGCGTATCAGCAGG

GCCAGAACCAACTGTATAACGAGCTCAACCTGGGACGCAGGGAAGAGTATGACGTTTTGGA

CAAGCGCAGAGGACGGGACCCTGAGATGGGTGGCAAACCAAGACGAAAAAACCCCCAGGAG

GGTCTCTATAATGAGCTGCAGAAGGATAAGATGGCTGAAGCCTATTCTGAAATAGGCATGA

AAGGAGAGCGGAGAAGGGGAAAAGGGCACGACGGTTTGTACCAGGGACTCAGCACTGCTAC

GAAGGATACTTATGACGCTCTCCACATGCAAGCCCTGCCACCTAGG

Clone RD-26578 CAR HxL
(SEQ ID NO: 408)
MALPVTALLL PLALLLHAAR PQVQLVESGG GVVQPGRSLR

LSCAASGFTF SSRGMHWVRQ APGKGLEWVA VIGYDGQEKY

YADSVKGRFT ISRDNSKNTL YLQMNSLRAE DTAVYYCVKG

PLQEPPYDYG MDVWGQGTTV TVSSGSTSGS GKPGSGEGST

KGEIVMTQSP ATLSVSPGER ATLSCRASQS VSSNLAWYQQ

```
KPGQAPRLLI YSASTRATGI PARFSGSGSG TEFTLTISSL

QSEDFAVYYC QQHHVWPLTF GGGTKVEIKR AAALDNEKSN

GTIIHVKGKH LCPSPLFPGP SKPFWVLVVV GGVLACYSLL

VTVAFIIFWV RSKRSRLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL

PPR

Clone RD-26578 CAR DNA LxH
                                              (SEQ ID NO: 409)
ATGGCACTCCCCGTAACTGCTCTGCTGCTGCCGTTGGCATTGCTCCTGCACGCCGCACGCC

CGGAAATAGTGATGACGCAGTCTCCAGCCACCCTGTCTGTGTCTCCAGGGGAAAGAGCCAC

CCTCTCCTGCAGGGCCAGTCAGAGTGTTAGCAGCAACTTAGCCTGGTACCAGCAGAAACCT

GGCCAGGCTCCCAGGCTCCTCATCTATAGCGCATCCACCAGGGCCACTGGTATCCCAGCCA

GGTTCAGTGGCAGTGGGTCTGGGACAGAGTTCACTCTCACCATCAGCAGCCTGCAGTCTGA

AGATTTTGCAGTTTATTACTGTCAGCAGCACCACGTCTGGCCTCTCACTTTTGGCGGAGGG

ACCAAGGTTGAGATCAAACGGGGGTCTACATCCGGCTCCGGGAAGCCCGGAAGTGGCGAAG

GTAGTACAAAGGGGCAGGTGCAGCTGGTGGAGTCTGGGGGAGGCGTGGTCCAGCCTGGGAG

GTCCCTGAGACTCTCCTGTGCAGCGTCTGGATTCACCTTCAGTAGCCGTGGCATGCACTGG

GTCCGCCAGGCTCCAGGCAAGGGGCTGGAGTGGGTGGCAGTTATAGGGTATGATGGACAGG

AGAAATACTATGCAGACTCCGTGAAGGGCCGATTCACCATCTCCAGAGACAATTCCAAGAA

CACGCTGTATCTGCAAATGAACAGCCTGAGAGCCGAGGACACGGCGGTGTACTACTGCGTC

AAGGGGCCGTTGCAGGAGCCGCCATACGATTATGGAATGGACGTATGGGGCCAGGGAACAA

CTGTCACCGTCTCCTCAGCCGCTGCCCTTGATAATGAAAAGTCAAACGGAACAATCATTCA

CGTGAAGGGCAAGCACCTCTGTCCGTCACCCTTGTTCCCTGGTCCATCCAAGCCATTCTGG

GTGTTGGTCGTAGTGGGTGGAGTCCTCGCTTGTTACTCTCTGCTCGTCACCGTGGCTTTTA

TAATCTTCTGGGTTAGATCCAAAAGAAGCCGCCTGCTCCATAGCGATTACATGAATATGAC

TCCACGCCGCCCTGGCCCCACAAGGAAACACTACCAGCCTTACGCACCACCTAGAGATTTC

GCTGCCTATCGGAGCAGGGTGAAGTTTTCCAGATCTGCAGATGCACCAGCGTATCAGCAGG

GCCAGAACCAACTGTATAACGAGCTCAACCTGGGACGCAGGGAAGAGTATGACGTTTTGGA

CAAGCGCAGAGGACGGGACCCTGAGATGGGTGGCAAACCAAGACGAAAAAACCCCCAGGAG

GGTCTCTATAATGAGCTGCAGAAGGATAAGATGGCTGAAGCCTATTCTGAAATAGGCATGA

AAGGAGAGCGGAGAAGGGGAAAAGGGCACGACGGTTTGTACCAGGGACTCAGCACTGCTAC

GAAGGATACTTATGACGCTCTCCACATGCAAGCCCTGCCACCTAGG

Clone RD-26578 CAR LxH
                                              (SEQ ID NO: 410)
MALPVTALLL PLALLLHAAR PEIVMTQSPA TLSVSPGERA

TLSCRASQSV SSNLAWYQQK PGQAPRLLIY SASTRATGIP

ARFSGSGSGT EFTLTISSLQ SEDFAVYYCQ QHHVWPLTFG

GGTKVEIKRG STSGSGKPGS GEGSTKGQVQ LVESGGGVVQ

PGRSLRLSCA ASGFTFSSRG MHWVRQAPGK GLEWVAVIGY

DGQEKYYADS VKGRFTISRD NSKNTLYLQM NSLRAEDTAV
```

-continued

YYCVKGPLQE PPYDYGMDVW GQGTTVTVSS AAALDNEKSN

GTIIHVKGKH LCPSPLFPGP SKPFWVLVVV GGVLACYSLL

VTVAFIIFWV RSKRSRLLHS DYMNMTPRRP GPTRKHYQPY

APPRDFAAYR SRVKFSRSAD APAYQQGQNQ LYNELNLGRR

EEYDVLDKRR GRDPEMGGKP RRKNPQEGLY NELQKDKMAE

AYSEIGMKGE RRRGKGHDGL YQGLSTATKD TYDALHMQAL

PPR

---

We claim:

1. An isolated polynucleotide encoding an antibody, a chimeric antigen receptor (CAR), or a T cell receptor (TCR) comprising an antigen binding molecule that specifically binds to B-cell maturation antigen (BCMA), wherein the antigen binding molecule comprises:
   (a) a VH CDR1 region comprising the amino acid sequence of SEQ ID NO: 301; a VH CDR2 region comprising the amino acid sequence of SEQ ID NO: 302; a VH CDR3 region comprising the amino acid sequence of SEQ ID NO: 303; a VL CDR1 region comprising the amino acid sequence of SEQ ID NO: 306; a VL CDR2 region comprising the amino acid sequence of SEQ ID NO: 307; and a VL CDR3 region comprising the amino acid sequence of SEQ ID NO: 308;
   (b) a VH CDR1 region comprising the amino acid sequence of SEQ ID NO: 315; a VH CDR2 region comprising the amino acid sequence of SEQ ID NO: 316; a VH CDR3 region comprising the amino acid sequence of SEQ ID NO: 317; a VL CDR1 region comprising the amino acid sequence of SEQ ID NO: 320; a VL CDR2 region comprising the amino acid sequence of SEQ ID NO: 321; and a VL CDR3 region comprising the amino acid sequence of SEQ ID NO: 322;
   (c) a VH CDR1 region comprising the amino acid sequence of SEQ ID NO: 357; a VH CDR2 region comprising the amino acid sequence of SEQ ID NO: 358; a VH CDR3 region comprising the amino acid sequence of SEQ ID NO: 359; a VL CDR1 region comprising the amino acid sequence of SEQ ID NO: 362; a VL CDR2 region comprising the amino acid sequence of SEQ ID NO: 363; and a VL CDR3 region comprising the amino acid sequence of SEQ ID NO: 364;
   (d) a VH CDR1 region comprising the amino acid sequence of SEQ ID NO: 385; a VH CDR2 region comprising the amino acid sequence of SEQ ID NO: 386; a VH CDR3 region comprising the amino acid sequence of SEQ ID NO: 387; a VL CDR1 region comprising the amino acid sequence of SEQ ID NO: 390; a VL CDR2 region comprising the amino acid sequence of SEQ ID NO: 391; and a VL CDR3 region comprising the amino acid sequence of SEQ ID NO: 392.

2. The polynucleotide of claim 1, wherein the antigen binding molecule comprises:
   (a) a VH comprising the amino acid sequence of SEQ ID NO: 300; and a VL comprising the amino acid sequence of SEQ ID NO: 305;
   (b) a VH comprising the amino acid sequence of SEQ ID NO: 314; and a VL comprising the amino acid sequence of SEQ ID NO: 319;
   (c) a VH comprising the amino acid sequence of SEQ ID NO: 356; and a VL comprising the amino acid sequence of SEQ ID NO: 361;
   (d) a VH comprising the amino acid sequence of SEQ ID NO: 384; and a VL comprising the amino acid sequence of SEQ ID NO: 389.

3. The polynucleotide of claim 2, which comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 299, 313, 355, and 383, respectively, wherein the nucleotide sequence encodes the VH of the antigen binding molecule.

4. The polynucleotide of claim 2, which comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 304, 318, 360, and 388, respectively, wherein the nucleotide sequence encodes the VL of the antigen binding molecule.

5. The polynucleotide of claim 1, wherein the antigen binding molecule is selected from the group consisting of scFv, Fab, Fab', Fv, F(ab')2, dAb, and any combination thereof.

6. The polynucleotide of claim 1, wherein the VH and the VL are connected by a linker.

7. The polynucleotide of claim 1, wherein the TCR further comprises a CDR4.

8. The polynucleotide of claim 1, wherein the TCR further comprises a constant region.

9. The polynucleotide of claim 1, wherein the CAR comprises a transmembrane domain.

10. The polynucleotide of claim 9, wherein the CAR comprises a hinge region between the transmembrane domain and the antigen binding molecule.

11. The polynucleotide of claim 1, wherein the CAR or TCR comprises a costimulatory region.

12. The polynucleotide of claim 11, wherein the costimulatory region is a signaling region of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1)(CD11a/CD18), CD3 gamma, CD3 delta, CD3 epsilon, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD (CD11d), ITGAE (CD103), ITGAL (CD11a), LFA-1, ITGAM (CD11b), ITGAX (CD11C), ITGB1, CD29, ITGB2, CD18, ITGB7, NKG2D, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, or any combination thereof.

13. The polynucleotide of claim 1, wherein the CAR or TCR comprises an activation domain.

14. The polynucleotide of claim 1, wherein the CAR or TCR further comprises a leader peptide.

15. The polynucleotide of claim 1 encoding a CAR comprising the amino acid sequence of SEQ ID NO: 310, 324, 366, or 394.

16. A vector comprising the polynucleotide of claim 1.

17. An antibody, CAR, or TCR encoded by the polynucleotide of claim 1.

18. A cell comprising the polynucleotide of claim 1, the vector of claim 16, the antibody, CAR, or TCR of claim 17, or any combination thereof.

19. A composition comprising the polynucleotide of claim 1, the vector of claim 16, or the antibody, CAR, or TCR of claim 17.

20. A composition comprising the cell of claim 18.

21. A method of inducing an immunity against a tumor comprising administering to a subject an effective amount of a T-cell or NK-cell comprising one or more of following: the polynucleotide of claim 1, the vector of claim 16, the CAR of claim 17, and the TCR of claim 17; wherein the antigen binding molecule of the CAR or TCR, including that encoded by the polynucleotide of claim 1, is linked to an intracellular signaling domain comprising at least one costimulatory domain and at least one activating domain.

22. A method of treating a cancer in a subject in need thereof comprising administering to the subject an effective amount of T-cell or NK-cell comprising one or more of following: the polynucleotide of claim 1, the vector of claim 16, the CAR of claim 17, and the TCR of claim 17; wherein the antigen binding molecule of the CAR or TCR, including that encoded by the polynucleotide of claim 1, is linked to an intracellular signaling domain comprising at least one costimulatory domain and at least one activating domain.

* * * * *

SEQUENCE LISTING

<160> NUMBER OF SEQ ID NOS: 413

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      VH FR1 peptide

```
<400> SEQUENCE: 4

Gln Leu Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 9
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 9

Gly Phe Thr Phe Ser Ser Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 10

Gly Phe Thr Phe Ser Ser Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 11

Gly Tyr Thr Phe Thr Ser Tyr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 12

Gly Gly Ser Ile Ser Ser Ser Ser Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 13

Gly Phe Thr Phe Ser Ser Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 14

Gly Phe Thr Phe Ser Ser Tyr
```

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 15

Gly Gly Thr Phe Ser Ser Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 16

Gly Phe Thr Phe Ser Ser Tyr
1               5

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 17

Ala Met Ser Trp Val Arg Gln Ala Pro Gly Lys Gly Leu Glu Trp Val
1               5                   10                  15
Ser

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 18

Gly Met His Trp Val Arg Gln Ala Pro Gly Lys Gly Leu Glu Trp Val
1               5                   10                  15
Ala

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 19

Tyr Met His Trp Val Arg Gln Ala Pro Gly Gln Gly Leu Glu Trp Met
1               5                   10                  15
Gly

```
<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 20

Tyr Trp Gly Trp Ile Arg Gln Pro Pro Gly Lys Gly Leu Glu Trp Ile
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 21

Ser Met Asn Trp Val Arg Gln Ala Pro Gly Lys Gly Leu Glu Trp Val
1               5                   10                  15

Ser

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 22

Gly Met His Trp Val Arg Gln Ala Pro Gly Lys Gly Leu Glu Trp Val
1               5                   10                  15

Ala

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 23

Ala Ile Ser Trp Val Arg Gln Ala Pro Gly Gln Gly Leu Glu Trp Met
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 24

Gly Met His Trp Val Arg Gln Ala Pro Gly Lys Gly Leu Glu Trp Val
1               5                   10                  15

Ala
```

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide

<400> SEQUENCE: 25

Ala Ile Ser Gly Ser Gly Gly Ser Thr Tyr Tyr Ala Asp Ser Val Lys
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide

<400> SEQUENCE: 26

Val Ile Ser Tyr Asp Gly Ser Asn Lys Tyr Tyr Ala Asp Ser Val Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide

<400> SEQUENCE: 27

Ile Ile Asn Pro Gly Gly Gly Ser Thr Ser Tyr Ala Gln Lys Phe Gln
1               5                   10                  15

Gly

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      VH CDR2 peptide

<400> SEQUENCE: 28

Ser Ile Ser Tyr Ser Gly Ser Thr Tyr Tyr Asn Pro Ser Leu Lys Ser
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide

<400> SEQUENCE: 29

Thr Ile Ser Ser Ser Ser Ser Thr Ile Tyr Tyr Ala Asp Ser Val Lys
1               5                   10                  15

Gly

```
<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide

<400> SEQUENCE: 30

Val Ile Ser Tyr Asp Gly Ser Asn Lys Tyr Tyr Ala Asp Ser Val Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide

<400> SEQUENCE: 31

Gly Ile Ile Pro Ile Phe Gly Thr Ala Asn Tyr Ala Gln Lys Phe Gln
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide

<400> SEQUENCE: 32

Val Ile Ser Tyr Asp Gly Ser Asn Lys Tyr Tyr Ala Asp Ser Val Lys
1               5                   10                  15

Gly

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 33

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 34

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
```

20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 35

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 36

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 37

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 38

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

```
<400> SEQUENCE: 39

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 40

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 41

Ala Arg Ala Glu Met Gly Ala Val Phe Asp Ile
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 42

Ala Arg Asp Gly Thr Tyr Leu Gly Gly Leu Trp Tyr Phe Asp Leu
1               5                   10                  15

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 43

Ala Arg Glu Ser Trp Pro Met Asp Val
1               5

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 44

Ala Arg Gly Arg Gly Tyr Ala Thr Ser Leu Ala Phe Asp Ile
```

```
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 45

Ala Arg Gly Ser Gln Glu His Leu Ile Phe Asp Tyr
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 46

Ala Arg Thr Asp Phe Trp Ser Gly Ser Pro Pro Gly Leu Asp Tyr
1               5                   10                  15

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 47

Ala Arg Thr Pro Glu Tyr Ser Ser Ser Ile Trp His Tyr Tyr Tyr Gly
1               5                   10                  15

Met Asp Val

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 48

Val Lys Gly Pro Leu Gln Glu Pro Pro Tyr Asp Tyr Gly Met Asp Val
1               5                   10                  15

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 49

Trp Gly Gln Gly Thr Met Val Thr Val Ser Ser
1               5                   10

<210> SEQ ID NO 50
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      VH FR4 peptide

<400> SEQUENCE: 50

Trp Gly Arg Gly Thr Leu Val Thr Val Ser Ser
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 51

Trp Gly Gln Gly Thr Thr Val Thr Val Ser Ser
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 52

Trp Gly Gln Gly Thr Met Val Thr Val Ser Ser
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 53

Trp Gly Gln Gly Thr Leu Val Thr Val Ser Ser
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 54

Trp Gly Gln Gly Thr Leu Val Thr Val Ser Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 55

Trp Gly Gln Gly Thr Thr Val Thr Val Ser Ser
1               5                   10
```

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 56

Trp Gly Gln Gly Thr Thr Val Thr Val Ser Ser
1               5                   10

<210> SEQ ID NO 57
<211> LENGTH: 354
<212> TYPE: DNA
<213> ORGANISM: Artificial Sequence
<220> FEATURE:
<223> OTHER INFORMATION: Description of Artificial Sequence: Synthetic
      VH polynucleotide

<400> SEQUENCE: 57
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggcggtgt actactgcgc aagagccgag     300
atgggagccg tattcgacat atggggtcag ggtacaatgg tcaccgtctc ctca           354

<210> SEQ ID NO 58
<211> LENGTH: 366
<212> TYPE: DNA
<213> ORGANISM: Artificial Sequence
<220> FEATURE:
<223> OTHER INFORMATION: Description of Artificial Sequence: Synthetic
      VH polynucleotide

<400> SEQUENCE: 58
caggtgcagc tggtggagtc tgggggaggc gtggtccagc ctggggaggtc cctgagactc     60 tcctgtgcag cgtctggatt caccttcagt agctatggca tgcactgggt ccgccaggct    120
ccaggcaagg ggctggagtg ggtggcagtt atatcgtatg atggaagtaa taaatactat    180
gcagactccg tgaagggccg attcaccatc tccagagaca attccaagaa cacgctgtat    240
ctgcaaatga acagcctgag agccgaggac acggcggtgt actactgcgc agagacggt    300 acttatctag gtggtctctg gtacttcgac ttatggggga gaggtacctt ggtcaccgtc    360
tcctca                                                                366

<210> SEQ ID NO 59
<211> LENGTH: 348
<212> TYPE: DNA
<213> ORGANISM: Artificial Sequence
<220> FEATURE:
<223> OTHER INFORMATION: Description of Artificial Sequence: Synthetic
      VH polynucleotide

<400> SEQUENCE: 59
caggtgcagc tggtgcagtc tggggctgag gtgaagaagc ctggggcctc agtgaaggtt      60
tcctgcaagg catctggata caccttcacc agctactata tgcactgggt gcgacaggcc    120
cctggacaag gcttgagtg gatgggaata atcaaccctg gtggtggtag cacaagctac    180

```
gcacagaagt tccagggcag agtcaccatg accagggaca cgtccacgag cacagtctac    240
atggagctga gcagcctgag atctgaggac acggcggtgt actactgcgc cagagagagt    300
tggccaatgg acgtatgggg ccagggaaca actgtcaccg tctcctca                 348
```

<210> SEQ ID NO 60
<211> LENGTH: 366
<212> TYPE: DNA
<213> ORGANISM: Artificial Sequence
<220> FEATURE:
<223> OTHER INFORMATION: Description of Artificial Sequence: Synthetic
      VH polynucleotide

<400> SEQUENCE: 60

```
cagctgcagc tgcaggagtc gggcccagga ctggtgaagc cttcggagac cctgtccctc    60
acctgcactg tctctggtgg ctccatcagc agtagtagtt actactgggg ctggatccgc    120
cagcccccag gaaggggct ggagtggatt gggagtatct cctatagtgg gagcacctac    180
tacaacccgt ccctcaagag tcgagtcacc atatccgtag acacgtccaa gaaccagttc    240
tccctgaagc tgagttctgt gaccgccgca gacacggcgg tgtactactg cgccagaggc    300
aggggatatg caaccagctt agccttcgat atctggggtc agggtacaat ggtcaccgtc    360
tcctca                                                               366
```

<210> SEQ ID NO 61
<211> LENGTH: 357
<212> TYPE: DNA
<213> ORGANISM: Artificial Sequence
<220> FEATURE:
<223> OTHER INFORMATION: Description of Artificial Sequence: Synthetic
      VH polynucleotide

<400> SEQUENCE: 61

```
gaggtgcagc tggtggagtc tgggggaggc ttggtacagc ctggggggtc cctgagactc    60
tcctgtgcag cctctggatt caccttcagt agctatagca tgaactgggt ccgccaggct    120
ccagggaagg ggctggagtg ggtttcaacc attagtagta gtagtagtac catatactac    180
gcagactctg tgaagggccg attcaccatc tccagagaca tgccaagaa ctcactgtat     240 ctgcaaatga acagcctgag agctgaggac acggcggtgt actactgcgc cagaggttct    300
caggagcacc tgattttcga ttattgggga caggtacat ggtcaccgt ctcctca         357
```

<210> SEQ ID NO 62
<211> LENGTH: 366
<212> TYPE: DNA
<213> ORGANISM: Artificial Sequence
<220> FEATURE:
<223> OTHER INFORMATION: Description of Artificial Sequence: Synthetic
      VH polynucleotide

<400> SEQUENCE: 62

```
caggtgcagc tggtggagtc tgggggaggc gtggtccagc ctggggaggtc cctgagactc    60 tcctgtgcag cgtctggatt caccttcagt agctatgca tgcactgggt ccgccaggct      120
ccaggcaagg ggctggagtg ggtggcagtt atatcgtatg atggaagtaa taaatactat     180
gcagactccg tgaagggccg attcaccatc tccagagaca attccaagaa cacgctgtat     240
ctgcaaatga acagcctgag agccgaggac acggcggtgt actactgcgc cagaactgac    300
ttctggagcg gatcccctcc aggcttagat tactggggac agggtacatt ggtcaccgtc    360
tcctca                                                               366
```

<210> SEQ ID NO 63
<211> LENGTH: 378
<212> TYPE: DNA
<213> ORGANISM: Artificial Sequence
<220> FEATURE:
<223> OTHER INFORMATION: Description of Artificial Sequence: Synthetic
      VH polynucleotide

<400> SEQUENCE: 63
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac      180
gcacagaagt tccagggcag agtcacgatt accgcggacg aatccacgag cacagcctac     240
atggagctga gcagcctgag atctgaggac acggcggtgt actactgcgc cagaactcct     300
gaatactcct ccagcatatg gcactattac tacggcatgg acgtatgggg ccagggaaca     360
actgtcaccg tctcctca                                                   378

<210> SEQ ID NO 64
<211> LENGTH: 369
<212> TYPE: DNA
<213> ORGANISM: Artificial Sequence
<220> FEATURE:
<223> OTHER INFORMATION: Description of Artificial Sequence: Synthetic
      VH polynucleotide

<400> SEQUENCE: 64
caggtgcagc tggtggagtc tgggggaggc gtggtccagc ctggggaggtc cctgagactc     60 tcctgtgcag cgtctggatt caccttcagt agctatggca tgcactgggt ccgccaggct    120
ccaggcaagg gctggagtg gtggcagtt atatcgtatg atggaagtaa taatactat       180 gcagactccg tgaagggccg attcaccatc tccagagaca attccaagaa cacgctgtat    240
ctgcaaatga acagcctgag agccgaggac acggcggtgt actactgcgt caaggggccg    300
ttgcaggagc cgccatacga ttatggaatg gacgtatggg gccagggaac aactgtcacc    360
gtctcctca                                                             369

<210> SEQ ID NO 65
<211> LENGTH: 118
<212> TYPE: PRT
<213> ORGANISM: Artificial Sequence
<220> FEATURE:
<223> OTHER INFORMATION: Description of Artificial Sequence: Synthetic
      VH polypeptide

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Ala Glu Met Gly Ala Val Phe Asp Ile Trp Gly Gln Gly Thr
            100                 105                 110

Met Val Thr Val Ser Ser
        115
```

<210> SEQ ID NO 66
<211> LENGTH: 122
<212> TYPE: PRT
<213> ORGANISM: Artificial Sequence
<220> FEATURE:
<223> OTHER INFORMATION: Description of Artificial Sequence: Synthetic
      VH polypeptide

<400> SEQUENCE: 66

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser
        115                 120
```

<210> SEQ ID NO 67
<211> LENGTH: 116
<212> TYPE: PRT
<213> ORGANISM: Artificial Sequence
<220> FEATURE:
<223> OTHER INFORMATION: Description of Artificial Sequence: Synthetic
      VH polypeptide

<400> SEQUENCE: 67

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Gly Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
            100                 105                 110

Thr Val Ser Ser
        115
```

<210> SEQ ID NO 68
<211> LENGTH: 122

```
<212> TYPE: PRT
<213> ORGANISM: Artificial Sequence
<220> FEATURE:
<223> OTHER INFORMATION: Description of Artificial Sequence: Synthetic
      VH polypeptide

<400> SEQUENCE: 68

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Gly Tyr Ala Thr Ser Leu Ala Phe Asp Ile Trp
            100                 105                 110

Gly Gln Gly Thr Met Val Thr Val Ser Ser
        115                 120

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
      VH polypeptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Thr Ile Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gln Glu His Leu Ile Phe Asp Tyr Trp Gly Gln Gly
            100                 105                 110

Thr Leu Val Thr Val Ser Ser
        115

<210> SEQ ID NO 70
<211> LENGTH: 122
<212> TYPE: PRT
<213> ORGANISM: Artificial Sequence
<220> FEATURE:
<223> OTHER INFORMATION: Description of Artificial Sequence: Synthetic
      VH polypeptide

<400> SEQUENCE: 70

Gln Val Gln Leu Val Glu Ser Gly Gly Gly Val Val Gln Pro Gly Arg
```

```
1               5                   10                  15
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Phe Trp Ser Gly Ser Pro Pro Gly Leu Asp Tyr Trp
            100                 105                 110

Gly Gln Gly Thr Leu Val Thr Val Ser Ser
            115                 120
```

<210> SEQ ID NO 71
<211> LENGTH: 126
<212> TYPE: PRT
<213> ORGANISM: Artificial Sequence
<220> FEATURE:
<223> OTHER INFORMATION: Description of Artificial Sequence: Synthetic
      VH polypeptide

<400> SEQUENCE: 71

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Glu Tyr Ser Ser Ser Ile Trp His Tyr Tyr Tyr Gly
            100                 105                 110

Met Asp Val Trp Gly Gln Gly Thr Thr Val Thr Val Ser Ser
            115                 120                 125
```

<210> SEQ ID NO 72
<211> LENGTH: 123
<212> TYPE: PRT
<213> ORGANISM: Artificial Sequence
<220> FEATURE:
<223> OTHER INFORMATION: Description of Artificial Sequence: Synthetic
      VH polypeptide

<400> SEQUENCE: 72

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Lys Gly Pro Leu Gln Glu Pro Pro Tyr Asp Tyr Gly Met Asp Val
                100                 105                 110

Trp Gly Gln Gly Thr Thr Val Thr Val Ser Ser
            115                 120

<210> SEQ ID NO 73
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 73

Glu Ile Val Leu Thr Gln Ser Pro Ala Thr Leu Ser Leu Ser Pro Gly
 1               5                  10                  15

Glu Arg Ala Thr Leu Ser Cys
            20

<210> SEQ ID NO 74
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 74

Asp Ile Val Met Thr Gln Ser Pro Leu Ser Leu Pro Val Thr Pro Gly
 1               5                  10                  15

Glu Pro Ala Ser Ile Ser Cys
            20

<210> SEQ ID NO 75
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 75

Glu Ile Val Met Thr Gln Ser Pro Ala Thr Leu Ser Val Ser Pro Gly
 1               5                  10                  15

Glu Arg Ala Thr Leu Ser Cys
            20

<210> SEQ ID NO 76
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 76

Glu Ile Val Leu Thr Gln Ser Pro Ala Thr Leu Ser Leu Ser Pro Gly
 1               5                  10                  15
```

Glu Arg Ala Thr Leu Ser Cys
            20

<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 78

Asp Ile Gln Leu Thr Gln Ser Pro Ser Ser Val Ser Ala Ser Val Gly
1               5                   10                  15

Asp Arg Val Thr Ile Thr Cys
            20

<210> SEQ ID NO 79
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 79

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence: Synthetic
      VL FR1 peptide

<400> SEQUENCE: 80

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR1 peptide

```
<400> SEQUENCE: 81

Arg Ala Ser Gln Ser Val Ser Arg Tyr Leu Ala
1               5                   10

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      VL CDR1 peptide

<400> SEQUENCE: 82

Arg Ser Ser Gln Ser Leu Leu His Ser Asn Gly Tyr Asn Tyr Leu Asp
1               5                   10                  15

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR1 peptide

<400> SEQUENCE: 83

Arg Ala Ser Gln Ser Val Ser Ser Asn Leu Ala
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR1 peptide

<400> SEQUENCE: 84

Arg Ala Ser Gln Ser Val Ser Ser Tyr Leu Ala
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR1 peptide

<400> SEQUENCE: 85

Arg Ala Ser Gln Ser Val Ser Arg Tyr Leu Ala
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR1peptide

<400> SEQUENCE: 86

Arg Ala Ser Gln Gly Ile Ser Ser Trp Leu Ala
1               5                   10

<210> SEQ ID NO 87
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      VL CDR1 peptide

<400> SEQUENCE: 87

Lys Ser Ser Gln Ser Val Leu Tyr Ser Ser Asn Asn Lys Asn Tyr Leu
1               5                   10                  15

Ala

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR1 peptide

<400> SEQUENCE: 88

Arg Ala Ser Gln Ser Val Ser Ser Asn Leu Ala
1               5                   10

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 89

Trp Tyr Gln Gln Lys Pro Gly Gln Ala Pro Arg Leu Leu Ile Tyr
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 90

Trp Tyr Leu Gln Lys Pro Gly Gln Ser Pro Gln Leu Leu Ile Tyr
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 91

Trp Tyr Gln Gln Lys Pro Gly Gln Ala Pro Arg Leu Leu Ile Tyr
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 92
```

Trp Tyr Gln Gln Lys Pro Gly Gln Ala Pro Arg Leu Leu Ile Tyr
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 93

Trp Tyr Gln Gln Lys Pro Gly Gln Ala Pro Arg Leu Leu Ile Tyr
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 94

Trp Tyr Gln Gln Lys Pro Gly Lys Ala Pro Lys Leu Leu Ile Tyr
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 95

Trp Tyr Gln Gln Lys Pro Gly Gln Pro Pro Lys Leu Leu Ile Tyr
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      VL FR2 peptide

<400> SEQUENCE: 96

Trp Tyr Gln Gln Lys Pro Gly Gln Ala Pro Arg Leu Leu Ile Tyr
1               5                   10                  15

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 97

Asp Ala Ser Asn Arg Ala Thr
1               5

<210> SEQ ID NO 98
<211> LENGTH: 7
<212> TYPE: PRT
<213> ORGANISM: Artificial Sequence

```
<220> FEATURE:
<223> OTHER INFORMATION: Description of Artificial Sequence: Synthetic
      VL CDR2 peptide

<400> SEQUENCE: 98

Leu Gly Ser Asn Arg Ala Ser
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 99

Gly Ala Ser Thr Arg Ala Thr
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 100

Asp Ala Ser Asn Arg Ala Thr
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 101

Asp Ala Ser Asn Arg Ala Thr
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 102

Gly Ala Ser Ser Leu Gln Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 103

Trp Ala Ser Thr Arg Glu Ser
1               5
```

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide

<400> SEQUENCE: 104

Ser Ala Ser Thr Arg Ala Thr
1               5

<210> SEQ ID NO 105
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 105

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
                20                  25                  30

<210> SEQ ID NO 106
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 106

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
                20                  25                  30

<210> SEQ ID NO 107
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 107

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
                20                  25                  30

<210> SEQ ID NO 108
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 108

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 109
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 109

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 110

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 111
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 111

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Description of Artificial Sequence: Synthetic
      VL FR3 polypeptide

<400> SEQUENCE: 112

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide

```
<400> SEQUENCE: 113

Gln Gln Arg Ile Ser Trp Pro Phe Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 114

Met Gln Gly Leu Gly Leu Pro Leu Thr
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 115

Gln Gln Tyr Ala Ala Tyr Pro Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 116

Gln Gln Arg His Val Trp Pro Pro Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 117

Gln Gln Arg Phe Tyr Tyr Pro Trp Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 118

Gln Gln Ile Tyr Thr Phe Pro Phe Thr
1               5

<210> SEQ ID NO 119
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 119

Gln Gln Phe Ala His Thr Pro Phe Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide

<400> SEQUENCE: 120

Gln Gln His His Val Trp Pro Leu Thr
1               5

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 121

Phe Gly Gly Gly Thr Lys Val Glu Ile Lys
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 122

Phe Gly Gly Gly Thr Lys Val Glu Ile Lys
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 123

Phe Gly Gly Gly Thr Lys Val Glu Ile Lys
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 124

Phe Gly Gly Gly Thr Lys Val Glu Ile Lys
```

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 125

Phe Gly Gly Gly Thr Lys Val Glu Ile Lys
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 126

Phe Gly Gly Gly Thr Lys Val Glu Ile Lys
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 127

Phe Gly Gly Gly Thr Lys Val Glu Ile Lys
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      VL FR4 peptide

<400> SEQUENCE: 128

Phe Gly Gly Gly Thr Lys Val Glu Ile Lys
1               5                   10

<210> SEQ ID NO 129
<211> LENGTH: 321
<212> TYPE: DNA
<213> ORGANISM: Artificial Sequence
<220> FEATURE:
<223> OTHER INFORMATION: Description of Artificial Sequence: Synthetic
      VL polynucleotide

<400> SEQUENCE: 129
gaaattgtgt tgacacagtc tccagccacc ctgtctttgt ctccagggga aagagccacc      60
ctctcctgca gggccagtca gagtgttagc aggtacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag agaatctcct ggcctttcac ttttggcgga    300

```
gggaccaagg ttgagatcaa a                                              321
```

<210> SEQ ID NO 130
<211> LENGTH: 336
<212> TYPE: DNA
<213> ORGANISM: Artificial Sequence
<220> FEATURE:
<223> OTHER INFORMATION: Description of Artificial Sequence: Synthetic
      VL polynucleotide

<400> SEQUENCE: 130

```
gatattgtga tgactcagtc tccactctcc ctgcccgtca cccctggaga gccggcctcc     60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcagggact cggcctccct   300
ctcacttttg gcggagggac caaggttgag atcaaa                             336
```

<210> SEQ ID NO 131
<211> LENGTH: 318
<212> TYPE: DNA
<213> ORGANISM: Artificial Sequence
<220> FEATURE:
<223> OTHER INFORMATION: Description of Artificial Sequence: Synthetic
      VL polynucleotide

<400> SEQUENCE: 131

```
gaaatagtga tgacgcagtc tccagccacc ctgtctgtgt ctccagggga aagagccacc     60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tacgccgcct accctacttt tggcggaggg   300
accaaggttg agatcaaa                                                 318
```

<210> SEQ ID NO 132
<211> LENGTH: 321
<212> TYPE: DNA
<213> ORGANISM: Artificial Sequence
<220> FEATURE:
<223> OTHER INFORMATION: Description of Artificial Sequence: Synthetic
      VL polynucleotide

<400> SEQUENCE: 132

```
gaaattgtgt tgacacagtc tccagccacc ctgtctttgt ctccagggga aagagccacc     60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag agacacgtct ggcctcctac ttttggcgga   300
gggaccaagg ttgagatcaa a                                             321
```

<210> SEQ ID NO 133
<211> LENGTH: 321
<212> TYPE: DNA
<213> ORGANISM: Artificial Sequence
<220> FEATURE:
<223> OTHER INFORMATION: Description of Artificial Sequence: Synthetic
      VL polynucleotide

<400> SEQUENCE: 133

```
gaaattgtgt tgacacagtc tccagccacc ctgtctttgt ctccagggga aagagccacc    60
ctctcctgca gggccagtca gagtgttagc aggtacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag agattctact acccttggac ttttggcgga   300
gggaccaagg ttgagatcaa a                                             321
```

<210> SEQ ID NO 134
<211> LENGTH: 321
<212> TYPE: DNA
<213> ORGANISM: Artificial Sequence
<220> FEATURE:
<223> OTHER INFORMATION: Description of Artificial Sequence: Synthetic
      VL polynucleotide

<400> SEQUENCE: 134

```
gacatccagt tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatggt gcatccagtt gcaaagtggg gtcccatca    180
aggttcagcg gcagtggatc tgggacagat ttcactctca ccatcagcag cctgcagcct   240
gaagattttg caacttatta ctgtcagcag atatacacct tccctttcac ttttggcgga   300
gggaccaagg ttgagatcaa a                                             321
```

<210> SEQ ID NO 135
<211> LENGTH: 339
<212> TYPE: DNA
<213> ORGANISM: Artificial Sequence
<220> FEATURE:
<223> OTHER INFORMATION: Description of Artificial Sequence: Synthetic
      VL polynucleotide

<400> SEQUENCE: 135

```
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcagtt cgcccacact   300
cctttcactt ttggcggagg gaccaaggtt gagatcaaa                          339
```

<210> SEQ ID NO 136
<211> LENGTH: 321
<212> TYPE: DNA
<213> ORGANISM: Artificial Sequence
<220> FEATURE:
<223> OTHER INFORMATION: Description of Artificial Sequence: Synthetic
      VL polynucleotide

<400> SEQUENCE: 136

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatagc gcatccacca gggccactgg tatcccagcc   180
aggttcagtg gcagtgggtc tgggacagag ttcactctca ccatcagcag cctgcagtct   240
```

```
gaagattttg cagtttatta ctgtcagcag caccacgtct ggcctctcac ttttggcgga      300
gggaccaagg ttgagatcaa a                                                321
```

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 137

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Ser Trp Pro Phe
                85                  90                  95

Thr Phe Gly Gly Gly Thr Lys Val Glu Ile Lys
            100                 105
```

<210> SEQ ID NO 138
<211> LENGTH: 112
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 138

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gly Leu Pro Leu Thr Phe Gly Gly Gly Thr Lys Val Glu Ile Lys
            100                 105                 110
```

<210> SEQ ID NO 139
<211> LENGTH: 106
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 139

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Ala Tyr Pro Thr
                85                  90                  95

Phe Gly Gly Gly Thr Lys Val Glu Ile Lys
            100                 105

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 140

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg His Val Trp Pro Pro
                85                  90                  95

Thr Phe Gly Gly Gly Thr Lys Val Glu Ile Lys
            100                 105

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 141

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Phe Tyr Tyr Pro Trp
                85                  90                  95
Thr Phe Gly Gly Gly Thr Lys Val Glu Ile Lys
            100                 105
```

<210> SEQ ID NO 142
<211> LENGTH: 107
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 142

```
Asp Ile Gln Leu Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
        35                  40                  45
Tyr Gly Ala Ser Ser Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ile Tyr Thr Phe Pro Phe
                85                  90                  95
Thr Phe Gly Gly Gly Thr Lys Val Glu Ile Lys
            100                 105
```

<210> SEQ ID NO 143
<211> LENGTH: 113
<212> TYPE: PRT
<213> ORGANISM: Artificial Sequence
<220> FEATURE:
<223> OTHER INFORMATION: Description of Artificial Sequence: Synthetic
      VL polypeptide

<400> SEQUENCE: 143

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Phe Ala His Thr Pro Phe Thr Phe Gly Gly Gly Thr Lys Val Glu Ile
            100                 105                 110
Lys
```

<210> SEQ ID NO 144
<211> LENGTH: 107
<212> TYPE: PRT
<213> ORGANISM: Artificial Sequence
<220> FEATURE:

<223> OTHER INFORMATION: Description of Artificial Sequence: Synthetic
      VL polypeptide

<400> SEQUENCE: 144

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95

Thr Phe Gly Gly Gly Thr Lys Val Glu Ile Lys
            100                 105

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide
<220> FEATURE:
<221> NAME/KEY: MISC_FEATURE
<222> LOCATION: (2)..(3)
<223> OTHER INFORMATION: May or may not be present
<220> FEATURE:
<221> NAME/KEY: MOD_RES
<222> LOCATION: (4)..(4)
<223> OTHER INFORMATION: Phe, Gly, Ile or Tyr
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Phe or Ser
<220> FEATURE:
<221> NAME/KEY: MOD_RES
<222> LOCATION: (7)..(7)
<223> OTHER INFORMATION: Ser or Thr

<400> SEQUENCE: 145

Gly Gly Ser Xaa Xaa Xaa Xaa Ser Tyr
1               5

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide
<220> FEATURE:
<221> NAME/KEY: MOD_RES
<222> LOCATION: (1)..(1)
<223> OTHER INFORMATION: Ala, Gly, Ile, Ser, Thr or Val
<220> FEATURE:
<221> NAME/KEY: MOD_RES
<222> LOCATION: (3)..(3)
<223> OTHER INFORMATION: Ile, Asn or Ser
<220> FEATURE:
<221> NAME/KEY: MOD_RES
<222> LOCATION: (4)..(4)

<223> OTHER INFORMATION: Gly, Pro, Ser or Tyr
<220> FEATURE:
<221> NAME/KEY: MOD_RES
<222> LOCATION: (5)..(5)
<223> OTHER INFORMATION: Asp, Gly, Ile or Ser
<220> FEATURE:
<221> NAME/KEY: MOD_RES
<222> LOCATION: (6)..(6)
<223> OTHER INFORMATION: Phe, Gly or Ser
<220> FEATURE:
<221> NAME/KEY: MOD_RES
<222> LOCATION: (7)..(7)
<223> OTHER INFORMATION: Gly, Ser or absent
<220> FEATURE:
<221> NAME/KEY: MOD_RES
<222> LOCATION: (8)..(8)
<223> OTHER INFORMATION: Asn, Ser or Thr
<220> FEATURE:
<221> NAME/KEY: MOD_RES
<222> LOCATION: (9)..(9)
<223> OTHER INFORMATION: Ala, Ile, Lys or Thr
<220> FEATURE:
<221> NAME/KEY: MOD_RES
<222> LOCATION: (10)..(10)
<223> OTHER INFORMATION: Asn, Ser or Tyr
<220> FEATURE:
<221> NAME/KEY: MOD_RES
<222> LOCATION: (12)..(12)
<223> OTHER INFORMATION: Ala or Asn
<220> FEATURE:
<221> NAME/KEY: MOD_RES
<222> LOCATION: (13)..(13)
<223> OTHER INFORMATION: Asp, Pro or Gln
<220> FEATURE:
<221> NAME/KEY: MOD_RES
<222> LOCATION: (14)..(14)
<223> OTHER INFORMATION: Lys or Ser
<220> FEATURE:
<221> NAME/KEY: MOD_RES
<222> LOCATION: (15)..(15)
<223> OTHER INFORMATION: Phe, Leu or Val
<220> FEATURE:
<221> NAME/KEY: MOD_RES
<222> LOCATION: (16)..(16)
<223> OTHER INFORMATION: Lys or Gln
<220> FEATURE:
<221> NAME/KEY: MOD_RES
<222> LOCATION: (17)..(17)
<223> OTHER INFORMATION: Gln or Ser

<400> SEQUENCE: 146

Xaa Ile Xaa Xaa Xaa Xaa Xaa Xaa Xaa Xaa Tyr Xaa Xaa Xaa Xaa Xaa
1               5                   10                  15

Xaa

<210> SEQ ID NO 147
<211> LENGTH: 19
<212> TYPE: PRT
<213> ORGANISM: Artificial Sequence
<220> FEATURE:
<223> OTHER INFORMATION: Description of Artificial Sequence: Synthetic
      VH CDR3 peptide
<220> FEATURE:
<221> NAME/KEY: MOD_RES
<222> LOCATION: (1)..(1)
<223> OTHER INFORMATION: Ala or Val
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
<223> OTHER INFORMATION: Asp, Gly, Thr or absent
<220> FEATURE:
<221> NAME/KEY: MOD_RES

```
<222> LOCATION: (4)..(4)
<223> OTHER INFORMATION: Ala, Asp, Gly, Pro, Arg, Ser or absent
<220> FEATURE:
<221> NAME/KEY: MOD_RES
<222> LOCATION: (5)..(5)
<223> OTHER INFORMATION: Glu, Phe, Gly, Leu, Gln, Thr or absent
<220> FEATURE:
<221> NAME/KEY: MOD_RES
<222> LOCATION: (6)..(6)
<223> OTHER INFORMATION: Glu, Met, Gln, Trp, Tyr or absent
<220> FEATURE:
<221> NAME/KEY: MOD_RES
<222> LOCATION: (7)..(7)
<223> OTHER INFORMATION: Ala, Glu, Leu, Ser or absent
<220> FEATURE:
<221> NAME/KEY: MOD_RES
<222> LOCATION: (8)..(8)
<223> OTHER INFORMATION: Gly, Pro, Ser, Thr or absent
<220> FEATURE:
<221> NAME/KEY: MOD_RES
<222> LOCATION: (9)..(9)
<223> OTHER INFORMATION: Gly, Pro, Ser or absent
<220> FEATURE:
<221> NAME/KEY: MOD_RES
<222> LOCATION: (10)..(10)
<223> OTHER INFORMATION: Ile, Leu, Pro, Tyr or absent
<220> FEATURE:
<221> NAME/KEY: MISC_FEATURE
<222> LOCATION: (11)..(12)
<223> OTHER INFORMATION: May or may not be present
<220> FEATURE:
<221> NAME/KEY: MOD_RES
<222> LOCATION: (13)..(13)
<223> OTHER INFORMATION: Glu, Tyr or absent
<220> FEATURE:
<221> NAME/KEY: MOD_RES
<222> LOCATION: (14)..(14)
<223> OTHER INFORMATION: Asp, Gly, His, Pro, Ser, Trp, Tyr or absent
<220> FEATURE:
<221> NAME/KEY: MOD_RES
<222> LOCATION: (15)..(15)
<223> OTHER INFORMATION: Ala, Gly, Leu, Trp or Tyr
<220> FEATURE:
<221> NAME/KEY: MOD_RES
<222> LOCATION: (16)..(16)
<223> OTHER INFORMATION: Ala, Gly, Ile, Pro, Val or absent
<220> FEATURE:
<221> NAME/KEY: MOD_RES
<222> LOCATION: (17)..(17)
<223> OTHER INFORMATION: Phe, Leu or Met
<220> FEATURE:
<221> NAME/KEY: MOD_RES
<222> LOCATION: (19)..(19)
<223> OTHER INFORMATION: Ile, Leu, Val or Tyr

<400> SEQUENCE: 147

Xaa Xaa Xaa Xaa Xaa Xaa Xaa Xaa Xaa Xaa Trp His Xaa Xaa Xaa Xaa
1               5                   10                  15

Xaa Asp Xaa

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      VL CDR1 peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Ala or Ser
<220> FEATURE:
```

```
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Ile, Leu or Val
<220> FEATURE:
<221> NAME/KEY: MOD_RES
<222> LOCATION: (7)..(7)
<223> OTHER INFORMATION: Leu or Ser
<220> FEATURE:
<221> NAME/KEY: MOD_RES
<222> LOCATION: (8)..(8)
<223> OTHER INFORMATION: His, Tyr or absent
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Asn, Ser or absent
<220> FEATURE:
<221> NAME/KEY: MOD_RES
<222> LOCATION: (11)..(11)
<223> OTHER INFORMATION: Gly, Asn or absent
<220> FEATURE:
<221> NAME/KEY: MISC_FEATURE
<222> LOCATION: (12)..(12)
<223> OTHER INFORMATION: May or may not be present
<220> FEATURE:
<221> NAME/KEY: MOD_RES
<222> LOCATION: (13)..(13)
<223> OTHER INFORMATION: Lys, Tyr or absent
<220> FEATURE:
<221> NAME/KEY: MOD_RES
<222> LOCATION: (14)..(14)
<223> OTHER INFORMATION: Asn, Arg or Ser
<220> FEATURE:
<221> NAME/KEY: MOD_RES
<222> LOCATION: (15)..(15)
<223> OTHER INFORMATION: Asn, Trp or Tyr
<220> FEATURE:
<221> NAME/KEY: MOD_RES
<222> LOCATION: (17)..(17)
<223> OTHER INFORMATION: Ala or Asp

<400> SEQUENCE: 148

Xaa Xaa Ser Gln Xaa Xaa Xaa Xaa Ser Xaa Xaa Asn Xaa Xaa Xaa Leu
1               5                   10                  15

Xaa

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide
<220> FEATURE:
<221> NAME/KEY: MOD_RES
<222> LOCATION: (1)..(1)
<223> OTHER INFORMATION: Asp, Gly, Leu, Ser or Trp
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Asn, Ser or Thr
<220> FEATURE:
<221> NAME/KEY: MOD_RES
<222> LOCATION: (5)..(5)
<223> OTHER INFORMATION: Leu or Arg
```

```
<220> FEATURE:
<221> NAME/KEY: MOD_RES
<222> LOCATION: (6)..(6)
<223> OTHER INFORMATION: Ala, Glu or Gln
<220> FEATURE:
<221> NAME/KEY: MOD_RES
<222> LOCATION: (7)..(7)
<223> OTHER INFORMATION: Ser or Thr

<400> SEQUENCE: 149

Xaa Xaa Ser Xaa Xaa Xaa Xaa
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide
<220> FEATURE:
<221> NAME/KEY: MOD_RES
<222> LOCATION: (1)..(1)
<223> OTHER INFORMATION: Met or Gln
<220> FEATURE:
<221> NAME/KEY: MOD_RES
<222> LOCATION: (3)..(3)
<223> OTHER INFORMATION: Phe, Gly, His, Ile, Arg or Tyr
<220> FEATURE:
<221> NAME/KEY: MOD_RES
<222> LOCATION: (4)..(4)
<223> OTHER INFORMATION: Ala, Phe, His, Ile, Leu or Tyr
<220> FEATURE:
<221> NAME/KEY: MOD_RES
<222> LOCATION: (5)..(5)
<223> OTHER INFORMATION: Ala, Gly, His, Ser, Thr, Val or Tyr
<220> FEATURE:
<221> NAME/KEY: MOD_RES
<222> LOCATION: (6)..(6)
<223> OTHER INFORMATION: Phe, Leu, Thr, Trp or Tyr
<220> FEATURE:
<221> NAME/KEY: MOD_RES
<222> LOCATION: (8)..(8)
<223> OTHER INFORMATION: Phe, Leu, Pro or Trp

<400> SEQUENCE: 150

Xaa Gln Xaa Xaa Xaa Xaa Pro Xaa Thr
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1 peptide
<220> FEATURE:
<221> NAME/KEY: MOD_RES
<222> LOCATION: (2)..(2)
<223> OTHER INFORMATION: Phe or Gly

<400> SEQUENCE: 151

Gly Xaa Thr Phe Ser Ser Tyr
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide
<220> FEATURE:
```

```
<221> NAME/KEY: MISC_FEATURE
<222> LOCATION: (2)..(3)
<223> OTHER INFORMATION: May or may not be present
<220> FEATURE:
<221> NAME/KEY: MOD_RES
<222> LOCATION: (4)..(4)
<223> OTHER INFORMATION: Phe, Gly or Ile
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Phe or Ser

<400> SEQUENCE: 152

Gly Gly Ser Xaa Xaa Xaa Ser Ser Tyr
1               5

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide
<220> FEATURE:
<221> NAME/KEY: MOD_RES
<222> LOCATION: (1)..(1)
<223> OTHER INFORMATION: Ala, Gly, Ile, Thr or Val
<220> FEATURE:
<221> NAME/KEY: MOD_RES
<222> LOCATION: (3)..(3)
<223> OTHER INFORMATION: Ile, Asn or Ser
<220> FEATURE:
<221> NAME/KEY: MOD_RES
<222> LOCATION: (4)..(4)
<223> OTHER INFORMATION: Gly, Pro, Ser or Tyr
<220> FEATURE:
<221> NAME/KEY: MOD_RES
<222> LOCATION: (5)..(5)
<223> OTHER INFORMATION: Asp, Gly, Ile or Ser
<220> FEATURE:
<221> NAME/KEY: MOD_RES
<222> LOCATION: (6)..(6)
<223> OTHER INFORMATION: Phe, Gly or Ser
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Asn, Ser or Thr
<220> FEATURE:
<221> NAME/KEY: MOD_RES
<222> LOCATION: (9)..(9)
<223> OTHER INFORMATION: Ala, Ile, Lys or Thr
<220> FEATURE:
<221> NAME/KEY: MOD_RES
<222> LOCATION: (10)..(10)
<223> OTHER INFORMATION: Asn, Ser or Tyr
<220> FEATURE:
<221> NAME/KEY: MOD_RES
<222> LOCATION: (13)..(13)
<223> OTHER INFORMATION: Asp or Gln
<220> FEATURE:
<221> NAME/KEY: MOD_RES
<222> LOCATION: (14)..(14)
<223> OTHER INFORMATION: Lys or Ser
<220> FEATURE:
<221> NAME/KEY: MOD_RES
<222> LOCATION: (15)..(15)
<223> OTHER INFORMATION: Phe or Val
<220> FEATURE:
<221> NAME/KEY: MOD_RES
```

```
<222> LOCATION: (16)..(16)
<223> OTHER INFORMATION: Lys or Gln

<400> SEQUENCE: 153

Xaa Ile Xaa Xaa Xaa Xaa Xaa Xaa Xaa Xaa Tyr Ala Xaa Xaa Xaa Xaa
1               5                   10                  15
Gly

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2 peptide
<220> FEATURE:
<221> NAME/KEY: MOD_RES
<222> LOCATION: (1)..(1)
<223> OTHER INFORMATION: Ala, Thr or Val
<220> FEATURE:
<221> NAME/KEY: MOD_RES
<222> LOCATION: (4)..(4)
<223> OTHER INFORMATION: Gly, Ser or Tyr
<220> FEATURE:
<221> NAME/KEY: MOD_RES
<222> LOCATION: (5)..(5)
<223> OTHER INFORMATION: Asp or Ser
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Asn, Ser or Thr
<220> FEATURE:
<221> NAME/KEY: MOD_RES
<222> LOCATION: (9)..(9)
<223> OTHER INFORMATION: Ile, Lys or Thr

<400> SEQUENCE: 154

Xaa Ile Ser Xaa Xaa Xaa Xaa Xaa Xaa Tyr Tyr Ala Asp Ser Val Lys
1               5                   10                  15
Gly

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ile
<220> FEATURE:
<221> NAME/KEY: MOD_RES
<222> LOCATION: (3)..(3)
<223> OTHER INFORMATION: Ile or Asn
<220> FEATURE:
<221> NAME/KEY: MOD_RES
<222> LOCATION: (5)..(5)
<223> OTHER INFORMATION: Gly or Ile
<220> FEATURE:
<221> NAME/KEY: MOD_RES
<222> LOCATION: (6)..(6)
<223> OTHER INFORMATION: Phe or Gly
<220> FEATURE:
```

```
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (10)..(10)
<223> OTHER INFORMATION: Asn or Ser

<400> SEQUENCE: 155

Xaa Ile Xaa Pro Xaa Xaa Gly Xaa Xaa Xaa Tyr Ala Gln Lys Phe Gln
 1               5                  10                  15

Gly

<210> SEQ ID NO 156
<211> LENGTH: 19
<212> TYPE: PRT
<213> ORGANISM: Artificial Sequence
<220> FEATURE:
<223> OTHER INFORMATION: Description of Artificial Sequence: Synthetic
      VH CDR3 peptide
<220> FEATURE:
<221> NAME/KEY: MOD_RES
<222> LOCATION: (3)..(3)
<223> OTHER INFORMATION: Asp, Gly, Thr or absent
<220> FEATURE:
<221> NAME/KEY: MOD_RES
<222> LOCATION: (4)..(4)
<223> OTHER INFORMATION: Ala, Asp, Gly, Pro, Arg, Ser or absent
<220> FEATURE:
<221> NAME/KEY: MOD_RES
<222> LOCATION: (5)..(5)
<223> OTHER INFORMATION: Glu, Phe, Gly, Gln, Thr or absent
<220> FEATURE:
<221> NAME/KEY: MOD_RES
<222> LOCATION: (6)..(6)
<223> OTHER INFORMATION: Glu, Met, Trp, Tyr or absent
<220> FEATURE:
<221> NAME/KEY: MOD_RES
<222> LOCATION: (7)..(7)
<223> OTHER INFORMATION: Ala, Leu, Ser or absent
<220> FEATURE:
<221> NAME/KEY: MOD_RES
<222> LOCATION: (8)..(8)
<223> OTHER INFORMATION: Gly, Ser, Thr or absent
<220> FEATURE:
<221> NAME/KEY: MOD_RES
<222> LOCATION: (9)..(9)
<223> OTHER INFORMATION: Gly, Ser or absent
<220> FEATURE:
<221> NAME/KEY: MOD_RES
<222> LOCATION: (10)..(10)
<223> OTHER INFORMATION: Ile, Leu, Phe or absent
<220> FEATURE:
<221> NAME/KEY: MISC_FEATURE
<222> LOCATION: (11)..(12)
<223> OTHER INFORMATION: May or may not be present
<220> FEATURE:
<221> NAME/KEY: MOD_RES
<222> LOCATION: (13)..(13)
<223> OTHER INFORMATION: Glu, Tyr or absent
<220> FEATURE:
<221> NAME/KEY: MOD_RES
<222> LOCATION: (14)..(14)
<223> OTHER INFORMATION: Gly, His, Pro, Ser, Trp, Tyr or absent
<220> FEATURE:
<221> NAME/KEY: MOD_RES
<222> LOCATION: (15)..(15)
<223> OTHER INFORMATION: Ala, Gly, Leu, Trp or Tyr
<220> FEATURE:
<221> NAME/KEY: MOD_RES
<222> LOCATION: (16)..(16)
<223> OTHER INFORMATION: Ala, Gly, Ile, Pro, Val or absent
```

```
<220> FEATURE:
<221> NAME/KEY: MOD_RES
<222> LOCATION: (17)..(17)
<223> OTHER INFORMATION: Phe, Leu or Met
<220> FEATURE:
<221> NAME/KEY: MOD_RES
<222> LOCATION: (19)..(19)
<223> OTHER INFORMATION: Ile, Leu, Val or Tyr

<400> SEQUENCE: 156

Ala Arg Xaa Xaa Xaa Xaa Xaa Xaa Xaa Trp His Xaa Xaa Xaa Xaa
1               5                   10                  15

Xaa Asp Xaa

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR1 peptide
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (8)..(8)
<223> OTHER INFORMATION: Arg or Ser
<220> FEATURE:
<221> NAME/KEY: MOD_RES
<222> LOCATION: (9)..(9)
<223> OTHER INFORMATION: Asn, Trp or Tyr

<400> SEQUENCE: 157

Arg Ala Ser Gln Xaa Xaa Ser Xaa Xaa Leu Ala
1               5                   10

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      VL CDR1 peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (6)..(6)
<223> OTHER INFORMATION: Leu or Val
<220> FEATURE:
<221> NAME/KEY: MOD_RES
<222> LOCATION: (8)..(8)
<223> OTHER INFORMATION: His or Tyr
<220> FEATURE:
<221> NAME/KEY: MOD_RES
<222> LOCATION: (10)..(10)
<223> OTHER INFORMATION: Asn or Ser
<220> FEATURE:
<221> NAME/KEY: MOD_RES
<222> LOCATION: (11)..(11)
<223> OTHER INFORMATION: Gln or Asn
<220> FEATURE:
<221> NAME/KEY: MISC_FEATURE
<222> LOCATION: (12)..(12)
<223> OTHER INFORMATION: May or may not be present
<220> FEATURE:
```

-continued

```
<221> NAME/KEY: MOD_RES
<222> LOCATION: (13)..(13)
<223> OTHER INFORMATION: Lys or Tyr
<220> FEATURE:
<221> NAME/KEY: MOD_RES
<222> LOCATION: (17)..(17)
<223> OTHER INFORMATION: Ala or Asp

<400> SEQUENCE: 158

Xaa Ser Ser Gln Ser Xaa Leu Xaa Ser Xaa Xaa Asn Xaa Asn Tyr Leu
1               5                   10                  15

Xaa

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide
<220> FEATURE:
<221> NAME/KEY: MOD_RES
<222> LOCATION: (1)..(1)
<223> OTHER INFORMATION: Asp, Gly or Ser
<220> FEATURE:
<221> NAME/KEY: MOD_RES
<222> LOCATION: (4)..(4)
<223> OTHER INFORMATION: Asn or Thr

<400> SEQUENCE: 159

Xaa Ala Ser Xaa Arg Ala Thr
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide
<220> FEATURE:
<221> NAME/KEY: MOD_RES
<222> LOCATION: (1)..(1)
<223> OTHER INFORMATION: Asp, Gly or Ser
<220> FEATURE:
<221> NAME/KEY: MOD_RES
<222> LOCATION: (4)..(4)
<223> OTHER INFORMATION: Asn, Ser or Thr
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (6)..(6)
<223> OTHER INFORMATION: Ala or Gln
<220> FEATURE:
<221> NAME/KEY: MOD_RES
<222> LOCATION: (7)..(7)
<223> OTHER INFORMATION: Ser or Thr

<400> SEQUENCE: 160

Xaa Ala Ser Xaa Xaa Xaa Xaa
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR2 peptide
```

```
<220> FEATURE:
<221> NAME/KEY: MOD_RES
<222> LOCATION: (1)..(1)
<223> OTHER INFORMATION: Leu or Trp
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Asn or Thr
<220> FEATURE:
<221> NAME/KEY: MOD_RES
<222> LOCATION: (6)..(6)
<223> OTHER INFORMATION: Ala or Glu

<400> SEQUENCE: 161

Xaa Xaa Ser Xaa Arg Xaa Ser
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3 peptide
<220> FEATURE:
<221> NAME/KEY: MOD_RES
<222> LOCATION: (3)..(3)
<223> OTHER INFORMATION: His, Ile, Arg or Tyr
<220> FEATURE:
<221> NAME/KEY: MOD_RES
<222> LOCATION: (4)..(4)
<223> OTHER INFORMATION: Ala, Phe, His, Ile or Tyr
<220> FEATURE:
<221> NAME/KEY: MOD_RES
<222> LOCATION: (5)..(5)
<223> OTHER INFORMATION: Ala, Ser, Thr, Val or Tyr
<220> FEATURE:
<221> NAME/KEY: MOD_RES
<222> LOCATION: (6)..(6)
<223> OTHER INFORMATION: Phe, Trp or Tyr
<220> FEATURE:
<221> NAME/KEY: MOD_RES
<222> LOCATION: (8)..(8)
<223> OTHER INFORMATION: Phe, Leu, Pro, Trp or absent

<400> SEQUENCE: 162

Gln Gln Xaa Xaa Xaa Xaa Pro Xaa Thr
1               5

<210> SEQ ID NO 163
<211> LENGTH: 184
<212> TYPE: PRT
<213> ORGANISM: Homo sapiens

<400> SEQUENCE: 163

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80
```

```
Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 164
<211> LENGTH: 63
<212> TYPE: DNA
<213> ORGANISM: Artificial Sequence
<220> FEATURE:
<223> OTHER INFORMATION: Description of Artificial Sequence: Synthetic
      Signal Peptide

<400> SEQUENCE: 164
atggcactcc cgtaactgc tctgctgctg ccgttggcat tgctcctgca cgccgcacgc      60
ccg                                                                   63

<210> SEQ ID NO 165
<211> LENGTH: 21
<212> TYPE: PRT
<213> ORGANISM: Artificial Sequence
<220> FEATURE:
<223> OTHER INFORMATION: Description of Artificial Sequence: Synthetic
      Signal Peptide

<400> SEQUENCE: 165

Met Ala Leu Pro Val Thr Ala Leu Leu Leu Pro Leu Ala Leu Leu Leu
1               5                   10                  15

His Ala Ala Arg Pro
            20

<210> SEQ ID NO 166
<211> LENGTH: 90
<212> TYPE: DNA
<213> ORGANISM: Artificial Sequence
<220> FEATURE:
<223> OTHER INFORMATION: Description of Artificial Sequence: Synthetic
      CD28 Hinge Domain

<400> SEQUENCE: 166
cttgataatg aaaagtcaaa cggaacaatc attcacgtga agggcaagca cctctgtccg      60 tcaccttgt ccctggtcc atccaagcca                                        90

<210> SEQ ID NO 167
<211> LENGTH: 30
<212> TYPE: PRT
<213> ORGANISM: Artificial Sequence
<220> FEATURE:
<223> OTHER INFORMATION: Description of Artificial Sequence: Synthetic
      CD28 Hinge Domain

<400> SEQUENCE: 167
```

```
Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30
```

<210> SEQ ID NO 168
<211> LENGTH: 81
<212> TYPE: DNA
<213> ORGANISM: Artificial Sequence
<220> FEATURE:
<223> OTHER INFORMATION: Description of Artificial Sequence: Synthetic
      CD28 TM Domain

<400> SEQUENCE: 168

```
ttctgggtgt tggtcgtagt gggtggagtc ctcgcttgtt actctctgct cgtcaccgtg    60
gcttttataa tcttctgggt t                                              81
```

<210> SEQ ID NO 169
<211> LENGTH: 27
<212> TYPE: PRT
<213> ORGANISM: Artificial Sequence
<220> FEATURE:
<223> OTHER INFORMATION: Description of Artificial Sequence: Synthetic
      CD28 TM Domain

<400> SEQUENCE: 169

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 170
<211> LENGTH: 123
<212> TYPE: DNA
<213> ORGANISM: Artificial Sequence
<220> FEATURE:
<223> OTHER INFORMATION: Description of Artificial Sequence: Synthetic
      CD28 Signaling Domain

<400> SEQUENCE: 170

```
agatccaaaa gaagccgcct gctccatagc gattacatga atatgactcc acgccgccct    60
ggccccacaa ggaaacacta ccagccttac gcaccaccta gagatttcgc tgcctatcgg   120
agc                                                                 123
```

<210> SEQ ID NO 171
<211> LENGTH: 41
<212> TYPE: PRT
<213> ORGANISM: Artificial Sequence
<220> FEATURE:
<223> OTHER INFORMATION: Description of Artificial Sequence: Synthetic
      CD28 Signaling Domain

<400> SEQUENCE: 171

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40
```

<210> SEQ ID NO 172
<211> LENGTH: 336
<212> TYPE: DNA

<213> ORGANISM: Artificial Sequence
<220> FEATURE:
<223> OTHER INFORMATION: Description of Artificial Sequence: Synthetic
    CD3z Activation Domain

<400> SEQUENCE: 172

```
agggtgaagt tttccagatc tgcagatgca ccagcgtatc agcagggcca gaaccaactg    60
tataacgagc tcaacctggg acgcagggaa gagtatgacg ttttggacaa gcgcagagga   120
cgggaccctg agatgggtgg caaaccaaga cgaaaaaacc cccaggaggg tctctataat   180
gagctgcaga aggataagat ggctgaagcc tattctgaaa taggcatgaa aggagagcgg   240
agaaggggaa aagggcacga cggtttgtac cagggactca gcactgctac gaaggatact   300
tatgacgctc tccacatgca agccctgcca cctagg                             336
```

<210> SEQ ID NO 173
<211> LENGTH: 112
<212> TYPE: PRT
<213> ORGANISM: Artificial Sequence
<220> FEATURE:
<223> OTHER INFORMATION: Description of Artificial Sequence: Synthetic
    CD3z Activation Domain

<400> SEQUENCE: 173

```
Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
                100                 105                 110
```

<210> SEQ ID NO 174
<211> LENGTH: 18
<212> TYPE: PRT
<213> ORGANISM: Artificial Sequence
<220> FEATURE:
<223> OTHER INFORMATION: Description of Artificial Sequence: Synthetic
    Linker peptide

<400> SEQUENCE: 174

```
Gly Ser Thr Ser Gly Ser Gly Lys Pro Gly Ser Gly Glu Gly Ser Thr
1               5                   10                  15
Lys Gly
```

<210> SEQ ID NO 175
<211> LENGTH: 1437
<212> TYPE: DNA
<213> ORGANISM: Artificial Sequence
<220> FEATURE:
<223> OTHER INFORMATION: Description of Artificial Sequence: Synthetic
    FS-21495CARDNAHxL polynucleotide

<400> SEQUENCE: 175

```
atggcactcc ccgtaactgc tctgctgctg ccgttggcat tgctcctgca cgccgcacgc    60
```

```
ccggaggtgc agctgttgga gtctgggga ggcttggtac agcctggggg gtccctgaga      120
ctctcctgtg cagcctctgg attcacctt agcagctatg ccatgagctg ggtccgccag      180
gctccaggga aggggctgga gtgggtctca gctattagtg gtagtggtgg tagcacatac      240
tacgcagact ccgtgaaggg ccggttcacc atctccagag acaattccaa gaacacgctg      300
tatctgcaaa tgaacagcct gagagccgag gacacggcgg tgtactactg cgcaagagcc      360
gagatgggag ccgtattcga catatggggt cagggtacaa tggtcaccgt ctcctcaggg      420
tctacatccg gctccgggaa gcccggaagt ggcgaaggta gtacaaaggg ggaaattgtg      480
ttgacacagt ctccagccac cctgtctttg tctccagggg aaagagccac cctctcctgc      540
agggccagtc agagtgttag caggtactta gcctggtacc aacagaaacc tggccaggct      600
cccaggctcc tcatctatga tgcatccaac agggccactg gcatcccagc caggttcagt      660
ggcagtgggt ctgggacaga cttcactctc accatcagca gcctagagcc tgaagatttt      720
gcagtttatt actgtcagca gagaatctcc tggcctttca cttttggcgg agggaccaag      780
gttgagatca aacgggccgc tgcccttgat aatgaaaagt caaacggaac aatcattcac      840
gtgaagggca agcacctctg tccgtcaccc ttgttccctg gtccatccaa gccattctgg      900
gtgttggtcg tagtgggtgg agtcctcgct tgttactctc tgctcgtcac cgtggctttt      960
ataatcttct gggttagatc caaaagaagc cgcctgctcc atagcgatta catgaatatg     1020
actccacgcc gccctggccc cacaaggaaa cactaccagc cttacgcacc acctagagat     1080
ttcgctgcct atcggagcag ggtgaagttt tccagatctg cagatgcacc agcgtatcag     1140
cagggccaga accaactgta taacgagctc aacctgggac gcagggaaga gtatgacgtt     1200
ttggacaagc gcagaggacg ggaccctgag atgggtggca aaccaagacg aaaaaacccc     1260
caggagggtc tctataatga gctgcagaag gataagatgg ctgaagccta ttctgaaata     1320
ggcatgaaag agagcggag aaggggaaaa gggcacgacg gtttgtacca gggactcagc     1380
actgctacga aggatactta tgacgctctc cacatgcaag ccctgccacc taggtaa       1437
```

<210> SEQ ID NO 176
<211> LENGTH: 478
<212> TYPE: PRT
<213> ORGANISM: Artificial Sequence
<220> FEATURE:
<223> OTHER INFORMATION: Description of Artificial Sequence: Synthetic
    FS-21495CARHxL polypeptide

<400> SEQUENCE: 176

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ala Glu Met Gly Ala Val Phe Asp Ile
            115                 120                 125

Trp Gly Gln Gly Thr Met Val Thr Val Ser Ser Gly Ser Thr Ser Gly
130                 135                 140

Ser Gly Lys Pro Gly Ser Gly Glu Gly Ser Thr Lys Gly Glu Ile Val
145                 150                 155                 160

Leu Thr Gln Ser Pro Ala Thr Leu Ser Leu Ser Pro Gly Glu Arg Ala
            165                 170                 175

Thr Leu Ser Cys Arg Ala Ser Gln Ser Val Ser Arg Tyr Leu Ala Trp
        180                 185                 190

Tyr Gln Gln Lys Pro Gly Gln Ala Pro Arg Leu Leu Ile Tyr Asp Ala
    195                 200                 205

Ser Asn Arg Ala Thr Gly Ile Pro Ala Arg Phe Ser Gly Ser Gly Ser
210                 215                 220

Gly Thr Asp Phe Thr Leu Thr Ile Ser Ser Leu Glu Pro Glu Asp Phe
225                 230                 235                 240

Ala Val Tyr Tyr Cys Gln Gln Arg Ile Ser Trp Pro Phe Thr Phe Gly
            245                 250                 255

Gly Gly Thr Lys Val Glu Ile Lys Arg Ala Ala Ala Leu Asp Asn Glu
        260                 265                 270

Lys Ser Asn Gly Thr Ile Ile His Val Lys Gly Lys His Leu Cys Pro
    275                 280                 285

Ser Pro Leu Phe Pro Gly Pro Ser Lys Pro Phe Trp Val Leu Val Val
290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
            325                 330                 335

Tyr Met Asn Met Thr Pro Arg Arg Pro Gly Pro Thr Arg Lys His Tyr
        340                 345                 350

Gln Pro Tyr Ala Pro Pro Arg Asp Phe Ala Ala Tyr Arg Ser Arg Val
    355                 360                 365

Lys Phe Ser Arg Ser Ala Asp Ala Pro Ala Tyr Gln Gln Gly Gln Asn
370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
            405                 410                 415

Arg Lys Asn Pro Gln Glu Gly Leu Tyr Asn Glu Leu Gln Lys Asp Lys
        420                 425                 430

Met Ala Glu Ala Tyr Ser Glu Ile Gly Met Lys Gly Glu Arg Arg Arg
    435                 440                 445

Gly Lys Gly His Asp Gly Leu Tyr Gln Gly Leu Ser Thr Ala Thr Lys
450                 455                 460

Asp Thr Tyr Asp Ala Leu His Met Gln Ala Leu Pro Pro Arg
465                 470                 475

<210> SEQ ID NO 177
<211> LENGTH: 1437
<212> TYPE: DNA
<213> ORGANISM: Artificial Sequence
<220> FEATURE:
<223> OTHER INFORMATION: Description of Artificial Sequence: Synthetic
      FS-21495CARDNALxH polynucleotide

<400> SEQUENCE: 177

```
atggcactcc ccgtaactgc tctgctgctg ccgttggcat tgctcctgca cgccgcacgc    60
ccggaaattg tgttgacaca gtctccagcc accctgtctt tgtctccagg ggaaagagcc   120
accctctcct gcagggccag tcagagtgtt agcaggtact tagcctggta ccaacagaaa   180
cctggccagg ctcccaggct cctcatctat gatgcatcca acagggccac tggcatccca   240
gccaggttca gtggcagtgg gtctgggaca gacttcactc tcaccatcag cagcctagag   300
cctgaagatt ttgcagttta ttactgtcag cagagaatct cctggccttt cacttttggc   360
ggagggacca aggttgagat caaacggggg tctacatccg gctccgggaa gcccggaagt   420
ggcgaaggta gtacaaaggg ggaggtgcag ctgttggagt ctggggggag cttggtacag   480
cctgggggt ccctgagact ctcctgtgca gcctctggat tcacctttag cagctatgcc    540
atgagctggg tccgccaggc tccagggaag gggctggagt gggtctcagc tattagtggt   600
agtggtggta gcacatacta cgcagactcc gtgaagggcc ggttcaccat ctccagagac   660
aattccaaga acacgctgta tctgcaaatg aacagcctga gagccgagga cacggcggtg   720
tactactgcg caagagccga gatgggagcc gtattcgaca tatgggtca gggtacaatg     780
gtcaccgtct cctcagccgc tgcccttgat aatgaaaagt caaacggaac aatcattcac   840
gtgaagggca agcacctctg tccgtcaccc ttgttccctg gtccatccaa gccattctgg   900
gtgttggtcg tagtgggtgg agtcctcgct tgttactctc tgctcgtcac cgtggctttt   960
ataatcttct gggttagatc caaaagaagc cgcctgctcc atagcgatta catgaatatg  1020
actccacgcc gccctggccc cacaaggaaa cactaccagc cttacgcacc acctagagat  1080
ttcgctgcct atcggagcag ggtgaagttt tccagatctg cagatgcacc agcgtatcag  1140
cagggccaga accaactgta taacgagctc aacctgggac gcaggaaga gtatgacgtt   1200
ttggacaagc gcagaggacg ggaccctgag atgggtggca accaagacg aaaaaacccc    1260
caggagggtc tctataatga gctgcagaag gataagatgg ctgaagccta ttctgaaata  1320
ggcatgaaag gagagcggag aaggggaaaa gggcacgacg gtttgtacca gggactcagc  1380
actgctacga aggatactta tgacgctctc cacatgcaag ccctgccacc taggtaa     1437
```

<210> SEQ ID NO 178
<211> LENGTH: 478
<212> TYPE: PRT
<213> ORGANISM: Artificial Sequence
<220> FEATURE:
<223> OTHER INFORMATION: Description of Artificial Sequence: Synthetic
      FS-21495CARLxH polypeptide

<400> SEQUENCE: 178

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
                20                  25                  30

Ser Leu Ser Pro Gly Glu Arg Ala Thr Leu Ser Cys Arg Ala Ser Gln
            35                  40                  45

Ser Val Ser Arg Tyr Leu Ala Trp Tyr Gln Gln Lys Pro Gly Gln Ala
        50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg 100                 105                 110
Ile Ser Trp Pro Phe Thr Phe Gly Gly Gly Thr Lys Val Glu Ile Lys
            115                 120                 125
Arg Gly Ser Thr Ser Gly Ser Gly Lys Pro Gly Ser Gly Glu Gly Ser
130                 135                 140
Thr Lys Gly Glu Val Gln Leu Leu Glu Ser Gly Gly Gly Leu Val Gln
145                 150                 155                 160
Pro Gly Gly Ser Leu Arg Leu Ser Cys Ala Ala Ser Gly Phe Thr Phe
                165                 170                 175
Ser Ser Tyr Ala Met Ser Trp Val Arg Gln Ala Pro Gly Lys Gly Leu
            180                 185                 190
Glu Trp Val Ser Ala Ile Ser Gly Ser Gly Gly Ser Thr Tyr Tyr Ala
        195                 200                 205
Asp Ser Val Lys Gly Arg Phe Thr Ile Ser Arg Asp Asn Ser Lys Asn
210                 215                 220
Thr Leu Tyr Leu Gln Met Asn Ser Leu Arg Ala Glu Asp Thr Ala Val
225                 230                 235                 240
Tyr Tyr Cys Ala Arg Ala Glu Met Gly Ala Val Phe Asp Ile Trp Gly
                245                 250                 255
Gln Gly Thr Met Val Thr Val Ser Ser Ala Ala Ala Leu Asp Asn Glu
            260                 265                 270
Lys Ser Asn Gly Thr Ile Ile His Val Lys Lys Tyr Lys Leu Cys Pro
        275                 280                 285
Ser Pro Leu Phe Pro Gly Pro Ser Lys Pro Phe Trp Val Leu Val Val
290                 295                 300
Val Gly Gly Val Leu Ala Cys Tyr Ser Leu Leu Val Thr Val Ala Phe
305                 310                 315                 320
Ile Ile Phe Trp Val Arg Ser Lys Arg Ser Arg Leu Leu His Ser Asp
                325                 330                 335
Tyr Met Asn Met Thr Pro Arg Arg Pro Gly Pro Thr Arg Lys His Tyr
            340                 345                 350
Gln Pro Tyr Ala Pro Pro Arg Asp Phe Ala Ala Tyr Arg Ser Arg Val
        355                 360                 365
Lys Phe Ser Arg Ser Ala Asp Ala Pro Ala Tyr Gln Gln Gly Gln Asn
370                 375                 380
Gln Leu Tyr Asn Glu Leu Asn Leu Gly Arg Arg Glu Glu Tyr Asp Val
385                 390                 395                 400
Leu Asp Lys Arg Arg Gly Arg Asp Pro Glu Met Gly Gly Lys Pro Arg
                405                 410                 415
Arg Lys Asn Pro Gln Glu Gly Leu Tyr Asn Glu Leu Gln Lys Asp Lys
            420                 425                 430
Met Ala Glu Ala Tyr Ser Glu Ile Gly Met Lys Gly Glu Arg Arg Arg
        435                 440                 445
Gly Lys Gly His Asp Gly Leu Tyr Gln Gly Leu Ser Thr Ala Thr Lys
450                 455                 460
Asp Thr Tyr Asp Ala Leu His Met Gln Ala Leu Pro Pro Arg
465                 470                 475

<210> SEQ ID NO 179
<211> LENGTH: 1464
<212> TYPE: DNA
<213> ORGANISM: Artificial Sequence
<220> FEATURE:
<223> OTHER INFORMATION: Description of Artificial Sequence: Synthetic
      PC-21497CARDNAHxL polynucleotide

<400> SEQUENCE: 179

```
atggcactcc ccgtaactgc tctgctgctg ccgttggcat tgctcctgca cgccgcacgc    60
ccgcaggtgc agctggtgga gtctggggga ggcgtggtcc agcctgggag gtccctgaga   120
ctctcctgtg cagcgtctgg attcaccttc agtagctatg gcatgcactg ggtccgccag   180
gctccaggca aggggctgga gtgggtggca gttatatcgt atgatggaag taataaatac   240
tatgcagact ccgtgaaggg ccgattcacc atctccagag acaattccaa gaacacgctg   300
tatctgcaaa tgaacagcct gagagccgag gacacggcgg tgtactactg cgccagagac   360
ggtacttatc taggtggtct ctggtacttc gacttatggg ggagaggtac cttggtcacc   420
gtctcctcag ggtctacatc cggctccggg aagcccggaa gtggcgaagg tagtacaaag   480
ggggatattg tgatgactca gtctccactc tccctgcccg tcacccctgg agagccggcc   540
tccatctcct gcaggtctag tcagagcctc ctgcatagta tggatacaa ctatttggat   600
tggtacctgc agaagccagg gcagtctcca cagctcctga tctatttggg ttctaatcgg   660
gcctccgggg tccctgacag gttcagtggc agtggatcag gcacagattt tacactgaaa   720
atcagcagag tggaggctga ggatgttggg gtttattact gcatgcaggg actcggcctc   780
cctctcactt ttggcggagg gaccaaggtt gagatcaaac gggccgctgc ccttgataat   840
gaaaagtcaa acggaacaat cattcacgtg aagggcaagc acctctgtcc gtcacccttg   900
ttccctggtc catccaagcc attctgggtg ttggtcgtag tgggtggagt cctcgcttgt   960
tactctctgc tcgtcaccgt ggcttttata atcttctggg ttagatccaa agaagccgc  1020
ctgctccata gcgattacat gaatatgact ccacgccgcc ctggccccac aaggaaacac  1080
taccagcctt acgcaccacc tagagatttc gctgcctatc ggagcagggt gaagttttcc  1140
agatctgcag atgcaccagc gtatcagcag ggccagaacc aactgtataa cgagctcaac  1200
ctgggacgca gggaagagta tgacgttttg acaagcgca gaggacggga ccctgagatg  1260
ggtggcaaac caagacgaaa aaaccccag gagggtctct ataatgagct gcagaaggat  1320
aagatggctg aagcctattc tgaaataggc atgaaaggag agcggagaag gggaaaaggg  1380
cacgacggtt tgtaccaggg actcagcact gctacgaagg atacttatga cgctctccac  1440
atgcaagccc tgccacctag gtaa                                         1464
```

<210> SEQ ID NO 180
<211> LENGTH: 487
<212> TYPE: PRT
<213> ORGANISM: Artificial Sequence
<220> FEATURE:
<223> OTHER INFORMATION: Description of Artificial Sequence: Synthetic
      PC-21497CARHxL polypeptide

<400> SEQUENCE: 180

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80
```

```
Tyr Ala Asp Ser Val Lys Gly Arg Phe Thr Ile Ser Arg Asp Asn Ser
                85                  90                  95
Lys Asn Thr Leu Tyr Leu Gln Met Asn Ser Leu Arg Ala Glu Asp Thr
            100                 105                 110
Ala Val Tyr Tyr Cys Ala Arg Asp Gly Thr Tyr Leu Gly Gly Leu Trp
        115                 120                 125
Tyr Phe Asp Leu Trp Gly Arg Gly Thr Leu Val Thr Val Ser Ser Gly
    130                 135                 140
Ser Thr Ser Gly Ser Gly Lys Pro Gly Ser Gly Glu Gly Ser Thr Lys
145                 150                 155                 160
Gly Asp Ile Val Met Thr Gln Ser Pro Leu Ser Leu Pro Val Thr Pro
                165                 170                 175
Gly Glu Pro Ala Ser Ile Ser Cys Arg Ser Ser Gln Ser Leu Leu His
            180                 185                 190
Ser Asn Gly Tyr Asn Tyr Leu Asp Trp Tyr Leu Gln Lys Pro Gly Gln
        195                 200                 205
Ser Pro Gln Leu Leu Ile Tyr Leu Gly Ser Asn Arg Ala Ser Gly Val
    210                 215                 220
Pro Asp Arg Phe Ser Gly Ser Gly Ser Gly Thr Asp Phe Thr Leu Lys
225                 230                 235                 240
Ile Ser Arg Val Glu Ala Glu Asp Val Gly Val Tyr Tyr Cys Met Gln
                245                 250                 255
Gly Leu Gly Leu Pro Leu Thr Phe Gly Gly Gly Thr Lys Val Glu Ile
            260                 265                 270
Lys Arg Ala Ala Ala Leu Asp Asn Glu Lys Ser Asn Gly Thr Ile Ile
        275                 280                 285
His Val Lys Gly Lys His Leu Cys Pro Ser Pro Leu Phe Pro Gly Pro
    290                 295                 300
Ser Lys Pro Phe Trp Val Leu Val Val Gly Gly Val Leu Ala Cys
305                 310                 315                 320
Tyr Ser Leu Leu Val Thr Val Ala Phe Ile Ile Phe Trp Val Arg Ser
                325                 330                 335
Lys Arg Ser Arg Leu Leu His Ser Asp Tyr Met Asn Met Thr Pro Arg
            340                 345                 350
Arg Pro Gly Pro Thr Arg Lys His Tyr Gln Pro Tyr Ala Pro Pro Arg
        355                 360                 365
Asp Phe Ala Ala Tyr Arg Ser Arg Val Lys Phe Ser Arg Ser Ala Asp
    370                 375                 380
Ala Pro Ala Tyr Gln Gln Gly Gln Asn Gln Leu Tyr Asn Glu Leu Asn
385                 390                 395                 400
Leu Gly Arg Arg Glu Glu Tyr Asp Val Leu Asp Lys Arg Arg Gly Arg
                405                 410                 415
Asp Pro Glu Met Gly Gly Lys Pro Arg Arg Lys Asn Pro Gln Glu Gly
            420                 425                 430
Leu Tyr Asn Glu Leu Gln Lys Asp Lys Met Ala Glu Ala Tyr Ser Glu
        435                 440                 445
Ile Gly Met Lys Gly Glu Arg Arg Arg Gly Lys Gly His Asp Gly Leu
    450                 455                 460
Tyr Gln Gly Leu Ser Thr Ala Thr Lys Asp Thr Tyr Asp Ala Leu His
465                 470                 475                 480
Met Gln Ala Leu Pro Pro Arg
                485
```

<210> SEQ ID NO 181
<211> LENGTH: 1464
<212> TYPE: DNA
<213> ORGANISM: Artificial Sequence
<220> FEATURE:
<223> OTHER INFORMATION: Description of Artificial Sequence: Synthetic
      PC-21497CARDNALxH polynucleotide

<400> SEQUENCE: 181

| | | | | |
|---|---|---|---|---|
| atggcactcc | ccgtaactgc | tctgctgctg | ccgttggcat | tgctcctgca cgccgcacgc | 60 |
| ccggatattg | tgatgactca | gtctccactc | tccctgcccg | tcaccctgg agagccggcc | 120 |
| tccatctcct | gcaggtctag | tcagagcctc | ctgcatagta | atggatacaa ctatttggat | 180 |
| tggtacctgc | agaagccagg | gcagtctcca | cagctcctga | tctatttggg ttctaatcgg | 240 |
| gcctccgggg | tccctgacag | gttcagtggc | agtggatcag | gcacagattt tacactgaaa | 300 |
| atcagcagag | tggaggctga | ggatgttggg | gtttattact | gcatgcaggg actcggcctc | 360 |
| cctctcactt | ttggcggagg | gaccaaggtt | gagatcaaac | gggggtctac atccggctcc | 420 |
| gggaagcccg | aagtggcga | aggtagtaca | aaggggcagg | tgcagctggt ggagtctggg | 480 |
| ggaggcgtgg | tccagcctgg | gaggtccctg | agactctcct | gtgcagcgtc tggattcacc | 540 |
| ttcagtagct | atggcatgca | ctgggtccgc | caggctccag | gcaaggggct ggagtgggtg | 600 |
| gcagttatat | cgtatgatgg | aagtaataaa | tactatgcag | actccgtgaa gggccgattc | 660 |
| accatctcca | gagacaattc | caagaacacg | ctgtatctgc | aaatgaacag cctgagagcc | 720 |
| gaggacacgg | cggtgtacta | ctgcgccaga | gacggtactt | atctaggtgg tctctggtac | 780 |
| ttcgacttat | gggggagagg | taccttggtc | accgtctcct | cagccgctgc ccttgataat | 840 |
| gaaaagtcaa | acggaacaat | cattcacgtg | aagggcaagc | acctctgtcc gtcacccttg | 900 |
| ttccctggtc | catccaagcc | attctgggtg | ttggtcgtag | tgggtggagt cctcgcttgt | 960 |
| tactctctgc | tcgtcaccgt | ggctttata | atcttctggg | ttagatccaa agaagccgc | 1020 |
| ctgctccata | gcgattacat | gaatatgact | ccacgccgcc | ctggccccac aaggaaacac | 1080 |
| taccagcctt | acgcaccacc | tagagatttc | gctgcctatc | ggagcagggt gaagttttcc | 1140 |
| agatctgcag | atgcaccagc | gtatcagcag | ggccagaacc | aactgtataa cgagctcaac | 1200 |
| ctgggacgca | gggaagagta | tgacgttttg | gacaagcgca | gaggacggga ccctgagatg | 1260 |
| ggtggcaaac | caagacgaaa | aaaccccag | gagggtctct | ataatgagct gcagaaggat | 1320 |
| aagatggctg | aagcctattc | tgaaataggc | atgaaaggag | agcggagaag gggaaaaggg | 1380 |
| cacgacggtt | tgtaccaggg | actcagcact | gctacgaagg | atacttatga cgctctccac | 1440 |
| atgcaagccc | tgccacctag | gtaa | | | 1464 |

<210> SEQ ID NO 182
<211> LENGTH: 487
<212> TYPE: PRT
<213> ORGANISM: Artificial Sequence
<220> FEATURE:
<223> OTHER INFORMATION: Description of Artificial Sequence: Synthetic
      PC-21497CARHxL polypeptide

<400> SEQUENCE: 182

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Leu Ser Leu
                20                  25                  30

Pro Val Thr Pro Gly Glu Pro Ala Ser Ile Ser Cys Arg Ser Ser Gln
            35                  40                  45

Ser Leu Leu His Ser Asn Gly Tyr Asn Tyr Leu Asp Trp Tyr Leu Gln
            50                  55                  60

Lys Pro Gly Gln Ser Pro Gln Leu Leu Ile Tyr Leu Gly Ser Asn Arg
 65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Gly Leu Gly Leu Pro Leu Thr Phe Gly Gly Gly Thr
            115                 120                 125

Lys Val Glu Ile Lys Arg Gly Ser Thr Ser Gly Ser Gly Lys Pro Gly
130                 135                 140

Ser Gly Glu Gly Ser Thr Lys Gly Gln Val Gln Leu Val Glu Ser Gly
145                 150                 155                 160

Gly Gly Val Val Gln Pro Gly Arg Ser Leu Arg Leu Ser Cys Ala Ala
                165                 170                 175

Ser Gly Phe Thr Phe Ser Ser Tyr Gly Met His Trp Val Arg Gln Ala
                180                 185                 190

Pro Gly Lys Gly Leu Glu Trp Val Ala Val Ile Ser Tyr Asp Gly Ser
            195                 200                 205

Asn Lys Tyr Tyr Ala Asp Ser Val Lys Gly Arg Phe Thr Ile Ser Arg
210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Asp Gly Tyr Tyr Leu Gly
                245                 250                 255

Gly Leu Trp Tyr Phe Asp Leu Trp Gly Arg Gly Thr Leu Val Thr Val
                260                 265                 270

Ser Ser Ala Ala Ala Leu Asp Asn Glu Lys Ser Asn Gly Thr Ile Ile
            275                 280                 285

His Val Lys Gly Lys His Leu Cys Pro Ser Pro Leu Phe Pro Gly Pro
290                 295                 300

Ser Lys Pro Phe Trp Val Leu Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
                340                 345                 350

Arg Pro Gly Pro Thr Arg Lys His Tyr Gln Pro Tyr Ala Pro Pro Arg
            355                 360                 365

Asp Phe Ala Ala Tyr Arg Ser Arg Val Lys Phe Ser Arg Ser Ala Asp
            370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 183
<211> LENGTH: 1428
<212> TYPE: DNA
<213> ORGANISM: Artificial Sequence
<220> FEATURE:
<223> OTHER INFORMATION: Description of Artificial Sequence: Synthetic
      AJ-21508CARDNAHxL polynucleotide

<400> SEQUENCE: 183

```
atggcactcc ccgtaactgc tctgctgctg ccgttggcat tgctcctgca cgccgcacgc      60
ccgcaggtgc agctggtgca gtctgggggct gaggtgaaga agcctggggc ctcagtgaag     120
gtttcctgca aggcatctgg atacaccttc accagctact atatgcactg ggtgcgacag     180
gcccctggac aagggcttga gtggatggga ataatcaacc ctggtggtgg tagcacaagc     240
tacgcacaga gttccaggg cagagtcacc atgaccaggg acacgtccac gagcacagtc      300
tacatggagc tgagcagcct gagatctgag gacacggcgg tgtactactg cgccagagag     360
agttggccaa tggacgtatg gggccaggga caactgtca ccgtctcctc agggtctaca      420
tccggctccg ggaagcccgg aagtggcgaa ggtagtacaa aggggggaaat agtgatgacg     480 cagtctccag ccaccctgtc tgtgtctcca ggggaaagag ccaccctctc ctgcagggcc     540
agtcagagtg ttagcagcaa cttagcctgg taccagcaga aacctggcca ggctcccagg     600
ctcctcatct atggtgcatc caccagggcc actggtatcc cagccaggtt cagtggcagt     660
gggtctggga cagagttcac tctcaccatc agcagcctgc agtctgaaga ttttgcagtt     720
tattactgtc agcagtacgc cgcctaccct actttggcg gagggaccaa ggttgagatc      780
aaacgggccg ctgcccttga taatgaaaag tcaaacggaa caatcattca cgtgaagggc     840
aagcacctct gtccgtcacc cttgttccct ggtccatcca agccattctg ggtgttggtc     900
gtagtgggtg gagtcctcgc ttgttactct ctgctcgtca ccgtggcttt tataatcttc     960
tgggttagat ccaaaagaag ccgcctgctc catagcgatt acatgaatat gactccacgc    1020
cgccctggcc ccacaaggaa acactaccag ccttacgcac cacctagaga tttcgctgcc    1080
tatcggagca gggtgaagtt ttccagatct gcagatgcac cagcgtatca gcagggccag    1140
aaccaactgt ataacgagct caacctggga cgcagggaag agtatgacgt tttggacaag    1200 cgcagagggac gggaccctga tgatggtggc aaaccaagac gaaaaaaccc ccaggagggt    1260
ctctataatg agctgcagaa ggataagatg gctgaagcct attctgaaat aggcatgaaa    1320
ggagagcgga agggggaaa aagggcacgac ggttttgtacc agggactcag cactgctacg    1380
aaggatactt atgacgctct ccacatgcaa gccctgccac ctaggtaa                 1428
```

<210> SEQ ID NO 184
<211> LENGTH: 475
<212> TYPE: PRT
<213> ORGANISM: Artificial Sequence
<220> FEATURE:
<223> OTHER INFORMATION: Description of Artificial Sequence: Synthetic
      AJ-21508CARHxL polypeptide

<400> SEQUENCE: 184

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Tyr Met His Trp Val Arg Gln Ala Pro Gly Gln
    50                  55                  60

Gly Leu Glu Trp Met Gly Ile Ile Asn Pro Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Glu Ser Trp Pro Met Asp Val Trp Gly
        115                 120                 125

Gln Gly Thr Thr Val Thr Val Ser Ser Gly Ser Thr Ser Gly Ser Gly
    130                 135                 140

Lys Pro Gly Ser Gly Glu Gly Ser Thr Lys Gly Glu Ile Val Met Thr
145                 150                 155                 160

Gln Ser Pro Ala Thr Leu Ser Val Ser Pro Gly Glu Arg Ala Thr Leu
                165                 170                 175

Ser Cys Arg Ala Ser Gln Ser Val Ser Ser Asn Leu Ala Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Ala Arg Phe Ser Gly Ser Gly Ser Gly Thr
    210                 215                 220

Glu Phe Thr Leu Thr Ile Ser Ser Leu Gln Ser Glu Asp Phe Ala Val
225                 230                 235                 240

Tyr Tyr Cys Gln Gln Tyr Ala Ala Tyr Pro Thr Phe Gly Gly Gly Thr
                245                 250                 255

Lys Val Glu Ile Lys Arg Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly

His Asp Gly Leu Tyr Gln Gly Leu Ser Thr Ala Thr Lys Asp Thr Tyr
        450                 455                 460

Asp Ala Leu His Met Gln Ala Leu Pro Pro Arg
465                 470                 475

<210> SEQ ID NO 185
<211> LENGTH: 1428
<212> TYPE: DNA
<213> ORGANISM: Artificial Sequence
<220> FEATURE:
<223> OTHER INFORMATION: Description of Artificial Sequence: Synthetic
      AJ-21508CARDNALxH polynucleotide

<400> SEQUENCE: 185

| | | | | | |
|---|---|---|---|---|---|
| atggcactcc | ccgtaactgc | tctgctgctg | ccgttggcat | tgctcctgca | cgccgcacgc | 60 |
| ccggaaatag | tgatgacgca | gtctccagcc | accctgtctg | tgtctccagg | ggaaagagcc | 120 |
| accctctcct | gcagggccag | tcagagtgtt | agcagcaact | tagcctggta | ccagcagaaa | 180 |
| cctggccagg | ctcccaggct | cctcatctat | ggtgcatcca | ccagggccac | tggtatccca | 240 |
| gccaggttca | gtggcagtgg | gtctgggaca | gagttcactc | tcaccatcag | cagcctgcag | 300 |
| tctgaagatt | ttgcagttta | ttactgtcag | cagtacgccg | cctaccctac | ttttggcgga | 360 |
| gggaccaagg | ttgagatcaa | acgggggtct | acatccggct | ccgggaagcc | cggaagtggc | 420 |
| gaaggtagta | caaggggca | ggtgcagctg | gtgcagtctg | gggctgaggt | gaagaagcct | 480 |
| ggggcctcag | tgaaggtttc | ctgcaaggca | tctggataca | ccttcaccag | ctactatatg | 540 |
| cactgggtgc | gacaggcccc | tggacaaggg | cttgagtgga | tgggaataat | caaccctggt | 600 |
| ggtggtagca | caagctacgc | acagaagttc | cagggcagag | tcaccatgac | cagggacacg | 660 |
| tccacgagca | cagtctacat | ggagctgagc | agcctgagat | ctgaggacac | ggcggtgtac | 720 |
| tactgcgcca | gagagagttg | gccaatggac | gtatggggcc | agggaacaac | tgtcaccgtc | 780 |
| tcctcagccg | ctgcccttga | taatgaaaag | tcaaacggaa | caatcattca | cgtgaagggc | 840 |
| aagcacctct | gtccgtcacc | cttgttccct | ggtccatcca | agccattctg | ggtgttggtc | 900 |
| gtagtgggtg | gagtcctcgc | ttgttactct | ctgctcgtca | ccgtggcttt | tataatcttc | 960 |
| tgggttagat | ccaaaagaag | ccgcctgctc | catagcgatt | acatgaatat | gactccacgc | 1020 |
| cgccctggcc | ccacaaggaa | acactaccag | ccttacgcac | acctagaga | tttcgctgcc | 1080 |
| tatcggagca | gggtgaagtt | ttccagatct | gcagatgcac | cagcgtatca | gcagggccag | 1140 |
| aaccaactgt | ataacgagct | caacctggga | cgcagggaag | agtatgacgt | tttggacaag | 1200 |
| cgcagaggac | gggaccctga | gatgggtggc | aaaccaagac | gaaaaaaccc | caggagggt | 1260 |
| ctctataatg | agctgcagaa | ggataagatg | gctgaagcct | attctgaaat | aggcatgaaa | 1320 |
| ggagagcgga | gaaggggaaa | agggcacgac | ggtttgtacc | agggactcag | cactgctacg | 1380 |
| aaggatactt | atgacgctct | ccacatgcaa | gccctgccac | ctaggtaa | | 1428 |

<210> SEQ ID NO 186
<211> LENGTH: 475
<212> TYPE: PRT
<213> ORGANISM: Artificial Sequence
<220> FEATURE:
<223> OTHER INFORMATION: Description of Artificial Sequence: Synthetic
      AJ-21508CARLxH polypeptide

<400> SEQUENCE: 186

Met Ala Leu Pro Val Thr Ala Leu Leu Leu Pro Leu Ala Leu Leu Leu

-continued

```
1               5                   10                  15
His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
            35                  40                  45

Ser Val Ser Ser Asn Leu Ala Trp Tyr Gln Gln Lys Pro Gly Gln Ala
        50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Ala Ala Tyr Pro Thr Phe Gly Gly Gly Thr Lys Val Glu Ile Lys Arg
            115                 120                 125

Gly Ser Thr Ser Gly Ser Gly Lys Pro Gly Ser Gly Glu Gly Ser Thr
        130                 135                 140

Lys Gly Gln Val Gln Leu Val Gln Ser Gly Ala Glu Val Lys Lys Pro
145                 150                 155                 160

Gly Ala Ser Val Lys Val Ser Cys Lys Ala Ser Gly Tyr Thr Phe Thr
                165                 170                 175

Ser Tyr Tyr Met His Trp Val Arg Gln Ala Pro Gly Gln Gly Leu Glu
            180                 185                 190

Trp Met Gly Ile Ile Asn Pro Gly Gly Gly Ser Thr Ser Tyr Ala Gln
            195                 200                 205

Lys Phe Gln Gly Arg Val Thr Met Thr Arg Asp Thr Ser Thr Ser Thr
        210                 215                 220

Val Tyr Met Glu Leu Ser Ser Leu Arg Ser Glu Asp Thr Ala Val Tyr
225                 230                 235                 240

Tyr Cys Ala Arg Glu Ser Trp Pro Met Asp Val Trp Gly Gln Gly Thr
                245                 250                 255

Thr Val Thr Val Ser Ser Ala Ala Ala Leu Asp Asn Glu Lys Ser Asn
            260                 265                 270

Gly Thr Ile Ile His Val Lys Gly Lys His Leu Cys Pro Ser Pro Leu
            275                 280                 285

Phe Pro Gly Pro Ser Lys Pro Phe Trp Val Leu Val Val Val Gly Gly
            290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
            355                 360                 365

Arg Ser Ala Asp Ala Pro Ala Tyr Gln Gln Gly Gln Asn Gln Leu Tyr
        370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430
```

Ala Tyr Ser Glu Ile Gly Met Lys Gly Glu Arg Arg Gly Lys Gly
            435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 187
<211> LENGTH: 1449
<212> TYPE: DNA
<213> ORGANISM: Artificial Sequence
<220> FEATURE:
<223> OTHER INFORMATION: Description of Artificial Sequence: Synthetic
      NM-21517CARDNAHxL polynucleotide

<400> SEQUENCE: 187

```
atggcactcc ccgtaactgc tctgctgctg ccgttggcat tgctcctgca cgccgcacgc      60
ccgcagctgc agctgcagga gtcgggccca ggactggtga agccttcgga gaccctgtcc     120
ctcacctgca ctgtctctgg tggctccatc agcagtagta gttactactg gggctggatc     180
cgccagcccc cagggaaggg gctggagtgg attgggagta tctcctatag tgggagcacc     240
tactacaacc cgtccctcaa gagtcgagtc accatatccg tagacacgtc caagaaccag     300
ttctccctga gctgagttc tgtgaccgcc gcagacacgg cggtgtacta ctgcgccaga     360
ggcagggat atgcaaccag cttagccttc gatatctggg gtcagggtac aatggtcacc     420
gtctcctcag gtctacatc cggctccggg aagcccggaa gtggcgaagg tagtacaaag     480
ggggaaattg tgttgacaca gtctccagcc accctgtctt tgtctccagg ggaagagcc     540
acctctcct gcagggccag tcagagtgtt agcagctact tagcctgta ccaacagaaa     600
cctggccagg ctcccaggct cctcatctat gatgcatcca cagggccac tggcatccca     660
gccaggttca gtggcagtgg gtctgggaca gacttcactc tcaccatcag cagcctagag     720
cctgaagatt ttgcagttta ttactgtcag cagagacacg tctggcctcc tacttttggc     780
ggagggacca aggttgagat caaacgggcc gctgcccttg ataatgaaaa gtcaaacgga     840
acaatcattc acgtgaaggg caagcacctc tgtccgtcac ccttgttccc tggtccatcc     900
aagccattct gggtgttggt cgtagtgggt ggagtcctcg cttgttactc tctgctcgtc     960
accgtggctt ttataatctt ctgggttaga tccaaaagaa gccgcctgct ccatagcgat    1020
tacatgaata tgactccacg ccgccctggc cccacaagga acactacca gccttacgca    1080
ccacctagag atttcgctgc ctatcggagc agggtgaagt tttccagatc tgcagatgca    1140
ccagcgtatc agcagggcca gaaccaactg tataacgagc tcaacctggg acgcagggaa    1200
gagtatgacg ttttggacaa gcgcagagga cgggaccctg agatgggtgg caaaccaaga    1260
cgaaaaaacc cccaggaggg tctctataat gagctgcaga aggataagat ggctgaagcc    1320
tattctgaaa taggcatgaa aggagagcgg agaaggggaa agggcacga cggtttgtac    1380
cagggactca gcactgctac gaaggatact tatgacgctc tccacatgca agccctgcca    1440
cctaggtaa                                                            1449
```

<210> SEQ ID NO 188
<211> LENGTH: 482
<212> TYPE: PRT
<213> ORGANISM: Artificial Sequence
<220> FEATURE:
<223> OTHER INFORMATION: Description of Artificial Sequence: Synthetic
      NM-21517CARHxL polypeptide

<400> SEQUENCE: 188

```
Met Ala Leu Pro Val Thr Ala Leu Leu Pro Leu Ala Leu Leu Leu
1               5                   10                  15

His Ala Ala Arg Pro Gln Leu Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Ser Ser Tyr Tyr Trp Gly Trp Ile Arg Gln Pro Pro
    50                  55                  60

Gly Lys Gly Leu Glu Trp Ile Gly Ser Ile Ser Tyr Ser Gly Ser Thr
65                  70                  75                  80

Tyr Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Gly Arg Gly Tyr Ala Thr Ser Leu
        115                 120                 125

Ala Phe Asp Ile Trp Gly Gln Gly Thr Met Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Glu Ile Val Leu Thr Gln Ser Pro Ala Thr Leu Ser Leu Ser Pro
                165                 170                 175

Gly Glu Arg Ala Thr Leu Ser Cys Arg Ala Ser Gln Ser Val Ser Ser
            180                 185                 190

Tyr Leu Ala Trp Tyr Gln Gln Lys Pro Gly Gln Ala Pro Arg Leu Leu
        195                 200                 205

Ile Tyr Asp Ala Ser Asn Arg Ala Thr Gly Ile Pro Ala Arg Phe Ser
    210                 215                 220

Gly Ser Gly Ser Gly Thr Asp Phe Thr Leu Thr Ile Ser Ser Leu Glu
225                 230                 235                 240

Pro Glu Asp Phe Ala Val Tyr Tyr Cys Gln Gln Arg His Val Trp Pro
                245                 250                 255

Pro Thr Phe Gly Gly Gly Thr Lys Val Glu Ile Lys Arg Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
```

```
                    405                 410                 415
Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 189
<211> LENGTH: 1449
<212> TYPE: DNA
<213> ORGANISM: Artificial Sequence
<220> FEATURE:
<223> OTHER INFORMATION: Description of Artificial Sequence: Synthetic
      NM-21517CARDNALxH polynucleotide

<400> SEQUENCE: 189
atggcactcc ccgtaactgc tctgctgctg ccgttggcat tgctcctgca cgccgcacgc      60
ccggaaattg tgttgacaca gtctccagcc accctgtctt tgtctccagg ggaaagagcc     120
accctctcct gcagggccag tcagagtgtt agcagctact tagcctggta ccaacagaaa     180
cctggccagg ctcccaggct cctcatctat gatgcatcca cagggccac tggcatccca      240
gccaggttca gtggcagtgg gtctgggaca gacttcactc tcaccatcag cagcctagag     300
cctgaagatt ttgcagttta ttactgtcag cagagacacg tctggcctcc tacttttggc    360
ggagggacca aggttgagat caaacggggg tctacatccg gctccgggaa gcccggaagt    420
ggcgaaggta gtacaaaggg gcagctgcag ctgcaggagt cgggcccagg actggtgaag    480
ccttcggaga ccctgtccct cacctgcact gtctctggtg gctccatcag cagtagtagt    540
tactactggg gctggatccg ccagccccca gggaaggggc tggagtggat tgggagtatc    600
tcctatagtg ggagcaccta ctacaacccg tccctcaaga gtcgagtcac catatccgta    660
gacacgtcca agaaccagtt ctccctgaag ctgagttctg tgaccgccgc agacacggcg    720
gtgtactact gcgccagagg caggggatat gcaaccagct tagccttcga tatctggggt    780
cagggtacaa tggtcaccgt ctcctcagcc gctgcccttg ataatgaaaa gtcaaacgga    840
acaatcattc acgtgaaggg caagcacctc tgtccgtcac ccttgttccc tggtccatcc    900
aagccattct gggtgttggt cgtagtgggt ggagtcctcg cttgttactc tctgctcgtc    960
accgtggctt ttataatctt ctgggttaga tccaaaagaa gccgcctgct ccatagcgat   1020
tacatgaata tgactccacg ccgccctggc cccacaagga aacactacca gccttacgca   1080
ccacctagag atttcgctgc ctatcggagc agggtgaagt tttccagatc tgcagatgca   1140
ccagcgtatc agcagggcca gaaccaactg tataacgagc tcaacctggg acgcagggaa   1200
gagtatgacg ttttggacaa gcgcagagga cgggaccctg agatgggtgg caaaccaaga   1260
cgaaaaaacc cccaggaggg tctctataat gagctgcaga aggataagat ggctgaagcc   1320
tattctgaaa taggcatgaa aggagagcgg agaaggggaa aagggcacga cggtttgtac   1380
cagggactca gcactgctac gaaggatact tatgacgctc tccacatgca agccctgcca   1440
cctaggtaa                                                          1449

<210> SEQ ID NO 190
```

<211> LENGTH: 482
<212> TYPE: PRT
<213> ORGANISM: Artificial Sequence
<220> FEATURE:
<223> OTHER INFORMATION: Description of Artificial Sequence: Synthetic
      NM-21517CARLxH polypeptide

<400> SEQUENCE: 190

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Ser Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

His Val Trp Pro Pro Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Leu Gln Leu Gln Glu Ser Gly Pro Gly Leu Val Lys
145                 150                 155                 160

Pro Ser Glu Thr Leu Ser Leu Thr Cys Thr Val Ser Gly Gly Ser Ile
                165                 170                 175

Ser Ser Ser Ser Tyr Tyr Trp Gly Trp Ile Arg Gln Pro Pro Gly Lys
            180                 185                 190

Gly Leu Glu Trp Ile Gly Ser Ile Ser Tyr Ser Gly Ser Thr Tyr Tyr
        195                 200                 205

Asn Pro Ser Leu Lys Ser Arg Val Thr Ile Ser Val Asp Thr Ser Lys
    210                 215                 220

Asn Gln Phe Ser Leu Lys Leu Ser Ser Val Thr Ala Ala Asp Thr Ala
225                 230                 235                 240

Val Tyr Tyr Cys Ala Arg Gly Arg Gly Tyr Ala Thr Ser Leu Ala Phe
                245                 250                 255

Asp Ile Trp Gly Gln Gly Thr Met Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln

| | | | | | | | | | | | | |
|---|---|---|---|---|---|---|---|---|---|---|---|---|
| | | | | 370 | | | 375 | | | 380 | | |
| Gln | Gly | Gln | Asn | Gln | Leu | Tyr | Asn | Glu | Leu | Asn | Leu | Gly | Arg | Arg | Glu |
| 385 | | | | 390 | | | | 395 | | | | 400 |
| Glu | Tyr | Asp | Val | Leu | Asp | Lys | Arg | Arg | Gly | Arg | Asp | Pro | Glu | Met | Gly |
| | | | 405 | | | | | 410 | | | | | 415 | | |
| Gly | Lys | Pro | Arg | Arg | Lys | Asn | Pro | Gln | Gly | Leu | Tyr | Asn | Glu | Leu |
| | | | 420 | | | | | 425 | | | | | 430 | | |
| Gln | Lys | Asp | Lys | Met | Ala | Glu | Ala | Tyr | Ser | Glu | Ile | Gly | Met | Lys | Gly |
| | | 435 | | | | | 440 | | | | | 445 | | | |
| Glu | Arg | Arg | Arg | Gly | Lys | Gly | His | Asp | Gly | Leu | Tyr | Gln | Gly | Leu | Ser |
| | 450 | | | | | 455 | | | | | 460 | | | | |
| Thr | Ala | Thr | Lys | Asp | Thr | Tyr | Asp | Ala | Leu | His | Met | Gln | Ala | Leu | Pro |
| 465 | | | | | 470 | | | | | 475 | | | | | 480 |
| Pro | Arg |

<210> SEQ ID NO 191
<211> LENGTH: 1440
<212> TYPE: DNA
<213> ORGANISM: Artificial Sequence
<220> FEATURE:
<223> OTHER INFORMATION: Description of Artificial Sequence: Synthetic
    TS-21522CARDNAHxL polynucleotide

<400> SEQUENCE: 191

```
atggcactcc ccgtaactgc tctgctgctg ccgttggcat tgctcctgca cgccgcacgc      60
ccggaggtgc agctggtgga gtctggggga ggcttggtac agcctggggg gtccctgaga     120
ctctcctgtg cagcctctgg attcaccttc agtagctata gcatgaactg ggtccgccag     180
gctccaggga aggggctgga gtgggtttca accattagta gtagtagtag taccatatac     240
tacgcagact ctgtgaaggg ccgattcacc atctccagag acaatgccaa gaactcactg     300
tatctgcaaa tgaacagcct gagagctgag gacacggcgg tgtactactg cgccagaggt     360
tctcaggagc acctgatttt cgattattgg ggacagggta cattggtcac cgtctcctca     420
gggtctacat ccggctccgg gaagcccgga agtggcgaag gtagtacaaa ggggggaaatt    480
gtgttgacac agtctccagc caccctgtct ttgtctccag ggaaagagc cacccctctcc    540
tgcagggcca gtcagagtgt tagcaggtac ttagcctggt accaacagaa acctggccag    600
gctcccaggc tcctcatcta tgatgcatcc aacagggcca ctggcatccc agccaggttc    660
agtggcagtg ggtctgggac agacttcact ctcaccatca gcagcctaga gcctgaagat    720
tttgcagttt attactgtca gcagagattc tactacccct tggacttttgg cggagggacc    780
aaggttgaga tcaaacgggc cgctgccctt gataatgaaa agtcaaacgg aacaatcatt    840
cacgtgaagg gcaagcacct ctgtccgtca cccttgttcc ctggtccatc caagccattc    900
tgggtgttgg tcgtagtggg tggagtcctc gcttgttact ctctgctcgt caccgtggct    960
tttataatct ctgggttag atccaaaaga agccgcctgc tccatagcga ttacatgaat   1020
atgactccac gccgccctgg ccccacaagg aaacactacc agccttacgc accacctaga   1080
gatttcgctg cctatcggag cagggtgaag ttttccagat ctgcagatgc accagcgtat   1140
cagcagggcc agaaccaact gtataacgag ctcaacctgg gacgcaggga gagtatgac    1200
gttttggaca gcgcagagg acgggaccct gagatgggtg gcaaaccaag acgaaaaaac   1260
ccccaggag gtctctataa tgagctgcag aaggataaga tggctgaagc ctattctgaa   1320
ataggcatga aggagagcg gagaagggga aaagggcacg acggtttgta ccagggactc   1380
```
agcactgcta cgaaggatac ttatgacgct ctccacatgc aagccctgcc acctaggtaa    1440

<210> SEQ ID NO 192
<211> LENGTH: 479
<212> TYPE: PRT
<213> ORGANISM: Artificial Sequence
<220> FEATURE:
<223> OTHER INFORMATION: Description of Artificial Sequence: Synthetic
    TS-21522CARHxL polypeptide

<400> SEQUENCE: 192

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ser Met Asn Trp Val Arg Gln Ala Pro Gly Lys
    50                  55                  60

Gly Leu Glu Trp Val Ser Thr Ile Ser Ser Ser Ser Thr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Gly Ser Gln Glu His Leu Ile Phe Asp
        115                 120                 125

Tyr Trp Gly Gln Gly Thr Leu Val Thr Val Ser Ser Gly Ser Thr Ser
    130                 135                 140

Gly Ser Gly Lys Pro Gly Ser Gly Glu Gly Ser Thr Lys Gly Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Arg Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Phe Tyr Pro Trp Thr Phe
                245                 250                 255

Gly Gly Gly Thr Lys Val Glu Ile Lys Arg Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350
```

| | | | | | | | | | | | |
|---|---|---|---|---|---|---|---|---|---|---|---|
|Tyr|Gln|Pro|Tyr|Ala|Pro|Pro|Arg|Asp|Phe|Ala|Ala|Tyr|Arg|Ser|Arg|
| | |355| | | |360| | | | |365| | | | |

Val Lys Phe Ser Arg Ser Ala Asp Ala Pro Ala Tyr Gln Gln Gly Gln
        370             375             380

Asn Gln Leu Tyr Asn Glu Leu Asn Leu Gly Arg Arg Glu Glu Tyr Asp
385             390             395             400

Val Leu Asp Lys Arg Arg Gly Arg Asp Pro Glu Met Gly Gly Lys Pro
            405             410             415

Arg Arg Lys Asn Pro Gln Glu Gly Leu Tyr Asn Glu Leu Gln Lys Asp
            420             425             430

Lys Met Ala Glu Ala Tyr Ser Glu Ile Gly Met Lys Gly Glu Arg Arg
        435             440             445

Arg Gly Lys Gly His Asp Gly Leu Tyr Gln Gly Leu Ser Thr Ala Thr
    450             455             460

Lys Asp Thr Tyr Asp Ala Leu His Met Gln Ala Leu Pro Pro Arg
465             470             475

```
<210> SEQ ID NO 193
<211> LENGTH: 1440
<212> TYPE: DNA
<213> ORGANISM: Artificial Sequence
<220> FEATURE:
<223> OTHER INFORMATION: Description of Artificial Sequence: Synthetic
      TS-21522CARDNALxH polynucleotide

<400> SEQUENCE: 193
```

| | | |
|---|---|---|
|atggcactcc cgtaactgc tctgctgctg ccgttggcat tgctcctgca cgccgcacgc|60|
|ccggaaattg tgttgacaca gtctccagcc accctgtctt tgtctccagg ggaaagagcc|120|
|accctctcct gcagggccag tcagagtgtt agcaggtact tagcctgta ccaacagaaa|180|
|cctggccagg ctcccaggct cctcatctat gatgcatcca acagggccac tggcatccca|240|
|gccaggttca gtggcagtgg gtctgggaca gacttcactc tcaccatcag cagcctagag|300|
|cctgaagatt ttgcagttta ttactgtcag cagagattct actacccttg gacttttggc|360|
|ggagggacca aggttgagat caaacggggg tctacatccg gctccgggaa gcccggaagt|420|
|ggcgaaggta gtacaaaggg ggaggtgcag ctggtggagt ctggggggag cttggtacag|480|
|cctgggggt ccctgagact ctcctgtgca gcctctggat tcaccttcag tagctatagc|540|
|atgaactggg tccgccaggc tccagggaag gggctgagtg ggtttcaac cattagtagt|600|
|agtagtagta ccatatacta cgcagactct gtgaagggcc gattcaccat ctccagagac|660|
|aatgccaaga actcactgta tctgcaaatg aacagcctga gagctgagga cacggcggtg|720|
|tactactgcg ccagaggttc tcaggagcac ctgattttcg attattgggg acagggtaca|780|
|ttggtcaccg tctcctcagc cgctgcccct gataatgaaa agtcaaacgg aacaatcatt|840|
|cacgtgaagg gcaagcacct ctgtccgtca cccttgttcc ctggtccatc caagccattc|900|
|tgggtgttgg tcgtagtggg tggagtcctc gcttgttact ctctgctcgt caccgtggct|960|
|tttataatct tctgggttag atccaaaaga agccgcctgc tccatagcga ttacatgaat|1020|
|atgactccac gccgccctgg ccccacaagg aaacactacc agccttacgc accacctaga|1080|
|gatttcgctg cctatcggag cagggtgaag ttttccagat ctgcagatgc accagcgtat|1140|
|cagcagggcc agaaccaact gtataacgag ctcaacctgg gacgcaggga agagtatgac|1200|
|gttttggaca gcgcagagg acgggaccct gagatgggtg gcaaaccaag acgaaaaaac|1260|
|ccccaggagg gtctctataa tgagctgcag aaggataaga tggctgaagc ctattctgaa|1320|

```
ataggcatga aaggagagcg gagaagggga aaagggcacg acggtttgta ccagggactc    1380
agcactgcta cgaaggatac ttatgacgct ctccacatgc aagccctgcc acctaggtaa    1440
```

<210> SEQ ID NO 194
<211> LENGTH: 479
<212> TYPE: PRT
<213> ORGANISM: Artificial Sequence
<220> FEATURE:
<223> OTHER INFORMATION: Description of Artificial Sequence: Synthetic
      TS-21522CARLxH polypeptide

<400> SEQUENCE: 194

| Met | Ala | Leu | Pro | Val | Thr | Ala | Leu | Leu | Pro | Leu | Ala | Leu | Leu | Leu |
|---|---|---|---|---|---|---|---|---|---|---|---|---|---|---|
| 1 | | | | 5 | | | | | 10 | | | | | 15 |

| His | Ala | Ala | Arg | Pro | Glu | Ile | Val | Leu | Thr | Gln | Ser | Pro | Ala | Thr | Leu |
|---|---|---|---|---|---|---|---|---|---|---|---|---|---|---|---|
| | | | 20 | | | | | 25 | | | | | 30 | | |

| Ser | Leu | Ser | Pro | Gly | Glu | Arg | Ala | Thr | Leu | Ser | Cys | Arg | Ala | Ser | Gln |
|---|---|---|---|---|---|---|---|---|---|---|---|---|---|---|---|
| | | 35 | | | | | 40 | | | | | 45 | | | |

| Ser | Val | Ser | Arg | Tyr | Leu | Ala | Trp | Tyr | Gln | Gln | Lys | Pro | Gly | Gln | Ala |
|---|---|---|---|---|---|---|---|---|---|---|---|---|---|---|---|
| | 50 | | | | | 55 | | | | | 60 | | | | |

| Pro | Arg | Leu | Leu | Ile | Tyr | Asp | Ala | Ser | Asn | Arg | Ala | Thr | Gly | Ile | Pro |
|---|---|---|---|---|---|---|---|---|---|---|---|---|---|---|---|
| 65 | | | | | 70 | | | | | 75 | | | | | 80 |

| Ala | Arg | Phe | Ser | Gly | Ser | Gly | Ser | Gly | Thr | Asp | Phe | Thr | Leu | Thr | Ile |
|---|---|---|---|---|---|---|---|---|---|---|---|---|---|---|---|
| | | | | 85 | | | | | 90 | | | | | 95 | |

| Ser | Ser | Leu | Glu | Pro | Glu | Asp | Phe | Ala | Val | Tyr | Tyr | Cys | Gln | Gln | Arg |
|---|---|---|---|---|---|---|---|---|---|---|---|---|---|---|---|
| | | | 100 | | | | | 105 | | | | | 110 | | |

| Phe | Tyr | Tyr | Pro | Trp | Thr | Phe | Gly | Gly | Gly | Thr | Lys | Val | Glu | Ile | Lys |
|---|---|---|---|---|---|---|---|---|---|---|---|---|---|---|---|
| | | 115 | | | | | 120 | | | | | 125 | | | |

| Arg | Gly | Ser | Thr | Ser | Gly | Ser | Gly | Lys | Pro | Gly | Ser | Gly | Glu | Gly | Ser |
|---|---|---|---|---|---|---|---|---|---|---|---|---|---|---|---|
| | 130 | | | | | 135 | | | | | 140 | | | | |

| Thr | Lys | Gly | Glu | Val | Gln | Leu | Val | Glu | Ser | Gly | Gly | Gly | Leu | Val | Gln |
|---|---|---|---|---|---|---|---|---|---|---|---|---|---|---|---|
| 145 | | | | | 150 | | | | | 155 | | | | | 160 |

| Pro | Gly | Gly | Ser | Leu | Arg | Leu | Ser | Cys | Ala | Ala | Ser | Gly | Phe | Thr | Phe |
|---|---|---|---|---|---|---|---|---|---|---|---|---|---|---|---|
| | | | | 165 | | | | | 170 | | | | | 175 | |

| Ser | Ser | Tyr | Ser | Met | Asn | Trp | Val | Arg | Gln | Ala | Pro | Gly | Lys | Gly | Leu |
|---|---|---|---|---|---|---|---|---|---|---|---|---|---|---|---|
| | | | 180 | | | | | 185 | | | | | 190 | | |

| Glu | Trp | Val | Ser | Thr | Ile | Ser | Ser | Ser | Ser | Thr | Ile | Tyr | Tyr | Ala |
|---|---|---|---|---|---|---|---|---|---|---|---|---|---|---|
| | | 195 | | | | | 200 | | | | | 205 | | |

| Asp | Ser | Val | Lys | Gly | Arg | Phe | Thr | Ile | Ser | Arg | Asp | Asn | Ala | Lys | Asn |
|---|---|---|---|---|---|---|---|---|---|---|---|---|---|---|---|
| | 210 | | | | | 215 | | | | | 220 | | | | |

| Ser | Leu | Tyr | Leu | Gln | Met | Asn | Ser | Leu | Arg | Ala | Glu | Asp | Thr | Ala | Val |
|---|---|---|---|---|---|---|---|---|---|---|---|---|---|---|---|
| 225 | | | | | 230 | | | | | 235 | | | | | 240 |

| Tyr | Tyr | Cys | Ala | Arg | Gly | Ser | Gln | Glu | His | Leu | Ile | Phe | Asp | Tyr | Trp |
|---|---|---|---|---|---|---|---|---|---|---|---|---|---|---|---|
| | | | | 245 | | | | | 250 | | | | | 255 | |

| Gly | Gln | Gly | Thr | Leu | Val | Thr | Val | Ser | Ser | Ala | Ala | Ala | Leu | Asp | Asn |
|---|---|---|---|---|---|---|---|---|---|---|---|---|---|---|---|
| | | | 260 | | | | | 265 | | | | | 270 | | |

| Glu | Lys | Ser | Asn | Gly | Thr | Ile | Ile | His | Val | Lys | Gly | Lys | His | Leu | Cys |
|---|---|---|---|---|---|---|---|---|---|---|---|---|---|---|---|
| | | 275 | | | | | 280 | | | | | 285 | | | |

| Pro | Ser | Pro | Leu | Phe | Pro | Gly | Pro | Ser | Lys | Pro | Phe | Trp | Val | Leu | Val |
|---|---|---|---|---|---|---|---|---|---|---|---|---|---|---|---|
| | 290 | | | | | 295 | | | | | 300 | | | | |

| Val | Val | Gly | Gly | Val | Leu | Ala | Cys | Tyr | Ser | Leu | Leu | Val | Thr | Val | Ala |
|---|---|---|---|---|---|---|---|---|---|---|---|---|---|---|---|
| 305 | | | | | 310 | | | | | 315 | | | | | 320 |

| Phe | Ile | Ile | Phe | Trp | Val | Arg | Ser | Lys | Arg | Ser | Arg | Leu | Leu | His | Ser |
|---|---|---|---|---|---|---|---|---|---|---|---|---|---|---|---|
| | | | | 325 | | | | | 330 | | | | | 335 | |

| Asp | Tyr | Met | Asn | Met | Thr | Pro | Arg | Arg | Pro | Gly | Pro | Thr | Arg | Lys | His |

```
            340                 345                 350
Tyr Gln Pro Tyr Ala Pro Pro Arg Asp Phe Ala Ala Tyr Arg Ser Arg
            355                 360                 365
Val Lys Phe Ser Arg Ser Ala Asp Ala Pro Ala Tyr Gln Gln Gly Gln
            370                 375                 380
Asn Gln Leu Tyr Asn Glu Leu Asn Leu Gly Arg Arg Glu Glu Tyr Asp
385                 390                 395                 400
Val Leu Asp Lys Arg Arg Gly Arg Asp Pro Glu Met Gly Gly Lys Pro
                405                 410                 415
Arg Arg Lys Asn Pro Gln Glu Gly Leu Tyr Asn Glu Leu Gln Lys Asp
                420                 425                 430
Lys Met Ala Glu Ala Tyr Ser Glu Ile Gly Met Lys Gly Glu Arg Arg
            435                 440                 445
Arg Gly Lys Gly His Asp Gly Leu Tyr Gln Gly Leu Ser Thr Ala Thr
        450                 455                 460
Lys Asp Thr Tyr Asp Ala Leu His Met Gln Ala Leu Pro Pro Arg
465                 470                 475

<210> SEQ ID NO 195
<211> LENGTH: 1449
<212> TYPE: DNA
<213> ORGANISM: Artificial Sequence
<220> FEATURE:
<223> OTHER INFORMATION: Description of Artificial Sequence: Synthetic
      RY-21527CARDNAHxL polynucleotide

<400> SEQUENCE: 195
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagctatg gcatgcactg ggtccgccag     180
gctccaggca aggggctgga gtgggtggca gttatatcgt atgatggaag taataaatac     240
tatgcagact ccgtgaaggg ccgattcacc atctccagag acaattccaa gaacacgctg     300
tatctgcaaa tgaacagcct gagagccgag gacacggcgg tgtactactg cgccagaact     360
gacttctgga gcggatcccc tccaggctta gattactggg gacagggtac attggtcacc     420
gtctcctcag gtctacatc  cggctccggg aagcccggaa gtggcgaagg tagtacaaag     480
ggggacatcc agttgaccca gtctccatct tccgtgtctg catctgtagg agacagagtc     540
accatcactt gtcgggcgag tcagggtatt agcagctggt tagcctggta tcagcagaaa     600
ccagggaaag cccctaagct cctgatctat ggtgcatcca gtttgcaaag tggggtccca     660
tcaaggttca gcggcagtgg atctgggaca gatttcactc tcaccatcag cagcctgcag     720
cctgaagatt ttgcaactta ttactgtcag cagatataca ccttcccttt cacttttggc     780
ggagggacca aggttgagat caaacgggcc gctgcccttg ataatgaaaa gtcaaacgga     840
acaatcattc acgtgaaggg caagcaccct cgtgtccgtca ccttgttccc tggtccatcc     900
aagccattct gggtgttggt cgtagtgggt ggagtcctcg cttgttactc tctgctcgtc     960
accgtggctt ttataatctt ctgggttaga tccaaaagaa gccgcctgct ccatagcgat    1020
tacatgaata tgactccacg ccgccctggc cccacaagga acactacca gccttacgca    1080 ccacctagag atttcgctgc ctatcggagc agggtgaagt tttccagatc tgcagatgca    1140
ccagcgtatc agcagggcca gaaccaactg tataacgagc tcaacctggg acgcagggaa    1200
gagtatgacg tttggacaa gcgcagagga cgggaccctg agatgggtgg caaaccaaga    1260
```

-continued

```
cgaaaaaacc cccaggaggg tctctataat gagctgcaga aggataagat ggctgaagcc    1320
tattctgaaa taggcatgaa aggagagcgg agaaggggaa aagggcacga cggtttgtac    1380
cagggactca gcactgctac gaaggatact tatgacgctc tccacatgca agccctgcca    1440
cctaggtaa                                                            1449
```

<210> SEQ ID NO 196
<211> LENGTH: 482
<212> TYPE: PRT
<213> ORGANISM: Artificial Sequence
<220> FEATURE:
<223> OTHER INFORMATION: Description of Artificial Sequence: Synthetic
      RY-21527CARHxL polypeptide

<400> SEQUENCE: 196

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Thr Asp Phe Trp Ser Gly Ser Pro Pro
        115                 120                 125

Gly Leu Asp Tyr Trp Gly Gln Gly Thr Leu Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Asp Ile Gln Leu Thr Gln Ser Pro Ser Ser Val Ser Ala Ser Val
                165                 170                 175

Gly Asp Arg Val Thr Ile Thr Cys Arg Ala Ser Gln Gly Ile Ser Ser
            180                 185                 190

Trp Leu Ala Trp Tyr Gln Gln Lys Pro Gly Lys Ala Pro Lys Leu Leu
        195                 200                 205

Ile Tyr Gly Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ile Tyr Thr Phe Pro
                245                 250                 255

Phe Thr Phe Gly Gly Gly Thr Lys Val Glu Ile Lys Arg Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320
```

```
Thr Val Ala Phe Ile Ile Phe Trp Val Arg Ser Lys Arg Ser Arg Leu
            325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
            355                 360                 365

Arg Ser Arg Val Lys Phe Ser Arg Ser Ala Asp Ala Pro Ala Tyr Gln
            370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
            405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
            450                 455                 460

Thr Ala Thr Lys Asp Thr Tyr Asp Ala Leu His Met Gln Ala Leu Pro
465                 470                 475                 480

Pro Arg

<210> SEQ ID NO 197
<211> LENGTH: 1449
<212> TYPE: DNA
<213> ORGANISM: Artificial Sequence
<220> FEATURE:
<223> OTHER INFORMATION: Description of Artificial Sequence: Synthetic
      RY-21527CARDNALxH polynucleotide

<400> SEQUENCE: 197
atggcactcc ccgtaactgc tctgctgctg ccgttggcat tgctcctgca cgccgcacgc      60
ccggacatcc agttgaccca gtctccatct tccgtgtctg catctgtagg agacagagtc     120
accatcactt gtcgggcgag tcagggtatt agcagctggt tagcctggta tcagcagaaa     180
ccagggaaag cccctaagct cctgatctat ggtgcatcca gtttgcaaag tggggtccca     240
tcaaggttca gcggcagtgg atctgggaca gatttcactc tcaccatcag cagcctgcag     300
cctgaagatt ttgcaactta ttactgtcag cagatataca ccttcccttt cacttttggc     360
ggagggacca aggttgagat caaacggggg tctacatccg gctccgggaa gcccggaagt     420
ggcgaaggta gtacaaaggg gcaggtgcag ctggtggagt ctgggggagg cgtggtccag     480
cctgggaggt ccctgagact ctcctgtgca gcgtctggat tcaccttcag tagctatggc     540
atgcactggg tccgccaggc tccaggcaag gggctggagt gggtggcagt tatatcgtat     600
gatggaagta ataaatacta tgcagactcc gtgaagggcc gattcaccat ctccagagac     660
aattccaaga cacgctgta tctgcaaatg aacagcctga gaccgagga cacggcggtg      720 tactactgcg ccagaactga cttctggagc ggatcccctc aggcttaga ttactgggga     780 cagggtacat ggtcaccgt ctcctcagcc gctgccttg ataatgaaaa gtcaaacgga      840
acaatcattc acgtgaaggg caagcacctc tgtccgtcac ccttgttccc tggtccatcc     900
aagccattct gggtgttggt cgtagtgggt ggagtcctcg cttgttactc tctgctcgtc     960
accgtggctt ttataatctt ctgggttaga tccaaaagaa gccgcctgct ccatagcgat    1020
tacatgaata tgactccacg ccgccctggc cccacaagga aacactacca gccttacgca    1080
```

```
ccacctagag atttcgctgc ctatcggagc agggtgaagt tttccagatc tgcagatgca    1140
ccagcgtatc agcagggcca gaaccaactg tataacgagc tcaacctggg acgcagggaa    1200
gagtatgacg ttttggacaa gcgcagagga cgggaccctg agatgggtgg caaaccaaga    1260
cgaaaaaacc cccaggaggg tctctataat gagctgcaga aggataagat ggctgaagcc    1320
tattctgaaa taggcatgaa aggagagcgg agaagggaa aagggcacga cggtttgtac    1380
cagggactca gcactgctac gaaggatact tatgacgctc tccacatgca agccctgcca    1440
cctaggtaa                                                            1449
```

<210> SEQ ID NO 198
<211> LENGTH: 482
<212> TYPE: PRT
<213> ORGANISM: Artificial Sequence
<220> FEATURE:
<223> OTHER INFORMATION: Description of Artificial Sequence: Synthetic
      RY-21527CARLxH polypeptide

<400> SEQUENCE: 198

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Val
            20                  25                  30

Ser Ala Ser Val Gly Asp Arg Val Thr Ile Thr Cys Arg Ala Ser Gln
        35                  40                  45

Gly Ile Ser Ser Trp Leu Ala Trp Tyr Gln Gln Lys Pro Gly Lys Ala
    50                  55                  60

Pro Lys Leu Leu Ile Tyr Gly Ala Ser Ser Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Ile
            100                 105                 110

Tyr Thr Phe Pro Phe Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Val Glu Ser Gly Gly Gly Val Val Gln
145                 150                 155                 160

Pro Gly Arg Ser Leu Arg Leu Ser Cys Ala Ala Ser Gly Phe Thr Phe
                165                 170                 175

Ser Ser Tyr Gly Met His Trp Val Arg Gln Ala Pro Gly Lys Gly Leu
            180                 185                 190

Glu Trp Val Ala Val Ile Ser Tyr Asp Gly Ser Asn Lys Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Arg Thr Asp Phe Trp Ser Gly Ser Pro Pro Gly Leu
                245                 250                 255

Asp Tyr Trp Gly Gln Gly Thr Leu Val Thr Val Ser Ser Ala Ala Ala
            260                 265                 270

Leu Asp Asn Glu Lys Ser Asn Gly Thr Ile Ile His Val Lys Gly Lys
        275                 280                 285
```

```
His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
                340                 345                 350

Arg Lys His Tyr Gln Pro Tyr Ala Pro Pro Arg Asp Phe Ala Ala Tyr
            355                 360                 365

Arg Ser Arg Val Lys Phe Ser Arg Ser Ala Asp Ala Pro Ala Tyr Gln
370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 199
<211> LENGTH: 1479
<212> TYPE: DNA
<213> ORGANISM: Artificial Sequence
<220> FEATURE:
<223> OTHER INFORMATION: Description of Artificial Sequence: Synthetic
      PP-21528CARDNAHxL polynucleotide

<400> SEQUENCE: 199
atggcactcc ccgtaactgc tctgctgctg ccgttggcat tgctcctgca cgccgcacgc      60
ccgcaggtgc agctggtgca gtctggggct gaggtgaaga agcctgggtc ctcggtgaag     120
gtctcctgca aggcttctgg aggcaccttc agcagctatg ctatcagctg ggtgcgacag     180
gcccctggac aagggcttga gtggatggga gggatcatcc ctatctttgg tacagcaaac     240
tacgcacaga agttccaggg cagagtcacg attaccgcgg acgaatccac gagcacagcc     300
tacatggagc tgagcagcct gagatctgag gacacggcgg tgtactactg cgccagaact     360
cctgaatact cctccagcat atggcactat tactacggca tggacgtatg gggccaggga     420
acaactgtca ccgtctcctc agggtctaca tccggctccg ggaagcccgg aagtggcgaa     480
ggtagtacaa agggggacat cgtgatgacc cagtctccag actccctggc tgtgtctctg     540
ggcgagaggg ccaccatcaa ctgcaagtcc agccagagtg ttttatacag ctccaacaat     600
aagaactact tagcttggta ccagcagaaa ccaggacagc ctcctaagct gctcatttac     660
tgggcatcta cccgggaatc cggggtccct gaccgattca gtggcagcgg gtctgggaca     720
gatttcactc tcaccatcag cagcctgcag gctgaagatg tggcagttta ttactgtcag     780
cagttcgccc acactccttt cactttggc ggagggacca aggttgagat caaacgggcc     840
gctgcccttg ataatgaaaa gtcaaacgga acaatcattc acgtgaaggg caagcacctc     900
```

-continued

```
tgtccgtcac ccttgttccc tggtccatcc aagccattct gggtgttggt cgtagtgggt    960
ggagtcctcg cttgttactc tctgctcgtc accgtggctt ttataatctt ctgggttaga   1020
tccaaaagaa gccgcctgct ccatagcgat tacatgaata tgactccacg ccgccctggc   1080
cccacaagga aacactacca gccttacgca ccacctagag atttcgctgc ctatcggagc   1140
agggtgaagt tttccagatc tgcagatgca ccagcgtatc agcagggcca gaaccaactg   1200
tataacgagc tcaacctggg acgcagggaa gagtatgacg ttttggacaa gcgcagagga   1260
cgggaccctg agatgggtgg caaaccaaga cgaaaaaacc cccaggaggg tctctataat   1320
gagctgcaga aggataagat ggctgaagcc tattctgaaa taggcatgaa aggagagcgg   1380
agaaggggaa aagggcacga cggtttgtac cagggactca gcactgctac gaaggatact   1440
tatgacgctc tccacatgca agccctgcca cctaggtaa                          1479
```

<210> SEQ ID NO 200
<211> LENGTH: 492
<212> TYPE: PRT
<213> ORGANISM: Artificial Sequence
<220> FEATURE:
<223> OTHER INFORMATION: Description of Artificial Sequence: Synthetic
      PP-21528CARHxL polypeptide

<400> SEQUENCE: 200

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Ala Ser Gly Gly
            35                  40                  45

Thr Phe Ser Ser Tyr Ala Ile Ser Trp Val Arg Gln Ala Pro Gly Gln
        50                  55                  60

Gly Leu Glu Trp Met Gly Gly Ile Ile Pro Ile Phe Gly Thr Ala Asn
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Thr Pro Glu Tyr Ser Ser Ser Ile Trp
        115                 120                 125

His Tyr Tyr Gly Met Asp Val Trp Gly Gln Gly Thr Thr Val Thr
    130                 135                 140

Val Ser Ser Gly Ser Thr Ser Gly Ser Gly Lys Pro Gly Ser Gly Glu
145                 150                 155                 160

Gly Ser Thr Lys Gly Asp Ile Val Met Thr Gln Ser Pro Asp Ser Leu
                165                 170                 175

Ala Val Ser Leu Gly Glu Arg Ala Thr Ile Asn Cys Lys Ser Ser Gln
            180                 185                 190

Ser Val Leu Tyr Ser Ser Asn Asn Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Leu Gln Ala Glu Asp Val Ala Val
                245                 250                 255
```

Tyr Tyr Cys Gln Gln Phe Ala His Thr Pro Phe Thr Phe Gly Gly
            260                 265                 270

Thr Lys Val Glu Ile Lys Arg Ala Ala Ala Leu Asp Asn Glu Lys Ser
            275                 280                 285

Asn Gly Thr Ile Ile His Val Lys Gly Lys His Leu Cys Pro Ser Pro
        290                 295                 300

Leu Phe Pro Gly Pro Ser Lys Pro Phe Trp Val Leu Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
            355                 360                 365

Tyr Ala Pro Pro Arg Asp Phe Ala Ala Tyr Arg Ser Arg Val Lys Phe
        370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
        450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

```
<210> SEQ ID NO 201
<211> LENGTH: 1479
<212> TYPE: DNA
<213> ORGANISM: Artificial Sequence
<220> FEATURE:
<223> OTHER INFORMATION: Description of Artificial Sequence: Synthetic
      PP-21528CARDNALxH polynucleotide

<400> SEQUENCE: 201
atggcactcc ccgtaactgc tctgctgctg ccgttggcat tgctcctgca cgccgcacgc      60
ccggacatcg tgatgaccca gtctccagac tccctggctg tgtctctggg cgagagggcc     120
accatcaact gcaagtccag ccagagtgtt ttatacagct ccaacaataa gaactactta     180
gcttggtacc agcagaaacc aggacagcct cctaagctgc tcatttactg ggcatctacc     240
cgggaatccg gggtccctga ccgattcagt ggcagcgggt ctgggacaga tttcactctc     300
accatcagca gcctgcaggc tgaagatgtg gcagtttatt actgtcagca gttcgcccac     360
actcctttca cttttggcgg agggaccaag gttgagatca acgggggtc tacatccggc     420 tccgggaagc ccggaagtgg cgaaggtagt acaaaggggc aggtgcagct ggtgcagtct     480
ggggctgagg tgaagaagcc tgggtcctcg gtgaaggtct cctgcaaggc ttctggaggc     540
accttcagca gctatgctat cagctggggtg cgacaggccc ctggacaagg gcttgagtgg     600
atgggaggga tcatccctat ctttggtaca gcaaactacg cacagaagtt ccagggcaga     660
gtcacgatta ccgcggacga atccacgagc acagcctaca tggagctgag cagcctgaga     720
```

```
tctgaggaca cggcggtgta ctactgcgcc agaactcctg aatactcctc cagcatatgg    780
cactattact acggcatgga cgtatggggc cagggaacaa ctgtcaccgt ctcctcagcc    840
gctgcccttg ataatgaaaa gtcaaacgga acaatcattc acgtgaaggg caagcacctc    900
tgtccgtcac ccttgttccc tggtccatcc aagccattct gggtgttggt cgtagtgggt    960
ggagtcctcg cttgttactc tctgctcgtc accgtggctt ttataatctt ctgggttaga   1020
tccaaaagaa gccgcctgct ccatagcgat tacatgaata tgactccacg ccgccctggc   1080
cccacaagga aacactacca gccttacgca ccacctagag atttcgctgc ctatcggagc   1140
agggtgaagt tttccagatc tgcagatgca ccagcgtatc agcagggcca gaaccaactg   1200
tataacgagc tcaacctggg acgcagggaa gagtatgacg ttttggacaa gcgcagagga   1260
cgggaccctg agatgggtgg caaaccaaga cgaaaaaacc cccaggaggg tctctataat   1320
gagctgcaga aggataagat ggctgaagcc tattctgaaa taggcatgaa aggagagcgg   1380
agaaggggaa aagggcacga cggtttgtac cagggactca gcactgctac gaaggatact   1440
tatgacgctc tccacatgca agccctgcca cctaggtaa                          1479
```

<210> SEQ ID NO 202
<211> LENGTH: 492
<212> TYPE: PRT
<213> ORGANISM: Artificial Sequence
<220> FEATURE:
<223> OTHER INFORMATION: Description of Artificial Sequence: Synthetic
      PP-21528CARLxH polypeptide

<400> SEQUENCE: 202

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Val Leu Tyr Ser Ser Asn Asn Lys Asn Tyr Leu Ala Trp Tyr Gln
    50                  55                  60

Gln Lys Pro Gly Gln Pro Pro Lys Leu Leu Ile Tyr Trp Ala Ser Thr
65                  70                  75                  80

Arg Glu Ser Gly Val Pro Asp Arg Phe Ser Gly Ser Gly Ser Gly Thr
                85                  90                  95

Asp Phe Thr Leu Thr Ile Ser Ser Leu Gln Ala Glu Asp Val Ala Val
            100                 105                 110

Tyr Tyr Cys Gln Gln Phe Ala His Thr Pro Phe Thr Phe Gly Gly Gly
        115                 120                 125

Thr Lys Val Glu Ile Lys Arg Gly Ser Thr Ser Gly Ser Gly Lys Pro
    130                 135                 140

Gly Ser Gly Glu Gly Ser Thr Lys Gly Gln Val Gln Leu Val Gln Ser
145                 150                 155                 160

Gly Ala Glu Val Lys Lys Pro Gly Ser Ser Val Lys Val Ser Cys Lys
                165                 170                 175

Ala Ser Gly Gly Thr Phe Ser Ser Tyr Ala Ile Ser Trp Val Arg Gln
            180                 185                 190

Ala Pro Gly Gln Gly Leu Glu Trp Met Gly Gly Ile Ile Pro Ile Phe
        195                 200                 205

Gly Thr Ala Asn Tyr Ala Gln Lys Phe Gln Gly Arg Val Thr Ile Thr
    210                 215                 220
```

Ala Asp Glu Ser Thr Ser Thr Ala Tyr Met Glu Leu Ser Ser Leu Arg
225                 230                 235                 240

Ser Glu Asp Thr Ala Val Tyr Tyr Cys Ala Arg Thr Pro Glu Tyr Ser
            245                 250                 255

Ser Ser Ile Trp His Tyr Tyr Gly Met Asp Val Trp Gly Gln Gly
        260                 265                 270

Thr Thr Val Thr Val Ser Ser Ala Ala Ala Leu Asp Asn Glu Lys Ser
        275                 280                 285

Asn Gly Thr Ile Ile His Val Lys Gly Lys His Leu Cys Pro Ser Pro
            290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 203
<211> LENGTH: 1452
<212> TYPE: DNA
<213> ORGANISM: Artificial Sequence
<220> FEATURE:
<223> OTHER INFORMATION: Description of Artificial Sequence: Synthetic
      RD-21530CARDNAHxL polynucleotide

<400> SEQUENCE: 203
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagctatg gcatgcactg ggtccgccag     180
gctccaggca aggggctgga gtgggtggca gttatatcgt atgatggaag taataaatac     240
tatgcagact ccgtgaaggg ccgattcacc atctccagag acaattccaa gaacacgctg     300
tatctgcaaa tgaacagcct gagagccgag gacacggcgg tgtactactg cgtcaagggg     360
ccgttgcagg agccgccata cgattatgga atggacgtat ggggccaggg aacaactgtc     420
accgtctcct cagggtctac atccggctcc gggaagcccg gaagtggcga aggtagtaca     480

```
aaggggggaaa tagtgatgac gcagtctcca gccaccctgt ctgtgtctcc aggggaaaga    540
gccaccctct cctgcagggc cagtcagagt gttagcagca acttagcctg gtaccagcag    600
aaacctggcc aggctcccag gctcctcatc tatagcgcat ccaccagggc cactggtatc    660
ccagccaggt tcagtggcag tgggtctggg acagagttca ctctcaccat cagcagcctg    720
cagtctgaag attttgcagt ttattactgt cagcagcacc acgtctggcc tctcactttt    780
ggcggaggga ccaaggttga gatcaaacgg gccgctgccc ttgataatga aaagtcaaac    840
ggaacaatca ttcacgtgaa gggcaagcac ctctgtccgt cacccttgtt ccctggtcca    900
tccaagccat tctgggtgtt ggtcgtagtg ggtggagtcc tcgcttgtta ctctctgctc    960
gtcaccgtgg cttttataat cttctgggtt agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa accccaggga gggtctctat aatgagctgc agaaggataa gatggctgaa   1320
gcctattctg aaataggcat gaaaggagag cggagaaggg gaaaagggca cgacggtttg   1380
taccagggac tcagcactgc tacgaaggat acttatgacg ctctccacat gcaagccctg   1440
ccacctaggt aa                                                       1452
```

<210> SEQ ID NO 204
<211> LENGTH: 483
<212> TYPE: PRT
<213> ORGANISM: Artificial Sequence
<220> FEATURE:
<223> OTHER INFORMATION: Description of Artificial Sequence: Synthetic
    RD-21530CARHxL polypeptide

<400> SEQUENCE: 204

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
```

180                 185                 190
    Ser Asn Leu Ala Trp Tyr Gln Gln Lys Pro Gly Gln Ala Pro Arg Leu
            195                 200                 205

Leu Ile Tyr Ser Ala Ser Thr Arg Ala Thr Gly Ile Pro Ala Arg Phe
            210                 215                 220

Ser Gly Ser Gly Ser Gly Thr Glu Phe Thr Leu Thr Ile Ser Ser Leu
    225                 230                 235                 240

Gln Ser Glu Asp Phe Ala Val Tyr Tyr Cys Gln Gln His His Val Trp
                        245                 250                 255

Pro Leu Thr Phe Gly Gly Gly Thr Lys Val Glu Ile Lys Arg Ala Ala
                260                 265                 270

Ala Leu Asp Asn Glu Lys Ser Asn Gly Thr Ile Ile His Val Lys Gly
            275                 280                 285

Lys His Leu Cys Pro Ser Pro Leu Phe Pro Gly Pro Ser Lys Pro Phe
            290                 295                 300

Trp Val Leu Val Val Val Gly Gly Val Leu Ala Cys Tyr Ser Leu Leu
    305                 310                 315                 320

Val Thr Val Ala Phe Ile Ile Phe Trp Val Arg Ser Lys Arg Ser Arg
                        325                 330                 335

Leu Leu His Ser Asp Tyr Met Asn Met Thr Pro Arg Arg Pro Gly Pro
                340                 345                 350

Thr Arg Lys His Tyr Gln Pro Tyr Ala Pro Pro Arg Asp Phe Ala Ala
            355                 360                 365

Tyr Arg Ser Arg Val Lys Phe Ser Arg Ser Ala Asp Ala Pro Ala Tyr
            370                 375                 380

Gln Gln Gly Gln Asn Gln Leu Tyr Asn Glu Leu Asn Leu Gly Arg Arg
    385                 390                 395                 400

Glu Glu Tyr Asp Val Leu Asp Lys Arg Arg Gly Arg Asp Pro Glu Met
                        405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
            450                 455                 460

Ser Thr Ala Thr Lys Asp Thr Tyr Asp Ala Leu His Met Gln Ala Leu
    465                 470                 475                 480

Pro Pro Arg

<210> SEQ ID NO 205
<211> LENGTH: 1452
<212> TYPE: DNA
<213> ORGANISM: Artificial Sequence
<220> FEATURE:
<223> OTHER INFORMATION: Description of Artificial Sequence: Synthetic
      RD-21530CARDNALxH polynucleotide

<400> SEQUENCE: 205
atggcactcc ccgtaactgc tctgctgctg ccgttggcat tgctcctgca cgccgcacgc      60
ccggaaatag tgatgacgca gtctccagcc accctgtctg tgtctccagg ggaaagagcc     120
accctctcct gcagggccag tcagagtgtt agcagcaact tagcctggta ccagcagaaa     180
cctggccagg ctcccaggct cctcatctat agcgcatcca ccagggccac tggtatccca     240
gccaggttca gtggcagtgg gtctgggaca gagttcactc tcaccatcag cagcctgcag     300

-continued

```
tctgaagatt tgcagttta ttactgtcag cagcaccacg tctggcctct cactttggc    360
ggagggacca aggttgagat caaacggggg tctacatccg gctccgggaa gcccggaagt    420
ggcgaaggta gtacaaaggg gcaggtgcag ctggtggagt ctgggggagg cgtggtccag    480
cctgggaggt ccctgagact ctcctgtgca gcgtctggat tcaccttcag tagctatggc    540
atgcactggg tccgccaggc tccaggcaag gggctggagt gggtggcagt tatatcgtat    600
gatgaagta ataaatacta tgcagactcc gtgaagggcc gattcaccat ctccagagac    660
aattccaaga acacgctgta tctgcaaatg aacagcctga gagccgagga cacggcggtg    720
tactactgcg tcaaggggcc gttgcaggag ccgccatacg attatggaat ggacgtatgg    780
ggccagggaa caactgtcac cgtctcctca gccgctgccc ttgataatga aaagtcaaac    840
ggaacaatca ttcacgtgaa gggcaagcac ctctgtccgt caccttgtt ccctggtcca    900
tccaagccat tctgggtgtt ggtcgtagtg ggtggagtcc tcgcttgtta ctctctgctc    960
gtcaccgtgg cttttataat cttctgggtt agatccaaaa gaagccgcct gctcccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa accccaggga gggtctctat aatgagctgc agaaggataa gatggctgaa   1320
gcctattctg aaataggcat gaaggagag cggagaaggg gaaaagggca cgacggtttg   1380
taccagggac tcagcactgc tacgaaggat acttatgacg ctctccacat gcaagccctg   1440
ccacctaggt aa                                                         1452
```

<210> SEQ ID NO 206
<211> LENGTH: 483
<212> TYPE: PRT
<213> ORGANISM: Artificial Sequence
<220> FEATURE:
<223> OTHER INFORMATION: Description of Artificial Sequence: Synthetic RD-21530CARLxH polypeptide

<400> SEQUENCE: 206

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Ser Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln His
            100                 105                 110

His Val Trp Pro Leu Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Val Glu Ser Gly Gly Gly Val Val Gln
```

```
            145                 150                 155                 160
    Pro Gly Arg Ser Leu Arg Leu Ser Cys Ala Ala Ser Gly Phe Thr Phe
                    165                 170                 175

Ser Ser Tyr Gly Met His Trp Val Arg Gln Ala Pro Gly Lys Gly Leu
                    180                 185                 190

Glu Trp Val Ala Val Ile Ser Tyr Asp Gly Ser Asn Lys Tyr Tyr Ala
                    195                 200                 205

Asp Ser Val Lys Gly Arg Phe Thr Ile Ser Arg Asp Asn Ser Lys Asn
        210                 215                 220

Thr Leu Tyr Leu Gln Met Asn Ser Leu Arg Ala Glu Asp Thr Ala Val
    225                 230                 235                 240

Tyr Tyr Cys Val Lys Gly Pro Leu Gln Glu Pro Pro Tyr Asp Tyr Gly
                    245                 250                 255

Met Asp Val Trp Gly Gln Gly Thr Thr Val Thr Val Ser Ser Ala Ala
                    260                 265                 270

Ala Leu Asp Asn Glu Lys Ser Asn Gly Thr Ile Ile His Val Lys Gly
                    275                 280                 285

Lys His Leu Cys Pro Ser Pro Leu Phe Pro Gly Pro Ser Lys Pro Phe
                    290                 295                 300

Trp Val Leu Val Val Val Gly Gly Val Leu Ala Cys Tyr Ser Leu Leu
    305                 310                 315                 320

Val Thr Val Ala Phe Ile Ile Phe Trp Val Arg Ser Lys Arg Ser Arg
                    325                 330                 335

Leu Leu His Ser Asp Tyr Met Asn Met Thr Pro Arg Arg Pro Gly Pro
                    340                 345                 350

Thr Arg Lys His Tyr Gln Pro Tyr Ala Pro Pro Arg Asp Phe Ala Ala
                    355                 360                 365

Tyr Arg Ser Arg Val Lys Phe Ser Arg Ser Ala Asp Ala Pro Ala Tyr
                    370                 375                 380

Gln Gln Gly Gln Asn Gln Leu Tyr Asn Glu Leu Asn Leu Gly Arg Arg
    385                 390                 395                 400

Glu Glu Tyr Asp Val Leu Asp Lys Arg Arg Gly Arg Asp Pro Glu Met
                    405                 410                 415

Gly Gly Lys Pro Arg Arg Lys Asn Pro Gln Glu Gly Leu Tyr Asn Glu
                    420                 425                 430

Leu Gln Lys Asp Lys Met Ala Glu Ala Tyr Ser Glu Ile Gly Met Lys
                    435                 440                 445

Gly Glu Arg Arg Arg Gly Lys Gly His Asp Gly Leu Tyr Gln Gly Leu
                    450                 455                 460

Ser Thr Ala Thr Lys Asp Thr Tyr Asp Ala Leu His Met Gln Ala Leu
    465                 470                 475                 480

Pro Pro Arg

<210> SEQ ID NO 207
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 207

Glu Val Gln Leu Leu Glu Ser Gly Gly Gly Leu Val Gln Pro Gly Gly
    1               5                   10                  15

Ser Leu Arg Leu Ser Cys Ala Ala Ser Gly
```

20                  25

<210> SEQ ID NO 208
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 208

Gln Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 209
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 210
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 210

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 211
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 212
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

```
<400> SEQUENCE: 212

Gln Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 213
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 213

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 214
<211> LENGTH: 26
<212> TYPE: PRT
<213> ORGANISM: Artificial Sequence
<220> FEATURE:
<223> OTHER INFORMATION: Description of Artificial Sequence: Synthetic
      VH FR1 peptide

<400> SEQUENCE: 214

Gln Val Gln Leu Val Glu Ser Gly Gly Gly Val Val Gln Pro Gly Arg
1               5                   10                  15

Ser Leu Arg Leu Ser Cys Ala Ala Ser Gly
            20                  25

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 215

Phe Thr Phe Ser Ser Tyr Ala Met Ser
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 216

Phe Thr Phe Ser Ser Tyr Gly Met His
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide
```

```
<400> SEQUENCE: 217

Tyr Thr Phe Thr Ser Tyr Tyr Met His
1               5

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 218

Gly Ser Ile Ser Ser Ser Ser Tyr Tyr Trp Gly
1               5                   10

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 219

Phe Thr Phe Ser Ser Tyr Ser Met Asn
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 220

Phe Thr Phe Ser Ser Tyr Gly Met His
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 221

Gly Thr Phe Ser Ser Tyr Ala Ile Ser
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide

<400> SEQUENCE: 222

Phe Thr Phe Ser Ser Tyr Gly Met His
1               5

<210> SEQ ID NO 223
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      VH FR2 peptide

<400> SEQUENCE: 223

Trp Val Arg Gln Ala Pro Gly Lys Gly Leu Glu Trp Val Ser
1               5                   10

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 224

Trp Val Arg Gln Ala Pro Gly Lys Gly Leu Glu Trp Val Ala
1               5                   10

<210> SEQ ID NO 225
<211> LENGTH: 14
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 225

Trp Val Arg Gln Ala Pro Gly Gln Gly Leu Glu Trp Met Gly
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 226

Trp Ile Arg Gln Pro Pro Gly Lys Gly Leu Glu Trp Ile Gly
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 227

Trp Val Arg Gln Ala Pro Gly Lys Gly Leu Glu Trp Val Ser
1               5                   10

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 228

Trp Val Arg Gln Ala Pro Gly Lys Gly Leu Glu Trp Val Ala
1               5                   10
```

```
<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 229

Trp Val Arg Gln Ala Pro Gly Gln Gly Leu Glu Trp Met Gly
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 230

Trp Val Arg Gln Ala Pro Gly Lys Gly Leu Glu Trp Val Ala
1               5                   10

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 231

Ala Ile Ser Gly Ser Gly Gly Ser Thr Tyr Tyr Ala Asp Ser Val Lys
1               5                   10                  15

Gly

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 232

Val Ile Ser Tyr Asp Gly Ser Asn Lys Tyr Tyr Ala Asp Ser Val Lys
1               5                   10                  15

Gly

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 233

Ile Ile Asn Pro Gly Gly Gly Ser Thr Ser Tyr Ala Gln Lys Phe Gln
1               5                   10                  15

Gly

<210> SEQ ID NO 234
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 234

Ser Ile Ser Tyr Ser Gly Ser Thr Tyr Tyr Asn Pro Ser Leu Lys Ser
1               5                   10                  15

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 235

Thr Ile Ser Ser Ser Ser Ser Thr Ile Tyr Tyr Ala Asp Ser Val Lys
1               5                   10                  15

Gly

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 236

Val Ile Ser Tyr Asp Gly Ser Asn Lys Tyr Tyr Ala Asp Ser Val Lys
1               5                   10                  15

Gly

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 237

Gly Ile Ile Pro Ile Phe Gly Thr Ala Asn Tyr Ala Gln Lys Phe Gln
1               5                   10                  15

Gly

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
      VH FR2 peptide

<400> SEQUENCE: 238

Val Ile Ser Tyr Asp Gly Ser Asn Lys Tyr Tyr Ala Asp Ser Val Lys
1               5                   10                  15

Gly

<210> SEQ ID NO 239
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 239

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 240
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 240

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 241
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 241

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 242
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 242

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 243
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 243

Arg Phe Thr Ile Ser Arg Asp Asn Ala Lys Asn Ser Leu Tyr Leu Gln
1               5                   10                  15
```

```
Met Asn Ser Leu Arg Ala Glu Asp Thr Ala Val Tyr Tyr Cys
            20                  25                  30

<210> SEQ ID NO 244
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 244

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 245
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 245

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 246
<211> LENGTH: 30
<212> TYPE: PRT
<213> ORGANISM: Artificial Sequence
<220> FEATURE:
<223> OTHER INFORMATION: Description of Artificial Sequence: Synthetic
      VH FR3 polypeptide

<400> SEQUENCE: 246

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 247

Ala Arg Ala Glu Met Gly Ala Val Phe Asp Ile
1               5                   10

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 248
```

Ala Arg Asp Gly Thr Tyr Leu Gly Gly Leu Trp Tyr Phe Asp Leu
1               5                   10                  15

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 249

Ala Arg Glu Ser Trp Pro Met Asp Val
1               5

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 250

Ala Arg Gly Arg Gly Tyr Ala Thr Ser Leu Ala Phe Asp Ile
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 251

Ala Arg Gly Ser Gln Glu His Leu Ile Phe Asp Tyr
1               5                   10

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 252

Ala Arg Thr Asp Phe Trp Ser Gly Ser Pro Pro Gly Leu Asp Tyr
1               5                   10                  15

<210> SEQ ID NO 253
<211> LENGTH: 19
<212> TYPE: PRT
<213> ORGANISM: Artificial Sequence
<220> FEATURE:
<223> OTHER INFORMATION: Description of Artificial Sequence: Synthetic
      VH CDR3 peptide

<400> SEQUENCE: 253

Ala Arg Thr Pro Glu Tyr Ser Ser Ser Ile Trp His Tyr Tyr Gly
1               5                   10                  15

Met Asp Val

<210> SEQ ID NO 254
<211> LENGTH: 16
<212> TYPE: PRT

```
<213> ORGANISM: Artificial Sequence
<220> FEATURE:
<223> OTHER INFORMATION: Description of Artificial Sequence: Synthetic
      VH CDR3 peptide

<400> SEQUENCE: 254

Val Lys Gly Pro Leu Gln Glu Pro Pro Tyr Asp Tyr Gly Met Asp Val
1               5                   10                  15

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 255

Trp Gly Gln Gly Thr Met Val Thr Val Ser Ser
1               5                   10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 256

Trp Gly Arg Gly Thr Leu Val Thr Val Ser Ser
1               5                   10

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 257

Trp Gly Gln Gly Thr Thr Val Thr Val Ser Ser
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 258

Trp Gly Gln Gly Thr Met Val Thr Val Ser Ser
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 259

Trp Gly Gln Gly Thr Leu Val Thr Val Ser Ser
1               5                   10
```

```
<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 260

Trp Gly Gln Gly Thr Leu Val Thr Val Ser Ser
1               5                   10

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 261

Trp Gly Gln Gly Thr Thr Val Thr Val Ser Ser
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      VH FR4 peptide

<400> SEQUENCE: 262

Trp Gly Gln Gly Thr Thr Val Thr Val Ser Ser
1               5                   10

<210> SEQ ID NO 263
<211> LENGTH: 11
<212> TYPE: PRT
<213> ORGANISM: Artificial Sequence
<220> FEATURE:
<223> OTHER INFORMATION: Description of Artificial Sequence: Synthetic
      VH CDR1 peptide
<220> FEATURE:
<221> NAME/KEY: MISC_FEATURE
<222> LOCATION: (1)..(2)
<223> OTHER INFORMATION: May or may not be present
<220> FEATURE:
<221> NAME/KEY: MOD_RES
<222> LOCATION: (3)..(3)
<223> OTHER INFORMATION: Phe, Gly, Ile or Tyr
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Phe or Ser
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (9)..(9)
<223> OTHER INFORMATION: Ala, Gly, Ser or Tyr
<220> FEATURE:
<221> NAME/KEY: MOD_RES
<222> LOCATION: (10)..(10)
<223> OTHER INFORMATION: Ile, Met or Trp
```

```
<220> FEATURE:
<221> NAME/KEY: MOD_RES
<222> LOCATION: (11)..(11)
<223> OTHER INFORMATION: Gly, His, Asn or Ser

<400> SEQUENCE: 263

Gly Ser Xaa Xaa Xaa Xaa Ser Tyr Xaa Xaa Xaa
1               5                   10

<210> SEQ ID NO 264
<211> LENGTH: 21
<212> TYPE: PRT
<213> ORGANISM: Artificial Sequence
<220> FEATURE:
<223> OTHER INFORMATION: Description of Artificial Sequence: Synthetic
      VH CDR3 peptide
<220> FEATURE:
<221> NAME/KEY: MOD_RES
<222> LOCATION: (1)..(1)
<223> OTHER INFORMATION: Ala or Val
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
<223> OTHER INFORMATION: Asp, Gly or Thr
<220> FEATURE:
<221> NAME/KEY: MOD_RES
<222> LOCATION: (4)..(4)
<223> OTHER INFORMATION: Asp, Gly, Pro or absent
<220> FEATURE:
<221> NAME/KEY: MOD_RES
<222> LOCATION: (5)..(5)
<223> OTHER INFORMATION: Phe, Leu, Thr or absent
<220> FEATURE:
<221> NAME/KEY: MOD_RES
<222> LOCATION: (6)..(6)
<223> OTHER INFORMATION: Pro, Gln, Arg, Trp, Tyr or absent
<220> FEATURE:
<221> NAME/KEY: MOD_RES
<222> LOCATION: (7)..(7)
<223> OTHER INFORMATION: Glu, Gly, Leu, Ser or absent
<220> FEATURE:
<221> NAME/KEY: MOD_RES
<222> LOCATION: (8)..(8)
<223> OTHER INFORMATION: Ala, Gly, Pro, Ser, Tyr or absent
<220> FEATURE:
<221> NAME/KEY: MOD_RES
<222> LOCATION: (9)..(9)
<223> OTHER INFORMATION: Ala, Glu, Gly, Pro, Gln, Ser or absent
<220> FEATURE:
<221> NAME/KEY: MOD_RES
<222> LOCATION: (10)..(10)
<223> OTHER INFORMATION: Glu, Leu, Met, Pro, Ser, Thr, Tyr or absent
<220> FEATURE:
<221> NAME/KEY: MOD_RES
<222> LOCATION: (11)..(11)
<223> OTHER INFORMATION: Asp, Gly, His, Pro, Ser, Trp or absent
<220> FEATURE:
<221> NAME/KEY: MOD_RES
<222> LOCATION: (12)..(12)
<223> OTHER INFORMATION: Ala, Gly, Ile, Leu, Tyr or absent
<220> FEATURE:
<221> NAME/KEY: MOD_RES
<222> LOCATION: (13)..(13)
<223> OTHER INFORMATION: Ala, Gly, Ile, Val, Trp or absent
<220> FEATURE:
<221> NAME/KEY: MISC_FEATURE
<222> LOCATION: (14)..(16)
<223> OTHER INFORMATION: May or may not be present
<220> FEATURE:
<221> NAME/KEY: MOD_RES
<222> LOCATION: (17)..(17)
<223> OTHER INFORMATION: Trp, Tyr or absent
<220> FEATURE:
```

```
<221> NAME/KEY: MOD_RES
<222> LOCATION: (18)..(18)
<223> OTHER INFORMATION: Pro, Gly or absent
<220> FEATURE:
<221> NAME/KEY: MOD_RES
<222> LOCATION: (19)..(19)
<223> OTHER INFORMATION: Phe, Leu or Met
<220> FEATURE:
<221> NAME/KEY: MOD_RES
<222> LOCATION: (21)..(21)
<223> OTHER INFORMATION: Ile, Leu, Val or Tyr

<400> SEQUENCE: 264

Xaa Xaa Xaa Xaa Xaa Xaa Xaa Xaa Xaa Xaa Xaa Xaa Xaa His Tyr Tyr
1               5                   10                  15

Xaa Xaa Xaa Asp Xaa
            20

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide
<220> FEATURE:
<221> NAME/KEY: MOD_RES
<222> LOCATION: (1)..(1)
<223> OTHER INFORMATION: Phe, Gly or Tyr
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (7)..(7)
<223> OTHER INFORMATION: Ala, Gly, Ser or Tyr
<220> FEATURE:
<221> NAME/KEY: MOD_RES
<222> LOCATION: (8)..(8)
<223> OTHER INFORMATION: Ile or Met
<220> FEATURE:
<221> NAME/KEY: MOD_RES
<222> LOCATION: (9)..(9)
<223> OTHER INFORMATION: His, Asn or Ser

<400> SEQUENCE: 265

Xaa Thr Phe Xaa Ser Tyr Xaa Xaa Xaa
1               5

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1 peptide
<220> FEATURE:
<221> NAME/KEY: MOD_RES
<222> LOCATION: (7)..(7)
<223> OTHER INFORMATION: Ala, Gly or Ser
<220> FEATURE:
<221> NAME/KEY: MOD_RES
<222> LOCATION: (9)..(9)
<223> OTHER INFORMATION: His, Asn or Ser

<400> SEQUENCE: 266

Phe Thr Phe Ser Ser Tyr Xaa Met Xaa
1               5

<210> SEQ ID NO 267
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      VH CDR3 peptide
<220> FEATURE:
<221> NAME/KEY: MOD_RES
<222> LOCATION: (3)..(3)
<223> OTHER INFORMATION: Asp, Thr or absent
<220> FEATURE:
<221> NAME/KEY: MOD_RES
<222> LOCATION: (4)..(4)
<223> OTHER INFORMATION: Asp, Gly or absent
<220> FEATURE:
<221> NAME/KEY: MOD_RES
<222> LOCATION: (5)..(5)
<223> OTHER INFORMATION: Phe, Thr or absent
<220> FEATURE:
<221> NAME/KEY: MOD_RES
<222> LOCATION: (6)..(6)
<223> OTHER INFORMATION: Pro, Arg, Trp, Tyr or absent
<220> FEATURE:
<221> NAME/KEY: MOD_RES
<222> LOCATION: (7)..(7)
<223> OTHER INFORMATION: Glu, Gly, Leu, Ser or absent
<220> FEATURE:
<221> NAME/KEY: MOD_RES
<222> LOCATION: (8)..(8)
<223> OTHER INFORMATION: Ala, Gly, Ser, Tyr or absent
<220> FEATURE:
<221> NAME/KEY: MOD_RES
<222> LOCATION: (9)..(9)
<223> OTHER INFORMATION: Ala, Glu, Gly, Gln or Ser
<220> FEATURE:
<221> NAME/KEY: MOD_RES
<222> LOCATION: (10)..(10)
<223> OTHER INFORMATION: Glu, Leu, Met, Pro, Ser or Thr
<220> FEATURE:
<221> NAME/KEY: MOD_RES
<222> LOCATION: (11)..(11)
<223> OTHER INFORMATION: Gly, His, Pro, Ser, Trp or absent
<220> FEATURE:
<221> NAME/KEY: MOD_RES
<222> LOCATION: (12)..(12)
<223> OTHER INFORMATION: Ala, Gly, Ile, Leu, Tyr or absent
<220> FEATURE:
<221> NAME/KEY: MOD_RES
<222> LOCATION: (13)..(13)
<223> OTHER INFORMATION: Ala, Ile, Val, Trp or absent
<220> FEATURE:
<221> NAME/KEY: MISC_FEATURE
<222> LOCATION: (14)..(16)
<223> OTHER INFORMATION: May or may not be present
<220> FEATURE:
<221> NAME/KEY: MOD_RES
<222> LOCATION: (17)..(17)
<223> OTHER INFORMATION: Trp, Tyr or absent
<220> FEATURE:
<221> NAME/KEY: MOD_RES
<222> LOCATION: (18)..(18)
<223> OTHER INFORMATION: Pro, Gly or absent
<220> FEATURE:
<221> NAME/KEY: MOD_RES
<222> LOCATION: (19)..(19)
<223> OTHER INFORMATION: Phe, Leu or Met
<220> FEATURE:
<221> NAME/KEY: MOD_RES
<222> LOCATION: (21)..(21)
<223> OTHER INFORMATION: Ile, Leu, Val or Tyr

<400> SEQUENCE: 267

Ala Arg Xaa Xaa Xaa Xaa Xaa Xaa Xaa Xaa Xaa Xaa Xaa His Tyr Tyr
1               5                   10                  15

Xaa Xaa Xaa Asp Xaa
            20
```

```
<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic
      scFv G4s linker

<400> SEQUENCE: 268

Gly Gly Gly Gly Ser Gly Gly Gly Gly Ser Gly Gly Gly Gly Ser
1               5                   10                  15

<210> SEQ ID NO 269
<211> LENGTH: 288
<212> TYPE: DNA
<213> ORGANISM: Artificial Sequence
<220> FEATURE:
<223> OTHER INFORMATION: Description of Artificial Sequence: Synthetic
      CD8 DNA extracellular & transmembrane domain
      polynucleotide

<400> SEQUENCE: 269
gctgcagcat tgagcaactc aataatgtat tttagtcact ttgtaccagt gttcttgccg      60
gctaagccta ctaccacacc cgctccacgg ccacctaccc cagctcctac catcgcttca     120
cagcctctgt ccctgcgccc agaggcttgc cgaccggccg caggggcgc tgttcatacc     180 agaggactgg atttcgcctg cgatatctat atctgggcac ccctggccgg aacctgcggc     240
gtactcctgc tgtccctggt catcacgctc tattgtaatc acaggaac                 288

<210> SEQ ID NO 270
<211> LENGTH: 97
<212> TYPE: PRT
<213> ORGANISM: Artificial Sequence
<220> FEATURE:
<223> OTHER INFORMATION: Description of Artificial Sequence: Synthetic
      CD8 AA extracellular & transmembrane domain
      polypeptide

<400> SEQUENCE: 270

Ala Ala Ala Leu Ser Asn Ser Ile Met Tyr Phe Ser His Phe Val Pro
1               5                   10                  15

Arg Val Phe Leu Pro Ala Lys Pro Thr Thr Pro Ala Pro Arg Pro
                20                  25                  30

Pro Thr Pro Ala Pro Thr Ile Ala Ser Gln Pro Leu Ser Leu Arg Pro
            35                  40                  45

Glu Ala Cys Arg Pro Ala Ala Gly Gly Ala Val His Thr Arg Gly Leu
    50                  55                  60

Asp Phe Ala Cys Asp Ile Tyr Ile Trp Ala Pro Leu Ala Gly Thr Cys
65                  70                  75                  80

Gly Val Leu Leu Leu Ser Leu Val Ile Thr Leu Tyr Cys Asn His Arg
                85                  90                  95

Asn

<210> SEQ ID NO 271
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271
gaggtgcagc tgttggagtc tgggggaggc ttggtacagc ctggggggtc cctgagactc      60
```

```
tcctgtgcag cctctggatt caccttggac gactatgcca tggcatgggt ccgccaggct    120
ccagggaagg ggctggagtg ggtctcagct attagtgatg caggtgacag aacatactac    180
gcagactccg tgaggggccg gttcaccatc tccagagaca attccaagaa cacactgtat    240
ctgcaaatga acagcctgag agccgaggac acggcggtgt actactgcgc aagagccgag    300
atgggagccg tattcgacat atggggtcag ggtacaatgg tcaccgtctc ctca          354
```

<210> SEQ ID NO 272
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 272

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
            20                  25                  30

Ala Met Ala Trp Val Arg Gln Ala Pro Gly Lys Gly Leu Glu Trp Val
        35                  40                  45

Ser Ala Ile Ser Asp Ala Gly Asp Arg Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Glu Met Gly Ala Val Phe Asp Ile Trp Gly Gln Gly Thr
            100                 105                 110

Met Val Thr Val Ser Ser
        115
```

<210> SEQ ID NO 273
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 273

```
Ser Cys Ala Ala Ser Gly Phe Thr Phe Asp Asp Tyr Ala Met Ala
 1               5                  10                  15
```

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 274

```
Ala Ile Ser Asp Ala Gly Asp Arg Thr Tyr Tyr Ala Asp Ser Val Arg
 1               5                  10                  15

Gly
```

<210> SEQ ID NO 275
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ala Arg Ala Glu Met Gly Ala Val Phe Asp Ile
1               5                   10

<210> SEQ ID NO 276
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
gaaattgtgt tgacacagtc tccagccacc ctgtctttgt ctccagggga aagagccacc      60
ctctcctgca gggccagtca gagtgttagc aggtacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag agaatctcct ggcctttcac ttttggcgga    300
gggaccaagg ttgagatcaa acgg                                            324

<210> SEQ ID NO 277
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Ser Trp Pro Phe
                85                  90                  95

Thr Phe Gly Gly Gly Thr Lys Val Glu Ile Lys Arg
            100                 105

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Arg Ala Ser Gln Ser Val Ser Arg Tyr Leu Ala
1               5                   10

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asp Ala Ser Asn Arg Ala Thr
1               5

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gln Gln Arg Ile Ser Trp Pro Phe Thr
1               5

<210> SEQ ID NO 281
<211> LENGTH: 1434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
atggcactcc ccgtaactgc tctgctgctg ccgttggcat tgctcctgca cgccgcacgc    60
ccggaggtgc agctgttgga gtctggggga ggcttggtac agcctggggg gtccctgaga   120
ctctcctgtg cagcctctgg attcaccttt gacgactatg ccatggcatg ggtccgccag   180
gctccaggga aggggctgga gtgggtctca gctattagtg atgcaggtga cagaacatac   240
tacgcagact ccgtgagggg ccggttcacc atctccagag acaattccaa gaacacactg   300
tatctgcaaa tgaacagcct gagagccgag gacacggcgg tgtactactg cgcaagagcc   360
gagatgggag ccgtattcga catatggggt cagggtacaa tggtcaccgt ctcctcaggg   420
tctacatccg gctccgggaa gcccggaagt ggcgaaggta gtacaaaggg ggaaattgtg   480
ttgacacagt ctccagccac cctgtctttg tctccagggg aaagagccac cctctcctgc   540
agggccagtc agagtgttag caggtactta gcctggtacc aacagaaacc tggccaggct   600
cccaggctcc tcatctatga tgcatccaac agggccactg gcatcccagc caggttcagt   660
ggcagtgggt ctgggacaga cttcactctc accatcagca gcctagagcc tgaagatttt   720
gcagtttatt actgtcagca gagaatctcc tggcctttca cttttggcgg agggaccaag   780
gttgagatca aacgggccgc tgcccttgat aatgaaaagt caaacggaac aatcattcac   840
gtgaagggca agcacctctg tccgtcaccc ttgttccctg tccatccaa gccattctgg    900 gtgttggtcg tagtgggtgg agtcctcgct tgttactctc tgctcgtcac cgtggctttt   960
ataatcttct gggttagatc caaaagaagc cgcctgctcc atagcgatta catgaatatg   1020
actccacgcc gcctggccc cacaaggaaa cactaccagc cttacgcacc acctagagat   1080
ttcgctgcct atcggagcag ggtgaagttt tccagatctg cagatgcacc agcgtatcag   1140
cagggccaga accaactgta taacgagctc aacctgggac gcagggaaga gtatgacgtt   1200

```
ttggacaagc gcagaggacg ggaccctgag atgggtggca aaccaagacg aaaaaacccc   1260
caggagggtc tctataatga gctgcagaag gataagatgg ctgaagccta ttctgaaata   1320
ggcatgaaag gagagcggag aagggggaaaa gggcacgacg gtttgtacca gggactcagc  1380
actgctacga aggatactta tgacgctctc cacatgcaag ccctgccacc tagg         1434
```

<210> SEQ ID NO 282
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Asp Asp Tyr Ala Met Ala Trp Val Arg Gln Ala Pro Gly Lys
    50                  55                  60

Gly Leu Glu Trp Val Ser Ala Ile Ser Asp Ala Gly Asp Arg Thr Tyr
65                  70                  75                  80

Tyr Ala Asp Ser Val Arg Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ala Glu Met Gly Ala Val Phe Asp Ile
        115                 120                 125

Trp Gly Gln Gly Thr Met Val Thr Val Ser Ser Gly Ser Thr Ser Gly
    130                 135                 140

Ser Gly Lys Pro Gly Ser Gly Glu Gly Ser Thr Lys Gly Glu Ile Val
145                 150                 155                 160

Leu Thr Gln Ser Pro Ala Thr Leu Ser Leu Ser Pro Gly Glu Arg Ala
                165                 170                 175

Thr Leu Ser Cys Arg Ala Ser Gln Ser Val Ser Arg Tyr Leu Ala Trp
            180                 185                 190

Tyr Gln Gln Lys Pro Gly Gln Ala Pro Arg Leu Leu Ile Tyr Asp Ala
        195                 200                 205

Ser Asn Arg Ala Thr Gly Ile Pro Ala Arg Phe Ser Gly Ser Gly Ser
    210                 215                 220

Gly Thr Asp Phe Thr Leu Thr Ile Ser Ser Leu Glu Pro Glu Asp Phe
225                 230                 235                 240

Ala Val Tyr Tyr Cys Gln Gln Arg Ile Ser Trp Pro Phe Thr Phe Gly
                245                 250                 255

Gly Gly Thr Lys Val Glu Ile Lys Arg Ala Ala Ala Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320
```

Ile Ile Phe Trp Val Arg Ser Lys Arg Ser Arg Leu Leu His Ser Asp
                325                 330                 335
Tyr Met Asn Met Thr Pro Arg Arg Pro Gly Pro Thr Arg Lys His Tyr
            340                 345                 350
Gln Pro Tyr Ala Pro Pro Arg Asp Phe Ala Ala Tyr Arg Ser Arg Val
        355                 360                 365
Lys Phe Ser Arg Ser Ala Asp Ala Pro Ala Tyr Gln Gln Gly Gln Asn
    370                 375                 380
Gln Leu Tyr Asn Glu Leu Asn Leu Gly Arg Arg Glu Glu Tyr Asp Val
385                 390                 395                 400
Leu Asp Lys Arg Arg Gly Arg Asp Pro Glu Met Gly Gly Lys Pro Arg
                405                 410                 415
Arg Lys Asn Pro Gln Glu Gly Leu Tyr Asn Glu Leu Gln Lys Asp Lys
            420                 425                 430
Met Ala Glu Ala Tyr Ser Glu Ile Gly Met Lys Gly Glu Arg Arg Arg
        435                 440                 445
Gly Lys Gly His Asp Gly Leu Tyr Gln Gly Leu Ser Thr Ala Thr Lys
    450                 455                 460
Asp Thr Tyr Asp Ala Leu His Met Gln Ala Leu Pro Pro Arg
465                 470                 475

<210> SEQ ID NO 283
<211> LENGTH: 1434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283
atggcactcc ccgtaactgc tctgctgctg ccgttggcat tgctcctgca cgccgcacgc      60
ccggaaattg tgttgacaca gtctccagcc accctgtctt tgtctccagg ggaaagagcc     120
accctctcct gcagggccag tcagagtgtt agcaggtact agcctggta ccaacagaaa      180
cctggccagg ctcccaggct cctcatctat gatgcatcca cagggccac tggcatccca     240
gccaggttca gtggcagtgg gtctgggaca gacttcactc tcaccatcag cagcctagag     300
cctgaagatt ttgcagttta ttactgtcag cagagaatct cctggccttt cacttttggc     360
ggagggacca aggttgagat caaacggggg tctacatccg gctccgggaa gcccggaagt     420
ggcgaaggta gtacaaaggg ggaggtgcag ctgttggagt ctgggggagg cttggtacag     480
cctggggggt ccctgagact ctcctgtgca gcctctggat tcacctttga cgactatgcc     540
atggcatggg tccgccaggc tccagggaag gggctggagt gggtctcagc tattagtgat     600
gcaggtgaca gaacatacta cgcagactcc gtgaggggcc ggttcaccat ctccagagac     660
aattccaaga cacactgta tctgcaaatg aacagcctga gagccgagga cacggcggtg     720
tactactgcg caagagccga gatgggagcc gtattcgaca tatggggtca gggtacaatg     780
gtcaccgtct cctcagccgc tgcccttgat aatgaaaagt caaacggaac aatcattcac     840
gtgaagggca gcaccctctg tccgtcaccc ttgttccctg tccatccaa gccattctgg     900
gtgttggtcg tagtgggtgg agtcctcgct tgttactctc tgctcgtcac cgtggctttt     960
ataatcttct gggttagatc caaaagaagc cgcctgctcc atagcgatta catgaatatg    1020
actccacgcc gccctggccc cacaaggaaa cactaccagc ttacgcacc acctagagat    1080
ttcgctgcct atcggagcag ggtgaagttt ccagatctg cagatgcacc agcgtatcag    1140

```
cagggccaga accaactgta taacgagctc aacctgggac gcagggaaga gtatgacgtt    1200
ttggacaagc gcagaggacg ggaccctgag atgggtggca aaccaagacg aaaaaacccc    1260
caggagggtc tctataatga gctgcagaag gataagatgg ctgaagccta ttctgaaata    1320
ggcatgaaag gagagcggag aaggggaaaa gggcacgacg gtttgtacca gggactcagc    1380
actgctacga aggatactta tgacgctctc cacatgcaag ccctgccacc tagg          1434
```

<210> SEQ ID NO 284
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Arg Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

Ile Ser Trp Pro Phe Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Asp Asp Tyr Ala Met Ala Trp Val Arg Gln Ala Pro Gly Lys Gly Leu
            180                 185                 190

Glu Trp Val Ser Ala Ile Ser Asp Ala Gly Asp Arg Thr Tyr Tyr Ala
        195                 200                 205

Asp Ser Val Arg Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Arg Ala Glu Met Gly Ala Val Phe Asp Ile Trp Gly
                245                 250                 255

Gln Gly Thr Met Val Thr Val Ser Ser Ala Ala Ala Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300
```

| | | | | | | | | | | | | | | | |
|---|---|---|---|---|---|---|---|---|---|---|---|---|---|---|---|
|Val|Gly|Gly|Val|Leu|Ala|Cys|Tyr|Ser|Leu|Leu|Val|Thr|Val|Ala|Phe|
|305| | | | |310| | | | |315| | | | |320|

Ile Ile Phe Trp Val Arg Ser Lys Arg Ser Arg Leu Leu His Ser Asp
                       325                   330                 335

Tyr Met Asn Met Thr Pro Arg Arg Pro Gly Pro Thr Arg Lys His Tyr
             340                     345                   350

Gln Pro Tyr Ala Pro Pro Arg Asp Phe Ala Ala Tyr Arg Ser Arg Val
                 355                     360                 365

Lys Phe Ser Arg Ser Ala Asp Ala Pro Ala Tyr Gln Gln Gly Gln Asn
    370                   375                   380

Gln Leu Tyr Asn Glu Leu Asn Leu Gly Arg Arg Glu Glu Tyr Asp Val
385                 390                   395                400

Leu Asp Lys Arg Arg Gly Arg Asp Pro Glu Met Gly Gly Lys Pro Arg
             405                     410                   415

Arg Lys Asn Pro Gln Glu Gly Leu Tyr Asn Glu Leu Gln Lys Asp Lys
                 420                   425                   430

Met Ala Glu Ala Tyr Ser Glu Ile Gly Met Lys Gly Glu Arg Arg Arg
             435                     440                   445

Gly Lys Gly His Asp Gly Leu Tyr Gln Gly Leu Ser Thr Ala Thr Lys
    450                   455                   460

Asp Thr Tyr Asp Ala Leu His Met Gln Ala Leu Pro Pro Arg
465                 470                   475

<210> SEQ ID NO 285
<211> LENGTH: 366
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 285
caggtgcagc tggtggagtc tgggggaggc gtggtccagc ctgggaggtc cctgagactc     60
tcctgtgcag cgtctggatt caccttcagt gagcatggca tgcactgggt ccgccaggct    120
ccaggcaagg ggctggagtg ggtggcagct atatcttatg atggaaggaa taaacactat    180
gcagactccg tgaagggccg attcaccatc tccagagaca attccaagaa cacgctgtat    240
ctgcaaatga acagcctgag agccgaggac acggcggtgt actactgcgc cagagacggt    300
acttatctag gtggtctctg gtacttcgac ttatggggga gaggtacctt ggtcaccgtc    360
tcctca    366

<210> SEQ ID NO 286
<211> LENGTH: 122
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 286

Gln Val Gln Leu Val Glu Ser Gly Gly Gly Val Val Gln Pro Gly Arg
1                 5                   10                   15

Ser Leu Arg Leu Ser Cys Ala Ala Ser Gly Phe Thr Phe Ser Glu His
             20                     25                   30

Gly Met His Trp Val Arg Gln Ala Pro Gly Lys Gly Leu Glu Trp Val
                 35                     40                 45

Ala Ala Ile Ser Tyr Asp Gly Arg Asn Lys His Tyr Ala Asp Ser Val

```
                   50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser
        115                 120
```

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

```
Phe Thr Phe Ser Glu His Gly Met His
 1               5
```

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

```
Ala Ile Ser Tyr Asp Gly Arg Asn Lys His Tyr Ala Asp Ser Val Lys
 1               5                  10                  15

Gly
```

<210> SEQ ID NO 289
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

```
Ala Arg Asp Gly Thr Tyr Leu Gly Gly Leu Trp Tyr Phe Asp Leu
 1               5                  10                  15
```

<210> SEQ ID NO 290
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180 tccgggggtcc ctgacaggtt cagtggcagt ggatcaggca cagattttac actgaaaatc   240
agcagagtgg aggctgagga tgttggggtt tattactgca tgcagggact cggcctccct   300
``` ctcactttg gcggagggac caaggttgag atcaaacgg        339

<210> SEQ ID NO 291
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gly Leu Pro Leu Thr Phe Gly Gly Gly Thr Lys Val Glu Ile Lys
            100                 105                 110

Arg

<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Ser Ser Gln Ser Leu Leu His Ser Asn Gly Tyr Asn Tyr Leu Asp
1               5                   10                  15

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Leu Gly Ser Asn Arg Ala Ser
1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Met Gln Gly Leu Gly Leu Pro Leu Thr
1               5

<210> SEQ ID NO 295
<211> LENGTH: 1461
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 295

```
atggcactcc cgtaactgc tctgctgctg ccgttggcat tgctcctgca cgccgcacgc      60
ccgcaggtgc agctggtgga gtctggggga ggcgtggtcc agcctgggag gtccctgaga    120
ctctcctgtg cagcgtctgg attcaccttc agtgagcatg gcatgcactg ggtccgccag    180
gctccaggca aggggctgga gtgggtggca gctatatctt atgatggaag gaataaacac    240
tatgcagact ccgtgaaggg ccgattcacc atctccagag acaattccaa gaacacgctg    300
tatctgcaaa tgaacagcct gagagccgag gacacggcgg tgtactactg cgccagagac    360
ggtacttatc taggtggtct ctggtacttc gacttatggg ggagaggtac cttggtcacc    420
gtctcctcag ggtctacatc cggctccggg aagcccggaa gtggcgaagg tagtacaaag    480
ggggatattg tgatgactca gtctccactc tccctgcccg tcacccctgg agagccggcc    540
tccatctcct gcaggtctag tcagagcctc ctgcatagta tggatacaa ctatttggat    600
tggtacctgc agaagccagg gcagtctcca cagctcctga tctatttggg ttctaatcgg    660
gcctccgggg tccctgacag gttcagtggc agtggatcag gcacagattt tacactgaaa    720
atcagcagag tggaggctga ggatgttggg gtttattact gcatgcaggg actcggcctc    780
cctctcactt ttggcggagg gaccaaggtt gagatcaaac gggccgctgc ccttgataat    840
gaaaagtcaa acggaacaat cattcacgtg aagggcaagc acctctgtcc gtcaccctgg    900
ttccctggtc catccaagcc attctgggtg ttggtcgtag tggtggagt cctcgcttgt    960
tactctctgc tcgtcaccgt ggcttttata atcttctggg ttagatccaa agaagccgc   1020
ctgctccata gcgattacat gaatatgact ccacgccgcc ctggccccac aaggaaacac   1080
taccagcctt acgcaccacc tagagatttc gctgcctatc ggagcagggt gaagttttcc   1140
agatctgcag atgcaccagc gtatcagcag ggccagaacc aactgtataa cgagctcaac   1200
ctgggacgca gggaagagta tgacgttttg gacaagcgca gaggacggga ccctgagatg   1260
ggtggcaaac caagacgaaa aaaccccccag gagggtctct ataatgagct gcagaaggat   1320
aagatggctg aagcctattc tgaaataggc atgaaggag agcggagaag gggaaaaggg   1380
cacgacggtt tgtaccaggg actcagcact gctacgaagg atacttatga cgctctccac   1440
atgcaagccc tgccacctag g                                             1461
```

<210> SEQ ID NO 296
<211> LENGTH: 487
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 296

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

```
Thr Phe Ser Glu His Gly Met His Trp Val Arg Gln Ala Pro Gly Lys
 50                  55                  60
Gly Leu Glu Trp Val Ala Ala Ile Ser Tyr Asp Gly Arg Asn Lys His
 65                  70                  75                  80
Tyr Ala Asp Ser Val Lys Gly Arg Phe Thr Ile Ser Arg Asp Asn Ser
                 85                  90                  95
Lys Asn Thr Leu Tyr Leu Gln Met Asn Ser Leu Arg Ala Glu Asp Thr
                100                 105                 110
Ala Val Tyr Tyr Cys Ala Arg Asp Gly Thr Tyr Leu Gly Gly Leu Trp
                115                 120                 125
Tyr Phe Asp Leu Trp Gly Arg Gly Thr Leu Val Thr Val Ser Ser Gly
                130                 135                 140
Ser Thr Ser Gly Ser Gly Lys Pro Gly Ser Gly Glu Gly Ser Thr Lys
145                 150                 155                 160
Gly Asp Ile Val Met Thr Gln Ser Pro Leu Ser Leu Pro Val Thr Pro
                165                 170                 175
Gly Glu Pro Ala Ser Ile Ser Cys Arg Ser Ser Gln Ser Leu Leu His
                180                 185                 190
Ser Asn Gly Tyr Asn Tyr Leu Asp Trp Tyr Leu Gln Lys Pro Gly Gln
                195                 200                 205
Ser Pro Gln Leu Leu Ile Tyr Leu Gly Ser Asn Arg Ala Ser Gly Val
                210                 215                 220
Pro Asp Arg Phe Ser Gly Ser Gly Ser Gly Thr Asp Phe Thr Leu Lys
225                 230                 235                 240
Ile Ser Arg Val Glu Ala Glu Asp Val Gly Val Tyr Tyr Cys Met Gln
                245                 250                 255
Gly Leu Gly Leu Pro Leu Thr Phe Gly Gly Gly Thr Lys Val Glu Ile
                260                 265                 270
Lys Arg Ala Ala Ala Leu Asp Asn Glu Lys Ser Asn Gly Thr Ile Ile
                275                 280                 285
His Val Lys Gly Lys His Leu Cys Pro Ser Pro Leu Phe Pro Gly Pro
                290                 295                 300
Ser Lys Pro Phe Trp Val Leu Val Val Gly Gly Val Leu Ala Cys
305                 310                 315                 320
Tyr Ser Leu Leu Val Thr Val Ala Phe Ile Ile Phe Trp Val Arg Ser
                325                 330                 335
Lys Arg Ser Arg Leu Leu His Ser Asp Tyr Met Asn Met Thr Pro Arg
                340                 345                 350
Arg Pro Gly Pro Thr Arg Lys His Tyr Gln Pro Tyr Ala Pro Pro Arg
                355                 360                 365
Asp Phe Ala Ala Tyr Arg Ser Arg Val Lys Phe Ser Arg Ser Ala Asp
                370                 375                 380
Ala Pro Ala Tyr Gln Gln Gly Gln Asn Gln Leu Tyr Asn Glu Leu Asn
385                 390                 395                 400
Leu Gly Arg Arg Glu Glu Tyr Asp Val Leu Asp Lys Arg Arg Gly Arg
                405                 410                 415
Asp Pro Glu Met Gly Gly Lys Pro Arg Arg Lys Asn Pro Gln Glu Gly
                420                 425                 430
Leu Tyr Asn Glu Leu Gln Lys Asp Lys Met Ala Glu Ala Tyr Ser Glu
                435                 440                 445
Ile Gly Met Lys Gly Glu Arg Arg Arg Gly Lys Gly His Asp Gly Leu
                450                 455                 460
```

```
Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 297
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297

```
atggcactcc ccgtaactgc tctgctgctg ccgttggcat tgctcctgca cgccgcacgc      60
ccggatattg tgatgactca gtctccactc tccctgcccg tcaccctgg agagccggcc     120
tccatctcct gcaggtctag tcagagcctc ctgcatagta atggatacaa ctatttggat     180
tggtacctgc agaagccagg gcagtctcca cagctcctga tctatttggg ttctaatcgg     240
gcctccgggg tccctgacag gttcagtggc agtggatcag gcacagattt tacactgaaa     300
atcagcagag tggaggctga ggatgttggg gtttattact gcatgcaggg actcggcctc     360
cctctcactt ttggcggagg gaccaaggtt gagatcaaac ggggtctac atccggctcc     420
ggaagcccg aagtggcga aggtagtaca aaggggcagg tgcagctggt ggagtctggg     480
ggaggcgtgg tccagcctgg gaggtccctg agactctcct gtgcagcgtc tggattcacc     540
ttcagtgagc atggcatgca ctgggtccgc caggctccag gcaagggct ggagtgggtg     600
gcagctatat cttatgatgg aaggaataaa cactatgcag actccgtgaa gggccgattc     660
accatctcca gagacaattc caagaacacg ctgtatctgc aaatgaacag cctgagagcc     720
gaggacacgg cggtgtacta ctgcgccaga gacggtactt atctaggtgg tctctggtac     780
ttcgacttat gggggagagg taccttggtc accgtctcct cagccgctgc ccttgataat     840
gaaaagtcaa acggaacaat cattcacgtg aagggcaagc acctctgtcc gtcacccttg     900
ttccctggtc catccaagcc attctggggt ttggtcgtag tggtggagt cctcgcttgt     960
tactctctgc tcgtcaccgt ggcttttata atcttctggg ttagatccaa aagaagccgc    1020
ctgctccata gcgattacat gaatatgact ccacgccgcc ctggccccac aaggaaacac    1080
taccagcctt acgcaccacc tagagatttc gctgcctatc ggagcagggt gaagttttcc    1140
agatctgcag atgcaccagc gtatcagcag ggccagaacc aactgtataa cgagctcaac    1200
ctgggacgca gggaagagta tgacgttttg gacaagcgca gaggacggga ccctgagatg    1260
ggtggcaaac caagacgaaa aaaccccag gagggtctct ataatgagct gcagaaggat    1320
aagatggctg aagcctattc tgaaataggc atgaaggag agcggagaag ggaaaaggg     1380
cacgacggtt tgtaccaggg actcagcact gctacgaagg atacttatga cgctctccac    1440
atgcaagccc tgccacctag g                                               1461
```

<210> SEQ ID NO 298
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Met Ala Leu Pro Val Thr Ala Leu Leu Leu Pro Leu Ala Leu Leu Leu

-continued

```
1               5                   10                  15
His Ala Ala Arg Pro Asp Ile Val Met Thr Gln Ser Pro Leu Ser Leu
            20                  25                  30

Pro Val Thr Pro Gly Glu Pro Ala Ser Ile Ser Cys Arg Ser Ser Gln
            35                  40                  45

Ser Leu Leu His Ser Asn Gly Tyr Asn Tyr Leu Asp Trp Tyr Leu Gln
            50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
            85                  90                  95

Phe Thr Leu Lys Ile Ser Arg Val Glu Ala Glu Asp Val Gly Val Tyr
            100                 105                 110

Tyr Cys Met Gln Gly Leu Gly Leu Pro Leu Thr Phe Gly Gly Gly Thr
            115                 120                 125

Lys Val Glu Ile Lys Arg Gly Ser Thr Ser Gly Ser Gly Lys Pro Gly
            130                 135                 140

Ser Gly Glu Gly Ser Thr Lys Gly Gln Val Gln Leu Val Glu Ser Gly
145                 150                 155                 160

Gly Gly Val Val Gln Pro Gly Arg Ser Leu Arg Leu Ser Cys Ala Ala
                165                 170                 175

Ser Gly Phe Thr Phe Ser Glu His Gly Met His Trp Val Arg Gln Ala
            180                 185                 190

Pro Gly Lys Gly Leu Glu Trp Val Ala Ala Ile Ser Tyr Asp Gly Arg
            195                 200                 205

Asn Lys His Tyr Ala Asp Ser Val Lys Gly Arg Phe Thr Ile Ser Arg
210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Asp Gly Thr Tyr Leu Gly
            245                 250                 255

Gly Leu Trp Tyr Phe Asp Leu Trp Gly Arg Gly Thr Leu Val Thr Val
            260                 265                 270

Ser Ser Ala Ala Ala Leu Asp Asn Glu Lys Ser Asn Gly Thr Ile Ile
            275                 280                 285

His Val Lys Gly Lys His Leu Cys Pro Ser Pro Leu Phe Pro Gly Pro
            290                 295                 300

Ser Lys Pro Phe Trp Val Leu Val Val Val Gly Gly Val Leu Ala Cys
305                 310                 315                 320

Tyr Ser Leu Leu Val Thr Val Ala Phe Ile Ile Phe Trp Val Arg Ser
            325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
            355                 360                 365

Asp Phe Ala Ala Tyr Arg Ser Arg Val Lys Phe Ser Arg Ser Ala Asp
            370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430
```

```
Leu Tyr Asn Glu Leu Gln Lys Asp Lys Met Ala Glu Ala Tyr Ser Glu
            435                 440                 445

Ile Gly Met Lys Gly Glu Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 299
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 299
caggtgcagc tggtgcagtc tggggctgag gtgaagaagc ctggggcctc agtgaaggtt       60
tcctgcaggg catctggata caccttcatg gagcactata tgcactgggt gcgacaggcc      120
cctggacaag gcttgagtg gatgggagta atcgggccta gtggtggtaa gacaagctac       180
gcacagaagt tccagggcag agtcaccatg accagggaca cgtccacgag cacagtctac      240
atggagctga gcagcctgag atctgaggac acggcggtgt actactgcgc cagagagaat      300
tggccaatgg acgtatgggg ccagggaaca actgtcaccg tctcctca                   348

<210> SEQ ID NO 300
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Met Glu His
            20                  25                  30

Tyr Met His Trp Val Arg Gln Ala Pro Gly Gln Gly Leu Glu Trp Met
        35                  40                  45

Gly Val Ile Gly Pro Ser Gly Gly Lys Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
            100                 105                 110

Thr Val Ser Ser
        115

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 301

Tyr Thr Phe Met Glu His Tyr Met His
1               5

<210> SEQ ID NO 302
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Val Ile Gly Pro Ser Gly Gly Lys Thr Ser Tyr Ala Gln Lys Phe Gln
1               5                   10                  15

Gly

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ala Arg Glu Ser Trp Pro Met Asp Val
1               5

<210> SEQ ID NO 304
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 304
gaaatagtga tgacgcagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagttttatta ctgtcagcag tacgccgcct accctacttt tggcggaggg    300
accaaggttg agatcaaacg g                                              321

<210> SEQ ID NO 305
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

```
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
 65                  70                  75                  80
Glu Asp Phe Ala Val Tyr Tyr Cys Gln Gln Tyr Ala Ala Tyr Pro Thr
                 85                  90                  95
Phe Gly Gly Gly Thr Lys Val Glu Ile Lys Arg
            100                 105
```

<210> SEQ ID NO 306
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

```
Arg Ala Ser Gln Ser Val Ser Ser Asn Leu Ala
 1               5                  10
```

<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

```
Gly Ala Ser Thr Arg Ala Thr
 1               5
```

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

```
Gln Gln Tyr Ala Ala Tyr Pro Thr
 1               5
```

<210> SEQ ID NO 309
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 309

```
atggcactcc ccgtaactgc tctgctgctg ccgttggcat tgctcctgca cgccgcacgc    60
ccgcaggtgc agctggtgca gtctggggct gaggtgaaga agcctggggc ctcagtgaag   120
gtttcctgca gggcatctgg atacacctcc atggagcact atatgcactg ggtgcgacag   180
gcccctggac aagggcttga gtggatggga gtaatcgggc tagtggtgg taagacaagc    240 tacgcacaga gttccagggg cagagtcacc atgaccaggg acacgtccac gagcacagtc   300
tacatggagc tgagcagcct gagatctgag gacacggcgg tgtactactg cgccagagag   360
aattggccaa tggacgtatg gggccaggga caactgtca ccgtctcctc agggtctaca    420
```

```
tccggctccg ggaagcccgg aagtggcgaa ggtagtacaa agggggaaat agtgatgacg    480
cagtctccag ccaccctgtc tgtgtctcca ggggaaagag ccaccctctc ctgcagggcc    540
agtcagagtg ttagcagcaa cttagcctgg taccagcaga aacctggcca ggctcccagg    600
ctcctcatct atggtgcatc caccagggcc actggtatcc cagccaggtt cagtggcagt    660
gggtctggga cagagttcac tctcaccatc agcagcctgc agtctgaaga ttttgcagtt    720
tattactgtc agcagtacgc cgcctaccct acttttggcg agggaccaa ggttgagatc    780
aaacgggccg ctgcccttga taatgaaaag tcaaacggaa caatcattca cgtgaagggc    840
aagcacctct gtccgtcacc cttgttccct ggtccatcca agccattctg ggtgttggtc    900
gtagtgggtg gagtcctcgc ttgttactct ctgctcgtca ccgtggcttt tataatcttc    960
tgggttagat ccaaaagaag ccgcctgctc catagcgatt acatgaatat gactccacgc   1020
cgccctggcc ccacaaggaa acactaccag ccttacgcac acctagaga tttcgctgcc   1080
tatcggagca gggtgaagtt ttccagatct gcagatgcac cagcgtatca gcagggccag   1140
aaccaactgt ataacgagct caacctggga cgcagggaag agtatgacgt tttggacaag   1200
cgcagaggac gggaccctga tgggtggc aaaccaagac gaaaaaaccc ccaggagggt    1260
ctctataatg agctgcagaa ggataagatg gctgaagcct attctgaaat aggcatgaaa   1320
ggagagcgga aagggggaaa agggcacgac ggtttgtacc agggactcag cactgctacg   1380
aaggatactt atgacgctct ccacatgcaa gccctgccac ctagg                   1425
```

<210> SEQ ID NO 310
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Arg Ala Ser Gly Tyr
        35                  40                  45

Thr Phe Met Glu His Tyr Met His Trp Val Arg Gln Ala Pro Gly Gln
    50                  55                  60

Gly Leu Glu Trp Met Gly Val Ile Gly Pro Ser Gly Gly Lys Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Glu Ser Trp Pro Met Asp Val Trp Gly
        115                 120                 125

Gln Gly Thr Thr Val Thr Val Ser Ser Gly Thr Ser Gly Ser Gly
    130                 135                 140

Lys Pro Gly Ser Gly Glu Gly Ser Thr Lys Gly Glu Ile Val Met Thr
145                 150                 155                 160

Gln Ser Pro Ala Thr Leu Ser Val Ser Pro Gly Glu Arg Ala Thr Leu
                165                 170                 175

Ser Cys Arg Ala Ser Gln Ser Val Ser Ser Asn Leu Ala Trp Tyr Gln

```
            180                 185                 190
Gln Lys Pro Gly Gln Ala Pro Arg Leu Leu Ile Tyr Gly Ala Ser Thr
            195                 200                 205

Arg Ala Thr Gly Ile Pro Ala Arg Phe Ser Gly Ser Gly Ser Gly Thr
            210                 215                 220

Glu Phe Thr Leu Thr Ile Ser Ser Leu Gln Ser Glu Asp Phe Ala Val
225                 230                 235                 240

Tyr Tyr Cys Gln Gln Tyr Ala Ala Tyr Pro Thr Phe Gly Gly Gly Thr
                245                 250                 255

Lys Val Glu Ile Lys Arg Ala Ala Ala Leu Asp Asn Glu Lys Ser Asn
            260                 265                 270

Gly Thr Ile Ile His Val Lys Gly Lys His Leu Cys Pro Ser Pro Leu
            275                 280                 285

Phe Pro Gly Pro Ser Lys Pro Phe Trp Val Leu Val Val Val Gly Gly
            290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
            355                 360                 365

Arg Ser Ala Asp Ala Pro Ala Tyr Gln Gln Gly Gln Asn Gln Leu Tyr
370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
            435                 440                 445

His Asp Gly Leu Tyr Gln Gly Leu Ser Thr Ala Thr Lys Asp Thr Tyr
            450                 455                 460

Asp Ala Leu His Met Gln Ala Leu Pro Pro Arg
465                 470                 475

<210> SEQ ID NO 311
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 311
atggcactcc ccgtaactgc tctgctgctg ccgttggcat tgctcctgca cgccgcacgc      60
ccggaaatag tgatgacgca gtctccagcc accctgtctg tgtctccagg ggaaagagcc     120
accctctcct gcagggccag tcagagtgtt agcagcaact tagcctggta ccagcagaaa     180
cctggccagg ctcccaggct cctcatctat ggtgcatcca ccagggccac tggtatccca     240
gccaggttca gtggcagtgg gtctgggaca gagttcactc tcaccatcag cagcctgcag     300
tctgaagatt ttgcagttta ttactgtcag cagtacgccg cctaccctac ttttggcgga     360
```

-continued

```
gggaccaagg ttgagatcaa acggggtct acatccggct ccgggaagcc cggaagtggc    420
gaaggtagta caaaggggca ggtgcagctg gtgcagtctg gggctgaggt gaagaagcct    480
ggggcctcag tgaaggtttc ctgcagggca tctggataca ccttcatgga gcactatatg    540
cactgggtgc gacaggcccc tggacaaggg cttgagtgga tgggagtaat cgggcctagt    600
ggtggtaaga caagctacgc acagaagttc cagggcagag tcaccatgac cagggacacg    660
tccacgagca cagtctacat ggagctgagc agcctgagat ctgaggacac ggcggtgtac    720
tactgcgcca gagagaattg gccaatggac gtatggggcc agggaacaac tgtcaccgtc    780
tcctcagccg ctgcccttga taatgaaaag tcaaacggaa caatcattca cgtgaagggc    840
aagcacctct gtccgtcacc cttgttccct ggtccatcca agccattctg ggtgttggtc    900
gtagtgggtg gagtcctcgc ttgttactct ctgctcgtca ccgtggcttt tataatcttc    960
tgggttagat ccaaaagaag ccgcctgctc catagcgatt acatgaatat gactccacgc   1020
cgccctggcc ccacaaggaa acactaccag ccttacgcac cacctagaga tttcgctgcc   1080
tatcggagca gggtgaagtt ttccagatct gcagatgcac agcgtatca gcagggccag   1140
aaccaactgt ataacgagct caacctggga cgcagggaag agtatgacgt tttggacaag   1200
cgcagaggac gggaccctga tggggtggc aaaccaagac gaaaaaaccc ccaggagggt   1260
ctctataatg agctgcagaa ggataagatg gctgaagcct attctgaaat aggcatgaaa   1320
ggagagcgga gaagggaaa aagggcacgac ggtttgtacc agggactcag cactgctacg   1380
aaggatactt atgacgctct ccacatgcaa gccctgccac ctagg               1425
```

<210> SEQ ID NO 312
<211> LENGTH: 475
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 312

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Val Ser Pro Gly Glu Arg Ala Thr Leu Ser Cys Arg Ala Ser Gln
            35                  40                  45

Ser Val Ser Ser Asn Leu Ala Trp Tyr Gln Gln Lys Pro Gly Gln Ala
        50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Ala Ala Tyr Pro Thr Phe Gly Gly Gly Thr Lys Val Glu Ile Lys Arg
        115                 120                 125

Gly Ser Thr Ser Gly Ser Gly Lys Pro Gly Ser Gly Glu Gly Ser Thr
    130                 135                 140

Lys Gly Gln Val Gln Leu Val Gln Ser Gly Ala Glu Val Lys Lys Pro
145                 150                 155                 160

Gly Ala Ser Val Lys Val Ser Cys Arg Ala Ser Gly Tyr Thr Phe Met
                165                 170                 175
```

Glu His Tyr Met His Trp Val Arg Gln Ala Pro Gly Gln Gly Leu Glu
             180                 185                 190

Trp Met Gly Val Ile Gly Pro Ser Gly Gly Lys Thr Ser Tyr Ala Gln
         195                 200                 205

Lys Phe Gln Gly Arg Val Thr Met Thr Arg Asp Thr Ser Thr Ser Thr
210                 215                 220

Val Tyr Met Glu Leu Ser Ser Leu Arg Ser Glu Asp Thr Ala Val Tyr
225                 230                 235                 240

Tyr Cys Ala Arg Glu Ser Trp Pro Met Asp Val Trp Gly Gln Gly Thr
                 245                 250                 255

Thr Val Thr Val Ser Ser Ala Ala Leu Asp Asn Glu Lys Ser Asn
             260                 265                 270

Gly Thr Ile Ile His Val Lys Gly Lys His Leu Cys Pro Ser Pro Leu
         275                 280                 285

Phe Pro Gly Pro Ser Lys Pro Phe Trp Val Leu Val Val Val Gly Gly
         290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                 325                 330                 335

Met Thr Pro Arg Arg Pro Gly Pro Thr Arg Lys His Tyr Gln Pro Tyr
             340                 345                 350

Ala Pro Pro Arg Asp Phe Ala Ala Tyr Arg Ser Arg Val Lys Phe Ser
             355                 360                 365

Arg Ser Ala Asp Ala Pro Ala Tyr Gln Gln Gly Gln Asn Gln Leu Tyr
370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                 405                 410                 415

Pro Gln Glu Gly Leu Tyr Asn Glu Leu Gln Lys Asp Lys Met Ala Glu
             420                 425                 430

Ala Tyr Ser Glu Ile Gly Met Lys Gly Glu Arg Arg Arg Gly Lys Gly
         435                 440                 445

His Asp Gly Leu Tyr Gln Gly Leu Ser Thr Ala Thr Lys Asp Thr Tyr
         450                 455                 460

Asp Ala Leu His Met Gln Ala Leu Pro Pro Arg
465                 470                 475

<210> SEQ ID NO 313
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 313
caggtgcagc tggtgcagtc tggggctgag gtgaagaagc ctggggcctc agtgaaggtt      60
tcctgcaagg catctggata caccttcacg gagcactata tgcactgggt gcgacaggcc    120
cctggacaaa ggcttgagtg gatgggagta atcgggccta gtggtggtaa gacaagctac    180
gcacagaagt tccagggcag agtcaccatg accaggagaca cgtccacgag cacagtctac    240
atggagctga gcagcctgag atctgaggac acggcggtgt actactgcgc cagagagagt    300
tggccaatgg acgtatgggg ccagggaaca actgtcaccg tctcctca 348

<210> SEQ ID NO 314
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Tyr Met His Trp Val Arg Gln Ala Pro Gly Gln Arg Leu Glu Trp Met
        35                  40                  45

Gly Val Ile Gly Pro Ser Gly Gly Lys Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
            100                 105                 110

Thr Val Ser Ser
        115
```

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

```
Tyr Thr Phe Thr Glu His Tyr Met His
1               5
```

<210> SEQ ID NO 316
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

```
Val Ile Gly Pro Ser Gly Gly Lys Thr Ser Tyr Ala Gln Lys Phe Gln
1               5                   10                  15

Gly
```

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

```
Ala Arg Glu Ser Trp Pro Met Asp Val
```

<210> SEQ ID NO 318
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 318

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tacgccgcct accctacttt tggcggaggg   300
accaaggttg agatcaaacg g                                             321
```

<210> SEQ ID NO 319
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 319

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Ala Ala Tyr Pro Thr
                85                  90                  95
Phe Gly Gly Gly Thr Lys Val Glu Ile Lys Arg
            100                 105
```

<210> SEQ ID NO 320
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 320

```
Arg Ala Ser Gln Ser Val Ser Ser Asn Leu Ala
1               5                   10
```

<210> SEQ ID NO 321
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 321

Gly Ala Ser Thr Arg Ala Thr
1               5

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Gln Tyr Ala Ala Tyr Pro Thr
1               5

<210> SEQ ID NO 323
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 323

| | | | |
|---|---|---|---|
| atggcactcc cgtaactgc tctgctgctg ccgttggcat tgctcctgca cgccgcacgc | 60 |
| ccgcaggtgc agctggtgca gtctggggct gaggtgaaga agcctggggc ctcagtgaag | 120 |
| gtttcctgca aggcatctgg atacaccttc acgagcact atatgcactg ggtgcgacag | 180 |
| gcccctggac aaaggcttga gtggatggga gtaatcgggc tagtggtgg taagacaagc | 240 |
| tacgcacaga agttccaggg cagagtcacc atgaccaggg acacgtccac gagcacagtc | 300 |
| tacatggagc tgagcagcct gagatctgag gacacggcgg tgtactactg cgccagagag | 360 |
| agttggccaa tggacgtatg gggccaggga caactgtca ccgtctcctc agggtctaca | 420 |
| tccggctccg ggaagcccgg aagtggcgaa ggtagtacaa agggggaaat agtgatgacg | 480 |
| cagtctccag ccaccctgtc tgtgtctcca ggggaaagag ccaccctctc ctgcagggcc | 540 |
| agtcagagtg ttagcagcaa cttagcctgg taccagcaga aacctggcca ggctcccagg | 600 |
| ctcctcatct atggtgcatc caccagggcc actggtatcc cagccaggtt cagtggcagt | 660 |
| gggtctggga cagagttcac tctcaccatc agcagcctgc agtctgaaga ttttgcagtt | 720 |
| tattactgtc agcagtacgc cgcctaccct acttttggcg agggaccaa ggttgagatc | 780 |
| aaacgggccg ctgcccttga taatgaaaag tcaaacggaa caatcattca cgtgaagggc | 840 |
| aagcacctct gtccgtcacc cttgttccct ggtccatcca agccattctg ggtgttggtc | 900 |
| gtagtgggtg gagtcctcgc ttgttactct ctgctcgtca ccgtggcttt tataatcttc | 960 |
| tgggttagat ccaaaagaag ccgcctgctc catagcgatt acatgaatat gactccacgc | 1020 |
| cgccctggcc ccacaaggaa acactaccag ccttacgcac acctagaga tttcgctgcc | 1080 |
| tatcggagca gggtgaagtt ttccagatct gcagatgcac cagcgtatca gcagggccag | 1140 |
| aaccaactgt ataacgagct caacctggga cgcaggaag agtatgacgt tttggacaag | 1200 |
| cgcagaggac gggaccctga gatgggtggc aaaccaagac gaaaaaaccc ccaggagggt | 1260 |
| ctctataatg agctgcagaa ggataagatg gctgaagcct attctgaaat aggcatgaaa | 1320 |
| ggagagcgga gaaggggaaa agggcacgac ggtttgtacc agggactcag cactgctacg | 1380 |
| aaggatactt atgacgctct ccacatgcaa gccctgccac ctagg | 1425 |

```
<210> SEQ ID NO 324
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324
```

| | | | | | | | | | | | | | | | |
|---|---|---|---|---|---|---|---|---|---|---|---|---|---|---|---|
| Met | Ala | Leu | Pro | Val | Thr | Ala | Leu | Leu | Pro | Leu | Ala | Leu | Leu | Leu | |
| 1 | | | | 5 | | | | | 10 | | | | | 15 | |
| His | Ala | Ala | Arg | Pro | Gln | Val | Gln | Leu | Val | Gln | Ser | Gly | Ala | Glu | Val |
| | | | 20 | | | | | 25 | | | | | 30 | | |
| Lys | Lys | Pro | Gly | Ala | Ser | Val | Lys | Val | Ser | Cys | Lys | Ala | Ser | Gly | Tyr |
| | | 35 | | | | | 40 | | | | | 45 | | | |
| Thr | Phe | Thr | Glu | His | Tyr | Met | His | Trp | Val | Arg | Gln | Ala | Pro | Gly | Gln |
| | 50 | | | | | 55 | | | | | 60 | | | | |
| Arg | Leu | Glu | Trp | Met | Gly | Val | Ile | Gly | Pro | Ser | Gly | Gly | Lys | Thr | Ser |
| 65 | | | | | 70 | | | | | 75 | | | | | 80 |
| Tyr | Ala | Gln | Lys | Phe | Gln | Gly | Arg | Val | Thr | Met | Thr | Arg | Asp | Thr | Ser |
| | | | | 85 | | | | | 90 | | | | | 95 | |
| Thr | Ser | Thr | Val | Tyr | Met | Glu | Leu | Ser | Ser | Leu | Arg | Ser | Glu | Asp | Thr |
| | | | 100 | | | | | 105 | | | | | 110 | | |
| Ala | Val | Tyr | Tyr | Cys | Ala | Arg | Glu | Ser | Trp | Pro | Met | Asp | Val | Trp | Gly |
| | | | 115 | | | | | 120 | | | | | 125 | | |
| Gln | Gly | Thr | Thr | Val | Thr | Val | Ser | Ser | Gly | Ser | Thr | Ser | Gly | Ser | Gly |
| | 130 | | | | | 135 | | | | | 140 | | | | |
| Lys | Pro | Gly | Ser | Gly | Glu | Gly | Ser | Thr | Lys | Gly | Glu | Ile | Val | Met | Thr |
| 145 | | | | | 150 | | | | | 155 | | | | | 160 |
| Gln | Ser | Pro | Ala | Thr | Leu | Ser | Val | Ser | Pro | Gly | Glu | Arg | Ala | Thr | Leu |
| | | | | 165 | | | | | 170 | | | | | 175 | |
| Ser | Cys | Arg | Ala | Ser | Gln | Ser | Val | Ser | Ser | Asn | Leu | Ala | Trp | Tyr | Gln |
| | | | 180 | | | | | 185 | | | | | 190 | | |
| Gln | Lys | Pro | Gly | Gln | Ala | Pro | Arg | Leu | Leu | Ile | Tyr | Gly | Ala | Ser | Thr |
| | | 195 | | | | | 200 | | | | | 205 | | | |
| Arg | Ala | Thr | Gly | Ile | Pro | Ala | Arg | Phe | Ser | Gly | Ser | Gly | Ser | Gly | Thr |
| | 210 | | | | | 215 | | | | | 220 | | | | |
| Glu | Phe | Thr | Leu | Thr | Ile | Ser | Ser | Leu | Gln | Ser | Glu | Asp | Phe | Ala | Val |
| 225 | | | | | 230 | | | | | 235 | | | | | 240 |
| Tyr | Tyr | Cys | Gln | Gln | Tyr | Ala | Ala | Tyr | Pro | Thr | Phe | Gly | Gly | Gly | Thr |
| | | | | 245 | | | | | 250 | | | | | 255 | |
| Lys | Val | Glu | Ile | Lys | Arg | Ala | Ala | Ala | Leu | Asp | Asn | Glu | Lys | Ser | Asn |
| | | | 260 | | | | | 265 | | | | | 270 | | |
| Gly | Thr | Ile | Ile | His | Val | Lys | Gly | Lys | His | Leu | Cys | Pro | Ser | Pro | Leu |
| | | 275 | | | | | 280 | | | | | 285 | | | |
| Phe | Pro | Gly | Pro | Ser | Lys | Pro | Phe | Trp | Val | Leu | Val | Val | Val | Gly | Gly |
| | 290 | | | | | 295 | | | | | 300 | | | | |
| Val | Leu | Ala | Cys | Tyr | Ser | Leu | Leu | Val | Thr | Val | Ala | Phe | Ile | Ile | Phe |
| 305 | | | | | 310 | | | | | 315 | | | | | 320 |
| Trp | Val | Arg | Ser | Lys | Arg | Ser | Arg | Leu | Leu | His | Ser | Asp | Tyr | Met | Asn |
| | | | | 325 | | | | | 330 | | | | | 335 | |
| Met | Thr | Pro | Arg | Arg | Pro | Gly | Pro | Thr | Arg | Lys | His | Tyr | Gln | Pro | Tyr |
| | | | 340 | | | | | 345 | | | | | 350 | | |
| Ala | Pro | Pro | Arg | Asp | Phe | Ala | Ala | Tyr | Arg | Ser | Arg | Val | Lys | Phe | Ser |
| | | 355 | | | | | 360 | | | | | 365 | | | |

```
Arg Ser Ala Asp Ala Pro Ala Tyr Gln Gln Gly Gln Asn Gln Leu Tyr
        370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 325
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 325
atggcactcc ccgtaactgc tctgctgctg ccgttggcat tgctcctgca cgccgcacgc     60
ccggaaatag tgatgacgca gtctccagcc accctgtctg tgtctccagg ggaaagagcc    120
accctctcct gcagggccag tcagagtgtt agcagcaact tagcctggta ccagcagaaa    180
cctggccagg ctcccaggct cctcatctat ggtgcatcca ccagggccac tggtatccca    240
gccaggttca gtggcagtgg gtctgggaca gagttcactc tcaccatcag cagcctgcag    300
tctgaagatt ttgcagttta ttactgtcag cagtacgccg cctaccctac ttttggcgga    360
gggaccaagg ttgagatcaa acgggggtct acatccggct ccgggaagcc cggaagtggc    420
gaaggtagta caaaggggca ggtgcagctg gtgcagtctg ggctgaggt gaagaagcct    480 ggggcctcag tgaaggtttc ctgcaaggca tctggataca ccttcacgga gcactatatg    540
cactgggtgc gacaggcccc tggacaaagg cttgagtgga tgggagtaat cgggcctagt    600
ggtggtaaga caagctacgc acagaagttc cagggcagag tcaccatgac cagggacacg    660
tccacgagca cagtctacat ggagctgagc agcctgagat ctgaggacac ggcggtgtac    720
tactgcgcca gagagagttg gccaatgaca gtatggggcc aggaacaac tgtcaccgtc    780 tcctcagccg ctgcccttga taatgaaaag tcaaacggaa caatcattca cgtgaagggc    840
aagcacctct gtccgtcacc cttgttccct ggtccatcca agccattctg ggtgttggtc    900
gtagtgggtg gagtcctcgc ttgttactct ctgctcgtca ccgtggcttt tataatcttc    960
tgggttagat ccaaaagaag ccgcctgctc catagcgatt acatgaatat gactccacgc   1020
cgccctggcc ccacaaggaa acactaccag ccttacgcac acctagaga tttcgctgcc   1080 tatcggagca gggtgaagtt ttccagatct gcagatgcac cagcgtatca gcagggccag   1140
aaccaactgt ataacgagct caacctggga cgcagggaag agtatgacgt tttggacaag   1200
cgcagaggac gggaccctga tgggtggc aaaccaagac gaaaaaaccc caggagggt    1260 ctctataatg agctgcagaa ggataagatg gctgaagcct attctgaaat aggcatgaaa   1320
ggagagcgga gaaggggaaa aggcacgac ggtttgtacc agggactcag cactgctacg    1380
```
aaggatactt atgacgctct ccacatgcaa gccctgccac ctagg         1425

<210> SEQ ID NO 326
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Ala Ala Tyr Pro Thr Phe Gly Gly Gly Thr Lys Val Glu Ile Lys Arg
        115                 120                 125

Gly Ser Thr Ser Gly Ser Gly Lys Pro Gly Ser Gly Glu Gly Ser Thr
    130                 135                 140

Lys Gly Gln Val Gln Leu Val Gln Ser Gly Ala Glu Val Lys Lys Pro
145                 150                 155                 160

Gly Ala Ser Val Lys Val Ser Cys Lys Ala Ser Gly Tyr Thr Phe Thr
                165                 170                 175

Glu His Tyr Met His Trp Val Arg Gln Ala Pro Gly Gln Arg Leu Glu
            180                 185                 190

Trp Met Gly Val Ile Gly Pro Ser Gly Gly Lys Thr Ser Tyr Ala Gln
        195                 200                 205

Lys Phe Gln Gly Arg Val Thr Met Thr Arg Asp Thr Ser Thr Ser Thr
    210                 215                 220

Val Tyr Met Glu Leu Ser Ser Leu Arg Ser Glu Asp Thr Ala Val Tyr
225                 230                 235                 240

Tyr Cys Ala Arg Glu Ser Trp Pro Met Asp Val Trp Gly Gln Gly Thr
                245                 250                 255

Thr Val Thr Val Ser Ser Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350
```

```
Ala Pro Pro Arg Asp Phe Ala Ala Tyr Arg Ser Arg Val Lys Phe Ser
            355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 327
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 327
caggtgcagc tgcaggagtc gggcccagga ctggtgaagc cttcacagac cctgtccctc      60
acctgtactg tctctggtgg ctccatcggg agtggtggta gttactggag ctggatccgc     120
cagcacccag ggaagggcct ggagtggatt gggttgatct attacgatgg gagcacctac     180
tacaacccgt ccctcaagag tcgagttacc atatcagtag acacgtctaa gaaccagttc     240
tccctgaagc tgagttctgt gaccgccgca gacacggcgg tgtactactg cgccagaggc     300 agggatatg agacttcttt agccttcgat atctggggtc aggtacaat ggtcaccgtc     360 tcctca                                                                366

<210> SEQ ID NO 328
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Gly Ser Gly
            20                  25                  30

Gly Ser Tyr Trp Ser Trp Ile Arg Gln His Pro Gly Lys Gly Leu Glu
        35                  40                  45

Trp Ile Gly Leu Ile Tyr Tyr Asp Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Gly Tyr Glu Thr Ser Leu Ala Phe Asp Ile Trp
```

```
              100                 105                 110

Gly Gln Gly Thr Met Val Thr Val Ser Ser
        115                 120

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Ser Ile Gly Ser Gly Gly Ser Tyr Trp Ser
1               5                   10

<210> SEQ ID NO 330
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Leu Ile Tyr Tyr Asp Gly Ser Thr Tyr Tyr Asn Pro Ser Leu Lys Ser
1               5                   10                  15

<210> SEQ ID NO 331
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Arg Gly Arg Gly Tyr Glu Thr Ser Leu Ala Phe Asp Ile
1               5                   10

<210> SEQ ID NO 332
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 332
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag agacacgtct ggcctcctac ttttggcgga     300
gggaccaagg ttgagatcaa acgg                                            324

<210> SEQ ID NO 333
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 333

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg His Val Trp Pro Pro
                85                  90                  95

Thr Phe Gly Gly Gly Thr Lys Val Glu Ile Lys Arg
            100                 105

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Arg Ala Ser Gln Ser Val Ser Ser Tyr Leu Ala
1               5                   10

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Asp Ala Ser Asn Arg Ala Thr
1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gln Gln Arg His Val Trp Pro Pro Thr
1               5

<210> SEQ ID NO 337
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 337
atggcactcc ccgtaactgc tctgctgctg ccgttggcat tgctcctgca cgccgcacgc       60
ccgcaggtgc agctgcagga gtcgggccca ggactggtga agccttcaca gaccctgtcc      120

```
ctcacctgta ctgtctctgg tggctccatc gggagtggtg gtagttactg gagctggatc    180
cgccagcacc cagggaaggg cctggagtgg attgggttga tctattacga tgggagcacc    240
tactacaacc cgtccctcaa gagtcgagtt accatatcag tagacacgtc taagaaccag    300
ttctccctga agctgagttc tgtgaccgcc gcagacacgg cggtgtacta ctgcgccaga    360
ggcaggggat atgagacttc tttagccttc gatatctggg gtcagggtac aatggtcacc    420
gtctcctcag gtctacatc cggctccggg aagcccggaa gtggcgaagg tagtacaaag    480
ggggaaattg tgttgacaca gtctccagcc accctgtctt tgtctccagg ggaagagcc    540 acctctcct gcagggccag tcagagtgtt agcagctact tagcctggta ccaacagaaa    600
cctggccagg ctcccaggct cctcatctat gatgcatcca acagggccac tggcatccca    660
gccaggttca gtggcagtgg gtctgggaca gacttcactc tcaccatcag cagcctagag    720
cctgaagatt ttgcagttta ttactgtcag cagagacacg tctggcctcc tacttttggc    780
ggagggacca aggttgagat caaacgggcc gctgcccttg taatgaaaa gtcaaacgga    840 acaatcattc acgtgaaggg caagcacctc tgtccgtcac ccttgttccc tggtccatcc    900
aagccattct gggtgttggt cgtagtgggt ggagtcctcg cttgttactc tctgctcgtc    960
accgtggctt ttataatctt ctgggttaga tccaaaagaa gccgcctgct ccatagcgat    1020
tacatgaata tgactccacg ccgcctggc cccacaagga acactacca gcttacgca    1080 ccacctagag atttcgctgc ctatcggagc agggtgaagt tttccagatc tgcagatgca    1140
ccagcgtatc agcagggcca gaaccaactg tataacgagc tcaacctggg acgcagggaa    1200
gagtatgacg ttttggacaa gcgcagagga cgggaccctg agatgggtgg caaaccaaga    1260
cgaaaaaacc cccaggaggg tctctataat gagctgcaga aggataagat ggctgaagcc    1320
tattctgaaa taggcatgaa aggagagcgg agaagggaa aagggcacga cggttttgtac    1380 cagggactca gcactgctac gaaggatact tatgacgctc tccacatgca agccctgcca    1440
cctagg                                                               1446
```

<210> SEQ ID NO 338
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Gly
        35                  40                  45

Ser Ile Gly Ser Gly Gly Ser Tyr Trp Ser Trp Ile Arg Gln His Pro
    50                  55                  60

Gly Lys Gly Leu Glu Trp Ile Gly Leu Ile Tyr Tyr Asp Gly Ser Thr
65                  70                  75                  80

Tyr Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
            100                 105                 110

```
Thr Ala Val Tyr Tyr Cys Ala Arg Gly Arg Gly Tyr Glu Thr Ser Leu
            115                 120                 125

Ala Phe Asp Ile Trp Gly Gln Gly Thr Met Val Thr Val Ser Ser Gly
130                 135                 140

Ser Thr Ser Gly Ser Gly Lys Pro Gly Ser Gly Glu Gly Ser Thr Lys
145                 150                 155                 160

Gly Glu Ile Val Leu Thr Gln Ser Pro Ala Thr Leu Ser Leu Ser Pro
                165                 170                 175

Gly Glu Arg Ala Thr Leu Ser Cys Arg Ala Ser Gln Ser Val Ser Ser
            180                 185                 190

Tyr Leu Ala Trp Tyr Gln Gln Lys Pro Gly Gln Ala Pro Arg Leu Leu
        195                 200                 205

Ile Tyr Asp Ala Ser Asn Arg Ala Thr Gly Ile Pro Ala Arg Phe Ser
210                 215                 220

Gly Ser Gly Ser Gly Thr Asp Phe Thr Leu Thr Ile Ser Ser Leu Glu
225                 230                 235                 240

Pro Glu Asp Phe Ala Val Tyr Tyr Cys Gln Gln Arg His Val Trp Pro
                245                 250                 255

Pro Thr Phe Gly Gly Gly Thr Lys Val Glu Ile Lys Arg Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg
```

<210> SEQ ID NO 339
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 339

```
atggcactcc ccgtaactgc tctgctgctg ccgttggcat tgctcctgca cgccgcacgc     60
ccggaaattg tgttgacaca gtctccagcc accctgtctt tgtctccagg ggaaagagcc    120
accctctcct gcagggccag tcagagtgtt agcagctact tagcctggta ccaacagaaa    180
cctggccagg ctcccaggct cctcatctat gatgcatcca acagggccac tggcatccca    240
gccaggttca gtggcagtgg gtctgggaca gacttcactc tcaccatcag cagcctagag    300
cctgaagatt ttgcagttta ttactgtcag cagagacacg tctggcctcc tacttttggc    360
ggagggacca aggttgagat caaacggggg tctacatccg gctccgggaa gcccggaagt    420
ggcgaaggta gtacaaaggg gcaggtgcag ctgcaggagt cgggcccagg actggtgaag    480
ccttcacaga ccctgtccct cacctgtact gtctctggtg gctccatcgg agtggtggt    540
agttactgga gctggatccg ccagcaccca gggaagggcc tggagtggat tgggttgatc    600
tattacgatg ggagcaccta ctacaacccg tccctcaaga gtcgagttac catatcagta    660
gacacgtcta agaaccagtt ctccctgaag ctgagttctg tgaccgccgc agacacggcg    720
gtgtactact gcgccagagg cagggggatat gagacttctt tagccttcga tatctggggt    780
cagggtacaa tggtcaccgt ctcctcagcc gctgcccttg taatgaaaa gtcaaacgga    840
acaatcattc acgtgaaggg caagcacctc tgtccgtcac ccttgttccc tggtccatcc    900
aagccattct gggtgttggt cgtagtgggt ggagtcctcg cttgttactc tctgctcgtc    960
accgtggctt ttataatctt ctgggttaga tccaaaagaa gccgcctgct ccatagcgat   1020
tacatgaata tgactccacg ccgccctggc cccacaagga acactacca gccttacgca   1080
ccacctagag atttcgctgc ctatcggagc agggtgaagt tttccagatc tgcagatgca   1140
ccagcgtatc agcagggcca gaaccaactg tataacgagc tcaacctggg acgcagggaa   1200
gagtatgacg ttttggacaa gcgcagagga cgggaccctg agatgggtgg caaaccaaga   1260
cgaaaaaacc cccaggaggg tctctataat gagctgcaga aggataagat ggctgaagcc   1320
tattctgaaa taggcatgaa aggagagcgg agaaggggaa aagggcacga cggtttgtac   1380
cagggactca gcactgctac gaaggatact tatgacgctc tccacatgca agccctgcca   1440
cctagg                                                              1446
```

<210> SEQ ID NO 340
<211> LENGTH: 482
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 340

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Ser Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80
```

-continued

```
Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

His Val Trp Pro Pro Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Gln Glu Ser Gly Pro Gly Leu Val Lys
145                 150                 155                 160

Pro Ser Gln Thr Leu Ser Leu Thr Cys Thr Val Ser Gly Gly Ser Ile
                165                 170                 175

Gly Ser Gly Gly Ser Tyr Trp Ser Trp Ile Arg Gln His Pro Gly Lys
            180                 185                 190

Gly Leu Glu Trp Ile Gly Leu Ile Tyr Tyr Asp Gly Ser Thr Tyr Tyr
        195                 200                 205

Asn Pro Ser Leu Lys Ser Arg Val Thr Ile Ser Val Asp Thr Ser Lys
    210                 215                 220

Asn Gln Phe Ser Leu Lys Leu Ser Ser Val Thr Ala Ala Asp Thr Ala
225                 230                 235                 240

Val Tyr Tyr Cys Ala Arg Gly Arg Gly Tyr Glu Thr Ser Leu Ala Phe
                245                 250                 255

Asp Ile Trp Gly Gln Gly Thr Met Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 341
```

<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 341

```
gaggtgcagc tggtggagtc tgggggaggc ttggtacagc ctgggggtc cctgagactc      60
tcctgtgcag cctctggatt caccttcagt agctatagca tgaactgggt ccgccaggct    120
ccagggaagg ggctggagtg ggtttcaacc attagtagta gtagtagtat catatactac    180
gcagactctg tgaagggccg attcaccatc tccagagaca tgccaagaa ctcactgtat     240
ctgcaaatga acagcctgag agctgaggac acggcggtgt actactgcgc cagaggttct    300
caggagcacc tgattttcga ttattgggga caggtacat tggtcaccgt ctcctca        357
```

<210> SEQ ID NO 342
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 342

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ser Met Asn Trp Val Arg Gln Ala Pro Gly Lys Gly Leu Glu Trp Val
        35                  40                  45
Ser Thr Ile Ser Ser Ser Ser Ile Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Ser Gln Glu His Leu Ile Phe Asp Tyr Trp Gly Gln Gly
            100                 105                 110
Thr Leu Val Thr Val Ser Ser
        115
```

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

```
Phe Thr Phe Ser Ser Tyr Ser Met Asn
1               5
```

<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic peptide -continued

```
<400> SEQUENCE: 344

Thr Ile Ser Ser Ser Ser Ile Ile Tyr Tyr Ala Asp Ser Val Lys
1               5                   10                  15

Gly

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ala Arg Gly Ser Gln Glu His Leu Ile Phe Asp Tyr
1               5                   10

<210> SEQ ID NO 346
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 346
gaaattgtgt tgacacagtc tccagccacc ctgtctttgt ctccagggga aagagccacc      60
ctctcctgca gggccagtca gagtgttagc aggtacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag agattctact acccttggac ttttggcgga     300
gggaccaagg ttgagatcaa acgg                                            324

<210> SEQ ID NO 347
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Tyr Tyr Pro Trp
                85                  90                  95

Thr Phe Gly Gly Gly Thr Lys Val Glu Ile Lys Arg
            100                 105

<210> SEQ ID NO 348
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Arg Ala Ser Gln Ser Val Ser Arg Tyr Leu Ala
1               5                   10

<210> SEQ ID NO 349
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Asp Ala Ser Asn Arg Ala Thr
1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gln Gln Arg Phe Tyr Tyr Pro Trp Thr
1               5

<210> SEQ ID NO 351
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 351
atggcactcc ccgtaactgc tctgctgctg ccgttggcat tgctcctgca cgccgcacgc     60
ccggaggtgc agctggtgga gtctggggga ggcttggtac agcctggggg gtccctgaga    120
ctctcctgtg cagcctctgg attcaccttc agtagctata gcatgaactg ggtccgccag    180
gctccaggga aggggctgga gtgggtttca accattagta gtagtagtag tatcatatac    240
tacgcagact ctgtgaaggg ccgattcacc atctccagag acaatgccaa gaactcactg    300
tatctgcaaa tgaacagcct gagagctgag gacacggcgg tgtactactg cgccagaggt    360
tctcaggagc acctgatttt cgattattgg ggacagggta cattggtcac cgtctcctca    420
gggtctacat ccggctccgg gaagcccgga agtggcgaag gtagtacaaa gggggaaatt    480
gtgttgacac agtctccagc caccctgtct ttgtctccag gggaagagc cacccctctcc    540 tgcagggcca gtcagagtgt tagcaggtac ttagcctggt accaacagaa acctggccag    600
gctcccaggc tcctcatcta tgatgcatcc aacagggcca ctggcatccc agccaggttc    660
agtggcagtg ggtctgggac agacttcact ctcaccatca gcagcctaga gcctgaagat    720
tttgcagttt attactgtca gcagagattc tactaccctt ggacttttgg cggagggacc    780
aaggttgaga tcaaacgggc cgctgccctt gataatgaaa agtcaaacgg aacaatcatt    840
cacgtgaagg gcaagcacct ctgtccgtca cccttgttcc ctggtccatc caagccattc    900
```

```
tgggtgttgg tcgtagtggg tggagtcctc gcttgttact ctctgctcgt caccgtggct    960
tttataatct tctggttag atccaaaaga agccgcctgc tccatagcga ttacatgaat    1020
atgactccac gccgccctgg ccccacaagg aaacactacc agccttacgc accacctaga    1080
gatttcgctg cctatcggag cagggtgaag ttttccagat ctgcagatgc accagcgtat    1140
cagcagggcc agaaccaact gtataacgag ctcaacctgg gacgcaggga gagtatgac    1200 gttttggaca gcgcagagg acgggaccct gagatgggtg gcaaaccaag acgaaaaaac    1260
ccccaggagg gtctctataa tgagctgcag aaggataaga tggctgaagc ctattctgaa    1320
ataggcatga aggagagcg gagaagggga aaagggcacg acggtttgta ccagggactc    1380
agcactgcta cgaaggatac ttatgacgct ctccacatgc aagccctgcc acctagg      1437
```

<210> SEQ ID NO 352
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 352

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ser Met Asn Trp Val Arg Gln Ala Pro Gly Lys
    50                  55                  60

Gly Leu Glu Trp Val Ser Thr Ile Ser Ser Ser Ser Ile Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Gly Ser Gln Glu His Leu Ile Phe Asp
        115                 120                 125

Tyr Trp Gly Gln Gly Thr Leu Val Thr Val Ser Ser Gly Ser Thr Ser
    130                 135                 140

Gly Ser Gly Lys Pro Gly Ser Gly Glu Gly Ser Thr Lys Gly Glu Ile
145                 150                 155                 160

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Arg Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Phe Tyr Tyr Pro Trp Thr Phe
                245                 250                 255

Gly Gly Gly Thr Lys Val Glu Ile Lys Arg Ala Ala Ala Leu Asp Asn
```

```
                260                265                270
Glu Lys Ser Asn Gly Thr Ile Ile His Val Lys Gly Lys His Leu Cys
            275                280                285
Pro Ser Pro Leu Phe Pro Gly Pro Ser Lys Pro Phe Trp Val Leu Val
            290                295                300
Val Val Gly Gly Val Leu Ala Cys Tyr Ser Leu Leu Val Thr Val Ala
305                310                315                320
Phe Ile Ile Phe Trp Val Arg Ser Lys Arg Ser Arg Leu Leu His Ser
                325                330                335
Asp Tyr Met Asn Met Thr Pro Arg Arg Pro Gly Pro Thr Arg Lys His
                340                345                350
Tyr Gln Pro Tyr Ala Pro Pro Arg Asp Phe Ala Ala Tyr Arg Ser Arg
            355                360                365
Val Lys Phe Ser Arg Ser Ala Asp Ala Pro Ala Tyr Gln Gln Gly Gln
            370                375                380
Asn Gln Leu Tyr Asn Glu Leu Asn Leu Gly Arg Arg Glu Glu Tyr Asp
385                390                395                400
Val Leu Asp Lys Arg Arg Gly Arg Asp Pro Glu Met Gly Gly Lys Pro
                405                410                415
Arg Arg Lys Asn Pro Gln Glu Gly Leu Tyr Asn Glu Leu Gln Lys Asp
                420                425                430
Lys Met Ala Glu Ala Tyr Ser Glu Ile Gly Met Lys Gly Glu Arg Arg
            435                440                445
Arg Gly Lys Gly His Asp Gly Leu Tyr Gln Gly Leu Ser Thr Ala Thr
        450                455                460
Lys Asp Thr Tyr Asp Ala Leu His Met Gln Ala Leu Pro Pro Arg
465                470                475
```

<210> SEQ ID NO 353
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 353

```
atggcactcc ccgtaactgc tctgctgctg ccgttggcat tgctcctgca cgccgcacgc      60
ccggaaattg tgttgacaca gtctccagcc accctgtctt tgtctccagg ggaaagagcc     120
accctctcct gcagggccag tcagagtgtt agcaggtact tagcctggta ccaacagaaa     180
cctggccagg ctcccaggct cctcatctat gatgcatcca acagggccac tggcatccca     240
gccaggttca gtggcagtgg gtctgggaca gacttcactc tcaccatcag cagcctagag     300
cctgaagatt ttgcagttta ttactgtcag cagagattct actacccttg gacttttggc     360
ggagggacca aggttgagat caaacggggg tctacatccg ctccgggaa gcccggaagt     420
ggcgaaggta gtacaaaggg ggaggtgcag ctggtggagt ctggggggagg cttggtacag     480
cctgggggt ccctgagact ctcctgtgca gcctctggat tcaccttcag tagctatagc     540
atgaactggg tccgccaggc tcagggaag gggctggagt gggtttcaac cattagtagt     600
agtagtagta tcatatacta cgcagactct gtgaagggcc gattcaccat ctccagagac     660
aatgccaaga actcactgta tctgcaaatg aacagcctga gagctgagga cacggcggtg     720
tactactgcg ccagaggttc tcaggagcac ctgattttcg attattgggg acagggtaca     780
ttggtcaccg tctcctcagc cgctgccctt gataatgaaa agtcaaacgg aacaatcatt     840
```

-continued

```
cacgtgaagg gcaagcacct ctgtccgtca cccttgttcc ctggtccatc caagccattc      900
tgggtgttgg tcgtagtggg tggagtcctc gcttgttact ctctgctcgt caccgtggct      960
tttataatct tctgggttag atccaaaaga agccgcctgc tccatagcga ttacatgaat     1020
atgactccac gccgccctgg ccccacaagg aaacactacc agccttacgc accacctaga     1080
gatttcgctg cctatcggag cagggtgaag ttttccagat ctgcagatgc accagcgtat     1140
cagcagggcc agaaccaact gtataacgag ctcaacctgg gacgcaggga agagtatgac     1200
gttttggaca gcgcagagg acgggaccct gagatgggtg gcaaaccaag acgaaaaaac     1260
ccccaggagg gtctctataa tgagctgcag aaggataaga tggctgaagc ctattctgaa     1320
ataggcatga aggagagcg gagaagggga aaagggcacg acggtttgta ccagggactc     1380
agcactgcta cgaaggatac ttatgacgct ctccacatgc aagccctgcc acctagg       1437
```

<210> SEQ ID NO 354
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 354

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Arg Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

Phe Tyr Tyr Pro Trp Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Tyr Ser Met Asn Trp Val Arg Gln Ala Pro Gly Lys Gly Leu
            180                 185                 190

Glu Trp Val Ser Thr Ile Ser Ser Ser Ser Ile Ile Tyr Tyr Ala
        195                 200                 205

Asp Ser Val Lys Gly Arg Phe Thr Ile Ser Arg Asp Asn Ala Lys Asn
    210                 215                 220

Ser Leu Tyr Leu Gln Met Asn Ser Leu Arg Ala Glu Asp Thr Ala Val
225                 230                 235                 240

Tyr Tyr Cys Ala Arg Gly Ser Gln Glu His Leu Ile Phe Asp Tyr Trp
                245                 250                 255
```

Gly Gln Gly Thr Leu Val Thr Val Ser Ser Ala Ala Ala Leu Asp Asn
                260                 265                 270

Glu Lys Ser Asn Gly Thr Ile Ile His Val Lys Gly Lys His Leu Cys
            275                 280                 285

Pro Ser Pro Leu Phe Pro Gly Pro Ser Lys Pro Phe Trp Val Leu Val
        290                 295                 300

Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
450                 455                 460

Lys Asp Thr Tyr Asp Ala Leu His Met Gln Ala Leu Pro Pro Arg
465                 470                 475

<210> SEQ ID NO 355
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 355
caggtgcagc tggtggagtc tgggggaggc gtggtccagc ctggggaggtc cctgagactc     60 tcctgtgcag cgtctggatt caccttcggg agctatggca tgcactgggt ccgccaggct    120
ccaggcaagg ggctggagtg ggtggcagtt atacattatg atggaagtgt tgaatactat    180
gcagactccg tgaagggccg attcaccatc tccagagaca attccaagga cacgctgtat    240
ctgcaaatga acagcctgag agccgaggac acggcggtgt actactgcgc cagaactgac    300
ttctggagcg gatcccctcc aagcttagat tactggggac agggtacatt ggtcaccgtc    360
tcctca                                                                366

<210> SEQ ID NO 356
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile His Tyr Asp Gly Ser Val Glu Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Phe Trp Ser Gly Ser Pro Pro Ser Leu Asp Tyr Trp
            100                 105                 110

Gly Gln Gly Thr Leu Val Thr Val Ser Ser
            115                 120
```

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

```
Phe Thr Phe Gly Ser Tyr Gly Met His
1               5
```

<210> SEQ ID NO 358
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

```
Val Ile His Tyr Asp Gly Ser Val Glu Tyr Tyr Ala Asp Ser Val Lys
1               5                   10                  15

Gly
```

<210> SEQ ID NO 359
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

```
Ala Arg Thr Asp Phe Trp Ser Gly Ser Pro Pro Ser Leu Asp Tyr
1               5                   10                  15
```

<210> SEQ ID NO 360
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 360

```
gacatccagt tgacccagtc tccatcttcc gtgtctgcat ctgtaggaga cagagtcacc    60
atcacttgtc gggcgagtcg gggtattagc agctggttag cctggtatca gcagaaacca   120
gggaaagccc ctaagctcct gatctatggt gcatccagtt tgcaaagtgg ggtcccatca   180
aggttcagcg gcagtggatc tgggacagat ttcactctca ccatcagcag cctgcagcct   240
gaagattttg caacttatta ctgtcagcag atatacacct tccctttcac ttttggcgga   300
gggaccaagg ttgagatcaa acgg                                          324
```

```
<210> SEQ ID NO 361
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361
```

Asp Ile Gln Leu Thr Gln Ser Pro Ser Ser Val Ser Ala Ser Val Gly
1               5                   10                  15

Asp Arg Val Thr Ile Thr Cys Arg Ala Ser Arg Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Tyr Thr Phe Pro Phe
                85                  90                  95

Thr Phe Gly Gly Gly Thr Lys Val Glu Ile Lys Arg
            100                 105

```
<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362
```

Arg Ala Ser Arg Gly Ile Ser Ser Trp Leu Ala
1               5                   10

```
<210> SEQ ID NO 363
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363
```

Gly Ala Ser Ser Leu Gln Ser
1               5

```
<210> SEQ ID NO 364
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 364

Gln Gln Ile Tyr Thr Phe Pro Phe Thr
1               5

<210> SEQ ID NO 365
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 365

```
atggcactcc ccgtaactgc tctgctgctg ccgttggcat tgctcctgca cgccgcacgc    60
ccgcaggtgc agctggtgga gtctggggga ggcgtggtcc agcctgggag gtccctgaga   120
ctctcctgtg cagcgtctgg attcaccttc gggagctatg gcatgcactg ggtccgccag   180
gctccaggca aggggctgga gtgggtggca gttatacatt atgatggaag tgttgaatac   240
tatgcagact ccgtgaaggg ccgattcacc atctccagag acaattccaa ggacacgctg   300
tatctgcaaa tgaacagcct gagagccgag gacacggcgg tgtactactg cgccagaact   360
gacttctgga gcggatcccc tccaagctta gattactggg gacagggtac attggtcacc   420
gtctcctcag gtctacatc cggctccggg aagcccggaa gtggcgaagg tagtacaaag   480
ggggacatcc agttgaccca gtctccatct tccgtgtctg catctgtagg agacagagtc   540
accatcactt gtcgggcgag tcgggggtatt agcagctggt tagcctggta tcagcagaaa   600
ccagggaaag cccctaagct cctgatctat ggtgcatcca gtttgcaaag tggggtccca   660
tcaaggttca gcggcagtgg atctgggaca gatttcactc tcaccatcag cagcctgcag   720
cctgaagatt ttgcaactta ttactgtcag cagatataca ccttcccttt cacttttggc   780
ggagggacca aggttgagat caaacgggcc gctgcccttg ataatgaaaa gtcaaacgga   840
acaatcattc acgtgaaggg caagcacctc tgtccgtcac ccttgttccc tggtccatcc   900
aagccattct gggtgttggt cgtagtgggt ggagtcctcg cttgttactc tctgctcgtc   960
accgtggctt ttataatctt ctgggttaga tccaaaagaa gccgcctgct ccatagcgat  1020
tacatgaata tgactccacg ccgccctggc ccacaagga aacactacca gccttacgca  1080
ccacctagag atttcgctgc ctatcggagc agggtgaagt tttccagatc tgcagatgca  1140
ccagcgtatc agcagggcca gaaccaactg tataacgagc tcaacctggg acgcagggaa  1200
gagtatgacg ttttggacaa gcgcagagga cgggaccctg atgggtgg caaaccaaga  1260
cgaaaaaacc cccaggaggg tctctataat gagctgcaga aggataagat ggctgaagcc  1320
tattctgaaa taggcatgaa aggagagcgg agaaggggaa aagggcacga cggtttgtac  1380
cagggactca gcactgctac gaaggatact tatgacgctc tccacatgca agccctgcca  1440
cctagg                                                             1446
```

<210> SEQ ID NO 366
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

-continued

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Gly Ser Tyr Gly Met His Trp Val Arg Gln Ala Pro Gly Lys
    50                  55                  60

Gly Leu Glu Trp Val Ala Val Ile His Tyr Asp Gly Ser Val Glu Tyr
65                  70                  75                  80

Tyr Ala Asp Ser Val Lys Gly Arg Phe Thr Ile Ser Arg Asp Asn Ser
                85                  90                  95

Lys Asp Thr Leu Tyr Leu Gln Met Asn Ser Leu Arg Ala Glu Asp Thr
            100                 105                 110

Ala Val Tyr Tyr Cys Ala Arg Thr Asp Phe Trp Ser Gly Ser Pro Pro
        115                 120                 125

Ser Leu Asp Tyr Trp Gly Gln Gly Thr Leu Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Asp Ile Gln Leu Thr Gln Ser Pro Ser Ser Val Ser Ala Ser Val
                165                 170                 175

Gly Asp Arg Val Thr Ile Thr Cys Arg Ala Ser Arg Gly Ile Ser Ser
            180                 185                 190

Trp Leu Ala Trp Tyr Gln Gln Lys Pro Gly Lys Ala Pro Lys Leu Leu
        195                 200                 205

Ile Tyr Gly Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ile Tyr Thr Phe Pro
                245                 250                 255

Phe Thr Phe Gly Gly Gly Thr Lys Val Glu Ile Lys Arg Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
```

```
                420                 425                 430
Gln Lys Asp Lys Met Ala Glu Ala Tyr Ser Glu Ile Gly Met Lys Gly
            435                 440                 445

Glu Arg Arg Gly Lys Gly His Asp Gly Leu Tyr Gln Gly Leu Ser
        450                 455                 460

Thr Ala Thr Lys Asp Thr Tyr Asp Ala Leu His Met Gln Ala Leu Pro
465                 470                 475                 480

Pro Arg

<210> SEQ ID NO 367
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 367
atggcactcc ccgtaactgc tctgctgctg ccgttggcat tgctcctgca cgccgcacgc        60
ccggacatcc agttgaccca gtctccatct tccgtgtctg catctgtagg agacagagtc      120
accatcactt gtcgggcgag tcgggggtatt agcagctggt tagcctggta tcagcagaaa      180
ccagggaaag cccctaagct cctgatctat ggtgcatcca gtttgcaaag tggggtccca      240
tcaaggttca gcggcagtgg atctgggaca gatttcactc tcaccatcag cagcctgcag      300
cctgaagatt ttgcaactta ttactgtcag cagatataca cttcccttt cacttttggc      360 ggagggacca aggttgagat caaacggggg tctacatccg gctccgggaa gccggaagt      420 ggcgaaggta gtacaaaggg gcaggtgcag ctggtggagt ctgggggagg cgtggtccag      480
cctgggaggt ccctgagact ctcctgtgca gcgtctggat tcaccttcgg agctatggc      540 atgcactggg tccgccaggc tccaggcaag gggctggagt gggtggcagt tatacattat      600
gatggaagtg ttgaatacta tgcagactcc gtgaagggcc gattcaccat ctccagagac      660
aattccaagg acacgctgta tctgcaaatg aacagcctga gagccgagga cacggcggtg      720
tactactgcg ccagaactga cttctggagc ggatcccctc aagcttaga ttactgggga      780 cagggtacat tggtcaccgt ctcctcagcc gctgcccttg ataatgaaaa gtcaaacgga      840
acaatcattc acgtgaaggg caagcaccc tgtccgtcac ccttgttccc tggtccatcc      900
aagccattct gggtgttggt cgtagtgggt ggagtcctcg cttgttactc tctgctcgtc      960
accgtggctt tataatcttt ctgggttaga tccaaaagaa gccgcctgct ccatagcgat     1020
tacatgaata tgactccacg ccgccctggc cccacaagga aacactacca gccttacgca     1080
ccacctagag atttcgctgc ctatcggagc agggtgaagt tttccagatc tgcagatgca     1140
ccagcgtatc agcagggcca gaaccaactg tataacgagc tcaacctggg acgcagggaa     1200
gagtatgacg ttttggacaa gcgcagagga cgggaccctg agatgggtgg caaaccaaga     1260
cgaaaaaacc cccaggaggg tctctataat gagctgcaga aggataagat ggctgaagcc     1320
tattctgaaa taggcatgaa aggagagcgg agaaggggaa aagggcacga cggtttgtac     1380
cagggactca gcactgctac gaaggatact tatgacgctc tccacatgca agccctgcca     1440
cctagg                                                                1446

<210> SEQ ID NO 368
<211> LENGTH: 482
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 368

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Val
            20                  25                  30

Ser Ala Ser Val Gly Asp Arg Val Thr Ile Thr Cys Arg Ala Ser Arg
        35                  40                  45

Gly Ile Ser Ser Trp Leu Ala Trp Tyr Gln Gln Lys Pro Gly Lys Ala
    50                  55                  60

Pro Lys Leu Leu Ile Tyr Gly Ala Ser Ser Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Ile
            100                 105                 110

Tyr Thr Phe Pro Phe Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Val Glu Ser Gly Gly Val Val Gln
145                 150                 155                 160

Pro Gly Arg Ser Leu Arg Leu Ser Cys Ala Ala Ser Gly Phe Thr Phe
                165                 170                 175

Gly Ser Tyr Gly Met His Trp Val Arg Gln Ala Pro Gly Lys Gly Leu
            180                 185                 190

Glu Trp Val Ala Val Ile His Tyr Asp Gly Ser Val Glu Tyr Tyr Ala
        195                 200                 205

Asp Ser Val Lys Gly Arg Phe Thr Ile Ser Arg Asp Asn Ser Lys Asp
    210                 215                 220

Thr Leu Tyr Leu Gln Met Asn Ser Leu Arg Ala Glu Asp Thr Ala Val
225                 230                 235                 240

Tyr Tyr Cys Ala Arg Thr Asp Phe Trp Ser Gly Ser Pro Pro Ser Leu
                245                 250                 255

Asp Tyr Trp Gly Gln Gly Thr Leu Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
```

Glu Tyr Asp Val Leu Asp Lys Arg Arg Gly Arg Asp Pro Glu Met Gly
            385                 390                 395                 400
                    405                 410                 415

Gly Lys Pro Arg Arg Lys Asn Pro Gln Glu Gly Leu Tyr Asn Glu Leu
                    420                 425                 430

Gln Lys Asp Lys Met Ala Glu Ala Tyr Ser Glu Ile Gly Met Lys Gly
                435                 440                 445

Glu Arg Arg Arg Gly Lys Gly His Asp Gly Leu Tyr Gln Gly Leu Ser
            450                 455                 460

Thr Ala Thr Lys Asp Thr Tyr Asp Ala Leu His Met Gln Ala Leu Pro
465                 470                 475                 480

Pro Arg

<210> SEQ ID NO 369
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 369
caggtgcagc tggtgcagtc tggggctgag gtgaagaagc ctgggtcctc ggtgaaggtc    60
tcctgcaagg cttctggagg caccctcagc agcctggcta tcagctgggt gcgacaggcc   120
cctggacaag ggcttgagtg gatgggaggg gtcatcccta tcttgggtcg ggcaaactac   180
gcacagaagt tccagggcag agtcacgatt accgcggacg agtccacgag cacagcctac   240
atggagctga gcagcctgag atctgaggac acggcggtgt actactgcgc cagaactcct   300
gaatactcct ccagcatatg gcactattac tacggcatgg acgtatgggg ccagggaaca   360
actgtcaccg tctcctca                                                 378

<210> SEQ ID NO 370
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Ser Leu
                20                  25                  30

Ala Ile Ser Trp Val Arg Gln Ala Pro Gly Gln Gly Leu Glu Trp Met
            35                  40                  45

Gly Gly Val Ile Pro Ile Leu Gly Arg Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Glu Tyr Ser Ser Ser Ile Trp His Tyr Tyr Tyr Gly
                100                 105                 110

Met Asp Val Trp Gly Gln Gly Thr Thr Val Thr Val Ser Ser
            115                 120                 125

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Gly Thr Leu Ser Ser Leu Ala Ile Ser
1               5

<210> SEQ ID NO 372
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Gly Val Ile Pro Ile Leu Gly Arg Ala Asn Tyr Ala Gln Lys Phe Gln
1               5                   10                  15

Gly

<210> SEQ ID NO 373
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ala Arg Thr Pro Glu Tyr Ser Ser Ser Ile Trp His Tyr Tyr Tyr Gly
1               5                   10                  15

Met Asp Val

<210> SEQ ID NO 374
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 374
gacatcgtga tgacccagtc tccagactcc ctggctgtgt ctctgggcga gagggccacc      60
atcaactgca gtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagtt cgcccacact     300
cctttcactt ttggcggagg gaccaaggtt gagatcaaac gg                        342

<210> SEQ ID NO 375
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Ala His Thr Pro Phe Thr Phe Gly Gly Gly Thr Lys Val Glu Ile
            100                 105                 110

Lys Arg
```

```
<210> SEQ ID NO 376
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Lys Ser Ser Gln Ser Val Leu Tyr Ser Ser Asn Asn Lys Asn Tyr Leu
1               5                   10                  15

Ala
```

```
<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Trp Ala Ser Thr Arg Glu Ser
1               5
```

```
<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gln Gln Phe Ala His Thr Pro Phe Thr
1               5
```

```
<210> SEQ ID NO 379
<211> LENGTH: 1476
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 379
```

```
atggcactcc ccgtaactgc tctgctgctg ccgttggcat tgctcctgca cgccgcacgc    60
ccgcaggtgc agctggtgca gtctgggggct gaggtgaaga agcctgggtc ctcggtgaag   120
gtctcctgca aggcttctgg aggcaccctc agcagcctgg ctatcagctg ggtgcgacag   180
gcccctggac aagggcttga gtggatggga ggggtcatcc ctatcttggg tcgggcaaac   240
tacgcacaga agttccaggg cagagtcacg attaccgcgg acgagtccac gagcacagcc   300
tacatggagc tgagcagcct gagatctgag gacacggcgg tgtactactg cgccagaact   360
cctgaatact cctccagcat atggcactat tactacggca tggacgtatg gggccaggga   420
acaactgtca ccgtctcctc agggtctaca tccggctccg ggaagcccgg aagtggcgaa   480
ggtagtacaa aggggggacat cgtgatgacc cagtctccag actccctggc tgtgtctctg   540
ggcgagaggg ccaccatcaa ctgcaagtcc agccagagtg ttttatacag ctccaacaat   600
aagaactact tagcttggta ccagcagaaa ccaggacagc ctcctaagct gctcatttac   660
tgggcatcta cccgggaatc cggggtccct gaccgattca gtggcagcgg gtctgggaca   720
gatttcactc tcaccatcag cagcctgcag gctgaagatg tggcagttta ttactgtcag   780
cagttcgccc acactccttt cacttttggc ggagggacca aggttgagat caaacgggcc   840
gctgcccttg ataatgaaaa gtcaaacgga acaatcattc acgtgaaggg caagcacctc   900
tgtccgtcac ccttgttccc tggtccatcc aagccattct gggtgttggt cgtagtgggt   960
ggagtcctcg cttgttactc tctgctcgtc accgtggctc ttataatctt ctgggttaga  1020
tccaaaagaa gccgcctgct ccatagcgat tacatgaata tgactccacg ccgccctggc  1080
cccacaagga aacactacca gccttacgca ccacctagag atttcgctgc ctatcggagc  1140
agggtgaagt tttccagatc tgcagatgca ccagcgtatc agcagggcca gaaccaactg  1200
tataacgagc tcaacctggg acgcaggaa gagtatgacg ttttggacaa gcgcagagga  1260
cgggaccctg agatgggtgg caaaccaaga cgaaaaaacc cccaggaggg tctctataat  1320
gagctgcaga aggataagat ggctgaagcc tattctgaaa taggcatgaa aggagagcgg  1380
agaagggaa aagggcacga cggtttgtac cagggactca gcactgctac gaaggatact  1440
tatgacgctc tccacatgca agccctgcca cctagg                            1476
```

<210> SEQ ID NO 380
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Leu Ser Ser Leu Ala Ile Ser Trp Val Arg Gln Ala Pro Gly Gln
    50                  55                  60

Gly Leu Glu Trp Met Gly Gly Val Ile Pro Ile Leu Gly Arg Ala Asn
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110
Ala Val Tyr Tyr Cys Ala Arg Thr Pro Glu Tyr Ser Ser Ile Trp
        115                 120                 125
His Tyr Tyr Gly Met Asp Val Trp Gly Gln Gly Thr Thr Val Thr
    130                 135                 140
Val Ser Ser Gly Ser Thr Ser Gly Ser Gly Lys Pro Gly Ser Gly Glu
145                 150                 155                 160
Gly Ser Thr Lys Gly Asp Ile Val Met Thr Gln Ser Pro Asp Ser Leu
                165                 170                 175
Ala Val Ser Leu Gly Glu Arg Ala Thr Ile Asn Cys Lys Ser Ser Gln
            180                 185                 190
Ser Val Leu Tyr Ser Ser Asn Asn Lys Asn Tyr Leu Ala Trp Tyr Gln
        195                 200                 205
Gln Lys Pro Gly Gln Pro Pro Lys Leu Leu Ile Tyr Trp Ala Ser Thr
    210                 215                 220
Arg Glu Ser Gly Val Pro Asp Arg Phe Ser Gly Ser Gly Ser Gly Thr
225                 230                 235                 240
Asp Phe Thr Leu Thr Ile Ser Ser Leu Gln Ala Glu Asp Val Ala Val
                245                 250                 255
Tyr Tyr Cys Gln Gln Phe Ala His Thr Pro Phe Thr Phe Gly Gly Gly
            260                 265                 270
Thr Lys Val Glu Ile Lys Arg Ala Ala Ala Leu Asp Asn Glu Lys Ser
        275                 280                 285
Asn Gly Thr Ile Ile His Val Lys Gly Lys His Leu Cys Pro Ser Pro
    290                 295                 300
Leu Phe Pro Gly Pro Ser Lys Pro Phe Trp Val Leu Val Val Val Gly
305                 310                 315                 320
Gly Val Leu Ala Cys Tyr Ser Leu Leu Val Thr Val Ala Phe Ile Ile
                325                 330                 335
Phe Trp Val Arg Ser Lys Arg Ser Arg Leu Leu His Ser Asp Tyr Met
            340                 345                 350
Asn Met Thr Pro Arg Arg Pro Gly Pro Thr Arg Lys His Tyr Gln Pro
        355                 360                 365
Tyr Ala Pro Pro Arg Asp Phe Ala Ala Tyr Arg Ser Arg Val Lys Phe
    370                 375                 380
Ser Arg Ser Ala Asp Ala Pro Ala Tyr Gln Gln Gly Gln Asn Gln Leu
385                 390                 395                 400
Tyr Asn Glu Leu Asn Leu Gly Arg Arg Glu Glu Tyr Asp Val Leu Asp
                405                 410                 415
Lys Arg Arg Gly Arg Asp Pro Glu Met Gly Gly Lys Pro Arg Arg Lys
            420                 425                 430
Asn Pro Gln Glu Gly Leu Tyr Asn Glu Leu Gln Lys Asp Lys Met Ala
        435                 440                 445
Glu Ala Tyr Ser Glu Ile Gly Met Lys Gly Glu Arg Arg Arg Gly Lys
    450                 455                 460
Gly His Asp Gly Leu Tyr Gln Gly Leu Ser Thr Ala Thr Lys Asp Thr
465                 470                 475                 480
Tyr Asp Ala Leu His Met Gln Ala Leu Pro Pro Arg
                485                 490

<210> SEQ ID NO 381
<211> LENGTH: 1476
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 381

```
atggcactcc ccgtaactgc tctgctgctg ccgttggcat tgctcctgca cgccgcacgc      60
ccggacatcg tgatgaccca gtctccagac tccctggctg tgtctctggg cgagagggcc     120
accatcaact gcaagtccag ccagagtgtt ttatacagct ccaacaataa gaactactta     180
gcttggtacc agcagaaacc aggacagcct cctaagctgc tcatttactg ggcatctacc     240
cgggaatccg gggtccctga ccgattcagt ggcagcgggt ctgggacaga tttcactctc     300
accatcagca gcctgcaggc tgaagatgtg gcagtttatt actgtcagca gttcgcccac     360
actcctttca cttttggcgg agggaccaag gttgagatca acggggggtc tacatccggc     420
tccgggaagc ccggaagtgg cgaaggtagt acaaaggggc aggtgcagct ggtgcagtct     480
ggggctgagg tgaagaagcc tgggtcctcg gtgaaggtct cctgcaaggc ttctggaggc     540
accctcagca gcctggctat cagctgggtg cgacaggccc ctggacaagg cttgagtgg      600
atgggagggg tcatccctat cttgggtcgg caaactacg cacagaagtt ccagggcaga      660
gtcacgatta ccgcggacga gtccacgagc acagcctaca tggagctgag cagcctgaga     720
tctgaggaca cggcggtgta ctactgcgcc agaactcctg aatactcctc agcatatgg      780
cactattact acggcatgga cgtatggggc cagggaacaa ctgtcaccgt ctcctcagcc     840
gctgcccttg ataatgaaaa gtcaaacgga acaatcattc acgtgaaggg caagcacctc     900
tgtccgtcac ccttgttccc tggtccatcc aagccattct gggtgttggt cgtagtgggt     960
ggagtcctcg cttgttactc tctgctcgtc accgtggctt ttataatctt ctgggttaga    1020
tccaaaagaa gccgcctgct ccatagcgat tacatgaata tgactccacg ccgccctggc    1080
cccacaagga aacactacca gccttacgca ccacctagag atttcgctgc ctatcggagc    1140
agggtgaagt tttccagatc tgcagatgca ccagcgtatc agcagggcca gaaccaactg    1200
tataacgagc tcaacctggg acgcaggaa gagtatgacg ttttggacaa gcgcagagga    1260
cgggaccctg agatgggtgg caaaccaaga cgaaaaaacc cccaggaggg tctctataat    1320
gagctgcaga aggataagat ggctgaagcc tattctgaaa taggcatgaa aggagagcgg    1380
agaaggggaa aagggcacga cggtttgtac cagggactca gcactgctac gaaggatact    1440
tatgacgctc tccacatgca agccctgcca cctagg                              1476
```

<210> SEQ ID NO 382
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 382

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Val Leu Tyr Ser Ser Asn Asn Lys Asn Tyr Leu Ala Trp Tyr Gln
    50                  55                  60
```

-continued

Gln Lys Pro Gly Gln Pro Pro Lys Leu Leu Ile Tyr Trp Ala Ser Thr
65                  70                  75                  80

Arg Glu Ser Gly Val Pro Asp Arg Phe Ser Gly Ser Gly Ser Gly Thr
            85                  90                  95

Asp Phe Thr Leu Thr Ile Ser Ser Leu Gln Ala Glu Asp Val Ala Val
            100                 105                 110

Tyr Tyr Cys Gln Gln Phe Ala His Thr Pro Phe Thr Phe Gly Gly Gly
            115                 120                 125

Thr Lys Val Glu Ile Lys Arg Gly Ser Thr Ser Gly Ser Gly Lys Pro
130                 135                 140

Gly Ser Gly Glu Gly Ser Thr Lys Gly Gln Val Gln Leu Val Gln Ser
145                 150                 155                 160

Gly Ala Glu Val Lys Lys Pro Gly Ser Ser Val Lys Val Ser Cys Lys
                165                 170                 175

Ala Ser Gly Gly Thr Leu Ser Ser Leu Ala Ile Ser Trp Val Arg Gln
            180                 185                 190

Ala Pro Gly Gln Gly Leu Glu Trp Met Gly Gly Val Ile Pro Ile Leu
            195                 200                 205

Gly Arg Ala Asn Tyr Ala Gln Lys Phe Gln Gly Arg Val Thr Ile Thr
210                 215                 220

Ala Asp Glu Ser Thr Ser Thr Ala Tyr Met Glu Leu Ser Ser Leu Arg
225                 230                 235                 240

Ser Glu Asp Thr Ala Val Tyr Tyr Cys Ala Arg Thr Pro Glu Tyr Ser
                245                 250                 255

Ser Ser Ile Trp His Tyr Tyr Gly Met Asp Val Trp Gly Gln Gly
            260                 265                 270

Thr Thr Val Thr Val Ser Ser Ala Ala Ala Leu Asp Asn Glu Lys Ser
            275                 280                 285

Asn Gly Thr Ile Ile His Val Lys Gly Lys His Leu Cys Pro Ser Pro
290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
            325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
            355                 360                 365

Tyr Ala Pro Pro Arg Asp Phe Ala Ala Tyr Arg Ser Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
            405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
            485                 490

<210> SEQ ID NO 383
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 383
caggtgcggc tggtggagtc tgggggggc gtggtccagc ctgggaggtc cctgagactc      60
tcctgtgcag cgtctggatt caccttcagt agctatggca tacactgggt ccgccaggct    120
ccaggcaagg ggctggagtg ggtggcagtt atagggtatg atggacagga gaaatactat    180
gcagactccg tgaagggccg attcaccatc tccagagaca attccaagaa cacgctgtat    240
ctgcaaatga acagcctgag agccgaggac acggcggtgt actactgcgt caaggggccg    300
ttgcaggagc cgccatacgc ttttgggatg gacgtatggg gccagggaac aactgtcacc    360
gtctcctca                                                            369

<210> SEQ ID NO 384
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Gln Val Arg Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Gly Tyr Asp Gly Gln Glu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Ala Phe Gly Met Asp Val
            100                 105                 110

Trp Gly Gln Gly Thr Thr Val Thr Val Ser Ser
        115                 120

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Phe Thr Phe Ser Ser Tyr Gly Ile His
1               5

<210> SEQ ID NO 386

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Val Ile Gly Tyr Asp Gly Gln Glu Lys Tyr Tyr Ala Asp Ser Val Lys
1               5                   10                  15
Gly

<210> SEQ ID NO 387
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Val Lys Gly Pro Leu Gln Glu Pro Pro Tyr Ala Phe Gly Met Asp Val
1               5                   10                  15

<210> SEQ ID NO 388
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 388
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatagc gcatccacca gggccactgg tatcccagcc     180
aggttcagtg gcagtgggtc tgggacagag ttcactctca ccatcagcag cctgcagtct     240
gaagattttg cagtttatta ctgtcagcag caccacgtct ggcctctcac ttttggcgga     300
gggaccaagg ttgagatcaa acgg                                            324

<210> SEQ ID NO 389
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95
```

Thr Phe Gly Gly Gly Thr Lys Val Glu Ile Lys Arg
            100                 105

<210> SEQ ID NO 390
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Ala Ser Gln Ser Val Ser Ser Asn Leu Ala
1               5                   10

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Ser Ala Ser Thr Arg Ala Thr
1               5

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gln Gln His His Val Trp Pro Leu Thr
1               5

<210> SEQ ID NO 393
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 393
atggcactcc ccgtaactgc tctgctgctg ccgttggcat tgctcctgca cgccgcacgc        60
ccgcaggtgc ggctggtgga gtctgggggg ggcgtggtcc agcctgggag gtccctgaga       120
ctctcctgtg cagcgtctgg attcaccttc agtagctatg catacactg ggtccgccag        180 gctccaggca aggggctgga gtgggtggca gttatagggt atgatggaca ggagaaatac       240
tatgcagact ccgtgaaggg ccgattcacc atctccagag acaattccaa gaacacgctg       300
tatctgcaaa tgaacagcct gagagccgag gacacggcgg tgtactactg cgtcaagggg       360
ccgttgcagg agccgccata cgcttttggg atggacgtat ggggccaggg aacaactgtc       420
accgtctcct cagggtctac atccggctcc gggaagcccg aagtggcga aggtagtaca        480 aaggggaaa tagtgatgac gcagtctcca gccaccctgt ctgtgtctcc aggggaaaga       540
gccaccctct cctgcagggc cagtcagagt gttagcagca acttagcctg gtaccagcag       600
aaacctggcc aggctcccag gctcctcatc tatagcgcat ccaccagggc cactggtatc       660

-continued

```
ccagccaggt tcagtggcag tgggtctggg acagagttca ctctcaccat cagcagcctg    720
cagtctgaag attttgcagt ttattactgt cagcagcacc acgtctggcc tctcactttt    780
ggcggaggga ccaaggttga gatcaaacgg gccgctgccc ttgataatga aaagtcaaac    840
ggaacaatca ttcacgtgaa gggcaagcac ctctgtccgt caccettgtt ccctggtcca    900 tccaagccat tctgggtgtt ggtcgtagtg ggtggagtcc tcgcttgtta ctctctgctc    960
gtcaccgtgg cttttataat cttctgggtt agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa acccccagga gggtctctat aatgagctgc agaaggataa gatggctgaa   1320
gcctattctg aaataggcat gaaaggagag cggagaaggg gaaaagggca cgacggtttg   1380 tacccaggggac tcagcactgc tacgaaggat acttatgacg ctctccacat gcaagccctg   1440
ccacctagg                                                           1449
```

<210> SEQ ID NO 394
<211> LENGTH: 483
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 394

```
Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Ile His Trp Val Arg Gln Ala Pro Gly Lys
        50                  55                  60

Gly Leu Glu Trp Val Ala Val Ile Gly Tyr Asp Gly Gln Glu Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Ala
        115                 120                 125

Phe Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
```

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
            245                 250                 255

Pro Leu Thr Phe Gly Gly Gly Thr Lys Val Glu Ile Lys Arg Ala Ala
        260                 265                 270

Ala Leu Asp Asn Glu Lys Ser Asn Gly Thr Ile Ile His Val Lys Gly
    275                 280                 285

Lys His Leu Cys Pro Ser Pro Leu Phe Pro Gly Pro Ser Lys Pro Phe
290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
            325                 330                 335

Leu Leu His Ser Asp Tyr Met Asn Met Thr Pro Arg Arg Pro Gly Pro
        340                 345                 350

Thr Arg Lys His Tyr Gln Pro Tyr Ala Pro Pro Arg Asp Phe Ala Ala
    355                 360                 365

Tyr Arg Ser Arg Val Lys Phe Ser Arg Ser Ala Asp Ala Pro Ala Tyr
370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
        420                 425                 430

Leu Gln Lys Asp Lys Met Ala Glu Ala Tyr Ser Glu Ile Gly Met Lys
    435                 440                 445

Gly Glu Arg Arg Arg Gly Lys Gly His Asp Gly Leu Tyr Gln Gly Leu
450                 455                 460

Ser Thr Ala Thr Lys Asp Thr Tyr Asp Ala Leu His Met Gln Ala Leu
465                 470                 475                 480

Pro Pro Arg

<210> SEQ ID NO 395
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 395
atggcactcc ccgtaactgc tctgctgctg ccgttggcat tgctcctgca cgccgcacgc    60
ccggaaatag tgatgacgca gtctccagcc accctgtctg tgtctccagg ggaaagagcc   120
accctctcct gcagggccag tcagagtgtt agcagcaact tagcctggta ccagcagaaa   180
cctggccagg ctcccaggct cctcatctat agcgcatcca ccagggccac tggtatccca   240
gccaggttca gtggcagtgg gtctgggaca gagttcactc tcaccatcag cagcctgcag   300
tctgaagatt ttgcagtttt ttactgtcag cagcaccacg tctggcctct cactttttggc   360 ggagggacca aggttgagat caaacggggg tctacatccg gctccgggaa gcccggaagt   420
ggcgaaggta gtacaaaggg gcaggtgcgg ctggtggagt ctggggggggg cgtggtccag   480

```
cctgggaggt ccctgagact ctcctgtgca gcgtctggat tcaccttcag tagctatggc    540
atacactggg tccgccaggc tccaggcaag gggctggagt gggtggcagt tatagggtat    600
gatggacagg agaaatacta tgcagactcc gtgaagggcc gattcaccat ctccagagac    660
aattccaaga acacgctgta tctgcaaatg aacagcctga gagccgagga cacggcggtg    720
tactactgcg tcaaggggcc gttgcaggag ccgccatacg cttttgggat ggacgtatgg    780
ggccagggaa caactgtcac cgtctcctca gccgctgccc ttgataatga aaagtcaaac    840
ggaacaatca ttcacgtgaa gggcaagcac ctctgtccgt cacccttgtt ccctggtcca    900
tccaagccat ctgggtgtt ggtcgtagtg ggtggagtcc tcgcttgtta ctctctgctc    960
gtcaccgtgg cttttataat cttctgggtt agatccaaaa gaagccgcct gctccatagc    1020
gattacatga atatgactcc acgccgccct ggccccacaa ggaaacacta ccagccttac    1080
gcaccaccta gagatttcgc tgcctatcgg agcagggtga agttttccag atctgcagat    1140
gcaccagcgt atcagcaggg ccagaaccaa ctgtataacg agctcaacct gggacgcagg    1200
gaagagtatg acgttttgga caagcgcaga ggacgggacc ctgagatggg tggcaaacca    1260
agacgaaaaa accccagga gggtctctat aatgagctgc agaaggataa gatggctgaa    1320
gcctattctg aaataggcat gaaggagag cggagaaggg gaaaagggca cgacggtttg    1380
taccagggac tcagcactgc tacgaaggat acttatgacg ctctccacat gcaagccctg    1440
ccacctagg                                                           1449
```

<210> SEQ ID NO 396
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Ser Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln His
            100                 105                 110

His Val Trp Pro Leu Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Arg Leu Val Glu Ser Gly Gly Gly Val Val Gln
145                 150                 155                 160

Pro Gly Arg Ser Leu Arg Leu Ser Cys Ala Ala Ser Gly Phe Thr Phe
                165                 170                 175

Ser Ser Tyr Gly Ile His Trp Val Arg Gln Ala Pro Gly Lys Gly Leu

```
            180                 185                 190
Glu Trp Val Ala Val Ile Gly Tyr Asp Gly Gln Glu Lys Tyr Tyr Ala
                195                 200                 205

Asp Ser Val Lys Gly Arg Phe Thr Ile Ser Arg Asp Asn Ser Lys Asn
            210                 215                 220

Thr Leu Tyr Leu Gln Met Asn Ser Leu Arg Ala Glu Asp Thr Ala Val
225                 230                 235                 240

Tyr Tyr Cys Val Lys Gly Pro Leu Gln Glu Pro Pro Tyr Ala Phe Gly
                245                 250                 255

Met Asp Val Trp Gly Gln Gly Thr Thr Val Thr Val Ser Ser Ala Ala
            260                 265                 270

Ala Leu Asp Asn Glu Lys Ser Asn Gly Thr Ile Ile His Val Lys Gly
            275                 280                 285

Lys His Leu Cys Pro Ser Pro Leu Phe Pro Gly Pro Ser Lys Pro Phe
            290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
                340                 345                 350

Thr Arg Lys His Tyr Gln Pro Tyr Ala Pro Pro Arg Asp Phe Ala Ala
                355                 360                 365

Tyr Arg Ser Arg Val Lys Phe Ser Arg Ser Ala Asp Ala Pro Ala Tyr
                370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
            450                 455                 460

Ser Thr Ala Thr Lys Asp Thr Tyr Asp Ala Leu His Met Gln Ala Leu
465                 470                 475                 480

Pro Pro Arg

<210> SEQ ID NO 397
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 397
caggtgcagc tggtggagtc tgggggaggc gtggtccagc ctgggaggtc cctgagactc      60
tcctgtgcag cgtctggatt caccttcagt agccgtggca tgcactgggt ccgccaggct    120
ccaggcaagg ggctggagtg ggtggcagtt atagggtatg atggacagga gaaatactat    180
gcagactccg tgaagggccg attcaccatc tccagagaca attccaagaa cacgctgtat    240
ctgcaaatga acagcctgag agccgaggac acggcggtgt actactgcgt caaggggccg    300
```

```
ttgcaggagc cgccatacga ttatggaatg gacgtatggg gccagggaac aactgtcacc    360
gtctcctca                                                            369
```

<210> SEQ ID NO 398
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Arg
            20                  25                  30

Gly Met His Trp Val Arg Gln Ala Pro Gly Lys Gly Leu Glu Trp Val
        35                  40                  45

Ala Val Ile Gly Tyr Asp Gly Gln Glu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
            100                 105                 110

Trp Gly Gln Gly Thr Thr Val Thr Val Ser Ser
        115                 120
```

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

```
Phe Thr Phe Ser Ser Arg Gly Met His
1               5
```

<210> SEQ ID NO 400
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

```
Val Ile Gly Tyr Asp Gly Gln Glu Lys Tyr Tyr Ala Asp Ser Val Lys
1               5                   10                  15

Gly
```

<210> SEQ ID NO 401
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Val Lys Gly Pro Leu Gln Glu Pro Pro Tyr Asp Tyr Gly Met Asp Val
1               5                   10                  15

<210> SEQ ID NO 402
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 402
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatagc gcatccacca gggccactgg tatcccagcc   180
aggttcagtg gcagtgggtc tgggacagag ttcactctca ccatcagcag cctgcagtct   240
gaagattttg cagtttatta ctgtcagcag caccacgtct ggcctctcac ttttggcgga   300
gggaccaagg ttgagatcaa acgg                                         324

<210> SEQ ID NO 403
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95

Thr Phe Gly Gly Gly Thr Lys Val Glu Ile Lys Arg
            100                 105

<210> SEQ ID NO 404
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Arg Ala Ser Gln Ser Val Ser Ser Asn Leu Ala
1               5                   10

<210> SEQ ID NO 405
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 405

Ser Ala Ser Thr Arg Ala Thr
1               5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gln Gln His His Val Trp Pro Leu Thr
1               5

<210> SEQ ID NO 407
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 407

```
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagccgtg gcatgcactg ggtccgccag     180
gctccaggca aggggctgga gtgggtggca gttatagggt atgatggaca ggagaaatac     240
tatgcagact ccgtgaaggg ccgattcacc atctccagag acaattccaa gaacacgctg     300
tatctgcaaa tgaacagcct gagagccgag gacacggcgg tgtactactg cgtcaagggg     360
ccgttgcagg agccgccata cgattatgga atggacgtat ggggccaggg aacaactgtc     420
accgtctcct caggggtcta catccggctc gggaagcccg aagtggcga aggtagtaca      480 aaggggggaaa tagtgatgac gcagtctcca gccaccctgt ctgtgtctcc aggggaaaga     540
gccaccctct cctgcagggc cagtcagagt gttagcagca acttagcctg gtaccagcag     600
aaacctggcc aggctcccag gctcctcatc tatagcgcat ccaccagggc cactggtatc     660
ccagccaggt tcagtggcag tgggtctggg acagagttca ctctcaccat cagcagcctg     720
cagtctgaag attttgcagt ttattactgt cagcagcacc acgtctggcc tctcactttt     780
ggcggaggga ccaaggttga gatcaaacgg ccgctgccc ttgataatga aaagtcaaac      840
ggaacaatca ttcacgtgaa gggcaagcac ctctgtccgt cacccttgtt ccctggtcca     900
tccaagccat tctgggtgtt ggtcgtagtg ggtggagtcc tcgcttgtta ctctctgctc     960
gtcaccgtgg cttttataat cttctgggtt agatccaaaa gaagccgcct gctccatagc    1020
gattacatga atatgactcc acgccgccct ggccccacaa ggaaacacta ccagccttac    1080
gcaccaccta gagatttcgc tgcctatcgg agcagggtga gtttttccag atctgcagat    1140
gcaccagcgt atcagcaggg ccagaaccaa ctgtataacg agctcaacct gggacgcagg    1200
gaagagtatg acgttttgga caagcgcaga ggacgggacc ctgagatggg tggcaaacca    1260
agacgaaaaa accccaggaa gggtctctat aatgagctgc agaaggataa gatggctgaa    1320
gcctattctg aaataggcat gaaggagag cggagaaggg gaaaagggca cgacggtttg    1380
```

```
taccagggac tcagcactgc tacgaaggat acttatgacg ctctccacat gcaagccctg    1440
ccacctagg                                                            1449
```

<210> SEQ ID NO 408
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Arg Gly Met His Trp Val Arg Gln Ala Pro Gly Lys
    50                  55                  60

Gly Leu Glu Trp Val Ala Val Ile Gly Tyr Asp Gly Gln Glu Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
```

```
              340                 345                 350
Thr Arg Lys His Tyr Gln Pro Tyr Ala Pro Pro Arg Asp Phe Ala Ala
            355                 360                 365
Tyr Arg Ser Arg Val Lys Phe Ser Arg Ser Ala Asp Ala Pro Ala Tyr
        370                 375                 380
Gln Gln Gly Gln Asn Gln Leu Tyr Asn Glu Leu Asn Leu Gly Arg Arg
385                 390                 395                 400
Glu Glu Tyr Asp Val Leu Asp Lys Arg Gly Arg Asp Pro Glu Met
                405                 410                 415
Gly Gly Lys Pro Arg Arg Lys Asn Pro Gln Glu Gly Leu Tyr Asn Glu
            420                 425                 430
Leu Gln Lys Asp Lys Met Ala Glu Ala Tyr Ser Glu Ile Gly Met Lys
            435                 440                 445
Gly Glu Arg Arg Arg Gly Lys Gly His Asp Gly Leu Tyr Gln Gly Leu
            450                 455                 460
Ser Thr Ala Thr Lys Asp Thr Tyr Asp Ala Leu His Met Gln Ala Leu
465                 470                 475                 480
Pro Pro Arg
```

<210> SEQ ID NO 409
<211> LENGTH: 1449
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 409

```
atggcactcc ccgtaactgc tctgctgctg ccgttggcat tgctcctgca cgccgcacgc      60
ccggaaatag tgatgacgca gtctccagcc accctgtctg tgtctccagg ggaaagagcc     120
accctctcct gcagggccag tcagagtgtt agcagcaact tagcctggta ccagcagaaa     180
cctggccagg ctcccaggct cctcatctat agcgcatcca caggccac tggtatccca      240
gccaggttca gtggcagtgg gtctgggaca gagttcactc tcaccatcag cagcctgcag     300
tctgaagatt ttgcagttta ttactgtcag cagcaccacg tctggcctct cacttttggc     360
ggagggacca aggttgagat caaacggggg tctacatccg gctccgggaa gcccggaagt     420
ggcgaaggta gtacaaaggg gcaggtgcag ctggtggagt ctggggag cgtggtccag     480
cctgggaggt ccctgagact ctcctgtgca gcgtctggat tcaccttcag tagccgtggc     540
atgcactggg tccgccaggc tccaggcaag gggctggagt gggtggcagt tatagggtat     600
gatggacagg agaaatacta tgcagactcc gtgaagggcc gattcaccat ctccagagac     660
aattccaaga cacgctgta tctgcaaatg aacagcctga gagccgagga cacggcggtg     720
tactactgcg tcaagggggcc gttgcaggag ccgccatacg attatggaat ggacgtatgg     780
ggccagggaa caactgtcac cgtctcctca gccgctgccc ttgataatga aaagtcaaac     840
ggaacaatca ttcacgtgaa gggcaagcac ctctgtccgt cacccttgtt ccctggtcca     900
tccaagccat tctgggtgtt ggtcgtagtg ggtggagtcc tcgcttgtta ctctctgctc     960
gtcaccgtgg cttttataat cttctgggtt agatccaaaa gaagccgcct gctccatagc    1020
gattacatga atatgactcc acgccgccct ggccccacaa ggaaacacta ccagccttac    1080
gcaccaccta gagatttcgc tgcctatcgg agcagggtga agttttccag atctgcagat    1140
gcaccagcgt atcagcaggg ccagaaccaa ctgtataacg agctcaacct gggacgcagg    1200
```

```
gaagagtatg acgttttgga caagcgcaga ggacgggacc ctgagatggg tggcaaacca    1260
agacgaaaaa accccaggga gggtctctat aatgagctgc agaaggataa gatggctgaa    1320
gcctattctg aaataggcat gaaggagag cggagaaggg gaaaagggca cgacggtttg    1380
taccagggac tcagcactgc tacgaaggat acttatgacg ctctccacat gcaagccctg    1440
ccacctagg                                                            1449
```

```
<210> SEQ ID NO 410
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410
```

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Ser Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln His
            100                 105                 110

His Val Trp Pro Leu Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Val Glu Ser Gly Gly Gly Val Val Gln
145                 150                 155                 160

Pro Gly Arg Ser Leu Arg Leu Ser Cys Ala Ala Ser Gly Phe Thr Phe
                165                 170                 175

Ser Ser Arg Gly Met His Trp Val Arg Gln Ala Pro Gly Lys Gly Leu
            180                 185                 190

Glu Trp Val Ala Val Ile Gly Tyr Asp Gly Gln Glu Lys Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Val Lys Gly Pro Leu Gln Glu Pro Pro Tyr Asp Tyr Gly
                245                 250                 255

Met Asp Val Trp Gly Gln Gly Thr Thr Val Thr Val Ser Ser Ala Ala
            260                 265                 270

Ala Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu

```
                305                 310                 315                 320
Val Thr Val Ala Phe Ile Ile Phe Trp Val Arg Ser Lys Arg Ser Arg
                    325                 330                 335

Leu Leu His Ser Asp Tyr Met Asn Met Thr Pro Arg Arg Pro Gly Pro
                    340                 345                 350

Thr Arg Lys His Tyr Gln Pro Tyr Ala Pro Pro Arg Asp Phe Ala Ala
                    355                 360                 365

Tyr Arg Ser Arg Val Lys Phe Ser Arg Ser Ala Asp Ala Pro Ala Tyr
                    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                    405                 410                 415

Gly Gly Lys Pro Arg Arg Lys Asn Pro Gln Glu Gly Leu Tyr Asn Glu
                    420                 425                 430

Leu Gln Lys Asp Lys Met Ala Glu Ala Tyr Ser Glu Ile Gly Met Lys
                    435                 440                 445

Gly Glu Arg Arg Arg Gly Lys Gly His Asp Gly Leu Tyr Gln Gly Leu
                    450                 455                 460

Ser Thr Ala Thr Lys Asp Thr Tyr Asp Ala Leu His Met Gln Ala Leu
465                 470                 475                 480

Pro Pro Arg

<210> SEQ ID NO 411
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Gly Gly Gly Ser Gly Gly Gly Gly Ser Gly Gly Gly Gly Ser Gly
1               5                   10                  15

Gly Gly Gly Ser
            20

<210> SEQ ID NO 412
<211> LENGTH: 112
<212> TYPE: PRT
<213> ORGANISM: Homo sapiens

<400> SEQUENCE: 412

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                    20                  25                  30

Asp Val Leu Asp Lys Arg Arg Gly Arg Asp Pro Glu Met Gly Gly Lys
                    35                  40                  45

Pro Arg Arg Lys Asn Pro Gln Glu Gly Leu Tyr Asn Glu Leu Gln Lys
                    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                    85                  90                  95

Thr Lys Asp Thr Tyr Asp Ala Leu His Met Gln Ala Leu Pro Pro Arg
                    100                 105                 110
```

<210> SEQ ID NO 413
<211> LENGTH: 6762
<212> TYPE: DNA
<213> ORGANISM: Lentivirus

<400> SEQUENCE: 413

| | | | | | |
|---|---|---|---|---|---|
| ctgacgcgcc | ctgtagcggc | gcattaagcg | cggcgggtgt | ggtggttacg | cgcagcgtga | 60 |
| ccgctacact | tgccagcgcc | ctagcgcccg | ctcctttcgc | tttcttccct | tcctttctcg | 120 |
| ccacgttcgc | cggctttccc | cgtcaagctc | taaatcgggg | gctcccttta | gggttccgat | 180 |
| ttagtgcttt | acggcacctc | gaccccaaaa | aacttgatta | gggtgatggt | tcacgtagtg | 240 |
| ggccatcgcc | ctgatagacg | gttttcgcc | ctttgacgtt | ggagtccacg | ttctttaata | 300 |
| gtggactctt | gttccaaact | ggaacaacac | tcaaccctat | ctcggtctat | tcttttgatt | 360 |
| tataagggat | tttgccgatt | tcggcctatt | ggttaaaaaa | tgagctgatt | taacaaaaat | 420 |
| ttaacgcgaa | ttttaacaaa | atattaacgc | ttacaatttg | ccattcgcca | ttcaggctgc | 480 |
| gcaactgttg | ggaagggcga | tcggtgcggg | cctcttcgct | attacgccag | ctggcgaaag | 540 |
| ggggatgtgc | tgcaaggcga | ttaagttggg | taacgccagg | gttttcccag | tcacgacgtt | 600 |
| gtaaaacgac | ggccagtgaa | ttgtaatacg | actcactata | gggcgacccg | gggatggcgc | 660 |
| gccagtaatc | aattacgggg | tcattagttc | atagcccata | tatggagttc | cgcgttacat | 720 |
| aacttacggt | aaatggcccg | cctggctgac | cgcccaacga | cccccgccca | ttgacgtcaa | 780 |
| taatgacgta | tgttcccata | gtaacgccaa | tagggacttt | ccattgacgt | caatgggtgg | 840 |
| agtatttacg | gtaaactgcc | cacttggcag | tacatcaagt | gtatcatatg | ccaagtacgc | 900 |
| cccctattga | cgtcaatgac | ggtaaatggc | ccgcctggca | ttatgcccag | tacatgacct | 960 |
| tatgggactt | tcctacttgg | cagtacatct | acgtattagt | catcgctatt | accatgctga | 1020 |
| tgcggttttg | gcagtacatc | aatgggcgtg | gatagcggtt | tgactcacgg | ggatttccaa | 1080 |
| gtctccaccc | cattgacgtc | aatgggagtt | tgttttggca | ccaaaatcaa | cgggactttc | 1140 |
| caaaatgtcg | taacaactcc | gccccattga | cgcaaatggg | cggtaggcgt | gtacggtggg | 1200 |
| aggtctatat | aagcagagct | ggtttagtga | accgggtct | ctctggttag | accagatctg | 1260 |
| agcctgggag | ctctctggct | aactagggaa | cccactgctt | aagcctcaat | aaagcttgcc | 1320 |
| ttgagtgctt | caagtagtgt | gtgcccgtct | gttgtgtgac | tctggtaact | agagatccct | 1380 |
| cagacccttt | tagtcagtgt | ggaaaatctc | tagcagtggc | gcccgaacag | ggacttgaaa | 1440 |
| gcgaaaggga | aaccagagga | gctctctcga | cgcaggactc | ggcttgctga | agcgcgcacg | 1500 |
| gcaagaggcg | aggggcggcg | actggtgagt | acgccaaaaa | ttttgactag | cggaggctag | 1560 |
| aaggagagag | atgggtgcga | gagcgtcagt | attaagcggg | ggagaattag | atcgcgatgg | 1620 |
| gaaaaaattc | ggttaaggcc | agggggaaag | aaaaaatata | aattaaaaca | tatagtatgg | 1680 |
| gcaagcaggg | agctagaacg | attcgcagtt | aatcctggcc | tgttagaaac | atcagaaggc | 1740 |
| tgtagacaaa | tactgggaca | gctacaacca | tcccttcaga | caggatcaga | agaacttaga | 1800 |
| tcattatata | atacagtagc | aaccctctat | tgtgtgcatc | aaaggataga | gataaaagac | 1860 |
| accaaggaag | ctttagacaa | gatagaggaa | gagcaaaaca | aaagtaagac | caccgcacag | 1920 |
| caagccgccg | ctgatcttca | gacctggagg | aggagatatg | agggacaatt | ggagaagtga | 1980 |
| attatataaa | tataaagtag | taaaaattga | accattagga | gtagcaccca | ccaaggcaaa | 2040 |
| gagaagagtg | gtgcagagag | aaaaaagagc | agtgggaata | ggagctttgt | tccttgggtt | 2100 |

```
cttgggagca gcaggaagca ctatgggcgc agcgtcaatg acgctgacgg tacaggccag    2160
acaattattg tctggtatag tgcagcagca gaacaatttg ctgagggcta ttgaggcgca    2220
acagcatctg ttgcaactca cagtctgggg catcaagcag ctccaggcaa gaatcctggc    2280
tgtggaaaga tacctaaagg atcaacagct cctggggatt tggggttgct ctggaaaact    2340
catttgcacc actgctgtgc cttggaatgc tagttggagt aataaatctc tggaacagat    2400
ttggaatcac acgacctgga tggagtggga cagagaaatt aacaattaca caagcttaat    2460
acactcctta attgaagaat cgcaaaacca gcaagaaaag aatgaacaag aattattgga    2520
attagataaa tgggcaagtt tgtggaattg gtttaacata acaaattggc tgtggtatat    2580
aaaattattc ataatgatag taggaggctt ggtaggttta agaatagttt ttgctgtact    2640
ttctatagtg aatagagtta ggcagggata ttcaccatta tcgtttcaga cccacctccc    2700
aaccccgagg ggacccgaca ggcccgaagg aatagaagaa gaaggtggag agagagacag    2760
agacagatcc attcgattag tgaacggatc tcgacggtat cggttaactt ttaaaagaaa    2820 agggggatt gggggtaca gtgcagggga aagaatagta gacataatag caacagacat    2880
acaaactaaa gaattacaaa aacaaattac aaaattcaaa attttatcgc gatcgcggaa    2940
tgaaagaccc cacctgtagg tttggcaagc tagcttaagt aacgccattt tgcaaggcat    3000
ggaaaataca taactgagaa tagagaagtt cagatcaagg ttaggaacag agagacagca    3060
gaatatgggc caaacaggat atctgtggta agcagttcct gccccggctc agggccaaga    3120
acagatggtc cccagatgcg gtcccgccct cagcagtttc tagagaacca tcagatgttt    3180
ccagggtgcc ccaaggacct gaaaatgacc ctgtgcctta tttgaactaa ccaatcagtt    3240
cgcttctcgc ttctgttcgc gcgcttctgc tccccgagct caataaaaga gcccacaacc    3300
cctcactcgg cgcgccagtc cttcgaagta gatctttgtc gatcctacca tccactcgac    3360 acaccccgcca gcggccgctg ccaagcttcc gagctctcga attaattcac ggtacccacc    3420
atggcctagg gagactagtc gaatcgatat caacctctgg attacaaaat ttgtgaaaga    3480
ttgactggta ttcttaacta tgttgctcct tttacgctat gtggatacgc tgctttaatg    3540
cctttgtatc atgctattgc ttcccgtatg gctttcattt tctcctcctt gtataaatcc    3600
tggttgctgt ctctttatga ggagttgtgg cccgttgtca ggcaacgtgg cgtggtgtgc    3660
actgtgtttg ctgacgcaac ccccactggt tggggcattg ccaccacctg tcagctcctt    3720
tccgggactt tcgctttccc cctccctatt gccacggcgg aactcatcgc cgcctgcctt    3780
gcccgctgct ggacagggc tcggctgttg ggcactgaca attccgtggt gttgtcgggg    3840
aagctgacgt ccttttcatg gctgctcgcc tgtgttgcca cctggattct gcgcgggacg    3900
tccttctgct acgtcccttc ggccctcaat ccagcggacc ttccttcccg cggcctgctg    3960
ccggctctgc ggcctcttcc gcgtcttcgc cttcgccctc agacgagtcg gatctccctt    4020
tgggccgcct ccccgcctgg ttaattaaag tacctttaag accaatgact acaaggcag    4080 ctgtagatct tagccacttt ttaaaagaaa agggggact ggaagggcga attcactccc    4140
aacgaagaca agatctgctt tttgcttgta ctgggtctct ctggttagac cagatctgag    4200
cctgggagct ctctggctaa ctagggaacc cactgcttaa gcctcaataa agcttgcctt    4260
gagtgcttca agtagtgtgt gcccgtctgt tgtgtgactc tggtaactag agatccctca    4320
gaccctttta gtcagtgtgg aaaatctcta gcaggcatgc cagacatgat aagatacatt    4380
gatgagtttg gacaaaccac aactagaatg cagtgaaaaa aatgctttat ttgtgaaatt    4440
tgtgatgcta ttgctttatt tgtaaccatt ataagctgca ataaacaagt aacaacaac    4500
```

```
aattgcattc attttatgtt tcaggttcag ggggaggtgt gggaggtttt ttggcgcgcc      4560
atcgtcgagg ttccctttag tgagggttaa ttgcgagctt ggcgtaatca tggtcatagc      4620
tgtttcctgt gtgaaattgt tatccgctca caattccaca caacatacga gccggaagca      4680
taaagtgtaa agcctggggt gcctaatgag tgagctaact cacattaatt gcgttgcgct      4740
cactgcccgc tttccagtcg ggaaacctgt cgtgccagct gcattaatga atcggccaac      4800
gcgcggggag aggcggtttg cgtattgggc gctcttccgc ttcctcgctc actgactcgc      4860
tgcgctcggt cgttcggctg cggcgagcgg tatcagctca ctcaaaggcg gtaatacggt      4920
tatccacaga atcaggggat aacgcaggaa agaacatgtg agcaaaaggc cagcaaaagg      4980
ccaggaaccg taaaaaggcc gcgttgctgg cgtttttcca taggctccgc cccccccgacg      5040 agcatcacaa aaatcgacgc tcaagtcaga ggtggcgaaa cccgacagga ctataaagat      5100
accaggcgtt tccccctgga agctccctcg tgcgctctcc tgttccgacc ctgccgctta      5160
ccggatacct gtccgccttt ctcccttcgg aagcgtggc gctttctcat agctcacgct      5220
gtaggtatct cagttcggtg taggtcgttc gctccaagct gggctgtgtg cacgaacccc      5280
ccgttcagcc cgaccgctgc gccttatccg gtaactatcg tcttgagtcc aacccggtaa      5340
gacacgactt atcgccactg gcagcagcca ctggtaacag gattagcaga gcgaggtatg      5400
taggcggtgc tacagagttc ttgaagtggt ggcctaacta cggctacact agaagaacag      5460
tatttggtat ctgcgctctg ctgaagccag ttaccttcgg aaaaagagtt ggtagctctt      5520
gatccggcaa acaaaccacc gctggtagcg gtggtttttt tgtttgcaag cagcagatta      5580
cgcgcagaaa aaaggatct caagaagatc ctttgatctt ttctacgggg tctgacgctc      5640
agtggaacga aaactcacgt taagggattt tggtcatgag attatcaaaa aggatcttca      5700
cctagatcct tttaaattaa aaatgaagtt ttaaatcaat ctaaagtata tatgagtaaa      5760
cttggtctga cagttaccaa tgcttaatca gtgaggcacc tatctcagcg atctgtctat      5820
ttcgttcatc catagttgcc tgactccccg tcgtgtagat aactacgata cgggagggct      5880
taccatctgg ccccagtgct gcaatgatac cgcgagaccc acgctcaccg gctccagatt      5940
tatcagcaat aaaccagcca gccggaaggg ccgagcgcag aagtggtcct gcaactttat      6000
ccgcctccat ccagtctatt aattgttgcc gggaagctag agtaagtagt tcgccagtta      6060
atagtttgcg caacgttgtt gccattgcta caggcatcgt ggtgtcacgc tcgtcgtttg      6120
gtatggcttc attcagctcc ggttcccaac gatcaaggcg agttacatga tcccccatgt      6180
tgtgcaaaaa agcggttagc tccttcggtc ctccgatcgt tgtcagaagt aagttggccg      6240
cagtgttatc actcatggtt atggcagcac tgcataattc tcttactgtc atgccatccg      6300
taagatgctt ttctgtgact ggtgagtact caaccaagtc attctgagaa tagtgtatgc      6360
ggcgaccgag ttgctcttgc ccggcgtcaa tacgggataa taccgcgcca catagcagaa      6420
ctttaaaagt gctcatcatt ggaaaacgtt cttcggggcg aaaactctca aggatcttac      6480
cgctgttgag atccagttcg atgtaaccca ctcgtgcacc caactgatct tcagcatctt      6540
ttactttcac cagcgtttct gggtgagcaa aaacaggaag gcaaaatgcc gcaaaaaagg      6600
gaataagggc gacacggaaa tgttgaatac tcatactctt cctttttcaa tattattgaa      6660
gcatttatca gggttattgt ctcatgagcg gatacatatt tgaatgtatt tagaaaaata      6720
aacaaatagg ggttccgcgc acatttcccc gaaaagtgcc ac                        6762
```